(12) United States Patent
Coburn et al.

(10) Patent No.: US 10,442,790 B2
(45) Date of Patent: *Oct. 15, 2019

(54) BENZAZEPINE COMPOUNDS, CONJUGATES, AND USES THEREOF

(71) Applicant: Silverback Therapeutics, Inc., Seattle, WA (US)

(72) Inventors: Craig Alan Coburn, Seattle, WA (US); Peter Robert Baum, Seattle, WA (US); Sean Wesley Smith, Seattle, WA (US)

(73) Assignee: Silverback Therapeutics, Inc., Seattle, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/274,132

(22) Filed: Feb. 12, 2019

(65) Prior Publication Data

US 2019/0169165 A1 Jun. 6, 2019

Related U.S. Application Data

(63) Continuation of application No. 15/774,262, filed as application No. PCT/US2018/022510 on Mar. 14, 2018.

(Continued)

(51) Int. Cl.
*C07D 401/12* (2006.01)
*C07D 223/16* (2006.01)
(Continued)

(52) U.S. Cl.
CPC ............ *C07D 401/12* (2013.01); *A61K 31/55* (2013.01); *A61K 47/6803* (2017.08); *A61P 35/00* (2018.01); *C07D 223/16* (2013.01); *C07D 401/14* (2013.01); *C07D 403/12* (2013.01); *C07D 471/04* (2013.01)

(58) Field of Classification Search
None
See application file for complete search history.

(56) References Cited

U.S. PATENT DOCUMENTS 5,846,514 A 12/1998 Foster et al.
6,043,238 A 3/2000 Cooper et al.
(Continued)

FOREIGN PATENT DOCUMENTS

CN 102753542 A 10/2012
CN 102781933 A 11/2012
(Continued)

OTHER PUBLICATIONS

Gadd et al., Bioconjugate Chem. 2015, 26, 1743-1752 (Year: 2015).*

(Continued)

*Primary Examiner* — Karl J Puttlitz
(74) *Attorney, Agent, or Firm* — Wilson Sonsini Goodrich & Rosati

(57) ABSTRACT

Benzazepine compounds, conjugates, and pharmaceutical compositions for use in the treatment of disease, such as cancer, are disclosed herein. The disclosed benzazepine compounds are useful, among other things, in the treating of cancer and modulating TLR8. Additionally, benzazepine compounds incorporated into a conjugate with an antibody construct are described herein.

41 Claims, 10 Drawing Sheets

Specification includes a Sequence Listing.

Related U.S. Application Data

(60) Provisional application No. 62/622,780, filed on Jan. 26, 2018, provisional application No. 62/573,630, filed on Oct. 17, 2017, provisional application No. 62/471,886, filed on Mar. 15, 2017.

(51) Int. Cl.

| | | |
|---|---|---|
| *A61K 31/55* | (2006.01) | |
| *C07D 401/14* | (2006.01) | |
| *C07D 403/12* | (2006.01) | |
| *A61K 47/68* | (2017.01) | |
| *C07D 471/04* | (2006.01) | |
| *A61P 35/00* | (2006.01) | |

(56) References Cited

U.S. PATENT DOCUMENTS

| | | | |
|---|---|---|---|
| 6,334,997 | B1 | 1/2002 | Foster et al. |
| 9,943,416 | B2 | 4/2018 | Arramon et al. |
| 9,944,573 | B2 | 4/2018 | Radaelli et al. |
| 9,956,091 | B2 | 5/2018 | de Villiers et al. |
| 2008/0234251 | A1 | 9/2008 | Doherty et al. |
| 2011/0117013 | A1 | 5/2011 | Mack et al. |
| 2013/0171152 | A1 | 7/2013 | Spriggs et al. |
| 2013/0309256 | A1 | 11/2013 | Lyon et al. |
| 2016/0199510 | A1 | 7/2016 | McDonald et al. |
| 2016/0250223 | A1 | 9/2016 | Smith et al. |
| 2016/0257653 | A1* | 9/2016 | Hoves ................ C07D 223/16 |
| 2017/0014423 | A1 | 1/2017 | Hoves et al. |
| 2018/0258048 | A1 | 9/2018 | Craig |

FOREIGN PATENT DOCUMENTS

| | | |
|---|---|---|
| CN | 103562186 A | 2/2014 |
| WO | WO-2007005874 A2 | 1/2007 |
| WO | WO-2007024612 A2 | 3/2007 |
| WO | WO-2007024612 A3 | 5/2007 |
| WO | WO-2007005874 A3 | 7/2007 |
| WO | WO-2011022508 A2 | 2/2011 |
| WO | WO-2011022509 A2 | 2/2011 |
| WO | WO-2011022508 A3 | 6/2011 |
| WO | WO-2011022509 A3 | 6/2011 |
| WO | WO-2012078688 A2 | 6/2012 |
| WO | WO-2012097173 A2 | 7/2012 |
| WO | WO-2012097177 A2 | 7/2012 |
| WO | WO-2012078688 A3 | 8/2012 |
| WO | WO-2012097173 A3 | 9/2012 |
| WO | WO-2012097177 A3 | 10/2012 |
| WO | WO-2014012479 A1 | 1/2014 |
| WO | WO-2015162293 A1 | 10/2015 |
| WO | WO-2016004875 A1 | 1/2016 |
| WO | WO-2016096778 A1 | 6/2016 |
| WO | WO-2016100302 A2 | 6/2016 |
| WO | WO-2016100302 A3 | 9/2016 |
| WO | WO-2016142250 A1 | 9/2016 |
| WO | WO-2017190669 A1 | 11/2017 |
| WO | WO-2017202703 A1 | 11/2017 |
| WO | WO-2017202704 A1 | 11/2017 |
| WO | WO-2017216054 A1 | 12/2017 |
| WO | 2018140831 * | 8/2018 |
| WO | WO-2018140831 A2 | 8/2018 |
| WO | WO-2018144955 A1 | 8/2018 |

OTHER PUBLICATIONS

Jain et al., Pharm Res (2015) 32:3526-3540 (Year: 2015).*

Berge et al. Pharmaceutically acceptable salts, J. Pharm. Sci, 1977, 66:1-19.

Database Caplus Chemical Abstracts Service, Columbus, Ohio, US; Database Accession No. 2017:1888322, Abstract of WO 2017202704, F. Hoffmann-La Roche AG, (Year: 2017).

Fedorak et al. A novel colon-specific steroid prodrug enhances sodium chloride absorption in rat colitis. Am. J. Physiol. 269:G210-218 (1995).

Hochhaus et al. A selective HPLC/RIA for dexamethasone and its prodrug dexamethasone-21-sulphobenzoate sodium in biological fluids. Biomed. Chrom. 6:283-286 (1992).

Larsen et al. Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).

Larsen et al. Prodrug forms for the sulfonamide group. II. water-soluble amino acid derivatives of N-methylsulfonylamindes as possible prodrug derivatives. Int'l J of Pharmaceutics 47:103-110 (1988).

McLoed et al. A Glucocorticoid Prodrug Facilitates Normal Mucosal Function in Rat Colitis Without Adrenal Suppression, Gastroenterol, 1994, 106:405-413.

PCT/CN2017/083031 International Search Report dated Aug. 3, 2017.

PCT/US2018/022510 International Search Report and Written Opinion dated Jul. 3, 2018.

Sinkula et al. Rationale for design of biologically reversible drug derivatives: prodrugs. J. Pharm. Sci. 64:181-210 (1975).

U.S. Appl. No. 15/774,262 Notice of Allowance dated Dec. 19, 2018.

U.S. Appl. No. 15/973,506 Office Action dated Dec. 6, 2018.

* cited by examiner

SEQUENCE LISTING

<160> NUMBER OF SEQ ID NOS: 27

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
 50                  55                  60

Lys Gly Arg Phe Ala Phe Ser Leu Asp Thr Ser Val Ser Thr Ala Tyr
 65                  70                  75                  80
```

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys
            100                 105

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
            100                 105                 110

Gly Thr Leu Val Thr Val Ser Ser
        115                 120

<210> SEQ ID NO 6

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Tyr Phe Gln Gln Arg Pro Gly Gln Ser
        35                  40                  45

Pro Arg Pro Leu Ile Tyr Lys Ile Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 9
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Thr Ser Gly Asp Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Lys Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Lys Phe His Phe Val Ser Gly Ser Pro Phe Gly Met Asp Val
            100                 105                 110

Trp Gly Gln Gly Thr Thr Val Thr Val Ser Ser
        115                 120

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105

<210> SEQ ID NO 13
<211> LENGTH: 123
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 13

Glu Val Lys Leu Gln Glu Ser Gly Gly Gly Phe Val Lys Pro Gly Gly
1               5                   10                  15

Ser Leu Lys Val Ser Cys Ala Ala Ser Gly Phe Thr Phe Ser Ser Tyr
            20                  25                  30

Ala Met Ser Trp Val Arg Leu Ser Pro Glu Met Arg Leu Glu Trp Val
        35                  40                  45

Ala Thr Ile Ser Ser Ala Gly Gly Tyr Ile Phe Tyr Ser Asp Ser Val
    50                  55                  60

Gln Gly Arg Phe Thr Ile Ser Arg Asp Asn Ala Lys Asn Thr Leu His
65                  70                  75                  80

Leu Gln Met Gly Ser Leu Arg Ser Gly Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110

Trp Gly Gln Gly Thr Thr Val Thr Val Ser Ser
        115                 120

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Val Lys
            100                 105                 110

<210> SEQ ID NO 15
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Lys Leu Glu Glu Ser Gly Gly Gly Phe Val Lys Pro Gly Gly
1               5                   10                  15

Ser Leu Lys Ile Ser Cys Ala Ala Ser Gly Phe Thr Phe Arg Asn Tyr
            20                  25                  30

Ala Met Ser Trp Val Arg Leu Ser Pro Glu Met Arg Leu Glu Trp Val

```
                35                  40                  45
Ala Thr Ile Ser Ser Ala Gly Gly Tyr Ile Phe Tyr Ser Asp Ser Val
     50                  55                  60

Gln Gly Arg Phe Thr Ile Ser Arg Asp Asn Ala Lys Asn Thr Leu His
65                  70                  75                  80

Leu Gln Met Gly Ser Leu Arg Ser Gly Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110

Trp Gly Gln Gly Thr Thr Val Thr Val Ser Ser
            115                 120

<210> SEQ ID NO 16
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Glu Leu Thr Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Gln Leu Ala Trp Tyr Gln Gln Lys Thr Gly Gln
        35                  40                  45

Ser Pro Glu Leu Leu Ile Tyr Trp Ala Ser Thr Arg Gln Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Thr Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Arg His Asp Ala His Tyr Gly Thr Trp Phe Ala Tyr Trp Gly Gln
```

```
                     100                 105                 110

Gly Thr Leu Val Thr Val Ser Ser
        115                 120

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ile Arg Asn
            20                  25                  30

Asp Gly Asn Thr Tyr Leu Glu Trp Tyr Gln Gln Arg Pro Gly Gln Ser
        35                  40                  45

Pro Arg Arg Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 19
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Ile Gln Leu Gln Gln Ser Gly Pro Glu Leu Met Lys Pro Gly Ala
1               5                   10                  15

Ser Val Lys Ile Ser Cys Lys Ala Ser Thr Tyr Ser Phe Thr Arg Tyr
            20                  25                  30

Phe Met His Trp Val Lys Gln Ser His Gly Glu Ser Leu Glu Trp Ile
        35                  40                  45

Gly Tyr Ile Asp Pro Phe Asn Gly Gly Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Val Thr Tyr Gly Ser Asp Tyr Phe Asp Tyr Trp Gly Gln Gly Thr Thr
            100                 105                 110

Leu Thr Val Ser Ser
        115

<210> SEQ ID NO 20
<211> LENGTH: 108
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 20

Asp Ile Val Met Thr Gln Pro Gln Lys Phe Met Ser Thr Ser Val Gly
1               5                   10                  15

Asp Arg Val Ser Val Thr Cys Lys Ala Ser Gln Asn Val Glu Thr Asp
            20                  25                  30

Val Val Trp Tyr Gln Gln Lys Pro Gly Gln Pro Pro Lys Ala Leu Ile
        35                  40                  45

Tyr Ser Ala Ser Tyr Arg His Ser Gly Val Pro Asp Arg Phe Thr Gly
    50                  55                  60

Ser Gly Ser Gly Thr Asn Phe Thr Leu Thr Ile Ser Thr Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Ile Arg
            100                 105

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Leu Thr Ile Glu Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Gly Pro Lys Phe
    50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Asp Thr Ala Val Tyr Tyr Cys
                85                  90                  95

Ala Val His Asn Ala His Tyr Gly Thr Trp Phe Ala Tyr Trp Gly Gln
                100                 105                 110

Gly Thr Leu Val Thr Val Ser Ser
            115                 120

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Glu Trp Tyr Gln Gln Arg Pro Gly Gln Ser
        35                  40                  45
```

Pro Arg Pro Leu Ile Tyr Lys Ile Ser Thr Arg Phe Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Thr Ser Gly Leu Asp Tyr Trp Gly Gln Gly Thr Leu Val
            100                 105                 110

Thr Val Ser Ser
            115

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
            35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys
            100                 105

```
<210> SEQ ID NO 25
<211> LENGTH: 5
<212> TYPE: PRT
<213> ORGANISM: Unknown
<220> FEATURE:
<223> OTHER INFORMATION: Description of Unknown:
      recognition motif sequence
<220> FEATURE:
<221> NAME/KEY: MOD_RES
<222> LOCATION: (3)..(3)
<223> OTHER INFORMATION: Any amino acid

<400> SEQUENCE: 25

Leu Pro Xaa Thr Gly
1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Leu Gly
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Leu Ala Leu
1
```

BENZAZEPINE COMPOUNDS, CONJUGATES, AND USES THEREOF

RELATED APPLICATION INFORMATION

This application is a continuation application of U.S. patent application Ser. No. 15/774,262 filed May 7, 2018, which is a national stage entry of International Application No. PCT/US2018/022510 filed Mar. 14, 2018, which claims the benefit of U.S. Provisional Application No. 62/622,780 filed Jan. 26, 2018, U.S. Provisional Application No. 62/573,630 filed Oct. 17, 2017, and U.S. Provisional Application No. 62/471,886 filed Mar. 15, 2017, the contents of each of which are incorporated herein by reference in their entirety.

SEQUENCE LISTING

The instant application contains a Sequence Listing which has been filed electronically in ASCII format and is hereby incorporated by reference in its entirety. Said ASCII copy, created on Nov. 8, 2018, is named 50358-716_831_SL.txt and is 28,096 bytes in size.

BACKGROUND OF THE INVENTION

One of the leading causes of death in the United States is cancer. The conventional methods of cancer treatment, like chemotherapy, surgery, or radiation therapy, tend to be either highly toxic or nonspecific to a cancer, or both, resulting in limited efficacy and harmful side effects. However, the immune system has the potential to be a powerful, specific tool in fighting cancers. In many cases tumors can specifically express genes whose products are required for inducing or maintaining the malignant state. These proteins may serve as antigen markers for the development and establishment of more specific anti-cancer immune response. The boosting of this specific immune response has the potential to be a powerful anti-cancer treatment that can be more effective than conventional methods of cancer treatment and can have fewer side effects.

SUMMARY OF THE INVENTION

In some aspects, the present disclosure provides a compound represented by the structure of Formula (IIA):

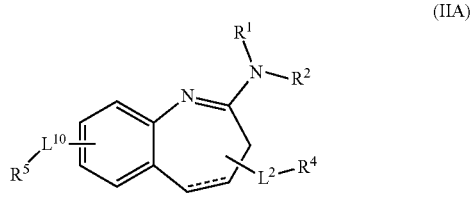

(IIA)

or a pharmaceutically acceptable salt thereof, wherein:

------ represents an optional double bond;

$L^{10}$ is $-X^{10}-$;

$L^2$ is selected from $-X^2-$, $-X^2-C_{1-6}$ alkylene-$X^2-$, $-X^2-C_{2-6}$ alkenylene-$X^2-$, and $-X^2-C_{2-6}$ alkynylene-$X^2-$, each of which is optionally substituted on alkylene, alkenylene or alkynylene with one or more $R^{12}$;

$X^{10}$ is selected from $-C(O)-$, and $-C(O)N(R^{10})-*$, wherein * represents where $X^{10}$ is bound to $R^5$;

$X^2$ at each occurrence is independently selected from a bond, $-O-$, $-S-$, $-N(R^{10})-$, $-C(O)-$, $-C(O)O-$, $-OC(O)-$, $-OC(O)O-$, $-C(O)N(R^{10})-$, $-C(O)N(R^{10})C(O)-$, $-C(O)N(R^{10})C(O)N(R^{10})-$, $-N(R^{10})C(O)-$, $-N(R^{10})C(O)N(R^{10})-$, $-N(R^{10})C(O)O-$, $-OC(O)N(R^{10})-$, $-C(NR^{10})-$, $-N(R^{10})C(NR^{10})-$, $-C(NR^{10})N(R^{10})-$, $-N(R^{10})C(NR^{10})N(R^{10})-$, $-S(O)_2-$, $-OS(O)-$, $-S(O)O-$, $-S(O)$, $-OS(O)_2-$, $-S(O)_2O$, $-N(R^{10})S(O)_2-$, $-S(O)_2N(R^{10})-$, $-N(R^{10})S(O)-$, $-S(O)N(R^{10})-$, $-N(R^{10})S(O)_2N(R^{10})-$, and $-N(R^{10})S(O)N(R^{10})-$;

$R^1$ and $R^2$ are independently selected from hydrogen; and $C_{1-10}$ alkyl, $C_{2-10}$ alkenyl, and $C_{2-10}$ alkynyl, each of which is optionally substituted with one or more substituents independently selected from halogen, $-OR^{10}$, $-SR^{10}$, $-C(O)N(R^{10})_2$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, and $-CN$;

$R^4$ is selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R^{10}$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl;

$R^5$ is selected from unsaturated $C_{4-8}$ carbocycle; bicyclic carbocycle; and fused 5-5, fused 5-6, and fused 6-6 bicyclic heterocycle, wherein $R^5$ is optionally substituted and wherein substituents are independently selected at each occurrence from: halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^5$ is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl;

$R^{10}$ is independently selected at each occurrence from hydrogen, $-NH_2$, $-C(O)OCH_2C_6H_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, $-OH$, $-CN$, $-NO_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and haloalkyl;

R$^{12}$ is independently selected at each occurrence from halogen, —OR$^{10}$, —SR$^{10}$, N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle.

In some embodiments, the compound of Formula (IIA) is represented by Formula (IIB):

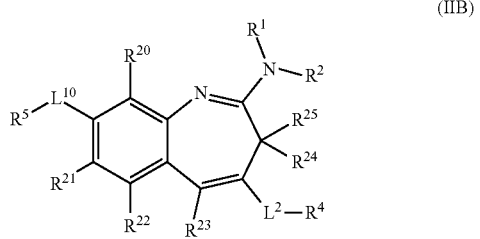

(IIB)

or a pharmaceutically acceptable salt thereof, wherein:

R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$, and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —OR$^{10}$, —NO$_2$, —CN, and C$_{1-10}$ alkyl. R$^{20}$, R$^{21}$, R$^{22}$, and R$^{23}$ may be each hydrogen. In certain embodiments, R$^{21}$ is halogen. In certain embodiments, R$^{21}$ is hydrogen. In certain embodiments, R$^{21}$ is —OR$^{10}$. For example, R$^{21}$ may be —OCH$_3$.

In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In certain embodiments, R$^{24}$ and R$^{25}$ are each hydrogen. In other embodiments, R$^{24}$ and R$^{25}$ taken together form an optionally substituted saturated C$_{3-5}$ carbocycle, wherein substituents are selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; and C$_{1-10}$ alkyl, C$_{2-10}$ alkenyl, C$_{2-10}$ alkynyl, each of which is independently optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle.

In some embodiments, R$^1$ is hydrogen. In some embodiments, R$^2$ is hydrogen. In some embodiments, R$^2$ is —C(O)—.

In some embodiments, L$^{10}$ is selected from —C(O)N(R$^{10}$)—*. In certain embodiments, R$^{10}$ of —C(O)N(R$^{10}$)—* is selected from hydrogen and C$_{1-6}$ alkyl. For example, L$^{10}$ may be —C(O)NH—*.

In some embodiments, R$^5$ is an optionally substituted bicyclic carbocycle. In certain embodiments, R$^5$ is an optionally substituted 8- to 12-membered bicyclic carbocycle. R$^5$ may be an optionally substituted 8- to 12-membered bicyclic carbocycle substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. In certain embodiments, R$^5$ is an optionally substituted 8- to 12-membered bicyclic carbocycle substituted with one or more substituents independently selected from —OR$^{10}$, —N(R$^{10}$)$_2$, and =O. In some embodiments, R$^5$ is an optionally substituted indane, and optionally substituted tetrahydronaphthalene. R$^5$ may be selected from:

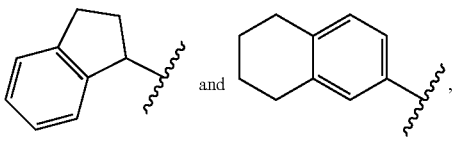 [SMILES: *C1CCc2ccccc21 ; *c1ccc2c(c1)CCCC2]

and any one of which is optionally substituted. For example, the R$^5$ is selected from:

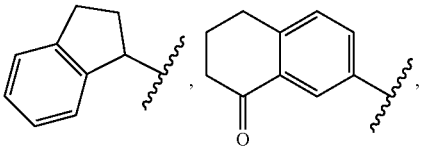

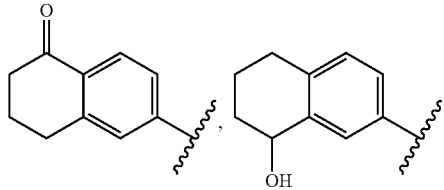

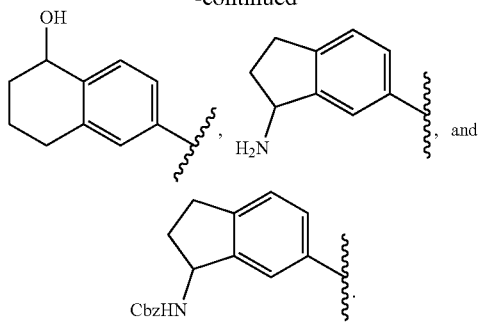

In some embodiments, $R^5$ is an optionally substituted unsaturated $C_{4-8}$ carbocycle. In certain embodiments, $R^5$ is an optionally substituted unsaturated $C_{4-6}$ carbocycle. In certain embodiments, $R^5$ is an optionally substituted unsaturated $C_{4-6}$ carbocycle with one or more substituents independently selected from optionally substituted $C_{3-12}$ carbocycle, and optionally substituted 3- to 12-membered heterocycle. $R^5$ may be an optionally substituted unsaturated $C_{4-6}$ carbocycle with one or more substituents independently selected from optionally substituted phenyl, optionally substituted 3- to 12-heterocycle, optionally substituted $C_{1-10}$ alkyl, optionally substituted $C_{2-10}$ alkenyl, and halogen.

In some embodiments, $R^5$ is selected from an optionally substituted fused 5-5, fused 5-6, and fused 6-6 bicyclic heterocycle. In certain embodiments, $R^5$ is an optionally substituted fused 5-5, fused 5-6, and fused 6-6 bicyclic heterocycle with one or more substituents independently selected from —C(O)OR$^{10}$, —N(R$^{10}$)$_2$, —OR$^{10}$, and optionally substituted $C_{1-10}$ alkyl. In certain embodiments, $R^5$ is an optionally substituted fused 5-5, fused 5-6, and fused 6-6 bicyclic heterocycle substituted with —C(O)OR$^{10}$. In certain embodiments, $R^5$ is an optionally substituted fused 6-6 bicyclic heterocycle. For example, the fused 6-6 bicyclic heterocycle may be an optionally substituted pyridine-piperidine. In some embodiments, $L^{10}$ is bound to a carbon atom of the pyridine of the fused pyridine-piperidine. In certain embodiments, $R^5$ is selected from tetrahydroquinoline, tetrahydroisoquinoline, tetrahydronaphthyridine, cyclopentapyridine, and dihydrobenzoxaborole, any one of which is optionally substituted. $R^5$ may be an optionally substituted tetrahydronaphthyridine. In some embodiments, $R^5$ is selected from:

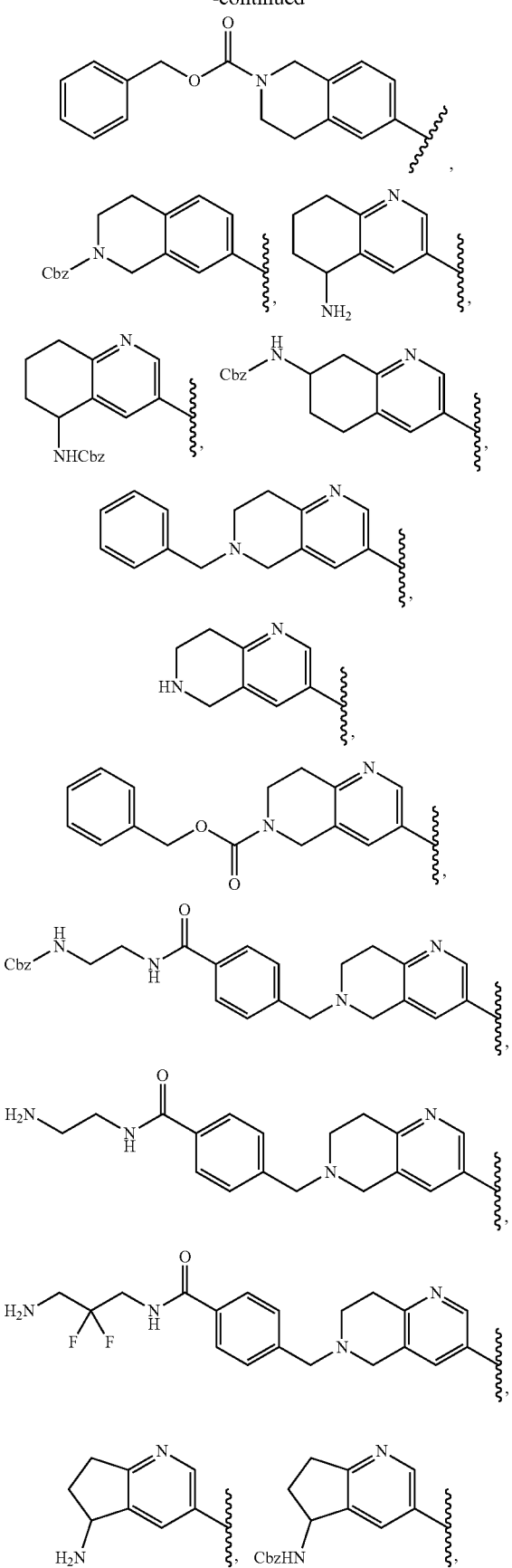

-continued

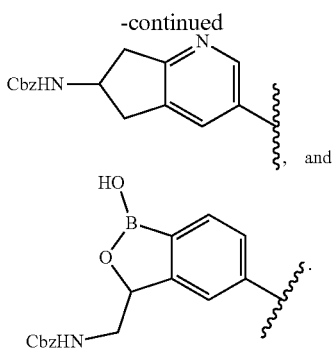

In some embodiments, when $R^5$ is substituted, substituents on $R^5$ are independently selected at each occurrence from: halogen, $-OR^{10}$, $-SR^{10}$, $-C(O)N(R^{10})_2$, $-N(R^{10})C(O)R^{10}$, $N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl. In certain embodiments, the substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle. In certain embodiments, the substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})_2$, $-C(O)R^{10}$, $-C(O)OR^{10}$, $OC(O)R^{10}$, $-NO_2$, $=O$, and $-CN$; and $C_{1-10}$ alkyl optionally substituted with one or more substituents independently selected from halogen, $-OR^{10}$, $-SR^{10}$, $-N(R^{10})_2$, $-C(O)R^{10}$, $-C(O)OR^{10}$, $-NO_2$, $=O$, and $-CN$. In some embodiments, $R^5$ is not substituted.

In some embodiments, $L^2$ is selected from $-C(O)-$, and $-C(O)NR^{10}-$. In some embodiments, $L^2$ is $-C(O)-$. In some embodiments, $L^2$ is selected from $-C(O)NR^{10}-$. $R^{10}$ of $-C(O)NR^{10}-$ may be selected from hydrogen and $C_{1-6}$ alkyl. For example, $L^2$ may be $-C(O)NH-$.

In some embodiments, $R^4$ is selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R^{10}$; $C_{1-10}$ alkyl, $C_{2-10}$ alkenyl, $C_{2-10}$ alkynyl, each of which is optionally substituted with one or substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{3-12}$ carbocycle, and 3- to 12-membered heterocycle; and $C_{3-12}$ carbocycle and 3- to 12-membered, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, $=O$, $=S$, $=N(R^{10})$, $-CN$, $C_{1-6}$ alkyl, $C_{2-6}$ alkenyl, and $C_{2-6}$ alkynyl. In some embodiments, $R^4$ is selected from: $-OR^{10}$, and $-N(R^{10})_2$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, $-OR^{10}$, $-SR^{10}$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl. In certain embodiments, $R^4$ is $-N(R^{10})_2$. $R^{10}$ of $-N(R^{10})_2$ may be independently selected at each occurrence from optionally substituted $C_{1-6}$ alkyl. In certain embodiments, $R^{10}$ of $-N(R^{10})_2$ is independently selected at each occurrence from methyl, ethyl, propyl, and butyl, any one of which is optionally substituted. For example, $R^4$ may be

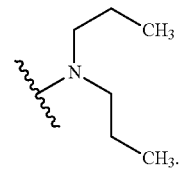

In certain embodiments, $-L^2-R^4$ is

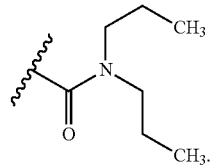

In some embodiments, $R^{12}$ is independently selected at each occurrence from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, $-CN$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, $-CN$, $C_{1-6}$ alkyl, $C_{2-6}$ alkenyl, and $C_{2-6}$ alkynyl. In certain embodiments, $R^{12}$ is independently selected at each occurrence from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-P(O)(OR^{10})_2$, $-OP(O)(OR^{10})_2$, $-NO_2$, $=O$, $=S$, $=N(R^{10})$, and $-CN$; and $C_{1-10}$ alkyl, $C_{2-10}$ alkenyl, $C_{2-10}$ alkynyl, each of which is optionally substituted with one or more substituents independently selected from halogen, —OR[10], —SR[10], —N(R[10])$_2$, —C(O)R[10], C(O)N(R[10])$_2$, —N(R[10])C(O)R[10], —C(O)OR[10], —OC(O)R[10], —S(O)R[10], —S(O)$_2$R[10], —P(O)(OR[10])$_2$, —OP(O)(OR[10])$_2$, —NO$_2$, =O, =S, =N(R[10]), —CN, C$_{3-10}$ carbocycle and 3- to 10-membered heterocycle.
In some embodiments, the compound is selected from:
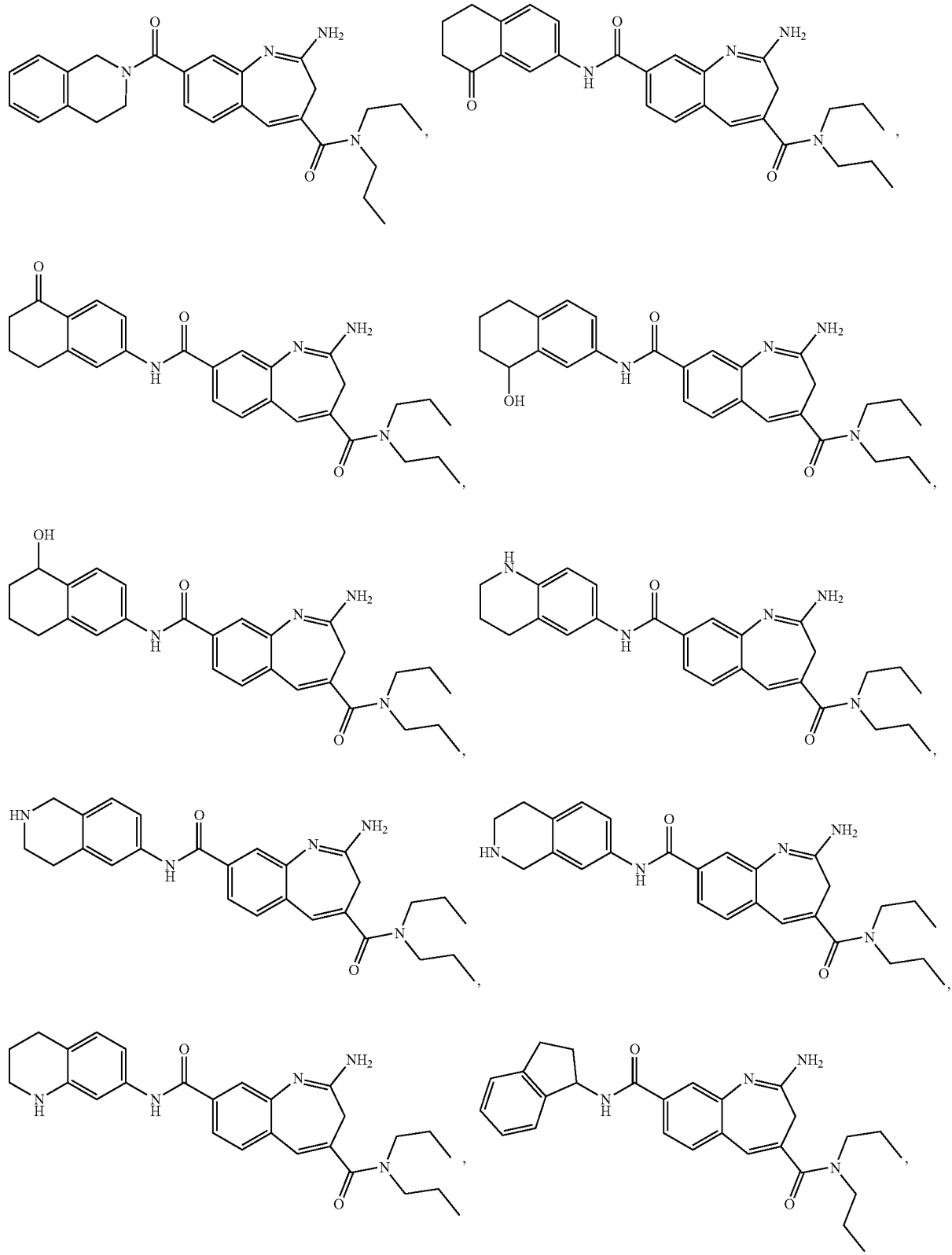

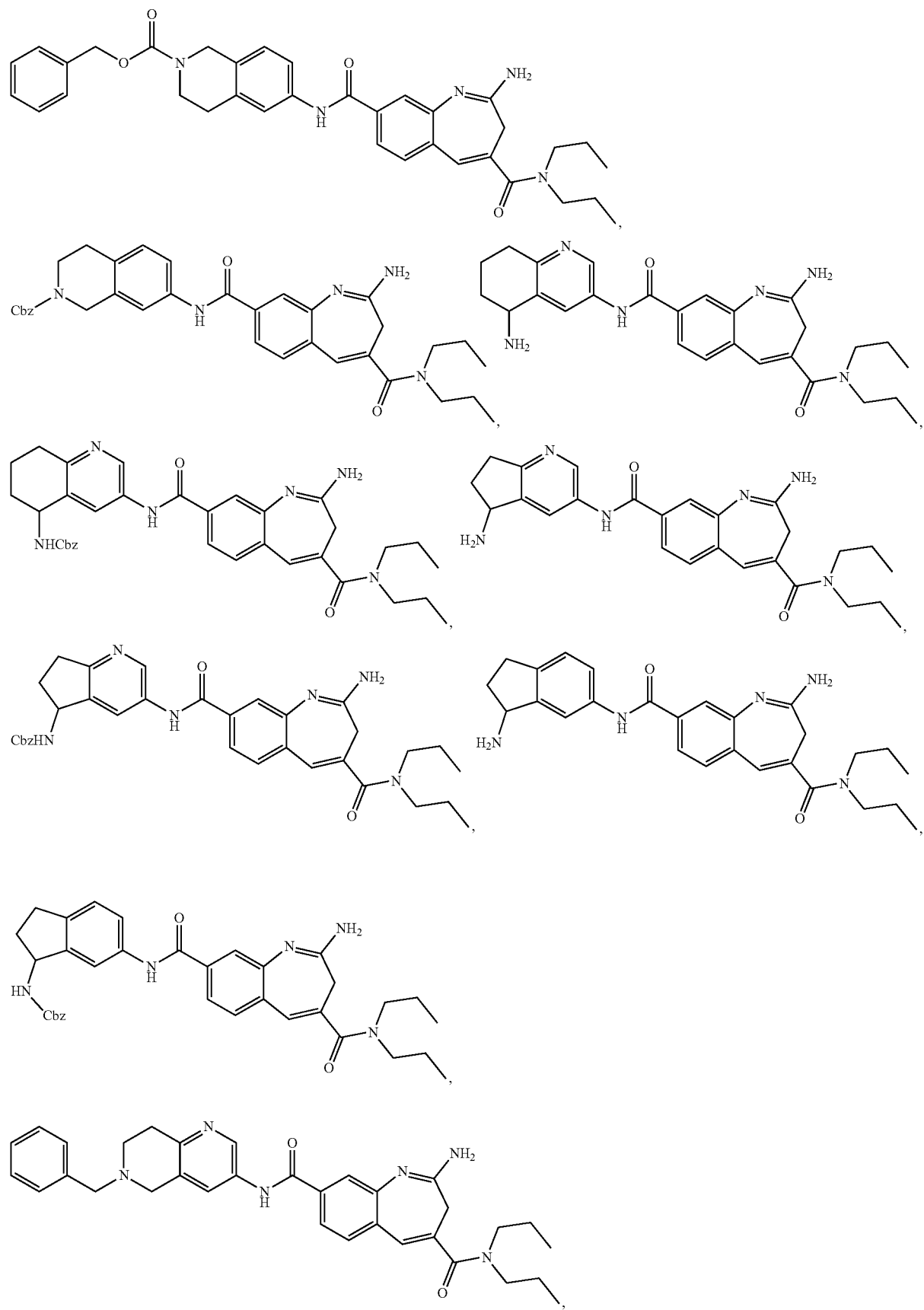

-continued
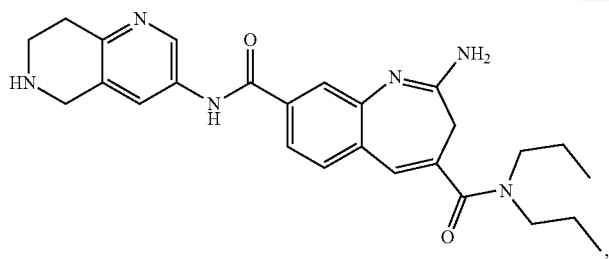
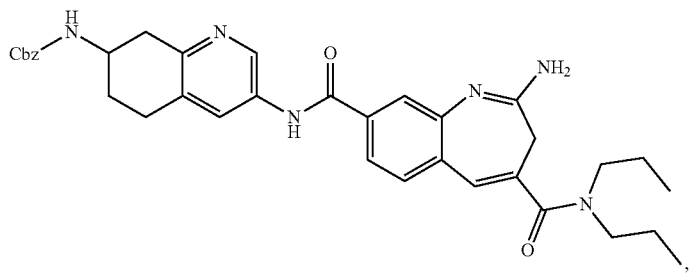
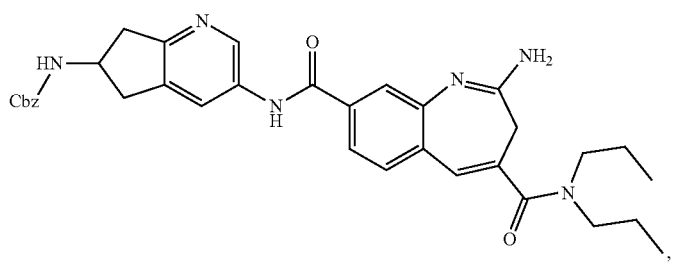
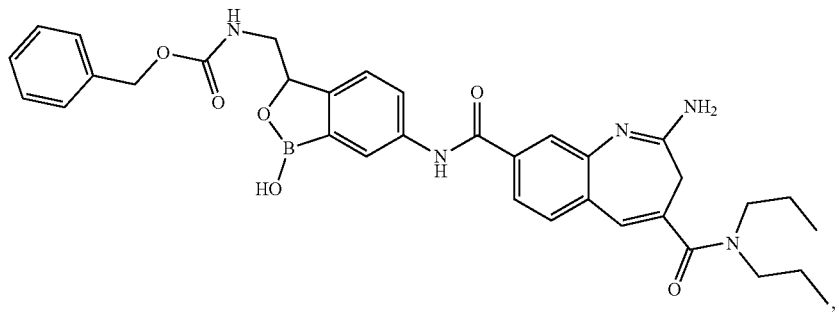
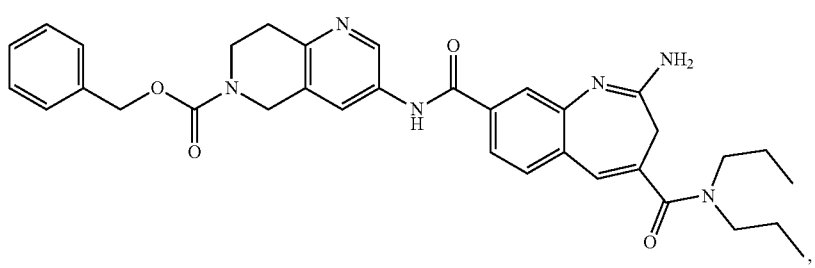
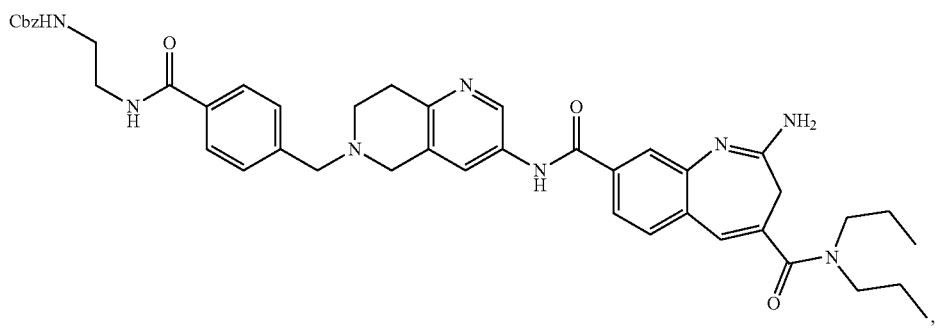

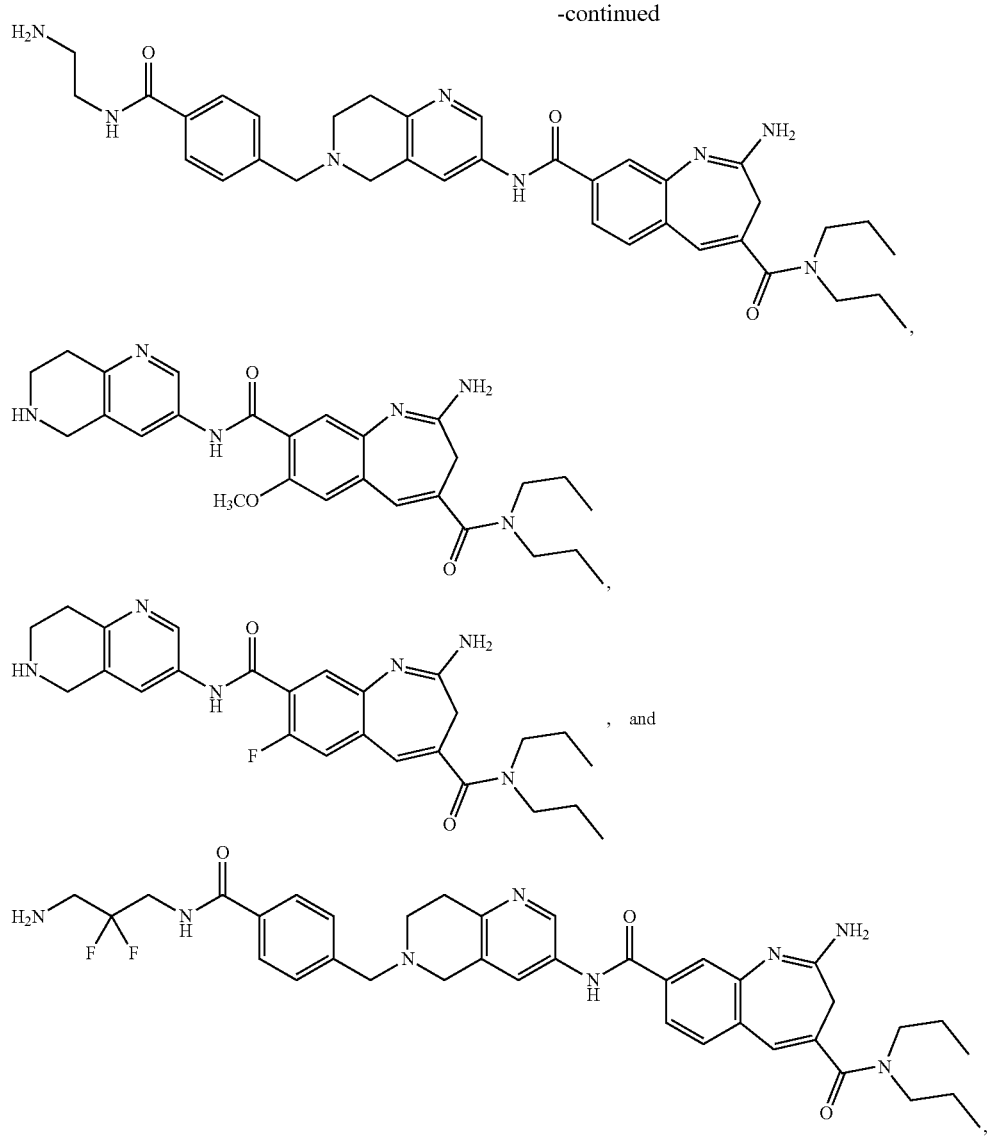

and a salt of any one thereof.

In some aspects, the present disclosure provides a compound represented by the structure of Formula (IIIA):

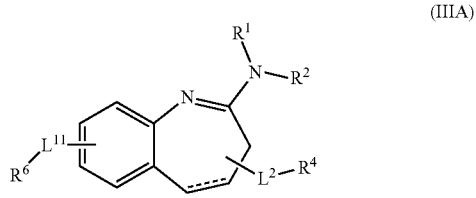

(IIIA)

or a pharmaceutically acceptable salt thereof, wherein:

------ represents an optional double bond;

$L^{11}$ is $-X^{11}-$;

$L^2$ is selected from $-X^2-$, $-X^2-C_{1-6}$ alkylene-$X^2-$, $-X^2-C_{2-6}$ alkenylene-$X^2-$, and $-X^2-C_{2-6}$ alkynylene-$X^2-$, each of which is optionally substituted on alkylene, alkenylene or alkynylene with one or more $R^{12}$;

$X^{11}$ is selected from $-C(O)-$ and $-C(O)N(R^{10})-$*, wherein * represents where $X^{11}$ is bound to $R^6$;

$X^2$ at each occurrence is independently selected from a bond, $-O-$, $-S-$, $-N(R^{10})-$, $-C(O)-$, $-C(O)O-$, $-OC(O)-$, $-OC(O)O-$, $-C(O)N(R^{10})-$, $-C(O)N(R^{10})C(O)-$, $-C(O)N(R^{10})C(O)N(R^{10})-$, $-N(R^{10})C(O)-$, $-N(R^{10})C(O)N(R^{10})-$, $-N(R^{10})C(O)O-$, $-OC(O)N(R^{10})-$, $-C(NR^{10})-$, $-N(R^{10})C(NR^{10})-$, $-C(NR^{10})N(R^{10})-$, $-N(R^{10})C(NR^{10})N(R^{10})-$, $-S(O)_2-$, $-OS(O)-$, $-S(O)O-$, $-S(O)-$, $-OS(O)_2-$, $-S(O)_2O-$, $-N(R^{10})S(O)_2-$, $-S(O)_2N(R^{10})-$, $-N(R^{10})S(O)-$, $-S(O)N(R^{10})-$, $-N(R^{10})S(O)_2N(R^{10})-$, and $-N(R^{10})S(O)N(R^{10})-$;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, $-OR^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;

R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$Ro; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^4$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;

R$^6$ is selected from phenyl and 5- or 6-membered heteroaryl, any one of which is substituted with one or more substituents selected from R$^7$ and R$^6$ is further optionally substituted by one or more additional substituents independently selected from R$^{12}$; R$^7$ is selected from —C(O)NHNH$_2$, —C(O)NH—C$_{1-3}$ alkylene-NH(R$^{10}$), —C(O)CH$_3$, —C$_{1-3}$ alkylene-NHC(O)OR$^{11}$, —C$_{1-3}$alkylene-NHC(O)R$^{10}$, —C$_{1-3}$alkylene-NHC(O)NHR$^{10}$, —C$_{1-3}$ alkylene-NHC(O)—C$_{1-3}$alkylene-R$^{10}$, and a 3- to 12-membered heterocycle optionally substituted with one or more substituents independently selected from R$^{12}$;

R$^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, —C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

R$^{11}$ is selected from C$_{3-12}$ carbocycle and 3- to 12-membered heterocycle, each of which is optionally substituted with one or more substituents independently selected from R$^{12}$;

R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle. In some embodiments, the compound of Formula (IIIA) is represented by Formula (IIIB):

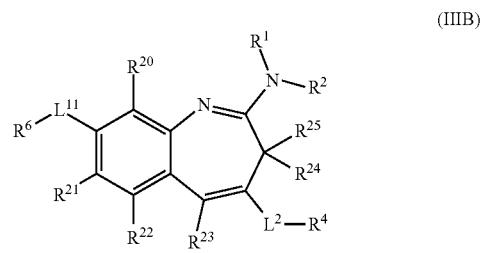

(IIIB)

or a pharmaceutically acceptable salt thereof, wherein:
R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$, and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —NO$_2$, —CN, and C$_{1-10}$ alkyl. In certain embodiments, R$^{20}$, R$^{21}$, R$^{22}$, and R$^{23}$ are each hydrogen. In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In certain embodiments, R$^{24}$ and R$^{25}$ are each hydrogen. In certain embodiments, R$^{24}$ and R$^{25}$ taken together form an optionally substituted saturated C$_{3-5}$ carbocycle.

In some embodiments, R$^1$ is hydrogen. In some embodiments, R$^2$ is hydrogen.

In some embodiments, L$^{11}$ is selected from —C(O)N(R$^{10}$)—*. In some embodiments, R$^{10}$ of —C(O)N(R$^{10}$)—* is selected from hydrogen and C$_{1-6}$ alkyl. For example, L$^{11}$ may be —C(O)NH—*.

In some embodiments, R$^6$ is phenyl substituted with R$^7$ and R$^6$ is further optionally substituted with one or more additional substituents independently selected from R$^{12}$. In some embodiments, R$^6$ is selected from phenyl substituted with one or more substituents independently selected from —C(O)NHNH$_2$, —C(O)NH—C$_{1-3}$alkylene-NH(R$^{10}$), —C$_{1-3}$alkylene-NHC(O)R$^{10}$, and —C(O)CH$_3$; and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$alkylene-(R$^{10}$) and R$^6$ is further optionally substituted with one or more additional substituents independently selected from R$^{12}$. For example, R$^6$ may be selected from:

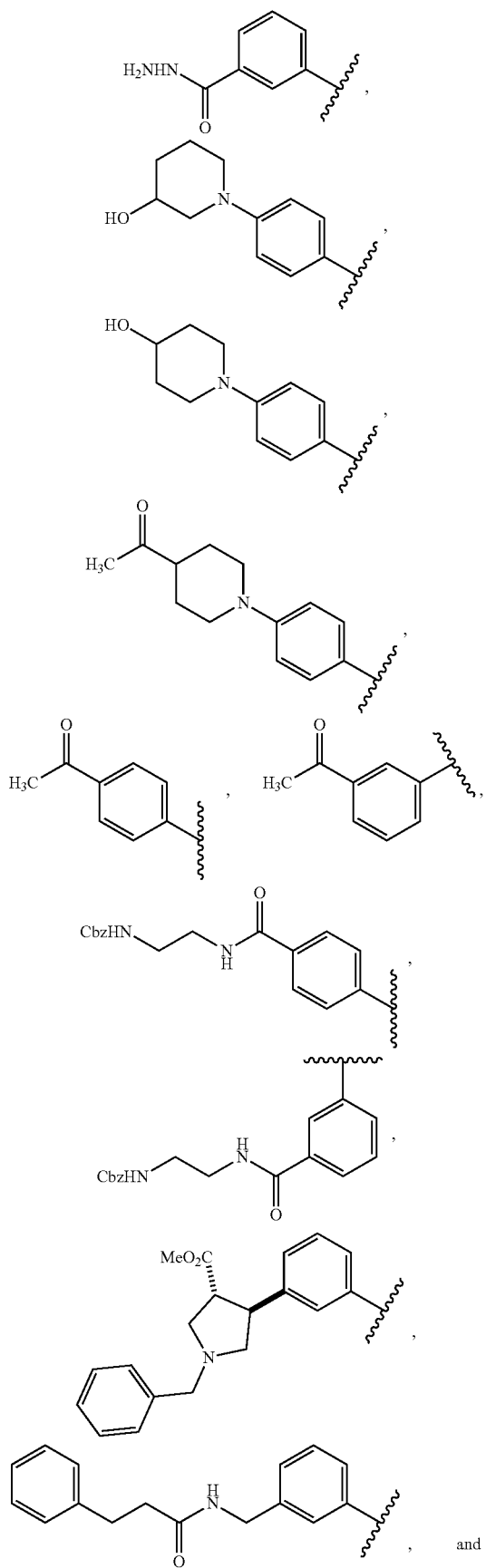

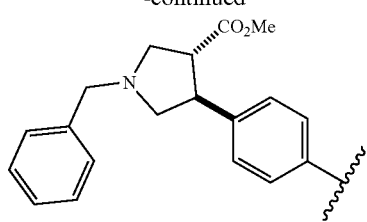

In some embodiments, $R^6$ is selected from a 5- and 6-membered heteroaryl substituted with one or more substituents independently selected from $R^7$, and $R^6$ is further optionally substituted with one or more additional substituents selected from $R^{12}$. In certain embodiments, $R^6$ is selected from 5- and 6-membered heteroaryl substituted with one or more substituents independently selected from —C(O)CH$_3$, —C$_{1-3}$alkylene-NHC(O)OR$^{10}$, —C$_{1-3}$alkylene-NHC(O)R$^{10}$, —C$_{1-3}$alkylene-NHC(O)NHR$^{10}$, and —C$_{1-3}$alkylene-NHC(O)—C$_{1-3}$alkylene-(R$^{10}$); and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$alkylene-(R$^{10}$), and $R^6$ is optionally further substituted with one or more additional substituents independently selected from $R^{12}$. $R^6$ may be selected from substituted pyridine, pyrazine, pyrimidine, pyridazine, furan, pyran, oxazole, thiazole, imidazole, pyrazole, oxadiazole, oxathiazole, and triazole, and $R^6$ is optionally further substituted with one or more additional substituents independently selected from $R^{12}$. In some embodiments, $R^6$ is substituted pyridine and $R^6$ is optionally further substituted with one or more additional substituents independently selected from $R^{12}$. $R^6$ may be represented as follows:

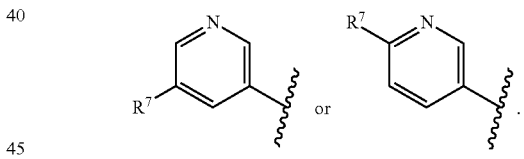

In some embodiments, $R^6$ is substituted pyridine, and wherein $R^7$ is —C$_{1-3}$alkylene-NHC(O)—C$_{1-3}$alkylene-R$^{10}$. In certain embodiments, $R^7$ is —C$_1$alkylene-NHC(O)—C$_1$alkylene-R$^{10}$. In certain embodiments, $R^7$ is —C$_1$alkylene-NHC(O)—C$_1$alkylene-NH$_2$. In some embodiments, $R^6$ is selected from:

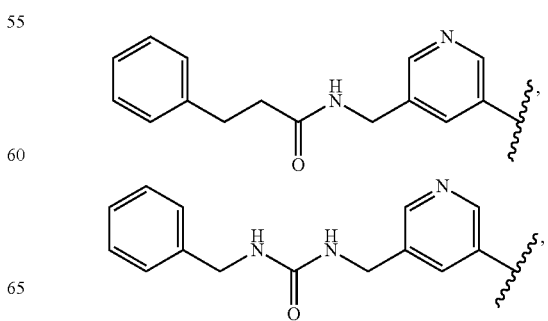

21

-continued

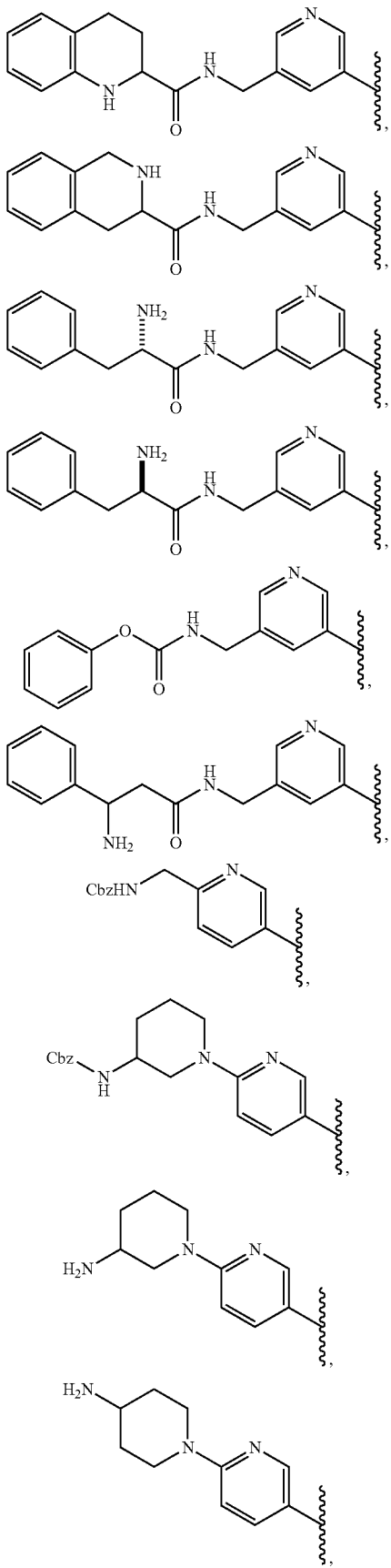

22

-continued

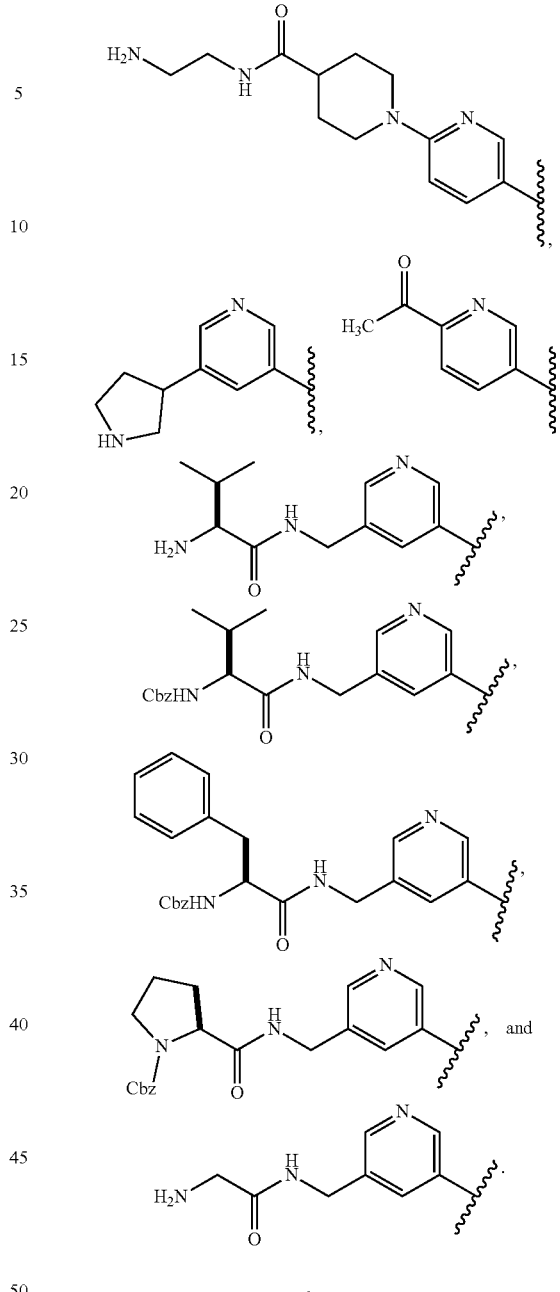

In certain embodiments, $R^6$ is

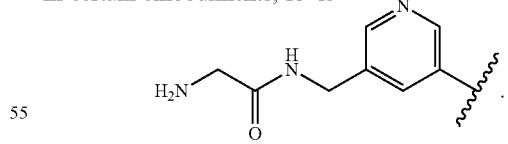

In some embodiments, $L^2$ is selected from —C(O)—, and —C(O)NR$^{10}$—. In some embodiments, $L^2$ is selected from —C(O)NR$^{10}$—. $R^1$ of —C(O)NR$^{10}$— may be selected from hydrogen and $C_{1-6}$ alkyl. For example, $L^2$ may be —C(O)NH—. In some embodiments, $L^2$ is —C(O)—.

In some embodiments, $R^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, $C_{3-12}$ carbocycle, and 3- to 12-membered heterocycle; and $C_{3-12}$ carbocycle and 3- to 12-membered, each of which is optionally substituted with one or more substituents independently selected from halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, $C_{1-6}$ alkyl, $C_{2-6}$ alkenyl, and $C_{2-6}$ alkynyl. In some embodiments, R⁴ is selected from: —OR¹⁰ and —N(R¹⁰)₂; and $C_{1-10}$ alkyl, $C_{2-10}$ alkenyl, $C_{2-10}$ alkynyl, $C_{3-12}$ carbocycle and 3- to 12-membered heterocycle, each of which is independently optionally substituted at each occurrence with one or more substituents selected from halogen, —OR¹⁰, —SR¹⁰, —N(R¹⁰)₂, —S(O)R¹⁰, —S(O)₂R¹⁰ —C(O)R¹⁰, —C(O)OR¹⁰, —OC(O)R¹⁰, —NO₂, =O, =S, =N(R¹⁰), —CN, $C_{1-10}$ alkyl, $C_{2-10}$ alkenyl, and $C_{2-10}$ alkynyl. In certain embodiments, R⁴ is —N(R¹⁰)₂. R¹⁰ of —N(R¹⁰)₂ may be independently selected at each occurrence from optionally substituted $C_{1-6}$ alkyl. In some embodiments, R¹⁰ of —N(R¹⁰)₂ is independently selected at each occurrence from methyl, ethyl, propyl, and butyl, any of which are optionally substituted. For example, R⁴ may be

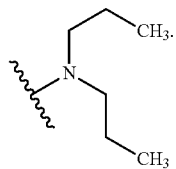

In some embodiments, -L²-R⁴ is

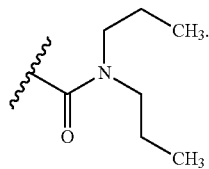 [SMILES: *C(=O)N(CCC)CCC]

In some embodiments, R¹² is independently selected at each occurrence from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, S(O)R¹⁰, —S(O)₂R¹⁰, —P(O)(OR¹⁰)₂, —OP(O)(OR¹⁰)₂, —NO₂, =O, =S, =N(R¹⁰), and —CN; $C_{1-10}$ alkyl, $C_{2-10}$ alkenyl, $C_{2-10}$ alkynyl, each of which is independently optionally substituted at each occurrence with one or more substituents selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), —CN, $C_{3-10}$ carbocycle and 3- to 10-membered heterocycle; and $C_{3-10}$ carbocycle and 3- to 10-membered heterocycle, each of which is independently optionally substituted at each occurrence with one or more substituents selected from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, —S(O)₂R¹⁰, —P(O)(OR¹⁰)₂, —OP(O)(OR¹⁰)₂, —NO₂, =O, =S, =N(R¹⁰), —CN, $C_{1-6}$ alkyl, $C_{2-6}$ alkenyl, and $C_{2-6}$ alkynyl. In certain embodiments, R¹² is independently selected at each occurrence from halogen, —OR¹⁰, —SR¹⁰, —N(R¹⁰)₂, —C(O)R¹⁰, —C(O)N(R¹⁰)₂, —N(R¹⁰)C(O)R¹⁰, —C(O)OR¹⁰, —OC(O)R¹⁰, —S(O)R¹⁰, S(O)₂R¹⁰, —P(O)(OR¹⁰)₂, —OP(O)(OR¹⁰)₂, —NO₂, =O, =S, =N(R¹⁰), and —CN; $C_{1-10}$ alkyl, $C_{2-10}$ alkenyl, $C_{2-10}$ alkynyl, each of which is independently optionally substituted at each occurrence with one or more substituents selected from halogen, —OR¹⁰, —SR¹⁰, —N(R¹⁰)₂, —C(O)R¹⁰, —C(O)N(R¹⁰)₂, —N(R¹⁰) C(O)R¹⁰, —C(O)OR¹⁰, —OC(O)R¹⁰, —S(O)R¹⁰, S(O)₂R¹⁰, —P(O)(OR¹⁰)₂, —OP(O)(OR¹⁰)₂, —NO₂, =O, =S, =N(R¹⁰), —CN, $C_{3-10}$ carbocycle and 3- to 10-membered heterocycle. In some embodiments, the compound is selected from:

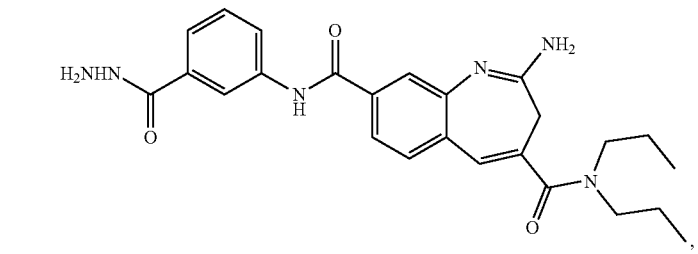

,

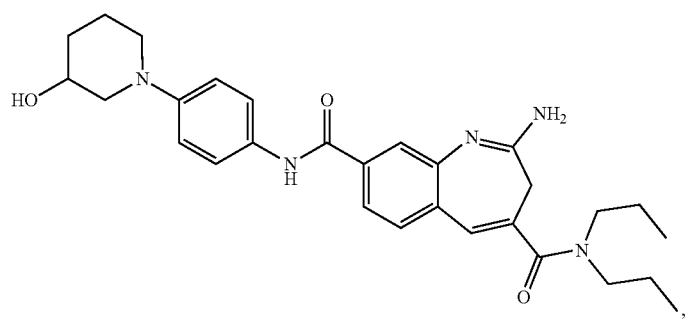

,

-continued
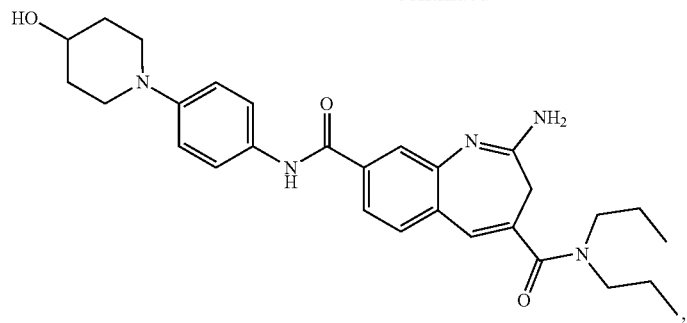
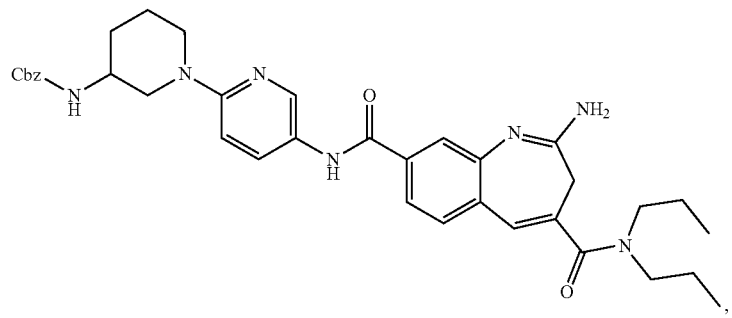
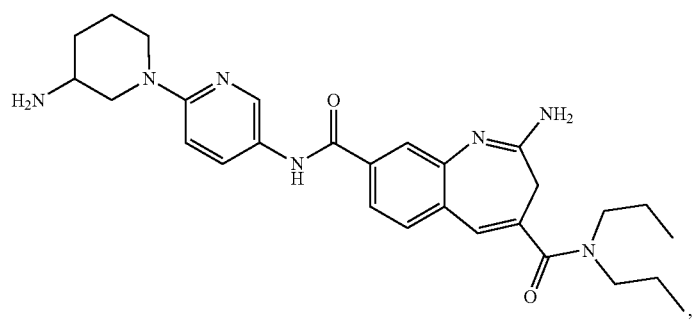
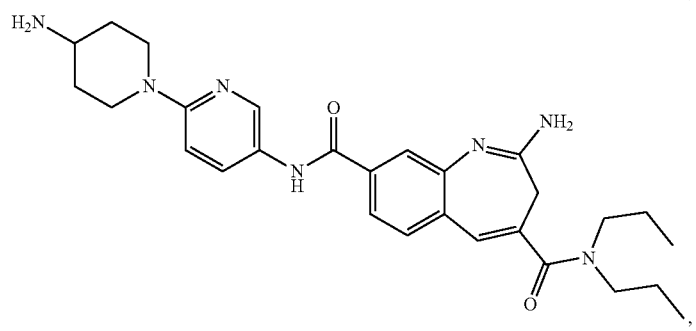
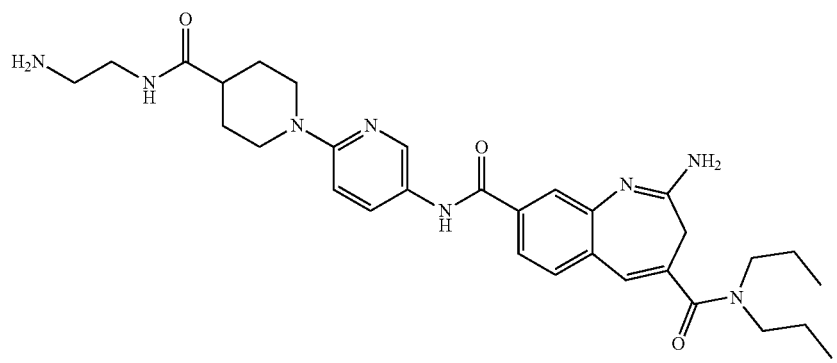

-continued
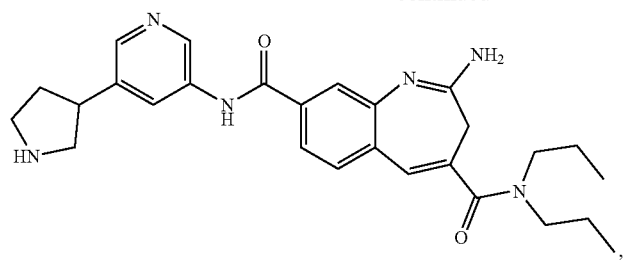
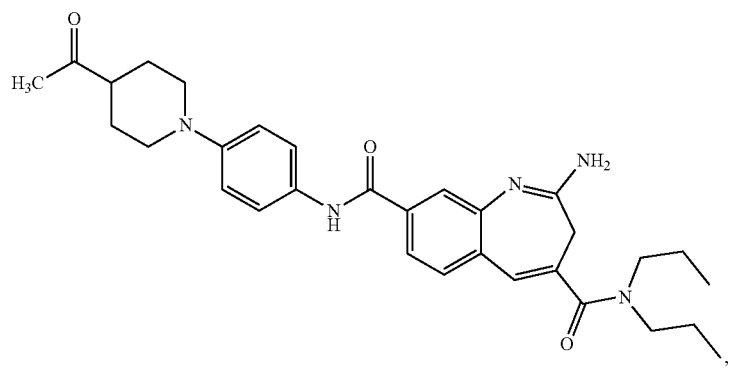
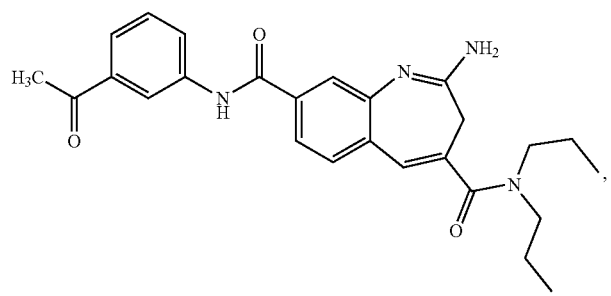
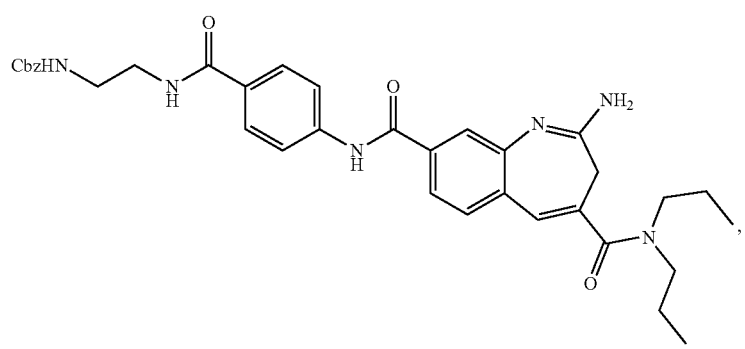
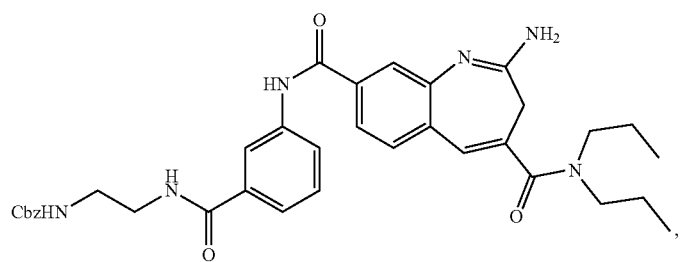

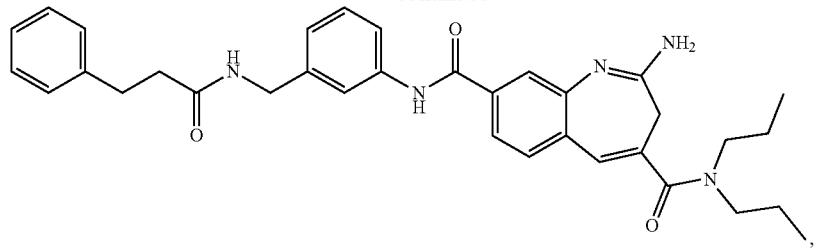
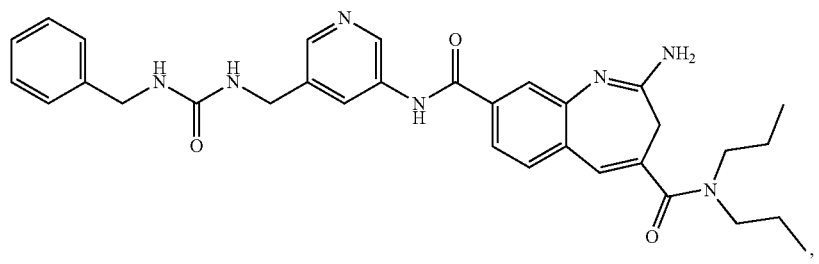
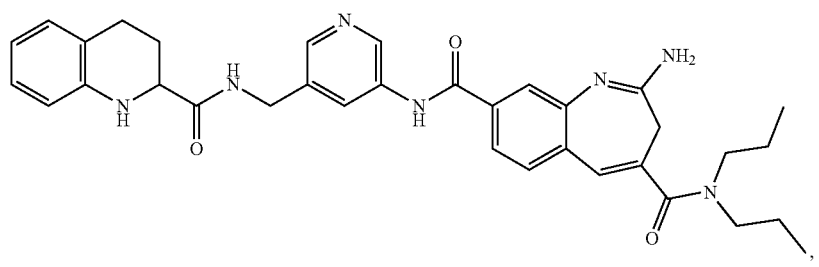
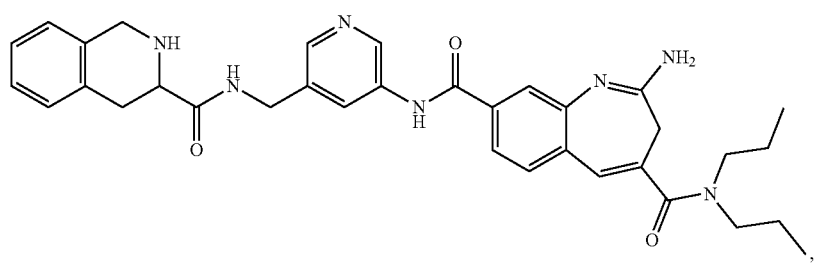
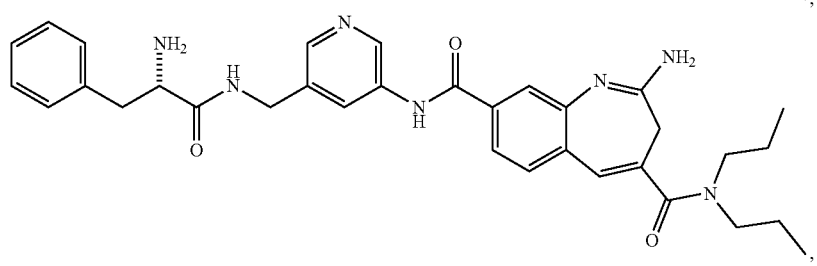
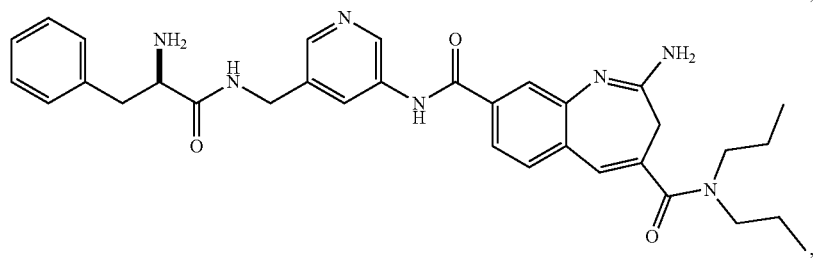

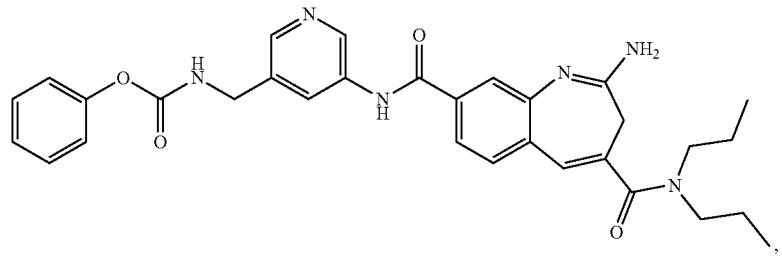
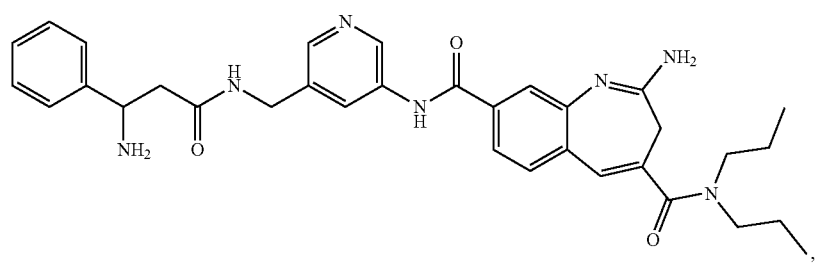
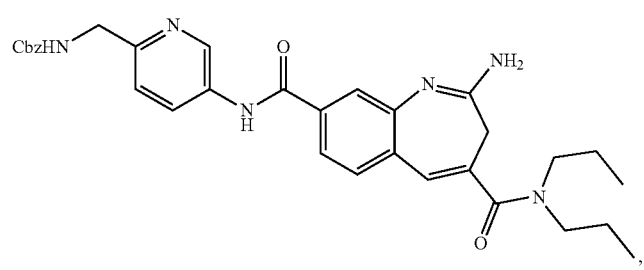
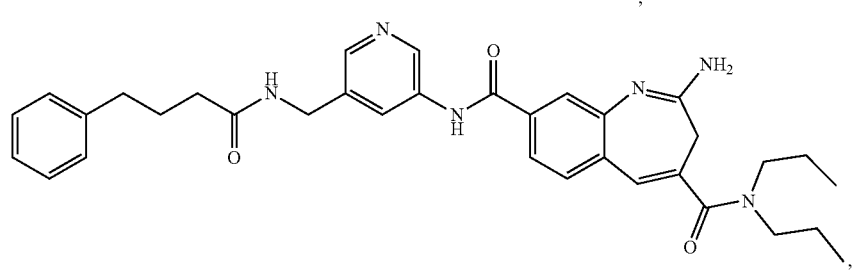
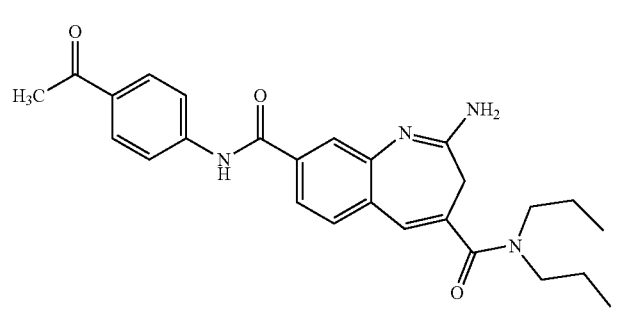
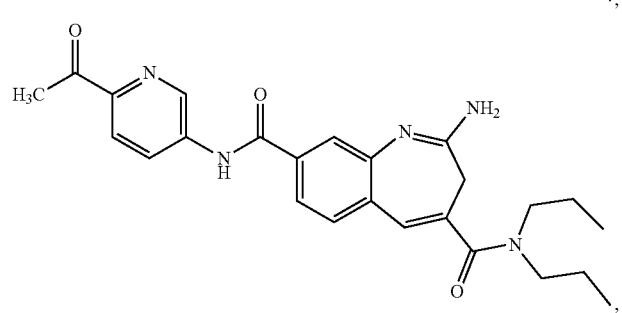

-continued
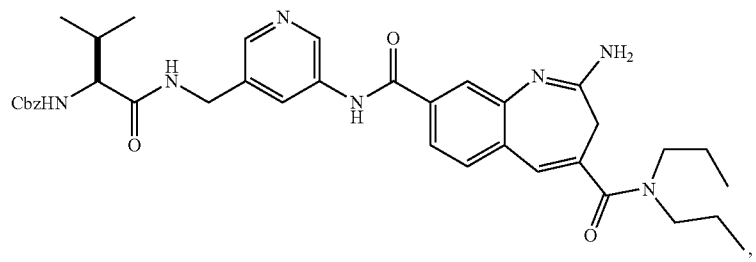
,
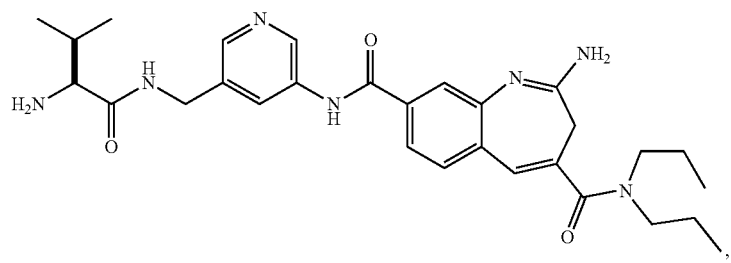
,
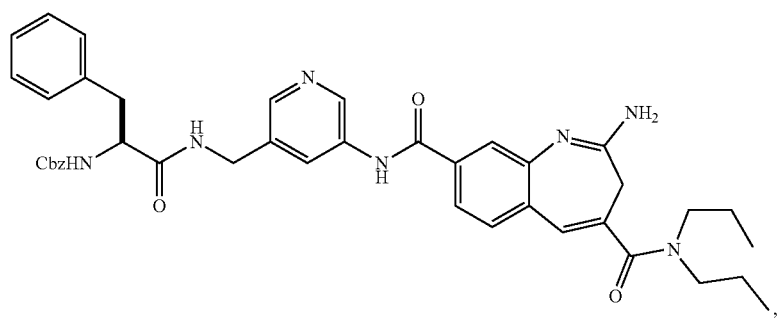
,
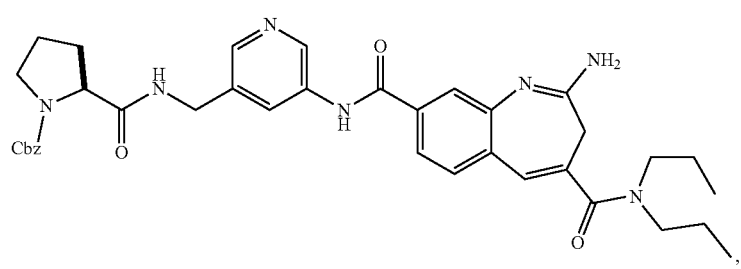
,
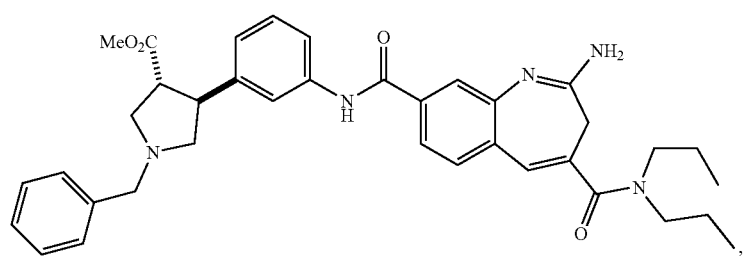
,
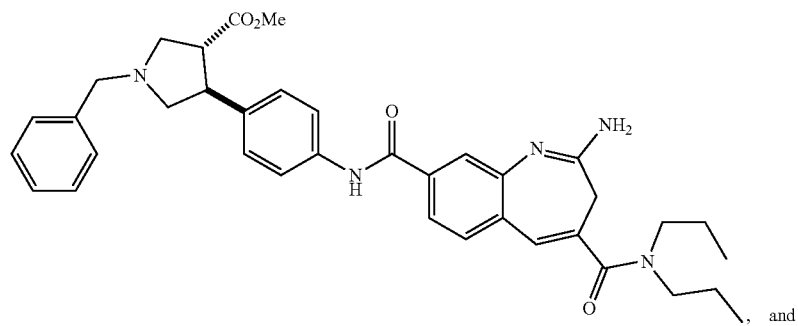
, and -continued

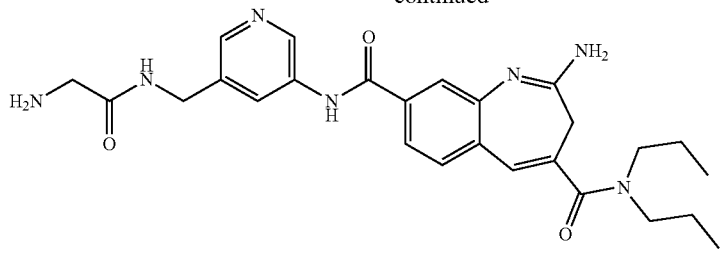

and a salt of any one thereof.

In some aspects, the present disclosure provides a compound represented by the structure of Formula (IA):

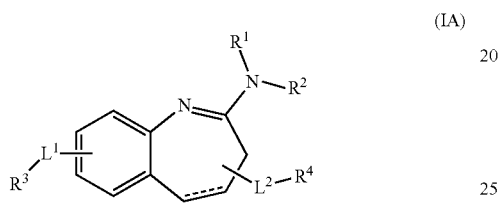

or a pharmaceutically acceptable salt thereof, wherein:

------ represents an optional double bond;

$L^1$ is selected from —$X^1$—, —$X^2$—$C_{1-6}$ alkylene-$X^2$— $C_{1-6}$ alkylene-, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$L^2$ is selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$X^1$ is selected from —S—*, —N($R^{10}$)—*, —C(O)O—*, —OC(O)—*, —OC(O)O—*, —C(O)N($R^{10}$)C(O)—*, —C(O)N($R^{10}$)C(O)N($R^{10}$)*, —N($R^{10}$)C(O)—*, —$CR^{10}_2$N($R^{10}$)C(O)—*, —N($R^{10}$)C(O)N($R^{10}$)—*, —N($R^{10}$)C(O)O—*, —OC(O)N($R^{10}$)—*, —C(N$R^{10}$)—*, —N($R^{10}$)C(N$R^{10}$)—*, —C(N$R^{10}$)N($R^{10}$)—*, —N($R^{10}$)C(N$R^{10}$)N($R^{10}$)—*, —S(O)$_2$—*, —OS(O)—*, —S(O)O—*, —S(O), —OS(O)$_2$—*, —S(O)$_2$O*, —N($R^{10}$)S(O)$_2$—*, —S(O)$_2$N($R^{10}$)—*, —N($R^{10}$)S(O)—*, —S(O)N($R^{10}$)—*, —N($R^{10}$)S(O)$_2$N($R^{10}$)—*, and —N($R^{10}$)S(O)N($R^{10}$)—*, wherein * represents where $X^1$ is bound to $R^3$;

$X^2$ is independently selected at each occurrence from —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$), —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, —$OR^{10}$, —$SR^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^3$ is selected from optionally substituted $C_{3-12}$ carbocycle, and optionally substituted 3- to 12-membered heterocycle, wherein substituents on $R^3$ are independently selected at each occurrence from: halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^3$ is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^4$ is selected from: —$OR^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —$OR^{10}$, —$SR^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^{10}$ is independently selected at each occurrence from: hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$R^{12}$ is independently selected at each occurrence from halogen, —$OR^{10}$, —$SR^{10}$, N($R^{10}$)$_2$, —C(O)$R^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle. In some embodiments, the compound of Formula (IA) is represented by Formula (IB):

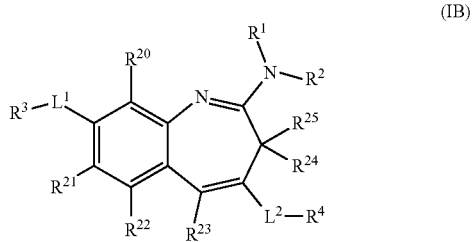

(IB)

or a pharmaceutically acceptable salt thereof, wherein:
R$^{20}$, R$^{21}$, R$^{22}$, and R$^{23}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and
R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

In some embodiments, R$^{20}$, R$^{21}$, R$^{22}$, and R$^{23}$ are independently selected from hydrogen, halogen, —OH, —NO$_2$, —CN, and C$_{1-10}$ alkyl. In certain embodiments, R$^{20}$, R$^{21}$, R$^{22}$, and R$^{23}$ are each hydrogen.

In some embodiments, R$^{24}$ and R$^{25}$ are independently selected from hydrogen, halogen, —OH, —NO$_2$, —CN, and C$_{1-10}$ alkyl, or R$^{24}$ and R$^{25}$ taken together form an optionally substituted saturated C$_{3-7}$ carbocycle. In some embodiments, R$^{24}$ and R$^{25}$ are each hydrogen. In some embodiments, R$^{24}$ and R$^{25}$ taken together form an optionally substituted saturated C$_{3-5}$ carbocycle.

In some embodiments, R$^1$ is hydrogen. In some embodiments, R$^2$ is hydrogen.

In some embodiments, L$^1$ is selected from —N(R$^{10}$)C(O)—*, —S(O)$_2$N(R$^{10}$)—*, —CR$^{10}$$_2$N(R$^{10}$)C(O)—* and —X$^2$—C$_{1-6}$ alkylene-X$^2$—C$_{1-6}$ alkylene-. In some embodiments, L$^1$ is selected from —N(R$^{10}$)C(O)—*. In certain embodiments, R$^{10}$ of —N(R$^{10}$)C(O)—* is selected from hydrogen and C$_{1-6}$ alkyl. For example, L$^1$ may be —NHC(O)—*. In some embodiments, L$^1$ is selected from —S(O)$_2$N(R$^{10}$)—*. In certain embodiments, R$^{10}$ of —S(O)$_2$N(R$^{10}$)—* is selected from hydrogen and C$_{1-6}$ alkyl. For example, L$^1$ is —S(O)$_2$NH—*. In some embodiments, L$^1$ is —CR$^{10}$$_2$N(R$^{10}$)C(O)—*. In certain embodiments, L$^1$ is selected from —CH$_2$N(H)C(O)—* and —CH(CH$_3$)N(H)C(O)—*.

In some embodiments, R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl. In certain embodiments, R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle.

In some embodiments, R$^3$ is selected from an optionally substituted aryl and an optionally substituted heteroaryl. In some embodiments, R$^3$ is an optionally substituted heteroaryl. R$^3$ may be an optionally substituted heteroaryl substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. In certain embodiments, R$^3$ is selected from an optionally substituted 6-membered heteroaryl. For example, R$^3$ may be an optionally substituted pyridine. In some embodiments, R$^3$ is an optionally substituted aryl. In certain embodiments, R$^3$ is an optionally substituted aryl substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, C$_{1-6}$ alkyl, C$_{2-6}$ alkenyl, and C$_{2-6}$ alkynyl. R$^3$ may be an optionally substituted phenyl. In certain embodiments, R$^3$ is selected from pyridine, phenyl, tetrahydronaphthalene, tetrahydroquinoline, tetrahydroisoquinoline, indane, cyclopropylbenzene, cyclopentapyridine, and dihydrobenzoxaborole, any one of which is optionally substituted. R$^3$ may be selected from:

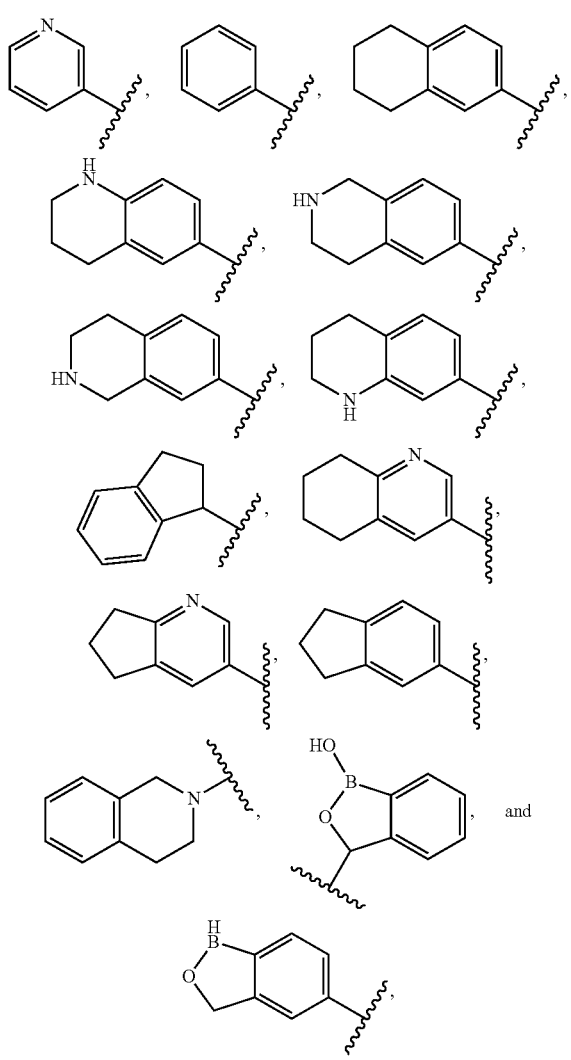
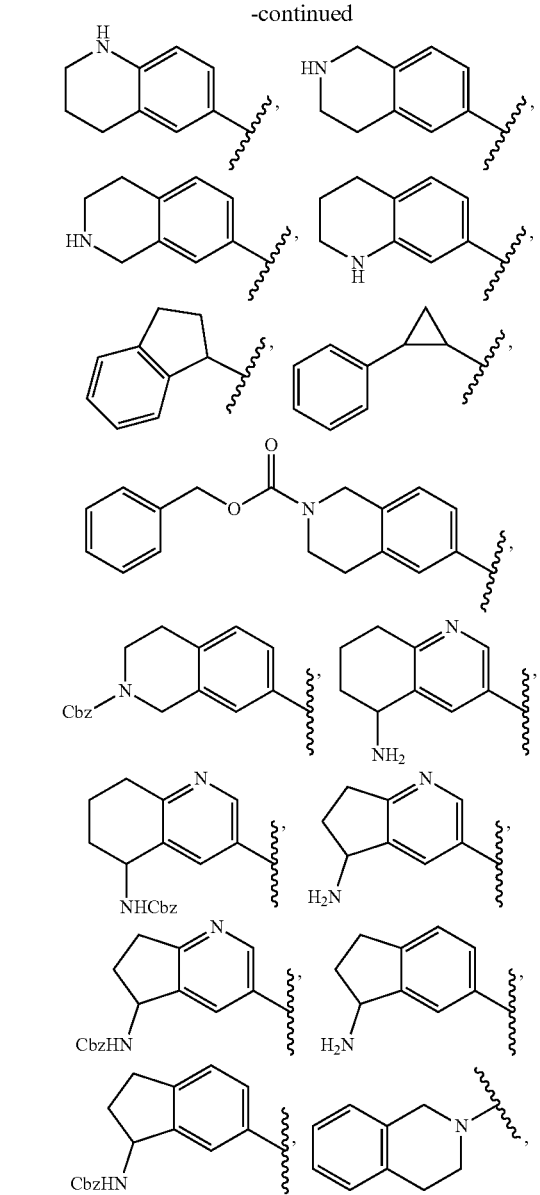
any one of which is optionally substituted. For example, $R^3$ may be selected from:
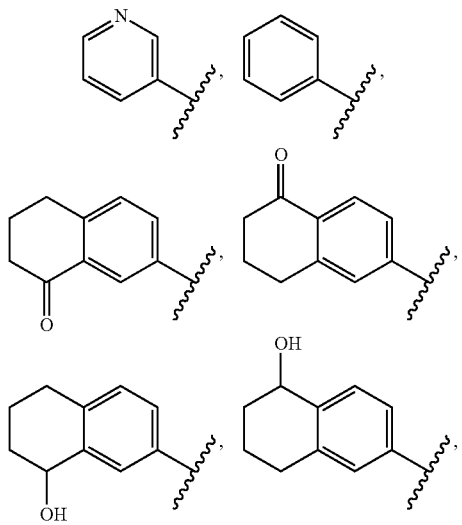
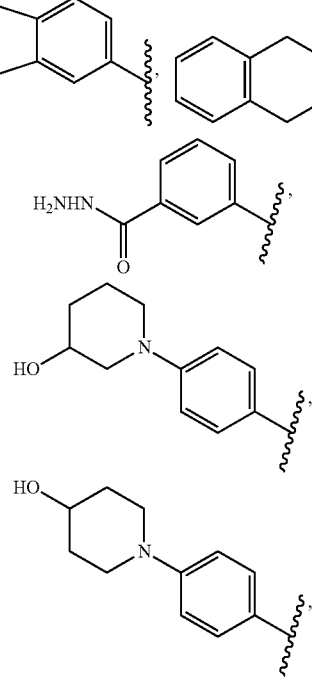

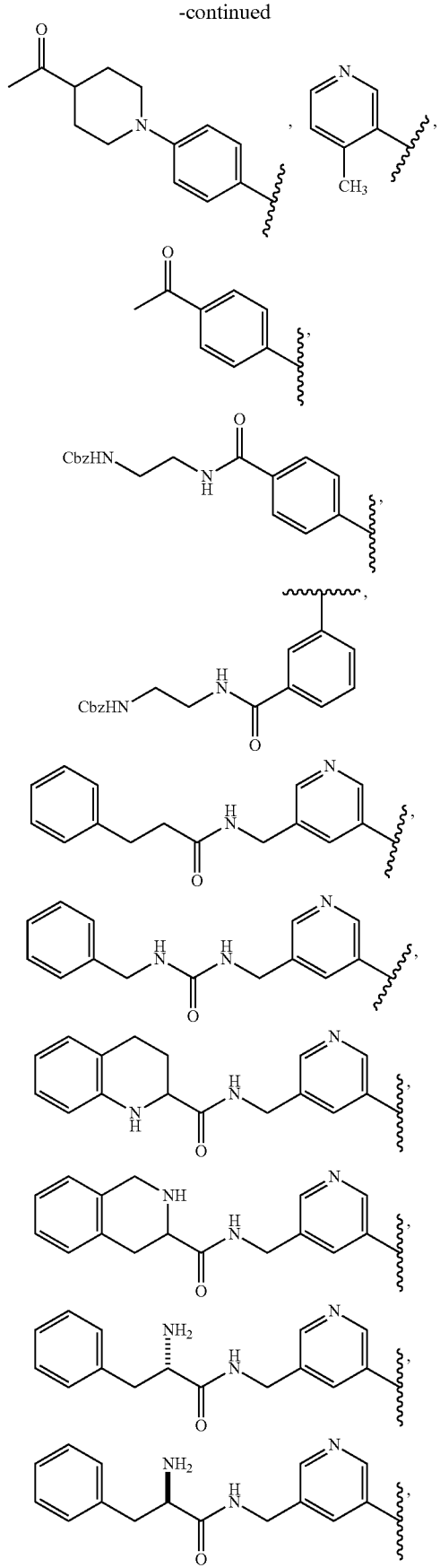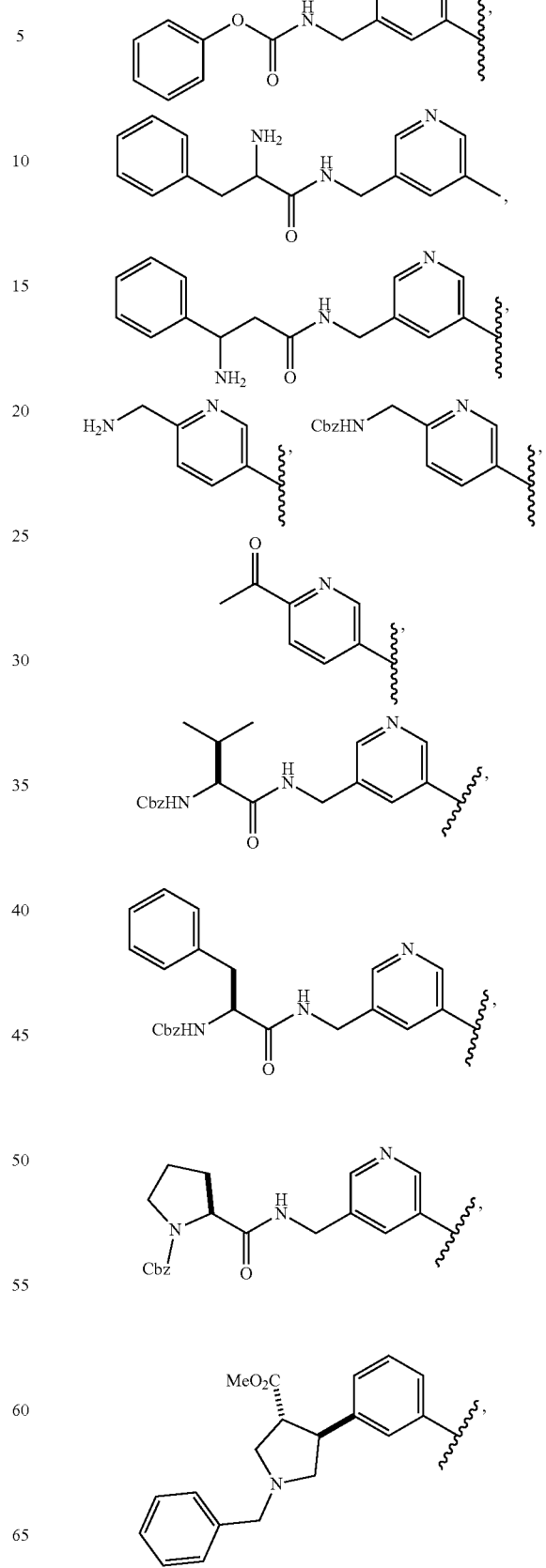

-continued

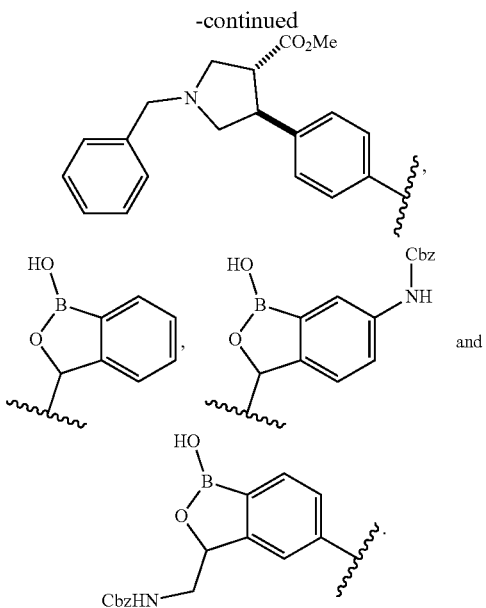

In some embodiments, $L^2$ is selected from —C(O)—, and —C(O)NR$^{10}$—. In certain embodiments, $L^2$ is —C(O)—. In certain embodiments, $L^2$ is selected from —C(O)NR$^{10}$—. $R^{10}$ of —C(O)NR$^{10}$— may be selected from hydrogen and $C_{1-6}$ alkyl. For example, $L^2$ may be —C(O)NH—.

In some embodiments, $R^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{1-6}$ alkyl, $C_{2-6}$ alkenyl, and $C_{2-6}$ alkynyl.

In some embodiments, $R^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{3-12}$ carbocycle, and 3- to 12-membered heterocycle. In some embodiments, $R^4$ is selected from: —OR$^{10}$, and —N(R$^{10}$)$_2$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, NO$_2$, =O, =S, =N(R$^{10}$), —CN, $C_{1-10}$ alkyl, $C_{2-10}$ alkenyl, and $C_{2-10}$ alkynyl. In certain embodiments, $R^4$ is —N(R$^{10}$)$_2$. $R^{10}$ of —N(R$^{10}$)$_2$ may be independently selected at each occurrence from optionally substituted $C_{1-6}$ alkyl. In certain embodiments, $R^{10}$ of —N(R$^{10}$)$_2$ is independently selected at each occurrence from methyl, ethyl, propyl, and butyl, any one of which is optionally substituted. For example, $R^4$ may be

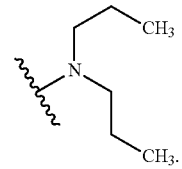

In certain embodiments, $L^2$-$R^4$ is

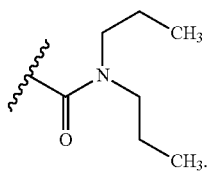

In some embodiments, $R^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{1-6}$ alkyl, $C_{2-6}$ alkenyl, $C_{2-6}$ alkynyl. In some embodiments, $R^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{3-10}$ carbocycle and 3- to 10-membered heterocycle.

In some embodiments, the compound is selected from:

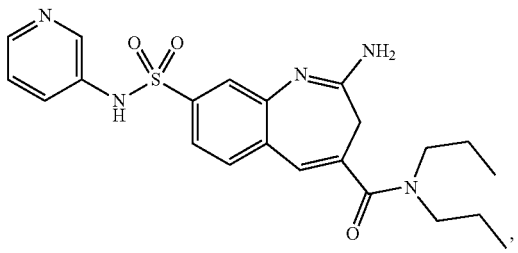

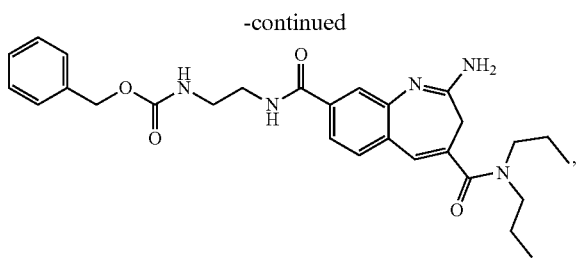

and a salt of any one thereof.

In some aspects, the present disclosure provides a compound represented by the structure of Formula (IVA):

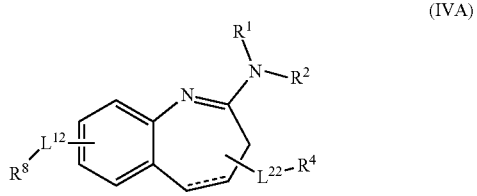

(IVA)

or a pharmaceutically acceptable salt thereof, wherein:

- - - - - - represents an optional double bond;

$L^{12}$ is selected from —$X^3$—, —$X^3$—$C_{1-6}$ alkylene-$X^3$—, —$X^3$—$C_{2-6}$ alkenylene-$X^3$—, and —$X^3$—$C_{2-6}$ alkynylene-$X^3$—, each of which is optionally substituted on alkylene, alkenylene, or alkynylene with one or more substituents independently selected from $R^{12}$;

$L^{22}$ is independently selected from —$X^4$—, —$X^4$—$C_{1-6}$ alkylene-$X^4$—, —$X^4$—$C_{2-6}$ alkenylene-$X^4$—, and —$X^4$—$C_{2-6}$ alkynylene-$X^4$—, each of which is optionally substituted on alkylene, alkenylene, or alkynylene with one or more substituents independently selected from $R^{10}$;

$X^3$ and $X^4$ are independently selected at each occurrence from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)N(R)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O)—, —OS(O)$_2$—, —S(O)$_2$O—, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from $L^3$, and hydrogen; and $C_{1-10}$ alkyl, $C_{2-10}$ alkenyl, and $C_{2-10}$ alkynyl, each of which is optionally substituted with one or more substituents independently selected from $L^3$, halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ and $R^8$ are independently selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is optionally substituted with one or more substituents independently selected from $L^3$, halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ and $R^8$ is optionally substituted with one or more substituents independently selected from $L^3$, halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^{10}$ is independently selected at each occurrence from $L^3$, hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$L^3$ is a linker moiety, wherein at least one of $R^1$, $R^2$, and $R^{10}$ is $L^3$ or at least one substituent on a group selected from $R^1$, $R^2$, $R^4$, $R^8$, $X^3$ and $X^4$ is $L^3$; and $R^{12}$ is independently selected at each occurrence from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^{12}$ is optionally substituted with one or more substituents independently selected from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), —CN, $C_{1-6}$ alkyl, $C_{2-6}$ alkenyl, $C_{2-6}$ alkynyl; and wherein any substitutable carbon on the benzazepine core is optionally substituted by a substituent independently selected from $R^{12}$ or two substituents on a single carbon atom combine to form a 3- to 7-membered carbocycle. In some embodiments, the compound of Formula (IVA) is represented by Formula (IVB):

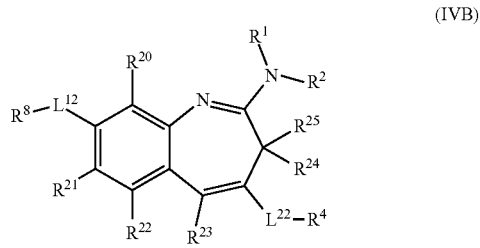

(IVB)

or a pharmaceutically acceptable salt thereof, wherein:

$R^{20}$, $R^{21}$, $R^{22}$, and $R^{23}$ are independently selected from hydrogen, halogen, —O$R^{10}$, —S$R^{10}$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), —CN, $C_{1-10}$ alkyl, $C_{2-10}$ alkenyl, and $C_{2-10}$ alkynyl; and $R^{24}$, and $R^{25}$ are independently selected from hydrogen, halogen, —$OR^{10}$, —$SR^{10}$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl; or $R^{24}$ and $R^{25}$ taken together form an optionally substituted saturated $C_{3-7}$ carbocycle.

In some embodiments, $R^1$ is $L^3$. In some embodiments, $R^2$ is $L^3$.

In some embodiments, $L^{12}$ is —C(O)N($R^{10}$)—. In some embodiments, $R^{10}$ of —C(O)N($R^{10}$)— is selected from hydrogen, $C_{1-6}$ alkyl, and $L^3$. For example, $L^{12}$ may be —C(O)NH—.

In some embodiments, $R^8$ is an optionally substituted 5- or 6-membered heteroaryl. $R^8$ may be an optionally substituted 5- or 6-membered heteroaryl, substituted with $L^3$. In some embodiments, $R^8$ is an optionally substituted pyridine, substituted with $L^3$.

In some embodiments, $L^{22}$ is selected from —C(O)—, and —C(O)N$R^{10}$—. In certain embodiments, $L^{22}$ is —C(O)—. In certain embodiments, $L^{22}$ is —C(O)N$R^{10}$—. $R^{10}$ of —C(O)N$R^{10}$— may be selected from hydrogen, $C_{1-6}$ alkyl, and -$L^3$. For example, $L^{22}$ may be —C(O)NH—.

In some embodiments, $R^4$ is selected from: —$OR^{10}$, and —$N(R^{10})_2$; and $C_{1-10}$ alkyl, $C_{2-10}$ alkenyl, $C_{2-10}$ alkynyl, $C_{3-12}$ carbocycle, 3- to 12-membered heterocycle, aryl, and heteroaryl, each of which is optionally substituted with one or more substituents independently selected from $L^3$, halogen, —$OR^{10}$, —$SR^{10}$, —$N(R^{10})_2$, —$S(O)R^{10}$, —$S(O)_2R^{10}$, —$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl. In some embodiments, $R^4$ is —$N(R^{10})_2$ and $R^{10}$ of —$N(R^{10})_2$ is selected from $L^3$ and hydrogen, and wherein at least one $R^{10}$ of —$N(R^{10})_2$ is $L^3$.

In some aspects, the present disclosure provides a compound of Table 1 or a salt thereof, selected from: 1.1, 1.2, 1.4, 1.5, 1.6, 1.7, 1.8, 1.9, 1.10, 1.11, 1.12, 1.13, 1.14, 1.15, 1.16, 1.17, 1.18, 1.19, 1.20, 1.23, 1.24, 1.25, 1.26, 1.27, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.48, 1.50, 1.51, 1.52, 1.53, 1.54, 1.55, 1.56, 1.57, 1.58, 1.59, 1.60, 1.61, and 1.63.

In some embodiments, the compound is further covalently bound to a linker, $L^3$. In some embodiments, $L^3$ is a noncleavable linker. In some embodiments, $L^3$ is a cleavable linker. $L^3$ may be cleavable by a lysosomal enzyme. In some embodiments, the compound is covalently attached to an antibody construct. In some embodiments, the compound is covalently attached to a targeting moiety, optionally through the linker. In some embodiments, the targeting moiety or antibody construct specifically binds to a tumor antigen. In some embodiments, the antibody construct or targeting moiety further comprises a target binding domain.

In some embodiments, $L^3$ is represented by the formula:

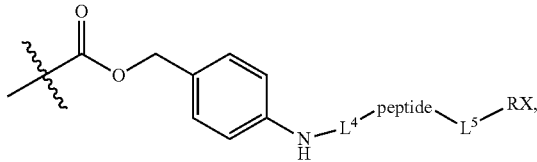

wherein:
$L^4$ represents the C-terminus of the peptide and $L^5$ is selected from a bond, alkylene and heteroalkylene, wherein $L^5$ is optionally substituted with one or more groups independently selected from $R^{32}$, and RX is a reactive moiety; and
$R^{32}$ is independently selected at each occurrence from halogen, —OH, —CN, —O-alkyl, —SH, =O, =S, —$NH_2$, —$NO_2$; and $C_{1-10}$ alkyl, $C_{2-10}$ alkenyl, $C_{2-10}$ alkynyl, each of which is optionally substituted with one or more substituents independently selected from halogen, —OH, —CN, —O— alkyl, —SH, =O, =S, —$NH_2$, —$NO_2$. In some embodiments, RX comprises a leaving group. In some embodiments, RX comprises a maleimide. In some embodiments, $L^3$ is further covalently bound to an antibody construct. In some embodiments, the antibody construct is directed against a tumor antigen. In some embodiments, the antibody construct further comprises target binding domain.

In some embodiments, $L^3$ is represented by the formula:

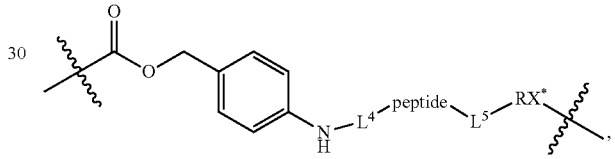

wherein $L^4$ represents the C-terminal of the peptide and $L^5$ is selected from a bond, alkylene and heteroalkylene, wherein $L^5$ is optionally substituted with one or more groups independently selected from $R^{32}$; RX* comprises a bond, a succinimide moiety, or a hydrolyzed succinimide moiety bound to a residue of an antibody construct, wherein ⁂ on RX* represents the point of attachment to the residue of the antibody construct; and,
$R^{32}$ is independently selected at each occurrence from halogen, —OH, —CN, —O-alkyl, —SH, =O, =S, —$NH_2$, —$NO_2$; and $C_{1-10}$ alkyl, $C_{2-10}$ alkenyl, $C_{2-10}$ alkynyl, each of which is optionally substituted with one or more substituents independently selected from halogen, —OH, —CN, —O— alkyl, —SH, =O, =S, —$NH_2$, —$NO_2$. In some embodiments, the peptide of $L^3$ comprises Val-Cit or Val-Ala.

In some aspects, the present disclosure provides a compound or salt selected from:

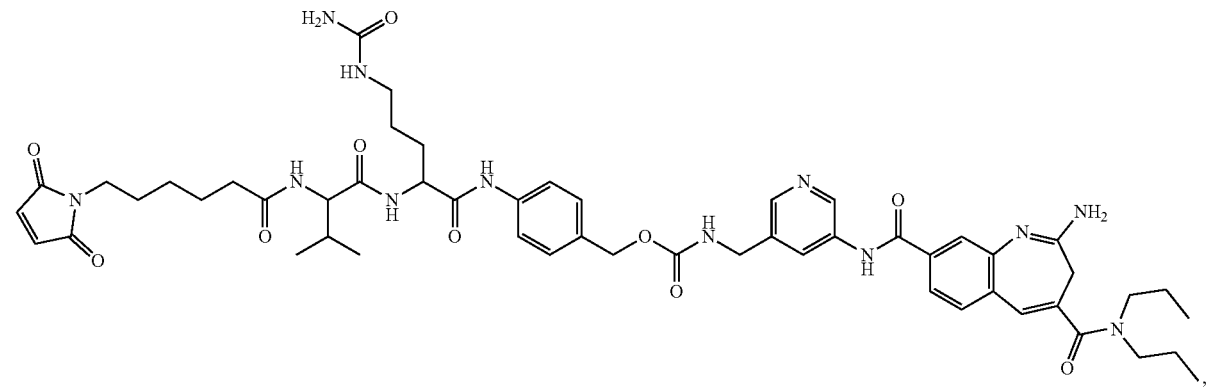

-continued
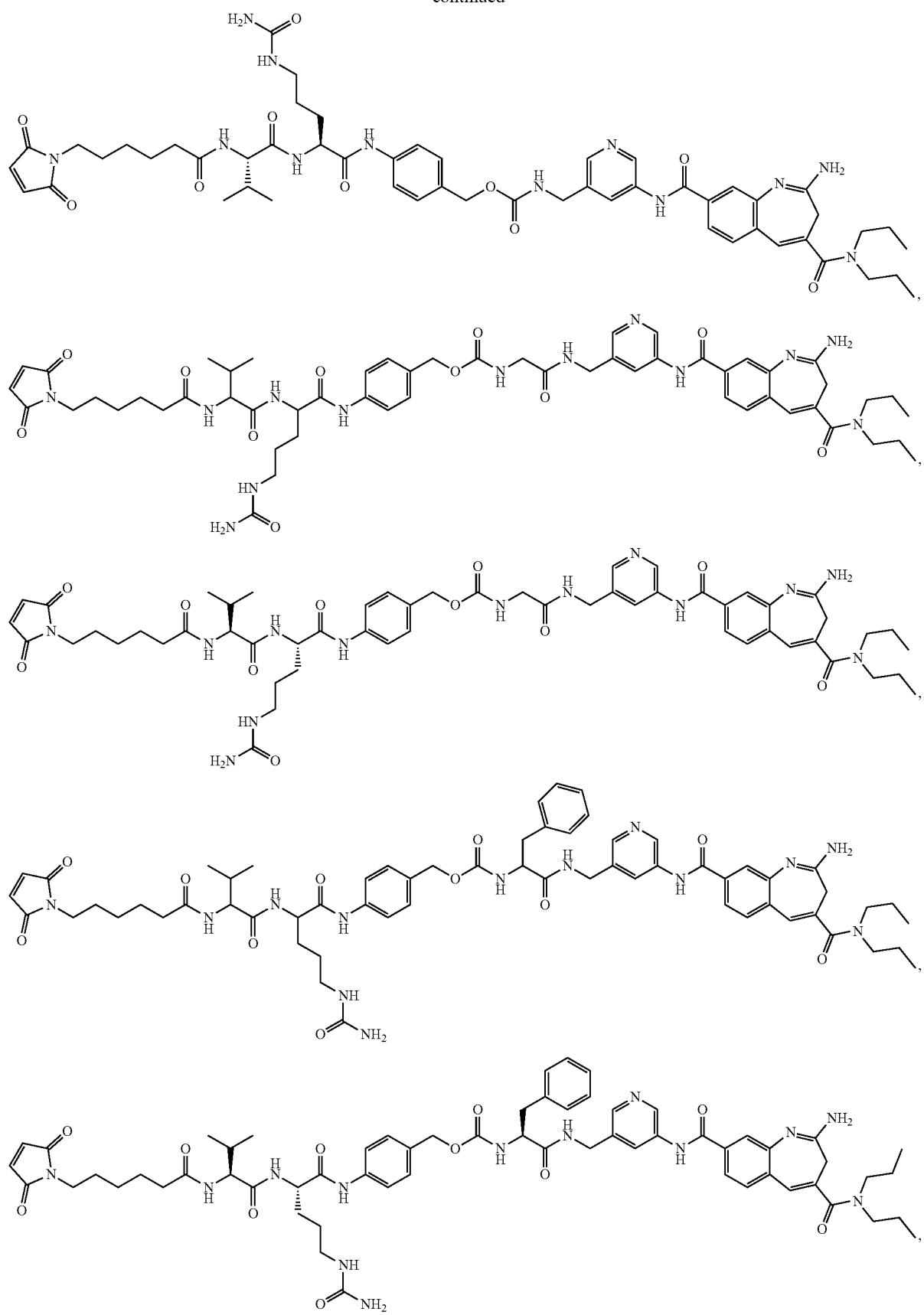

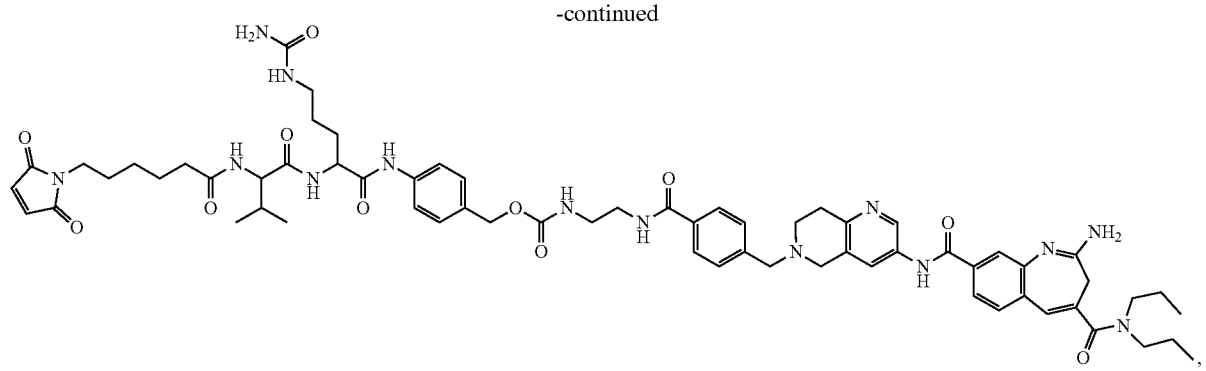
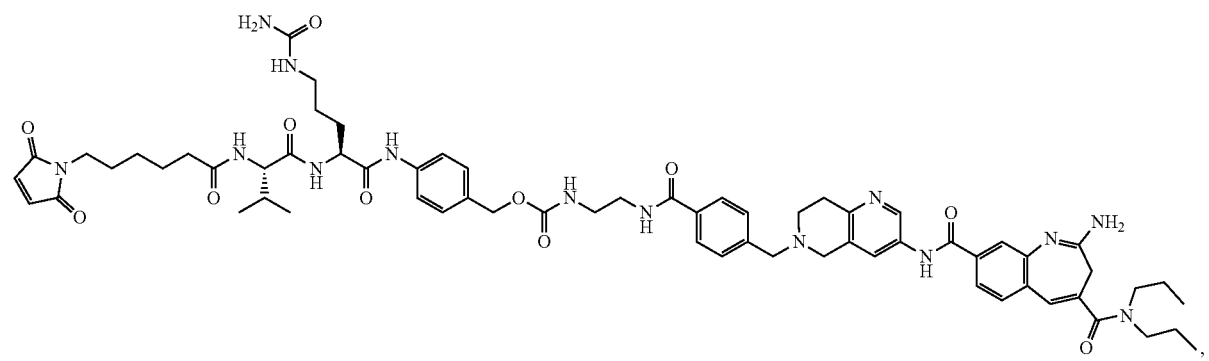
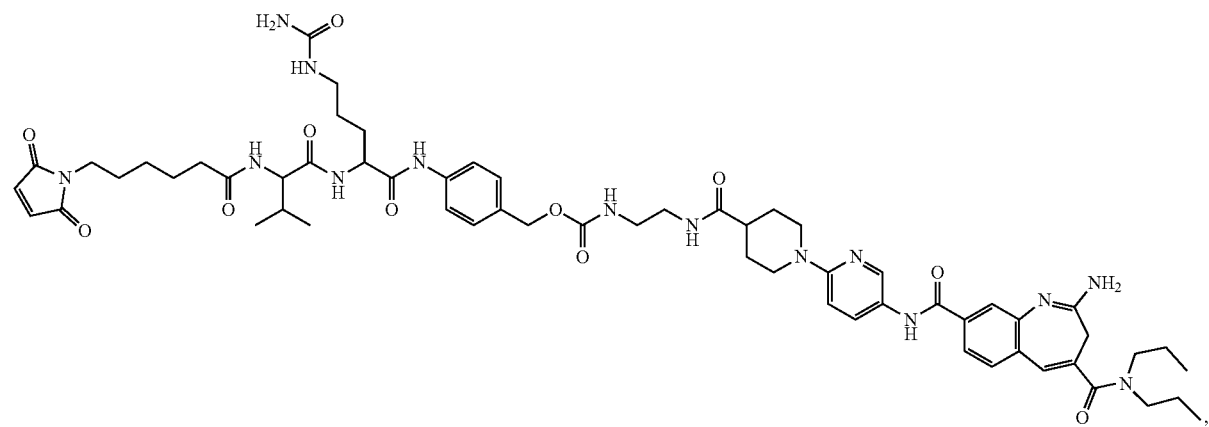
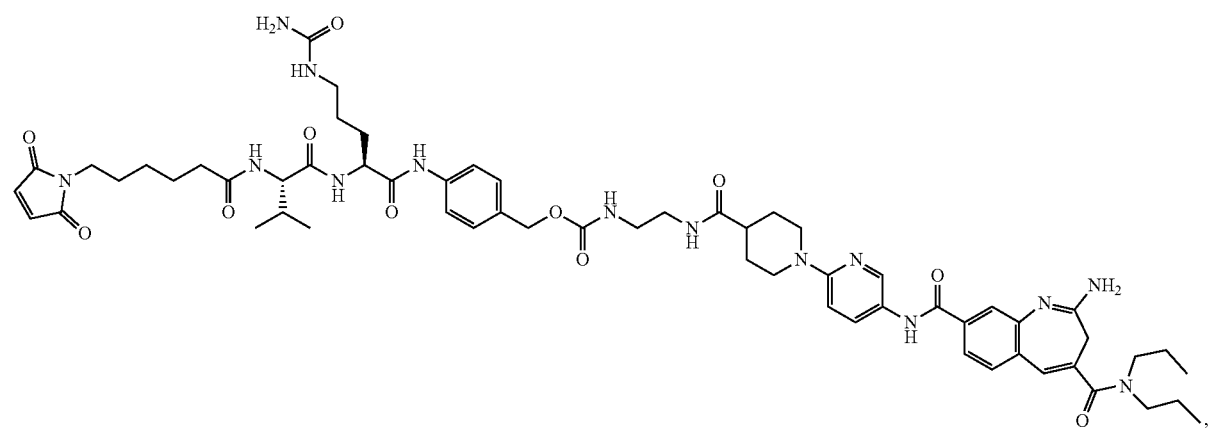

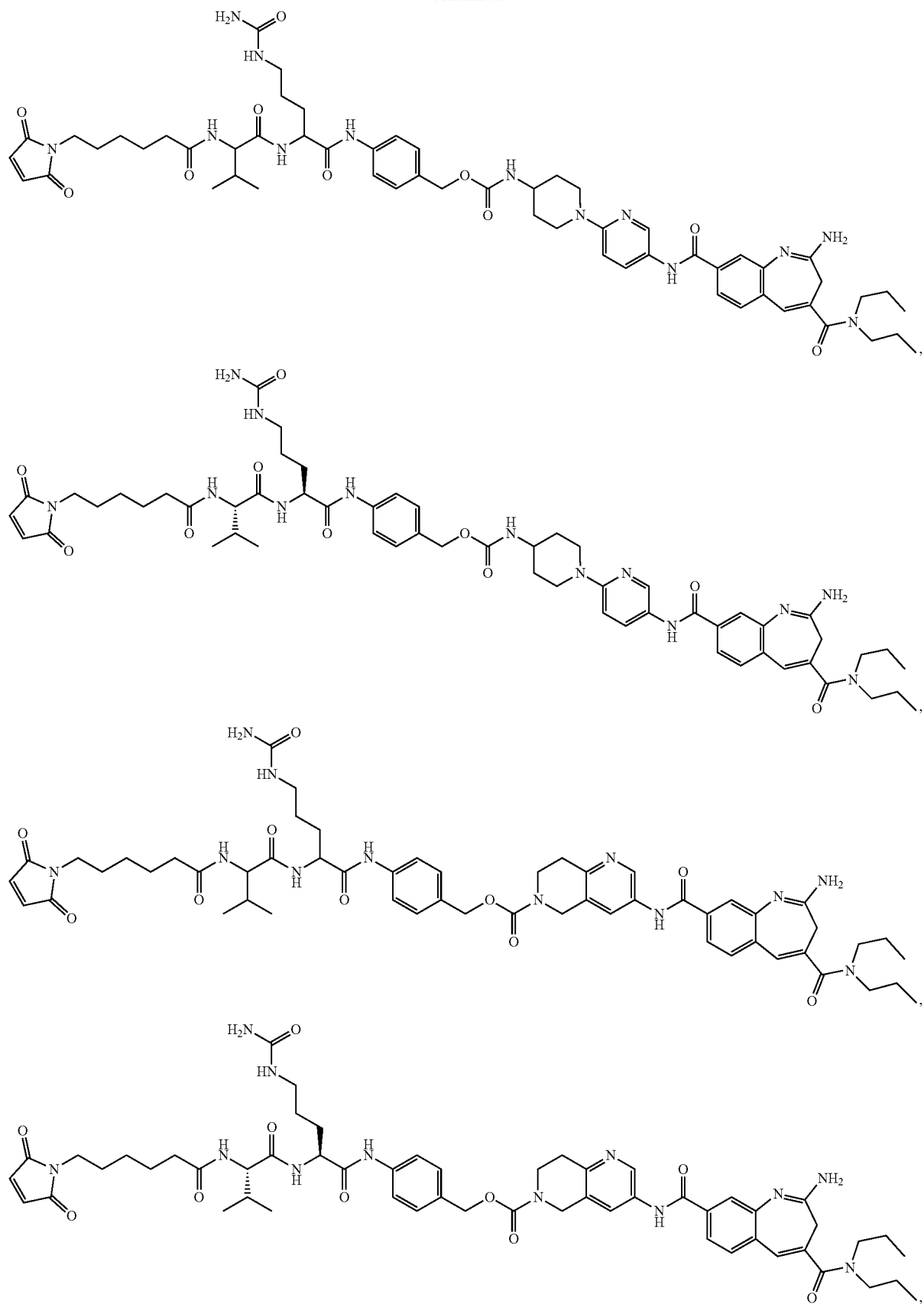

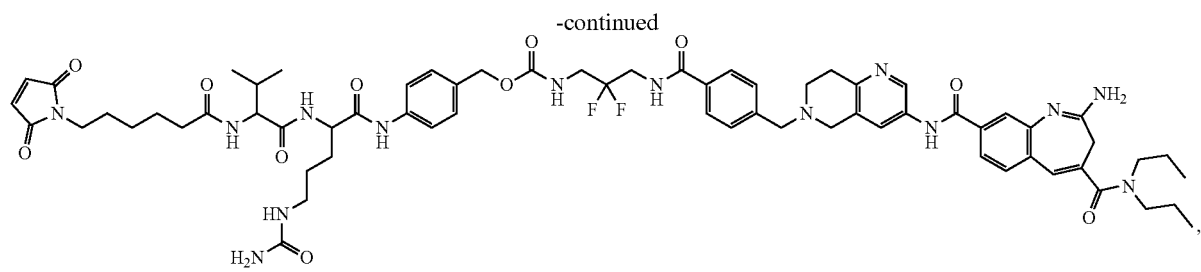
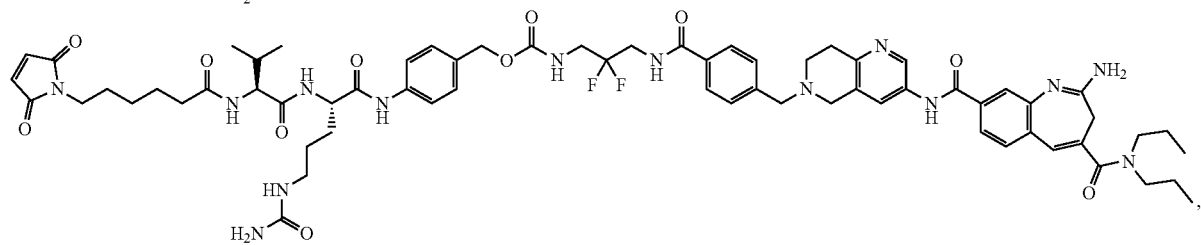
and a salt of any one thereof
In some aspects, the present disclosure provides a compound or salt selected from:
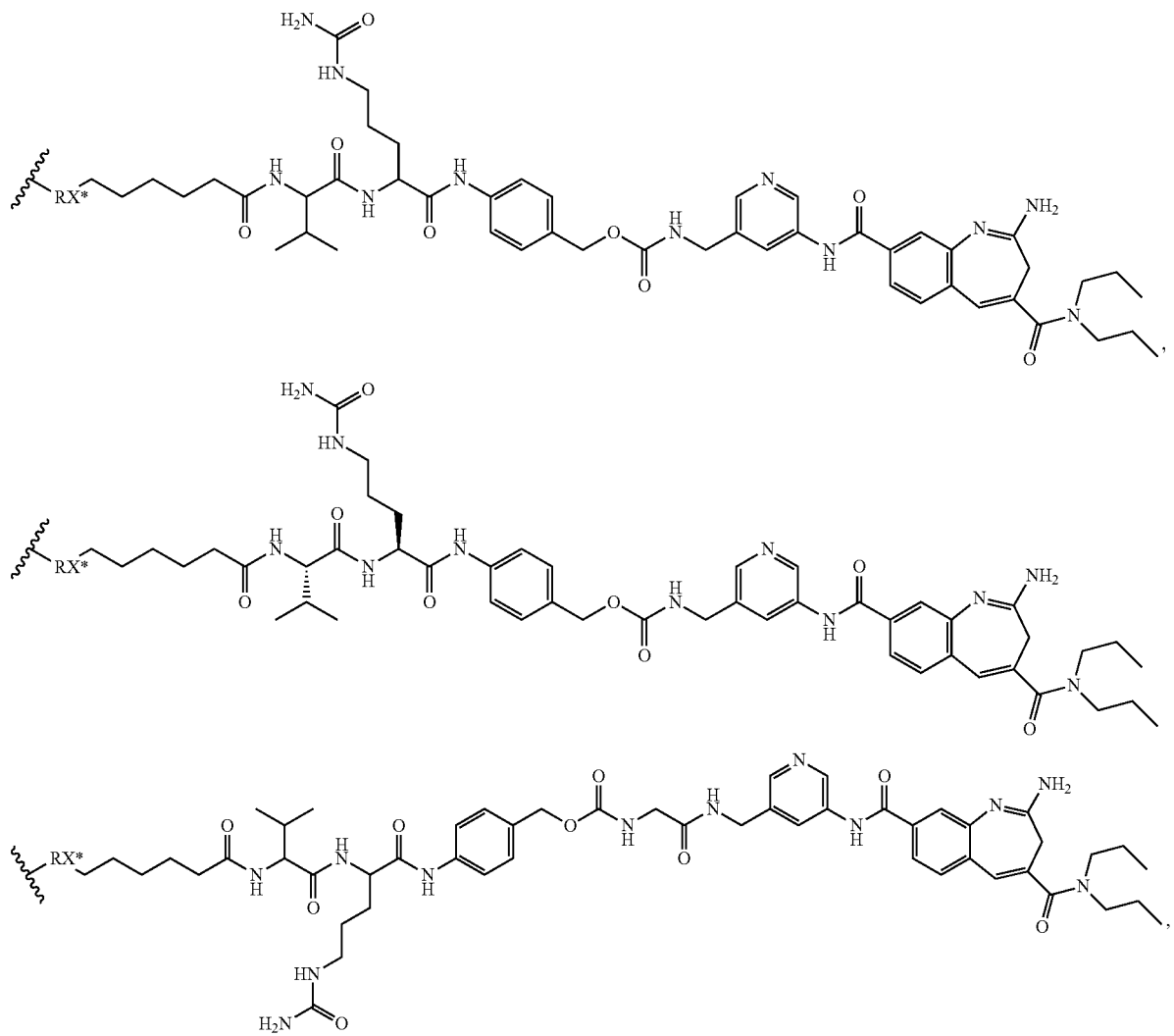

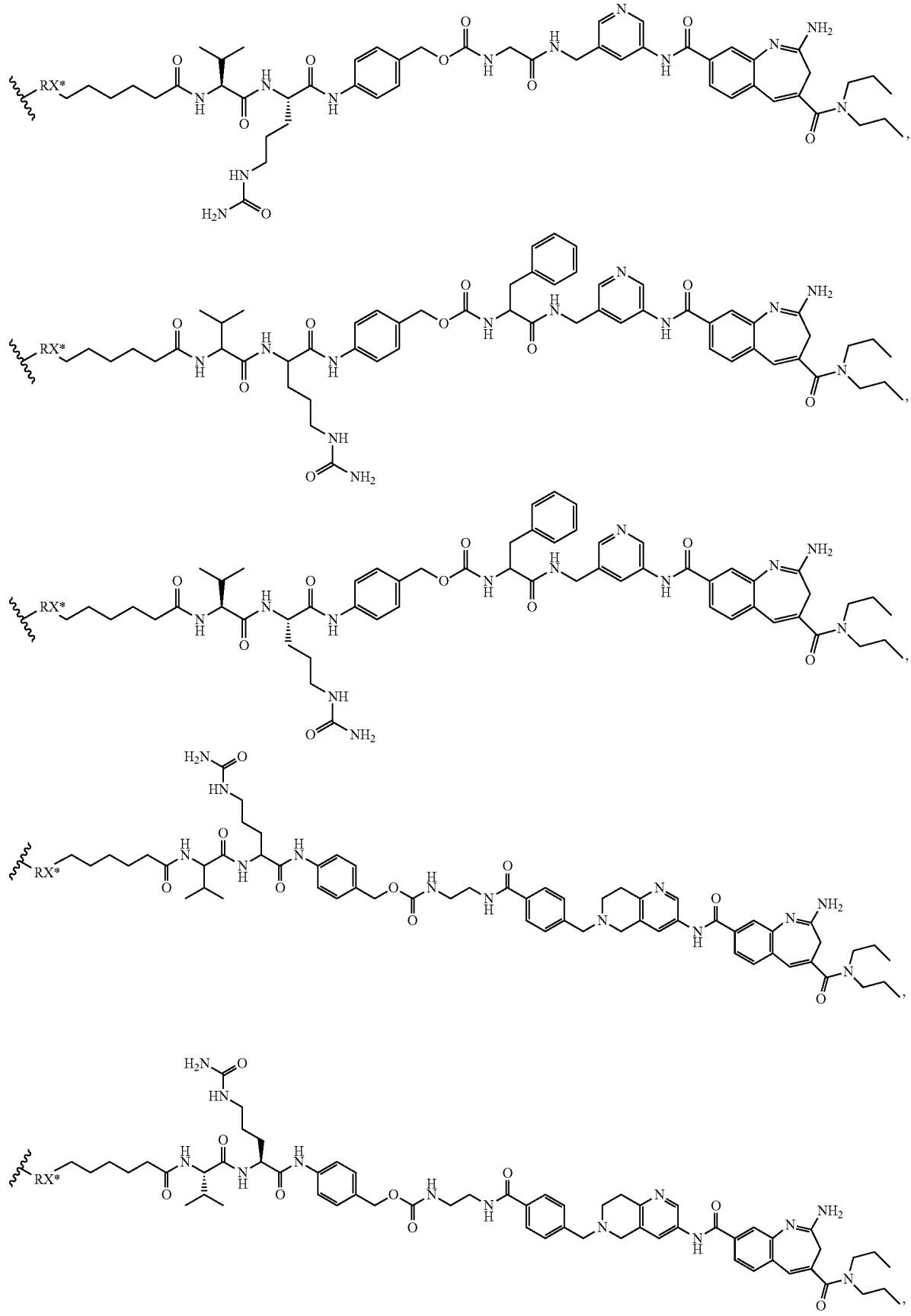

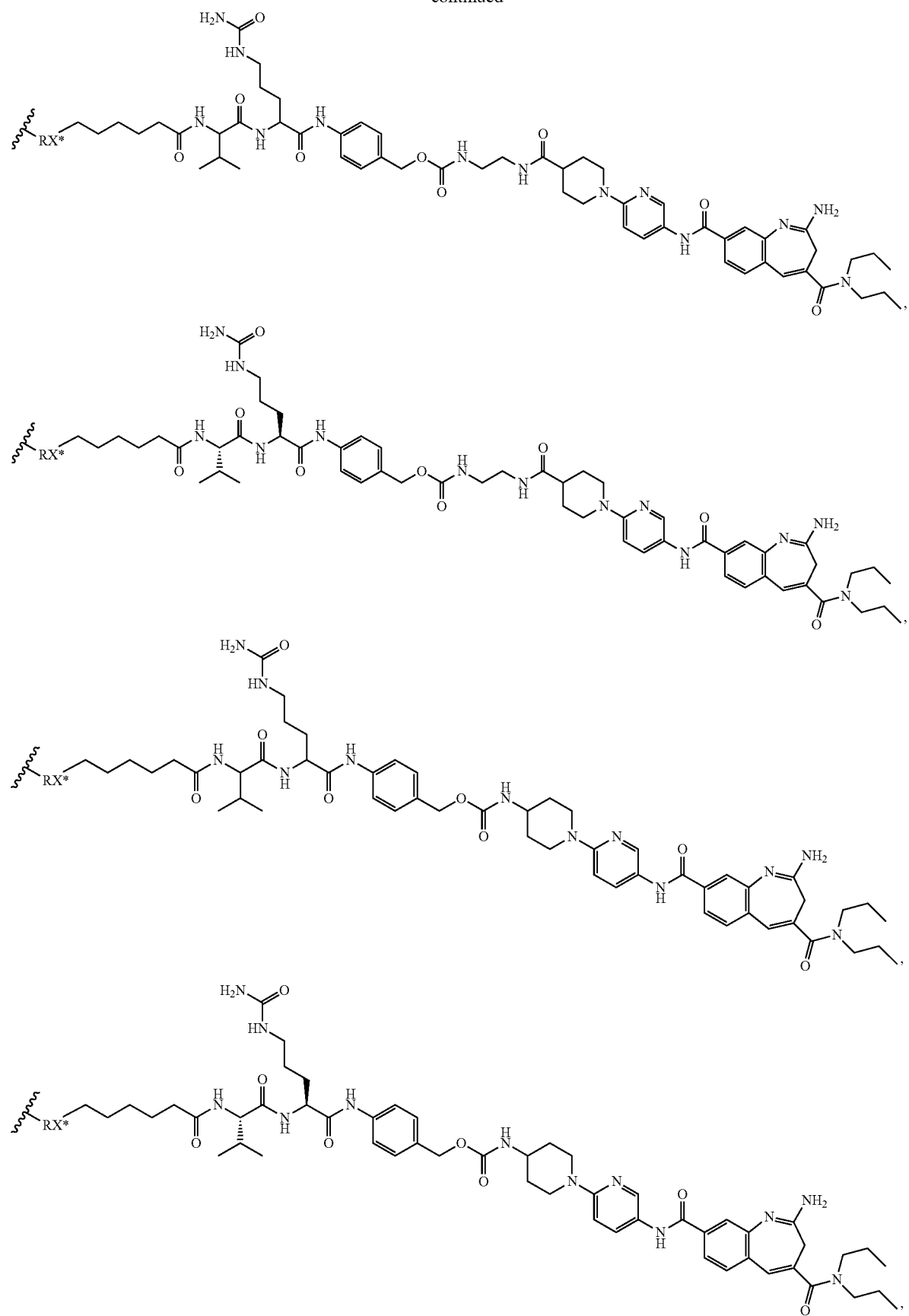

-continued

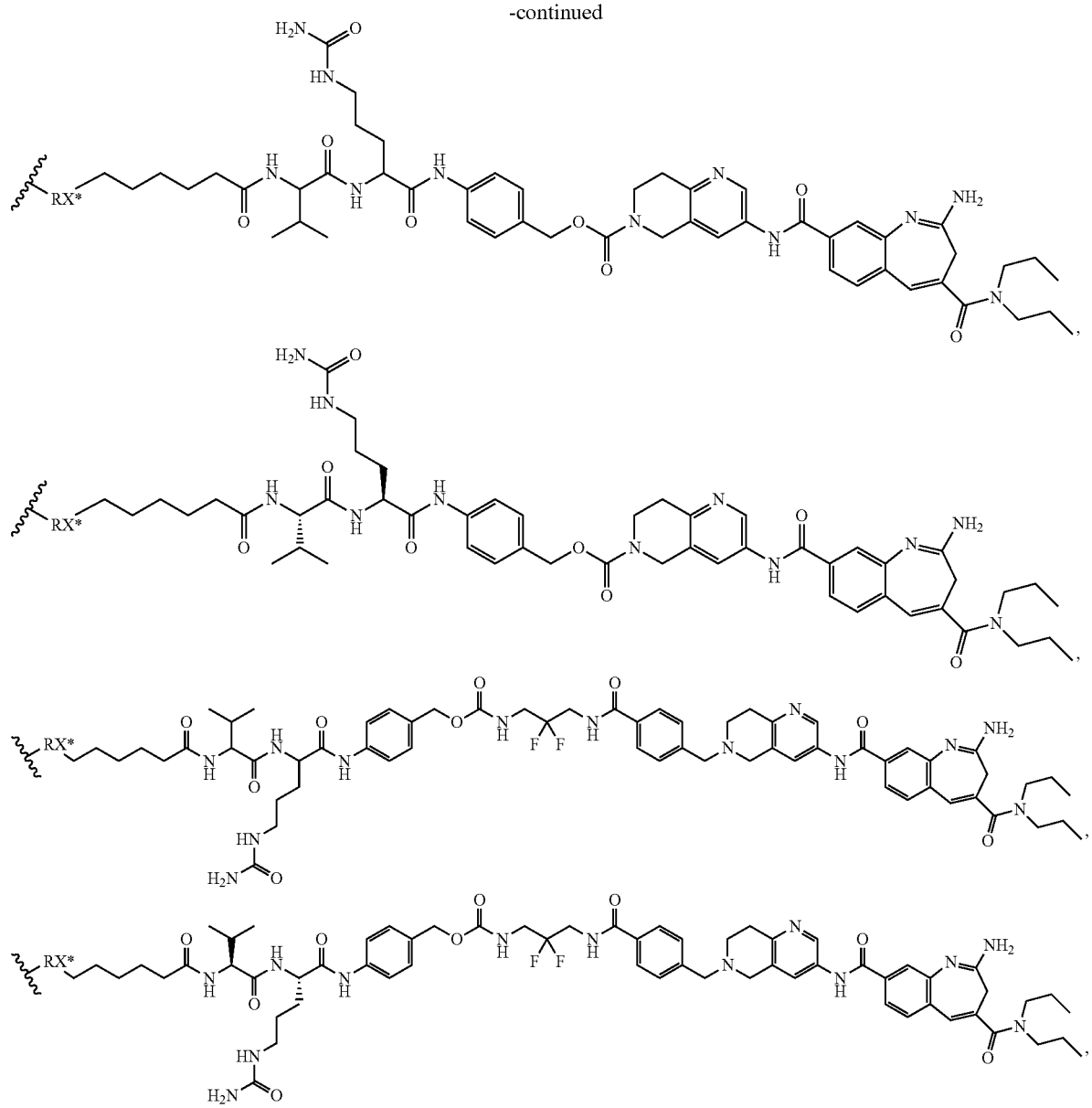

and a salt of any one thereof, wherein the RX* is a bond, a succinimide moiety, or a hydrolyzed succinimide moiety bound to a residue of an antibody construct, wherein ⋏ on RX* represents the point of attachment to the residue of the antibody construct.

In some embodiments, $L^3$ is represented by the formula:

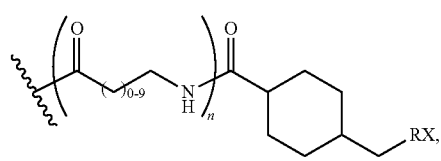

wherein RX comprises a reactive moiety, and n=0-9. In some embodiments, RX comprises a leaving group. In some embodiments, RX comprises a maleimide. In some embodiments, $L^3$ is represented as follows:

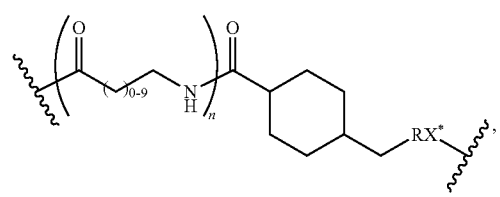

wherein RX* comprises a bond, a succinimide moiety, or a hydrolyzed succinimide moiety bound to a residue of an antibody construct, wherein ⋏ on RX* represents the point of attachment to the residue of the antibody construct, and n=0-9.

In some aspects, the present disclosure provides a compound or salt selected from:
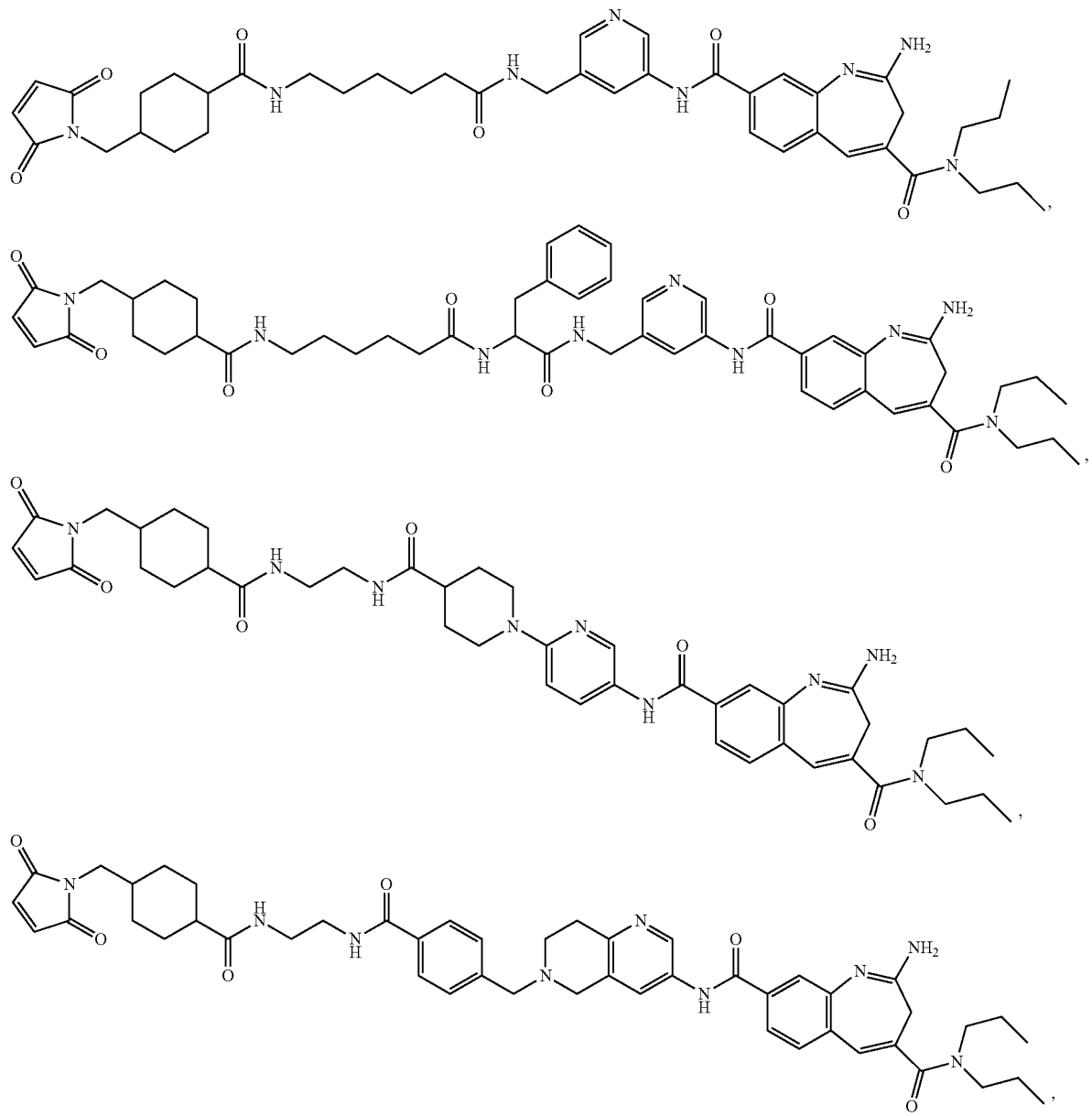
and a salt of any one thereof.
In some aspects, the present disclosure provides a compound or salt selected from:
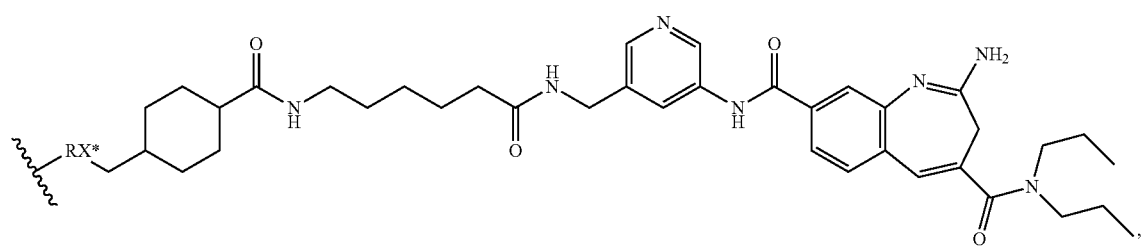

-continued

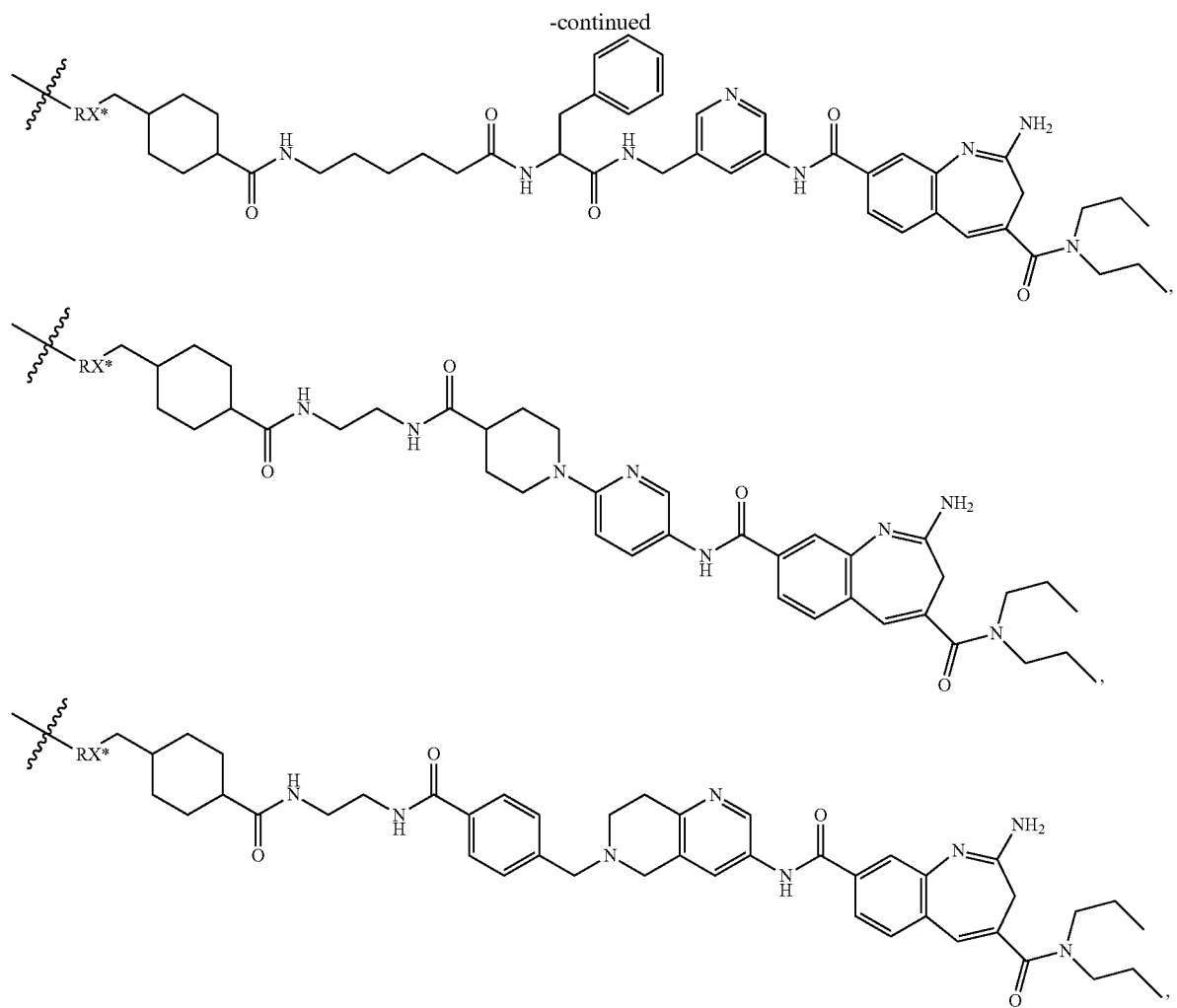

and a salt of any one thereof, wherein the RX* comprises a bond, a succinimide moiety, or a hydrolyzed succinimide moiety bound to a residue of an antibody construct, wherein ⸺ on RX* represents the point of attachment to the residue of the antibody construct.

In some embodiments, RX* comprises a succinamide moiety and is bound to a cysteine residue of an antibody construct. In some embodiments, RX* comprises a hydrolyzed succinamide moiety and is bound to a cysteine residue of an antibody construct. In some embodiments, the antibody construct comprises a HER2 antigen binding domain. In some embodiments, wherein the antibody construct comprises a TROP2 antigen binding domain. In some embodiments, the antibody construct is pertuzumab or an antigen binding fragment thereof. In some embodiments, the antibody construct is trastuzumab or an antigen binding fragment thereof. In some embodiments, the antibody construct is sacituzumab or an antigen binding fragment thereof.

In some aspects, the present disclosure provides a conjugate represented by the formula:

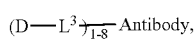

wherein Antibody is an antibody construct, D is a compound or salt disclosed herein, and $L^3$ is a linker moiety.

In some aspects, the present disclosure provides a conjugate represented by the formula:

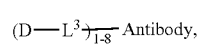

wherein Antibody is an antibody construct and D-$L^3$ is a compound or salt disclosed herein.

In some embodiments, the antibody construct comprises a HER2 antigen binding domain. In some embodiments, the antibody construct comprises a TROP2 antigen binding domain. In some embodiments, the antibody construct is pertuzumab or an antigen binding fragment thereof. In some embodiments, the antibody construct is trastuzumab or an antigen binding fragment thereof. In some embodiments, the antibody construct is sacituzumab or an antigen binding fragment thereof.

In some aspects, the present disclosure provides a pharmaceutical composition comprising the compound or salt disclosed herein and at least one pharmaceutically acceptable excipient.

In some aspects, the present disclosure provides a pharmaceutical composition, comprising the conjugate disclosed herein and at least one pharmaceutically acceptable excipient.

In some embodiments, the average DAR of the conjugate is from about 2 to about 8, or about 1 to about 3, or about 3 to about 5.

In some aspects, the present disclosure provides a method of killing tumor cells in vivo, comprising contacting a tumor cell population with a conjugate disclosed herein.

In some aspects, the present disclosure provides a method for treatment, comprising administering to a subject a conjugate disclosed herein.

In some aspects, the present disclosure provides a method for treatment, comprising administering to a subject in need thereof a compound or salt disclosed herein.

In some aspects, the present disclosure provides a method for treating cancer, comprising administering to a subject in need thereof a conjugate disclosed herein.

In some aspects, the present disclosure provides a method for treating cancer, comprising administering to a subject in need thereof a compound or salt disclosed herein.

In some aspects, the present disclosure provides a compound or salt disclosed herein for use in a method of treatment of a subject's body by therapy.

In some aspects, the present disclosure provides a compound or salt disclosed herein for use in a method of treating cancer.

In some aspects, the present disclosure provides a conjugate disclosed herein for use in a method of treatment of a subject's body by therapy.

In some aspects, the present disclosure provides a conjugate disclosed herein for use in a method of treating cancer.

In some aspects, the present disclosure provides a method of delivering a benzazepine compound to a cancer cell in a subject comprising administering a conjugate disclosed herein to a subject in need thereof.

In some aspects, the present disclosure provides a method for the treatment of cancer, comprising administering an effective amount of an antibody conjugate, wherein the antibody conjugate comprises an antibody construct covalently bound through a linker to a TLR8 agonist, wherein the TLR8 agonist has a $K_d$ for TLR7 that is two times or greater than two times the $K_d$ for TLR8, and wherein the antibody conjugate comprises from 1 to 20 TLR8 agonists per antibody construct, preferably from 1-8, 3-5 or 1-3.

In some aspects, the present disclosure provides a method for the treatment of cancer, comprising administering an effective amount of an antibody conjugate, wherein the antibody conjugate comprises an antibody construct covalently bound through a linker to a TLR8 agonist, wherein the TLR8 agonist agonizes TLR8 with at least an $EC_{50}$ of an order of magnitude less than the amount of the same compound required to show an agonizing effect on TLR7, and wherein the antibody conjugate comprises from 1 to 20 TLR8 agonists per antibody construct, preferably from 1-8, 3-5 or 1-3.

In some aspects, the present disclosure provides a method for the treatment of cancer, comprising administering an effective amount of an antibody conjugate, wherein the antibody conjugate comprises an antibody construct covalently bound through a linker to a TLR8 agonist, wherein the TLR8 agonist comprises a benzazepine substituted with a bicyclic heterocycle, and wherein the antibody conjugate comprises from 1 to 20 TLR8 agonists per antibody construct, preferably from 1-8, 3-5 or 1-3.

In some aspects, the present disclosure provides a method of preparing an antibody conjugate of the formula

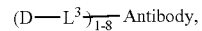

wherein Antibody is an antibody construct, and $L^3$-D is selected from a compound or salt disclosed herein comprising contacting $L^3$-D with an antibody construct.

In some embodiments, the antibody construct comprises a HER2 antigen binding domain. In some embodiments, the antibody construct comprises a TROP2 antigen binding domain. In some embodiments, the antibody construct is pertuzumab or an antigen binding fragment thereof. In some embodiments, the antibody construct is trastuzumab or an antigen binding fragment thereof. In some embodiments, the antibody construct is sacituzumab or an antigen binding fragment thereof. In some embodiments, the methods further comprising purifying the antibody conjugate.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings of which:

INCORPORATION BY REFERENCE

Figure 1:
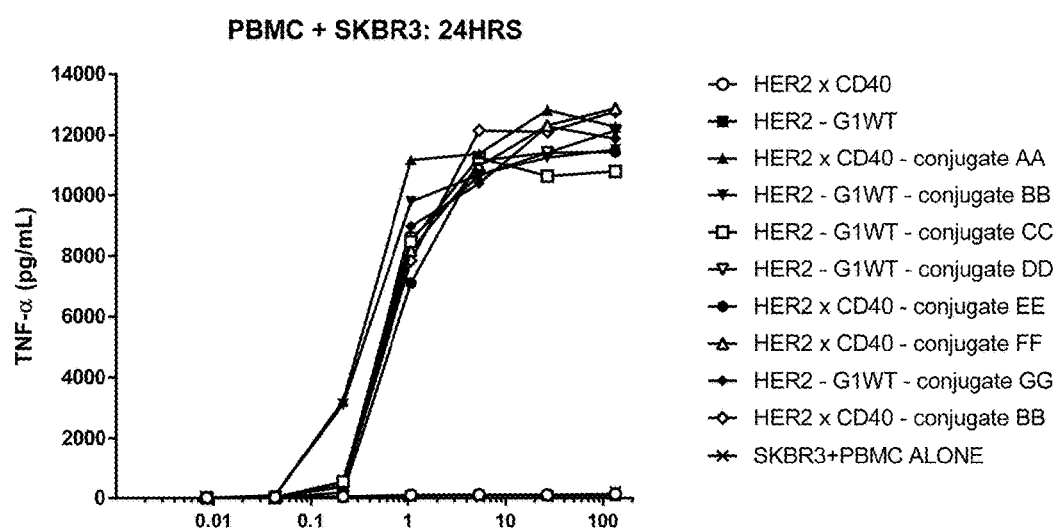
FIG. 1 shows that HER2-TLR8 agonist conjugates and HER2×CD40 TLR8 agonist conjugates were active in the presence of PBMCs and SKBR3 cells that express HER2, as measured by TNFα production.

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present disclosure provides compounds, conjugates and pharmaceutical compositions for use in the treatment of disease. In certain embodiments, the compounds of the disclosure are TLR8 modulators. In certain embodiments, the compounds are TLR8 agonists. Toll-like receptors (TLRs) are a family of membrane-spanning receptors that are expressed on cells of the immune system like dendritic cells, macrophages, monocytes, T cells, B cells, NK cells and mast cells but also on a variety of non-immune cells such as endothelial cells, epithelial cells and even tumor cells. TLRs can have many isoforms, including TLR4, TLR7 and TLR8.

TLR8 are localized to the endolysosomal/phagosomal compartment and predominantly found to be expressed by cells of the myeloid lineage. TLR ligation leads to activation of NF-κB and IRF-dependent pathways with the specific activation sequence and response with respect to the specific TLR and cell type. While TLR7 is mainly expressed in all dendritic cells subtypes (DC and here highly in pDC, plasmacytoid DC) and can be induced in B cells upon IFNα stimulation, TLR8 expression is rather restricted to monocytes, macrophages and myeloid DC. TLR8 signaling via MyD88 can be activated by bacterial single stranded RNA, small molecule agonists and microRNAs. The activation of TLR8 results in the production of various pro-inflammatory cytokines such as IL-6, IL-12 and TNF-α as well as enhanced expression of co-stimulatory molecules, such as CD80, CD86, and chemokine receptors. In addition, TLR8 activation can induce type I interferon (IFNβ) in primary human monocytes.

Several agonists targeting activation of different TLRs can be used in various immunotherapies, including vaccine adjuvants and in cancer immunotherapies. TLR agonists can range from simple molecules to complex macromolecules. Likewise, the sizes of TLR agonists can range from small to large. TLR agonists can be synthetic or biosynthetic agonists. TLR agonists can also be Pathogen-Associated Molecular Pattern molecules (PAMPs).

The compounds of the present disclosure may be useful for the treatment and prevention, e.g., vaccination, of cancer, autoimmune diseases, inflammation, sepsis, allergy, asthma, graft rejection, graft-versus-host disease, immunodeficiencies, and infectious diseases.

In certain embodiments, the compounds have utility in the treatment of cancer either as single agents or in combination therapy. In certain embodiments, the compounds have utility as single agent immunomodulators, vaccine adjuvants and in combination with conventional cancer therapies. In certain embodiments, the compounds are incorporated into a conjugate that can be utilized, for example, to enhance an immune response. In certain embodiments, the disclosure provides antibody construct-benzazepine compound conjugates and their use for treating cancer.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, the term "antibody" can refer to an immunoglobulin molecule that specifically binds to, or is immunologically reactive toward, a specific antigen. Antibody can include, for example, polyclonal, monoclonal, genetically engineered, and antigen binding fragments thereof. An antibody can be, for example, murine, chimeric, humanized, heteroconjugate, bispecific, a diabody, a triabody, or a tetrabody. The antigen binding fragment can include, for example, Fab', F(ab')$_2$, Fab, Fv, rIgG, and scFv.

As used herein, an "antigen binding domain" refers to a region on of a molecule that binds to an antigen. An antigen binding domain of the disclosure may be a domain that can specifically bind to an antigen. An antigen binding domain can be an antigen-binding portion of an antibody or an antibody fragment. An antigen binding domain can be one or more fragments of an antibody that can retain the ability to specifically bind to an antigen. An antigen binding domain can be an antigen binding fragment. An antigen binding domain can recognize a single antigen. An antigen binding domain can recognize, for example, two, three, four, five, six, seven, eight, nine, ten, or more antigens.

As used herein, an "antibody construct" refers to a molecule, e.g., a protein, peptide, antibody or portion thereof, that contains an antigen binding domain and an Fc domain. An antibody construct can recognize, for example, multiple antigens.

As used herein, the abbreviations for amino acids are conventional and can be as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Other amino acids include citrulline (Cit); homocysteine (Hcy); hydroxyproline (Hyp); ornithine (Orn); and thyroxine (Thx).

"Conjugate", as used herein, refers to an antibody construct that is linked, e.g., covalently linked, either directly or through a linker to a compound or compound-linker described herein, e.g., a compound or salt of any one of Formulas (IA), (IB), (IC), (IIA), (IIB), (IIC), (IIIA), (IIIB), (IIIC), (IVA), (IVB), or (IVC).

As used herein, an "Fc domain" can be an Fc domain from an antibody or from a non-antibody that can bind to an Fc receptor.

As used herein, "recognize" with regard to antibody interactions can refer to the association or binding between an antigen binding domain of an antibody or portion thereof and an antigen.

As used herein, a "target binding domain" can refer to a construct that contains an antigen binding domain from an antibody or from a non-antibody that can bind to the antigen.

As used herein, a "tumor antigen" can be an antigenic substance associated with a tumor or cancer cell, and can trigger an immune response in a host.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

In some embodiments, the pharmaceutically acceptable base addition salt is chosen from ammonium, potassium, sodium, calcium, and magnesium salts.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons. The term —$C_{x-y}$alkylene-refers to a substituted or unsubstituted alkylene chain with from x to y carbons in the alkylene chain. For example —$C_{1-6}$alkylene-may be selected from methylene, ethylene, propylene, butylene, pentylene, and hexylene, any one of which is optionally substituted.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively. The term —$C_{x-y}$alkenylene-refers to a substituted or unsubstituted alkenylene chain with from x to y carbons in the alkenylene chain. For example, —$C_{2-6}$alkenylene-may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene-refers to a substituted or unsubstituted alkynylene chain with from x to y carbons in the alkenylene chain. For example, —$C_{2-6}$alkenylene-may be selected from ethynylene, propynylene, butynylene, pentynylene, and hexynylene, any one of which is optionally substituted. An alkynylene chain may have one triple bond or more than one triple bond in the alkynylene chain.

"Alkylene" refers to a straight divalent hydrocarbon chain linking the rest of the molecule to a radical group, consisting solely of carbon and hydrogen, containing no unsaturation, and preferably having from one to twelve carbon atoms, for example, methylene, ethylene, propylene, butylene, and the like. The alkylene chain is attached to the rest of the molecule through a single bond and to the radical group through a single bond. The points of attachment of the alkylene chain to the rest of the molecule and to the radical group are through the terminal carbons respectively. In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Unless stated otherwise specifically in the specification, an alkylene chain is optionally substituted by one or more substituents such as those substituents described herein.

"Alkenylene" refers to a straight divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group are through the terminal carbons respectively. In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene). Unless stated otherwise specifically in the specification, an alkenylene chain is optionally substituted by one or more substituents such as those substituents described herein.

"Alkynylene" refers to a straight divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group are through the terminal carbons respectively. In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene). Unless stated otherwise specifically in the specification, an alkynylene chain is optionally substituted by one or more substituents such as those substituents described herein.

"Heteroalkylene" refers to a straight divalent hydrocarbon chain including at least one heteroatom in the chain, containing no unsaturation, and preferably having from one to twelve carbon atoms and from one to 6 heteroatoms, e.g., —O—, —NH—, —S—. The heteroalkylene chain is attached to the rest of the molecule through a single bond and to the radical group through a single bond. The points of attachment of the heteroalkylene chain to the rest of the molecule and to the radical group are through the terminal atoms of the chain. In other embodiments, a heteroalkylene comprises one to five carbon atoms and from one to three heteroatoms. In other embodiments, a heteroalkylene comprises one to four carbon atoms and from one to three heteroatoms. In other embodiments, a heteroalkylene comprises one to three carbon atoms and from one to two heteroatoms. In other embodiments, a heteroalkylene comprises one to two carbon atoms and from one to two heteroatoms. In other embodiments, a heteroalkylene comprises one carbon atom and from one to two heteroatoms. In other embodiments, a heteroalkylene comprises five to eight carbon atoms and from one to four heteroatoms. In other embodiments, a heteroalkylene comprises two to five carbon atoms and from one to three heteroatoms. In other embodiments, a heteroalkylene comprises three to five carbon atoms and from one to three heteroatoms. Unless stated otherwise specifically in the specification, a heteroalkylene chain is optionally substituted by one or more substituents such as those substituents described herein.

The term "carbocycle" as used herein refers to a saturated, unsaturated or aromatic ring in which each atom of the ring is carbon. Carbocycle includes 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexene. A bicyclic carbocycle includes any combination of saturated, unsaturated and aromatic bicyclic rings, as valence permits. A bicyclic carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, and naphthyl. The term "unsaturated carbocycle" refers to carbocycles with at least one degree of unsaturation and excluding aromatic carbocycles. Examples of unsaturated carbocycles include cyclohexadiene, cyclohexene, and cyclopentene.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, and 6- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. The term "unsaturated heterocycle" refers to heterocycles with at least one degree of unsaturation and excluding aromatic heterocycles. Examples of unsaturated heterocycles include dihydropyrrole, dihydrofuran, oxazoline, pyrazoline, and dihydropyridine.

The term "heteroaryl" includes aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes polycyclic ring systems having two or more rings in which two or more carbons are common to two adjoining rings wherein at least one of the rings is heteroaromatic, e.g., the other rings can be aromatic or non-aromatic carbocyclic, or heterocyclic. Heteroaryl groups include, for example, pyrrole, furan, thiophene, imidazole, oxazole, thiazole, pyrazole, pyridine, pyrazine, pyridazine, and pyrimidine, and the like.

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2), and —$R^b$—S(O)$_t$N($R^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each Rc is a straight or branched alkylene, alkenylene or alkynylene chain.

It will be understood by those skilled in the art that substituents can themselves be substituted, if appropriate. Unless specifically stated as "unsubstituted," references to chemical moieties herein are understood to include substituted variants. For example, reference to a "heteroaryl" group or moiety implicitly includes both substituted and unsubstituted variants, unless specified otherwise.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "targeting moiety" refers to a structure that has a selective affinity for a target molecule relative to other non-target molecules. The targeting moiety binds to a target molecule. A targeting moiety may include, for example, an antibody, a peptide, a ligand, a receptor, or a binding portion thereof. The target biological molecule may be a biological receptor or other structure of a cell such as a tumor antigen.

Antibody Construct

Disclosed herein are antibody constructs that may be used together with compounds of the disclosure. In certain embodiments, compounds of the disclosure are linked, e.g., covalently linked, either directly or through a linker to a compound of the disclosure forming conjugates. In certain embodiments, conjugates of the disclosure are represented by the following formula:

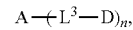

wherein A is an antibody construct, L$^3$ is a linker, D is a compound or salt of any one of Formulas (IA), (IB), (IC), (IIA), (IIB), (IIC), (IIIA), (IIIB) or (IIIC), or L$^3$-D is a compound or salt of any one of Formulas (IVA), (IVB) or (IVC), and n is from 1 to 20. In certain embodiments, n is from 1 to 10, such as from 1 to 9, such as from 1 to 8, such as from 2 to 8, such as from 1 to 6, such as from 3 to 5, or such as from 1 to 3. In certain embodiments, n is 4. In certain embodiments, each D or L$^3$-D are independently selected from Formulas (IA), (IB), (IC), (IIA), (IIB), (IIC), (IIIA), (IIIB) or (IIIC), or Formulas (IVA), (IVB) or (IVC), respectively.

In certain embodiments, a compound or salt of the disclosure, e.g., a compound or salt of Formula (IA), (IB), (IC), (IIA), (IIB), (IIC), (IIIA), (IIIB), (IIIC), (IVA), (IVB), or (IVC), may be referred to herein as a drug, D, a benzazepine compound, an immune-stimulatory compound, an ISC, or a payload, particularly when referenced as part of a conjugate. "LP", "linker-payload", "L$^3$-D", or "compound-linker" may be used herein to refer to a compound or salt of the disclosure bound to a linker.

An antibody construct of the disclosure may contain, for example, two, three, four, five, six, seven, eight, nine, ten, or more antigen binding domains. An antibody construct may contain two antigen binding domains in which each antigen binding domain can recognize the same antigen. An antibody construct may contain two antigen binding domains in which each antigen binding domain can recognize different antigens. An antigen binding domain may be in a scaffold, in which a scaffold is a supporting framework for the antigen binding domain. An antigen binding domain may be in a non-antibody scaffold. An antigen binding domain may be in an antibody scaffold. An antibody construct may comprise an antigen binding domain in a scaffold. The antibody construct may comprise a Fc fusion protein. In some embodiments, the antibody construct is a Fc fusion protein. An antigen binding domain may specifically bind to a tumor antigen. An antigen binding domain may specifically bind to an antigen that is at least 80%, at least 90%, at least 95%, at least 99%, or 100% homologous to a tumor antigen. An antigen binding domain may specifically bind to an antigen on an antigen presenting cell (APC). An antigen binding domain may specifically bind to an antigen that is at least 80%, at least 90%, at least 95%, at least 99%, or 100% homologous to an antigen on an antigen presenting cell (APC).

An antigen binding domain of an antibody may comprise one or more light chain (LC) CDRs and one or more heavy chain (HC) CDRs. For example, an antibody binding domain of an antibody may comprise one or more of the following: a light chain complementary determining region 1 (LC CDR1), a light chain complementary determining region 2 (LC CDR2), or a light chain complementary determining region 3 (LC CDR3). For another example, an antibody binding domain may comprise one or more of the following: a heavy chain complementary determining region 1 (HC CDR1), a heavy chain complementary determining region 2 (HC CDR2), or a heavy chain complementary determining region 3 (HC CDR3). As an additional example, an antibody binding domain of an antibody may comprise one or more of the following: LC CDR1, LC CDR2, LC CDR3, HC CDR1, HC CDR2, and HC CDR3.

The antigen binding domain of an antibody construct may be selected from any domain that binds the antigen including, but not limited to, from a monoclonal antibody, a polyclonal antibody, a recombinant antibody, or an antigen binding fragment thereof, for example, a heavy chain variable domain ($V_H$) and a light chain variable domain ($V_L$), a DARPin, an affimer, an avimer, a knottin, a monobody, an affinity clamp, an ectodomain, a receptor ectodomain, a receptor, a T cell receptor, or a recombinant T cell receptor.

The antigen binding domain of an antibody construct may be at least 80% homologous to an antigen binding domain selected from, but not limited to, a monoclonal antibody, a polyclonal antibody, a recombinant antibody, or a functional fragment thereof, for example, a heavy chain variable domain ($V_H$) and a light chain variable domain ($V_L$), a DARPin, an affimer, an avimer, a knottin, a monobody, an affinity clamp, an ectodomain, a receptor ectodomain, a receptor, a cytokine, a ligand, an immunocytokine, a T cell receptor, or a recombinant T cell receptor.

In certain embodiments, an antibody construct of the disclosure comprises an Fc domain that may further comprise an Fc domain, in which the Fc domain may be the part of an Fc region that interacts with Fc receptors. The Fc domain of an antibody construct may interact with Fc-receptors (FcRs) found on immune cells. The Fc domain may also mediate the interaction between effector molecules and cells, which can lead to activation of the immune system. The Fc domain may be derived from IgG, IgA, or IgD antibody isotypes, and may comprise two identical protein fragments, which are derived from the second and third constant domains of the antibody's heavy chains. In an Fc domain derived from an IgG antibody isotype, the Fc region may comprise a highly-conserved N-glycosylation site, which may be essential for FcR-mediated downstream effects. The Fc domain may be derived from IgM or IgE antibody isotypes, in which the Fc domain may comprise three heavy chain constant domains.

An Fc domain may interact with different types of FcRs. The different types of FcRs may include, for example, FcγRI, FcγRIIA, FcγRIIB, FcγRIIIA, FcγRIIIB, FcαRI, FcμR, FcεRI, FcεRII, and FcRn. FcRs may be located on the membrane of certain immune cells including, for example, B lymphocytes, natural killer cells, macrophages, neutrophils, follicular dendritic cells, eosinophils, basophils, platelets, and mast cells. Once the FcR is engaged by the Fc domain, the FcR may initiate functions including, for example, clearance of an antigen-antibody complex via receptor—mediated endocytosis, antibody-dependent cell-mediated cytotoxicity (ADCC), antibody dependent cell-mediated phagocytosis (ADCP), and ligand-triggered transmission of signals across the plasma membrane that can result in alterations in secretion, exocytosis, and cellular metabolism. FcRs may deliver signals when FcRs are aggregated by antibodies and multivalent antigens at the cell surface. The aggregation of FcRs with immunoreceptor tyrosine-based activation motifs (ITAMs) may sequentially activate SRC family tyrosine kinases and SYK family tyrosine kinases. ITAM comprises a twice-repeated YxxL sequence flanking seven variable residues. The SRC and SYK kinases may connect the transduced signals with common activation pathways.

An antibody of the disclosure may consist of two identical light protein chains and two identical heavy protein chains, all held together covalently by disulfide linkages. The N-terminal regions of the light and heavy chains together may form the antigen recognition site of an antibody. Structurally, various functions of an antibody may be confined to discrete protein domains (i.e., regions). The sites that can recognize and can bind antigen may consist of three complementarities determining regions (CDRs) that may lie within the variable heavy chain region and variable light chain region at the N-terminal end of the heavy chain and the light chain. The constant domains may provide the general framework of the antibody and may not be involved directly in binding the antibody to an antigen, but may be involved in various effector functions, such as participation of the antibody in antibody-dependent cellular cytotoxicity, and may bind Fc receptors. The constant domains may include an Fc region. The constant domains may include an Fc domain. The domains of natural light and heavy chains may have the same general structures, and each domain may comprise four framework regions, whose sequences can be somewhat conserved, connected by three hyper-variable regions or CDRs. The four framework regions (FR) may largely adopt a β-sheet conformation and the CDRs can form loops connecting, and in some aspects forming part of, the β-sheet structure. The CDRs in each chain may be held in close proximity by the framework regions and, with the CDRs from the other chain, may contribute to the formation of the antigen binding site.

An antibody construct may comprise a light chain of an amino acid sequence having at least one, two, three, four, five, six, seven, eight, nine or ten modifications and in certain embodiments, not more than 40, 35, 30, 25, 20, 15 or 10 modifications of the amino acid sequence relative to the natural or original amino acid sequence. An antibody construct may comprise a heavy chain of an amino acid sequence having at least one, two, three, four, five, six, seven, eight, nine or ten modifications and in certain embodiments, not more than 40, 35, 30, 25, 20, 15 or 10 modifications of the amino acid sequence relative to the natural or original amino acid sequence.

An antibody of an antibody construct may include an antibody of any type, which may be assigned to different classes of immunoglobins, e.g., IgA, IgD, IgE, IgG, and IgM. Several different classes may be further divided into isotypes, e.g., IgG1, IgG2, IgG3, IgG4, IgA1, and IgA2. An antibody may further comprise a light chain and a heavy chain, often more than one chain. The heavy-chain constant regions (Fc) that corresponds to the different classes of immunoglobulins may be α, δ, ε, γ, and μ, respectively. The light chains may be one of either kappa (κ) or lambda (λ), based on the amino acid sequences of the constant domains. The Fc region may contain an Fc domain. An Fc receptor may bind an Fc domain. Antibody constructs may also include any fragment or recombinant forms thereof, including but not limited to, single chain variable fragments (scFvs), 'T-bodies', anti-calins, centyrins, affibodies, domain antibodies, or peptibodies.

An antibody construct may comprise an antibody fragment. An antibody fragment may include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; and (iii) a Fv fragment consisting of the $V_L$ and $V_H$ domains of a single arm of an antibody. Although the two domains of the Fv fragment, $V_L$ and $V_H$, may be coded for by separate genes, they may be linked by a synthetic linker to be made as a single protein chain in which the $V_L$ and $V_H$ regions pair to form monovalent molecules.

$F(ab')_2$ and Fab' moieties may be produced by genetic engineering or by treating immunoglobulin (e.g., monoclonal antibody) with a protease such as pepsin and papain, and may include an antibody fragment generated by digesting immunoglobulin near the disulfide bonds existing between the hinge regions in each of the two H chains. The Fab fragment may also contain the constant domain of the light chain and the first constant domain ($C_{H1}$) of the heavy chain. Fab' fragments may differ from Fab fragments by the addition of a few residues at the carboxyl terminus of the heavy chain $C_{H1}$ domain including one or more cysteine(s) from the antibody hinge region.

An Fv may be the minimum antibody fragment which contains a complete antigen-recognition and antigen-binding site. This region may consist of a dimer of one heavy chain and one light chain variable domain in tight, non-covalent association. In this configuration, the three hypervariable regions of each variable domain may interact to define an antigen-binding site on the surface of the $V_H$-$V_L$ dimer. A single variable domain (or half of an Fv comprising only three hypervariable regions specific for an antigen) may recognize and bind antigen, although the binding can be at a lower affinity than the affinity of the entire binding site.

An antibody may include an Fc region comprising an Fc domain. The Fc domain of an antibody may interact with FcRs found on immune cells. The Fc domain may also mediate the interaction between effector molecules and cells, which may lead to activation of the immune system. In the IgG, IgA, and IgD antibody isotypes, the Fc region may comprise two identical protein fragments, which can be derived from the second and third constant domains of the antibody's heavy chains. In the IgM and IgE antibody isotypes, the Fc regions may comprise three heavy chain constant domains. In the IgG antibody isotype, the Fc regions may comprise a highly-conserved N-glycosylation site, which may be important for FcR-mediated downstream effects.

An antibody used herein may be "humanized." Humanized forms of non-human (e.g., murine) antibodies can be chimeric immunoglobulins, immunoglobulin chains or fragments thereof (such as Fv, Fab, Fab', $F(ab')_2$ or other target-binding subdomains of antibodies), which may contain minimal sequences derived from non-human immunoglobulin. In general, the humanized antibody may comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody may also comprise at least a portion of an immunoglobulin constant region (Fc), typically that of a human immunoglobulin consensus sequence.

An antibody described herein may be a human antibody. As used herein, "human antibodies" can include antibodies having, for example, the amino acid sequence of a human immunoglobulin and may include antibodies isolated from human immunoglobulin libraries or from animals transgenic for one or more human immunoglobulins that do not express endogenous immunoglobulins. Human antibodies may be produced using transgenic mice which are incapable of expressing functional endogenous immunoglobulins, but which may express human immunoglobulin genes. Completely human antibodies that recognize a selected epitope may be generated using guided selection. In this approach, a selected non-human monoclonal antibody, e.g., a mouse antibody, may be used to guide the selection of a completely human antibody recognizing the same epitope.

An antibody described herein may be a bispecific antibody or a dual variable domain antibody (DVD). Bispecific and DVD antibodies may be monoclonal, often human or humanized, antibodies that can have binding specificities for at least two different antigens.

An antibody described herein may be a derivatized antibody. For example, derivatized antibodies may be modified by glycosylation, acetylation, pegylation, phosphorylation, amidation, derivatization by known protecting/blocking groups, proteolytic cleavage, linkage to a cellular ligand or other protein.

An antibody described herein may have a sequence that has been modified to alter at least one constant region-mediated biological effector function relative to the corresponding wild type sequence. For example, in some embodiments, the antibody can be modified to reduce at least one constant region-mediated biological effector function relative to an unmodified antibody, e.g., reduced binding to the Fc receptor (FcR). FcR binding may be reduced by, for example, mutating the immunoglobulin constant region segment of the antibody at particular regions necessary for FcR interactions.

An antibody or Fc domain as described herein may be modified to acquire or improve at least one constant region-mediated biological effector function relative to an unmodified antibody or Fc domain, e.g., to enhance FcγR interactions. For example, an antibody with a constant region that binds FcγRIIA, FcγRIIB and/or FcγRIIIA with greater affinity than the corresponding wild type constant region may be produced according to the methods described herein. An Fc domain that binds FcγRIIA, FcγRIIB and/or FcγRIIIA with greater affinity than the corresponding wild type Fc domain may be produced according to the methods described herein.

In certain embodiments, the antibody construct comprises an antigen binding domain and an IgG Fc domain, wherein a $K_d$ for binding of the antigen binding domain to a first antigen in a presence of the immune-stimulatory compound is less than about 100 nM and no greater than about 100 times a $K_d$ for binding of the antigen binding domain to the first antigen in the absence of the immune-stimulatory compound. In certain embodiments, the antibody construct comprises a $K_d$ for binding of the IgG Fc domain to an Fc receptor in the presence of the immune-stimulatory compound is no greater than about 100 times a $K_d$ for binding the IgG Fc domain to the Fc receptor in the absence of the immune-stimulatory compound. In certain embodiments, the first antigen is selected from CD5, CD19, CD20, CD25, CD37, CD30, CD33, CD40, CD45, CAMPATH-1, BCMA, CS-1, PD-L1, B7-H3, B7-DC, HLD-DR, carcinoembryonic antigen (CEA), TAG-72, EpCAM, MUC1, folate-binding protein, A33, G250, prostate-specific membrane antigen (PSMA), ferritin, GD2, GD3, GM2, Le, CA-125, CA19-9, epidermal growth factor, p185HER2, IL-2 receptor, EGFRvIII (de2-7 EGFR), fibroblast activation protein, tenascin, a metalloproteinase, endosialin, vascular endothelial growth factor, avB3, WT1, LMP2, HPV E6, HPV E7, Her-2/neu, MAGE A3, p53 nonmutant, NY-ESO-1, MelanA/MART1, Ras mutant, gp100, p53 mutant, PR1, bcr-abl, tyronsinase, survivin, PSA, hTERT, a Sarcoma translocation breakpoint protein, EphA2, PAP, ML-IAP, AFP, ERG, NA17, PAX3, ALK, androgen receptor, cyclin B 1, polysialic acid, MYCN, RhoC, TRP-2, fucosyl GM1, mesothelin (MSLN), PSCA, MAGE Al, sLe(animal), CYP1B1, PLAV1, GM3, BORIS, Tn, GloboH, ETV6-AML, NY-BR-1, RGS5, SART3, STn, Carbonic anhydrase IX, PAX5, OY-TESL Sperm protein 17, LCK, HMWMAA, AKAP-4, SSX2, XAGE 1, Legumain, Tie 3, VEGFR2, MAD-CT-1, PDGFR-B, MAD-CT-2, ROR2, TRAIL1, MUC16, MAGE A4, MAGE C2, GAGE, EGFR, CMET, HER3, MUC15, CA6, NAPI2B, TROP2, CLDN6, CLDN16, CLDN18.2, CLorf186, RON, LY6E, FRA, DLL3, PTK7, STRA6, TMPRSS3, TMPRSS4, TMEM238, UPK1B, VTCN1, LIV1, ROR1, or Fos-related antigen 1. In certain embodiments, the first antigen is expressed on an immune cell. In certain embodiments, the first antigen is CD40, HER2 or TROP2. In certain embodiments, the first antigen is HER2 or TROP2.

In certain embodiments, the antibody construct comprises a human antibody or a humanized antibody or an antigen binding portion thereof, e.g., a humanized CD40, humanized HER2 or humanized TROP2 antibody. In certain embodiments, the antibody construct comprises a TROP2 antibody, e.g., sacituzumab, or an antigen binding portion thereof. In certain embodiments, the antibody construct comprises the heavy and light chain variable region sequences of sacituxumab (SEQ ID NOs:3 and 4). In certain embodiments, the antibody construct comprises LC CDR1, LC CDR2 and LC CDR3 of the light chain variable region of sacituzumab (SEQ ID NO:4), and HC CDR1, HC CDR2 and HC CDR3 of the heavy chain variable region of sacituzumab (SEQ ID NO:3), as determined by the Kabat index. In certain embodiments, the antibody construct comprises LC CDR1, LC CDR2 and LC CDR3 of the light chain variable region of sacituzumab (SEQ ID NO:4), and HC CDR1, HC CDR2 and HC CDR3 of the heavy chain variable region of sacituzumab (SEQ ID NO:3), as determined by IMGT (ImMunoGeneTics). In certain embodiments, the antibody construct comprises a HER2 antibody, e.g., pertuzumab, trastuzumab, or an antigen binding portion thereof. In certain embodiments, the antibody construct comprises the heavy and light chain variable region sequences of pertuzumab (SEQ ID NOs:1 and 2). In certain embodiments, the antibody construct comprises LC CDR1, LC CDR2 and LC CDR3 of the light chain variable region of pertuzumab (SEQ ID NO:2), and HC CDR1, HC CDR2 and HC CDR3 of the heavy chain variable region of pertuzumab (SEQ ID NO: 1), as determined by the Kabat index. In certain embodiments, the antibody construct comprises LC CDR1, LC CDR2 and LC CDR3 of the light chain variable region of pertuzumab (SEQ ID NO:2), and HC CDR1, HC CDR2 and HC CDR3 of the heavy chain variable region of pertuzumab (SEQ ID NO: 1), as determined by IMGT. In certain embodiments, the antibody construct comprises the heavy and light chain variable region sequences of trastuzumab (SEQ ID NOs:7 and 8). In certain embodiments, the antibody construct comprises LC CDR1, LC CDR2 and LC CDR3 of the light chain variable region of trastuzumab (SEQ ID NO:8), and HC CDR1, HC CDR2 and HC CDR3 of the heavy chain variable region of trastuzumab (SEQ ID NO:7), as determined by the Kabat index. In certain embodiments, the antibody construct comprises LC CDR1, LC CDR2 and LC CDR3 of the light chain variable region of trastuzumab (SEQ ID NO:8), and HC CDR1, HC CDR2 and HC CDR3 of the heavy chain variable region of trastuzumab (SEQ ID NO:7), as determined by IMGT. In certain embodiments, the antibody construct comprises a CD40 antibody or an antigen binding portion thereof. In certain embodiments, the antibody construct comprises the heavy and light chain variable region sequence of sacituxumab (SEQ ID NO:3 and 4). In certain embodiments, the antibody construct comprises the LC CDR1, LC CDR2 and LC CDR3 of the light chain variable region of sacituzumab (SEQ ID NO:4), and HC CDR1, HC CDR2 and HC CDR3 of the heavy chain variable region of sacituzumab (SEQ ID NO:3), as determined by Kabat index.

In certain embodiments, the antibody construct comprises a Liv-1 antibody, e.g., ladiratuzumab, huLiv1-14 (WO 2012078688), Liv1-1.7A4 (US 2011/0117013), huLiv1-22 (WO 2012078688) or an antigen binding portion thereof. In certain embodiments, the antibody construct comprises the heavy and light chain variable region sequences of ladiratuzumab (SEQ ID NOs:5 and 6). In certain embodiments, the antibody construct comprises LC CDR1, LC CDR2 and LC CDR3 of the light chain variable region of ladiratuzumab (SEQ ID NO:6), and HC CDR1, HC CDR2 and HC CDR3 of the heavy chain variable region of ladiratuzumab (SEQ ID NO:5), as determined by Kabat index. In certain embodiments, the antibody construct comprises LC CDR1, LC CDR2 and LC CDR3 of the light chain variable region of ladiratuzumab (SEQ ID NO:6), and HC CDR1, HC CDR2 and HC CDR3 of the heavy chain variable region of ladiratuzumab (SEQ ID NO:5), as determined by IMGT. In certain embodiments, the antibody construct comprises the heavy and light chain variable region sequences of huLiv1-14 (SEQ ID NOs:17 and 18). In certain embodiments, the antibody construct comprises LC CDR1, LC CDR2 and LC CDR3 of the light chain variable region of huLiv1-14 (SEQ ID NO:18), and HC CDR1, HC CDR2 and HC CDR3 of the heavy chain variable region of huLiv1-14 (SEQ ID NO:17), as determined by Kabat index. In certain embodiments, the antibody construct comprises LC CDR1, LC CDR2 and LC CDR3 of the light chain variable region of huLiv1-14 (SEQ ID NO: 18), and HC CDR1, HC CDR2 and HC CDR3 of the heavy chain variable region of huLiv1-14 (SEQ ID NO:17), as determined by IMGT. In certain embodiments, the antibody construct comprises the heavy and light chain variable region sequences of Liv1-1.7A4 (SEQ ID NOs:19 and 20). In certain embodiments, the antibody construct comprises LC CDR1, LC CDR2 and LC CDR3 of the light chain variable region of Liv1-1.7A4 (SEQ ID NO:20), and HC CDR1, HC CDR2 and HC CDR3 of the heavy chain variable region of Liv1-1.7A4 (SEQ ID NO:19), as determined by Kabat index. In certain embodiments, the antibody construct comprises a humanized antibody or antigen binding fragment thereof comprising LC CDR1, LC CDR2 and LC CDR3 of the light chain variable region of Liv1-1.7A4 (SEQ ID NO:20), and HC CDR1, HC CDR2 and HC CDR3 of the heavy chain variable region of Liv1-1.7A4 (SEQ ID NO:19), as determined by Kabat index. In certain embodiments, the antibody construct comprises LC CDR1, LC CDR2 and LC CDR3 of the light chain variable region of Liv1-1.7A4 (SEQ ID NO:20), and HC CDR1, HC CDR2 and HC CDR3 of the heavy chain variable region of Liv1-1.7A4 (SEQ ID NO:19), as determined by IMGT. In certain embodiments, the antibody construct comprises a humanized antibody or antigen binding fragment thereof comprising LC CDR1, LC CDR2 and LC CDR3 of the light chain variable region of Liv1-1.7A4 (SEQ ID NO:20), and HC CDR1, HC CDR2 and HC CDR3 of the heavy chain variable region of Liv1-1.7A4 (SEQ ID NO:19), as determined by IMGT. In certain embodiments, the antibody construct comprises the heavy and light chain variable region sequences of huLiv1-22 (SEQ ID NOs:21 and 22). In certain embodiments, the antibody construct comprises LC CDR1, LC CDR2 and LC CDR3 of the light chain variable region of huLiv1-22 (SEQ ID NO:22), and HC CDR1, HC CDR2 and HC CDR3 of the heavy chain variable region of huLiv1-22 (SEQ ID NO:21), as determined by Kabat index. In certain embodiments, the antibody construct comprises LC CDR1, LC CDR2 and LC CDR3 of the light chain variable region of huLiv1-22 (SEQ ID NO:22), and HC CDR1, HC CDR2 and HC CDR3 of the heavy chain variable region of huLiv1-22 (SEQ ID NO:21), as determined by IMGT.

In certain embodiments, the antibody construct comprises a MUC16 antibody, e.g., sofituzumab, 4H11 (US2013/0171152), 4H5 (US2013/0171152) or an antigen binding portion thereof. In certain embodiments, the antibody construct comprises the heavy and light chain variable region sequences of sofituzumab (SEQ ID NOs:23 and 24). In certain embodiments, the antibody construct comprises LC CDR1, LC CDR2 and LC CDR3 of the light chain variable region of sofituzumab (SEQ ID NO:24), and HC CDR1, HC CDR2 and HC CDR3 of the heavy chain variable region of sofituzumab (SEQ ID NO:23), as determined by Kabat index. In certain embodiments, the antibody construct comprises LC CDR1, LC CDR2 and LC CDR3 of the light chain variable region of sofituzumab (SEQ ID NO:24), and HC CDR1, HC CDR2 and HC CDR3 of the heavy chain variable region of sofituzumab (SEQ ID NO:23), as determined by IMGT. In certain embodiments, the antibody construct comprises the heavy and light chain variable region sequences of antibody 4H11 (SEQ ID NOs:13 and 14). In certain embodiments, the antibody construct comprises LC CDR1, LC CDR2 and LC CDR3 of the light chain variable region of antibody 4H11 (SEQ ID NO: 14), and HC CDR1, HC CDR2 and HC CDR3 of the heavy chain variable region of antibody 4H11 (SEQ ID NO: 13), as determined by Kabat index. In certain embodiments, the antibody construct comprises a humanized antibody comprising LC CDR1, LC CDR2 and LC CDR3 of the light chain variable region of antibody 4H11 (SEQ ID NO: 14), and HC CDR1, HC CDR2 and HC CDR3 of the heavy chain variable region of antibody 4H11 (SEQ ID NO: 13), as determined by Kabat index. In certain embodiments, the antibody construct comprises LC CDR1, LC CDR2 and LC CDR3 of the light chain variable region of antibody 4H11 (SEQ ID NO: 14), and HC CDR1, HC CDR2 and HC CDR3 of the heavy chain variable region of 4H11 (SEQ ID NO: 13), as determined by IMGT. In certain embodiments, the antibody construct comprises a humanized antibody or antigen binding fragment thereof comprising LC CDR1, LC CDR2 and LC CDR3 of the light chain variable region of antibody 4H11 (SEQ ID NO: 14), and HC CDR1, HC CDR2 and HC CDR3 of the heavy chain variable region of 4H11 (SEQ ID NO: 13), as determined by IMGT. In certain embodiments, the antibody construct comprises the heavy and light chain variable region sequences of antibody 4A5 (SEQ ID NOs:15 and 16). In certain embodiments, the antibody construct comprises LC CDR1, LC CDR2 and LC CDR3 of the light chain variable region of antibody 4A5 (SEQ ID NO: 16), and HC CDR1, HC CDR2 and HC CDR3 of the heavy chain variable region of 4A5 (SEQ ID NO:15), as determined by Kabat index. In certain embodiments, the antibody construct comprises a humanized antibody or an antigen binding fragment thereof comprising LC CDR1, LC CDR2 and LC CDR3 of the light chain variable region of antibody 4A5 (SEQ ID NO: 16), and HC CDR1, HC CDR2 and HC CDR3 of the heavy chain variable region of antibody 4A5 (SEQ ID NO: 15), as determined by Kabat index. In certain embodiments, the antibody construct comprises LC CDR1, LC CDR2 and LC CDR3 of the light chain variable region of antibody 4A5 (SEQ ID NO: 16), and HC CDR1, HC CDR2 and HC CDR3 of the heavy chain variable region of antibody 4A5 (SEQ ID NO:15), as determined by IMGT. In certain embodiments, the antibody construct comprises a humanized antibody or antigen binding fragment thereof comprising LC CDR1, LC CDR2 and LC CDR3 of the light chain variable region of 4A5 (SEQ ID NO:16), and HC CDR1, HC CDR2 and HC CDR3 of the heavy chain variable region of 4A5 (SEQ ID NO:15), as determined by IMGT.

In certain embodiments, the antibody construct comprises a PD-L1 antibody, e.g., atezolizumab, MDX-1105 (WO 2007/005874) or an antigen binding portion thereof. In certain embodiments, the antibody construct comprises the heavy and light chain variable region sequences of atezolizumab (SEQ ID NOs: 11 and 12). In certain embodiments, the antibody construct comprises LC CDR1, LC CDR2 and LC CDR3 of the light chain variable region of atezolizumab (SEQ ID NO: 12), and HC CDR1, HC CDR2 and HC CDR3 of the heavy chain variable region of atezolizumab (SEQ ID NO: 11), as determined by Kabat index. In certain embodiments, the antibody construct comprises LC CDR1, LC CDR2 and LC CDR3 of the light chain variable region of atezolizumab (SEQ ID NO:12), and HC CDR1, HC CDR2 and HC CDR3 of the heavy chain variable region of atezolizumab (SEQ ID NO: 11), as determined by IMGT. In certain embodiments, the antibody construct comprises the heavy and light chain variable region sequences of MDX-1105 (SEQ ID NOs:9 and 10). In certain embodiments, the antibody construct comprises LC CDR1, LC CDR2 and LC CDR3 of the light chain variable region of MDX-1105 (SEQ ID NO: 10), and HC CDR1, HC CDR2 and HC CDR3 of the heavy chain variable region of MDX-1105 (SEQ ID NO:9), as determined by Kabat index. In certain embodiments, the antibody construct comprises a humanized antibody or antigen binding fragment thereof comprising LC CDR1, LC CDR2 and LC CDR3 of the light chain variable region of MDX-1105 (SEQ ID NO: 10), and HC CDR1, HC CDR2 and HC CDR3 of the heavy chain variable region of MDX-1105 (SEQ ID NO:9), as determined by Kabat index. In certain embodiments, the antibody construct comprises LC CDR1, LC CDR2 and LC CDR3 of the light chain variable region of MDX-1105 (SEQ ID NO: 10), and HC CDR1, HC CDR2 and HC CDR3 of the heavy chain variable region of MDX-1105 (SEQ ID NO:9), as determined by IMGT. In certain embodiments, the antibody construct comprises a humanized antibody or antigen binding fragment thereof comprising LC CDR1, LC CDR2 and LC CDR3 of the light chain variable region of MDX-1105 (SEQ ID NO: 10), and HC CDR1, HC CDR2 and HC CDR3 of the heavy chain variable region of MDX-1105 (SEQ ID NO:9), as determined by IMGT.

An antibody construct may comprise an antibody with modifications of at least one amino acid residue. Modifications may be substitutions, additions, mutations, deletions, or the like. An antibody modification can be an insertion of an unnatural amino acid.

The exemplary antibody construct $V_H$ sequences and $V_L$ sequences are illustrated in Table A below.

TABLE A

Exemplary Antibody Construct VH sequences and VL sequences

| Antibody | Region | SEQ ID NO: | Sequence |
|---|---|---|---|
| Pertuzumab | $V_H$ | 1 | EVQLVESGGGLVQPGGSLRLSCAAS GFTFTDYTMDWVRQAPGKGLEWVAD |

TABLE A-continued

Exemplary Antibody Construct VII sequences and VL sequences

| Antibody | Region | SEQ ID NO: | Sequence |
|---|---|---|---|
| | | | VNPNSGGSIYNQRFKGRFTLSVDRS KNTLYLQMNSLRAEDTAVYYCARNL GPSFYFDYWGQGTLVTVSS |
| | $V_L$ | 2 | DIQMTQSPSSLSASVGDRVTITCKA SQDVSIGVAWYQQKPGKAPKLLIYS ASYRYTGVPSRFSGSGSGTDFTLTI SSLQPEDFATYYCQQYYIYPYTFGQ GTKVEIK |
| Sacituzumab | $V_H$ | 3 | QVQLQQSGSELKKPGASVKVSCKAS GYTFTNYGMNWVKQAPGQGLKWMGW INTYTGEPTYTDDFKGRFAFSLDTS VSTAYLQISSLKADDTAVYFCARGG FGSSYWYFDVWGQGSLVTVSS |
| | $V_L$ | 4 | DIQLTQSPSSLSASVGDRVSITCKA SQDVSIAVAWYQQKPGKAPKLLIYS ASYRYTGVPDRFSGSGSGTDFTLTI SSLQPEDFAVYYCQQHYITPLTFGA GTKVEIK |
| Ladiratuzumab | $V_H$ | 5 | QVQLVQSGAEVKKPGASVKVSCKAS GLTIEDYYMHWVRQAPGQGLEWMGW IDPENGDTEYGPKFQGRVTMTRDTS INTAYMELSRLSDDTAVYYCAVHN AHYGTWFAYWGQGTLVTVSS |
| | $V_L$ | 6 | DVVMTQSPLSLPVTLGQPASISCRS SQSLLHSSGNTYLEYFQQRPGQSPR PLIYKISTRFSGVPDRFSGSGSGTD FTLKISRVEAEDVGVYYCFQGSHVP YTFGGGTKVEIK |
| Trastuzumab | $V_H$ | 7 | EVQLVESGGGLVQPGGSLRLSCAAS GFNIKDTYIHWVRQAPGKGLEWVAR IYPTNGYTRYADSVKGRFTISADTS KNTAYLQMNSLRAEDTAVYYCSRWG GDGFYAMDYWGQGTLVTVSS |
| | $V_L$ | 8 | DIQMTQSPSSLSASVGDRVTITCRA SQDVNTAVAWYQQKPGKAPKLLIYS ASFLYSGVPSRFSGSRSGTDFTLTI SSLQPEDFATYYCQQHYTTPPTFGQ GTKVEIK |
| MDX-1105 | $V_H$ | 9 | QVQLVQSGAEVKKPGSSVKVSCKTS GDTFSTYAISWVRQAPGQGLEWMGG IIPIFGKAHYAQKFQGRVTITADES TSTAYMELSSLRSEDTAVYFCARKF HFVSGSPFGMDVWGQGTTVTVSS |
| | $V_L$ | 10 | EIVLTQSPATLSLSPGERATLSCRA SQSVSSYLAWYQQKPGQAPRLLIYD ASNRATGIPARFSGSGSGTDFTLTI SSLEPEDFAVYYCQQRSNWPTFGQG TKVEIK |
| Atezolizumab | $V_H$ | 11 | EVQLVESGGGLVQPGGSLRLSCAAS GFTFSDSWIHWVRQAPGKGLEWVAW ISPYGGSTYYADSVKGRFTISADTS KNTAYLQMNSLRAEDTAVYYCARRH WPGGFDYWGQGTLVTVSS |
| | $V_L$ | 12 | DIQMTQSPSSLSASVGDRVTITCRA SQDVSTAVAWYQQKPGKAPKLLIYS ASFLYSGVPSRFSGSGSGTDFTLTI SSLQPEDFATYYCQQYLYHPATFGQ GTKVEIK |
| 4H11 | $V_H$ | 13 | EVKLQESGGGFVKPGGSLKVSCAAS GFTFSSYAMSWVRLSPEMRLEWVAT ISSAGGYIFYSDSVQGRFTISRDNA |
| | | | KNTLHLQMGSLRSGDTAMYYCARQG FGNYGDYYAMDYWGQGTTVTVSS |
| | $V_L$ | 14 | DIELTQSPSSLAVSAGEKVTMSCKS SQSLLNSRTRKNQLAWYQQKPGQSP ELLIYWASTRQSGVPDRFTGSGSGT DFTLTISSVQAEDLAVYYCQQSYNL LTFGPGTKLEVK |
| 4A5 | $V_H$ | 15 | EVKLEESGGGFVKPGGSLKISCAAS GFTFRNYAMSWVRLSPEMRLEWVAT ISSAGGYIFYSDSVQGRFTISRDNA KNTLHLQMGSLRSGDTAMYYCARQG FGNYGDYYAMDYWGQGTTVTVSS |
| | $V_L$ | 16 | DIELTQSPSSLAVSAGEKVTMSCKS SQSLLNSRTRKNQLAWYQQKTGQSP ELLIYWASTRQSGVPDRFTGSGSGT DFTLTISSVQAEDLAVYYCQQSYNL LTFGPGTKLEIK |
| huLiv1-14 | $V_H$ | 17 | QVQLVQSGAEVKKPGASVKVSCKAS GYTIEDYYMHWVRQAPGQGLEWMGW IDPENGDTEYAPTFQGRVTMTRDTS INTAYMELSRLRSDDTAVYYCARHD AHYGTWFAYWGQGTLVTVSS |
| | $V_L$ | 18 | DVVMTQSPLSLPVTLGQPASISCRS SQSIIRNDGNTYLEWYQQRPGQSPR RLIYRVSNRFSGVPDRFSGSGSGTD FTLKISRVEAEDVGVYYCFQGSHVP YTFGGGTKVEIK |
| Liv1-1.7A4 | $V_H$ | 19 | EIQLQQSGPELMKPGASVKISCKAS TYSFTRYFMHWVKQSHGESLEWIGY IDPFNGGTGYNQKFKGKATLTVDKS SSTAYMHLSSLTSEDSAVYYCVTYG SDYFDYWGQGTTLTVSS |
| | $V_L$ | 20 | DIVMTQPQKFMSTSVGDRVSVTCKA SQNVETDVVWYQQKPGQPPKALIYS ASYRHSGVPDRFTGSGSGTNFTLTI STVQSEDLAEYFCQQYNNYPFTFGS GTKLEIR |
| huLiv1-22 | $V_H$ | 21 | QVQLVQSGAEVKKPGASVKVSCKAS GLTIEDYYMHWVRQAPGQGLEWMGW IDPENGDTEYGPKFQGRVTMTRDTS INTAYMELSRLSDDTAVYYCAVHN AHYGTWFAYWGQGTLVTVSS |
| | $V_L$ | 22 | DVVMTQSPLSLPVTLGQPASISCRS SQSLLHSSGNTYLEWYQQRPGQSPR PLIYKISTRFSGVPDRFSGSGSGTD FTLKISRVEAEDVGVYYCFQGSHVP YTFGGGTKVEIK |
| Sofituzumab | $V_H$ | 23 | EVQLVESGGGLVQPGGSLRLSCAAS GYSITNDYAWNWVRQAPGKGLEWVG YISYSGYTTYNPSLKSRFTISRDTS KNTLYLQMNSLRAEDTAVYYCARWT SGLDYWGQGTLVTVSS |
| | $V_L$ | 24 | DIQMTQSPSSLSASVGDRVTITCKA SDLIHNWLAWYQQKPGKAPKLLIYG ATSLETGVPSRFSGSGSGTDFTLTI SSLQPEDFATYYCQQYWTTPFTFGQ GTKVEIK |

Target Binding Domain of an Antibody Construct

An antibody construct may further comprise a target binding domain. A target binding domain may comprise a domain that binds to a target. A target may be an antigen. A target binding domain may comprise an antigen binding domain. A target binding domain may be a domain that can specifically bind to an antigen. A target binding domain may be an antigen-binding portion of an antibody or an antibody fragment. A target binding domain may be one or more fragments of an antibody that can retain the ability to specifically bind to an antigen. A target binding domain may be any antigen binding fragment. A target binding domain may be in a scaffold, in which a scaffold is a supporting framework for the antigen binding domain. A target binding domain may comprise an antigen binding domain in a scaffold.

A target binding domain may comprise an antigen binding domain which can refer to a portion of an antibody comprising the antigen recognition portion, i.e., an antigenic determining variable region of an antibody sufficient to confer recognition and binding of the antigen recognition portion to a target, such as an antigen, i.e., the epitope. A target binding domain may comprise an antigen binding domain of an antibody. In certain embodiments, a target binding domain is a CD40 agonist.

An Fv can be the minimum antibody fragment which contains a complete antigen-recognition and antigen-binding site. This region may consist of a dimer of one heavy chain and one light chain variable domain in tight, non-covalent association. In this configuration, the three hypervariable regions of each variable domain may interact to define an antigen-binding site on the surface of the $V_H$-$V_L$ dimer. A single variable domain (or half of an Fv comprising only three hypervariable regions specific for an antigen) can recognize and bind antigen, although at a lower affinity than the entire binding site.

A target binding domain may be at least 80% homologous to an antigen binding domain selected from, but not limited to, a monoclonal antibody, a polyclonal antibody, a recombinant antibody, or a functional fragment thereof, for example, a heavy chain variable domain ($V_H$) and a light chain variable domain ($V_L$), a single chain variable fragment (scFv), a DARPin, an affimer, an avimer, a knottin, a monobody, an affinity clamp, an ectodomain, a receptor ectodomain, a receptor, a cytokine, a ligand, an immunocytokine, a T cell receptor, or a recombinant T cell receptor.

A target binding domain may be attached to an antibody construct. For example, an antibody construct may be fused with a target binding domain to create an antibody construct target binding domain fusion. The antibody construct-target binding domain fusion may be the result of the nucleic acid sequence of the target binding domain being expressed in frame with the nucleic acid sequence of the antibody construct. The antibody construct-target binding domain fusion may be the result of an in-frame genetic nucleotide sequence or a contiguous peptide sequence encoding the antibody construct with the target binding domain. As another example, a target binding domain may be linked to an antibody construct. A target binding domain may be linked to an antibody construct by a chemical conjugation. A target binding domain may be attached to a terminus of an Fc region. A target binding domain may be attached to a terminus of an Fc region. A target binding domain may be attached to a terminus of an antibody construct. A target binding domain may be attached to a terminus of an antibody. A target binding domain may be attached to a light chain of an antibody. A target binding domain may be attached to a terminus of a light chain of an antibody. A target binding domain may be attached to a heavy chain of an antibody. A target binding domain may be attached to a terminus of a heavy chain of an antibody. The terminus may be a C-terminus. An antibody construct may be attached to 1, 2, 3, and/or 4 target binding domains. The target binding domain may direct the antibody construct to, for example, a particular cell or cell type. A target binding domain of an antibody construct may be selected in order to recognize an antigen, e.g., an antigen expressed on an immune cell. An antigen can be a peptide or fragment thereof. An antigen may be expressed on an antigen-presenting cell. An antigen may be expressed on a dendritic cell, a macrophage, or a B cell. As another example, an antigen may be a tumor antigen. The tumor antigen may be any tumor antigen described herein. When multiple target binding domains are attached to an antibody construct, the target binding domains may bind to the same antigen. When multiple target binding domains are attached to an antibody construct, the target binding domains may bind different antigens.

In certain embodiments, an antibody construct described herein specifically binds a second antigen. In certain embodiments, the target binding domain is linked, e.g., covalently bound, to the antibody construct at a C-terminal end of the Fc domain.

Compounds

The following is a discussion of compounds and salts thereof that may be used in the methods of the disclosure. The compounds and salts described in Formulas (IA), (IB), (IC), (IIA), (IIB), (IIC), (IIIA), (IIIB), and (IIIC) may be covalently bound, to linkers, $L^3$, which may further be covalently bound to antibody constructs. The compound and salts described in Formulas (IVA), (IVB), (IVC) are covalently bound to linkers, $L^3$, which may further be covalently bound to antibody constructs.

In some aspects, the present disclosure provides a compound represented by the structure of Formula (IA):

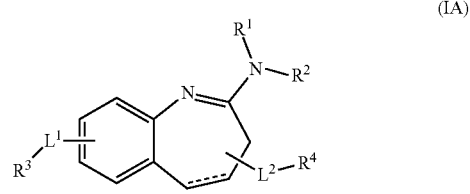

(IA)

or a pharmaceutically acceptable salt thereof, wherein:

- - - - - - represents an optional double bond;

$L^1$ is selected from —$X^1$—, —$X^2$—$C_{1-6}$ alkylene-$X^2$—$C_{1-6}$ alkylene-, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$L^2$ is selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$X^1$ is selected from —S—*, —N($R^{10}$)—*, —C(O)O—*, —OC(O)—*, —OC(O)O—*, —C(O)N($R^{10}$)C(O)—*, —C(O)N($R^{10}$)C(O)N($R^{10}$)*, —N($R^{10}$)C(O)—*, —CR$^{10}_2$N($R^{10}$)C (O)—*, —N($R^{10}$)C(O)N($R^{10}$)—*, —N($R^{10}$)C(O)O—*, —OC(O)N($R^{10}$)—*, —C(NR$^{10}$)—*, —N($R^{10}$)C(NR$^{10}$)—*, —C(NR$^{10}$)N ($R^{10}$)—*, —N($R^{10}$)C(NR$^{10}$)N($R^{10}$)—*, —S(O)$_2$—*, —OS(O)—*, —S(O)O—*, —S(O), —OS(O)$_2$—*, —S(O)$_2$O*, —N($R^{10}$)S(O)$_2$—*, —S(O)$_2$N($R^{10}$)—*, —N(R$^{10}$)S(O)—\*, —S(O)N(R$^{10}$)—\*, —N(R$^{10}$)S(O)$_2$N(R$^{10}$)—\*, and —N(R$^{10}$)S(O)N(R$^{10}$)—\*, wherein \* represents where X$^1$ is bound to R$^3$;

X$^2$ is independently selected at each occurrence from a bond, —O—, —S—, —N(R$^{10}$)—, —C(O)—, —C(O)O—, —OC(O)—, —OC(O)O—, —C(O)N(R$^{10}$)—, —C(O)N(R$^{10}$)C(O)—, —C(O)N(R$^{10}$)C(O)N(R$^{10}$), —N(R$^{10}$)C(O)—, —N(R$^{10}$)C(O)N(R$^{10}$)—, —N(R$^{10}$)C(O)O—, —OC(O)N(R$^{10}$)—, —C(NR$^{10}$)—, —N(R$^{10}$)C(NR$^{10}$)—, —C(NR$^{10}$)N(R$^{10}$)—, —N(R$^{10}$)C(NR$^{10}$)N(R$^{10}$)—, —S(O)$_2$—, —OS(O)—, —S(O)O—, —S(O), —OS(O)$_2$—, —S(O)$_2$O, —N(R$^{10}$)S(O)$_2$—, —S(O)$_2$N(R$^{10}$)—, —N(R$^{10}$)S(O)—, —S(O)N(R$^{10}$)—, —N(R$^{10}$)S(O)$_2$N(R$^{10}$)—, and —N(R$^{10}$)S(O)N(R$^{10}$)—;

R$^1$ and R$^2$ are independently selected from hydrogen; C$_{1-10}$ alkyl, C$_{2-10}$ alkenyl, and C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;

R$^3$ is selected from optionally substituted C$_{3-12}$ carbocycle, and optionally substituted 3- to 12-membered heterocycle, wherein substituents on R$^3$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^3$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;

R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^4$ is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;

R$^{10}$ is independently selected at each occurrence from: hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and haloalkyl;

R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, and C$_{2-6}$ alkynyl; and wherein any substitutable carbon on the benzazepine core is optionally substituted by a substituent independently selected from R$^{12}$ or two substituents on a single carbon atom combine to form a 3- to 7-membered carbocycle.

In certain embodiments, for a compound or salt of Formula (IA), X$^2$ is independently selected at each occurrence from —O—, —S—, —N(R$^{10}$)—, —C(O)—, —C(O)O—, —OC(O)—, —OC(O)O—, —C(O)N(R$^{10}$)—, —C(O)N(R$^{10}$)C(O)—, —C(O)N(R$^{10}$)C(O)N(R$^{10}$), —N(R$^{10}$)C(O)—, —N(R$^{10}$)C(O)N(R$^{10}$)—, —N(R$^{10}$)C(O)O—, —OC(O)N(R$^{10}$)—, —C(NR$^{10}$)—, —N(R$^{10}$)C(NR$^{10}$)—, —C(NR$^{10}$)N(R$^{10}$)—, —N(R$^{10}$)C(NR$^{10}$)N(R$^{10}$)—, —S(O)$_2$—, —OS(O)—, —S(O)O—, —S(O), —OS(O)$_2$—, —S(O)$_2$O, —N(R$^{10}$)S(O)$_2$—, —S(O)$_2$N(R$^{10}$)—, —N(R$^{10}$)S(O)—, —S(O)N(R$^{10}$)—, —N(R$^{10}$)S(O)$_2$N(R$^{10}$)—, and —N(R$^{10}$)S(O)N(R$^{10}$)—.

In certain embodiments, for a compound of Formula (IA):

------ represents an optional double bond;

L$^1$ is independently selected from —X$^1$—, —X$^2$—C$_{1-6}$ alkyl-X$^2$—, —X$^2$—C$_{2-6}$ alkenyl-X$^2$—, and —X$^2$—C$_{2-6}$ alkynyl-X$^2$, each of which is optionally substituted at each occurrence with one or more R$^{10}$;

L$^2$ is independently selected from —X$^2$—, —X$^2$—C$_{1-6}$ alkyl-X$^2$—, —X$^2$—C$_{2-6}$ alkenyl-X$^2$—, and —X$^2$—C$_{2-6}$ alkynyl-X$^2$—, each of which is optionally substituted at each occurrence with one or more R$^{10}$;

X$^1$ at each occurrence is independently selected from —S—\*, —N(R$^{10}$)—\*, —C(O)O—\*, —OC(O)—\*, —OC(O)O—\*, —C(O)N(R$^{10}$)C(O)—\*, —C(O)N(R$^{10}$)C(O)N(R$^{10}$)—\*, —N(R$^{10}$)C(O)—\*, —CR$^{10}$$_2$N(R$^{10}$)C (O)—\*, —N(R$^{10}$)C(O)N(R$^{10}$)—\*, —N(R$^{10}$)C(O)O—\*, —OC(O)N(R$^{10}$)—\*, —C(NR$^{10}$)—\*, —N(R$^{10}$)C(NR$^{10}$)—\*, —C(NR$^{10}$)N(R$^{10}$)—\*, —N(R$^{10}$)C(NR$^{10}$)N(R$^{10}$)—\*, —S(O)$_2$—\*, —OS(O)—\*, —S(O)O—\*, —S(O)—\*, —OS(O)$_2$—\*, —S(O)$_2$O\*, —N(RO)S(O)$_2$—\*, —S(O)$_2$N(R$^{10}$)—\*, —N(R$^{10}$)S(O)—\*, —S(O)N(R$^{10}$)—\*, —N(R$^{10}$)S(O)$_2$N(R$^{10}$)—\*, and —N(R$^{10}$)S(O)N(R$^{10}$)—\*, wherein \* represents where X$^1$ is bound to R$^3$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N(RO)C(O)—, —N($R^{10}$)C(O)N($R^{10}$)—, —N($R^{10}$)C(O)O—, —OC(O)N($R^{10}$), —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O) O—, —S(O)—, —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; and $C_{1-10}$ alkyl, $C_{2-10}$ alkenyl, and $C_{2-10}$ alkynyl, each of which is independently optionally substituted at each occurrence with one or more substituents selected from halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^3$ is selected from optionally substituted $C_{3-12}$ carbocycle, and optionally substituted 3- to 12-membered heterocycle, wherein substituents are independently selected at each occurrence from: halogen, —O$R^{10}$, —S$R^{10}$, —C(O)N($R^{10}$)$_2$, —N($R^{10}$)C(O)$R^{10}$, N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN; $C_{1-10}$ alkyl, $C_{2-10}$ alkenyl, $C_{2-10}$ alkynyl, each of which is independently optionally substituted at each occurrence with one or more substituents selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^3$ is independently optionally substituted with one or more substituents selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is independently optionally substituted at each occurrence with one or more substituents selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is independently optionally substituted with one or more substituents selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl; $R^{10}$ is independently selected at each occurrence from: hydrogen, —NH$_2$, —C(O)OCH$_2C_6H_5$; and $C_{1-10}$ alkyl, $C_{2-10}$ alkenyl, $C_{2-10}$ alkynyl, $C_{3-12}$ carbocycle, and 3- to 12-membered heterocycle, each of which is independently optionally substituted at each occurrence with one or more substituents selected from halogen, —CN, —NO$_2$, —NH$_2$, =O, =S, —C(O)OCH$_2C_6H_5$, —NHC(O)OCH$_2C_6H_5$, $C_{1-10}$ alkyl, $C_{2-10}$ alkenyl, $C_{2-10}$ alkynyl, $C_{3-12}$ carbocycle, 3- to 12-membered heterocycle, and haloalkyl; and wherein any substitutable carbon on the benzazepine core is optionally substituted by a substituent selected from halogen, —O$R^{10}$, —S$R^{10}$, —C(O)N($R^{10}$)$_2$, —N($R^{10}$)$_2$, —S(O)$R^{10}$, S(O)$_2R^{10}$, —C(O)$R^{10}$, —C(O)O$R^{10}$, —OC(O)$R^{10}$, —NO$_2$, =O, =S, =N($R^{10}$), —P(O)(O$R^{10}$)$_2$, —OP(O)(O$R^{10}$)$_2$, —CN, $C_{1-10}$ alkyl, $C_{2-10}$ alkenyl, and $C_{2-10}$ alkynyl, or two substituents on a single carbon atom combine to form a 3- to 7-membered carbocycle. "Benzazepine core" as used herein refers to both a benzazepine and a 4,5-dihydrobenzazepine core ring system.

In some embodiments for a compound or salt of Formula (IA), $L^2$ can be attached at C2, C3, C4 or C5 of the benzazepine core, wherein the numbering of the benzazepine is as follows:

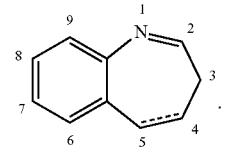

In certain embodiments, for a compound or salt of Formula (IA), $L^2$ is attached to the benzazepine core at C4. In certain embodiments for a compound or salt of Formula (IA), ------ represents a double bond and $L^2$ is attached to the benzazepine core at C4.

In some embodiments for a compound or salt of Formula (IA), $L^1$ can be attached at C6, C7, C8 or C9. In certain embodiments, for a compound or salt of Formula (IA), $L^1$ is attached to the benzazepine core at C8. In certain embodiments for a compound or salt of Formula (IA), ------ represents a double bond, $L^2$ is attached to the benzazepine core at C4 and $L^1$ is attached to the benzazepine core at C8.

In some embodiments for a compound or salt of Formula (IA), the substitutable carbon on the benzazepine core is selected from C2, C3, C4, C5, C6, C7, C8, and C9. The benzazepine core for a compound or salt of Formula (IA), can be optionally substituted by a substituent selected from halogen, —O$R^{10}$, —S$R^{10}$, —C(O)N($R^{10}$)$_2$, —N($R^{10}$)$_2$, —S(O)$R^{10}$, —S(O)$_2R^{10}$—C(O)$R^{10}$, —C(O)O$R^{10}$, —OC(O)$R^{10}$, —NO$_2$, =O, =S, =N($R^{10}$), —P(O)(O$R^{10}$)$_2$, —OP(O)(O$R^{10}$)$_2$, —CN, $C_{1-10}$ alkyl, $C_{2-10}$ alkenyl, and $C_{2-10}$ alkynyl, or two substituents on a single carbon atom combine to form a 3- to 7-membered carbocycle. In some embodiments for a compound or salt of Formula (IA), a moiety at any one of C2, C3, C4, C5, C6, C7, C8, and C9 of the benzazepine core is independently selected from hydrogen, halogen, —O$R^{10}$, —S$R^{10}$, —N($R^{10}$)$_2$, —S(O)$R^{10}$, —S(O)$_2R^{10}$—C(O)$R^{10}$, —C(O)O$R^{10}$, —OC(O)$R^{10}$, —NO$_2$, =O, =S, =N($R^{10}$), —CN, $C_{1-10}$ alkyl, $C_{2-10}$ alkenyl, and $C_{2-10}$ alkynyl.

In one embodiment, the compound of Formula (IA) is represented by Formula (IB):

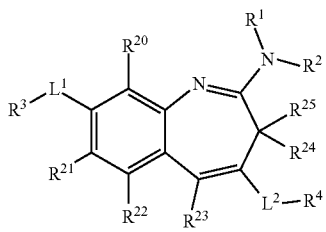

(IB)

or a pharmaceutically acceptable salt thereof, wherein:
$R^{20}$, $R^{21}$, $R^{22}$, and $R^{23}$ are independently selected from hydrogen, halogen, —$OR^{10}$, —$SR^{10}$, —$N(R^{10})_2$, —$S(O)R^{10}$, —$S(O)_2R^{10}$—$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl; and
$R^{24}$ and $R^{25}$ are independently selected from hydrogen, halogen, —$OR^{10}$, —$SR^{10}$, —$N(R^{10})_2$, —$S(O)R^{10}$, —$S(O)_2R^{10}$—$C(O)R^{10}$, —$C(O)OR^{10}$, —$OC(O)R^{10}$, —$NO_2$, =O, =S, =$N(R^{10})$, —CN, $C_{1-10}$ alkyl, $C_{2-10}$ alkenyl, and $C_{2-10}$ alkynyl; or $R^{24}$ and $R^{25}$ taken together form an optionally substituted saturated $C_{3-7}$ carbocycle.

In certain embodiments, the compound of Formula (IA) is represented by Formula (IC):

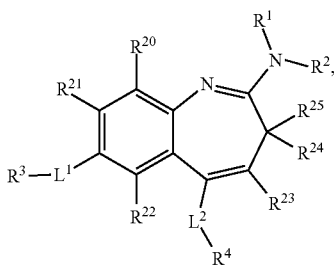

or a pharmaceutically acceptable salt thereof.

In some embodiments, for a compound or salt of Formula (IA), (IB) or (IC), $L^1$ is selected from —$N(R^{10})C(O)$—*, —$S(O)_2N(R^{10})$—*, $CR^{10}{}_2N(R^{10})C(O)$—* and —$X^2$—$C_{1-6}$ alkylene-$X^2$—$C_{1-6}$ alkylene wherein each $C_{1-6}$ alkylene is optionally substituted with one or more $R^{12}$. In some embodiments, $L^1$ is selected from —$N(R^{10})C(O)$—*. In some embodiments, $R^{10}$ of —$N(R^{10})C(O)$—* is selected from hydrogen and $C_{1-6}$ alkyl. In some embodiments for a compound or salt of Formula (IA), (IB) or (IC), $L^1$ is —NHC(O)—*.

In some embodiments, for a compound or salt of Formula (IA), (IB) or (IC), $L^1$ is selected from —$S(O)_2N(R^{10})$—*. In some embodiments, $R^{10}$ of —$S(O)_2N(R^{10})$—* is selected from hydrogen and $C_{1-6}$ alkyl. In some embodiments, $L^1$ is selected from —$S(O)_2NH$—*.

In some embodiments, for a compound or salt of Formula (IA), (IB) or (IC), $L^1$ is selected from —$CR^{10}{}_2N(R^{10})C(O)$—*. In certain embodiments, $L^1$ is selected from —$CH_2N(H)C(O)$—* and —$CH(CH_3)N(H)C(O)$—*.

In some embodiments, for a compound or salt of Formula (IA), (IB) or (IC), $R^3$ is selected from optionally substituted $C_{3-12}$ carbocycle, and optionally substituted 3- to 12-membered heterocycle, wherein substituents on $R^3$ are independently selected at each occurrence from: halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, and —CN; $C_{1-10}$ alkyl, $C_{2-10}$ alkenyl, $C_{2-10}$ alkynyl, each of which is independently optionally substituted at each occurrence with one or more substituents selected from halogen, —$OR^{10}$, —$SR^{10}$, —$C(O)N(R^{10})_2$, —$N(R^{10})C(O)R^{10}$, $N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^3$ is independently optionally substituted with one or more substituents selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{1-6}$ alkyl, $C_{2-6}$ alkenyl, and $C_{2-6}$ alkynyl.

$R^3$ may be selected from optionally substituted $C_{3-12}$ carbocycle, and optionally substituted 3- to 12-membered heterocycle, wherein substituents on $R^3$ are independently selected at each occurrence from: halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})$ $C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)$ $OR^{10}$, —$OC(O)R^{10}$, —$NO_2$, =O, =S, =$N(R^{10})$, —CN, $C_{1-6}$ alkyl, $C_{2-6}$ alkenyl, and $C_{2-6}$ alkynyl.

In certain embodiments, $R^3$ is selected from optionally substituted $C_{3-12}$ carbocycle, and optionally substituted 3- to 12-membered heterocycle, wherein substituents on $R^3$ are independently selected at each occurrence from: halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)$ $OR^{10}$, —$OC(O)R^{10}$, —$NO_2$, =O, =S, =$N(R^{10})$, and —CN; $C_{1-10}$ alkyl, $C_{2-10}$ alkenyl, $C_{2-10}$ alkynyl, each of which is optionally substituted with one or more substituents independently selected from halogen, —$OR^{10}$, —$SR^{10}$, —$C(O)N(R^{10})_2$, —$N(R^{10})C(O)R^{10}$, —$N(R^{10})C(O)N(R^{10})_2$, —$N(R^{10})_2$, —$C(O)R^{10}$, —$C(O)OR^{10}$, —$OC(O)R^{10}$, —$NO_2$, =O, =S, =$N(R^{10})$, —CN, $C_{3-12}$ carbocycle, and 3- to 12-membered heterocycle.

In some embodiments, for a compound or salt of Formula (IA), (IB) or (IC), $R^3$ is selected from an optionally substituted aryl and an optionally substituted heteroaryl, such as $R^3$ is an optionally substituted heteroaryl. In some embodiments, $R^3$ is an optionally substituted heteroaryl substituted with one or more substituents independently selected from halogen, —$OR^{10}$, —$SR^{10}$, —$N(R^{10})_2$, —$C(O)R^{10}$, —$C(O)$ $OR^{10}$, —$OC(O)R^{10}$, —$NO_2$, =O, =S, —CN, $C_{1-6}$ alkyl, $C_{2-6}$ alkenyl, and $C_{2-6}$ alkynyl. $R^3$ may be selected from an optionally substituted 5- or 6-membered heteroaryl. For example, $R^3$ may be selected from:

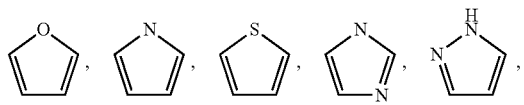

-continued

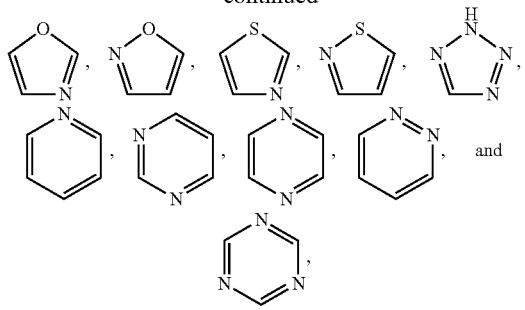

any one of which is optionally substituted. In some embodiments, $R^3$ is selected from an optionally substituted 6-membered heteroaryl, e.g., $R^3$ is optionally substituted pyridine.

In some embodiments for a compound or salt of Formula (IA), (IB) or (IC), $R^3$ is an optionally substituted aryl, such as $R^3$ is an aryl optionally substituted with one or more substituents independently selected from halogen, —OR$^{10}$, —SR$^{10}$, —N(R$^{10}$)$_2$, —C(O)R$^{10}$, —C(O)OR$^{10}$, —OC(O)R$^{10}$, —NO$_2$, =O, =S, —CN, $C_{1-6}$ alkyl, $C_{2-6}$ alkenyl, and $C_{2-6}$ alkynyl. $R^3$ may be selected from an optionally substituted phenyl and an optionally substituted naphthyl. In certain embodiments, $R^3$ is an optionally substituted phenyl.

In some embodiments, for a compound or salt of Formula (IA), (IB) or (IC), $R^3$ is selected from pyridine, phenyl, tetrahydronaphthalene, tetrahydroquinoline, tetrahydroisoquinoline, indane, cyclopropylbenzene, cyclopentapyridine, and dihydrobenzoxaborole, any one of which is optionally substituted. $R^3$ may be selected from:

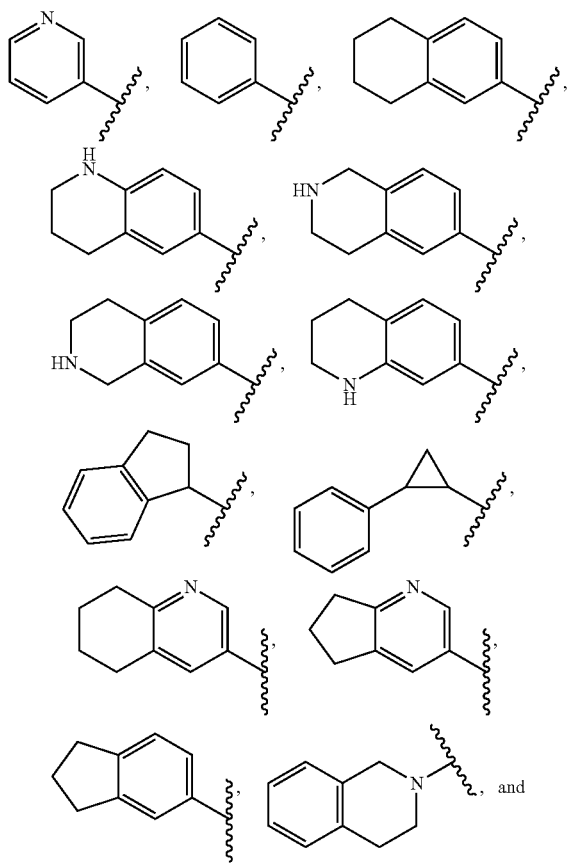

-continued

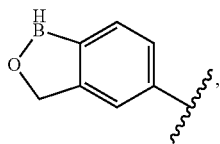

any one of which is optionally substituted. $R^3$ may be selected from:

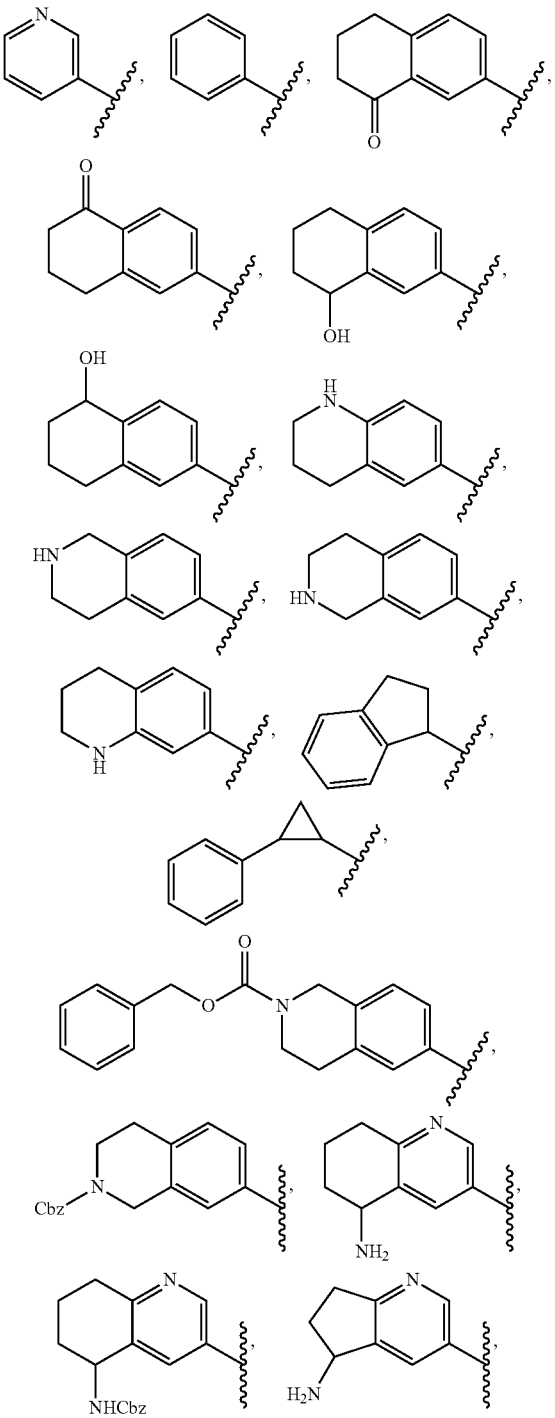

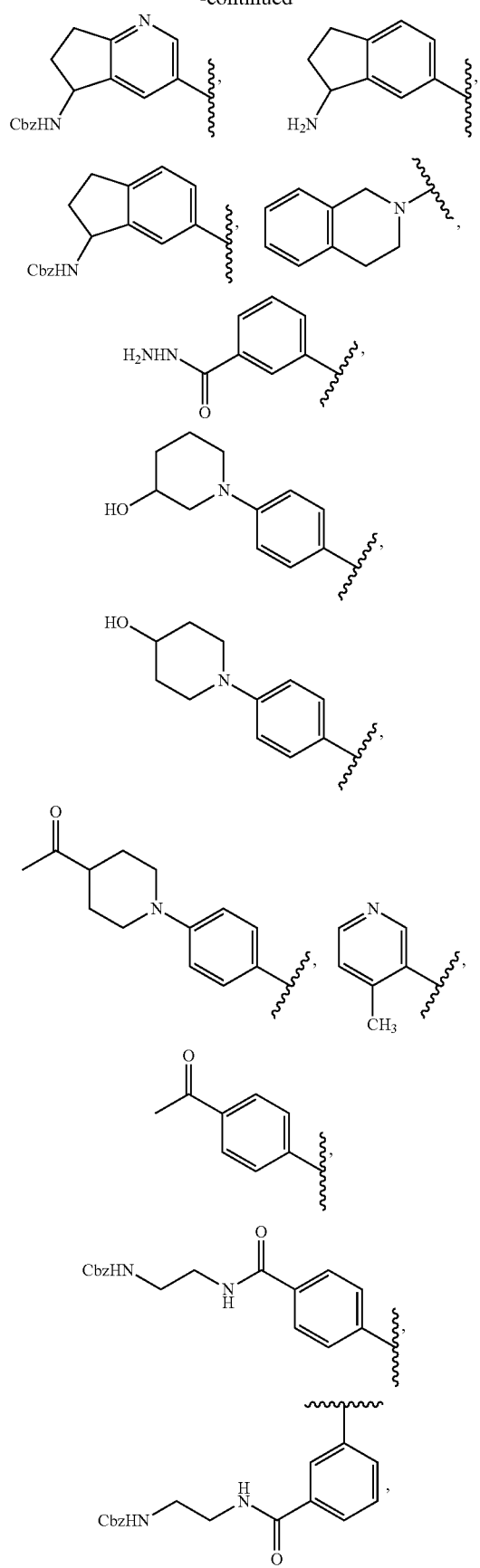
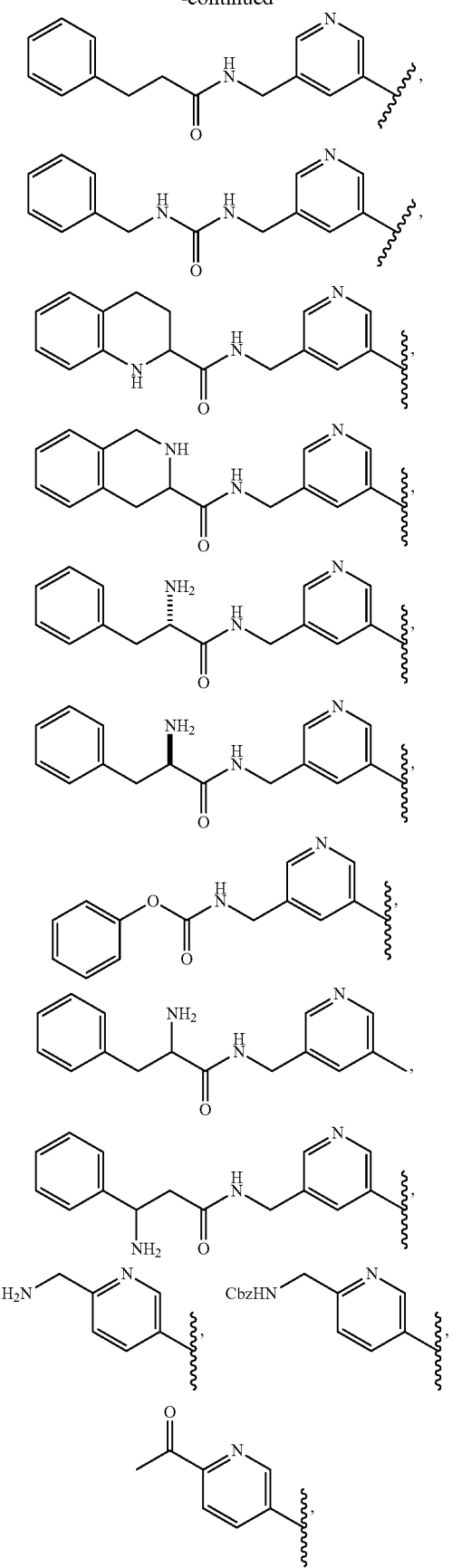

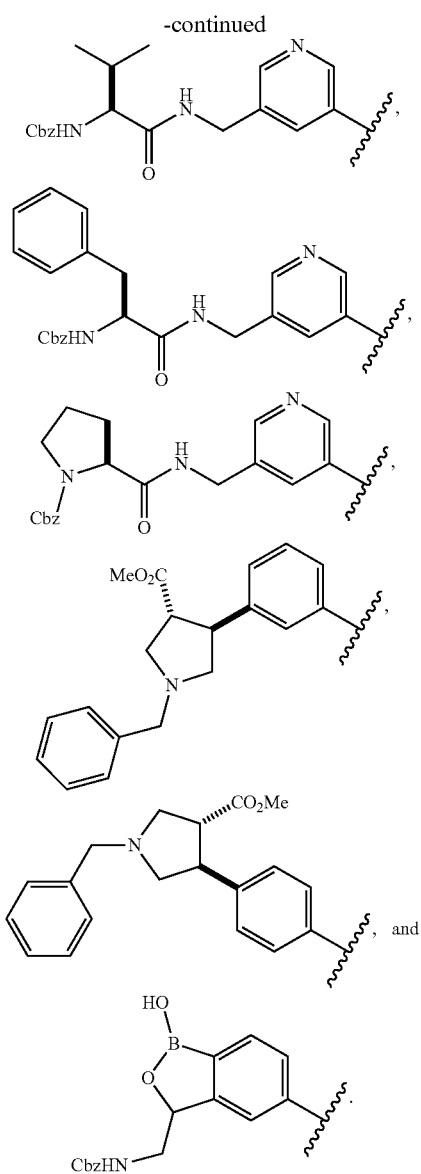

In some embodiments, for a compound of Formula (IA), (IB), or (IC) or a pharmaceutically acceptable salt thereof:

$L^1$ is selected from $-N(R^{10})C(O)-*$, $-S(O)_2N(R^{10})-*$, $-CR^{10}{}_2N(R^{10})C(O)-*$ and $-X^2-C_{1-6}$ alkylene-$X^2-C_{1-6}$ alkylene-;

$L^2$ is $-C(O)-$;

$X^2$ at each occurrence is independently selected from $-O-$, $-S-$, $-N(R^{10})-$, $-C(O)-$, $-C(O)O-$, $-OC(O)-$, $-OC(O)O-$, $-C(O)N(R^{10})-$, $-C(O)N(R^{10})C(O)-$, $-C(O)N(R^{10})C(O)N(R^{10})-$, $-N(R^{10})C(O)-$, $-N(R^{10})C(O)N(R^{10})-$, and $-N(R^{10})C(O)O-$;

$R^1$ and $R^2$ are independently selected from hydrogen; and $C_{1-10}$ alkyl optionally substituted with one or more substituents selected from halogen, $-OR^{10}$, $-SR^{10}$, $-C(O)N(R^{10})_2$, $-N(R^{10})_2$, $-NO_2$, $=O$, $=S$, $=N(R^{10})$, and $-CN$;

$R^3$ is selected from an optionally substituted phenyl, heteroaryl and 9- or 10-membered bicyclic carbocycle wherein substituents are independently selected at each occurrence from: halogen, $-OR^{10}$, $-SR^{10}$, $-C(O)N(R^{10})_2$, $-NO_2$, $=O$, $=S$, $=N(R^{10})$, and $-CN$; $C_{1-10}$ alkyl optionally substituted at each occurrence with one or more substituents selected from halogen, $-OR^{10}$, $-SR^{10}$, $-N(R^{10})_2$, $-C(O)R^{10}$, $-NO_2$, $=O$, $=S$, $=N(R^{10})$, $-CN$, $C_{3-12}$ carbocycle, and 3- to 12-membered heterocycle;

$R^4$ is selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R^{10}$; $C_{1-10}$ alkyl optionally substituted at each occurrence with one or more substituents selected from halogen, $-OR^{10}$, $-SR^{10}$, $-N(R^{10})_2$, $-C(O)R^{10}$, $-NO_2$, $=O$, $=S$, $=N(R^{10})$, $-CN$, $C_{3-12}$ carbocycle, and 3- to 12-membered heterocycle;

$R^{10}$ is independently selected at each occurrence from: hydrogen, $-NH_2$, $-C(O)OCH_2C_6H_5$; and $C_{1-10}$ alkyl, $C_{2-10}$ alkenyl, $C_{2-10}$ alkynyl, $C_{3-12}$ carbocycle, and 3- to 12-membered heterocycle, each of which is independently optionally substituted at each occurrence with one or more substituents selected from halogen, $-CN$, $-NO_2$, $-NH_2$, $=O$, $=S$, $-C(O)OCH_2C_6H_5$, $-NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and haloalkyl; and wherein any substitutable carbon on the benzazepine core is optionally substituted with one or more $R^{12}$, wherein $R^{12}$ is independently selected at each occurrence from halogen, $-OR^{10}$, $-SR^{10}$, $-N(R^{10})_2$, $-C(O)R^{10}$, $-C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, and $-CN$; and $C_{1-10}$ alkyl optionally substituted with one or more substituents independently selected from halogen, $-OR^{10}$, $-SR^{10}$, $-N(R^{10})_2$, $-C(O)R^{10}$, $C(O)N(R^{10})_2$, $-N(R^{10})C(O)R^{10}$, $-C(O)OR^{10}$, $-OC(O)R^{10}$, $-S(O)R^{10}$, $-S(O)_2R^{10}$, $-NO_2$, $=O$, $=S$, $=N(R^{10})$, $-CN$, $C_{3-10}$ carbocycle and 3- to 10-membered heterocycle.

In certain embodiments for a compound or salt of Formula (IA), (IB) or (IC), the compound may further comprise a linker ($L^3$). The linker may be covalently bound to any position, valence permitting, on a compound or salt of Formula (IA), (IB) or (IC). For example, the linker may be bound to $R^1$, $R^2$, $R^4$, $R^3$, $X^1$ or $X^2$. In certain embodiments, the linker is bound to a nitrogen or oxygen atom of a compound or salt of Formula (IA), (IB) or (IC). The linker may comprise a reactive moiety, e.g., an electrophile that can react to form a covalent bond with a moiety of an antibody, e.g., a lysine, serine, threonine, cysteine, tyrosine, aspartic acid, glutamine, a non-natural amino acid residue, or glutamic acid residue of an antibody. In some embodiments, a compound or salt of Formula (IA), (IB) or (IC), may be covalently bound through the linker to an antibody.

In some aspects, the present disclosure provides a compound represented by the structure of Formula (IIA):

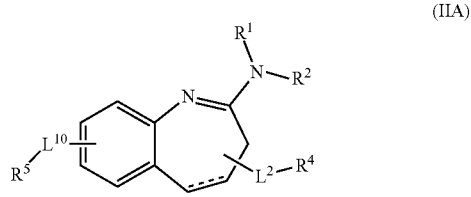

(IIA)

or a pharmaceutically acceptable salt thereof, wherein:

------- represents an optional double bond;

$L^{10}$ is $-X^{10}-$;

$L^2$ is selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted on alkylene, alkenylene or alkynylene with one or more $R^{12}$;

$X^{10}$ is selected from —C(O)—, and —C(O)N($R^{10}$)—*, wherein * represents where $X^{10}$ is bound to $R^5$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$), —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; and $C_{1-10}$ alkyl, $C_{2-10}$ alkenyl, and $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^5$ is selected from unsaturated $C_{4-8}$ carbocycle; bicyclic carbocycle; and fused 5-5, fused 5-6, and fused 6-6 bicyclic heterocycle, wherein $R^5$ is optionally substituted and wherein substituents are independently selected at each occurrence from: halogen, —O$R^{10}$—S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN; $C_{1-10}$alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^5$ is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^{10}$ is independently selected at each occurrence from hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and haloalkyl;

$R^{12}$ is independently selected at each occurrence from halogen, —O$R^{10}$, —S$R^{10}$, N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), and —CN; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^{12}$ is optionally substituted with one or more substituents independently selected from halogen, —O$R^{10}$, —S$R^{10}$, —N($R^{10}$)$_2$, —C(O)$R^{10}$, —C(O)N($R^{10}$)$_2$, —N($R^{10}$)C(O)$R^{10}$, —C(O)O$R^{10}$, —OC(O)$R^{10}$, —S(O)$R^{10}$, —S(O)$_2R^{10}$, —P(O)(O$R^{10}$)$_2$, —OP(O)(O$R^{10}$)$_2$, —NO$_2$, =O, =S, =N($R^{10}$), —CN, $C_{1-6}$ alkyl, $C_{2-6}$ alkenyl, $C_{2-6}$ alkynyl; and wherein any substitutable carbon on the benzazepine core is optionally substituted by a substituent independently selected from $R^{12}$ or two substituents on a single carbon atom combine to form a 3- to 7-membered carbocycle.

In certain embodiments, for a compound of Formula (IIA):

------ represents an optional double bond;

$L^{10}$ is independently selected from —$X^{10}$—;

$L^2$ is independently selected from —$X^2$—, —$X^2$—$C_{1-6}$ alkyl-$X^2$—, —$X^2$—$C_{2-6}$ alkenyl-$X^2$—, and —$X^2$—$C_{2-6}$ alkynyl-$X^2$—, each of which is optionally substituted at each occurrence with one or more $R^{10}$;

$X^{10}$ at each occurrence is independently selected from —C(O)—, and —C(O)N($R^{10}$)—*, wherein * represents where $X^{10}$ is bound to $R^5$;

$X^2$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$), —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O), —OS(O)$_2$—, —S(O)$_2$O, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; and $C_{1-10}$ alkyl, $C_{2-10}$ alkenyl, and $C_{2-10}$ alkynyl, each of which is independently optionally substituted at each occurrence with one or more substituents selected from halogen, —OR¹⁰, —SR¹⁰, —C(O)N(R¹⁰)₂, —N(R¹⁰)₂, —S(O)R¹⁰, —S(O)₂R¹⁰, —C(O)R¹⁰, —C(O)OR¹⁰, —OC(O)R¹⁰, —NO₂, =O, =S, =N(R¹⁰), and —CN;

R⁴ is selected from: —OR¹⁰, —N(R¹⁰)₂, —C(O)N(R¹⁰)₂, —C(O)R¹⁰, —C(O)OR¹⁰, —S(O)R¹⁰, and —S(O)₂R¹⁰; C₁₋₁₀ alkyl, C₂₋₁₀ alkenyl, C₂₋₁₀ alkynyl, each of which is independently optionally substituted at each occurrence with one or more substituents selected from halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, C₃₋₁₂ carbocycle, and 3- to 12-membered heterocycle; and C₃₋₁₂ carbocycle, and 3- to 12-membered heterocycle, wherein each C₃₋₁₂ carbocycle, and 3- to 12-membered heterocycle in R⁴ is independently optionally substituted with one or more substituents selected from halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, C₁₋₆ alkyl, C₂₋₆ alkenyl, and C₂₋₆ alkynyl;

R⁵ is selected from optionally substituted saturated and unsaturated C₃₋₈ carbocycle, optionally substituted saturated and unsaturated 3- to 8-membered heterocycle, optionally substituted bicyclic carbocycle, and optionally substituted bicyclic heterocycle wherein substituents are independently selected at each occurrence from: halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), and —CN; C₁₋₁₀ alkyl, C₂₋₁₀ alkenyl, C₂₋₁₀ alkynyl, each of which is independently optionally substituted at each occurrence with one or more substituents selected from halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, C₃₋₁₂ carbocycle, and 3- to 12-membered heterocycle; and C₃₋₁₂ carbocycle, and 3- to 12-membered heterocycle, wherein each C₃₋₁₂ carbocycle, and 3- to 12-membered heterocycle in R⁵ is independently optionally substituted with one or more substituents selected from halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, C₁₋₆ alkyl, C₂₋₆ alkenyl, and C₂₋₆ alkynyl;

R¹⁰ is independently selected at each occurrence from hydrogen, —NH₂, —C(O)OCH₂C₆H₅; and C₁₋₁₀ alkyl, C₂₋₁₀ alkenyl, C₂₋₁₀ alkynyl, C₃₋₁₂ carbocycle, and 3- to 12-membered heterocycle, each of which is independently optionally substituted at each occurrence with one or more substituents selected from halogen, —CN, —NO₂, —N₂, =O, =S, —C(O)OCH₂C₆H₅, —NHC(O)OCH₂C₆H₅, C₁₋₁₀ alkyl, C₂₋₁₀ alkenyl, C₂₋₁₀ alkynyl, C₃₋₁₂ carbocycle, 3- to 12-membered heterocycle, and haloalkyl; and wherein any substitutable carbon on the benzazepine core is optionally substituted by a substituent selected from halogen, —OR¹⁰, —SR¹⁰, —C(O)N(R¹⁰)₂, —N(R¹⁰)₂, —S(O)R¹⁰, S(O)₂R¹⁰, —C(O)R¹⁰, —C(O)OR¹⁰, —OC(O)R¹⁰, —NO₂, =O, =S, =N(R¹⁰), —P(O)(OR¹⁰)₂, —OP(O)(OR¹⁰)₂, —CN, C₁₋₁₀ alkyl, C₂₋₁₀ alkenyl, and C₂₋₁₀ alkynyl, or two substituents on a single carbon atom combine to form a 3- to 7-membered carbocycle.

In some embodiments for a compound or salt of Formula (IIA), L² can be attached at C2, C3, C4, or C5 of the benzazepine core, wherein the numbering of the benzazepine is as follows:

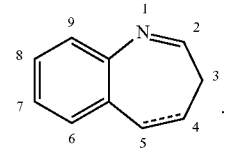

In certain embodiments, L² is attached to the benzazepine core at C4. In certain embodiments ------- represents a double bond and L² is attached to the benzazepine core at C4.

In some embodiments, for a compound or salt of Formula (IIA), L10 can be attached at C6, C7, C8 or C9. In certain embodiments, L¹⁰ is attached to the benzazepine core at C8. In certain embodiments ------- represents a double bond, L² is attached to the benzazepine core at C4 and L¹⁰ is attached to the benzazepine core at C8.

In some embodiments, for a compound or salt of Formula (IIA), the substitutable carbon on the benzazepine core is selected from C2, C3, C4, C5, C6, C7, C8, and C9. The benzazepine core for a compound or salt of Formula (IIA), can be optionally substituted by a substituent selected from halogen, —OR¹⁰, —SR¹⁰, —C(O)N(R¹⁰)₂, —N(R¹⁰)₂, —S(O)R¹⁰, —S(O)₂R¹⁰, —C(O)R¹⁰, —C(O)OR¹⁰, —OC(O)R¹⁰, —NO₂, =O, =S, =N(R¹⁰), —P(O)(OR¹⁰)₂, —OP(O)(OR¹⁰)₂, —CN, C₁₋₁₀ alkyl, C₂₋₁₀ alkenyl, and C₂₋₁₀ alkynyl, or two substituents on a single carbon atom combine to form a 3- to 7-membered carbocycle. In some embodiments for a compound or salt of Formula (IIA), a moiety at any one of C2, C3, C4, C5, C6, C7, C8, and C9 of the benzazepine core is independently selected from hydrogen, halogen, —OR¹⁰, —SR¹⁰, —N(R¹⁰)₂, —S(O)R¹⁰, —S(O)₂R¹⁰, —C(O)R¹⁰, —C(O)OR¹⁰, —OC(O)R¹⁰, —NO₂, =O, =S, =N(R¹⁰), —CN, C₁₋₁₀ alkyl, C₂₋₁₀ alkenyl, and C₂₋₁₀ alkynyl. In one embodiment, the compound of Formula (IIA) is represented by Formula (IIB):

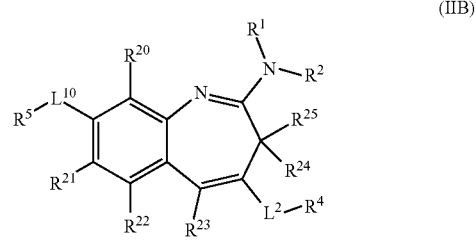

(IIB)

or a pharmaceutically acceptable salt thereof, wherein:

R²⁰, R²¹, R²², and R²³ are independently selected from hydrogen, halogen, —OR¹⁰, —SR¹⁰, —N(R¹⁰)₂, —S(O)R¹⁰, —S(O)₂R¹⁰, —C(O)R¹⁰, —C(O)OR¹⁰, —OC(O)R¹⁰, —NO₂, =O, =S, =N(R¹⁰), —CN, C₁₋₁₀ alkyl, C₂₋₁₀ alkenyl, and C₂₋₁₀ alkynyl; and R²⁴, and R²⁵ are independently selected from hydrogen, halogen, —OR¹⁰, —SR¹⁰, —N(R¹⁰)₂, —S(O)R¹⁰, —S(O)₂R¹⁰, —C(O)R¹⁰, —C(O)OR¹⁰, —OC(O)R¹⁰, —NO₂, =O, =S, =N(R¹⁰), —CN, C₁₋₁₀ alkyl, C₂₋₁₀ alkenyl, and $C_{2-10}$ alkynyl; or $R^{24}$ and $R^{25}$ taken together form an optionally substituted saturated $C_{3-7}$ carbocycle.

In one embodiment, the compound of Formula (IIA) is represented by Formula (IIC):

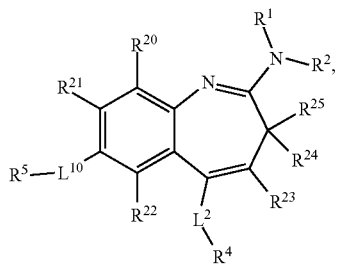

(IIC)

or a pharmaceutically acceptable salt thereof.

In certain embodiments, for a compound or salt of Formula (IIA), (IIB), or (IIC), $L^{10}$ is —C(O)—. In certain embodiments, $L^{10}$ is selected from —C(O)N($R^{10}$)—*. In certain embodiments, $R^{10}$ of —C(O)N($R^{10}$)—* is selected from hydrogen and $C_{1-6}$ alkyl. In certain embodiments, $L^{10}$ is —C(O)NH—*.

In certain embodiments, for a compound or salt of Formula (IIA), (IIB), or (IIC), $R^5$ is an optionally substituted 8- to 12-membered bicyclic carbocycle. In some embodiments, $R^5$ is an optionally substituted bicyclic carbocycle, e.g., an optionally substituted 8- to 12-membered bicyclic carbocycle, such as indane, naphthalene, dihydronaphthalene, tetrahydronaphthalene. In some embodiments, $R^5$ is an optionally substituted 8- to 12-membered bicyclic carbocycle with one or more substituents independently selected from halogen, —$OR^{10}$, —$SR^{10}$, —$N(R^{10})_2$, —$C(O)R^{10}$, —$C(O)OR^{10}$, —$OC(O)R^{10}$, —$NO_2$, =O, =S, —CN, $C_{1-6}$ alkyl, $C_{2-6}$ alkenyl, and $C_{2-6}$ alkynyl. In some embodiments, $R^5$ is an optionally substituted 8- to 12-membered bicyclic carbocycle with one or more substituents independently selected from —$OR^{10}$, —$N(R^{10})_2$, and =O. In some embodiments, $R^5$ is an optionally substituted indane or an optionally substituted tetrahydronaphthalene. In some embodiments, $R^5$ is selected from:

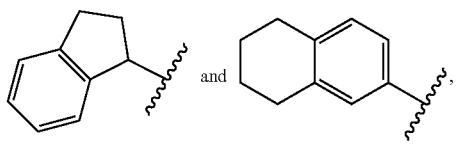 [SMILES: *C1CCc2ccccc21 ; *c1ccc2c(c1)CCCC2]

either of which is optionally substituted. In some embodiments for a compound or salt of Formula (IIA), (IIB) or (IIC), $R^5$ is selected from:

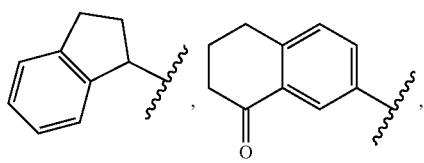

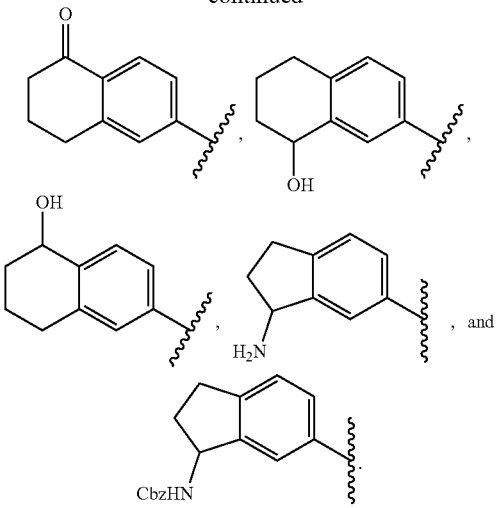

, and

In some embodiments, for a compound or salt of Formula (IIA), (IIB) or (IIC), $R^5$ is an optionally substituted unsaturated $C_{4-8}$ carbocycle. In some embodiments, $R^5$ is an optionally substituted unsaturated $C_{4-6}$ carbocycle, e.g., cyclopentene, cyclopentadiene, cyclohexene, cyclobutene. In some embodiments, $R^5$ is an optionally substituted unsaturated $C_{4-6}$ carbocycle with one or more substituents independently selected from optionally substituted $C_{3-12}$ carbocycle, and optionally substituted 3- to 12-membered heterocycle. In some embodiments, $R^5$ is an optionally substituted unsaturated $C_{4-6}$ carbocycle with one or more substituents independently selected from optionally substituted phenyl, optionally substituted 3- to 12-heterocycle, optionally substituted $C_{1-10}$ alkyl, optionally substituted $C_{2-10}$ alkenyl, and halogen.

In certain embodiments, for a compound or salt of Formula (IIA), (IIB) or (IIC), $R^5$ is an optionally substituted fused 5-5, fused 5-6, and fused 6-6 bicyclic heterocycle. In some embodiments, $R^5$ is an optionally substituted fused 5-5, fused 5-6, and fused 6-6 bicyclic heterocycle with one or more substituents independently selected from —C(O)$OR^{10}$, —$N(R^{10})_2$, —$OR^{10}$, and optionally substituted $C_{1-10}$ alkyl. In some embodiments, $R^5$ is an optionally substituted fused 5-5, fused 5-6, and fused 6-6 bicyclic heterocycle substituted with —C(O)$OR^{10}$. In some embodiments, $R^5$ is an optionally substituted fused 6-6 bicyclic heterocycle. The fused 6-6 bicyclic heterocycle may be an optionally substituted pyridine-piperidine. In some embodiments, $L^{10}$ is bound to a carbon atom of the pyridine of the fused pyridine-piperidine. In some embodiments, $R^5$ is selected from tetrahydroquinoline, tetrahydroisoquinoline, tetrahydronaphthyridine, cyclopentapyridine, and dihydrobenzoxaborole, any one of which is optionally substituted. In some embodiments, $R^5$ is an optionally substituted tetrahydronaphthyridine. In some embodiments for a compound or salt of Formula (IIA), (IIB) or (IIC), $R^5$ is selected from:

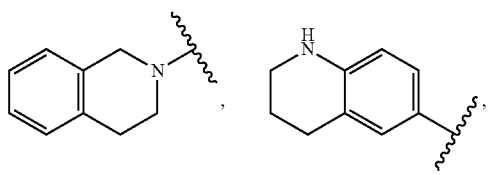

107
-continued

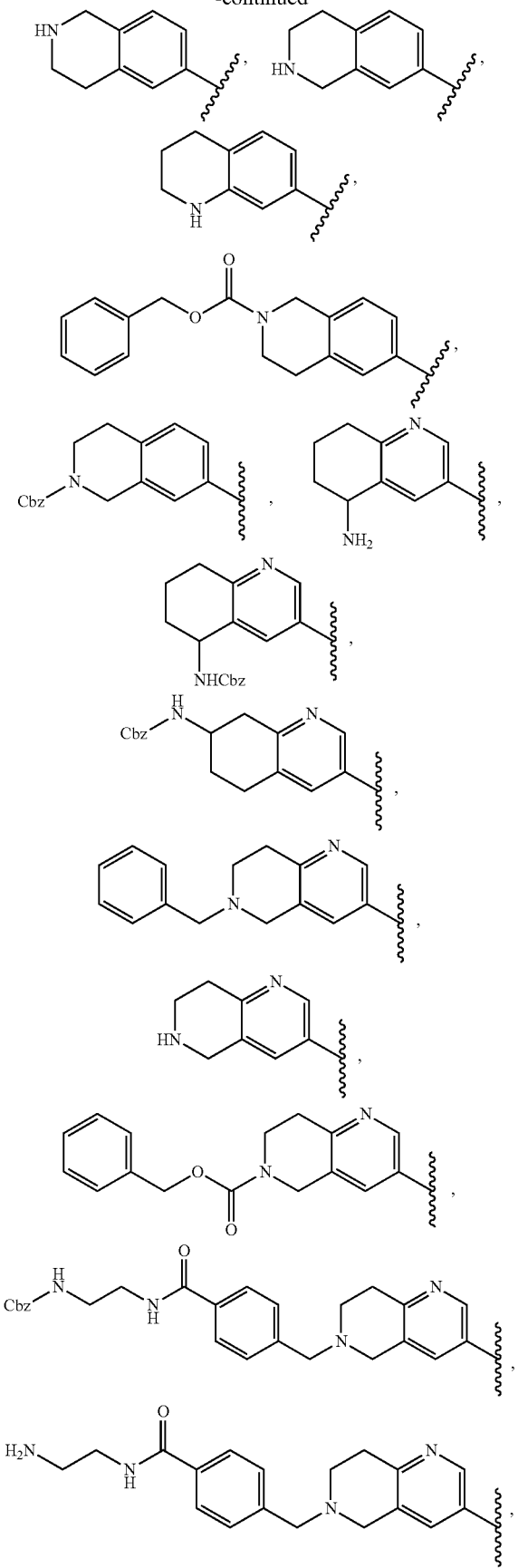

108
-continued

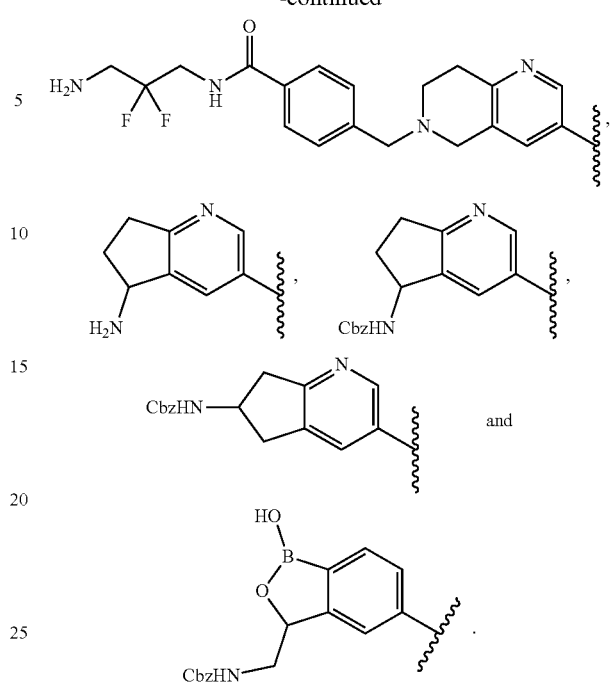

In some embodiments, for a compound or salt of Formula (IIA), (IIB) or (IIC), $R^5$ is selected from tetrahydronaphthalene, tetrahydroquinoline, tetrahydroisoquinoline, indane, cyclopropylbenzene, cyclopentapyridine, and dihydrobenzoxaborole, any one of which is optionally substituted. In some embodiments for a compound or salt of Formula (IIA), (IIB) or (IIC), $R^5$ is selected from:

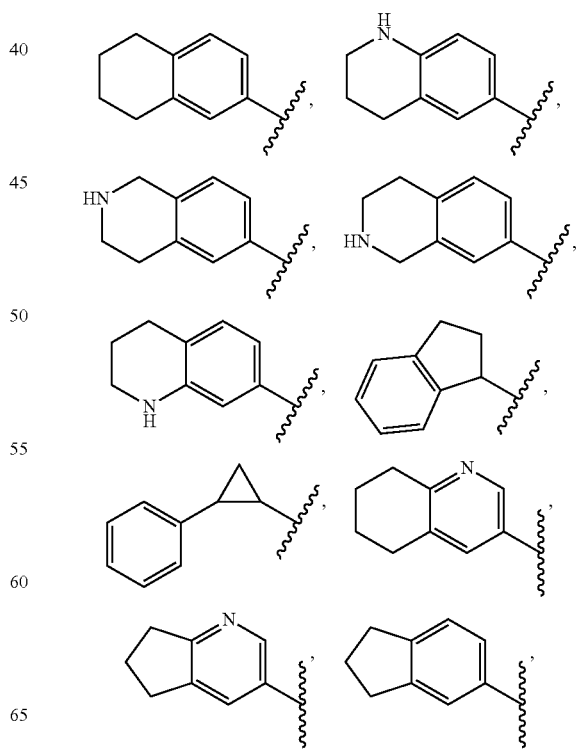

-continued

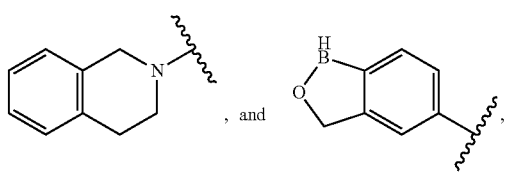
, and any one of which is optionally substituted. In some embodiments for a compound or salt of Formula (IIA), (IIB) or (IIC), $R^5$ is selected from:

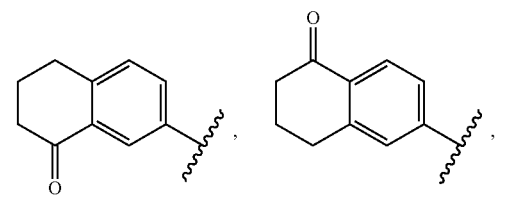

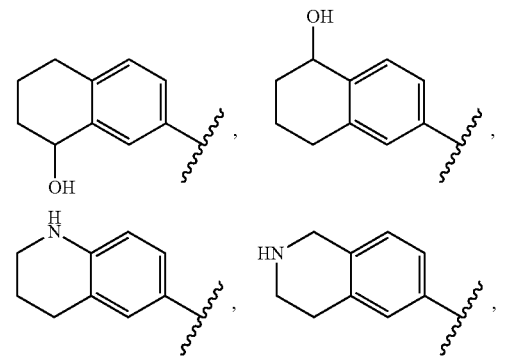

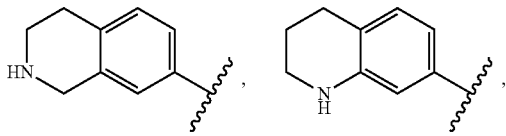

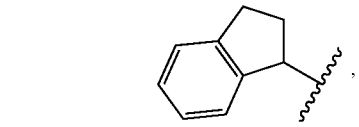

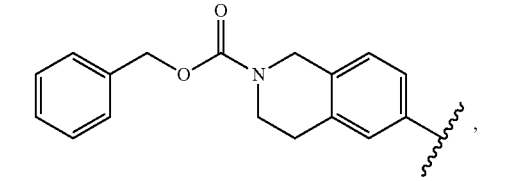

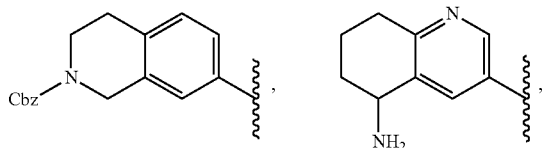

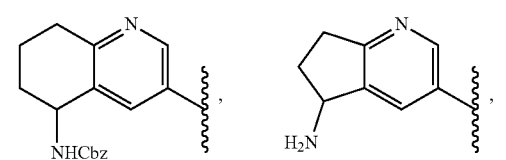

-continued

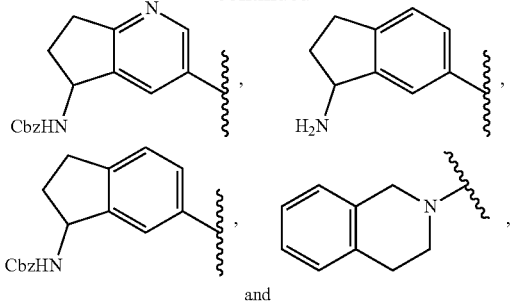

and

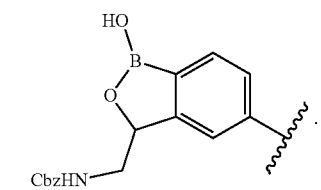

In some embodiments, for a compound or salt of Formula (IIA), (IIB) or (IIC), when $R^5$ is substituted, substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, =O, =S, =N($R^{10}$), and $-CN$; $C_{1-10}$ alkyl, $C_{2-10}$ alkenyl, $C_{2-10}$ alkynyl, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, =O, =S, =N($R^{10}$), $-CN$, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, $-NO_2$, =O, =S, =N($R^{10}$), $-CN$, $C_{1-6}$ alkyl, $C_{2-6}$ alkenyl, and $C_{2-6}$ alkynyl.

In some embodiments, for a compound or salt of Formula (IIA), (IIB) or (IIC), when $R^5$ is substituted, substituents on $R^5$ are independently selected at each occurrence from: halogen, $-OR^{10}$, $-SR^{10}$, $-C(O)N(R^{10})_2$, $-N(R_{10})C(O)R_{10}$, $-N(R_{10})C(O)N(R_{10})_2$, $-N(R^{10})_2$, $-C(O)R^{10}$, $-C(O)OR^{10}$, $-OC(O)R^{10}$, $-NO_2$, =O, =S, =N($R^{10}$), and $-CN$; $C_{1-10}$alkyl, $C_{2-10}$ alkenyl, $C_{2-10}$ alkynyl, each of which is independently optionally substituted at each occurrence with one or more substituents selected from halogen, $-OR^{10}$, $-SR^{10}$, $-C(O)N(R^{10})_2$, $-N(R^{10})C(O)R^{10}$, $N(R^{10})C(O)N(R^{10})_2$, $-N(R^{10})_2$, $-C(O)R^{10}$, $-C(O)OR^{10}$, $-OC(O)R^{10}$, $-NO_2$, =O, =S, =N($R^{10}$), $-CN$, $C_{3-12}$ carbocycle, and 3- to 12-membered heterocycle.

In some embodiments, for a compound or salt of Formula (IIA), (IIB) or (IIC), when $R^5$ is substituted, substituents on $R^5$ are independently selected at each occurrence from: halogen, $-OR^{10}$, $-SR^{10}$, $-C(O)N(R^{10})_2$, $-N(R_{10})C(O)R_{10}$, $-N(R_{10})C(O)N(R_{10})_2$, $-N(R^{10})_2$, $-C(O)R^{10}$, $-C(O)OR^{10}$, $-OC(O)R^{10}$, $-NO_2$, =O, =S, =N($R^{10}$), and $-CN$; $C_{1-10}$ alkyl, $C_{2-10}$ alkenyl, $C_{2-10}$ alkynyl, each of which is independently optionally substituted at each occurrence with one or more substituents selected from halogen, $-OR^{10}$, $-SR^{10}$, $-NO_2$, =O, =S, =N($R^{10}$), and $-CN$.

In certain embodiments, substituents on $R^5$ are independently selected at each occurrence from: halogen, $-OR^{10}$, $-SR^{10}$, $-C(O)N(R^{10})_2$, $-N(R^{10})C(O)R^{10}$, $-N(R^{10})_2$, —C(O)R$^{10}$, —C(O)OR$^{10}$, —OC(O)R$^{10}$, —NO$_2$, =O, and —CN; and C$_{1-10}$ alkyl optionally substituted with one or more substituents independently selected from halogen, —OR$^{10}$, —SR$^{10}$, —N(R$^{10}$)$_2$, —C(O)R$^{10}$, —C(O)OR$^{10}$, —NO$_2$, =O, and —CN. In certain embodiments, R$^5$ is not substituted.

In some embodiments for a compound or salt of Formula (IIA), (IIB) or (IIC), R$^5$ is selected from saturated and unsaturated C$_{3-8}$ carbocycle, bicyclic carbocycle, and bicyclic heterocycle, any of which is optionally substituted and wherein substituents are independently selected at each occurrence from: halogen, —OR$^{10}$, —SR$^{10}$, —C(O)N(R$^{10}$)$_2$, —N(R$_{10}$)C(O)R$_{10}$, —N(R$_{10}$)C(O)N(R$_{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^5$ is independently optionally substituted with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl.

In some embodiments, for a compound or salt of Formula (IIA), (IIB) or (IIC), R$^{20}$, R$^{21}$, R$^{22}$, and R$^{23}$ are independently selected from hydrogen, halogen, —OH, —OR$^{10}$, —NO$_2$, —CN, and C$_{1-10}$ alkyl. In some embodiments, R$^{20}$, R$^{21}$, R$^{22}$, and R$^{23}$ are each hydrogen. In some embodiments, R$^{21}$ is halogen, e.g. fluorine. In an exemplary embodiment, R$^{21}$ is hydrogen. In other embodiments, R$^{21}$ is —OR$^{10}$. For example, R$^{21}$ may be —OCH$_3$.

In some embodiments, for a compound of Formula (IIA), (IIB) or (IIC), or a pharmaceutically acceptable salt thereof:
  L$^{10}$ is selected from —C(O)N(R$^{10}$)—* and —C(O)—;
  L$^2$ is —C(O)—;
  R$^1$ and R$^2$ are independently selected from hydrogen; and C$_{1-10}$alkyl optionally substituted at each occurrence with one or more substituents selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;
  R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; and C$_{1-10}$ alkyl optionally substituted at each occurrence with one or more substituents selected from halogen, —OR$^{10}$, —SR$^{10}$, —C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle;
  R$^5$ is selected from optionally substituted unsaturated C$_{4-8}$ carbocycle, optionally substituted bicyclic carbocycle, and optionally substituted fused 5-5, fused 5-6, and fused 6-6 bicyclic heterocycle wherein substituents on R$^5$ are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —C(O)N(R$^{10}$)$_2$, —N(R$^{10}$)C(O)R$^{10}$, N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^5$ is independently optionally substituted with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;
  R$^{10}$ is independently selected at each occurrence from hydrogen, —NH$_2$, —C(O)OCH$_2$C$_6$H$_5$; and C$_{1-10}$ alkyl optionally substituted with one or more substituents independently selected from halogen, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and haloalkyl; and
  wherein any substitutable carbon on the benzazepine core is optionally substituted by a substituent independently selected from R$^{12}$.

In some embodiments, for a compound of Formula (IIA), (IIB) or (IIC), or a pharmaceutically acceptable salt thereof:
  L$^{10}$ is selected from —C(O)N(R$^{10}$)—* and —C(O)—;
  L$^2$ is —C(O)—;
  R$^1$ and R$^2$ are each hydrogen;
  R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$;
  R$^5$ is selected from optionally substituted optionally substituted fused 5-5, fused 5-6, and fused 6-6 bicyclic heterocycle wherein substituents are independently selected at each occurrence from: halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^5$ is independently optionally substituted with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;
  R$^{10}$ is independently selected at each occurrence from hydrogen, —NH$_2$, —C(O)OCH$_2$C$_6$H$_5$; and C$_{1-10}$ alkyl optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{3-12}$ carbocycle, and 3- to 12-membered heterocycle; and
  wherein any substitutable carbon on the benzazepine core is optionally substituted by a substituent independently selected from R$^{12}$.

In some embodiments, for a compound of Formula (IIB) or (IIC), or a pharmaceutically acceptable salt thereof:

$L^{10}$ is selected from —C(O)N($R^{10}$)—*, such as —C(O)NH—*;

$L^2$ is —C(O)—;

$R^1$ and $R^2$ are each hydrogen;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$, such as $R^4$ is —N($R^{10}$)$_2$;

$R^5$ is selected from optionally substituted optionally substituted fused 5-5, fused 5-6, and fused 6-6 bicyclic heterocycle, such as $R^5$ is selected from a tetrahydroquinoline, tetrahydroisoquinaline, dihydroindene, wherein substituents on $R^5$ are independently selected at each occurrence from: halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN; and $C_{1-10}$ alkyl optionally substituted at each occurrence with one or more substituents selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle;

$R^{10}$ is independently selected at each occurrence from hydrogen, —NH$_2$, —C(O)OCH$_2$C$_6$H$_5$; and $C_{1-10}$ alkyl optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, $C_{3-12}$ carbocycle, and 3- to 12-membered heterocycle;

$R^{20}$, $R^{21}$, $R^{22}$, and $R^{23}$ are independently selected from hydrogen, halogen, —O$R^{10}$, —S$R^{10}$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), —CN, $C_{1-10}$ alkyl, $C_{2-10}$ alkenyl, and $C_{2-10}$ alkynyl, such as $R^{20}$, $R^{21}$, $R^{22}$, and $R^{23}$ are each hydrogen; and $R^{24}$, and $R^{25}$ are independently selected from hydrogen, halogen, —O$R^{10}$, —S$R^{10}$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), —CN, $C_{1-10}$ alkyl, $C_{2-10}$ alkenyl, and $C_{2-10}$ alkynyl, such as $R^{24}$ and $R^{25}$ are each hydrogen.

In certain embodiments for a compound or salt of Formula (IIA), (IIB) or (IIC), the compound may further comprise a linker ($L^3$). The linker may be covalently bound to any position, valence permitting, on a compound or salt of Formula (IIA), (IIB) or (IIC). For example, the linker may be bound to $R^1$, $R^2$, $R^4$, $R^5$, $X^{10}$ or $X^2$. In certain embodiments, the linker may be bound to a nitrogen atom, or an oxygen atom of a compound or salt of Formula (IIA), (IIB) or (IIC). The linker may comprise a reactive moiety, e.g., an electrophile that can react to form a covalent bond with a moiety of an antibody, e.g., lysine, serine, threonine, cysteine, tyrosine, aspartic acid, glutamine, a non-natural amino acid residue, or glutamic acid residue of the antibody. In some embodiments, a compound or salt of Formula (IIA), (IIB) or (IIC), may be covalently bound through the linker to an antibody construct.

In some aspects, the present disclosure provides a compound represented by the structure of Formula (IIIA):

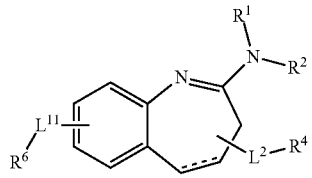

(IIIA)

or a pharmaceutically acceptable salt thereof, wherein:

- - - - - - represents an optional double bond;

$L^{11}$ is —$X^{11}$—;

$L^2$ is selected from —$X^{21}$—, —$X^{21}$—$C_{1-6}$ alkylene-$X^{21}$—, —$X^{21}$—$C_{2-6}$ alkenylene-$X^{21}$—, and —$X^2$—$C_{2-6}$ alkynylene-$X^2$—, each of which is optionally substituted on alkylene, alkenylene or alkynylene with one or more $R^{12}$;

$X^{11}$ is selected from —C(O)— and —C(O)N($R^{10}$)—*, wherein * represents where $X^{11}$ is bound to $R^6$;

$X^{21}$ at each occurrence is independently selected from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)$^{10}$N($R^{10}$)—, —N($R^{10}$)C(N$R^{10}$)N($R^{10}$)—, —S(O)$_2$—, —OS(O)—, —S(O)O—, —S(O)—, —OS(O)$_2$—, —S(O)$_2$O—, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from hydrogen; $C_{1-10}$ alkyl, $C_{2-10}$ alkenyl, and $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^6$ is selected from phenyl and 5- or 6-membered heteroaryl, any one of which is substituted with one or more substituents selected from $R^7$ and $R^6$ is further optionally substituted by one or more additional substituents independently selected from $R^{12}$ $R^7$ is selected from —C(O)NHNH$_2$, —C(O)NH—$C_{1-3}$ alkylene-NH($R^{10}$), —C(O)CH$_3$, —$C_{1-3}$ alkylene-NHC(O)OR—, —$C_{1-3}$alkylene-NHC(O)$R^{10}$, —$C_{1-3}$alkylene-NHC(O)NHR$^{10}$, —$C_{1-3}$ alkylene-NHC(O)—

$C_{1-3}$alkylene-$R^{10}$, and a 3- to 12-membered heterocycle optionally substituted with one or more substituents independently selected from $R^{12}$;

$R^{10}$ is independently selected at each occurrence from hydrogen, —$NH_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is optionally substituted with one or more substituents independently selected from halogen, —OH, —CN, —$NO_2$, —$NH_2$, =O, =S, —C(O)OCH$_2$C$_6$H$_5$, —NHC(O)OCH$_2$C$_6$H$_5$, —$C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle;

$R^{11}$ is selected from $C_{3-12}$ carbocycle and 3- to 12-membered heterocycle, each of which is optionally substituted with one or more substituents independently selected from $R^{12}$;

$R^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; $C_{1-10}$ alkyl, $C_{2-10}$ alkenyl, $C_{2-10}$ alkynyl, each of which is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{3-10}$ carbocycle and 3- to 10-membered heterocycle; and $C_{3-10}$ carbocycle and 3- to 10-membered heterocycle, wherein each $C_{3-10}$ carbocycle and 3- to 10-membered heterocycle in $R^{12}$ is optionally substituted with one or more substituents independently selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, $C_{1-6}$ alkyl, $C_{2-6}$ alkenyl, and $C_{2-6}$ alkynyl; and wherein any substitutable carbon on the benzazepine core is optionally substituted by a substituent independently selected from $R^{12}$ or two substituents on a single carbon atom combine to form a 3- to 7-membered carbocycle.

In certain embodiments, for a compound or salt of Formula (IIIA):

------ represents an optional double bond;

$L^{11}$ is independently selected from —$X^{11}$—;

$L^2$ is independently selected from —$X^2$—, —$X^2$—$C_{1-6}$ alkylene-$X^2$—, —$X^2$—$C_{2-6}$ alkenylene-$X^2$—, and —$X^2$—$C_{2-6}$ alkynylene-$X^2$—, each of which is optionally substituted at each occurrence with one or more $R^{10}$;

$X^{11}$ at each occurrence is independently selected from —C(O)—, and —C(O)N(R$^{10}$)—*, wherein * represents where $X^{11}$ is bound to $R^6$;

$X^2$ at each occurrence is independently selected from a bond, —O—, —S—, —N(R$^{10}$)—, —C(O)—, —C(O)O—, —OC(O)—, —OC(O)O—, —C(O)N(R$^{10}$)—, —C(O)N(R$^{10}$)C(O)—, —(O)N(R$^{10}$)C(O)N(R$^{10}$), —N(R$^{10}$)C(O)—, —N(R$^{10}$)C(O)N(R$^{10}$)—, —N(R$^{10}$)C(O)O—, —OC(O)N(R$^{10}$)—, —C(NR$^{10}$)—, —N(R$^{10}$)C(NR$^{10}$)—, —C(NR$^{10}$)N(R$^{10}$)—, —N(R$^{10}$)C(NR$^{10}$)N(R$^{10}$)—, —S(O)$_2$—, —OS(O)—, —S(O)O—, —S(O)—, —OS(O)$_2$—, —S(O)$_2$O, —N(R$^{10}$)S(O)$_2$—, —S(O)$_2$N(R$^{10}$)—, —N(R$^{10}$)S(O)—, —S(O)N(R$^{10}$)—, —N(R$^{10}$)S(O)$_2$N(R$^{10}$)—, and —N(R$^{10}$)S(O)N(R$^{10}$)—;

$R^1$ and $R^2$ are independently selected from hydrogen; $C_{1-10}$ alkyl, $C_{2-10}$ alkenyl, and $C_{2-10}$ alkynyl, each of which is independently optionally substituted at each occurrence with one or more substituents selected from halogen, —OR$^{10}$, —SR$^{10}$, —C(O)N(R$^{10}$)$_2$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), and —CN;

$R^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; $C_{1-10}$ alkyl, $C_{2-10}$ alkenyl, $C_{2-10}$ alkynyl, each of which is independently optionally substituted at each occurrence with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is independently optionally substituted with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, $C_{1-6}$ alkyl, $C_{2-6}$ alkenyl, and $C_{2-6}$ alkynyl;

$R^6$ is selected from phenyl and 5- or 6-membered heteroaryl, any one of which is substituted with one or more substituents selected from $R^7$;

$R^7$ is selected from —C(O)NHNH$_2$, —C(O)NH—$C_{1-3}$alkylene-NH(R$^{10}$), —C(O)CH$_3$, —$C_{1-3}$alkylene-NHC(O)OR$^{10}$, —$C_{1-3}$alkylene-NHC(O)R$^{10}$, —$C_{1-3}$alkylene-NHC(O)NHR$^{10}$, and —$C_{1-3}$ alkylene-NHC(O)—$C_{1-3}$alkylene-(R$^{10}$)$_2$; and an optionally substituted 3- to 12-membered heterocycle;

$R^{10}$ is independently selected at each occurrence from hydrogen, —$NH_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is independently optionally substituted at each occurrence with one or more substituents selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl; and wherein any substitutable carbon on the benzazepine core is optionally substituted by a substituent selected from halogen, —OR$^{10}$, —SR$^{10}$, —C(O)N(R$^{10}$)$_2$, —N(R$^{10}$)$_2$, —S(O)R$^{10}$, S(O)$_2$R$^{10}$, —C(O)R$^{10}$, —C(O)OR$^{10}$, —OC(O)R$^{10}$, —NO$_2$, =O, =S, =N(R$^{10}$), —P(O)(OR$^{10}$)$_2$, —OP(O)(OR$^{10}$)$_2$, —CN, $C_{1-10}$ alkyl, $C_{2-10}$ alkenyl, and $C_{2-10}$ alkynyl, or two substituents on a single carbon atom combine to form a 3- to 7-membered carbocycle.

In some embodiments for a compound or salt of Formula (IIIA), $L^2$ can be attached at C2, C3, C4, or C5 of the benzazepine core, wherein the numbering of the benzazepine is as follows:

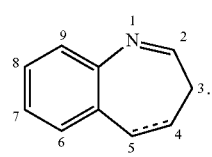

In certain embodiments, for a compound or salt of Formula (IIIA), $L^2$ is attached to the benzazepine core at C4. In certain embodiments for a compound or salt of Formula (IIIA), ------- represents a double bond and $L^2$ is attached to the benzazepine core at C4.

In some embodiments for a compound or salt of Formula (IIIA), $L^{11}$ can be attached at C6, C7, C8 or C9. In certain embodiments, for a compound or salt of Formula (IIIA), $L^{11}$ is attached to the benzazepine core at C8. In certain embodiments for a compound or salt of Formula (IIIA), ------- represents a double bond, $L^2$ is attached to the benzazepine core at C4 and $L^{11}$ is attached to the benzazepine core at C8.

In some embodiments for a compound or salt of Formula (IIIA), the substitutable carbon on the benzazepine core is selected from C2, C3, C4, C5, C6, C7, C8, and C9. The benzazepine core for a compound or salt of Formula (IIIA), can be optionally substituted by a substituent selected from halogen, $-OR^{10}$, $-SR^{10}$, $-C(O)N(R^{10})_2$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-P(O)(OR^{10})_2$, $-OP(O)(OR^{10})_2$, $-CN$, $C_{1-10}$ alkyl, $C_{2-10}$ alkenyl, and $C_{2-10}$ alkynyl, or two substituents on a single carbon atom combine to form a 3- to 7-membered carbocycle. In some embodiments for a compound or salt of Formula (IIIA), a moiety at any one of C2, C3, C4, C5, C6, C7, C8, and C9 of the benzazepine core is independently selected from hydrogen, halogen, $-OR^{10}$, $-SR^{10}$, $-N(R^{10})_2$, $-S(O)R^{10}$, $-S(O)_2R^{10}$$-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl.

In some embodiments, the compound of Formula (IIIA) is represented by Formula (IIIB):

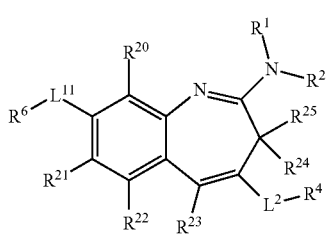

(IIIB)

or a pharmaceutically acceptable salt thereof, wherein:

$R^{20}$, $R^{21}$, $R^{22}$, and $R^{23}$ are independently selected from hydrogen, halogen, $-OR^{10}$, $-SR^{10}$, $-N(R^{10})_2$, $-S(O)R^{10}$, $-S(O)_2R^{10}$$-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl; and $R^{24}$, and $R^{25}$ are independently selected from hydrogen, halogen, $-OR^{10}$, $-SR^{10}$, $-N(R^{10})_2$, $-S(O)R^{10}$, $-S(O)_2R^{10}$$-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl; or $R^{24}$ and $R^{25}$ taken together form an optionally substituted saturated $C_{3-7}$ carbocycle.

In one embodiment, the compound of Formula (IIIA) is represented by Formula (IIIC):

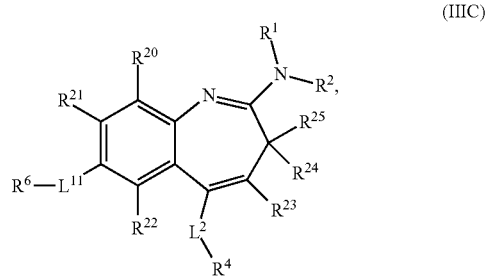

(IIIC)

or a pharmaceutically acceptable salt thereof.

In some embodiments, for a compound or salt of Formula (IIIA), (IIIB) or (IIIC), $L^{11}$ is selected from $-C(O)-$, and $-C(O)N(R^{10})-*$, wherein * represents where $L^{11}$ is bound to $R^6$. In certain embodiments, $L^{11}$ is $-C(O)-$. In certain embodiments, $L^{11}$ is selected from $-C(O)N(R^{10})-*$ In certain embodiments, $R^{10}$ or $L^{11}$ is selected from hydrogen and $C_{1-6}$ alkyl.

In certain embodiments, for a compound or salt of Formula (IIIA), (IIIB) or (IIIC), $R^6$ is further optionally substituted by one or more additional substituents independently selected from $R^{12}$.

In some embodiments, for a compound or salt of Formula (IIIA), (IIIB) or (IIIC), $R^7$ is selected from $-C(O)N(R^{10})N(R^{10})_2$, $-C(O)N(R^{10})-C_{1-3}$ alkylene-$N(R^{10})_2$, $-C(O)CH_3$, $-C_{1-3}$ alkylene-$N(R^{10})C(O)OR^{11}$, $-C_{1-3}$alkylene-$N(R^{10})C(O)R^{10}$, $-C_{1-3}$alkylene-$N(R^{10})C(O)N(R^{10})_2$, $-C_{1-3}$alkylene-$N(R^{10})C(O)-C_{1-3}$alkylene-$R^{10}$, and a 3- to 12-membered heterocycle optionally substituted with one or more substituents independently selected from $R^{12}$. $R^{11}$ may be selected from $C_{3-12}$ carbocycle and 3- to 12-membered heterocycle, each of which is independently optionally substituted with one or more substituents selected from $R^{12}$. In certain embodiments, for a compound or salt of Formula (IIIA), (IIIB) or (IIIC), $R^7$ is selected from $-C(O)NHNH_2$, $-C(O)NH-C_{1-3}$ alkylene-$NH(R^{10})$, $-C(O)CH_3$, $-C_{1-3}$ alkylene-$NHC(O)OR^{11}$, $-C_{1-3}$alkylene-$NHC(O)R^{10}$, $-C_{1-3}$alkylene-$NHC(O)NHR^{10}$, $-C_{1-3}$alkylene-$NHC(O)-C_{1-3}$alkylene-$R^{10}$, and a 3- to 12-membered heterocycle optionally substituted with one or more substituents independently selected from $R^{12}$. In certain embodiments, $R^7$ is selected from $-C(O)NHNH_2$, $-C(O)NH-C_{1-3}$ alkylene-$NH(R^{10})$, $-C(O)CH_3$, $-C_{1-3}$ alkylene-$NHC(O)OR^{11}$, $-C_{1-3}$alkylene-$NHC(O)NHR^{10}$, $-C_{1-3}$ alkylene-$NHC(O)-C_{1-3}$alkylene-$R^{10}$, and a 3- to 12-membered heterocycle optionally substituted with one or more substituents independently selected from $R^{12}$. In certain embodiment, $R^7$ is a 3- to 12-membered heterocycle optionally substituted with one or more substituents independently selected from $R^{12}$.

In some embodiments, for a compound or salt of Formula (IIIA), (IIIB) or (IIIC), $R^6$ is selected from an optionally substituted phenyl and an optionally substituted 5-6 membered heteroaryl, wherein $R^6$ is substituted with one or more substituents independently selected from $R^7$. In some embodiments, $R^6$ is selected from an optionally substituted phenyl, wherein the phenyl is substituted with one or more substituents independently selected from $R^7$. In some embodiments, $R^6$ is selected from an optionally substituted phenyl, wherein the phenyl is substituted with one or more substituents independently selected from $-C(O)NHNH_2$, $-C(O)NH-C_{1-3}$alkylene-$NH(R^{10})$, and $-C(O)CH_3$; and 3- to 12-membered heterocycle, which is optionally substituted with one or more substituents selected from $-OH$, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)$_2$R$^{10}$, and —C$_{1-3}$alkylene-(R$^{10}$), and optionally further substituted with one or more additional substituents. In some embodiments, for a compound or salt of Formula (IIIA), (IIIB) or (IIIC), R$^6$ is selected from:

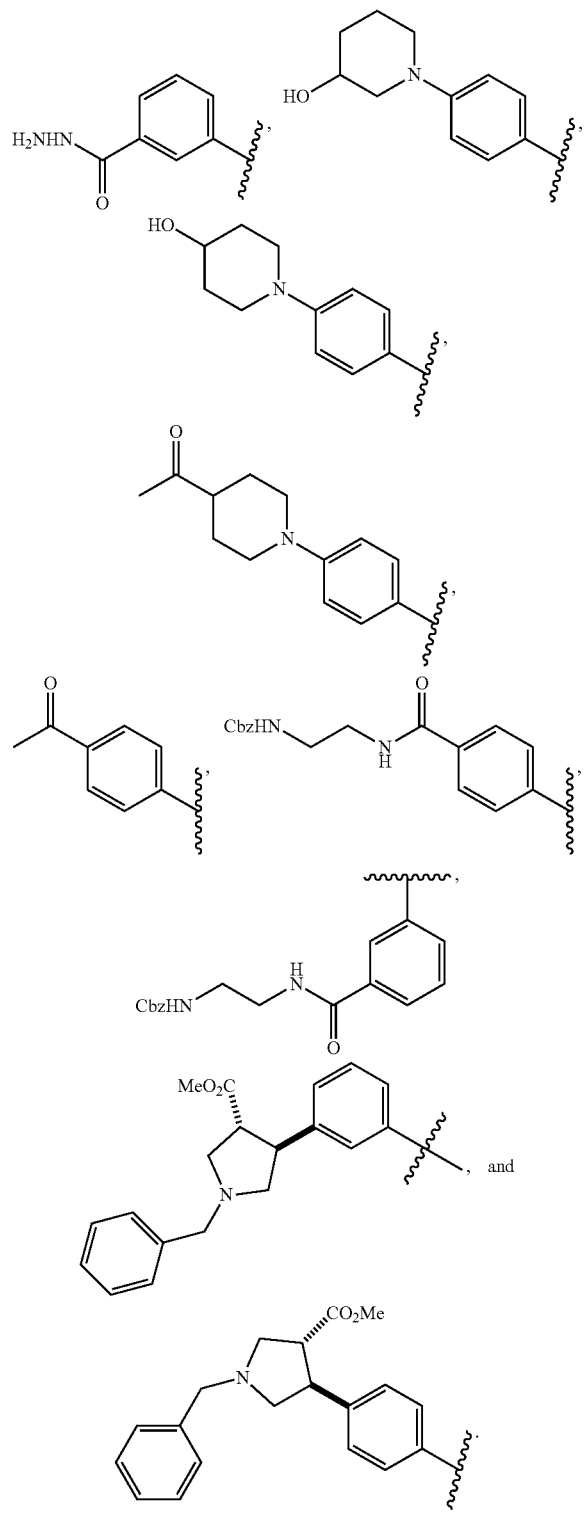

In some embodiments for a compound or salt of Formula (IIIA), (IIIB) or (IIIC), R$^6$ is selected from an optionally substituted 5-6 membered heteroaryl, wherein the heteroaryl is substituted with one or more substituents independently selected from R$^7$. R$^6$ may be selected from a 5- and 6-membered heteroaryl substituted with one or more substituents independently selected from R$^7$, and R$^6$ may be further optionally substituted with one or more additional substituents selected from R$^{12}$. In some embodiments, R$^6$ is selected from an optionally substituted 5-6 membered heteroaryl, wherein the heteroaryl is substituted with one or more substituents independently selected from —C(O)CH$_3$, —C$_{1-3}$alkylene-NHC(O)OR$^{10}$, —C$_{1-3}$alkylene-NHC(O)R$^{10}$, —C$_{1-3}$alkylene-NHC(O)NHR$^{10}$, and —C$_{1-3}$alkylene-NHC(O)—C$_{1-3}$alkylene-(R$^{10}$); and 3- to 12-membered heterocycle, which is optionally substituted with one or more substituents selected from —OH, —N(R$^{10}$)$_2$, —NHC(O)(R$^{10}$), —NHC(O)O(R$^{10}$), —NHC(O)N(R$^{10}$)$_2$, —C(O)R$^{10}$, —C(O)N(R$^{10}$)$_2$, —C(O)$_2$R$^{10}$, and —C$_{1-3}$ alkylene-(R$^{10}$), and R$^6$ is optionally further substituted with one or more additional substituents independently selected from R$^{12}$. In some embodiments, R$^6$ is selected from substituted pyridine, pyrazine, pyrimidine, pyridazine, furan, pyran, oxazole, thiazole, imidazole, pyrazole, oxadiazole, oxathiazole, and triazole, and R$^6$ is optionally further substituted with one or more additional substituents independently selected from R$^{12}$. R$^6$ may be an optionally substituted pyridine and R$^6$ is optionally further substituted with one or more additional substituents independently selected from R$^{12}$. In certain embodiments, R$^6$ may be represented as follows:

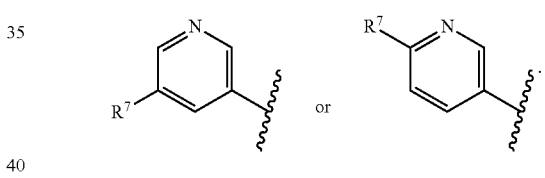

In some embodiments, R$^6$ is substituted pyridine, and wherein R$^7$ is —C$_{1-3}$alkylene-NHC(O)—C$_{1-3}$alkylene-R$^{10}$. R$^7$ may be —C$_1$alkylene-NHC(O)—C$_1$alkylene-R$^{10}$. R$^7$ may be —C$_1$alkylene-NHC(O)—C$_1$alkylene-NH$_2$. In some embodiments for a compound or salt of Formula (IIIA), (IIIB) or (IIIC), R$^6$ is selected from

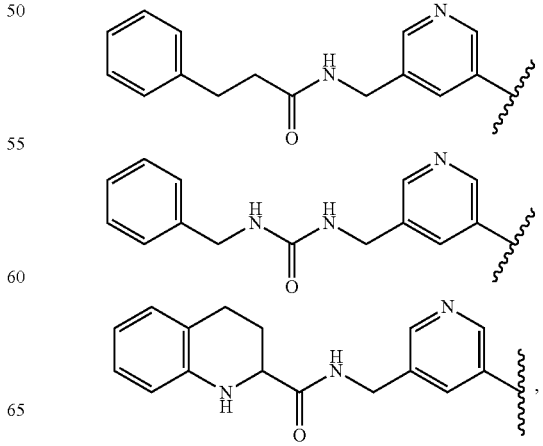

-continued

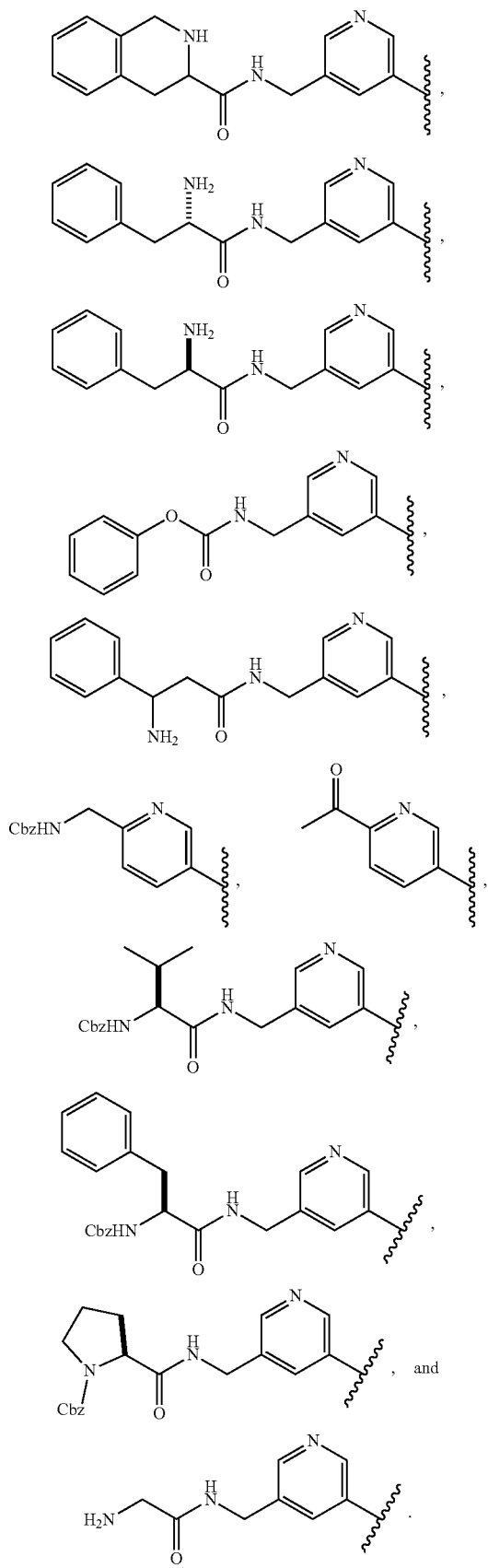

In an exemplary embodiment, $R^6$ is

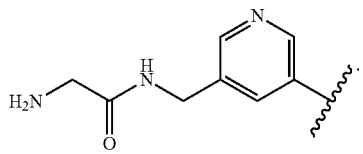 [SMILES: *c1cncc(CNC(=O)CN)c1]

In certain embodiments for a compound or salt of Formula (IIIA), (IIIB) or (IIIC), the compound may further comprise a linker ($L^3$). The linker may be covalently bound to any position, valence permitting, on a compound or salt of Formula (IIIA), (IIIB) or (IIIC). For example, the linker may be bound to $R^1$, $R^2$, , $R^6$, $X^{11}$ or $X^2$. In certain embodiments, the linker is bound to a nitrogen or oxygen atom of a compound or salt of Formula (IIIA), (IIIB) or (IIIC). The linker may comprise a reactive moiety, e.g., an electrophile, that can react to form a covalent bond with a moiety of an antibody construct, a lysine, serine, threonine, cysteine, tyrosine, aspartic acid, glutamine, a non-natural amino acid residue, or glutamic acid residue of an antibody. In some embodiments, a compound or salt of Formula (IIIA), (IIIB) or (IIIC), may be covalently bound through the linker moiety to an antibody construct.

In certain embodiments, for a compound or salt of Formula (IIIA), (IIIB) or (IIIC):

$L^{11}$ is —C(O)N($R^{10}$)—*, such as $L^{11}$ is —C(O)NH—;

$L^2$ is selected from —C(O)— and —C(O)N$R^{10}$—;

$R^1$ and $R^2$ are independently selected from hydrogen; and $C_{1-10}$ alkyl optionally substituted at each occurrence with one or more substituents selected from halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; and $C_{1-10}$ alkyl optionally substituted at each occurrence with one or more substituents selected from halogen, —O$R^{10}$, —S$R^{10}$, —C(O)N($R^{10}$)$_2$, —N($R^{10}$)$_2$, —C(O)$R^{10}$, —NO$_2$, =O, =S, =N($R^{10}$), —CN, $C_{3-12}$ carbocycle, and 3- to 12-membered heterocycle;

$R^6$ is selected from phenyl and 5- or 6-membered heteroaryl, any one of which is substituted with one or more substituents selected from $R^7$;

$R^7$ is selected from —C(O)NHNH$_2$, —C(O)NH—$C_{1-3}$alkylene-NH($R^{10}$), —C(O)CH$_3$, —$C_{1-3}$ alkylene-NHC(O)O$R^{11}$, —$C_{1-3}$alkylene-NHC(O)$R^{10}$, —$C_{1-3}$alkylene-NHC(O)NH$R^{10}$, and —$C_{1-3}$ alkylene-NHC(O)—$C_{1-3}$alkylene-($R^{10}$)$_2$; and a 3- to 12-membered heterocycle optionally substituted with one or more substituents independently selected from $R^{12}$;

$R^{10}$ is independently selected at each occurrence from hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is independently optionally substituted at each occurrence with one or more substituents selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$R^{11}$ is selected from $C_{3-12}$ carbocycle and 3- to 12-membered heterocycle, each of which is independently optionally substituted with one or more substituents selected from $R^{12}$; and wherein any substitutable carbon on the benzazepine core is optionally substituted by a substituent independently selected from $R^{12}$.

In certain embodiments, for a compound or salt of Formula (IIIA), (IIIB) or (IIIC):

$L^{11}$ is —C(O)N($R^{10}$)—*;
$L^2$ is —C(O)—;
$R^1$ and $R^2$ are each hydrogen;
$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$;
$R^6$ is selected from phenyl and 5- or 6-membered heteroaryl, any one of which is substituted with one or more substituents selected from $R^7$;
$R^7$ is selected from —C(O)NHNH$_2$, —C(O)NH—C$_{1-3}$alkylene-NH($R^{10}$), —C(O)CH$_3$, —C$_{1-3}$ alkylene-NHC(O)O$R^{11}$, —C$_{1-3}$alkylene-NHC(O)$R^{10}$, —C$_{1-3}$alkylene-NHC(O)NH$R^{10}$, and —C$_{1-3}$ alkylene-NHC(O)—C$_{1-3}$alkylene-($R^{10}$)$_2$;
$R^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is independently optionally substituted at each occurrence with one or more substituents selected from halogen, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and haloalkyl;
$R^{11}$ is selected from C$_{3-12}$ carbocycle and 3- to 12-membered heterocycle, each of which is independently optionally substituted with one or more substituents selected from $R^{12}$; and wherein any substitutable carbon on the benzazepine core is optionally substituted by a substituent independently selected from $R^{12}$.

In certain embodiments, for a compound or salt of Formula (IIIA), (IIIB) or (IIIC):

$L^{11}$ is —C(O)N($R^{10}$)—*, such as $L^{11}$ is —C(O)NH—;
$L^2$ is —C(O)—;
$R^1$ and $R^2$ are each hydrogen;
$R^4$ is selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$;
$R^6$ is selected from phenyl and 5- or 6-membered heteroaryl, e.g., pyridine, any one of which is substituted with one or more substituents selected from $R^7$;
$R^7$ is selected from —C(O)NHNH$_2$, —C(O)NH—C$_{1-3}$alkylene-NH($R^{10}$), —C(O)CH$_3$, —C$_{1-3}$ alkylene-NHC(O)O$R^{11}$, —C$_{1-3}$alkylene-NHC(O)NH$R^{10}$, and —C$_{1-3}$alkylene-NHC(O)—C$_{1-3}$ alkylene-($R^{10}$)$_2$; and a 3- to 12-membered heterocycle optionally substituted with one or more substituents independently selected from $R^{12}$;
$R^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is independently optionally substituted at each occurrence with one or more substituents selected from halogen, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, C$_{2-10}$ alkenyl, C$_{2-10}$ alkynyl, C$_{3-12}$ carbocycle, 3- to 12-membered heterocycle, and haloalkyl;

$R^{11}$ is selected from C$_{3-12}$ carbocycle and 3- to 12-membered heterocycle, each of which is independently optionally substituted with one or more substituents selected from $R^{12}$; and wherein any substitutable carbon on the benzazepine core is optionally substituted by a substituent independently selected from $R^{12}$.

In some embodiments, for a compound of any one of Formulas (IA), (IB), (IC), (IIA), (IB), (IIC), (IIIA), (IIIB), and (IIIC), $R^{20}$, $R^{21}$, $R^{22}$, and $R^{23}$ are independently selected from hydrogen, halogen, —OH, —NO$_2$, —CN, and C$_{1-10}$ alkyl. In some embodiments, $R^{20}$, $R^{21}$, $R^{22}$, and $R^{23}$ are each hydrogen.

In some embodiments, for a compound of any one of Formulas (IA), (IB), (IC), (IIA), (IB), (IIC), (IIIA), (IIIB), and (IIIC), $R^{24}$ and $R^{25}$ are independently selected from hydrogen, halogen, —OH, —NO$_2$, —CN, and C$_{1-10}$ alkyl, or $R^{24}$ and $R^{25}$ taken together form an optionally substituted saturated C$_{3-7}$ carbocycle. In some embodiments for a compound of any one of Formulas (IA), (IB), (IC), (IIA), (IIB), (IIC), (IIIA), (IIIB), and (IIIC), $R^{24}$ and $R^{25}$ are each hydrogen. In some embodiments for a compound of any one of Formulas (IA), (IB), (IC), (IIA), (IIB), (IIC), (IIIA), (IIIB), and (IIIC), $R^{24}$ and $R^{25}$ taken together form an optionally substituted saturated C$_{3-5}$ carbocycle, wherein substituents may be selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), and —CN; and C$_{1-10}$ alkyl, C$_{2-10}$ alkenyl, C$_{2-10}$ alkynyl, each of which is independently optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, C$_{3-12}$ carbocycle, and 3- to 12-membered heterocycle.

In some embodiments, for a compound of any one of Formulas (IA), (IB), (IC), (IIA), (IIB), (IIC), (IIIA), (IIIB), and (IIIC), $R^1$ and $R^2$ are independently selected from hydrogen; C$_{1-10}$ alkyl, C$_{2-10}$ alkenyl, and C$_{2-10}$ alkynyl, each of which is independently optionally substituted at each occurrence with one or more substituents selected from halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN. In some embodiments for a compound of any one of Formulas (IA), (IB), (IC), (IIA), (IIB), (IIC), (IIIA), (IIIB), and (IIIC), $R^1$ is hydrogen. In some embodiments for a compound of any one of Formulas (IA), (IB), (IC), (IIA), (IIB), (IIC), (IIIA), (IIIB), and (IIIC), $R^2$ is hydrogen. In some embodiments for a compound of any one of Formulas (IA), (IB), (IC), (IIA), (IIB), (IIC), (IIIA), (IIIB), and (IIIC), $R^1$ is hydrogen and $R^2$ is hydrogen.

In some embodiments, for a compound of any one of Formulas (IA), (IB), (IC), (IIA), (IIB), (IIC), (IIIA), (IIIB), and (IIIC), $L^2$ is independently selected from —X$^2$—, —X$^2$—C$_{1-6}$ alkyl-X$^2$—, —X$^2$—C$_{2-6}$ alkenyl-X$^2$—, and —X$^2$—C$_{2-6}$ alkynyl-X$^2$—, each of which is optionally substituted at each occurrence with one or more $R^{10}$. In some embodiments for a compound of any one of Formulas (IA), (IB), (IC), (IIA), (IIB), (IIC), (IIIA), (IIIB), and (IIIC), $L^2$ is selected from —C(O)—, and —C(O)N$R^{10}$—. In some embodiments for a compound of any one of Formulas (IA), (IB), (IC), (IIA), (IIB), (IIC), (IIIA), (IIIB), and (IIIC), $L^2$ is selected from —C(O)—. In some embodiments for a compound of any one of Formulas (IA), (IB), (IC), (IIA), (IIB), (IIC), (IIIA), (IIIB), and (IIIC), $L^2$ is selected from —C(O)

NR$^{10}$—. In some embodiments for a compound of any one of Formulas (IA), (IB), (IC), (IIA), (IIB), (IIC), (IIIA), (IIIB), and (IIIC), R$^{10}$ of —C(O)NR$^{10}$— is selected from hydrogen and C$_{1-6}$ alkyl. In some embodiments for a compound of any one of Formulas (IA), (IB), (IC), (IIA), (IIB), (IIC), (IIIA), (IIIB), and (IIIC), L$^2$ is —C(O)NH—.

In some embodiments, for a compound of any one of Formulas (IIA), (IIB), (IIC), (IIIA), (IIIB), and (IIIC), X$^2$ at each occurrence is independently selected from a bond, —O—, —S—, —N(R$^{10}$)—, —C(O)—, —C(O)O—, —OC(O)—, —OC(O)O—, —C(O)N(R$^{10}$)—, —C(O)N(R$^{10}$)C(O)—, —C(O)N(R$^{10}$)C(O)N(R$^{10}$), —N(R$^{10}$)C(O)—, —N(R$^{10}$)C(O)N(R$^{10}$)—, —N(R$^{10}$)C(O)O—, —OC(O)N(R$^{10}$)—, —C(NR$^{10}$)—, —N(R$^{10}$)C(NR$^{10}$)—, —C(NR$^{10}$)N(R$^{10}$)—, —N(R$^{10}$)C(NR$^{10}$)N(R$^{10}$)—, —S(O)$_2$—, —OS(O)—, —S(O)O—, —S(O), —OS(O)$_2$—, —S(O)$_2$O, —N(R$^{10}$)S(O)$_2$—, —S(O)$_2$N(R$^{10}$)—, —N(R$^{10}$)S(O)—, —S(O)N(R$^{10}$)—, —N(R$^{10}$)S(O)$_2$N(R$^{10}$)—, and —N(R$^{10}$)S(O)N(R$^{10}$)—. In some embodiments, for a compound of any one of Formulas (IA), (IB), (IC), X$^2$ at each occurrence is independently selected from a —O—, —S—, —N(R$^{10}$)—, —C(O)—, —C(O)O—, —OC(O)—, —OC(O)O—, —C(O)N(R$^{10}$)—, —C(O)N(R$^{10}$)C(O)—, —C(O)N(R$^{10}$)C(O)N(R$^{10}$)—, —N(R$^{10}$)C(O)—, —N(R$^{10}$)C(O)N(R$^{10}$)—, —N(R$^{10}$)C(O)O—, —OC(O)N(R$^{10}$)—, —C(NR$^{10}$)—, —N(R$^{10}$)C(NR$^{10}$)—, —C(NR$^{10}$)$^{10}$N(R$^{10}$)—, —N(R$^{10}$)C(NR$^{10}$)N(R$^{10}$)—, —S(O)$_2$—, —OS(O)—, —S(O)O—, —S(O), —OS(O)$_2$—, —S(O)$_2$O, —N(R$^{10}$)S(O)$_2$—, —S(O)$_2$N(R$^{10}$)—, —N(R$^{10}$)S(O)—, —S(O)N(R$^{10}$)—, —N(R$^{10}$)S(O)$_2$N(R$^{10}$)—, and —N(R$^{10}$)S(O)N(R$^{10}$)—. In certain embodiments for a compound of any one of Formulas (IA), (IB), (IC), (IIA), (IIB), (IIC), (IIIA), (IIIB), and (IIIC), X$^2$ is selected from —C(O)—, and —C(O)NR$^{10}$—. In some embodiments for a compound of any one of Formulas (IA), (IB), (IC), (IIA), (IIB), (IIC), (IIIA), (IIIB), and (IIIC), X$^2$ is selected from —C(O)—. In some embodiments for a compound of any one of Formulas (IA), (IB), (IC), (IIA), (IIB), (IIC), (IIIA), (IIIB), and (IIIC), X$^2$ is selected from —C(O)NR$^{10}$—. In some embodiments for a compound of any one of Formulas (IA), (IB), (IC), (IIA), (IIB), (IIC), (IIIA), (IIIB), and (IIIC), R$^{10}$ of —C(O)NR$^{10}$— is selected from hydrogen and C$_{1-6}$ alkyl. In some embodiments for a compound of any one of Formulas (IA), (IB), (IC), (IIA), (IIB), (IIC), (IIIA), (IIIB), and (IIIC), X$^2$ is —C(O)NH—.

In some embodiments, for a compound of any one of Formulas (IA), (IB), (IC), (IIA), (IIB), (IIC), (IIIA), (IIIB), and (IIIC), R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, wherein each C$_{3-12}$ carbocycle, and 3- to 12-membered heterocycle in R$^4$ is independently optionally substituted with one or more substituents selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl.

In some embodiments, for a compound of any one of Formulas (IA), (IB), (IC), (IIA), (IIB), (IIC), (IIIA), (IIIB), and (IIIC), R$^4$ is selected from: —OR$^{10}$, —N(R$^{10}$)$_2$, —C(O)N(R$^{10}$)$_2$, —C(O)R$^{10}$, —C(O)OR$^{10}$, —S(O)R$^{10}$, and —S(O)$_2$R$^{10}$; C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle and 3- to 12-membered heterocycle each of which is optionally substituted with one or more substituents selected from halogen, —OR$^{10}$, —SR$^{10}$, —C(O)N(R$^{10}$)—, —C(O)N(R$^{10}$)$_2$, —N(R$_{10}$)C(O)R$_{10}$, —N(R$_{10}$)C(O)N(R$_{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl.

In some embodiments for a compound of any one of Formulas (IA), (IB), (IC), (IIA), (IIB), (IIC), (IIIA), (IIIB), and (IIIC), R$^4$ is selected from: —OR$^{10}$, and —N(R$^{10}$)$_2$; and C$_{1-10}$ alkyl, C$_{2-10}$ alkenyl, C$_{2-10}$ alkynyl, C$_{3-12}$ carbocycle, 3- to 12-membered heterocycle, each of which is independently optionally substituted with one or more substituents selected from halogen, —OR$^{10}$, —SR$^{10}$, —N(R$^{10}$)$_2$, —S(O)R$^{10}$, —S(O)$_2$R$^{10}$—C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl. In some embodiments for a compound of any one of Formulas (IA), (IB), (IC), (IIA), (IIB), (IIC), (IIIA), (IIIB), and (IIIC), R$^4$ is —N(R$^{10}$)$_2$.

In some embodiments for a compound of any one of Formulas (IA), (IB), (IC), (IIA), (IIB), (IIC), (IIIA), (IIIB), and (IIIC), R$^{10}$ is independently selected at each occurrence from hydrogen, —NH$_2$, —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is independently optionally substituted at each occurrence with one or more substituents selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and haloalkyl.

In some embodiments, for a compound of any one of Formulas (IA), (IB), (IC), (IIA), (IIB), (IIC), (IIIA), (IIIB), and (IIIC), R$^4$ is —N(R$^{10}$)$_2$, and each R$^{10}$ is independently selected from optionally substituted C$_{1-6}$ alkyl. In some embodiments for a compound of any one of Formulas (IA), (IB), (IC), (IIA), (IIB), (IIC), (IIIA), (IIIB), and (IIIC), R$^4$ is —N(R$^{10}$)$_2$, and each R$^{10}$ is independently selected from methyl, ethyl, propyl, and butyl, any one of which is optionally substituted. In some embodiments for a compound of any one of Formulas (IA), (IB), (IC), (IIA), (IB), (IIC), (IIIA), (IIIB), and (IIIC), R$^4$ is

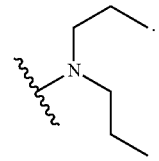 [SMILES: *N(CCC)CCC]

In some embodiments, for a compound or salt of Formula (IA), (IIA), (IIIA), any substitutable carbon on the benzazepine core is optionally substituted by a substituent independently selected from R$^{12}$ or two substituents on a single carbon atom combine to form a 3- to 7-membered carbocycle. In some embodiments, R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is independently optionally substituted with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$ alkynyl.

In some embodiments, for a compound or salt of Formula (IA), (IB), (IC), (IIA), (IIB), (IIC), (IIIA), (IIIB) or (IIIC), R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle each of which is optionally substituted with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$ alkynyl.

In some embodiments, for a compound or salt of Formula (IA), (IB), (IC), (IIA), (IIB), (IIC), (IIIA), (IIIB) or (IIIC), R$^{12}$ may be independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle.

In some embodiments, for a compound or salt of Formula (IA), (IB), (IC), (IIA), (IIB), (IIC), (IIIA), (IIIB) or (IIIC), R$^{12}$ may be independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; and C$_{1-10}$ alkyl optionally substituted with one or more substituents selected from halogen, —OR$^{10}$, —SR$^{10}$, —N(R$^{10}$)$_2$, —C(O)R$^{10}$, —NO$_2$, =O, =S, =N(R$^{10}$), and —CN.

In some embodiments, for a compound of any one of Formulas (IA), (IB), (IC), (IIA), (IB), (IIC), (IIIA), (IIIB), and (IIIC), R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, C$_{2-10}$ alkenyl, C$_{2-10}$ alkynyl, each of which is independently optionally substituted at each occurrence with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is independently optionally substituted with one or more substituents selected from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR$^{10}$, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), —CN, C$_{1-6}$ alkyl, C$_{2-6}$ alkenyl, C$_{2-6}$ alkynyl.

In some embodiments, for a compound of any one of Formulas (IA), (IB), (IC), (IIA), (IIB), (IIC), (IIIA), (IIIB), and (IIIC), R$^{12}$ is independently selected at each occurrence from halogen, —OR$^{10}$, —SR$^{10}$, —N(R$^{10}$)$_2$, —C(O)R$^{10}$, —C(O)N(R$^{10}$)$_2$, —N(R$^{10}$)C(O)R$^{10}$, —C(O)OR, —OC(O)R$^{10}$, —S(O)R$^{10}$, —S(O)$_2$R$^{10}$, —P(O)(OR$^{10}$)$_2$, —OP(O)(OR$^{10}$)$_2$, —NO$_2$, =O, =S, =N(R$^{10}$), and —CN; C$_{1-10}$ alkyl, optionally substituted at each occurrence with one or more substituents selected from halogen, —OR$^{10}$, —SR$^{10}$, —N(R$^{10}$)$_2$, —C(O)R$^{10}$, —NO$_2$, =O, =S, =N(R$^{10}$), —CN, C$_{3-10}$ carbocycle and 3- to 10-membered heterocycle; and C$_{3-10}$ carbocycle and 3- to 10-membered heterocycle, wherein each C$_{3-10}$ carbocycle and 3- to 10-membered heterocycle in R$^{12}$ is independently optionally substituted with one or more substituents selected from halogen, —OR$^{10}$, —SR$^{10}$, —N(R$^{10}$)$_2$, —C(O)R$^{10}$, —NO$_2$, =O, =S, =N(R$^{10}$), —CN, and C$_{1-6}$ alkyl.

Any combination of the groups described above for the various variables is contemplated herein. Throughout the specification, groups and substituents thereof can be chosen to provide stable moieties and compounds.

In certain embodiments, exemplary compounds may include, but are not limited to, a compound or salt of any one of compounds 1.1-1.67:

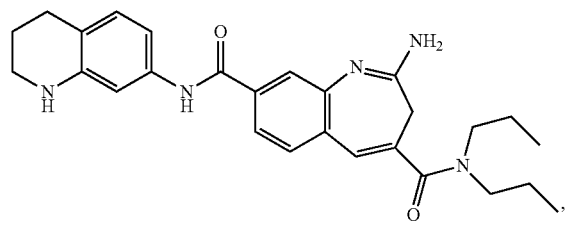

1.1

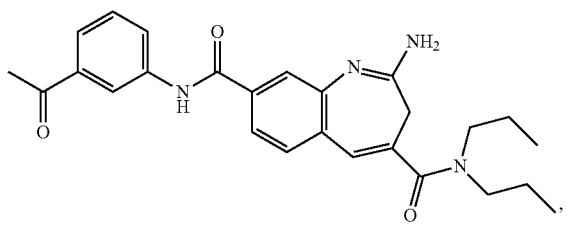

1.2

-continued
1.3
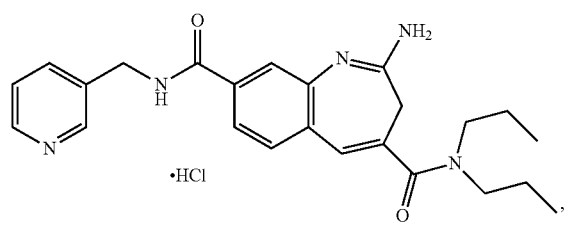
1.4
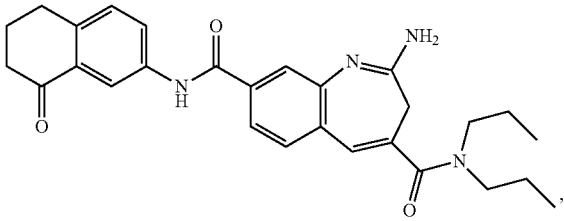
1.5
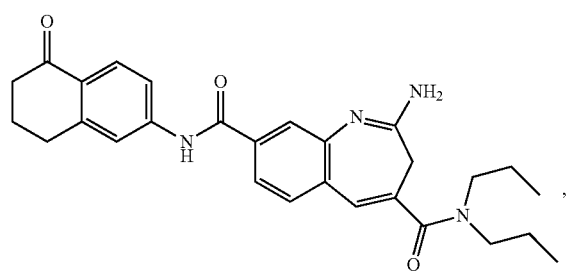
1.6
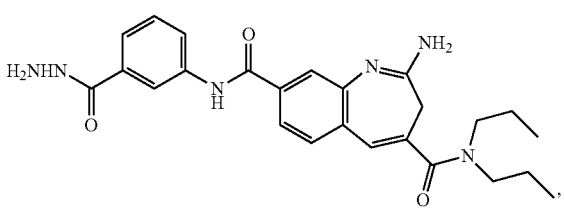
1.7
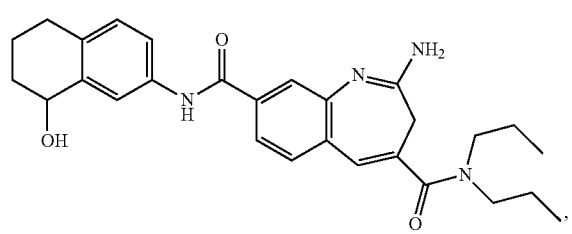
1.8
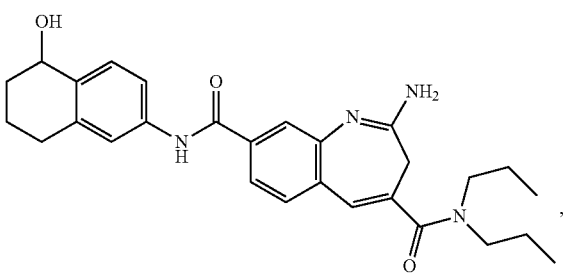
1.9
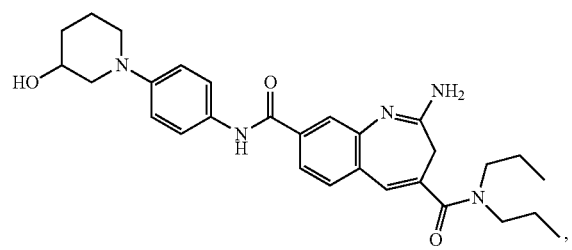
1.10
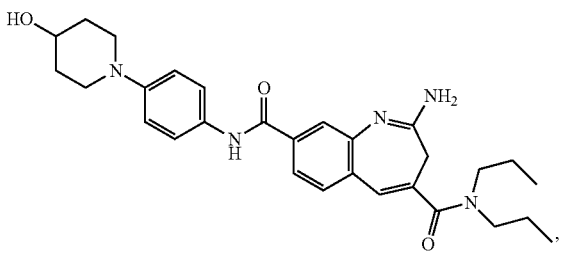
1.11
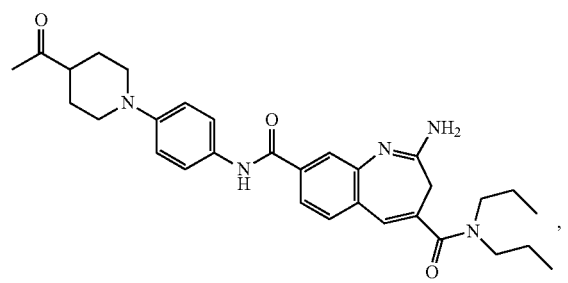
1.12
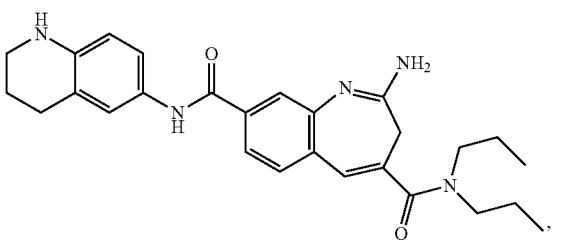
1.13
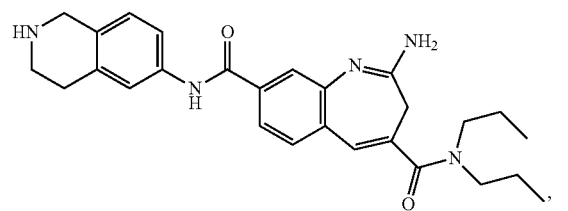
1.14
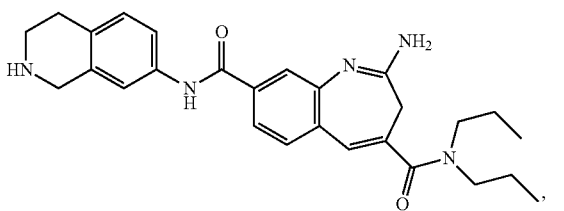

1.15
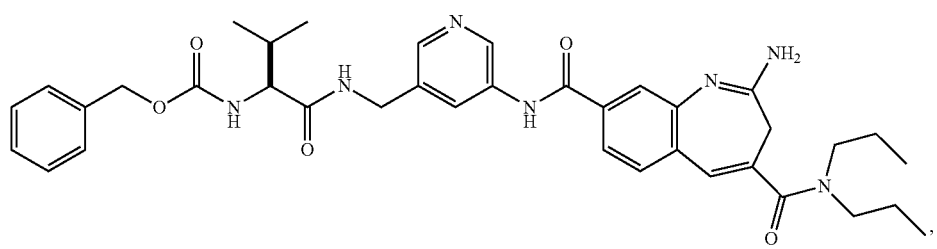
1.16
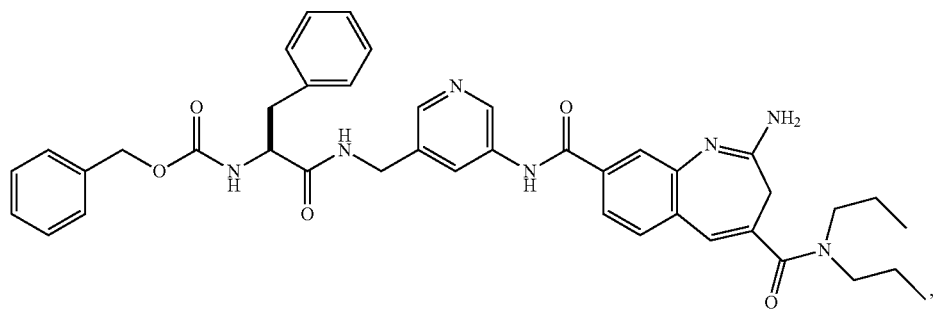
1.17
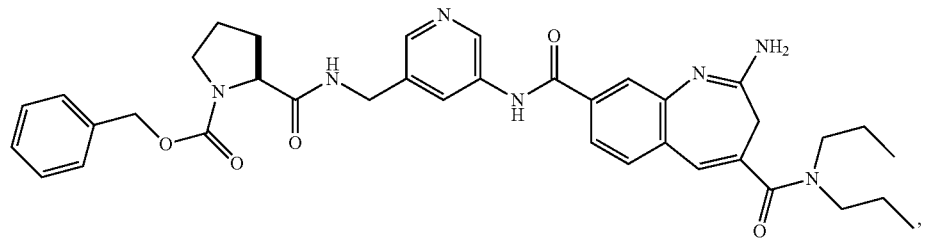
1.18 1.19
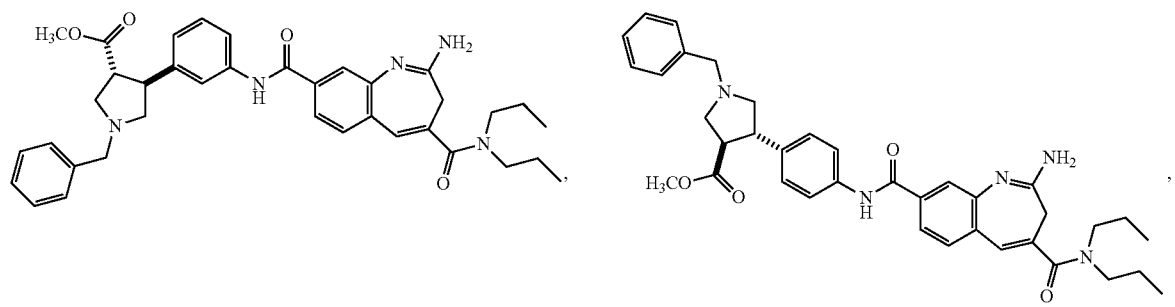
1.20
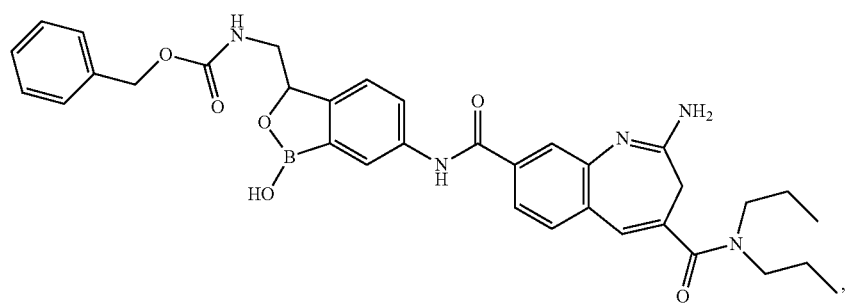

-continued
| 1.21 | 1.22 |
|---|---|
| 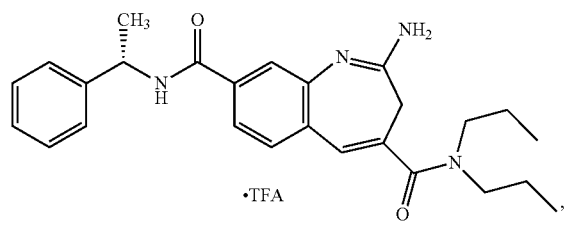 | 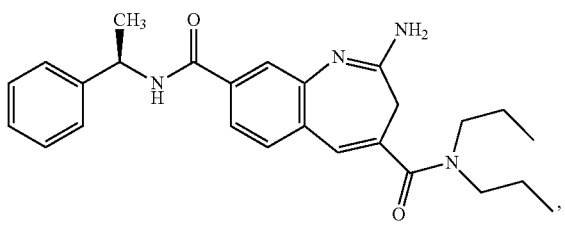 |
| 1.23 | 1.24 |
| 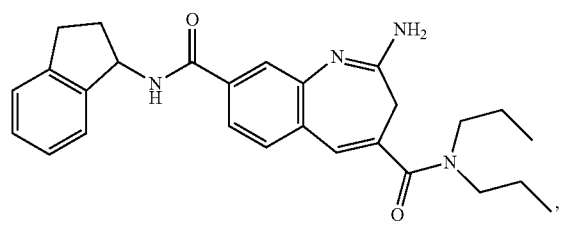 | 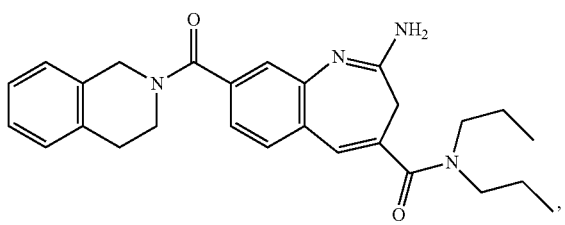 |
| 1.25 | 1.26 |
| 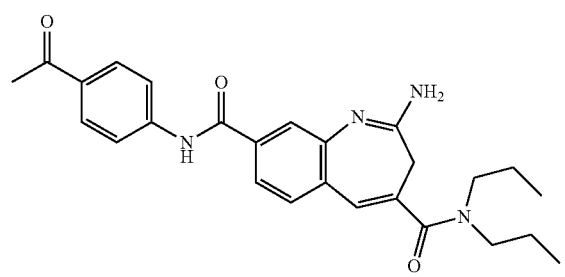 | 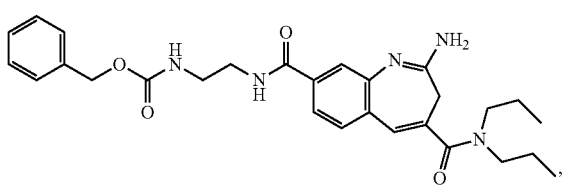 |
1.27
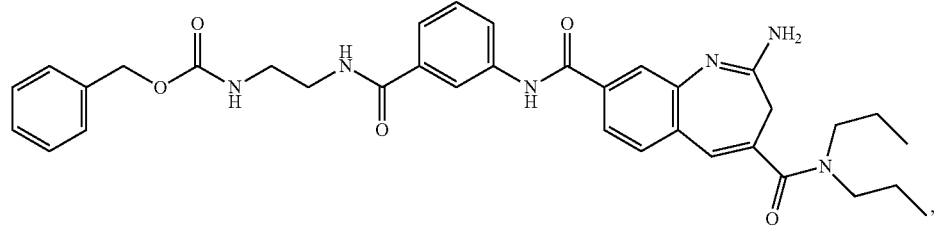
1.28
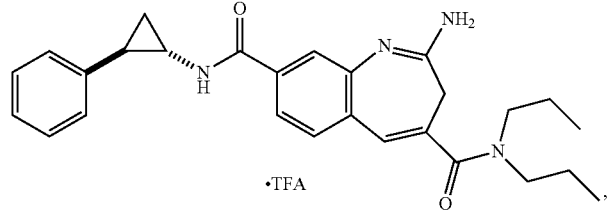
1.29
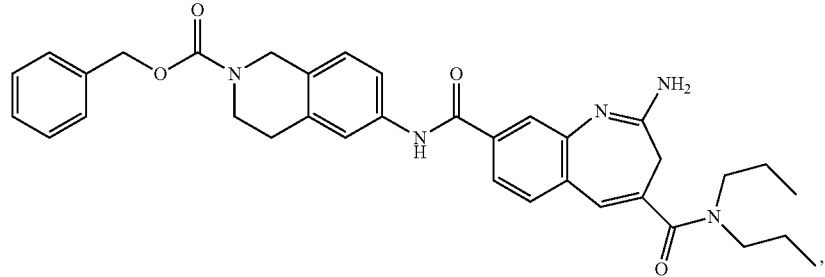

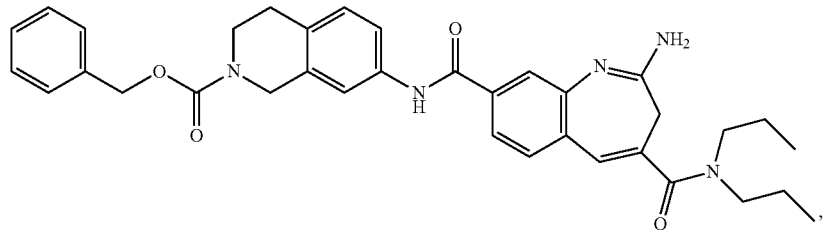
1.30
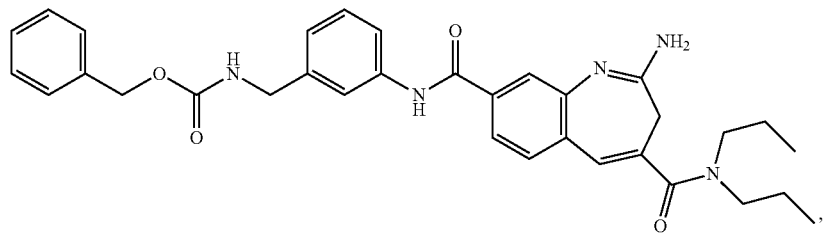
1.31
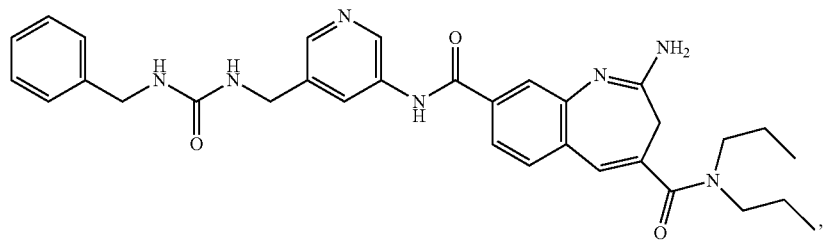
1.32
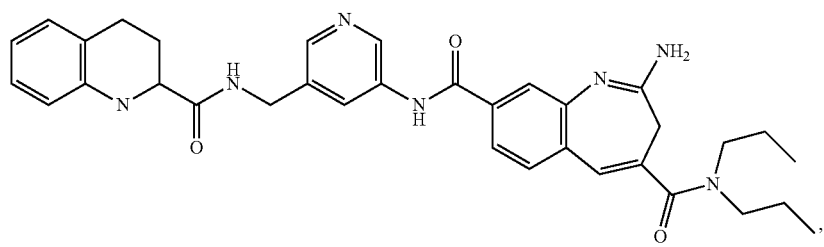
1.33
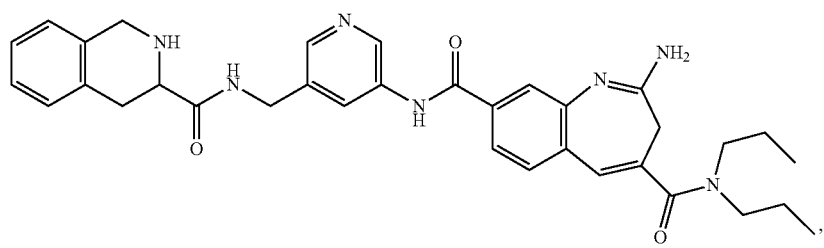
1.34
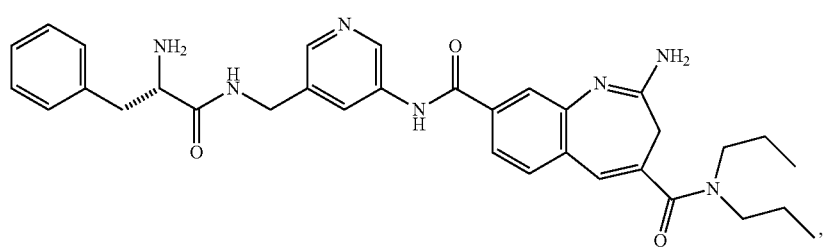
1.35

-continued
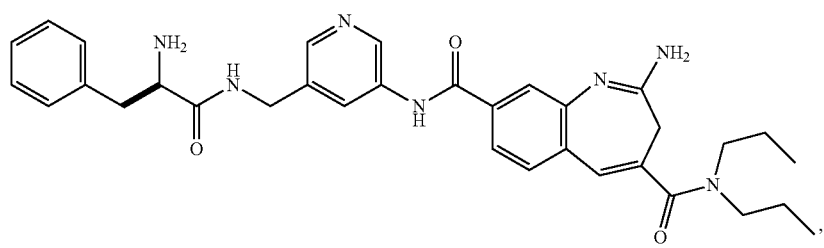
1.36
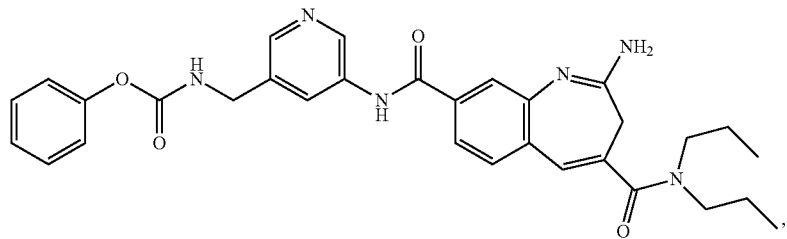
1.37
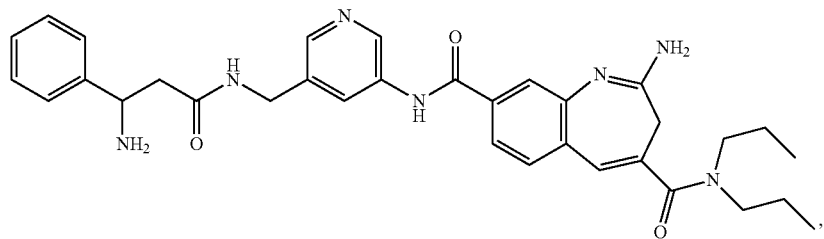
1.38
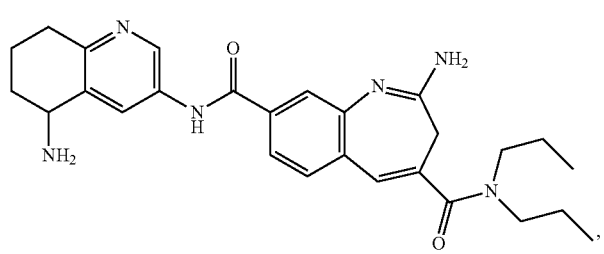
1.39
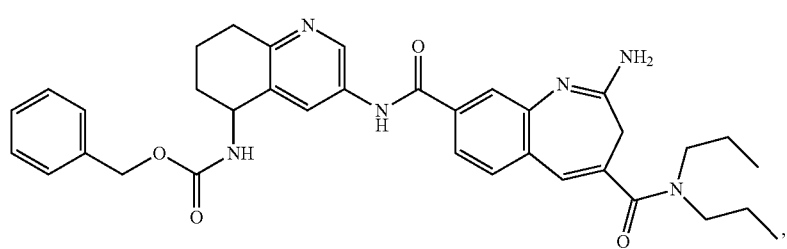
1.40
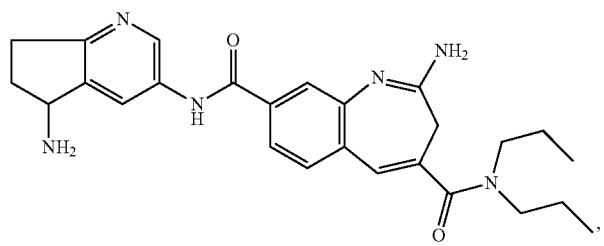
1.41

1.42
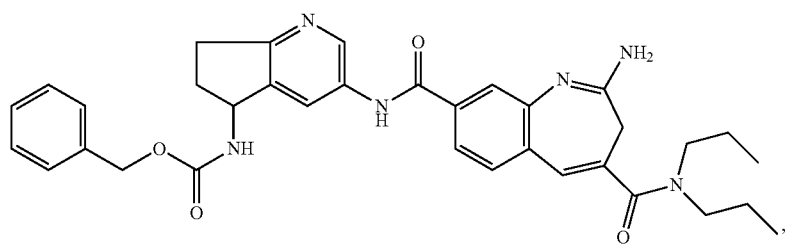
1.43
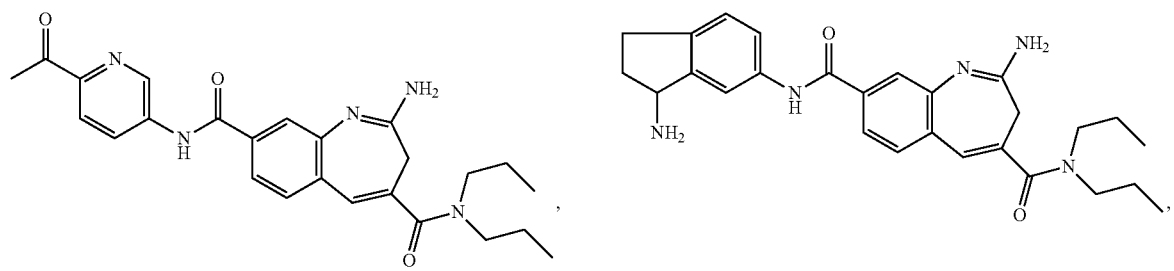
1.44
1.45
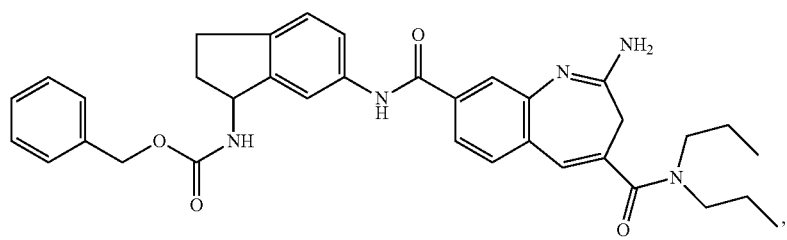
1.46
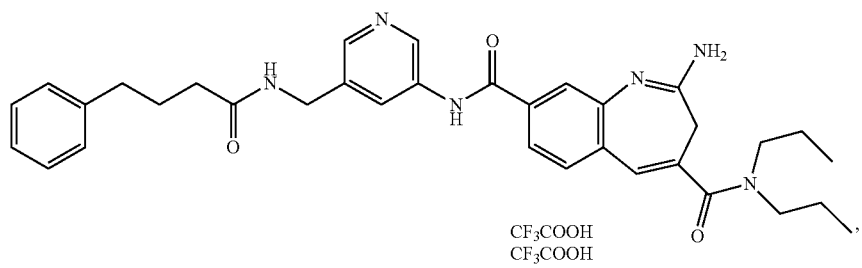
1.47
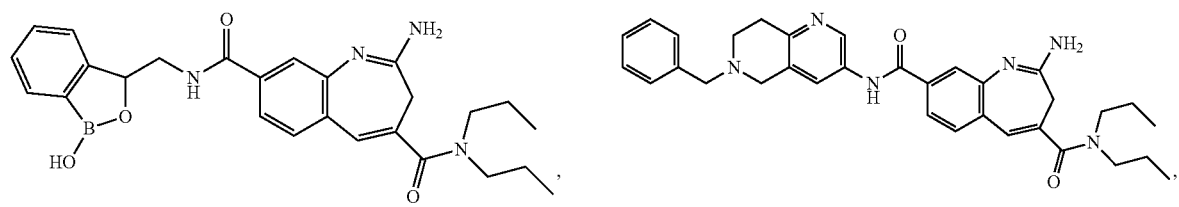
1.48
1.49
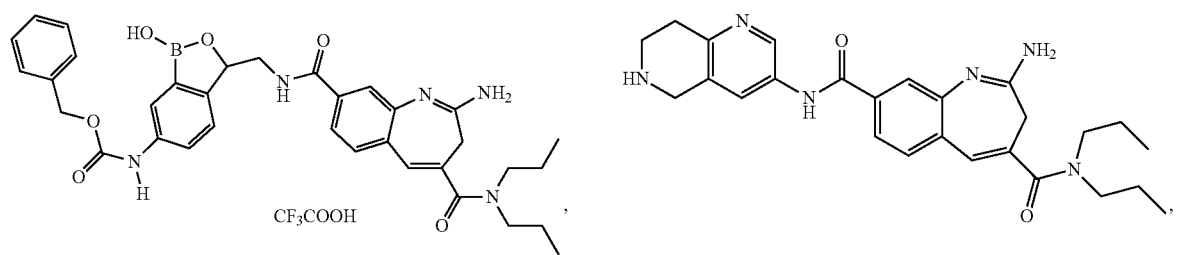
1.50

-continued
| 1.51 | 1.52 |
|---|---|
| 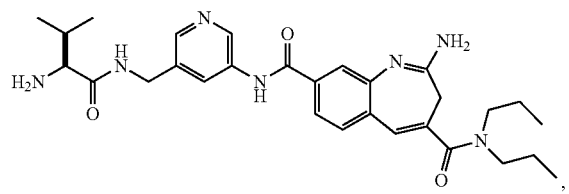 | 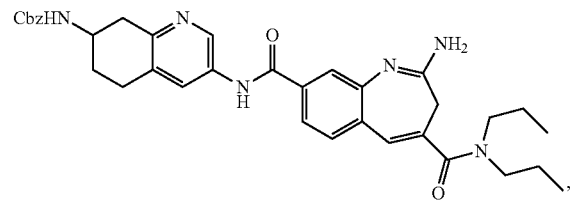 |
1.53
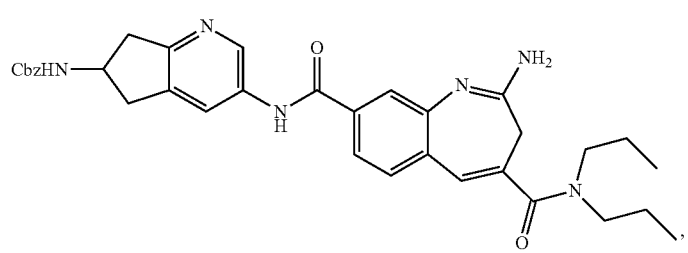
1.54
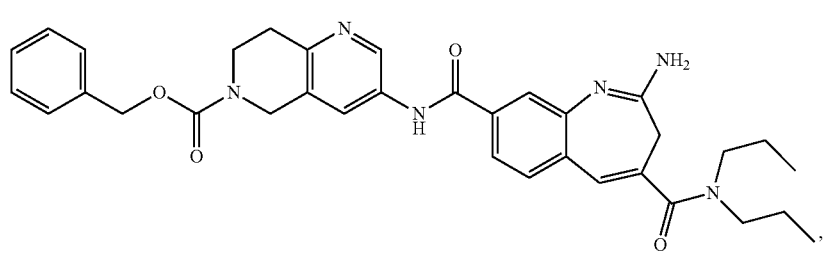
| 1.55 | 1.56 |
|---|---|
| 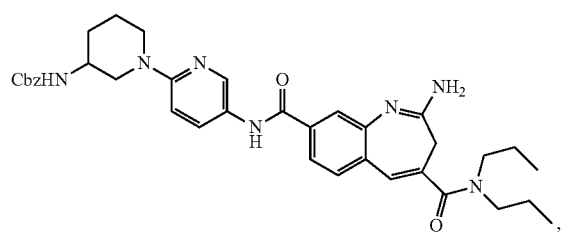 | 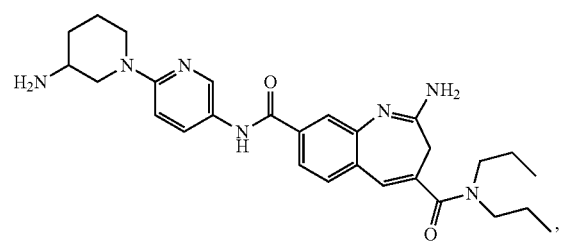 |
| 1.57 | 1.58 |
|---|---|
| 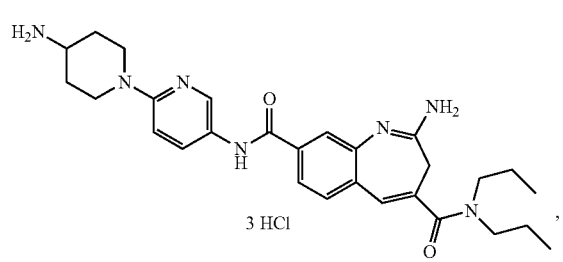 | 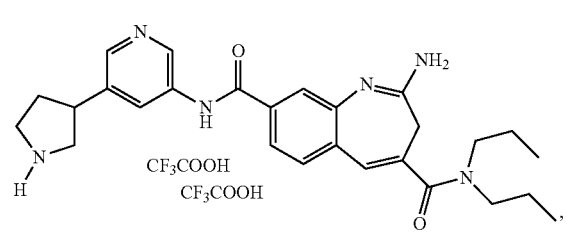 |
1.59
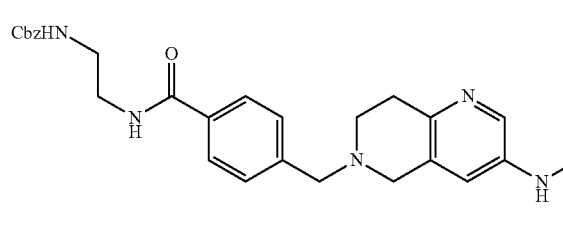

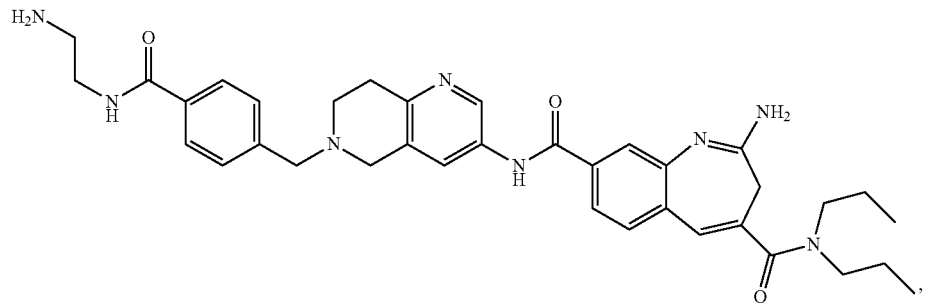
1.60
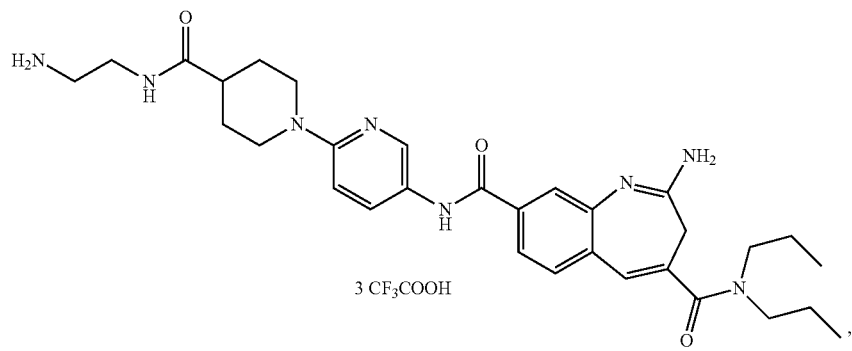
1.61
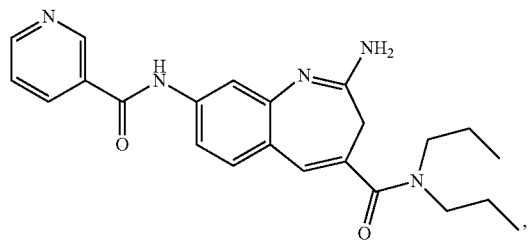
1.62
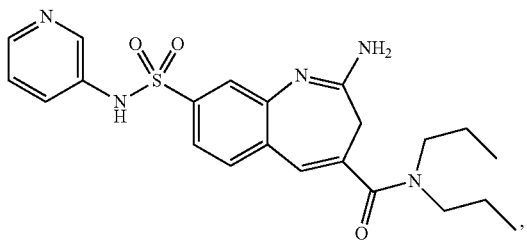
1.63
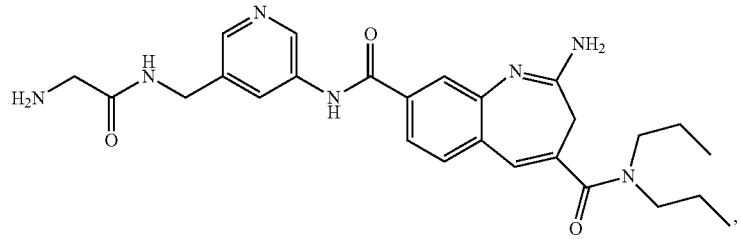
1.64
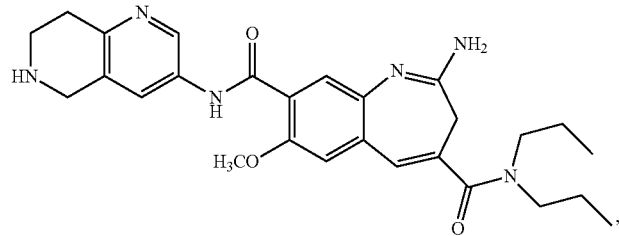
1.65
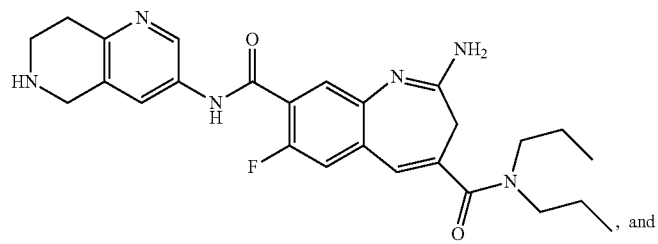
1.66

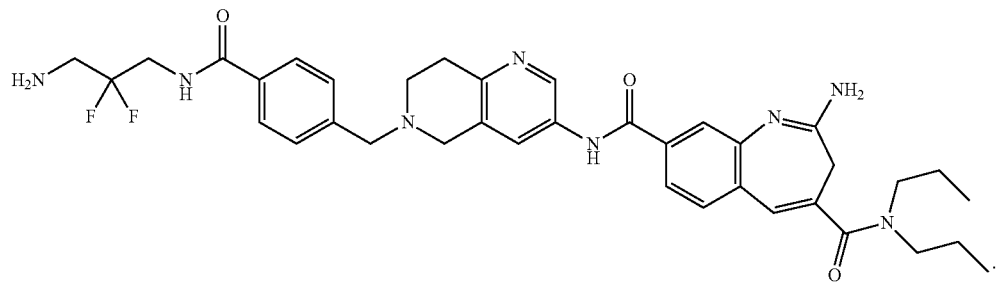

1.67

In certain embodiments, any one of compounds 1.1 to 1.67 is covalently bound to a linker ($L^3$). The linker may be covalently bound to any position, valence permitting, on a compound or salt of compounds 1.1 to 1.67. The linker may be bound to an amine on the benzazepine core. The linker may be bound to a substitutable nitrogen or oxygen atom of any one of compounds 1.1 to 1.67. In some embodiments, at least one of $R^1$, $R^2$, and $R^{10}$ is replaced with $L^3$. In some embodiments, at least one substituent on a group selected from $R^1$, $R^2$, $R^3$, $R^4$, $R^5$, $R^6$, $X^1$ and $X^2$ is -$L^3$. The linker may comprise a reactive moiety, e.g., an electrophile, that can react to form a covalent bond with a moiety of an antibody construct such as, for example, a lysine, serine, threonine, cysteine, tyrosine, aspartic acid, glutamine, a non-natural amino acid residue, or glutamic acid residue of any antibody. In some embodiments, a compound or salt of compounds 1.1 to 1.67, may be covalently bound through the linker to an antibody construct.

A compound may be represented by

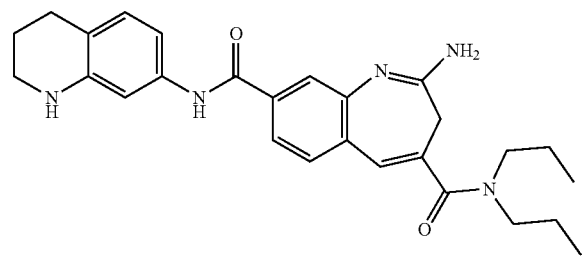 [SMILES: CCCN(CCC)C(=O)C1=Cc2ccc(C(=O)Nc3ccc4c(c3)NCCC4)cc2N=C(N)C1]

or a salt thereof. A compound may be represented by

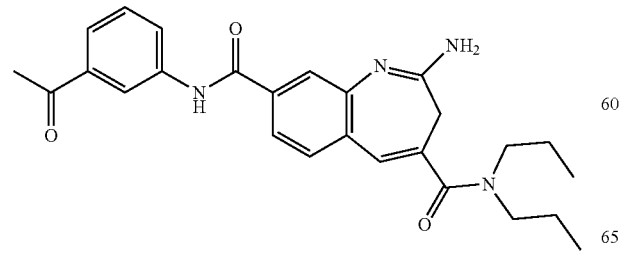

or a salt thereof. A compound may be represented by

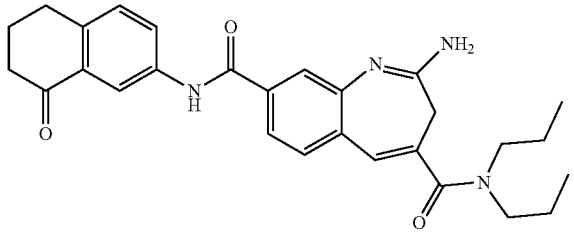 [SMILES: CCCN(CCC)C(=O)C1=Cc2ccc(C(=O)Nc3ccc4c(c3)C(=O)CCC4)cc2N=C(N)C1]

or a salt thereof. A compound may be represented by

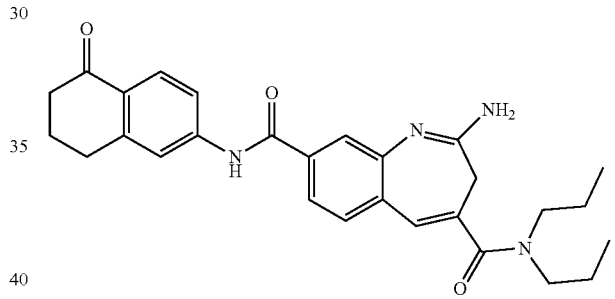

or a salt thereof. A compound may be represented by

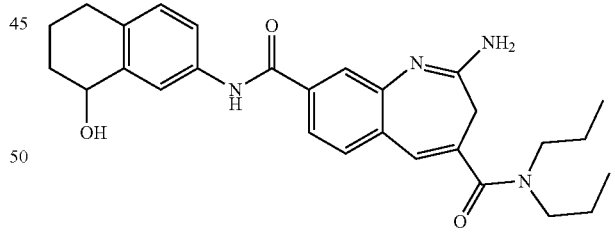

or a salt thereof. A compound may be represented by

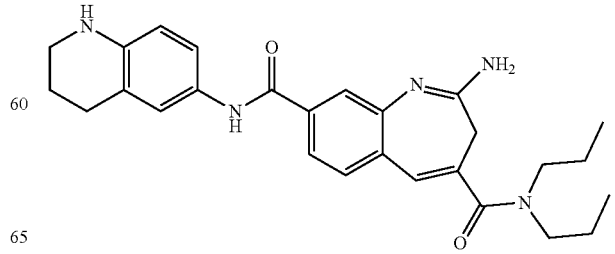

or a salt thereof. A compound may be represented by or a salt thereof. A compound may be represented by
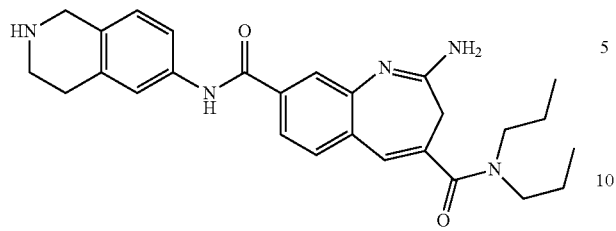
or a salt thereof. A compound may be represented by
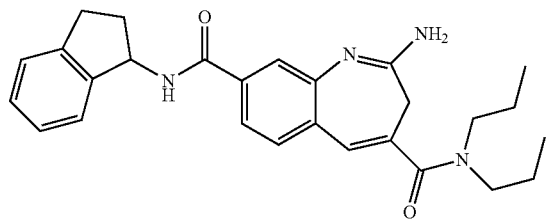 [SMILES: CCCN(CCC)C(=O)C1=Cc2ccc(C(=O)NC3CCc4ccccc43)cc2N=C(N)C1]
or a salt thereof. A compound may be represented by
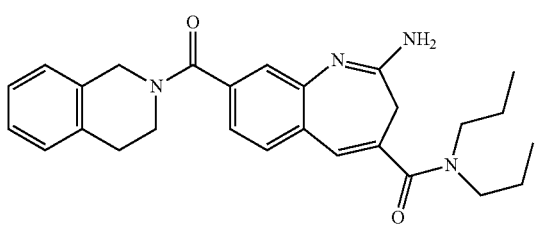 [SMILES: CCCN(CCC)C(=O)C1=Cc2ccc(C(=O)N3CCc4ccccc4C3)cc2N=C(N)C1]
or a salt thereof. A compound may be represented by
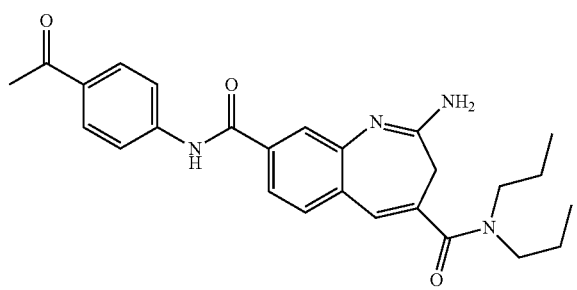 [SMILES: CCCN(CCC)C(=O)C1=Cc2ccc(C(=O)Nc3ccc(C(C)=O)cc3)cc2N=C(N)C1]
or a salt thereof. A compound may be represented by
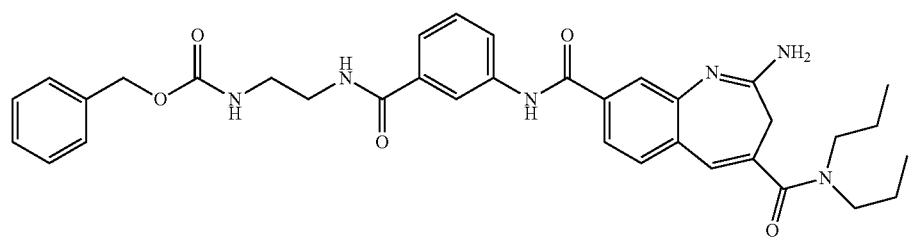 [SMILES: CCCN(CCC)C(=O)C1=Cc2ccc(C(=O)Nc3cccc(C(=O)NCCNC(=O)OCc4ccccc4)c3)cc2N=C(N)C1]
or a salt thereof. A compound may be represented by
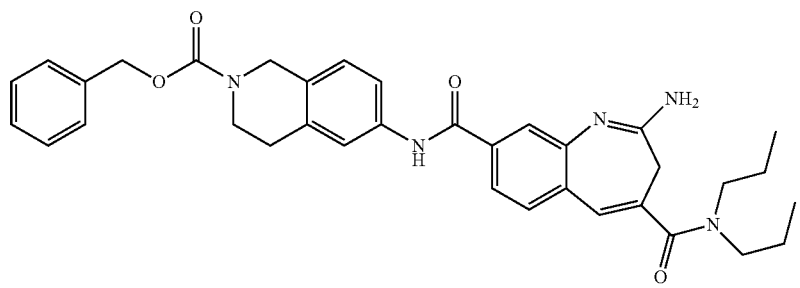 [SMILES: CCCN(CCC)C(=O)C1=Cc2ccc(C(=O)Nc3ccc4c(c3)CCN(C(=O)OCc3ccccc3)C4)cc2N=C(N)C1]

or a salt thereof. A compound may be represented by
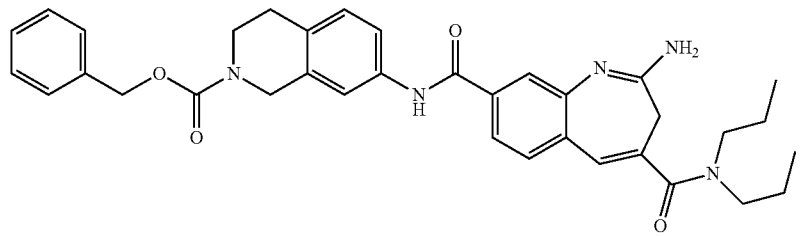 [SMILES: CCCN(CCC)C(=O)C1=Cc2ccc(C(=O)Nc3ccc4c(c3)CN(C(=O)OCc3ccccc3)CC4)cc2N=C(N)C1]
or a salt thereof. A compound may be represented by
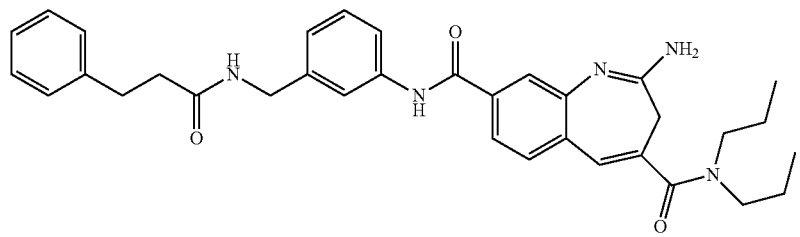 [SMILES: CCCN(CCC)C(=O)C1=Cc2ccc(C(=O)Nc3cccc(CNC(=O)CCc4ccccc4)c3)cc2N=C(N)C1]
or a salt thereof. A compound may be represented by
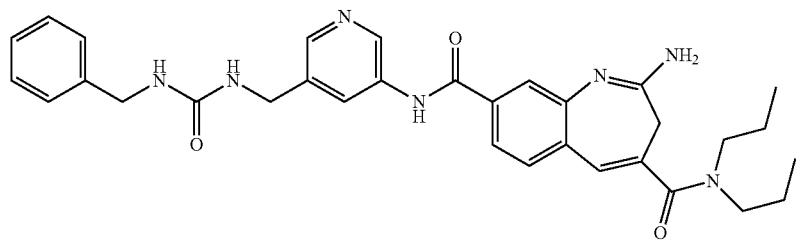 [SMILES: CCCN(CCC)C(=O)C1=Cc2ccc(C(=O)Nc3cncc(CNC(=O)NCc4ccccc4)c3)cc2N=C(N)C1]
or a salt thereof. A compound may be represented by
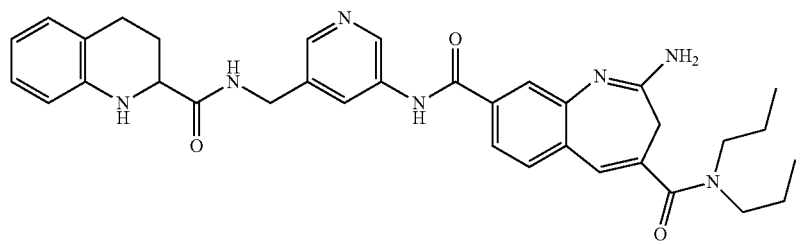 [SMILES: CCCN(CCC)C(=O)C1=Cc2ccc(C(=O)Nc3cncc(CNC(=O)C4CCc5ccccc5N4)c3)cc2N=C(N)C1]
or a salt thereof. A compound may be represented by
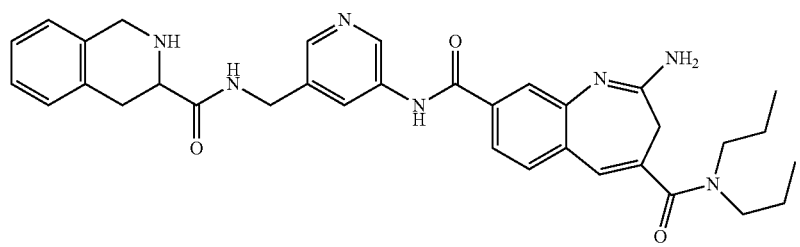 [SMILES: CCCN(CCC)C(=O)C1=Cc2ccc(C(=O)Nc3cncc(CNC(=O)C4Cc5ccccc5CN4)c3)cc2N=C(N)C1]

or a salt thereof. A compound may be represented by
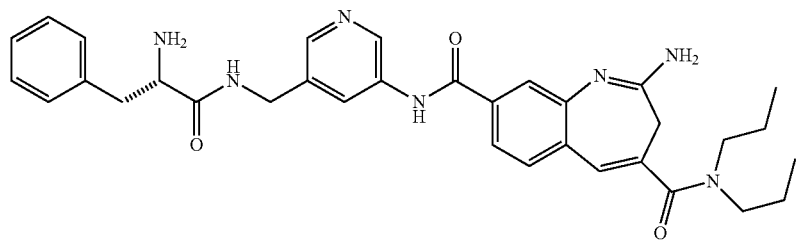 [SMILES: CCCN(CCC)C(=O)C1=Cc2ccc(C(=O)Nc3cncc(CNC(=O)[C@@H](N)Cc4ccccc4)c3)cc2N=C(N)C1]
or a salt thereof. A compound may be represented by
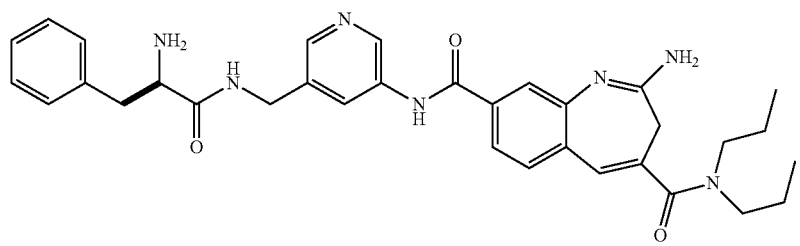 [SMILES: CCCN(CCC)C(=O)C1=Cc2ccc(C(=O)Nc3cncc(CNC(=O)[C@H](N)Cc4ccccc4)c3)cc2N=C(N)C1]
or a salt thereof. A compound may be represented by
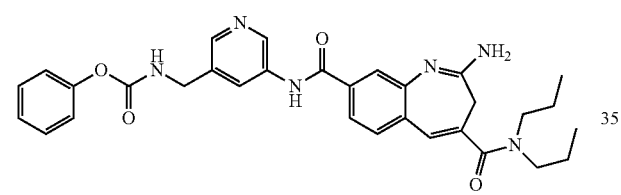
or a salt thereof. A compound may be represented by
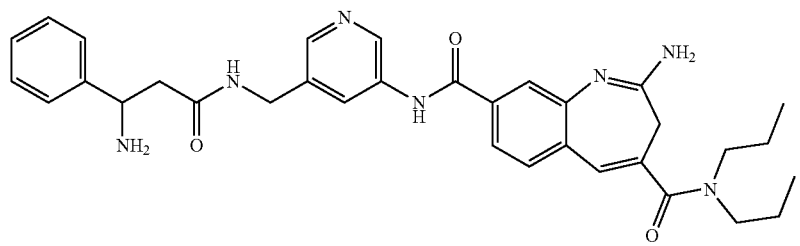 [SMILES: CCCN(CCC)C(=O)C1=Cc2ccc(C(=O)Nc3cncc(CNC(=O)CC(N)c4ccccc4)c3)cc2N=C(N)C1]
or a salt thereof. A compound may be represented by
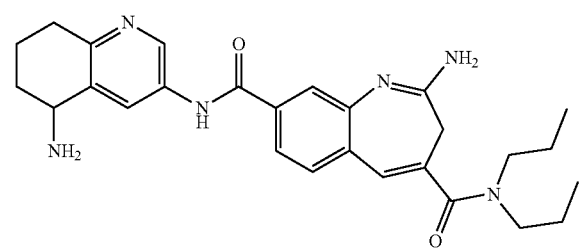 [SMILES: CCCN(CCC)C(=O)C1=Cc2ccc(C(=O)Nc3cnc4c(c3)C(N)CCC4)cc2N=C(N)C1]
or a salt thereof. A compound may be represented by
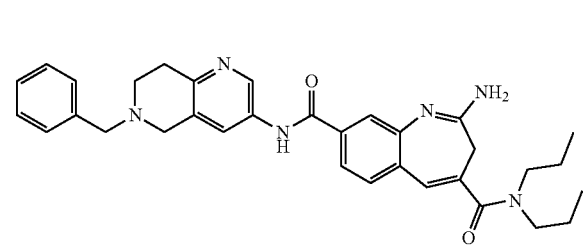 [SMILES: CCCN(CCC)C(=O)C1=Cc2ccc(C(=O)Nc3cnc4c(c3)CN(Cc3ccccc3)CC4)cc2N=C(N)C1]

or a salt thereof. A compound may be represented by
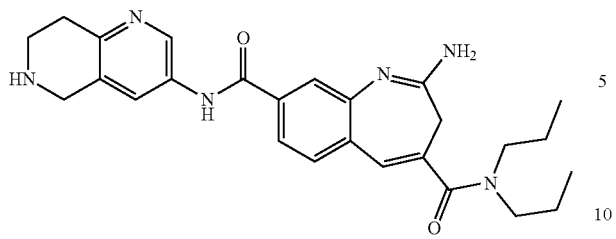
or a salt thereof. A compound may be represented by
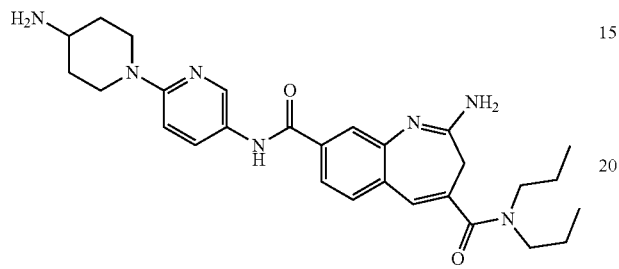
or a salt thereof. A compound may be represented by
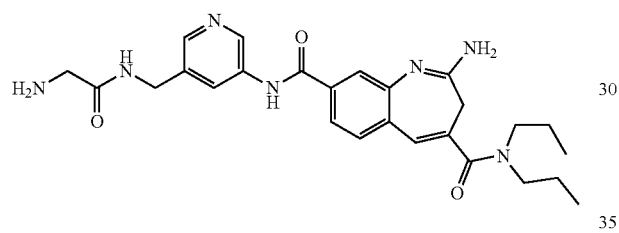
or a salt thereof. A compound may be represented by
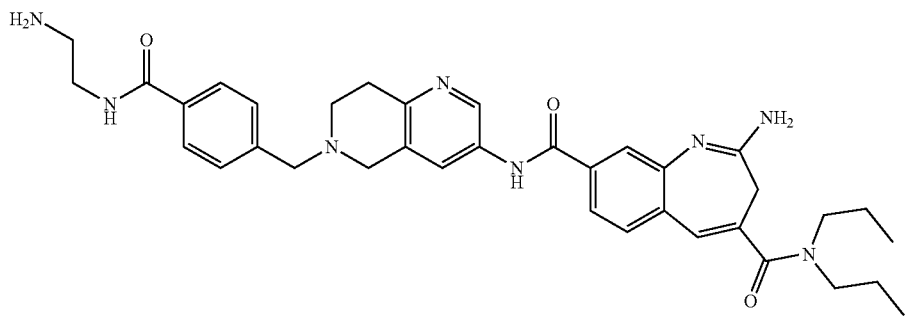 [SMILES: CCCN(CCC)C(=O)C1=Cc2ccc(C(=O)Nc3cnc4c(c3)CN(Cc3ccc(C(=O)NCCN)cc3)CC4)cc2N=C(N)C1]
or a salt thereof. A compound may be represented by
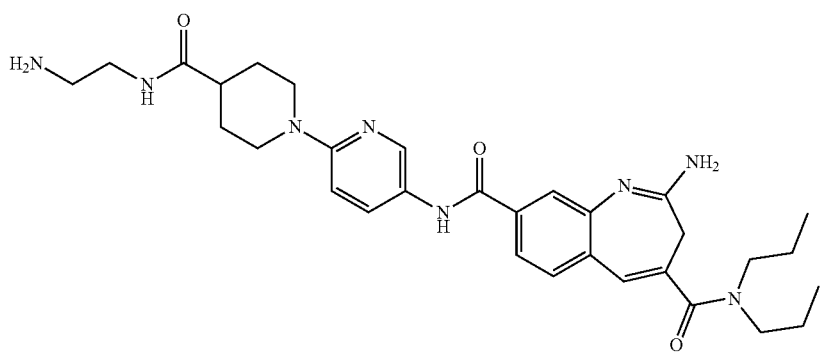 [SMILES: CCCN(CCC)C(=O)C1=Cc2ccc(C(=O)Nc3ccc(N4CCC(C(=O)NCCN)CC4)nc3)cc2N=C(N)C1]

or a salt thereof. A compound may be represented by

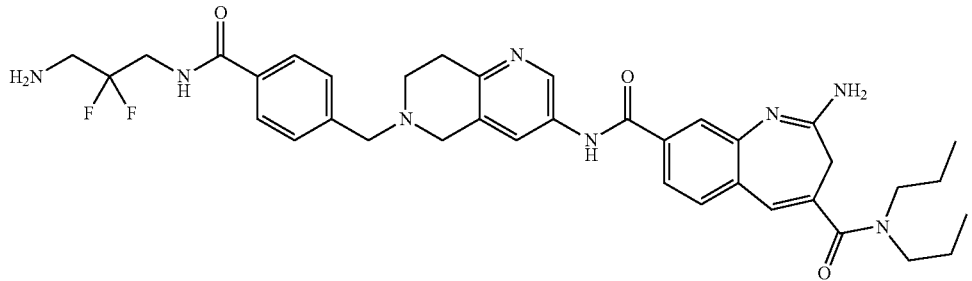 [SMILES: CCCN(CCC)C(=O)C1=Cc2ccc(C(=O)Nc3cnc4c(c3)CN(Cc3ccc(C(=O)NCC(F)(F)CN)cc3)CC4)cc2N=C(N)C1]

or a salt thereof.

In some aspects, the disclosure provides compounds that include a linker, $L^3$. In certain embodiments, a compound bound to a linker is represented by the structure of Formula (IVA):

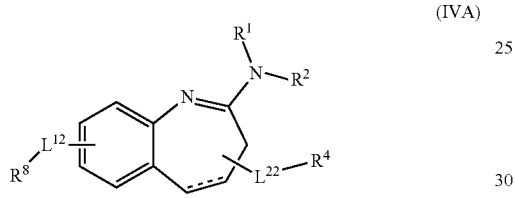

or a pharmaceutically acceptable salt thereof, wherein:

- - - - - - represents an optional double bond;

$L^{12}$ is independently selected from —$X^3$—, —$X^3$—$C_{1-6}$ alkyl-$X^3$—, —$X^3$—$C_{2-6}$ alkenyl-$X^3$—, and —$X^3$—$C_{2-6}$ alkynyl-$X^3$—, each of which is optionally substituted at each occurrence with one or more $R^{10}$;

$L^{22}$ is independently selected from —$X^4$—, —$X^4$—$C_{1-6}$ alkyl-$X^4$—, —$X^4$—$C_{2-6}$ alkenyl-$X^4$—, and —$X^4$—$C_{2-6}$ alkynyl-$X^4$—, each of which is optionally substituted at each occurrence with one or more $R^{10}$;

$X^3$ and $X^4$ are independently selected at each occurrence from a bond, —O—, —S—, —N($R^{10}$)—, —C(O)—, —C(O)O—, —OC(O)—, —OC(O)O—, —C(O)N($R^{10}$)—, —C(O)N($R^{10}$)C(O)—, —C(O)N($R^{10}$)C(O)N($R^{10}$)—, —N($R^{10}$)C(O)—, —N($R^{10}$)C(O)N($R^{10}$)—, —N($R^{10}$)C(O)O—, —OC(O)N($R^{10}$)—, —C(N$R^{10}$)—, —N($R^{10}$)C(N$R^{10}$)—, —C(N$R^{10}$)N($R^{10}$)—, —N($R^{10}$)C(N$R^{10}$)N($R^{10}$)—, —S(O)$_2$—, —OS(O)—, —S(O)O—, —S(O), —OS(O)$_2$—, —S(O)$_2$O—, —N($R^{10}$)S(O)$_2$—, —S(O)$_2$N($R^{10}$)—, —N($R^{10}$)S(O)—, —S(O)N($R^{10}$)—, —N($R^{10}$)S(O)$_2$N($R^{10}$)—, and —N($R^{10}$)S(O)N($R^{10}$)—;

$R^1$ and $R^2$ are independently selected from $L^3$, and hydrogen; and $C_{1-10}$ alkyl, $C_{2-10}$ alkenyl, and $C_{2-10}$ alkynyl, each of which is independently optionally substituted at each occurrence with one or more substituents selected from $L^3$, halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ and $R^8$ are independently selected from: —O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; $C_{1-10}$ alkyl, $C_{2-10}$ alkenyl, $C_{2-10}$ alkynyl, each of which is independently optionally substituted at each occurrence with one or more substituents selected from $L^3$, halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ and $R^8$ is independently optionally substituted with one or more substituents selected from $L^3$, halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^{10}$ is independently selected at each occurrence from $L^3$, hydrogen, —NH$_2$, —C(O)OCH$_2$C$_6$H$_5$; and $C_{1-10}$ alkyl, $C_{2-10}$ alkenyl, $C_{2-10}$ alkynyl, $C_{3-12}$ carbocycle, and 3- to 12-membered heterocycle, each of which is independently optionally substituted at each occurrence with one or more substituents selected from halogen, —CN, —NO$_2$, —NH$_2$, =O, =S, —C(O)OCH$_2$C$_6$H$_5$, —NHC(O)OCH$_2$C$_6$H$_5$, $C_{1-10}$ alkyl, $C_{2-10}$ alkenyl, $C_{2-10}$ alkynyl, $C_{3-12}$ carbocycle, 3- to 12-membered heterocycle, and haloalkyl;

$L^3$ is a linker moiety, wherein at least one of $R^1$, $R^2$, and $R^{10}$ is $L^3$ or at least one substituent on $R^1$, $R^2$, $R^4$, $R^8$, $X^3$ and $X^4$ is -$L^3$; and wherein any substitutable carbon on the benzazepine core is optionally substituted by a substituent selected from halogen, —O$R^{10}$, —S$R^{10}$, —C(O)N($R^{10}$)$_2$—, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), —P(O)(O$R^{10}$)$_2$, —OP(O)(O$R^{10}$)$_2$, —CN, $C_{1-10}$ alkyl, $C_{2-10}$ alkenyl, and $C_{2-10}$ alkynyl, or two substituents on a single carbon atom combine to form a 3- to 7-membered carbocycle.

In some embodiments, for a compound or salt of Formula (IVA), $L^{22}$ can be attached at C2, C3, C4, or C5 of the benzazepine core, wherein the numbering of the benzazepine is as follows:

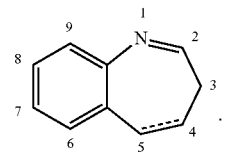

In certain embodiments, for a compound or salt of Formula (IVA), $L^{22}$ is attached to the benzazepine core at C4. In certain embodiments for a compound or salt of Formula (IIA), ------ represents a double bond and $L^{22}$ is attached to the benzazepine core at C4.

In some embodiments for a compound or salt of Formula (IVA), $L^{12}$ can be attached at C6, C7, C8 or C9. In certain embodiments, for a compound or salt of Formula (IVA), $L^{12}$ is attached to the benzazepine core at C8. In certain embodiments for a compound or salt of Formula (IVA), ------ represents a double bond, $L^{22}$ is attached to the benzazepine core at C4 and $L^{12}$ is attached to the benzazepine core at C8.

In some embodiments for a compound or salt of Formula (IVA), the substitutable carbon on the benzazepine core is selected from C2, C3, C4, C5, C6, C7, C8, and C9. The benzazepine core for a compound or salt of Formula (IVA), can be optionally substituted by a substituent selected from halogen, $-OR^{10}$, $-SR^{10}$, $-C(O)N(R^{10})_2-$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-P(O)(OR^{10})_2$, $-OP(O)(OR^{10})_2$, $-CN$, $C_{1-10}$ alkyl, $C_{2-10}$ alkenyl, and $C_{2-10}$ alkynyl, or two substituents on a single carbon atom combine to form a 3- to 7-membered carbocycle. In some embodiments for a compound or salt of Formula (IVA), a moiety at any one of C2, C3, C4, C5, C6, C7, C8, and C9 of the benzazepine core is independently selected from hydrogen, halogen, $-OR^{10}$, $-SR^{10}$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl.

In one embodiment, the compound of Formula (IVA) is represented by Formula (IVB):

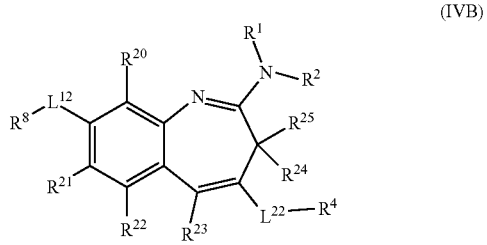

(IVB)

or a pharmaceutically acceptable salt thereof, wherein:

$R^{20}$, $R^{21}$, $R^{22}$, and $R^{23}$ are independently selected from hydrogen, halogen, $-OR^{10}$, $-SR^{10}$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl; and $R^{24}$ and $R^{25}$ are independently selected from hydrogen, halogen, $-OR^{10}$, $-SR^{10}$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, $-CN$, $C_{1-10}$ alkyl, $C_{2-10}$ alkenyl, and $C_{2-10}$ alkynyl; or $R^{24}$ and $R^{25}$ taken together form an optionally substituted saturated $C_{3-7}$ carbocycle.

In certain embodiments, the compound of Formula (IVA) is represented by Formula (IVC):

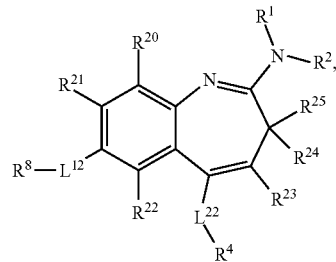

(IVC)

or a pharmaceutically acceptable salt thereof.

In certain embodiments, for a compound or salt of any one of Formulas (IVA), (IVB), and (IVC), $L^{12}$ is selected from $-X^3-$, $-X^3-C_{1-6}$ alkylene-$X^3-$, $-X^3-C_{2-6}$ alkenylene-$X^3-$, and $-X^3-C_{2-6}$ alkynylene-$X^3-$, each of which is optionally substituted on the alkylene, alkenylene and alkyneylene with one or more $R^{12}$.

In certain embodiments, for a compound or salt of any one of Formulas (IVA), (IVB), and (IVC), $L^{22}$ is selected from $-X^4-$, $-X^4-C_{1-6}$ alkylene-$X^4-$, $-X^4-C_{2-6}$ alkenylene-$X^4-$, and $-X^4-C_{2-6}$ alkynylene-$X^4-$, optionally substituted on the alkylene, alkenylene and alkynylene with one or more $R^{12}$.

In some embodiments, for a compound of any one of Formulas (IVA), (IVB), and (IVC), $R^1$ and $R^2$ are independently selected from -$L^3$, hydrogen; $C_{1-10}$ alkyl, $C_{2-10}$ alkenyl, and $C_{2-10}$ alkynyl, each of which is independently optionally substituted at each occurrence with one or more substituents selected from -$L^3$, halogen, $-OR^{10}$, $-SR^{10}$, $-C(O)N(R^{10})_2$, $-N(R^{10})_2$, $-S(O)R^{10}$, $-S(O)_2R^{10}$, $-C(O)R^{10}$, $-C(O)OR^{10}$, $-OC(O)R^{10}$, $-NO_2$, $=O$, $=S$, $=N(R^{10})$, and $-CN$.

In some embodiments, for a compound or salt of Formula (IVA), (IVB) or (IVC), $R^1$ is selected from -$L^3$. In some embodiments, for a compound or salt of Formula (IVA), (IVB) or (IVC), $R^2$ is selected from -$L^3$. In some embodiments, for a compound of any one of Formulas (IVA), (IVB), and (IVC), $R^1$ is -$L^3$ and $R^2$ is hydrogen.

In some embodiments, for a compound or salt of Formula (IVA), (IVB) or (IVC), $L^{12}$ is independently selected from $-X^3-$, $-X^3-C_{1-6}$ alkyl-$X^3-$, $-X^3-C_{2-6}$ alkenyl-$X^3-$, and $-X^3-C_{2-6}$ alkynyl-$X^3-$, each of which is optionally substituted at each occurrence with one or more $R^{10}$. In some embodiments, for a compound or salt of Formula (IVA), (IVB) or (IVC), $L^{12}$ is selected from $-C(O)-$, and $-C(O)NR^{10}-$. In some embodiments, for a compound or salt of Formula (IVA), (IVB) or (IVC), $L^{12}$ is $-C(O)N(R^{10})-$. In some embodiments, for a compound or salt of Formula (IVA), (IVB) or (IVC), $R^{10}$ of $-C(O)N(R^{10})-$ is selected from hydrogen, $C_{1-6}$ alkyl, and -$L^3$. In some embodiments for a compound or salt of Formula (IVA), (IVB) or (IVC), $L^{12}$ is $-C(O)NH-$. In some embodiments for a compound or salt of Formula (IVA), (IVB) or (IVC), $L^{12}$ is $-C(O)N(L^3)-$.

In certain embodiments, for a compound or salt of Formula (IVA), (IVB) or (IVC), $R^4$ and $R^8$ are independently selected from: $-OR^{10}$, $-N(R^{10})_2$, $-C(O)N(R^{10})_2$, $-C(O)R^{10}$, $-C(O)OR^{10}$, $-S(O)R^{10}$, and $-S(O)_2R^{10}$; $C_{1-10}$ alkyl, $C_{2-10}$ alkenyl, $C_{2-10}$ alkynyl, each of which is independently optionally substituted at each occurrence with one or more substituents selected from $L^3$, halogen, $-OR^{10}$, $-SR^{10}$, $-C(O)N(R^{10})_2$, $-N(R^{10})C(O)R^{10}$, $-N(R^{10})C(O)N(R^{10})_2$, $-N(R^{10})_2$, $-C(O)R^{10}$, $-C(O)OR^{10}$, $-OC(O)R^{10}$, —NO₂, =O, =S, =N(R¹⁰), —CN, $C_{3-12}$ carbocycle, and 3- to 12-membered heterocycle; and $C_{3-12}$ carbocycle, and 3- to 12-membered heterocycle, each of which is independently optionally substituted with one or more substituents selected from $L^3$, halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, $C_{1-6}$ alkyl, $C_{2-6}$ alkenyl, and $C_{2-6}$ alkynyl.

In some embodiments, for a compound or salt of Formula (IVA), (IVB) or (IVC), $R^8$ is an optionally substituted 5-6 membered heteroaryl. In some embodiments, $R^8$ is an optionally substituted 5-6 membered heteroaryl, substituted with -$L^3$. $R^8$ may be an optionally substituted pyridine, substituted with -$L^3$.

In some embodiments, for a compound or salt of Formula (IVA), (IVB) or (IVC), $L^{22}$ is independently selected from —$X^4$—, —$X^4$—$C_{1-6}$ alkyl-$X^4$—, —$X^4$—$C_{2-6}$ alkenyl-$X^4$—, and —$X^4$—$C_{2-6}$ alkynyl-$X^4$—, each of which is optionally substituted at each occurrence with one or more $R^{10}$. In some embodiments for a compound or salt of Formula (IVA), (IVB) or (IVC), $L^{22}$ is selected from —C(O)—, and —C(O)NR¹⁰—. $L^{22}$ may be —C(O)—. In some embodiments, $L^{22}$ is —C(O)NR¹⁰—, wherein, $R^{10}$ of —C(O)NR¹⁰— may be selected from hydrogen, $C_{1-6}$ alkyl, and -$L^3$. In some embodiments, $L^{22}$ is —C(O)NH—. In certain embodiments, $L^{12}$ is —C(O)N($L^3$)-.

In some embodiments, for a compound of Formulas (IVA), (IVB) or (IVC), $R^4$ is selected from: —OR¹⁰, —N(R¹⁰)₂, —C(O)N(R¹⁰)₂, —C(O)R¹⁰, —C(O)OR¹⁰, —S(O)R¹⁰, and —S(O)₂R¹⁰; $C_{1-10}$ alkyl, $C_{2-10}$ alkenyl, $C_{2-10}$ alkynyl, each of which is independently optionally substituted at each occurrence with one or more substituents selected from -$L^3$, halogen, —OR¹⁰, —SR¹⁰, —C(O)N(R¹⁰)₂, —N(R¹⁰)C(O)R¹⁰, —N(R₁₀)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, $C_{3-12}$ carbocycle, and 3- to 12-membered heterocycle; and $C_{3-12}$ carbocycle, and 3- to 12-membered heterocycle, wherein each $C_{3-12}$ carbocycle, and 3- to 12-membered heterocycle in $R^4$ is independently optionally substituted with one or more substituents selected from -$L^3$, halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, $C_{1-6}$ alkyl, $C_{2-6}$ alkenyl, and $C_{2-6}$ alkynyl. In some embodiments, $R^4$ is selected from: —OR¹⁰, and —N(R¹⁰)₂; and $C_{1-10}$ alkyl, $C_{2-10}$ alkenyl, $C_{2-10}$ alkynyl, $C_{3-12}$ carbocycle, 3- to 12-membered heterocycle, aryl, and heteroaryl, each of which is independently optionally substituted at each occurrence with one or more substituents selected from -$L^3$, halogen, —OR¹⁰, —SR¹⁰, —N(R¹⁰)₂, —S(O)R¹⁰, —S(O)₂R¹⁰, —C(O)R¹⁰, —C(O)OR¹⁰, —OC(O)R¹⁰, —NO₂, =O, =S, =N(R¹⁰), —CN, $C_{1-10}$ alkyl, $C_{2-10}$ alkenyl, and $C_{2-10}$ alkynyl. In some embodiments, for a compound or salt of Formula (IVA), (IVB) or (IVC), $R^{10}$ of —N(R¹⁰)₂ is selected from -$L^3$ and hydrogen, and wherein at least one $R^{10}$ of —N(R¹⁰)₂ is -$L^3$.

In certain embodiments, for a compound or salt of Formula (IVA), (IVB) or (IVC), $R^4$ is selected from: —OR¹⁰, —N(R¹⁰)₂, —C(O)N(R¹⁰)₂, —C(O)R¹⁰, —C(O)OR¹⁰, —S(O)R¹⁰, and —S(O)₂R¹⁰; and $C_{1-10}$ alkyl, $C_{2-10}$ alkenyl, and $C_{2-10}$ alkynyl, each of which is independently optionally substituted at each occurrence with one or more substituents selected from $L^3$, halogen, —OR¹⁰, —SR¹⁰, —C(O)N(R¹⁰)₂, —N(R¹⁰)C(O)R¹⁰, —N(R¹⁰)C(O)N(R¹⁰)₂, —N(R¹⁰)₂, —C(O)R¹⁰, —C(O)OR¹⁰, —OC(O)R¹⁰, —NO₂, =O, =S, =N(R¹⁰), —CN, $C_{3-12}$ carbocycle, and 3- to 12-membered heterocycle.

In certain embodiments, for a compound or salt of Formula (IA), (IB), (IC), (IIA), (IIB), (IIC), (IIIA), (IIIB), (IIIC), (IVA), (IVB) or (IVC), $L^3$ is a noncleavable linker. In some embodiments, for a compound or salt of Formula (IVA), (IVB) or (IVC), $L^3$ is cleavable linker such as a linker cleavable by a lysosomal enzyme.

In certain embodiments, a moiety described herein includes the symbol ⸺ which indicates the point of attachment, e.g., the point of attachment of a chemical moiety to the remainder of the compound, the point of attachment of a linker to a compound of the disclosure, or the point of attachment of a linker to an antibody construct, as described herein.

Some examplary linkers ($L^3$) are described in the following paragraphs and additional linkers are described in the subsequent section entitled "Linkers". In some embodiments for a compound or salt of Formula (IA), (IB), (IC), (IIA), (IIB), (IIC), (IIIA), (IIIB), (IIIC), (IVA), (IVB) or (IVC), -$L^3$ is represented by the formula:

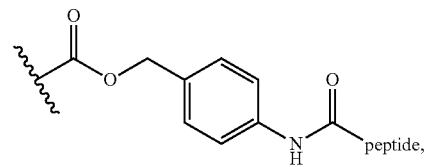

wherein peptide is a group comprising from one to ten amino acids.

In some embodiments for a compound or salt of Formula (IA), (IB), (IC), (IIA), (IIB), (IIC), (IIIA), (IIIB), (IIIC), (IVA), (IVB) or (IVC), -$L^3$ is represented by the formula:

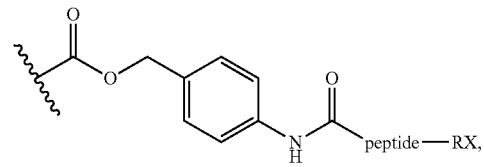

wherein peptide is a group comprising from one to ten amino acids and RX is a reactive moiety, and ⸺

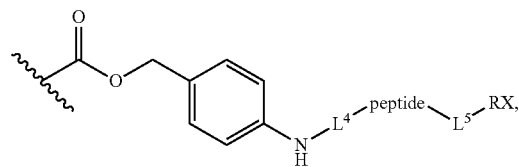

in which $L^4$ represents the C-terminus of the peptide and $L^5$ is selected from a bond, alkylene and heteroalkylene, wherein $L^5$ is optionally substituted with one or more groups independently selected from $R^{32}$, RX is a reactive moiety; and $R^{32}$ is independently selected at each occurrence from halogen, —OH, —CN, —O-alkyl, —SH, =O, =S, —NH₂, —NO₂; and $C_{1-10}$ alkyl, $C_{2-10}$ alkenyl, and $C_{2-10}$ alkynyl, each of which is independently optionally substituted at each occurrence with one or more substituents selected from halogen, —OH, —CN, —O-alkyl, —SH, =O, =S, —NH₂, and —NO₂.

In certain embodiments, for a compound of any one of Formulas (IA), (IB), (IC), (IIA), (IIB), (IIC), (IIIA), (IIIB), (IIIC), (IVA), (IVB) or (IVC), -L³ is represented by the formula:

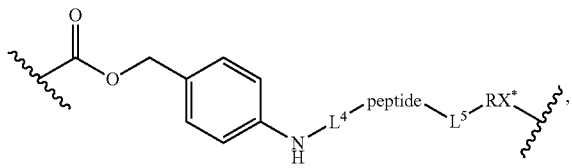

in which L⁴ represents the C-terminal of the peptide and L⁵ is selected from a bond, alkylene and heteroalkylene, wherein L⁵ is optionally substituted with one or more groups independently selected from $R^{32}$; RX* is a bond, a succinimide moiety, or a hydrolyzed succinimide moiety bound to a residue of an antibody construct, wherein 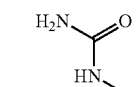 on RX* represents the point of attachment to the residue of the antibody construct; and, $R^{32}$ is independently selected at each occurrence from halogen, —OH, —CN, —O— alkyl, —SH, =O, =S, —NH₂, —NO₂; and $C_{1-10}$ alkyl, $C_{2-10}$ alkenyl, and $C_{2-10}$ alkynyl, each of which is independently optionally substituted at each occurrence with one or more substituents selected from halogen, —OH, —CN, —O-alkyl, —SH, =O, =S, —NH₂, and —NO₂. The reactive moiety may be selected from an electrophile, e.g., an α,β-unsaturated carbonyl, such as a maleimide, and a leaving group.

In some embodiments for a compound or salt of Formula (IA), (IB), (IC), (IIA), (IIB), (IIC), (IIIA), (IIIB), (IIIC), (IVA), (IVB) or (IVC), -L³ is represented by the formula:

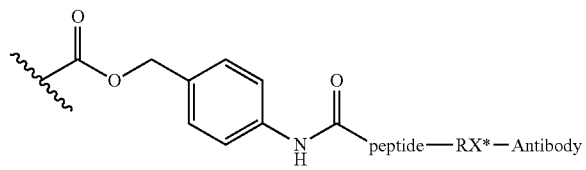

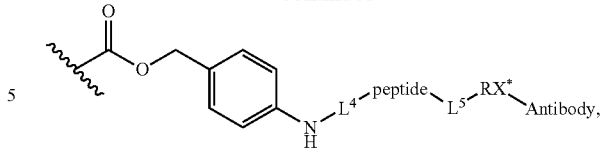

in which L⁴ represents the C-terminal of the peptide and L⁵ is selected from a bond, alkylene and heteroalkylene, wherein L⁵ is optionally substituted with one or more groups independently selected from $R^{32}$; RX* is a bond, a succinimide moiety, or a hydrolyzed succinimide moiety bound to a residue of an antibody construct, wherein Antibody is an antibody construct; and, $R^{32}$ is independently selected at each occurrence from halogen, —OH, —CN, —O-alkyl, —SH, =O, =S, —NH₂, —NO₂; and $C_{1-10}$ alkyl, $C_{2-10}$ alkenyl, and $C_{2-10}$ alkynyl, each of which is independently optionally substituted at each occurrence with one or more substituents selected from halogen, —OH, —CN, —O-alkyl, —SH, =O, =S, —NH₂, and —NO₂. L³ may be represented by the formula:

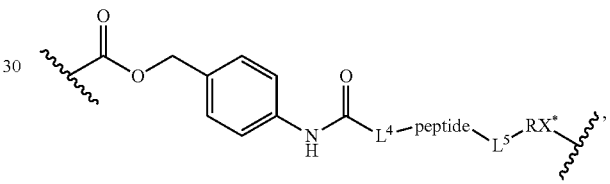

wherein L⁴ and L⁵ are independently selected from a bond, an alkylene and a heteroalkylene, each of which is optionally substituted with one or more groups independently selected from $R^{12}$; ⸺ on the left represents the point of attachment to the remainder of the compound, RX* is a bond, a succinimide moiety, or a hydrolyzed succinimide moiety attached at the ⸺ on the right to a residue of an antibody construct; peptide is a group comprising from one to 10 amino acids.

In some embodiments, the compound is:

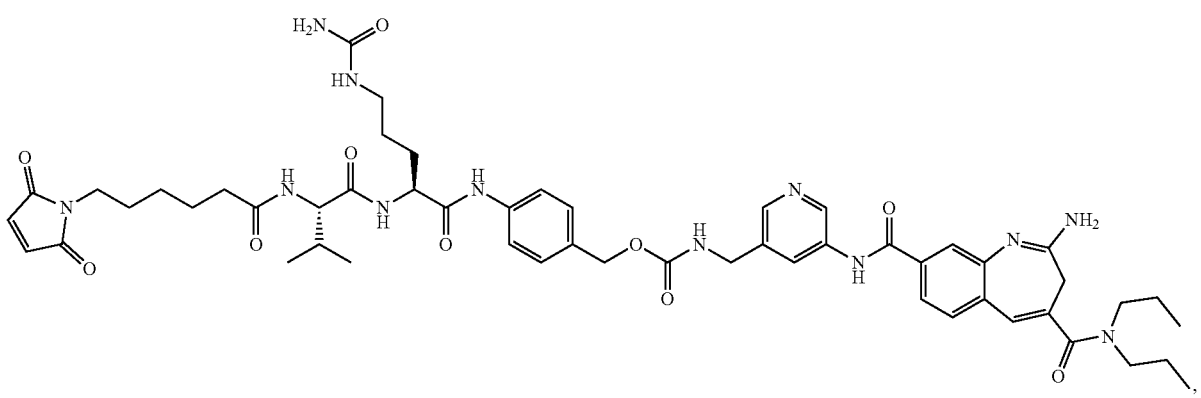 [SMILES: CCCN(CCC)C(=O)C1=Cc2ccc(C(=O)Nc3cncc(CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1]

or a salt thereof.

In some embodiments for a compound or salt of Formula (IA), (IB), (IC), (IIA), (IIB), (IIC), (IIIA), (IIIB), (IIIC), (IVA), (IVB) or (IVC), -L³ is represented by the formula:

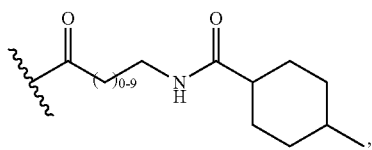

and ⁏ represents the point of attachment to the remainder of the compound.

In some embodiments for a compound or salt of Formula (IA), (IB), (IC), (IIA), (IIB), (IIC), (IIIA), (IIIB), (IIIC), (IVA), (IVB) or (IVC), -L³ is represented by the formula:

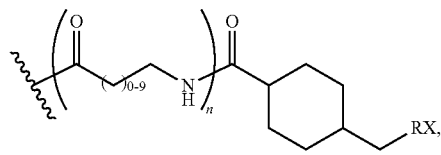

wherein RX comprises a reactive moiety, e.g., a maleimide or a leaving group, n=0-9 and ⁏ represents the point of attachment to the remainder of the compound.

In some embodiments, for a compound or salt of Formula (IA), (IB), (IC), (IIA), (IIB), (IIC), (IIIA), (IIIB), (IIIC), (IVA), (IVB) or (IVC), -L³ is represented by the formula:

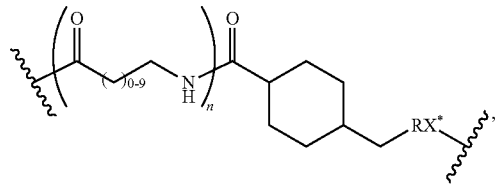

RX* is a bond, a succinimide moiety, or a hydrolyzed succinimide moiety attached at the ⁏ on the right to a residue of an antibody construct, n=0-9 and ⁏ on the left represents the point of attachment to the remainder of the compound.

In certain embodiments, the compound is:

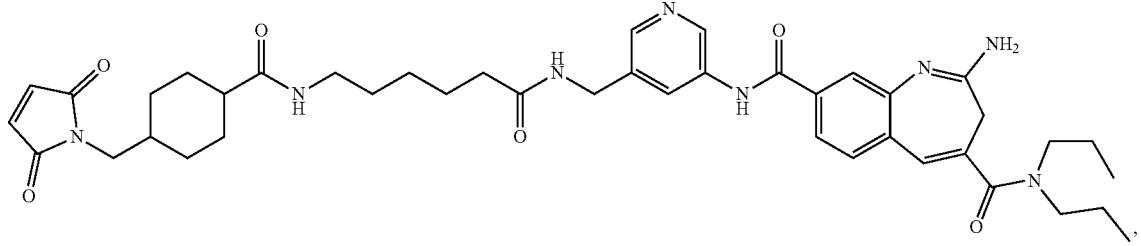 [SMILES: CCCN(CCC)C(=O)C1=Cc2ccc(C(=O)Nc3cncc(CNC(=O)CCCCCNC(=O)C4CCC(CN5C(=O)C=CC5=O)CC4)c3)cc2N=C(N)C1]

or a salt thereof.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

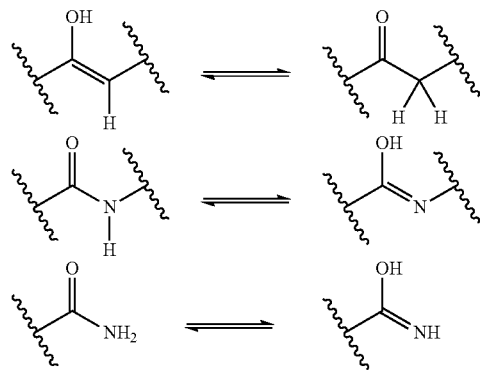

-continued

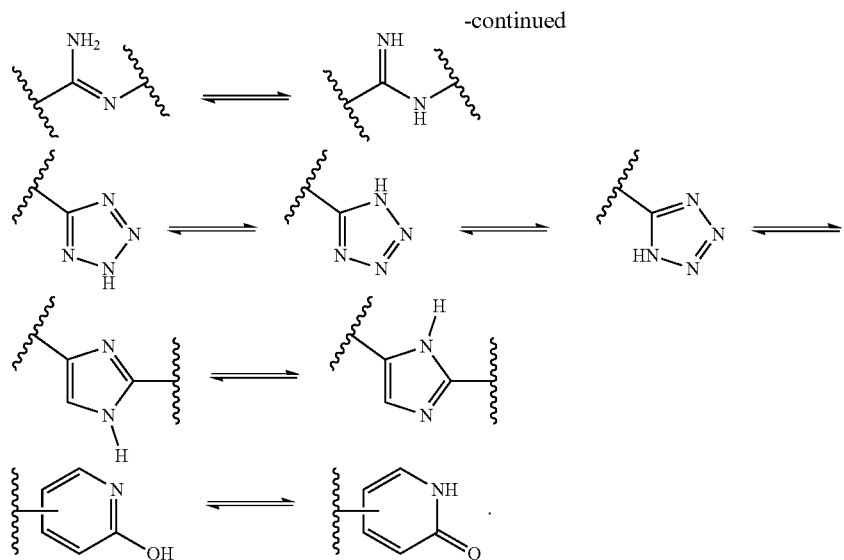

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, and $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

In some aspects, the present disclosure provides a method for treating cancer. In some embodiments, the present disclosure provides a method comprising administering a conjugate, compound or salt of Formula (IA), (IB), (IC), (IIA), (IIB), (IIC), (IIIA), (IIIB), (IIIC), (IVA), (IVB), or (IVC) to a subject in need thereof.

In some aspects, the compounds of the disclosure exhibit selective binding or agonizing properties for one receptor over another receptor. In some embodiments, a compound described herein selectively binds or modulates the activity of one toll-like receptor over another, e.g., TLR8 and TLR7. For example, a compound or salt of Formula (IA), (IB), (IC), (IIA), (IIB), (IIC), (IIIA), (IIIB), (IIIC), (IVA), (IVB), or (IVC) may have weaker binding to TLR7 as compared to TLR8, as measured by the $K_d$ values, e.g., a compound's $K_d$ for TLR7 is two times or greater than two times the $K_d$ for TLR8, or an order of magnitude or greater, or even two orders of magnitude or greater than the $K_d$ for TLR8. In certain embodiments, a compound or salt of of Formula (IA), (IB), (IC), (IIA), (IIB), (IIC), (IIIA), (IIIB), (IIIC), (IVA), (IVB), or (IVC) has greater activity for one toll-like receptor over another, e.g., TLR8 and TLR7. In certain embodiments, a compound of the disclosure agonizes TLR8 with an $EC_{50}$ of 500 nM or less while the same compound agonizes TLR7 with an $ED_{50}$ of greater than 1 µM. In certain embodiments, a compound of the disclosure agonizes TLR8 with at least an $EC_{50}$ of an order of magnitude or even two orders of magnituge less than the amount of the same compound required to show an agonizing effect on TLR7.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds of any one of Formulas (IA), (IB), (IC), (IIA), (IIB), (IIC), (IIIA), (IIIB), (IIIC), (IVA), (IVB), or (IVC) may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound of any one of Formulas (IA), (IB), (IC), (IIA), (IIB), (IIC), (IIIA), (IIIB), (IIIC), (IVA), (IVB), or (IVC) as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Linkers

The compounds and salts described herein may be bound to a linker also referred to herein as $L^3$, e.g., a peptide linker. In certain embodiments, the linker is also bound to an antibody construct and referred to as an antibody construct conjugate or conjugate. Linkers of the conjugates described herein may not affect the binding of active portions of a conjugate, e.g., the antigen binding domains, Fc domains, target binding domains, antibodies, agonists or the like, to a target, which can be a cognate binding partner such as an antigen. A conjugate can comprise multiple linkers, each having one or more compounds attached. These linkers can be the same linkers or different linkers. Some examplary linkers ($L^3$) are described in the preceding section entitled "Compounds" and additional linkers are described in this section.

A linker can be short, flexible, rigid, cleavable, non-cleavable, hydrophilic, or hydrophobic. A linker can contain segments that have different characteristics, such as segments of flexibility or segments of rigidity. The linker can be chemically stable to extracellular environments, for example, chemically stable in the blood stream, or may include linkages that are not stable or selectively stable. The linker can include linkages that are designed to cleave and/or immolate or otherwise breakdown specifically or non-specifically inside cells. A cleavable linker can be sensitive to enzymes. A cleavable linker can be cleaved by enzymes such as proteases. A cleavable linker may comprise a valine-citrulline linker or a valine-alanine peptide. A valine-citrulline- or valine-alanine-containing linker can contain a pentafluorophenyl group. A valine-citrulline- or valine-alanine-containing linker can contain a maleimide or succinimide group. A valine-citrulline- or valine-alanine-containing linker can contain a para aminobenzyl alcohol (PABA) group or para-aminobenzyl carbamate (PABC).

A valine-citrulline- or valine-alanine-containing linker can contain a PABA group and a pentafluorophenyl group. A valine-citrulline- or valine-alanine-containing linker can contain a PABA group and a maleimide or succinimide group.

A non-cleavable linker can be protease insensitive. A non-cleavable linker can be maleimidocaproyl linker. A maleimidocaproyl linker can comprise N-maleimidomethylcyclohexane-1-carboxylate. A maleimidocaproyl linker can contain a succinimide group. A maleimidocaproyl linker can contain pentafluorophenyl group. A linker can be a combination of a maleimidocaproyl group and one or more polyethylene glycol molecules. A linker can be a maleimide-PEG4 linker. A linker can be a combination of a maleimidocaproyl linker containing a succinimide group and one or more polyethylene glycol molecules. A linker can be a combination of a maleimidocaproyl linker containing a pentafluorophenyl group and one or more polyethylene glycol molecules. A linker can contain maleimides linked to polyethylene glycol molecules in which the polyethylene glycol can allow for more linker flexibility or can be used lengthen the linker. A linker can be a (maleimidocaproyl)-(valine-citrulline)-(para-aminobenzyloxycarbonly) linker. A linker can be a linker suitable for attachment to an engineered cysteine (THIOMAB). A THIOMAB linker can be a (maleimidocaproyl)-(valine-citrulline)-(para-aminobenzyloxycarbonly)-linker.

A linker can also comprise alkylene, alkenylene, alkynylene, polyether, polyester, polyamide group(s) and also, polyamino acids, polypeptides, cleavable peptides, or aminobenzylcarbamates. A linker can contain a maleimide at one end and an N-hydroxysuccinimidyl ester at the other end. A linker can contain a lysine with an N-terminal amine acetylated, and a valine-citrulline cleavage site. A linker can be a link created by a microbial transglutaminase, wherein the link can be created between an amine-containing moiety and a moiety engineered to contain glutamine as a result of the enzyme catalyzing a bond formation between the acyl group of a glutamine side chain and the primary amine of a lysine chain. A linker can contain a reactive primary amine. A linker can be a Sortase A linker. A Sortase A linker can be created by a Sortase A enzyme fusing an LPXTG recognition motif (SEQ ID NO: 25) to an N-terminal GGG motif to regenerate a native amide bond. The linker created can therefore link a moiety attached to the LPXTG recognition motif (SEQ ID NO: 25) with a moiety attached to the N-terminal GGG motif.

In the conjugates described herein, a compound or salt of any one of Formulas (IA), (IB), (IC), (IIA), (IIB), (IIC), (IIIA), (IIIB), (IIIC), (IVA), (IVB), or (IVC) is linked to the antibody construct by way of a linker(s), also referred to herein as $L^3$. $L^3$, as used herein, may be selected from any of the linker moieties discussed herein. The linker linking the compound or salt to the antibody construct of a conjugate may be short, long, hydrophobic, hydrophilic, flexible or rigid, or may be composed of segments that each independently have one or more of the above-mentioned properties such that the linker may include segments having different properties. The linkers may be polyvalent such that they covalently link more than one compound or salt to a single site on the antibody construct, or monovalent such that covalently they link a single compound or salt to a single site on the antibody construct.

Linkers of the disclosure ($L^3$) may have from about 10 to about 500 atoms in a linker, such as from about 10 to about 400 atoms, such as about 10 to about 300 atoms in a linker. In certain embodiments, linkers of the disclosure have from about 30 to about 400 atoms, such as from about 30 to about 300 atoms in the linker.

As will be appreciated by skilled artisans, the linkers may link a compound or salt of any one of Formulas (IA), (IB), (IC), (IIA), (IIB), (IIC), (IIIA), (IIIB), (IIIC), (IVA), (IVB), or (IVC) to the antibody construct by a covalent linkages between the linker and the antibody construct and compound. As used herein, the expression "linker" is intended to include (i) unconjugated forms of the linker that include a functional group capable of covalently linking the linker to a benzazepine compound(s) and a functional group capable of covalently linking the linker to an antibody construct; (ii) partially conjugated forms of the linker that include a functional group capable of covalently linking the linker to an antibody construct and that is covalently linked to a compound(s) or salt(s) of any one of Formulas (IA), (IB), (IC), (IIA), (IIB), (IIC), (IIIA), (IIIB), (IIIC), (IVA), (IVB), or (IVC), or vice versa; and (iii) fully conjugated forms of the linker that is covalently linked to both a compound(s) or salt(s) of any one of Formulas (IA), (IB), (IC), (IIA), (IIB), (IIC), (IIIA), (IIIB), (IIIC), (IVA), (IVB), or (IVC) and an antibody construct. One embodiment pertains to a conjugate formed by contacting an antibody construct that binds a cell surface receptor or tumor associated antigen expressed on a tumor cell with a linker-compound described herein under conditions in which the linker-compound covalently links to the antibody construct. One embodiment pertains to a method of making a conjugate formed by contacting a linker-compound described herein under conditions in which the linker-compound covalently links to the antibody construct. One embodiment pertains to a method of stimulating immune activity in a cell that expresses CD40, comprising contacting the cell with a conjugate described herein that is capable of binding the cell, under conditions in which the conjugate binds the cell.

Exemplary polyvalent linkers that may be used to link many benzazepine compounds to an antibody construct are described. For example, Fleximer® linker technology has the potential to enable high-DAR conjugates with good physicochemical properties. As shown below, the Fleximer® linker technology is based on incorporating drug molecules into a solubilizing poly-acetal backbone via a sequence of ester bonds. The methodology renders highly-loaded conjugates (DAR up to 20) whilst maintaining good physicochemical properties. This methodology could be utilized with a benzazepine compound as shown in the Scheme below.

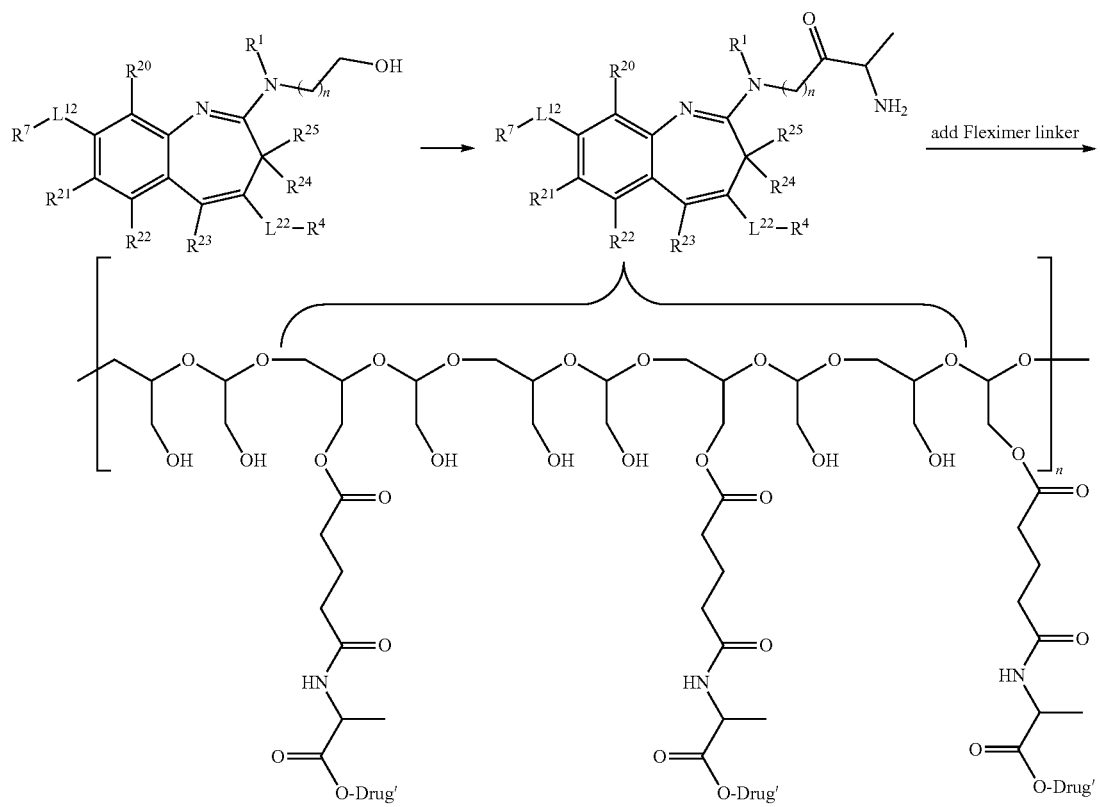

To utilize the Fleximer® linker technology depicted in the scheme above, an aliphatic alcohol can be present or introduced into the benzazepine compound. The alcohol moiety is then conjugated to an alanine moiety, which is then synthetically incorporated into the Fleximer® linker. Liposomal processing of the conjugate in vitro releases the parent alcohol-containing drug.

By way of example and not limitation, some cleavable and noncleavable linkers that may be included in the conjugates described herein are described below.

Cleavable linkers can be cleavable in vitro and in vivo. Cleavable linkers can include chemically or enzymatically unstable or degradable linkages. Cleavable linkers can rely on processes inside the cell to liberate a benzazepine compound, such as reduction in the cytoplasm, exposure to acidic conditions in the lysosome, or cleavage by specific proteases or other enzymes within the cell. Cleavable linkers can incorporate one or more chemical bonds that are either chemically or enzymatically cleavable while the remainder of the linker can be non-cleavable.

A linker can contain a chemically labile group such as hydrazone and/or disulfide groups.

Linkers comprising chemically labile groups can exploit differential properties between the plasma and some cytoplasmic compartments. The intracellular conditions that can facilitate benzazepine compound release for hydrazone containing linkers can be the acidic environment of endosomes and lysosomes, while the disulfide containing linkers can be reduced in the cytosol, which can contain high thiol concentrations, e.g., glutathione. The plasma stability of a linker containing a chemically labile group can be increased by introducing steric hindrance using substituents near the chemically labile group.

Acid-labile groups, such as hydrazone, can remain intact during systemic circulation in the blood's neutral pH environment (pH 7.3-7.5) and can undergo hydrolysis and can release the benzazepine compound once the antibody construct benzazepine compound conjugate is internalized into mildly acidic endosomal (pH 5.0-6.5) and lysosomal (pH 4.5-5.0) compartments of the cell. This pH dependent release mechanism can be associated with nonspecific release of the drug. To increase the stability of the hydrazone group of the linker, the linker can be varied by chemical modification, e.g., substitution, allowing tuning to achieve more efficient release in the lysosome with a minimized loss in circulation.

Hydrazone-containing linkers can contain additional cleavage sites, such as additional acid-labile cleavage sites and/or enzymatically labile cleavage sites. Antibody construct benzazepine compound conjugates including exemplary hydrazone-containing linkers can include, for example, the following structures:

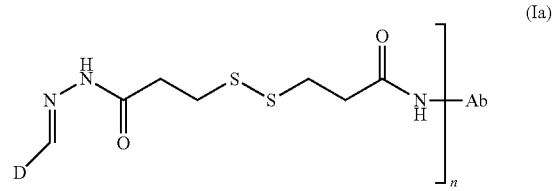

(Ia)

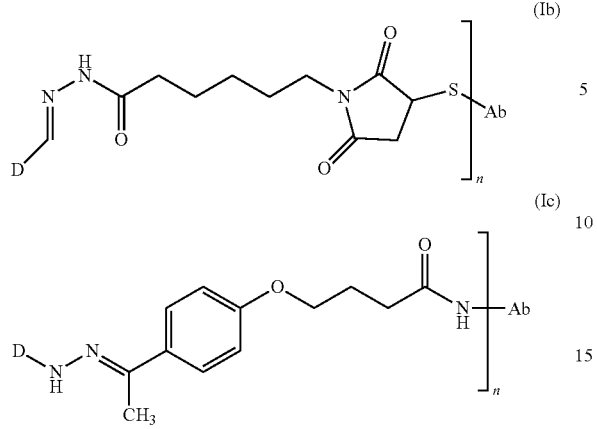

(Ib)

(Ic)

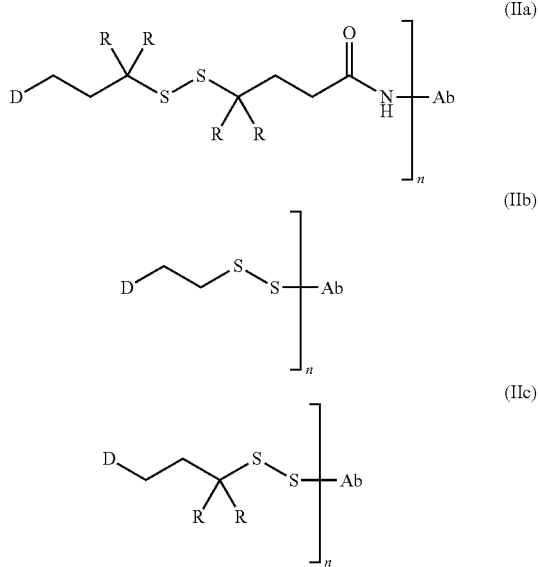

(IIa)

(IIb)

(IIc)

wherein D is a compound or salt of any one of Formulas (IA), (IB), (IC), (IIA), (IIB), (IIC), (IIIA), (IIIB), (IIIC) and Ab is an antibody construct, respectively, and n represents the number of compound-bound linkers (LP) bound to the antibody construct. In certain linkers, such as linker (Ia), the linker can comprise two cleavable groups, a disulfide and a hydrazone moiety. For such linkers, effective release of the unmodified free benzazepine compound can require acidic pH or disulfide reduction and acidic pH. Linkers such as (Ib) and (Ic) can be effective with a single hydrazone cleavage site.

Other acid-labile groups that can be included in linkers include cis-aconityl-containing linkers. cis-Aconityl chemistry can use a carboxylic acid juxtaposed to an amide bond to accelerate amide hydrolysis under acidic conditions.

Cleavable linkers can also include a disulfide group. Disulfides can be thermodynamically stable at physiological pH and can be designed to release the benzazepine compound upon internalization inside cells, wherein the cytosol can provide a significantly more reducing environment compared to the extracellular environment. Scission of disulfide bonds can require the presence of a cytoplasmic thiol cofactor, such as (reduced) glutathione (GSH), such that disulfide-containing linkers can be reasonably stable in circulation, selectively releasing the benzazepine compound in the cytosol. The intracellular enzyme protein disulfide isomerase, or similar enzymes capable of cleaving disulfide bonds, can also contribute to the preferential cleavage of disulfide bonds inside cells. GSH can be present in cells in the concentration range of 0.5-10 mM compared with a significantly lower concentration of GSH or cysteine, the most abundant low-molecular weight thiol, in circulation at approximately 5 µM. Tumor cells, where irregular blood flow can lead to a hypoxic state, can result in enhanced activity of reductive enzymes and therefore even higher glutathione concentrations. The in vivo stability of a disulfide-containing linker can be enhanced by chemical modification of the linker, e.g., use of steric hindrance adjacent to the disulfide bond.

Antibody construct benzazepine compound conjugates including exemplary disulfide-containing linkers can include the following structures:

wherein D is a compound or salt of any one of Formulas (IA), (IIA), (IB), (IIB), (IIIA), and (IIIB) and Ab is an antibody construct, respectively, n represents the number of compounds bound to linkers ($L^3$) bound to the antibody construct and R is independently selected at each occurrence from hydrogen or alkyl, for example. Increasing steric hindrance adjacent to the disulfide bond can increase the stability of the linker. Structures such as (IIa) and (IIc) can show increased in vivo stability when one or more R groups is selected from a lower alkyl such as methyl.

Another type of linker that can be used is a linker that is specifically cleaved by an enzyme. For example, the linker can be cleaved by a lysosomal enzyme. Such linkers can be peptide-based or can include peptidic regions that can act as substrates for enzymes. Peptide based linkers can be more stable in plasma and extracellular milieu than chemically labile linkers.

Peptide bonds can have good serum stability, as lysosomal proteolytic enzymes can have very low activity in blood due to endogenous inhibitors and the unfavorably high pH value of blood compared to lysosomes. Release of a benzazepine compound from an antibody construct can occur due to the action of lysosomal proteases, e.g., cathepsin and plasmin. These proteases can be present at elevated levels in certain tumor tissues. The linker can be cleavable by a lysosomal enzyme. The lysosomal enzyme can be, for example, cathepsin B, cathepsin S, β-glucuronidase, or β-galactosidase.

The cleavable peptide can be selected from tetrapeptides such as Gly-Phe-Leu-Gly (SEQ ID NO: 26), Ala-Leu-Ala-Leu (SEQ ID NO: 27) or dipeptides such as Val-Cit, Val-Ala, and Phe-Lys. Dipeptides can have lower hydrophobicity compared to longer peptides.

A variety of dipeptide-based cleavable linkers can be used in the antibody constructs benzazepine compound conjugates described herein.

Enzymatically cleavable linkers can include a self-immolative spacer to spatially separate the benzazepine compound from the site of enzymatic cleavage. The direct attachment of a benzazepine compound to a peptide linker can result in proteolytic release of the benzazepine compound or of an amino acid adduct of the benzazepine compound, thereby impairing its activity. The use of a self-immolative spacer can allow for the elimination of the fully active, chemically unmodified benzazepine compound upon amide bond hydrolysis.

One self-immolative spacer can be a bifunctional para-aminobenzyl alcohol group, which can link to the peptide through the amino group, forming an amide bond, while amine containing benzazepine compounds can be attached through carbamate functionalities to the benzylic hydroxyl group of the linker (to give ap-amidobenzylcarbamate, PABC). The resulting pro-benzazepine compound can be activated upon protease-mediated cleavage, leading to a 1,6-elimination reaction releasing the unmodified benzazepine compound, carbon dioxide, and remnants of the linker. The following scheme depicts the fragmentation of p-amidobenzyl carbamate and release of the benzazepine compound:

The enzymatically cleavable linker can be a β-glucuronic acid-based linker. Facile release of the benzazepine compound can be realized through cleavage of the β-glucuronide glycosidic bond by the lysosomal enzyme β-glucuronidase. This enzyme can be abundantly present within lysosomes and can be overexpressed in some tumor types, while the enzyme activity outside cells can be low. β-Glucuronic acid-based linkers can be used to circumvent the tendency of an antibody construct benzazepine compound conjugate to undergo aggregation due to the hydrophilic nature of β-glucuronides. In certain embodiments, β-glucuronic acid-based linkers can link an antibody construct to a hydrophobic benzazepine compound. The following scheme depicts the release of a benzazepine compound (D) from an antibody construct benzazepine compound conjugate containing a β-glucuronic acid-based linker:

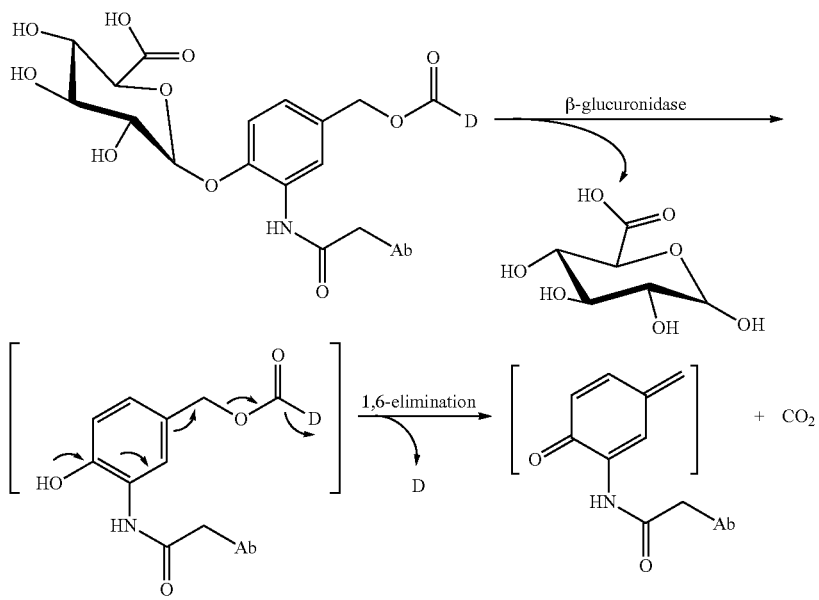

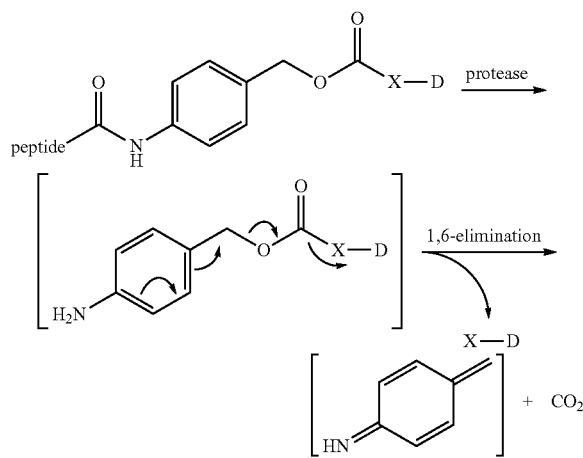

wherein X-D represents the unmodified benzazepine compound.

Heterocyclic variants of this self-immolative group have also been described.

wherein Ab indicates the antibody construct.

A variety of cleavable β-glucuronic acid-based linkers useful for linking drugs such as auristatins, camptothecin and doxorubicin analogues, CBI minor—groove binders, and psymberin to antibodies have been described. These β-glucuronic acid-based linkers may be used in the conjugates described herein. In certain embodiments, the enzymatically cleavable linker is a β-galactoside-based linker. β-Galactoside is present abundantly within lysosomes, while the enzyme activity outside cells is low.

Additionally, benzazepine compounds containing a phenol group can be covalently bonded to a linker through the phenolic oxygen. One such linker relies on a methodology in which a diamino-ethane "Space Link" is used in conjunction with traditional "PABO"-based self-immolative groups to deliver phenols.

Cleavable linkers can include non-cleavable portions or segments, and/or cleavable segments or portions can be included in an otherwise non-cleavable linker to render it cleavable. By way of example only, polyethylene glycol (PEG) and related polymers can include cleavable groups in the polymer backbone. For example, a polyethylene glycol or polymer linker can include one or more cleavable groups such as a disulfide, a hydrazone or a dipeptide.

Other degradable linkages that can be included in linkers can include ester linkages formed by the reaction of PEG carboxylic acids or activated PEG carboxylic acids with alcohol groups on a benzazepine compound, wherein such ester groups can hydrolyze under physiological conditions to release the benzazepine compound. Hydrolytically degradable linkages can include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

A linker can contain an enzymatically cleavable peptide moiety, for example, a linker comprising structural formula (IIIa), (IIIb), (IIIc), or (IIId):

alkyl-$(O)_r$—$(C_{1-4}$ alkylene$)_s$-$G^1$ or $C_{1-4}$ alkyl-(N)—$[(C_{1-4}$ alkylene)-$G^1]_2$; $R^z$ is $C_{1-4}$ alkyl-$(O)_r(C_{1-4}$ alkylene$)_s$-$G^2$; $G^1$ is $SO_3H$, $CO_2H$, PEG 4-32, or a sugar moiety; $G^2$ is $SO_3H$, $CO_2H$, or a PEG 4-32 moiety; r is 0 or 1; s is 0 or 1; p is an integer ranging from 0 to 5; q is 0 or 1; x is 0 or 1; y is 0 or 1; ∤ represents the point of attachment of the linker to a compound or salt of any one of Formulas (IA), (IB), (IC), (IIA), (IIB), (IIC), (IIIA), (IIIB), or (IIIC); and * represents the point of attachment to the remainder of the linker.

In certain embodiments, the peptide can be selected from natural amino acids, unnatural amino acids or combinations thereof. In certain embodiments, the peptide can be selected from a tripeptide or a dipeptide. In particular embodiments, the dipeptide can comprise L-amino acids and be selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Lys-Phe; Val-Lys; Lys-Val; Ala-Lys; Lys-Ala; Phe-Cit; Cit-

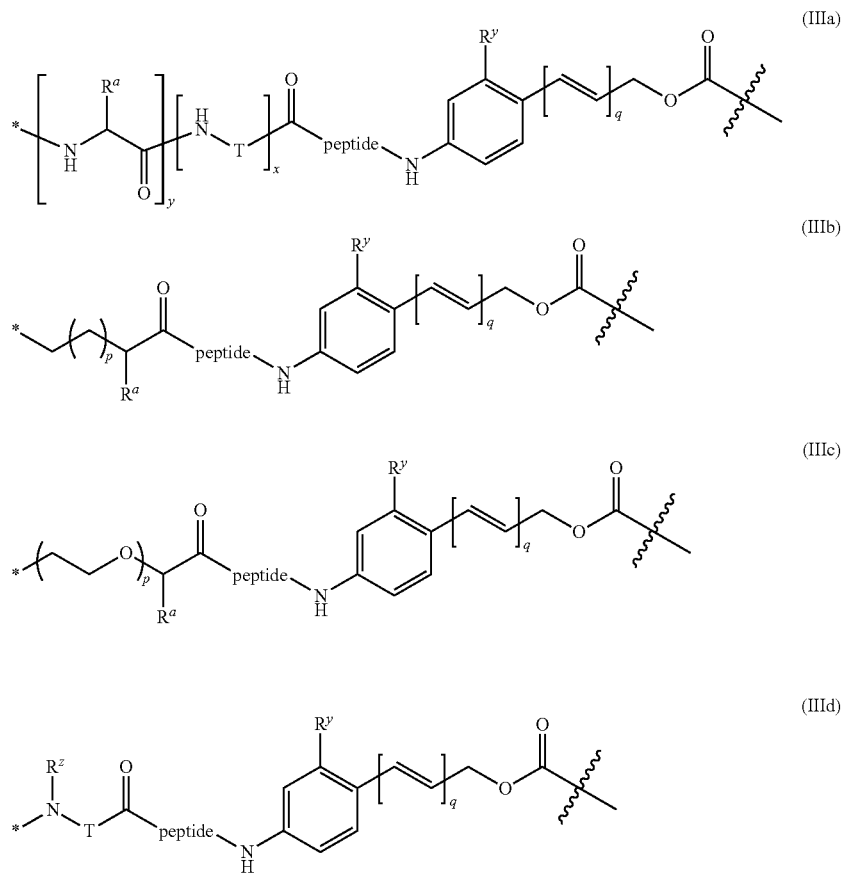

or a salt thereof, wherein: "peptide" represents a peptide (illustrated in N→C orientation, wherein peptide includes the amino and carboxy "termini") that is cleavable by a lysosomal enzyme; T represents a polymer comprising one or more ethylene glycol units or an alkylene chain, or combinations thereof; $R^a$ is selected from hydrogen, alkyl, sulfonate and methyl sulfonate; $R^Y$ is hydrogen or $C_{1-4}$ Phe; Leu-Cit; Cit-Leu; Ile-Cit; Cit-Ile; Phe-Arg; Arg-Phe; Cit-Trp; and Trp-Cit, or salts thereof.

Exemplary embodiments of linkers according to structural formula (IIIa) are illustrated below (as illustrated, the linkers include a reactive group suitable for covalently linking the linker to an antibody construct):

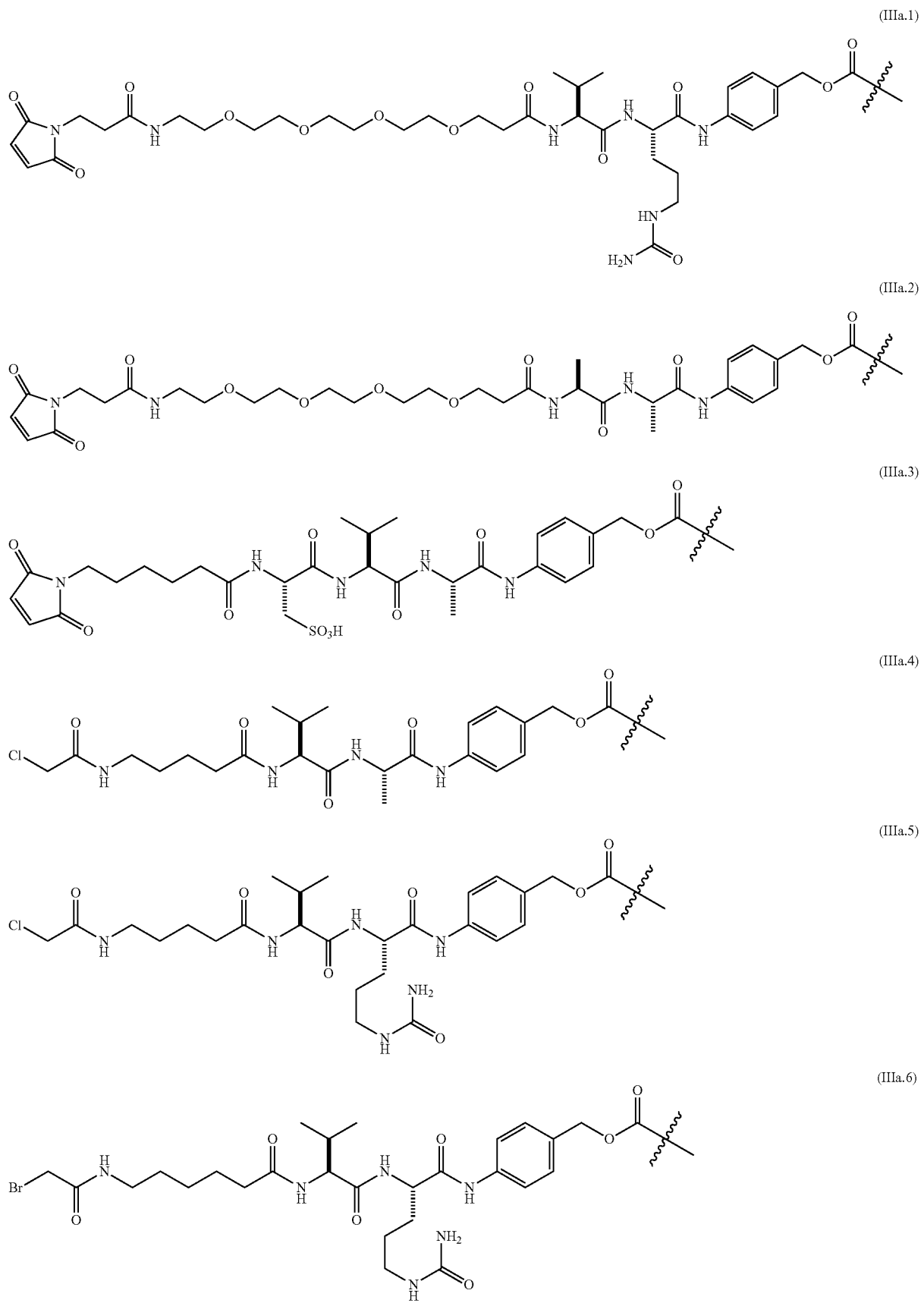

(IIIa.7)

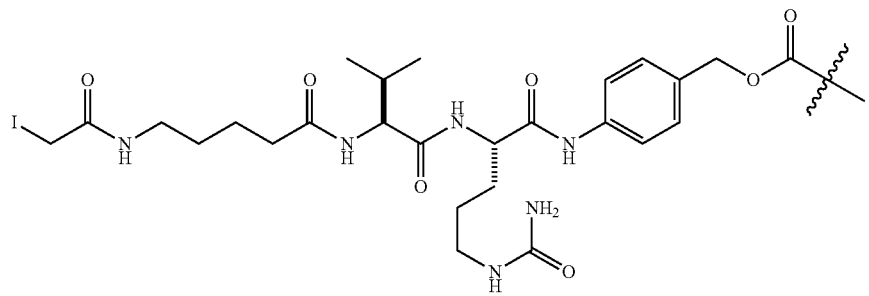

(IIIa.8)

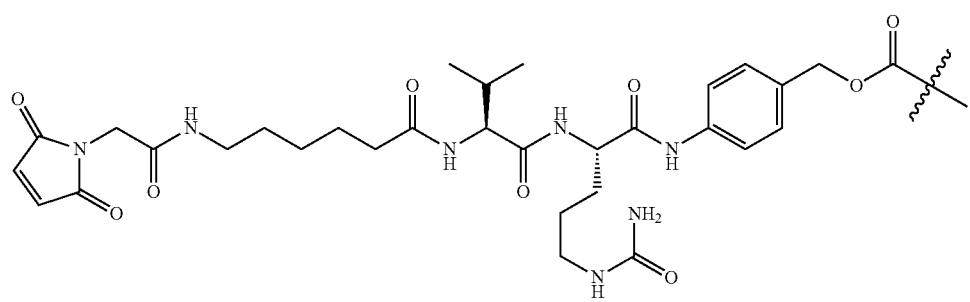

wherein ⸹ indicates an attachment site of a linker (L³) to a compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (IIIb), (IIIc), or (IIId) that can be included in the conjugates described herein can include the linkers illustrated below (as illustrated, the linkers can include a reactive group suitable for covalently linking the linker to an antibody construct):

(IIIb.1)

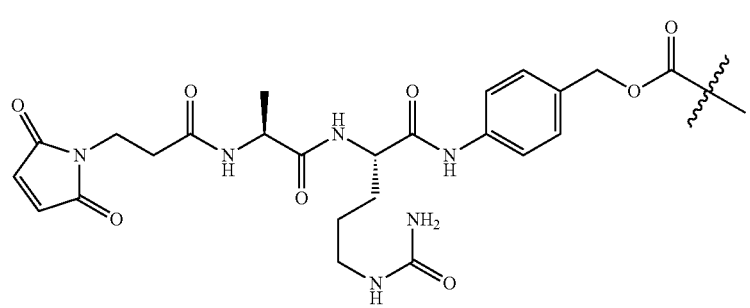

(IIIb.2)

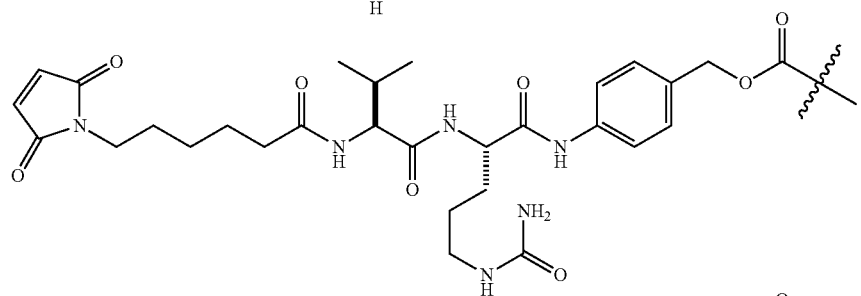

(IIIb.3)

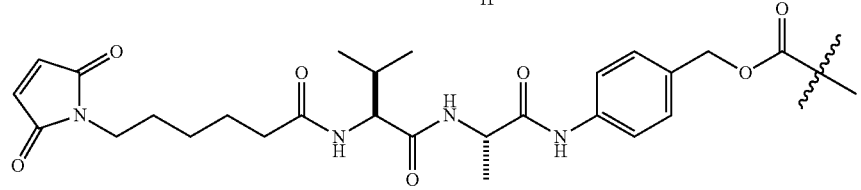

-continued
(IIIb.4)
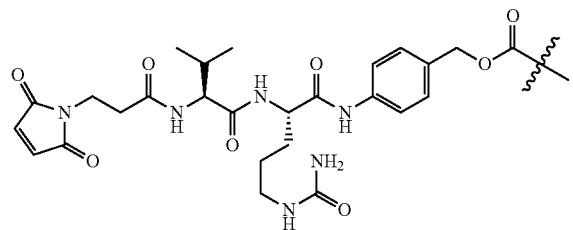
(IIIb.5)
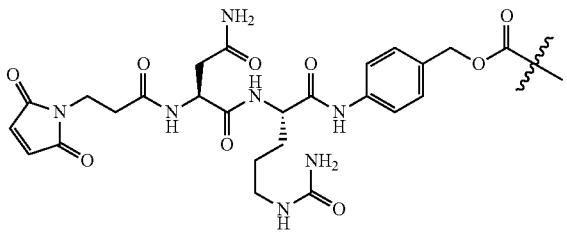
(IIIb.6)
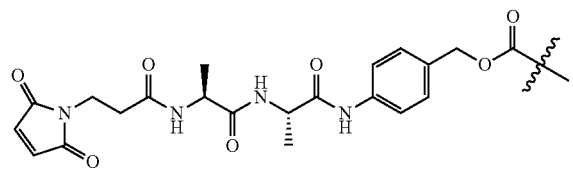
(IIIb.7)
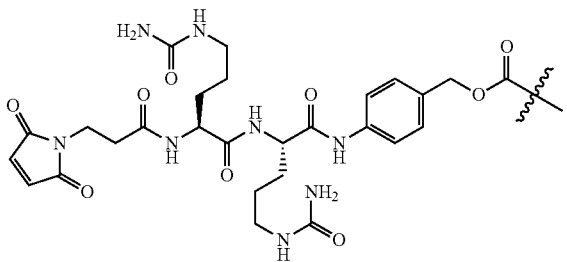
(IIIb.8)
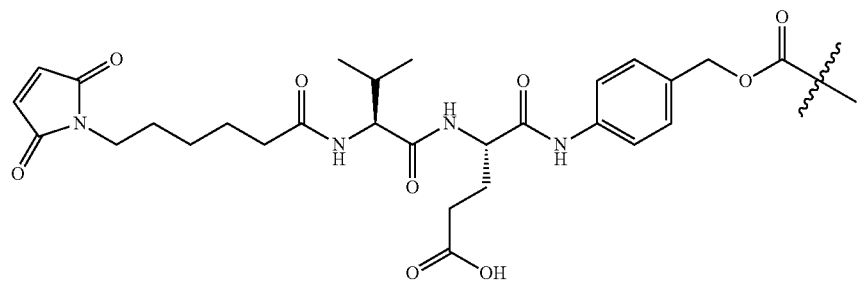
(IIIb.9)
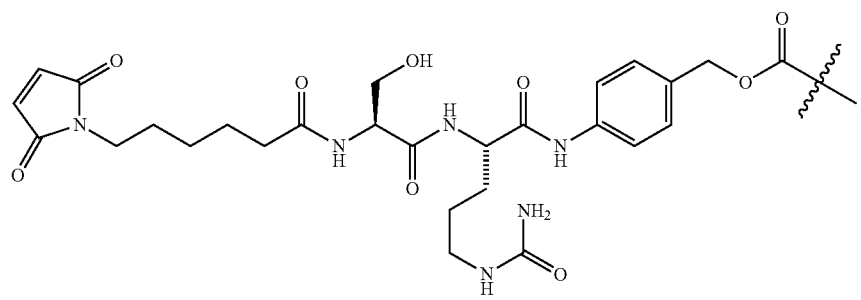
(IIIb.10)
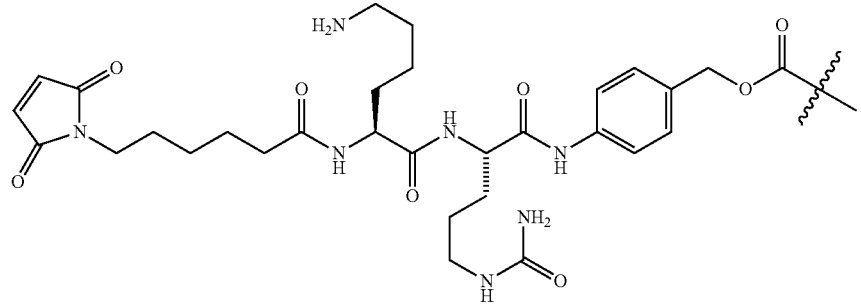

-continued
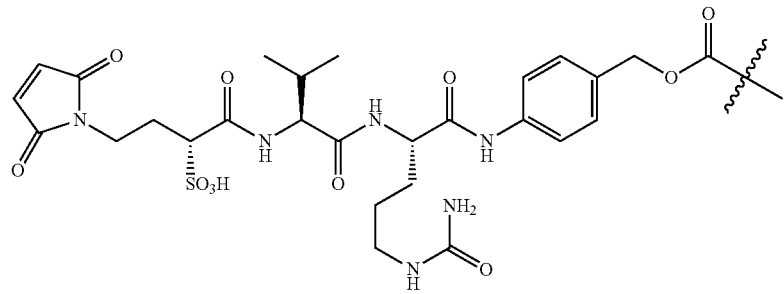
(IIIb.11)
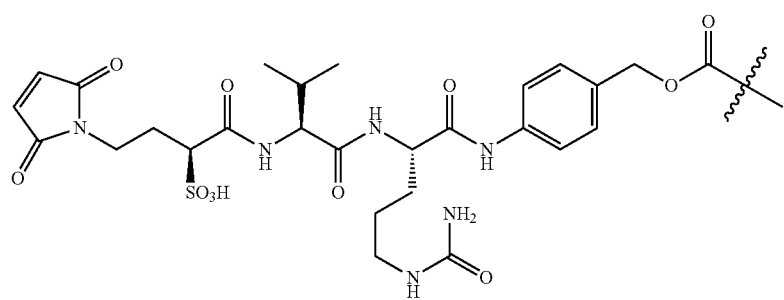
(IIIb.12)
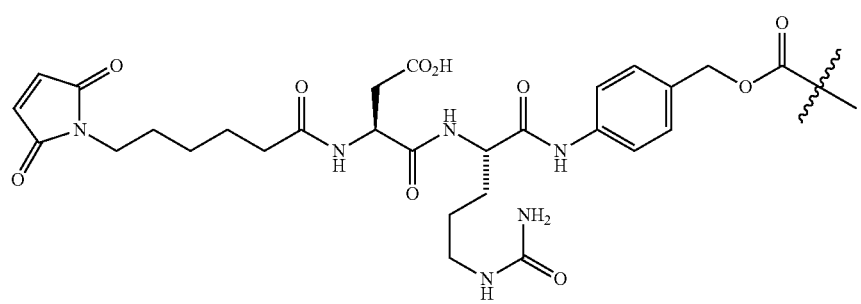
(IIIb.13)
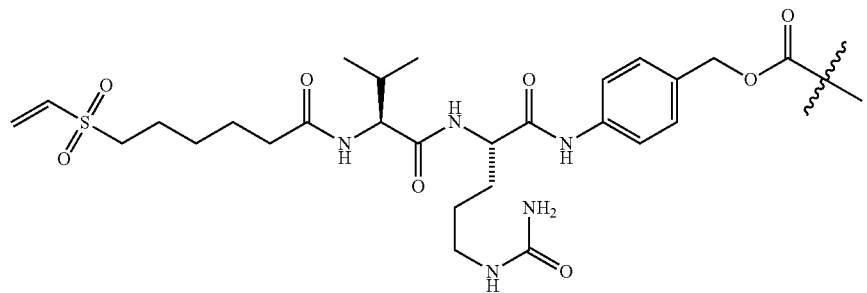
(IIIb.14)
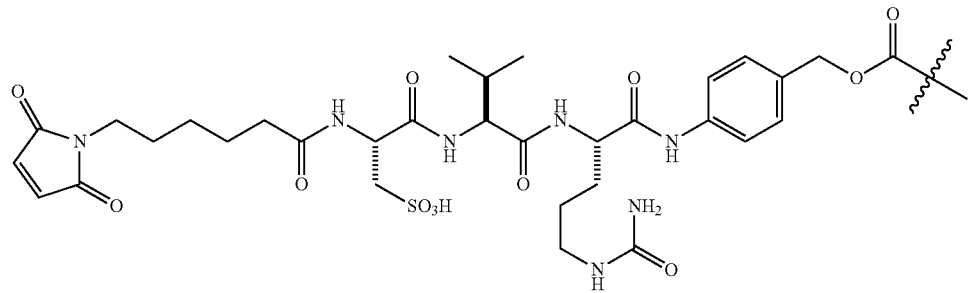
(IIIb.15)

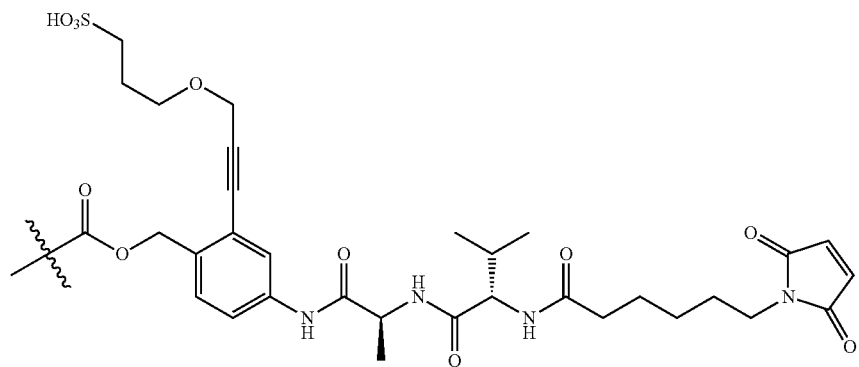
(IIIb.16)
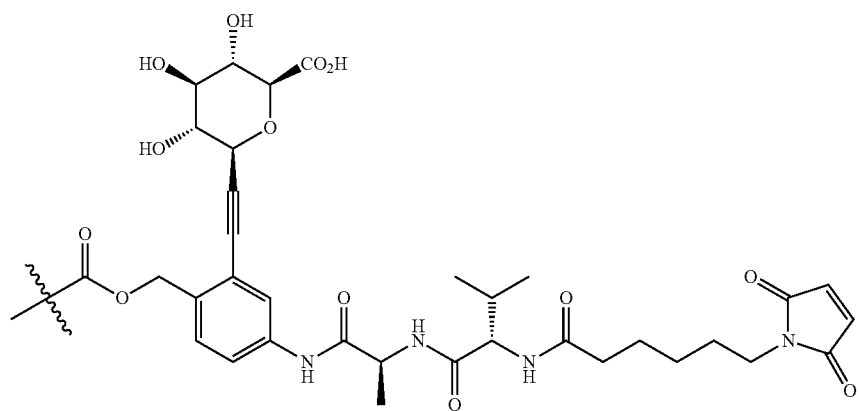
(IIIb.17)
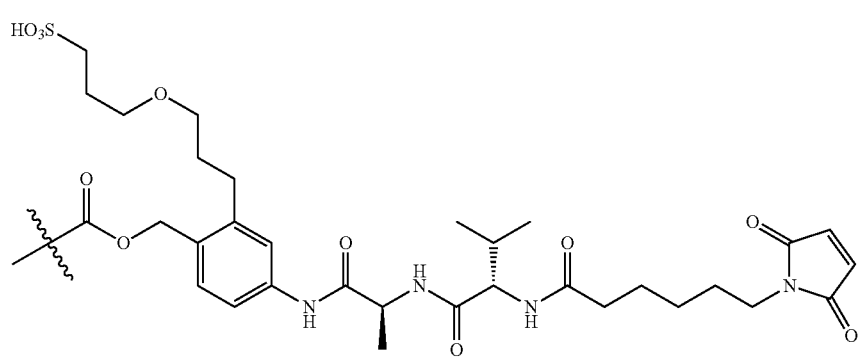
(IIIb.18)
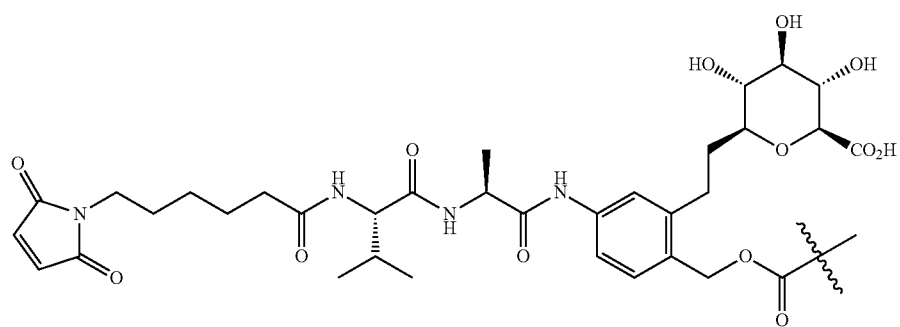
(IIIb.19)

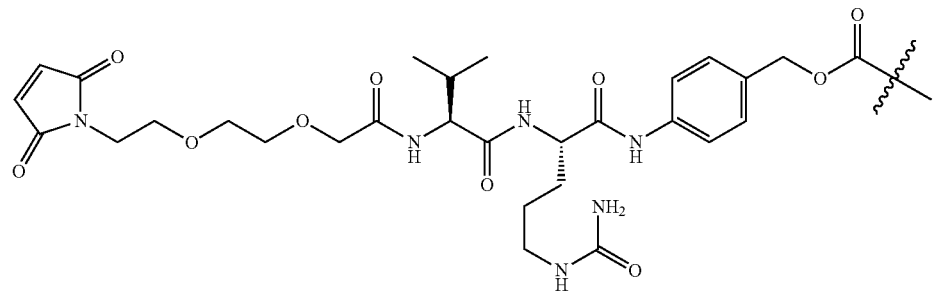
(IIIc.1)
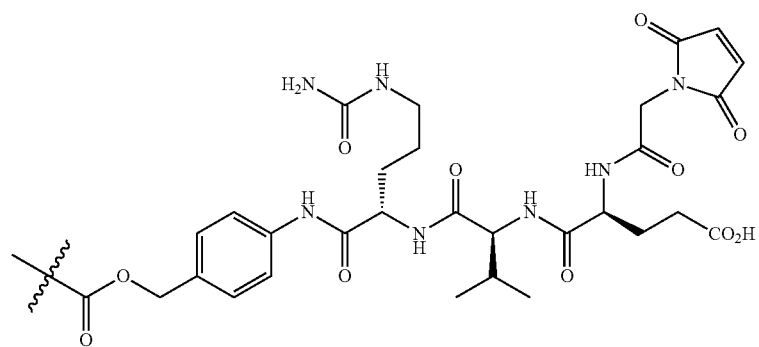
(IIIc.2)
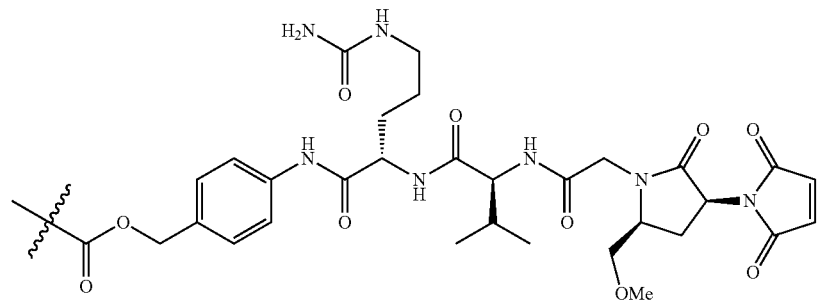
(IIIc.3)
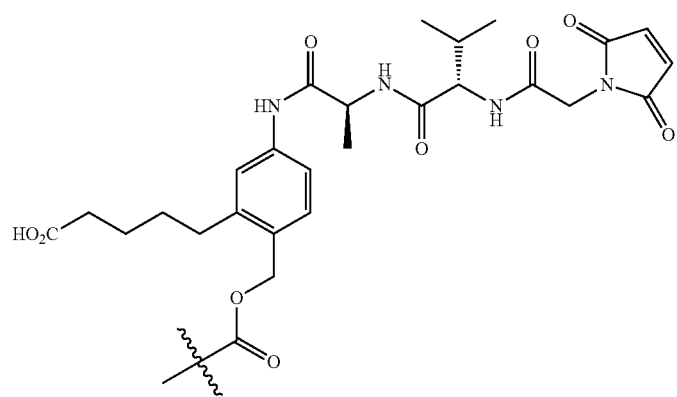
(IIIc.4)

-continued
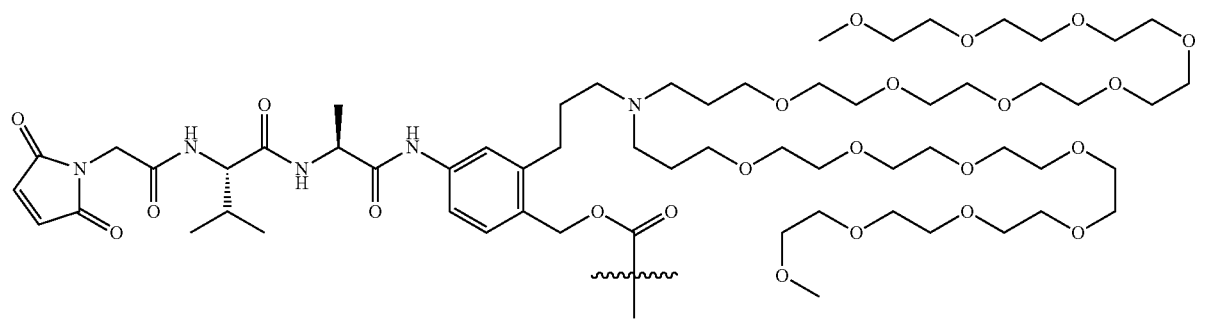
(IIIc.5)
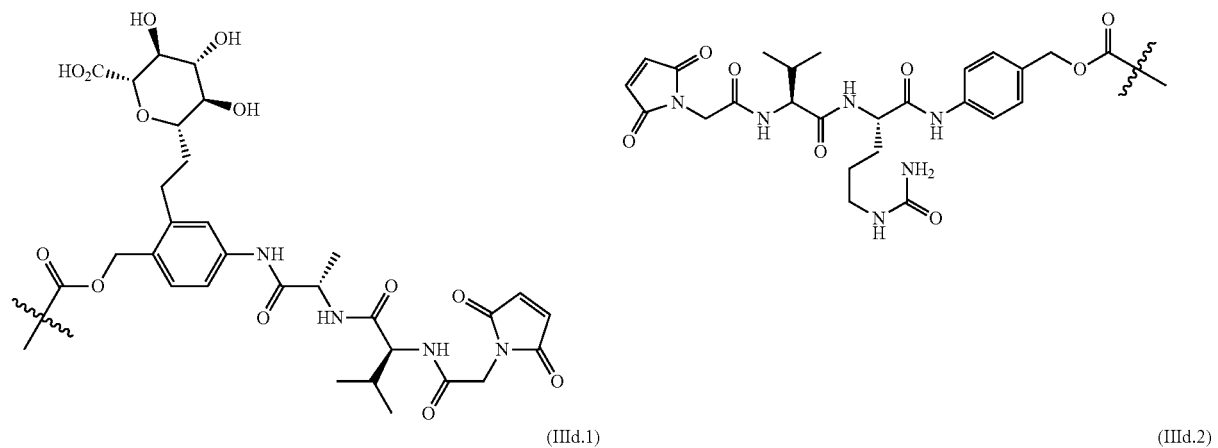
(IIIc.6) (IIIc.7)
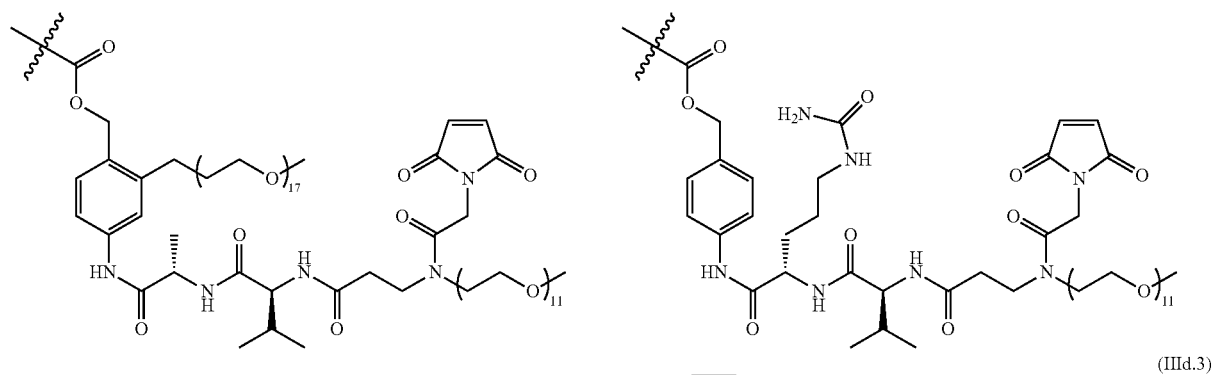
(IIId.1) (IIId.2)
(IIId.3)
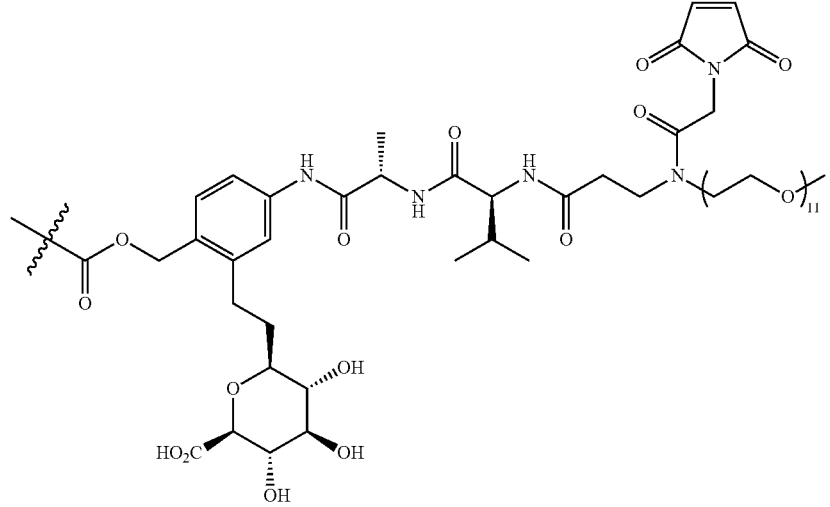

(IIId.4)

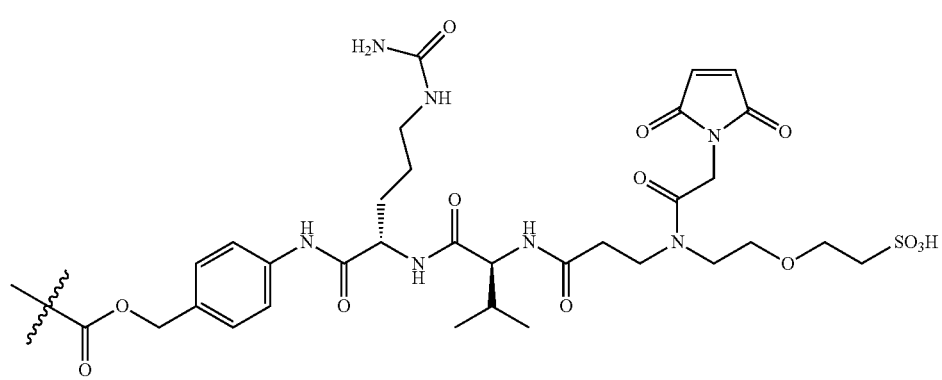

wherein ⁎ indicates an attachment site to a compound or salt of any one of Formulas (IA), (IB), (IC), (IIA), (IIB), (IIC), (IIIA), (IIIB), (IIIC), (IVA), (IVB), or (IVC).

The linker can contain an enzymatically cleavable sugar moiety, for example, a linker comprising structural formula (IVa), (IVb), (IVc), (IVd), or (IVe):

(IVa)

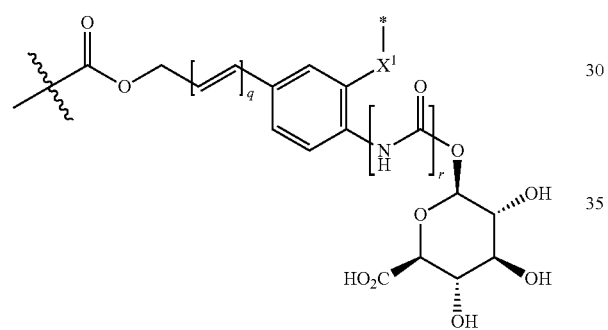

(IVb)

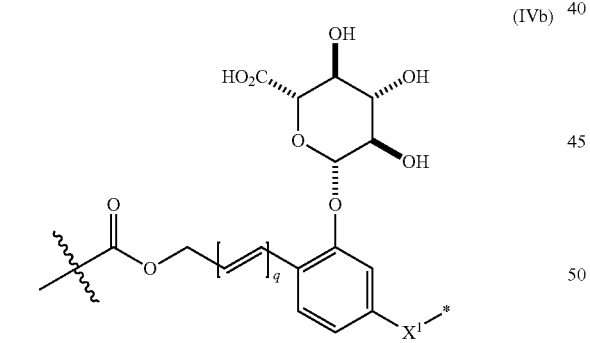

(IVc)

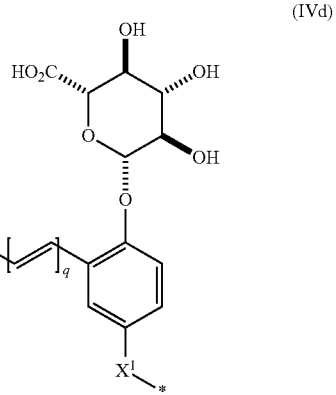

(IVd)

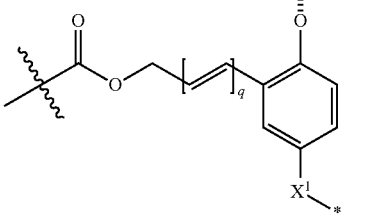

(IVe)

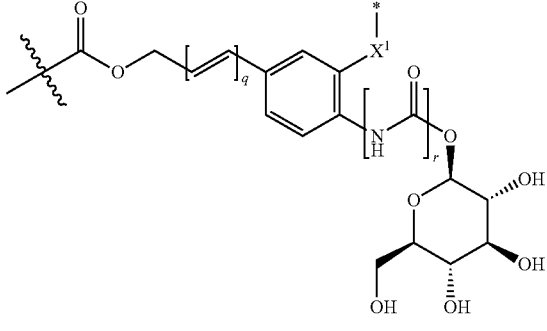

or a salt thereof, wherein: q is 0 or 1; r is 0 or 1; $X^1$ is $CH_2$, O or NH; ⁎ represents the point of attachment of the linker ($L^3$) to the compound or salt of any one of Formulas (IA), (IB), (IC), (IIA), (IIB), (IIC), (IIIA), (IIIB), (IIIC), (IVA), (IVB), or (IVC); and * represents the point of attachment to the remainder of the linker.

Exemplary embodiments of linkers according to structural formula (IVa) that may be included in the antibody construct benzazepine compound conjugates described herein can include the linkers illustrated below (as illustrated, the linkers include a group suitable for covalently linking the linker to an antibody construct):

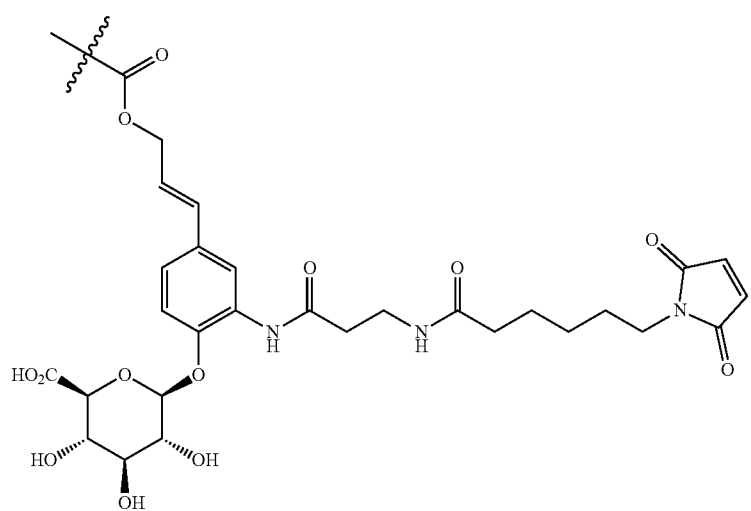
(IVa.1)
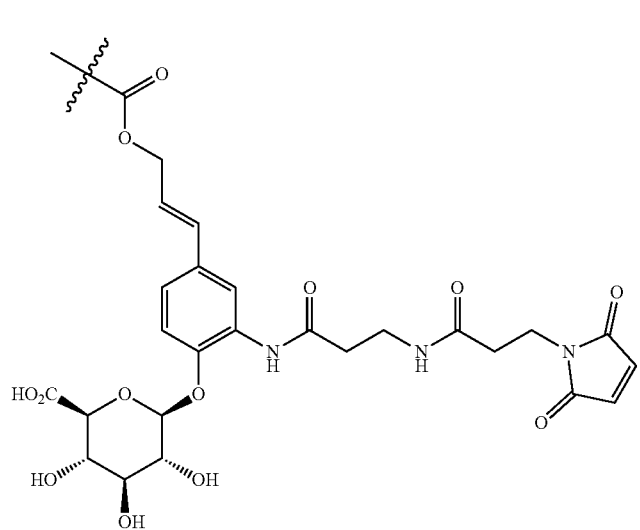
(IVa.2)
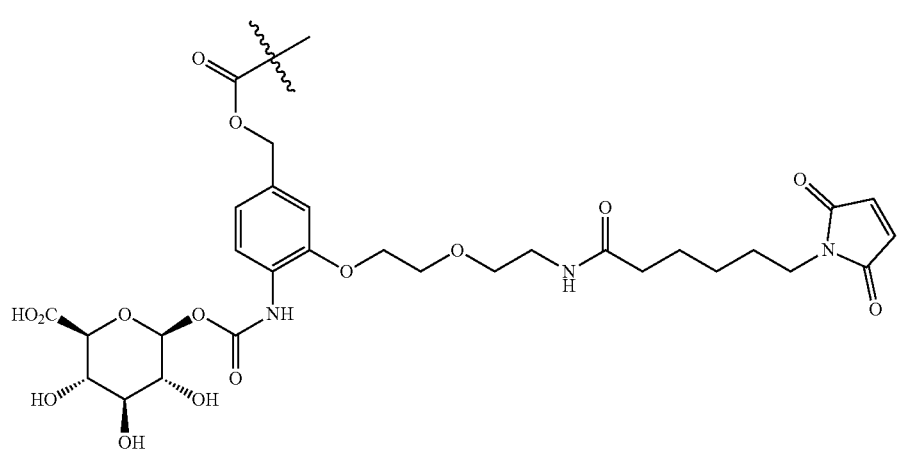
(IVa.3)

(IVa.4)
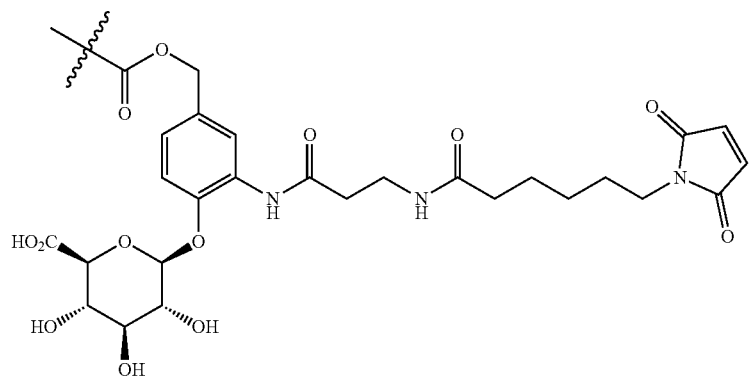
(IVa.5)
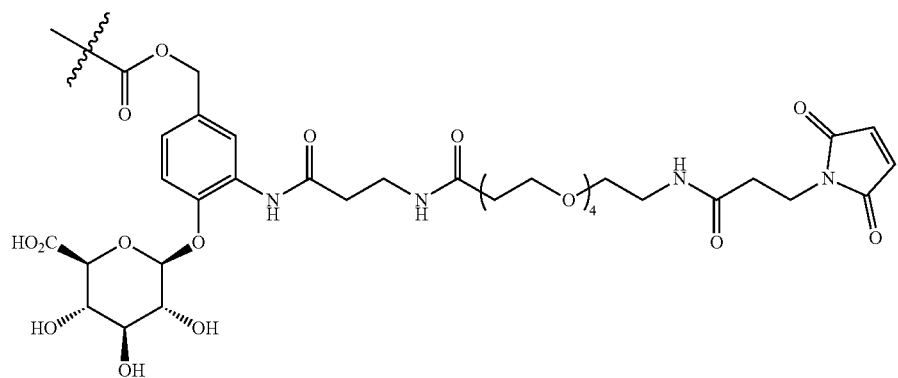
(IVa.6)
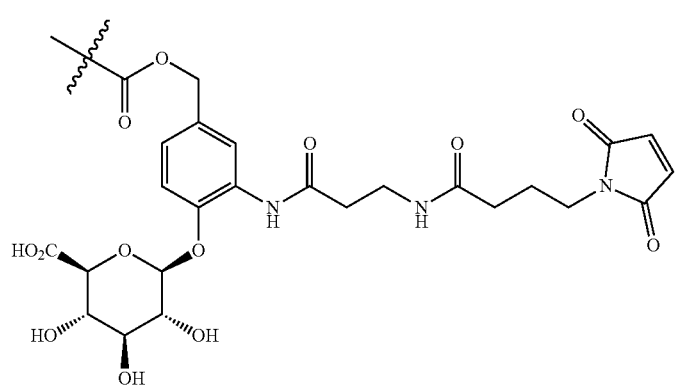
(IVa.7)
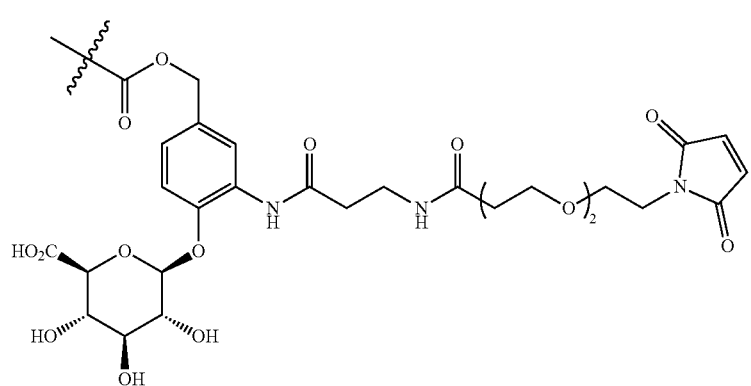

(IVa.8)
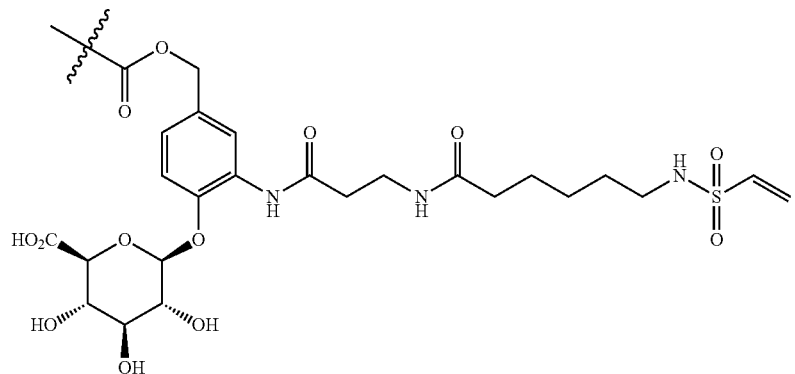
(IVa.9)
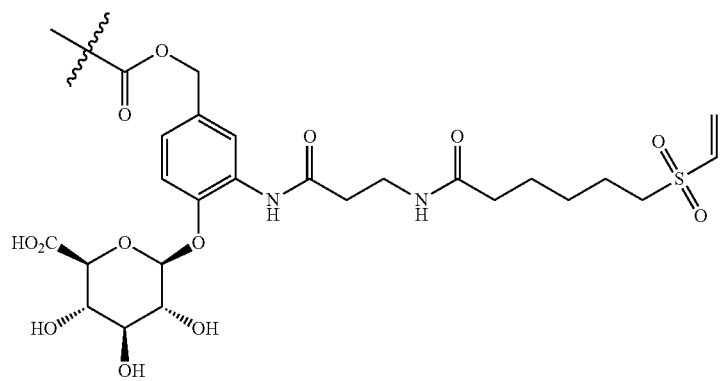
(IVa.10)
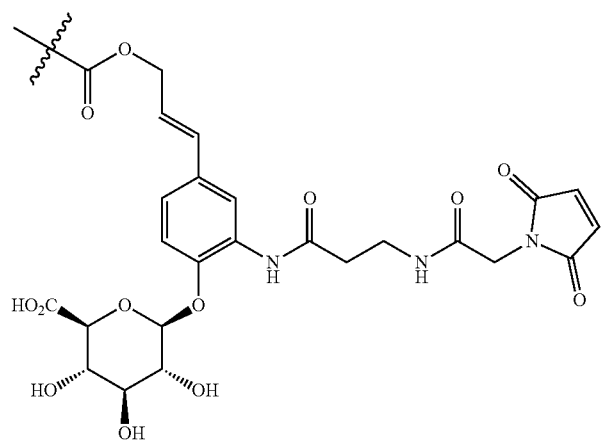
(IVa.11)
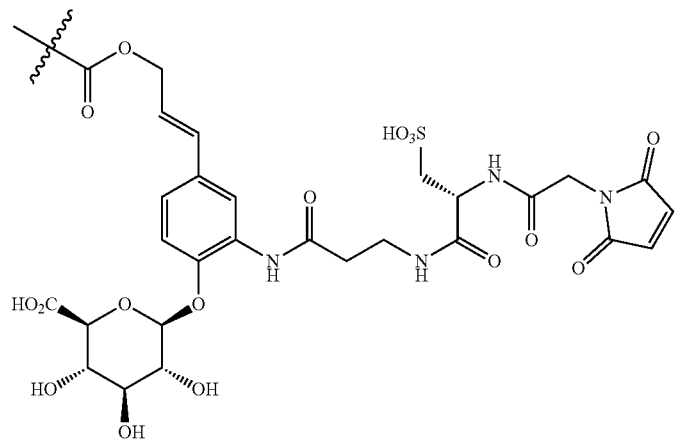

(IVa.12)

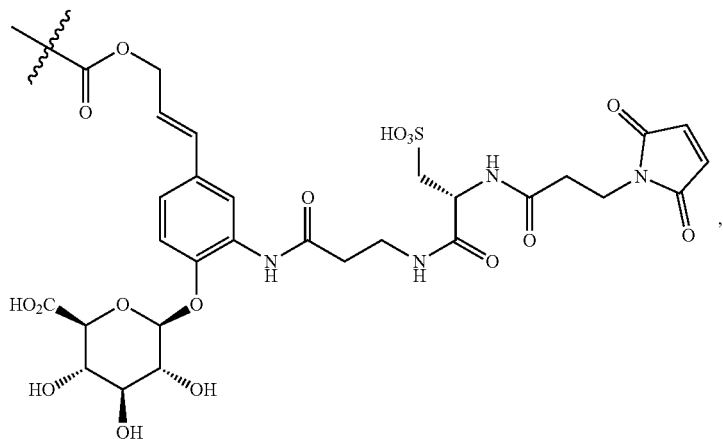

wherein ∫ represents the point of attachment of the linker (L³) to the compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (IVb) that may be included in the conjugates described herein include the linkers illustrated below (as illustrated, the linkers include a group suitable for covalently linking the linker to an antibody construct):

(IVb.1)

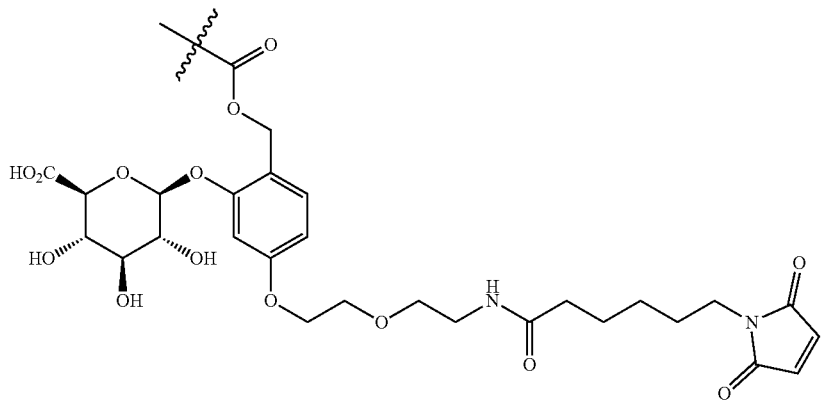

(IVb.1)

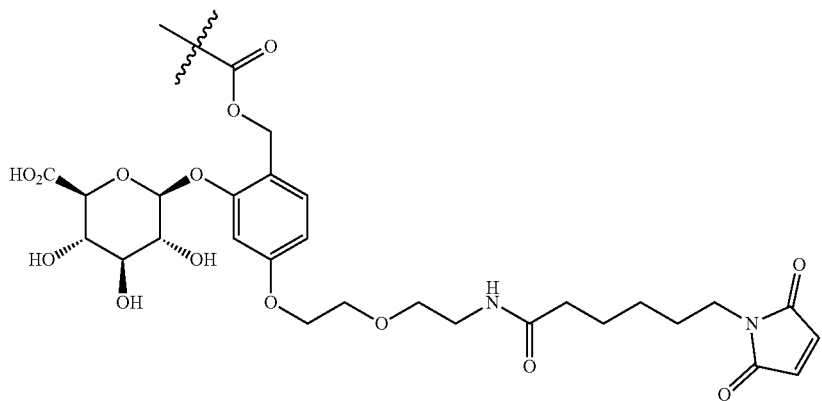

(IVb.2)
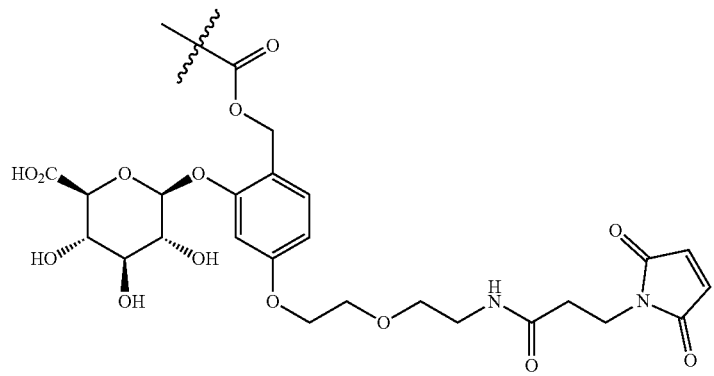
(IVb.3)
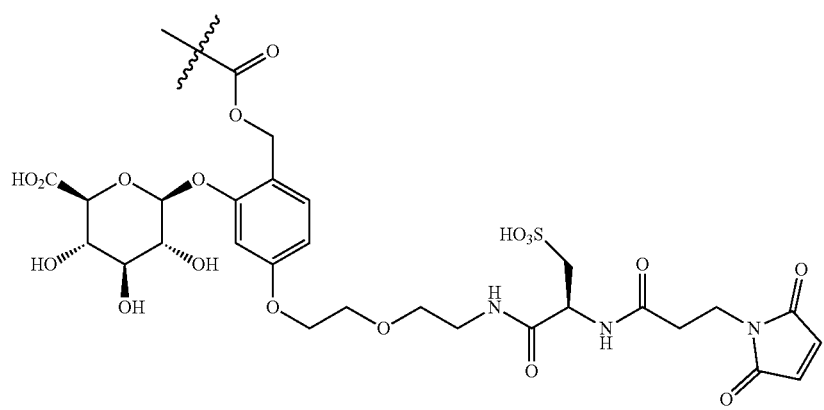
(IVb.4)
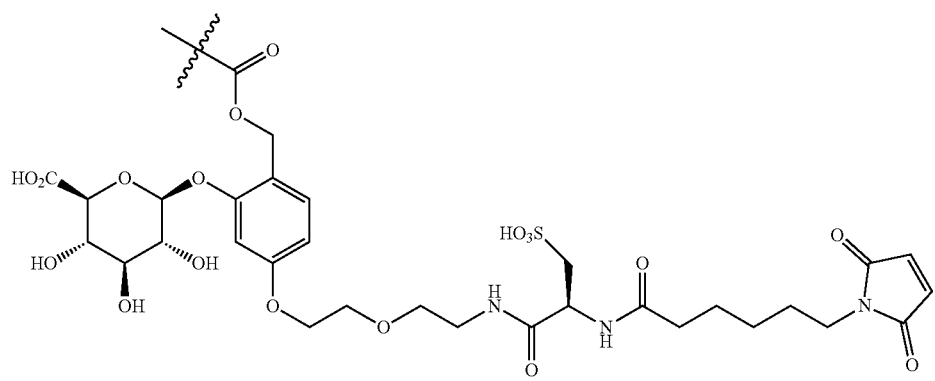
(IVb.5)
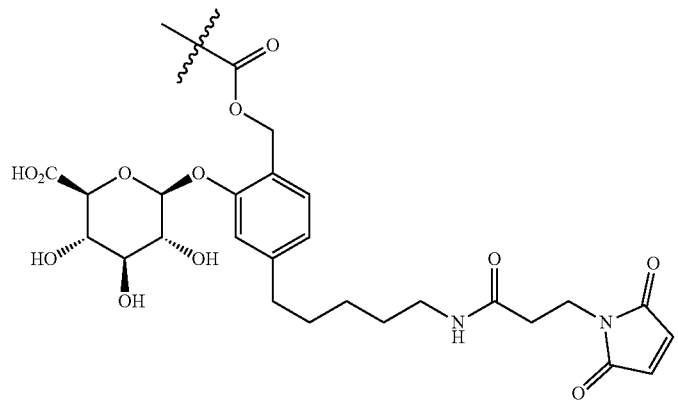

(IVb.6)
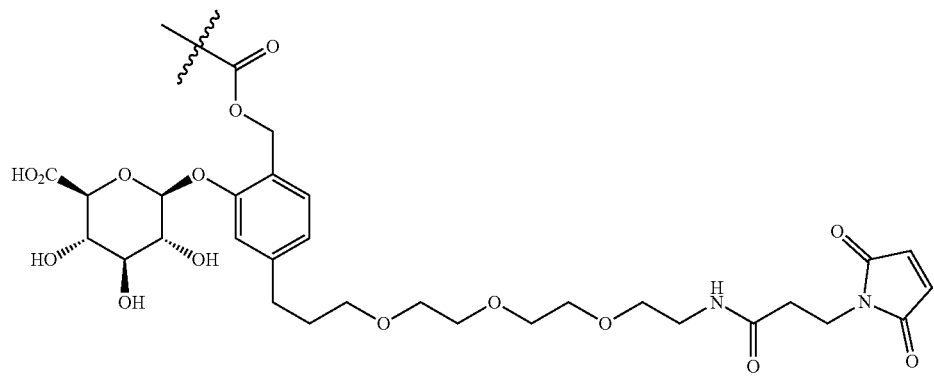
(IVb.7)
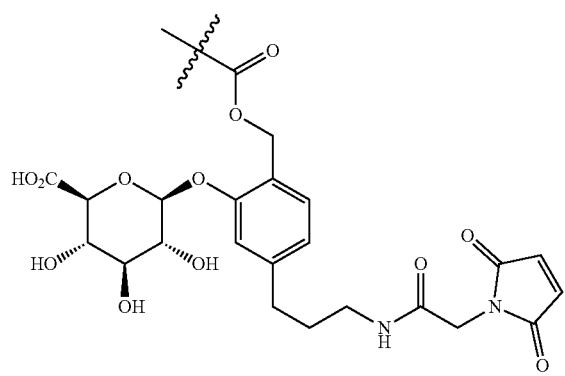
(IVb.8)
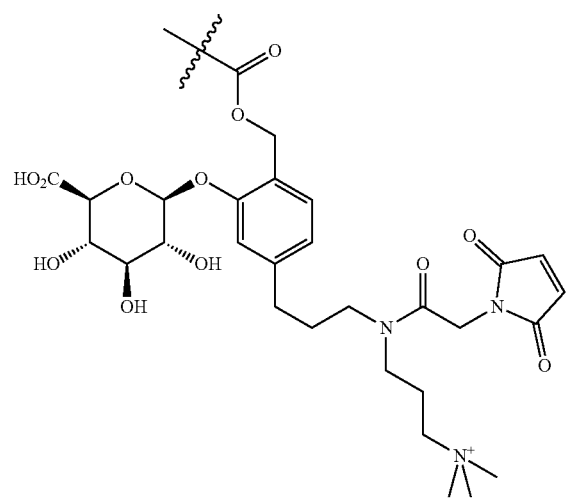
(IVb.9)
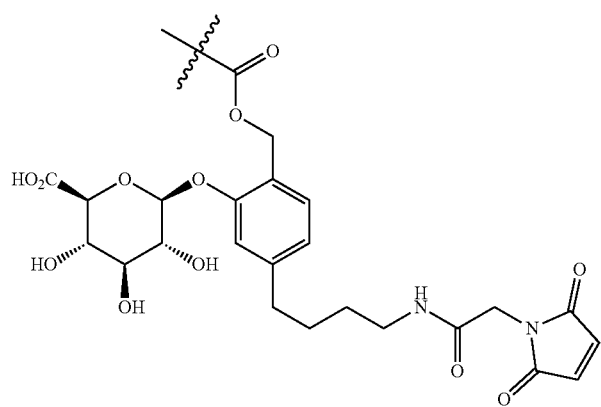

(IVb.10)

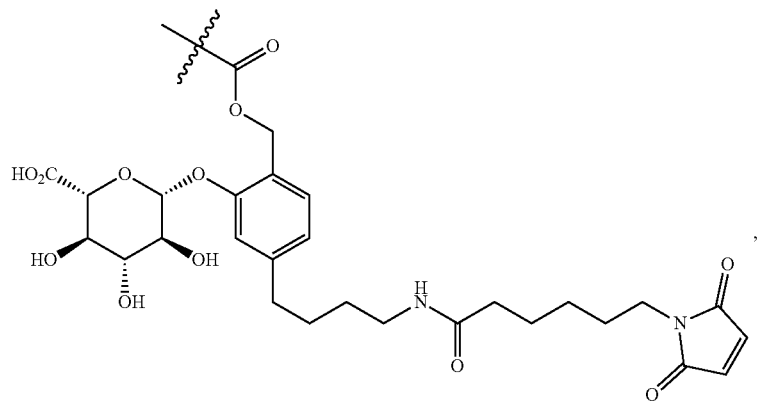

wherein ∤ represents the point of attachment of the linker ($L^3$) to the compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (IVc) that may be included in the conjugates described herein include the linkers illustrated below (as illustrated, the linkers include a group suitable for covalently linking the linker to an antibody construct):

(IVc.1)

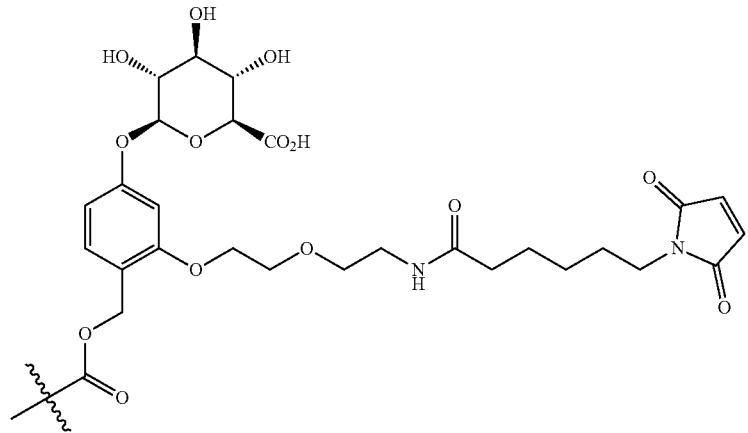

(IVc.2)

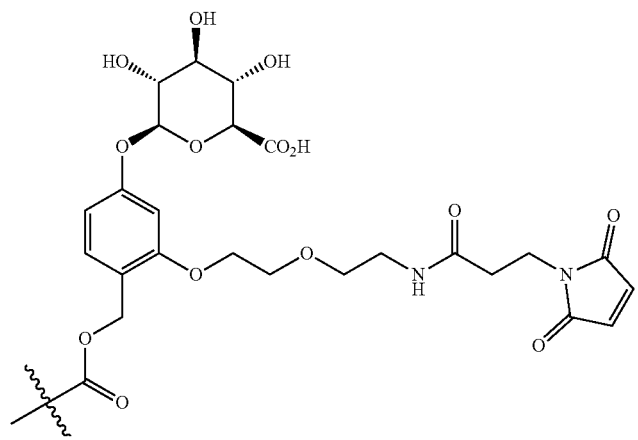

(IVc.3)
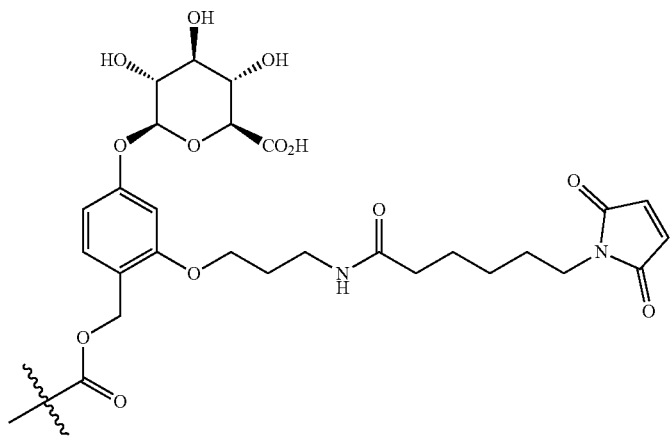
(IVc.4)
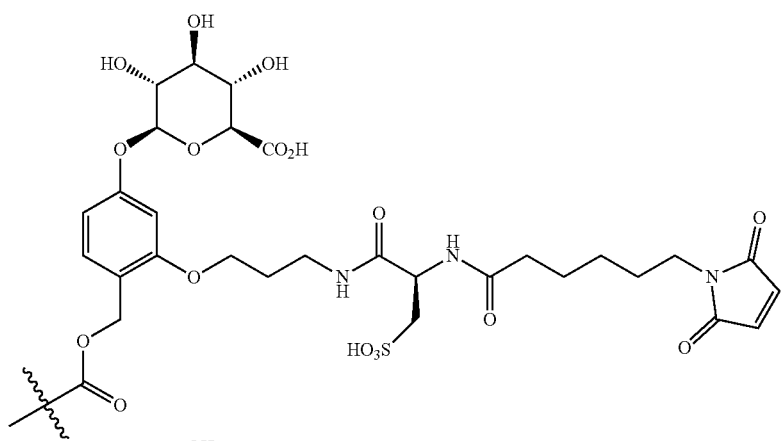
(IVc.5)
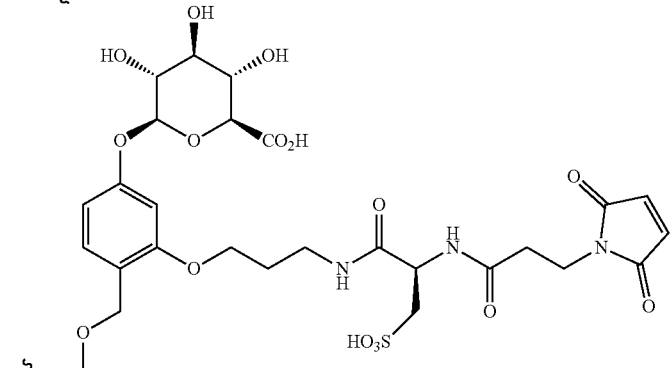
(IVc.6)
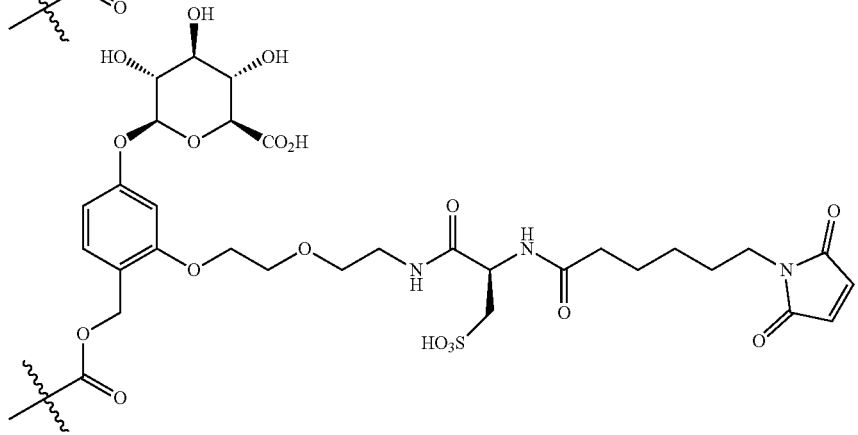

-continued
(IVc.7)
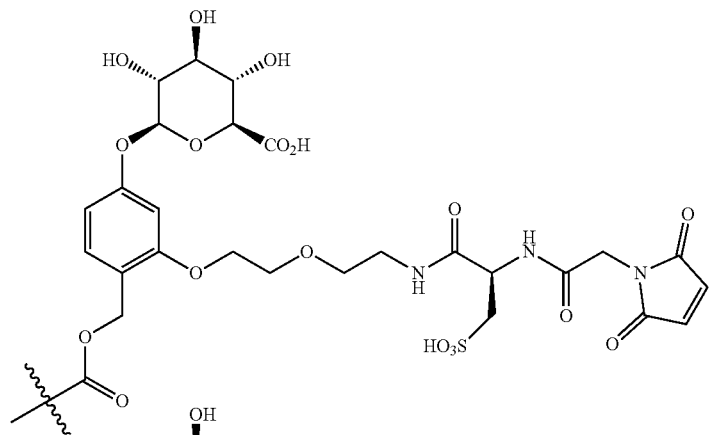
(IVc.8)
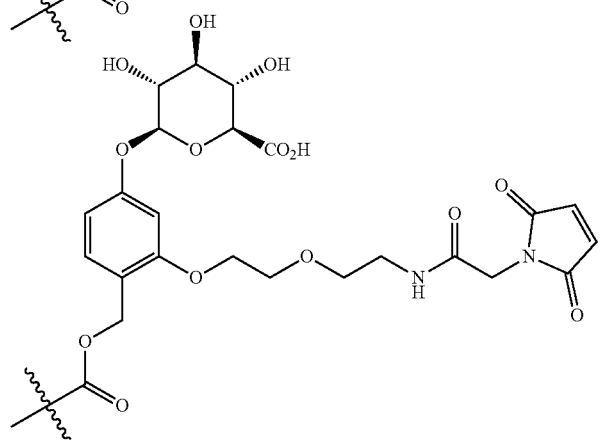
(IVc.9)
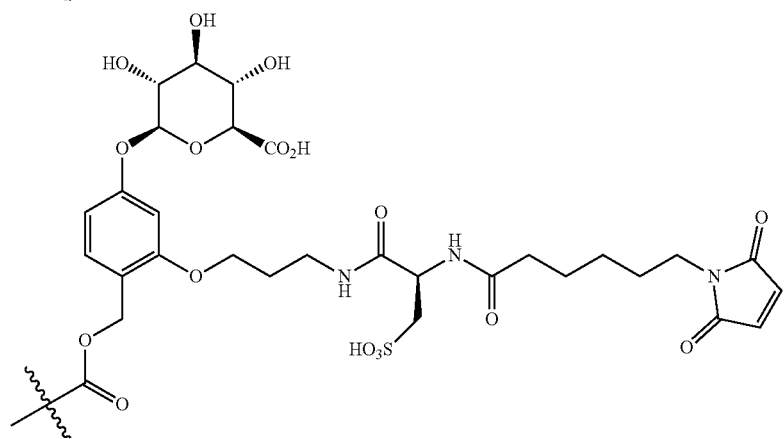
(IVc.10)
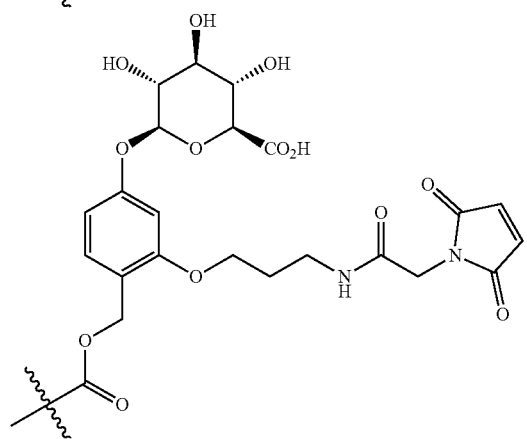

(IVc.11)

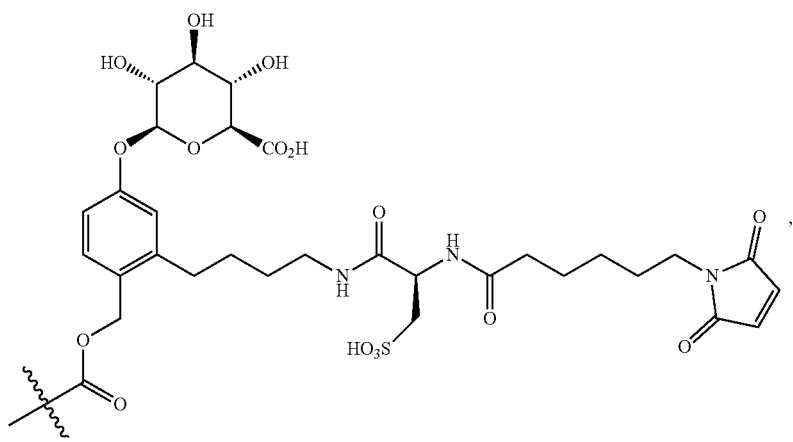

wherein ⁄ represents the point of attachment of the linker (L³) to the compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (IVd) that may be included in the conjugates described herein include the linkers illustrated below (as illustrated, the linkers include a group suitable for covalently linking the linker to an antibody construct):

(IVd.1)

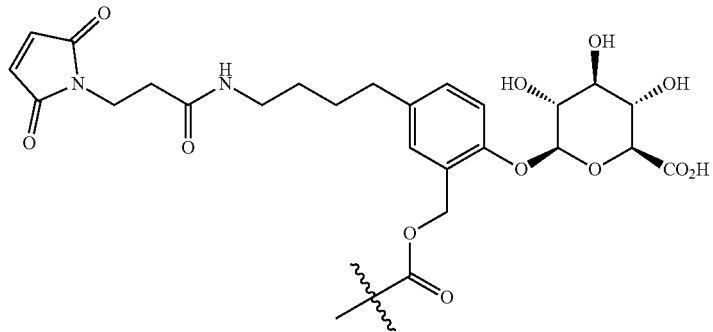

(IVd.2)

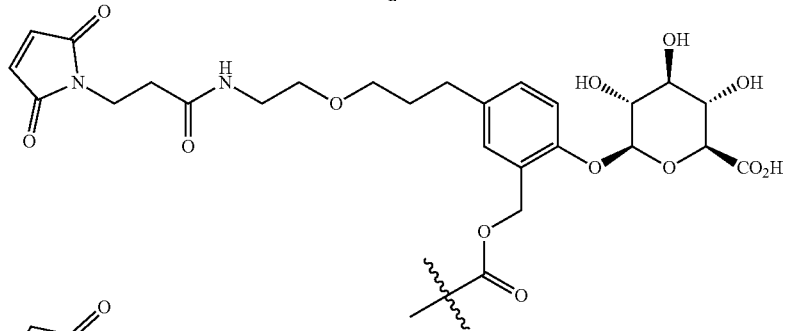

(IVd.3)

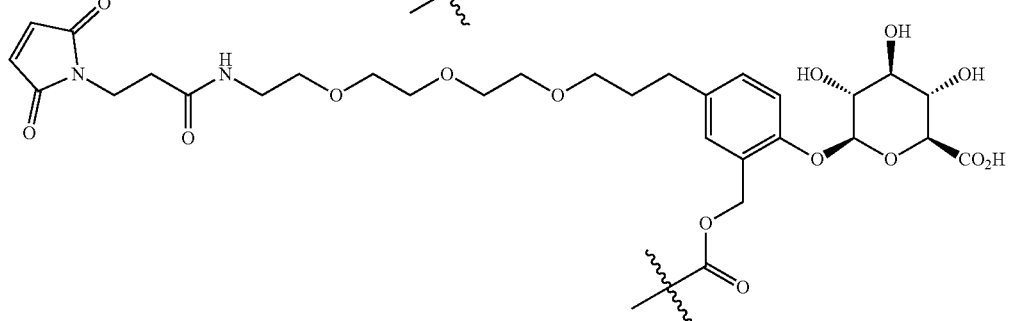

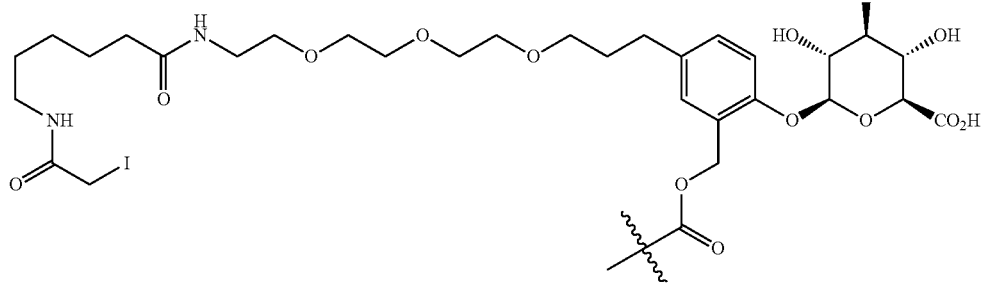 (IVd.4)

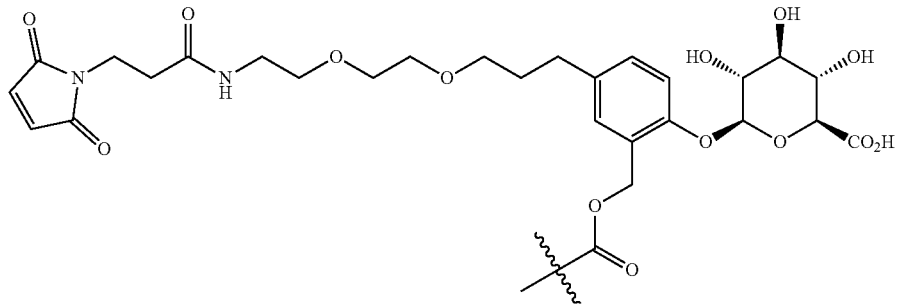 (IVd.5)

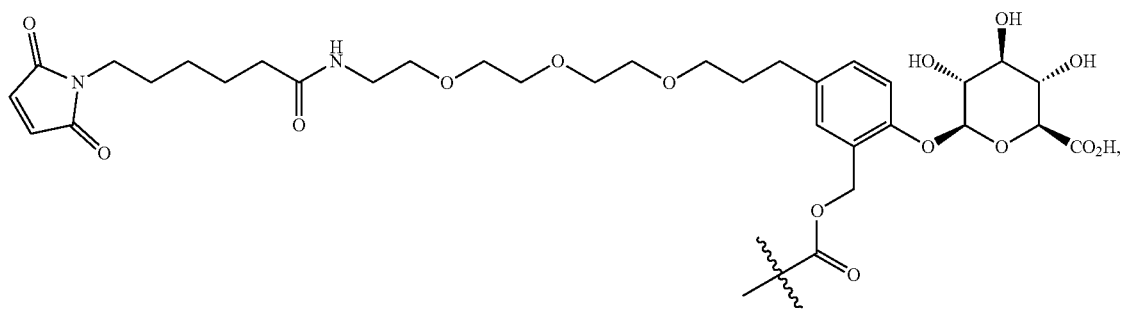 [SMILES: *C(=O)OCc1cc(CCCOCCOCCOCCNC(=O)CCCCCN2C(=O)C=CC2=O)ccc1O[C@@H]1O[C@H](C(=O)O)[C@@H](O)[C@H](O)[C@H]1O]

wherein ƒ represents the point of attachment of the linker (L³) to the compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (IVe) that may be included in the conjugates described herein include the linkers illustrated below (as illustrated, the linkers include a group suitable for covalently linking the linker to an antibody construct):

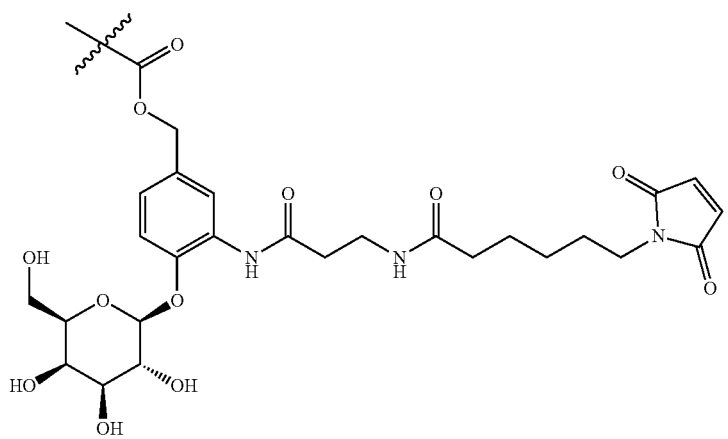 (IVe.1)

(IVe.2)

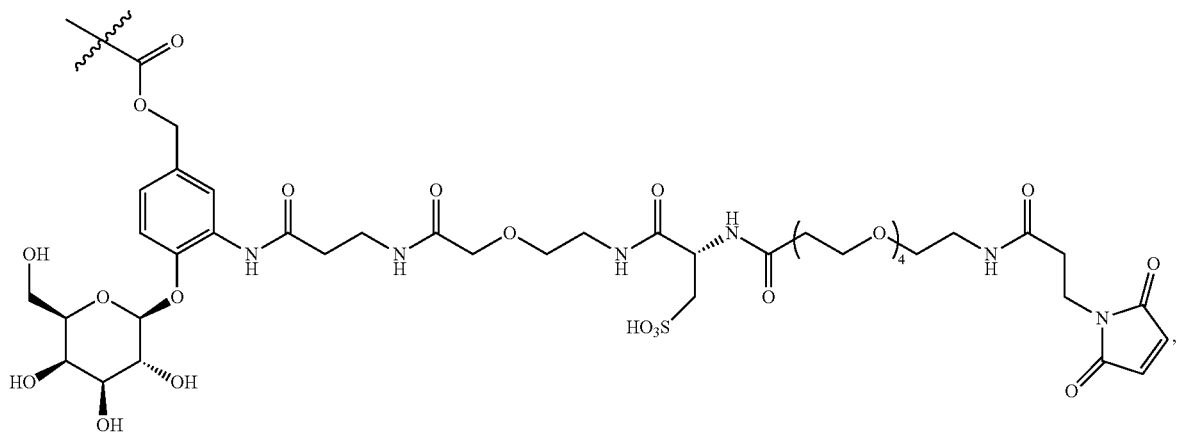

wherein ⫽ represents the point of attachment of the linker ($L^3$) to the compound or salt of any one of Formulas (IA), (IB), (IC), (IIA), (IIB), (IIC), (IIIA), (IIIB), (IIIC), (IVA), (IVB), or (IVC).

Although cleavable linkers can provide certain advantages, the linkers comprising the conjugate described herein need not be cleavable. For non-cleavable linkers, the benzazepine compound release may not depend on the differential properties between the plasma and some cytoplasmic compartments. The release of the benzazepine compound can occur after internalization of the antibody construct benzazepine compound conjugate via antigen-mediated endocytosis and delivery to lysosomal compartment, where the antibody construct can be degraded to the level of amino acids through intracellular proteolytic degradation. This process can release a benzazepine compound derivative, which is formed by the benzazepine compound, the linker, and the amino acid residue or residues to which the linker was covalently attached. The benzazepine compound derivative from antibody construct benzazepine compound conjugates with non-cleavable linkers can be more hydrophilic and less membrane permeable, which can lead to less bystander effects and less nonspecific toxicities compared to antibody construct benzazepine compound conjugates with a cleavable linker. Antibody construct benzazepine compound conjugates with non-cleavable linkers can have greater stability in circulation than antibody construct benzazepine compound conjugates with cleavable linkers. Non-cleavable linkers can include alkylene chains, or can be polymeric, such as, for example, based upon polyalkylene glycol polymers, amide polymers, or can include segments of alkylene chains, polyalkylene glycols and/or amide polymers. The linker can contain a polyethylene glycol segment having from 1 to 6 ethylene glycol units.

The linker can be non-cleavable in vivo, for example, a linker according to the formulations below:

(Va)

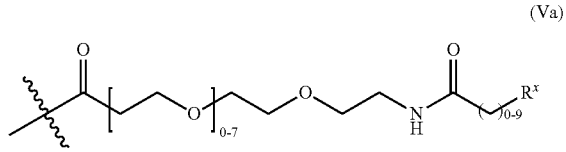

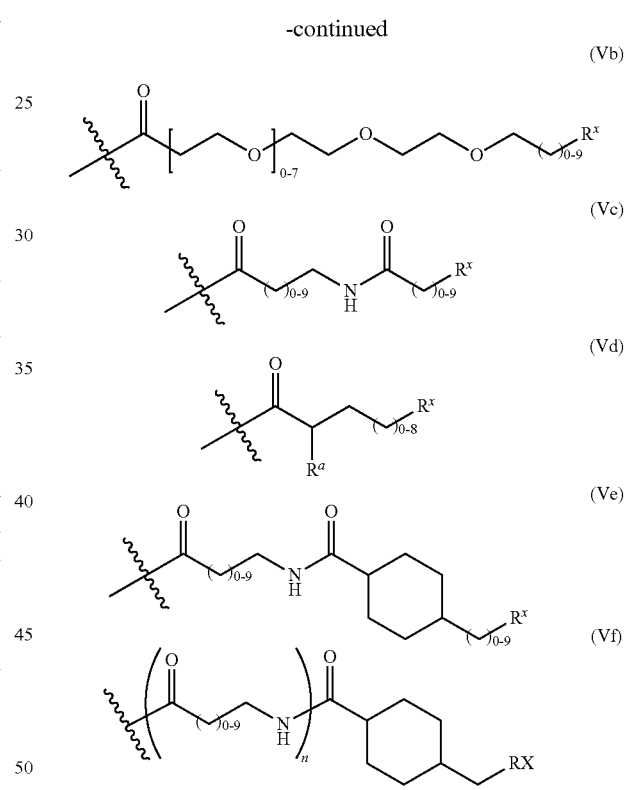

or salts thereof, wherein: $R^a$ is selected from hydrogen, alkyl, sulfonate and methyl sulfonate; $R^x$ is a reactive moiety including a functional group capable of covalently linking the linker to an antibody construct; and ⫽ represents the point of attachment of the linker ($L^3$) to the compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (Va)-(Vf) that may be included in the conjugates described herein include the linkers illustrated below (as illustrated, the linkers include a group suitable for covalently linking the linker to an antibody construct, and ⫽ represents the point of attachment of the linker ($L^3$) to the compound or salt of any one of Formulas (IA), (IB), (IC), (IIA), (IIB), (IIC), (IIIA), (IIIB), (IIIC), (IVA), (IVB), or (IVC):

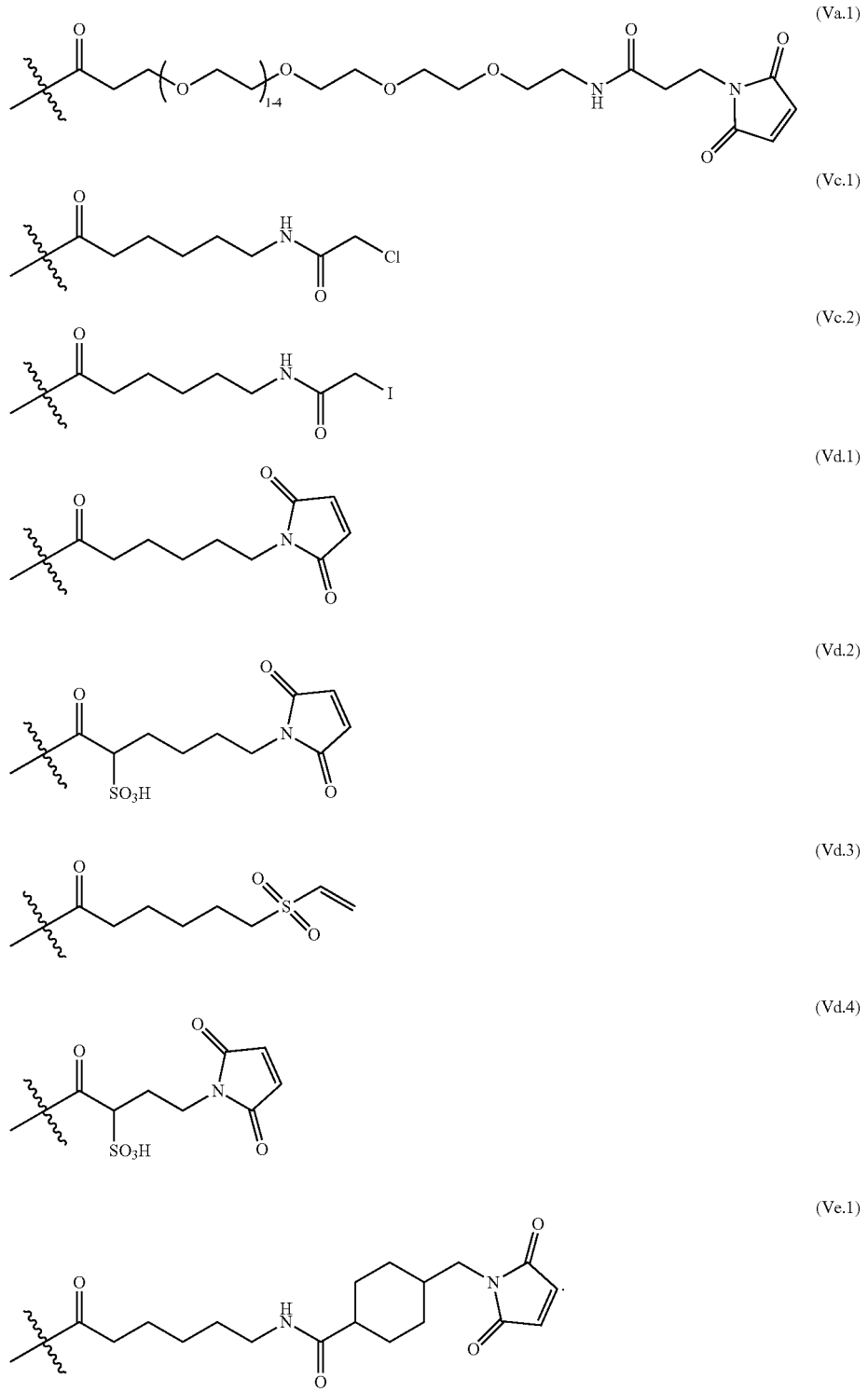

Attachment groups that are used to attach the linkers to an antibody construct can be electrophilic in nature and include, for example, maleimide groups, alkynes, alkynoates, allenes and allenoates, activated disulfides, active esters such as NHS esters and HOBt esters, haloformates, acid halides, alkyl, and benzyl halides such as haloacetamides. There are also emerging technologies related to "self-stabilizing" maleimides and "bridging disulfides" that can be used in accordance with the disclosure.

Maleimide groups are frequently used in the preparation of conjugates because of their specificity for reacting with thiol groups of, for example, cysteine groups of the antibody of a conjugate. The reaction between a thiol group of an antibody and a drug with a linker including a maleimide group proceeds according to the following scheme:

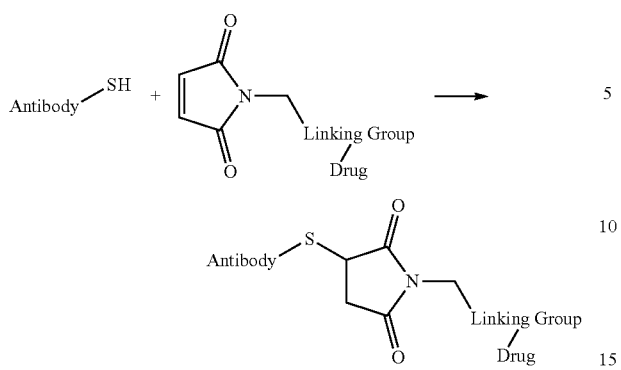

The reverse reaction leading to maleimide elimination from a thio-substituted succinimide may also take place. This reverse reaction is undesirable as the maleimide group may subsequently react with another available thiol group such as other proteins in the body having available cysteines. Accordingly, the reverse reaction can undermine the specificity of a conjugate. One method of preventing the reverse reaction is to incorporate a basic group into the linking group shown in the scheme above. Without wishing to be bound by theory, the presence of the basic group may increase the nucleophilicity of nearby water molecules to promote ring-opening hydrolysis of the succinimide group. The hydrolyzed form of the attachment group is resistant to deconjugation in the presence of plasma proteins. So-called "self-stabilizing" linkers provide conjugates with improved stability. A representative schematic is shown below:

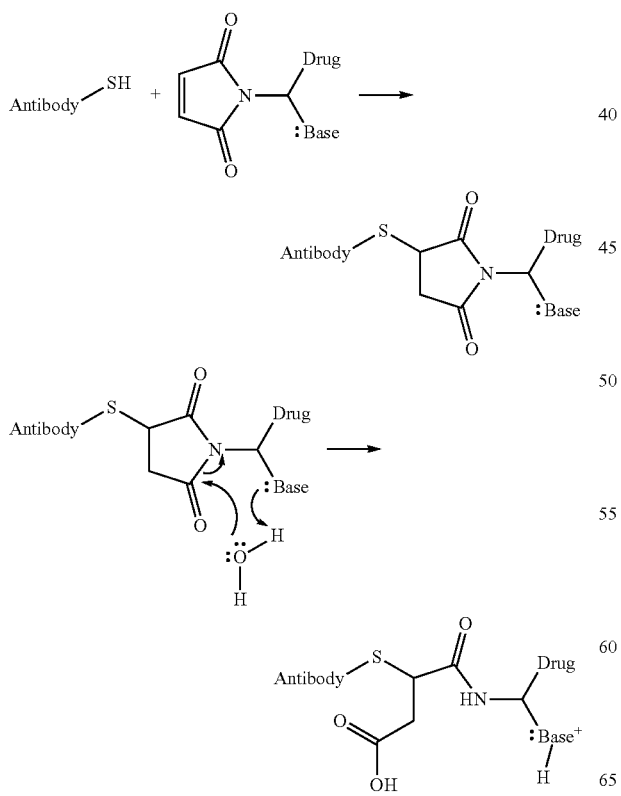

The hydrolysis reaction schematically represented above may occur at either carbonyl group of the succinimide group. Accordingly, two possible isomers may result, as shown below:

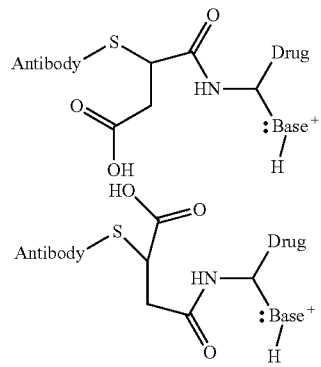

The identity of the base as well as the distance between the base and the maleimide group can be modified to tune the rate of hydrolysis of the thio-substituted succinimide group and optimize the delivery of a conjugate to a target by, for example, improving the specificity and stability of the conjugate.

Bases suitable for inclusion in a linker described herein, e.g., any $L^3$ described herein with a maleimide group prior to conjugating to an antibody construct, may facilitate hydrolysis of a nearby succinimide group formed after conjugation of the antibody construct to the linker. Bases may include, for example, amines (e.g., —N($R^{26}$)($R^{27}$), where $R^{26}$ and $R^{27}$ are independently selected from H and $C_{1-6}$ alkyl), nitrogen-containing heterocycles (e.g., a 3- to 12-membered heterocycle including one or more nitrogen atoms and optionally one or more double bonds), amidines, guanidines, and carbocycles or heterocycles substituted with one or more amine groups (e.g., a 3- to 12-membered aromatic or non-aromatic cycle optionally including a heteroatom such as a nitrogen atom and substituted with one or more amines of the type —N($R^{26}$)($R^{27}$), where $R^{26}$ and $R^{27}$ are independently selected from H or $C_{1-6}$ alkyl). A basic unit may be separated from a maleimide group by, for example, an alkylene chain of the form —(CH$_2$)$_m$—, where m is an integer from 0 to 10. An alkylene chain may be optionally substituted with other functional groups as described herein.

A linker ($L^3$) described herein with a maleimide group may include an electron withdrawing group such as, but not limited to, —C(O)R, =O, —CN, —NO$_2$, —CX$_3$, —X, —COOR, —CONR$_2$, —COR, —COX, —SO$_2$R, —SO$_2$OR, —SO$_2$NHR, —SO$_2$NR$_2$, PO$_3$R$^2$, —P(O)(CH$_3$)NHR, —NO, —NR$_3^+$, —CR=CR$_2$, and —C≡CR, where each R is independently selected from H and $C_{1-6}$ alkyl and each X is independently selected from F, Br, Cl, and I. Self-stabilizing linkers may also include aryl, e.g., phenyl, or heteroaryl, e.g., pyridine, groups optionally substituted with electron withdrawing groups such as those described herein.

Examples of self-stabilizing linkers are provided in, e.g., U.S. Patent Publication Number 2013/0309256, the linkers of which are incorporated by reference herein. It will be understood that a self-stabilizing linker useful in conjunction with the compounds of the present invention may be equivalently described as unsubstituted maleimide-including linkers, thio-substituted succinimide-including linkers, or hydrolyzed, ring-opened thio-substituted succinimide-including linkers.

In certain embodiments, a linker of the disclosure ($L^3$) comprises a stabilizing linker moiety selected from:

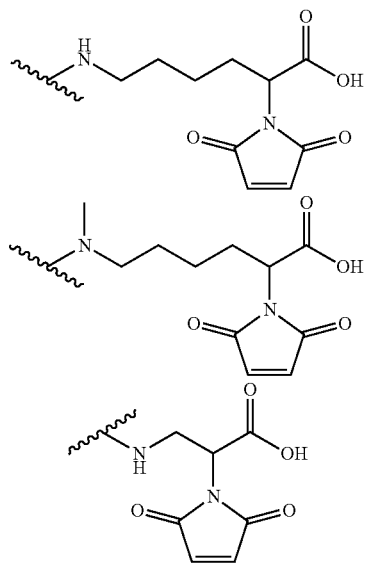

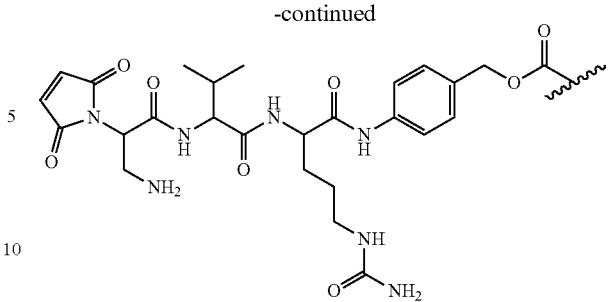

In the scheme provided above, the bottom structure may be referred to as (maleimido)-DPR-Val-Cit-PAB, where DPR refers to diaminopropinoic acid, Val refers to valine, Cit refers to citrulline, and PAB refers to para-aminobenzylcarbonyl. ʄ represents the point of attachment to compound or salt of any one of Formulas (IA), (IB), (IC), (IIA), (IIB), (IIC), (IIIA), (IIIB), (IIIC), (IVA), (IVB), or (IVC).

A method for bridging a pair of sulfhydryl groups derived from reduction of a native hinge disulfide bond has been disclosed and is depicted in the schematic below. An advantage of this methodology is the ability to synthesize homogenous DAR4 conjugates by full reduction of IgGs (to give 4 pairs of sulfhydryls from interchain disulfides) followed by reaction with 4 equivalents of the alkylating agent. Conjugates containing "bridged disulfides" are also claimed to have increased stability.

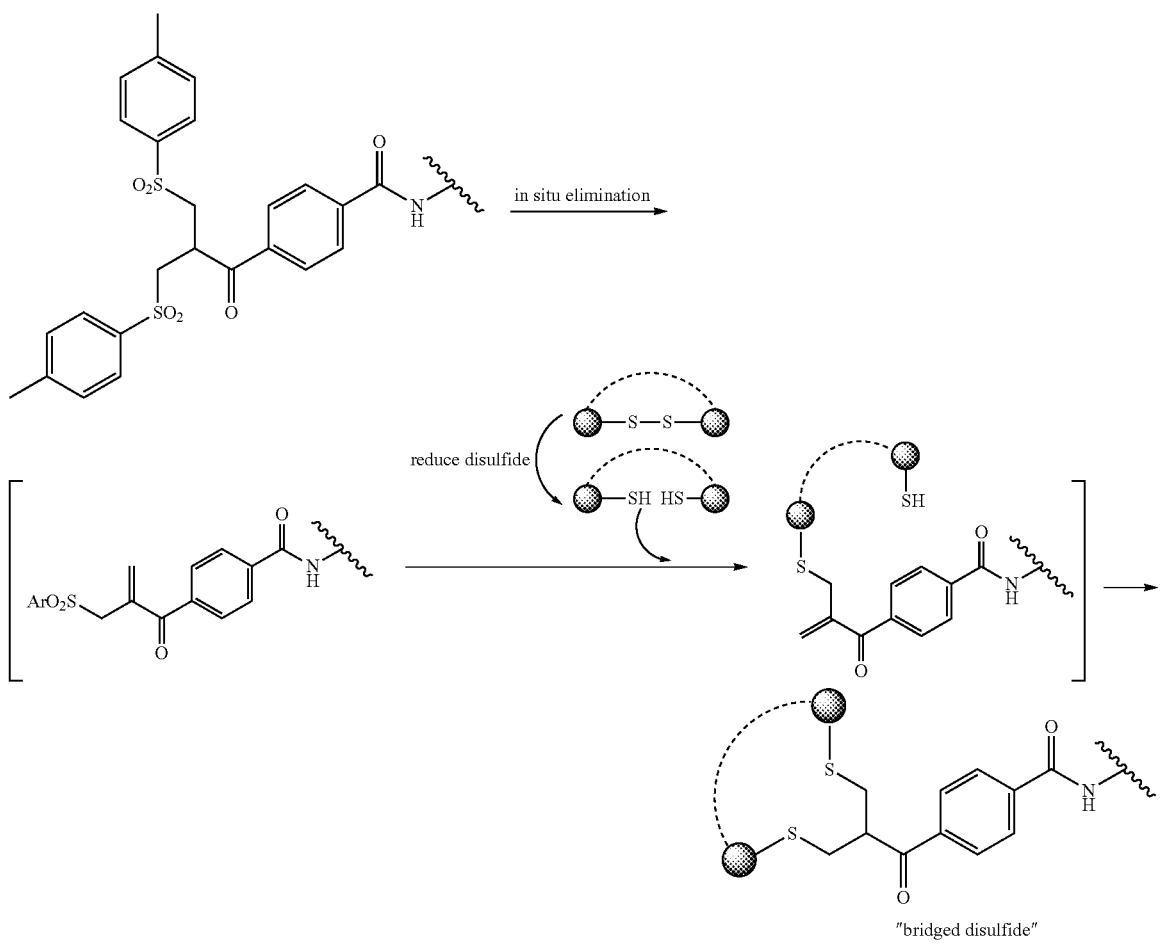
"bridged disulfide"

Similarly, as depicted below, a maleimide derivative that is capable of bridging a pair of sulfhydryl groups has been developed.

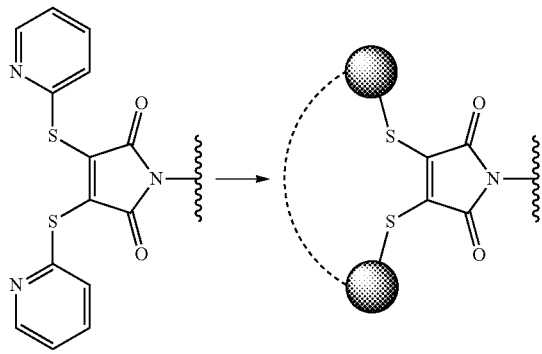 [SMILES: *N1C(=O)C(Sc2ccccn2)=C(Sc2ccccn2)C1=O ; *N1C(=O)C(SC)=C(SC)C1=O]

A linker of the disclosure, $L^3$, can contain the following structural formulas (VIa), (VIb), or (VIc):

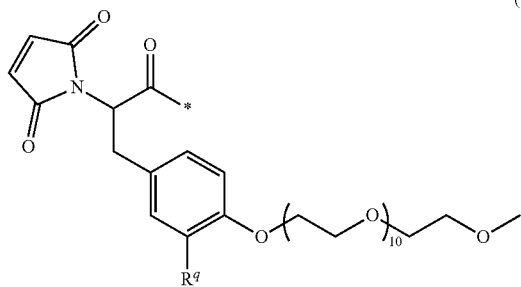
(VIa)

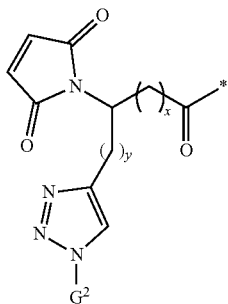
(VIb)

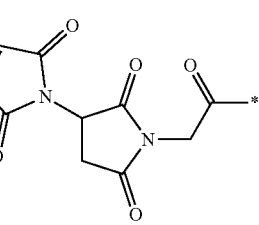
(VIc)

or salts thereof, wherein: $R^q$ is H or $-O-(CH_2CH_2O)_{11}-CH_3$; x is 0 or 1; y is 0 or 1; $G^2$ is $-CH_2CH_2CH_2SO_3H$ or $-CH_2CH_2O-(CH_2CH_2O)_{11}-CH_3$; $R^w$ is $-O-CH_2CH_2SO_3H$ or $-NH(CO)-CH_2CH_2O-(CH_2CH_2O)_{12}-CH_3$; and * represents the point of attachment to the remainder of the linker.

Exemplary embodiments of linkers according to structural formula (VIa) and (VIb) that can be included in the conjugates described herein can include the linkers illustrated below (as illustrated, the linkers can include a group suitable for covalently linking the linker to an antibody construct):

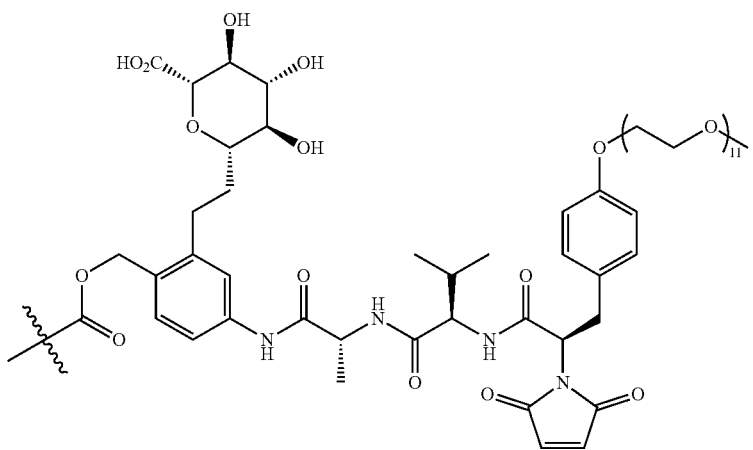
(VIa.1)

-continued
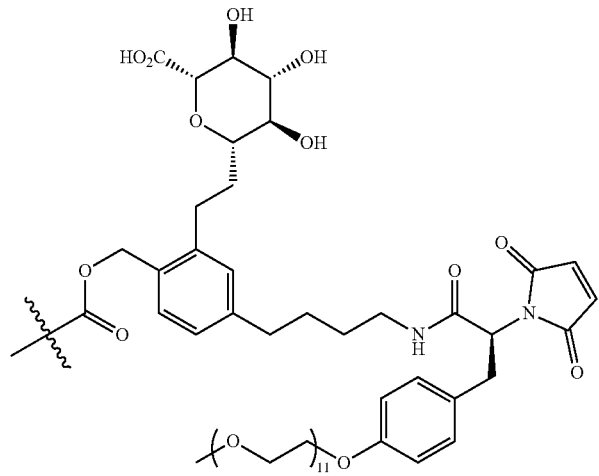
(VIa.2)
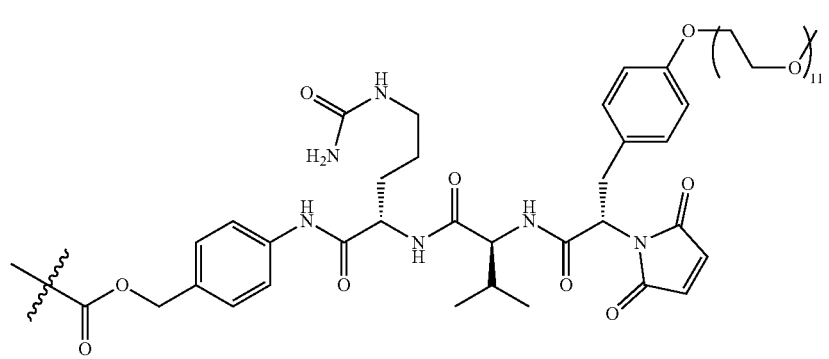
(VIa.3)
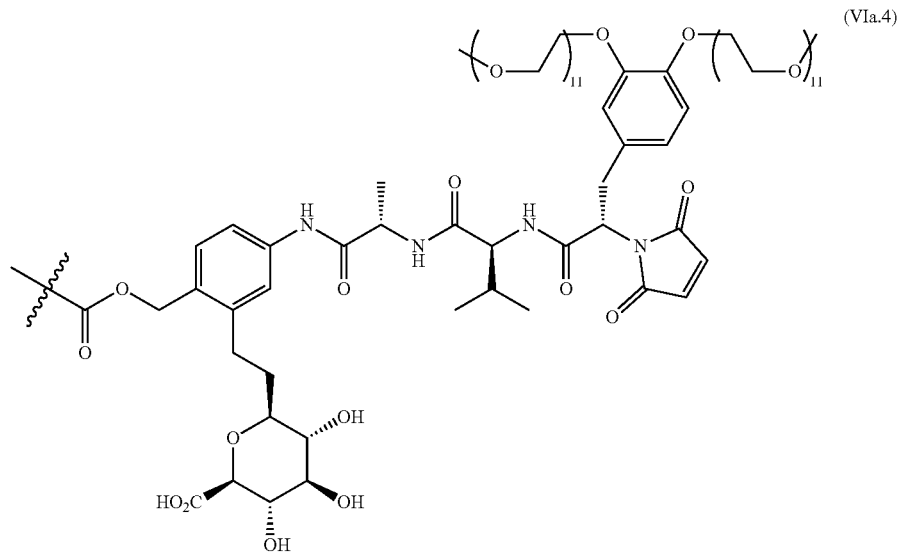
(VIa.4)

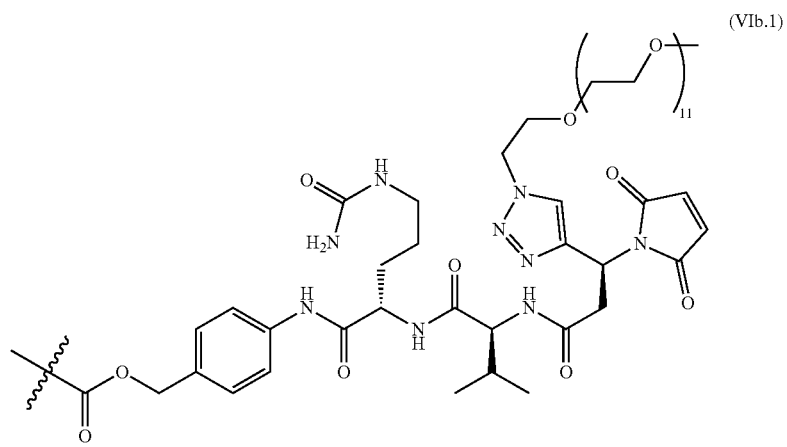
(VIb.1)
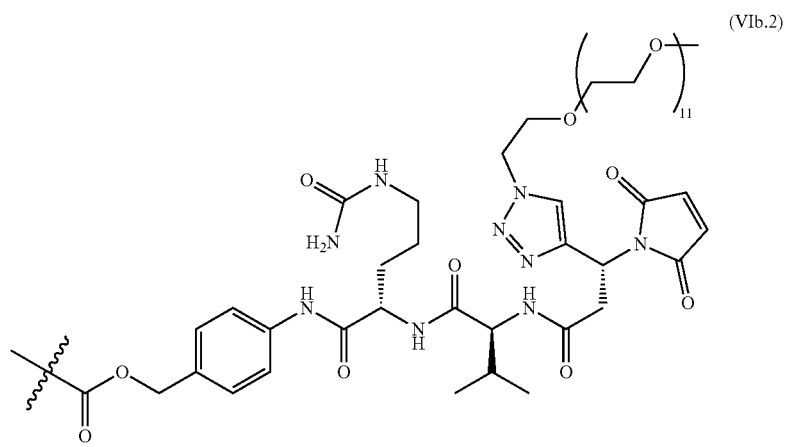
(VIb.2)
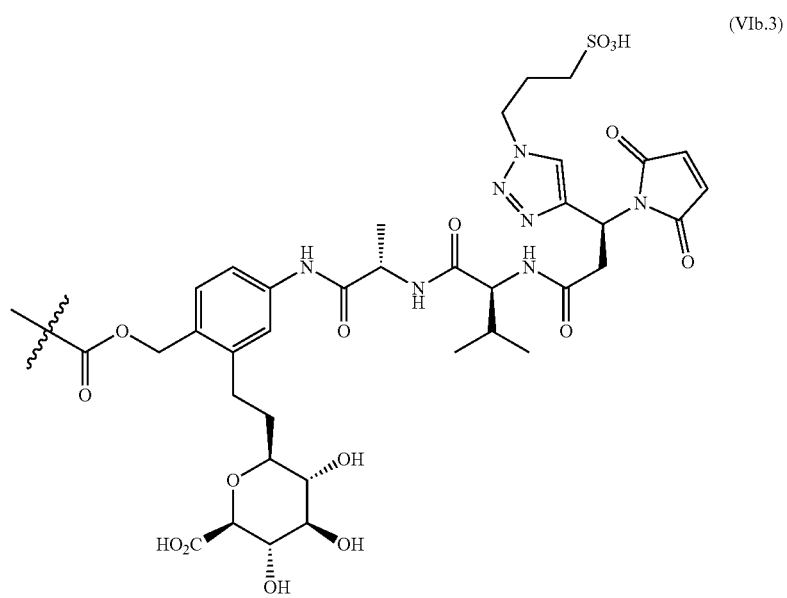
(VIb.3)

-continued
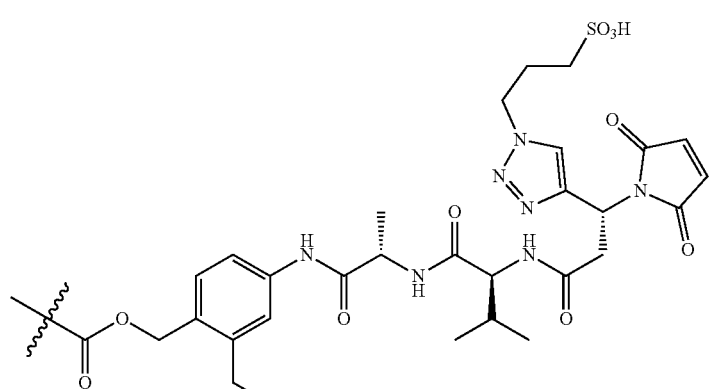
(VIb.4)
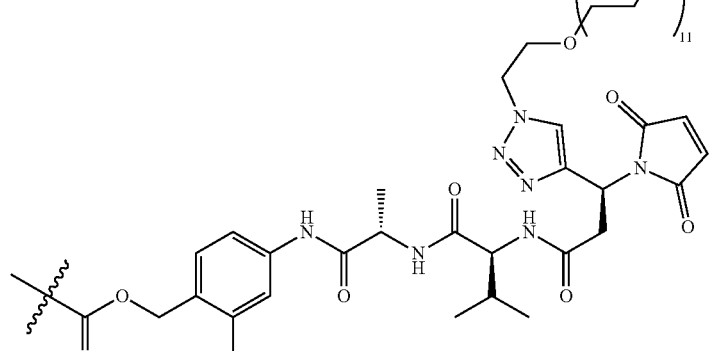
(VIb.6)
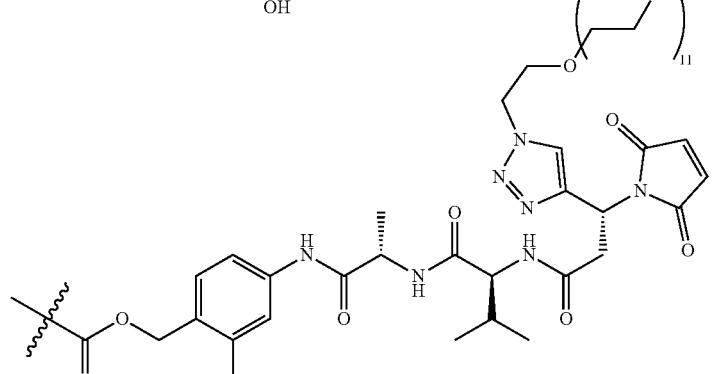
(VIIb.7)

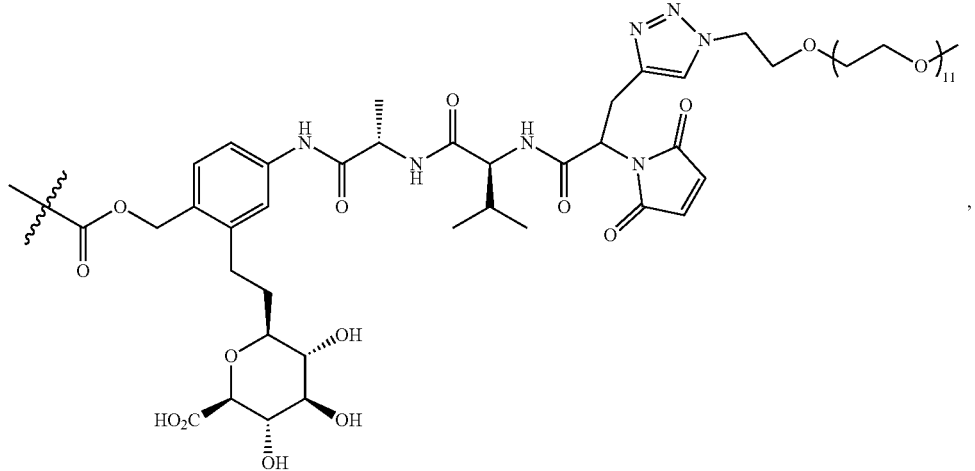

(VIIb.8)

wherein ∫ represents the point of attachment of the linker (L³) to the compound or salt of any one of Formulas (IA), (IB), (IC), (IIA), (IIB), (IIC), (IIIA), (IIIB), (IIIC), (IVA), (IVB), or (IVC).

Exemplary embodiments of linkers according to structural formula (VIc) that can be included in the antibody construct benzazepine compound conjugates described herein can include the linkers illustrated below (as illustrated, the linkers can include a group suitable for covalently linking the linker to an antibody construct):

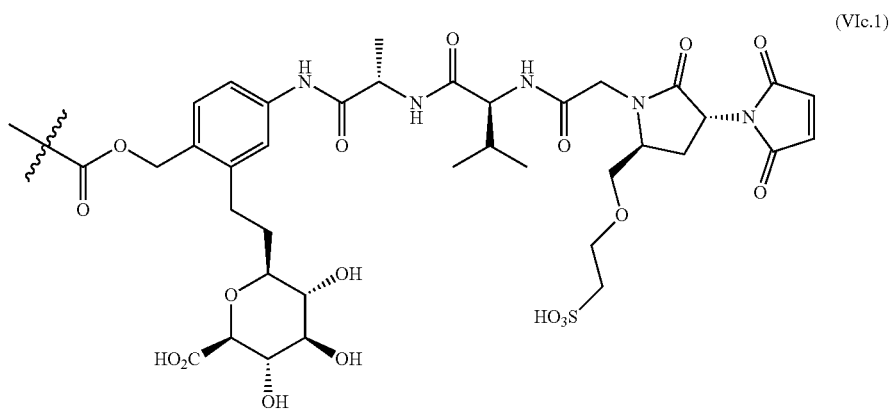

(VIc.1)

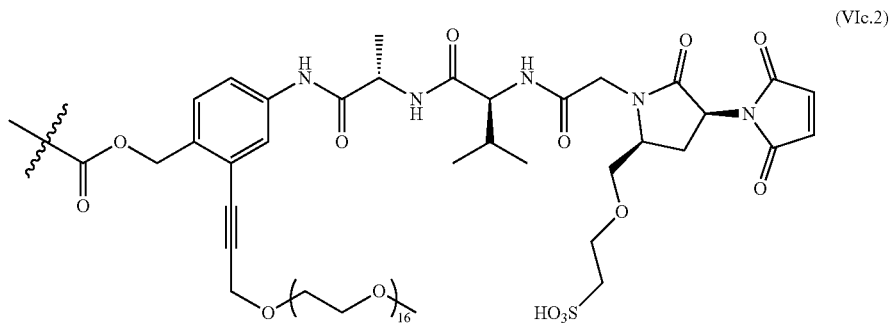

(VIc.2)

-continued (VIc.3)
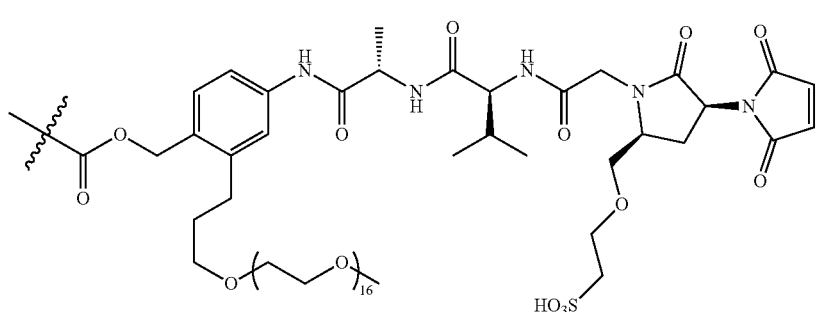

(VIc.4)
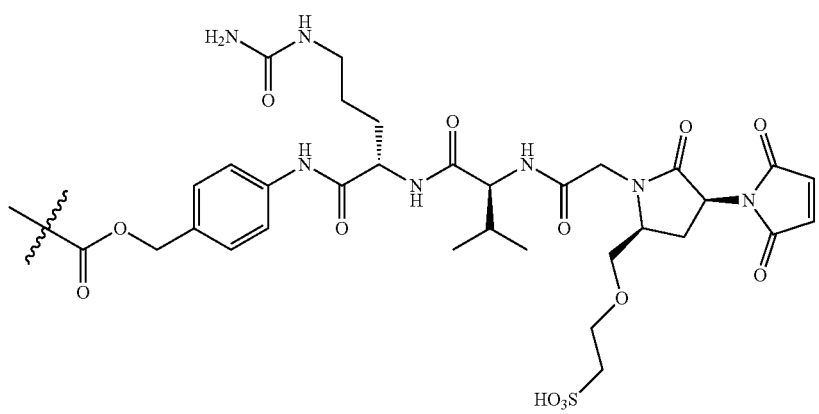

(VIc.5)
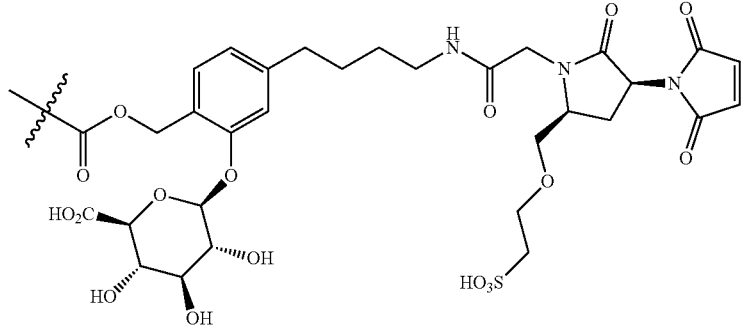

(VIc.6)
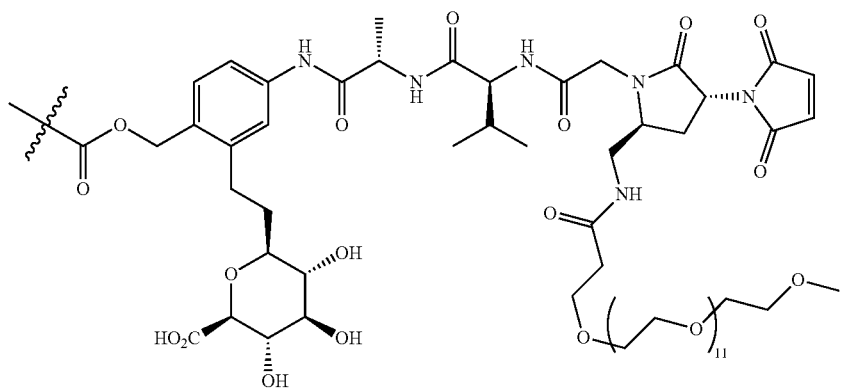

wherein ƒ represents the point of attachment of the linker ($L^3$) to the compound or salt of any one of Formulas (IA), (IB), (IC), (IIA), (IIB), (IIC), (IIIA), (IIIB), (IIIC), (IVA), (IVB), or (IVC).

As is known by skilled artisans, the linker selected for a particular conjugate may be influenced by a variety of factors, including but not limited to, the site of attachment to the antibody construct (e.g., lys, cys or other amino acid residues), structural constraints of the drug pharmacophore and the lipophilicity of the drug. The specific linker selected for a conjugate should seek to balance these different factors for the specific antibody construct/drug combination.

For example, conjugates have been observed to effect killing of bystander antigen-negative cells present in the vicinity of the antigen-positive tumor cells. The mechanism of bystander cell killing by conjugates has indicated that metabolic products formed during intracellular processing of the conjugates may play a role. Neutral cytotoxic metabolites generated by metabolism of the conjugates in antigen-positive cells appear to play a role in bystander cell killing while charged metabolites may be prevented from diffusing across the membrane into the medium, or from the medium across the membrane, and therefore cannot affect bystander killing. In certain embodiments, the linker is selected to attenuate the bystander killing effect caused by cellular metabolites of the conjugate. In certain embodiments, the linker is selected to increase the bystander killing effect.

The properties of the linker, or linker-compound, may also impact aggregation of the conjugate under conditions of use and/or storage. Typically, conjugates reported in the literature contain no more than 3-4 drug molecules per antibody molecule. Attempts to obtain higher drug-to-antibody ratios ("DAR") often failed, particularly if both the drug and the linker were hydrophobic, due to aggregation of the conjugate. In many instances, DARs higher than 3-4 could be beneficial as a means of increasing potency. In instances where the benzazepine compound is more hydrophobic in nature, it may be desirable to select linkers that are relatively hydrophilic as a means of reducing conjugate aggregation, especially in instances where DARs greater than 3-4 are desired. Thus, in certain embodiments, the linker incorporates chemical moieties that reduce aggregation of the conjugates during storage and/or use. A linker may incorporate polar or hydrophilic groups such as charged groups or groups that become charged under physiological pH to reduce the aggregation of the conjugates. For example, a linker may incorporate charged groups such as salts or groups that deprotonate, e.g., carboxylates, or protonate, e.g., amines, at physiological pH.

In particular embodiments, the aggregation of the conjugates during storage or use is less than about 40% as determined by size-exclusion chromatography (SEC). In particular embodiments, the aggregation of the conjugates during storage or use is less than 35%, such as less than about 30%, such as less than about 25%, such as less than about 20%, such as less than about 15%, such as less than about 10%, such as less than about 5%, such as less than about 4%, or even less, as determined by size-exclusion chromatography (SEC).

Attachment of Linkers to Antibody Construct

The conjugates described herein may comprise a linker, e.g., a cleavable linker such as a peptide linker or a non-cleavable linker. Linkers of the conjugates and methods described herein may not affect the binding of active portions of a conjugate (e.g., active portions include antigen binding domains, Fc domains, target binding domains, antibodies, compounds or salts of the disclosed, e.g., Formulas (IA), (IB), (IC), (IIA), (IIB), (IIC), (IIIA), (IIIB) or (IIIC), or linker-compounds of Formulas (IVA), (IVB), or (IVC) to a target, which can be a cognate binding partner such as an antigen. A linker sequence can form a linkage between different parts of a conjugate, e.g., between an antibody construct and a compound or salt of the disclosure. In certain embodiments, a conjugate comprises multiple linkers. In certain embodiments, wherein a conjugate comprises multiple linkers, the linkers may be the same linkers or different linkers.

A linker may be bound to an antibody construct by a bond between the antibody construct and the linker. A linker may be bound to an anti-tumor antigen antibody construct by a bond between the anti-tumor antigen antibody construct and the linker. A linker may be bound to a terminus of an amino acid sequence of an antibody construct, or could be bound to a side chain modification to the antibody construct, such as the side chain of a lysine, serine, threonine, cysteine, tyrosine, aspartic acid, glutamine, a non-natural amino acid residue, or glutamic acid residue. A linker may be bound to a terminus of an amino acid sequence of an Fc domain or Fc region of an antibody construct, or may be bound to a side chain modification of an Fc domain or Fc region of an antibody construct, such as the side chain of a lysine, serine, threonine, cysteine, tyrosine, aspartic acid, glutamine, a non-natural amino acid residue, or glutamic acid residue. A linker may be bound to a terminus of an amino acid sequence of an Fc domain of an antibody construct, or may be bound to a side chain modification of an Fc domain of an antibody construct, such as the side chain of a lysine, serine, threonine, cysteine, tyrosine, aspartic acid, glutamine, a non-natural amino acid residue, or glutamic acid residue.

A linker may be bound to an antibody construct at a hinge cysteine. A linker may be bound to an antibody construct at a light chain constant domain lysine. A linker may be bound to an antibody construct at a heavy chain constant domain lysine. A linker may be bound to an antibody construct at an engineered cysteine in the light chain. A linker may be bound to an antibody construct at an Fc region lysine. A linker may be bound to an antibody construct at an Fc domain lysine. A linker may be bound to an antibody construct at an Fc region cysteine. A linker may be bound to an antibody construct at an Fc domain cysteine. A linker may be bound to an antibody construct at a light chain glutamine, such as an engineered glutamine. A linker may be bound to an antibody construct at a heavy chain glutamine, such as an engineered glutamine. A linker may be bound to an antibody construct at an unnatural amino acid engineered into the light chain. A linker may be bound to an antibody construct at an unnatural amino acid engineered into the heavy chain. Amino acids can be engineered into an amino acid sequence of an antibody construct, for example, a linker of a conjugate. Engineered amino acids may be added to a sequence of existing amino acids. Engineered amino acids may be substituted for one or more existing amino acids of a sequence of amino acids.

A linker may be conjugated to an antibody construct via a sulfhydryl group on the antibody construct. A linker may be conjugated to an antibody construct via a primary amine on the antibody construct. A linker may be conjugated to an antibody construct via a residue of an unnatural amino acid on an antibody construct, e.g., a ketone moiety.

When one or more linkers are bound to an antibody construct at the sites described herein, an Fc domain of the antibody construct can bind to Fc receptors. In certain embodiments, an antibody construct bound through a linker or an antibody construct bound to a linker bound to a compound or salt of any one of Formulas (IA), (IB), (IC), (IIA), (IIB), (IIC), (IIIA), (IIIB) or (IIIC), or bound through a compound-linker of Formulas (IVA), (IVB) or (IVC), retains the ability of the Fc domain of the antibody to bind to Fc receptors. In certain embodiments, when a linker is connected to an antibody construct at the sites described herein, the antigen binding domain of an antibody construct bound to a linker or an antibody construct bound through a linker bound to a compound or salt of any one of Formulas (IA), (IB), (IC), (IIA), (IIB), (IIC), (IIIA), (IIIB) or (IIIC), or bound through a compound-linker of Formulas (IVA), (IVB), or (IVC) can bind its antigen. In certain embodiments, when a linker is connected to an antibody construct at the sites described herein, a target binding domain of an antibody construct bound to a linker or an antibody construct bound to a linker bound to a compound or salt of any one of Formulas (IA), (IB), (IC), (IIA), (IIB), (IIC), (IIIA), (IIIB), (IIIC), (IVA), (IVB), or (IVC) can bind its antigen.

In certain embodiments, a compound or a compound-linker of any one of Formulas (IA), (IB), (IC), (IIA), (IIB), (IIC), (IIIA), (IIIB), (IIIC), (IVA), (IVB), or (IVC) disclosed herein is attached to an antibody Fc region or domain at an engineered cysteine residue. In some embodiments, the engineered cysteine residue is at one or more of positions HC S239C, LC V205C, LC A114C, HC A140C, LC K149C, LC S168C, LC S153C, LC A127C, HC T116C, and HC S115C, where HC refers to heavy chain, LC refers t light chain and the numbering of amino acid residues in the Fc region is according to the EU index as in Kabat. In certain embodiments, a compound or a compound-linker of any one of Formulas (IA), (IB), (IC), (IIA), (IIB), (IIC), (IIIA), (IIIB), (IIIC), (IVA), (IVB), or (IVC) disclosed herein may not be attached to an amino acid residue of an IgG Fc domain disclosed herein selected from: 221, 222, 224, 227, 228, 230, 231, 223, 233, 234, 235, 236, 237, 238, 239, 240, 241, 243, 244, 245, 246, 247, 249, 250, 258, 262, 263, 264, 265, 266, 267, 268, 269, 270, 271, 272, 273, 274, 275, 276, 278, 280, 281, 283, 285, 286, 288, 290, 291, 292, 293, 294, 295, 296, 297, 298, 299, 300, 302, 305, 313, 317, 318, 320, 322, 323, 324, 325, 326, 327, 328, 329, 330, 331, 332, 333, 334, 335 336, 396, 428, or any subset thereof wherein numbering of amino acid residues in the Fc domain is according to the EU index as in Kabat.

Lysine-Based Bioconjugation

An antibody construct can be conjugated to a linker via lysine-based bioconjugation. An antibody construct can be exchanged into an appropriate buffer, for example, phosphate, borate, PBS, Tris-Acetate, Tris-Glycine, HEPES, MOPS, MES, EPS, HEPPS, Histidine, or HEPBS at a concentration of about 2 mg/mL to about 10 mg/mL. An appropriate number of equivalents of a compound-linker, e.g., a compound or salt of Formula (IVA), (IVB), or (IVC), described herein can be added as a solution with stirring. Dependent on the physical properties of the benzazepine-linker construct, a co-solvent can be introduced prior to the addition of the benzazepine-linker construct to facilitate solubility. The reaction can be stirred at room temperature for 2 hours to about 12 hours depending on the observed reactivity. The progression of the reaction can be monitored by LC-MS. Once the reaction is deemed complete, the remaining benzazepine-linker constructs can be removed by applicable methods and the antibody construct-benzazepine conjugate can be exchanged into the desired formulation buffer. Lysine-linked conjugates can be synthesized starting with antibody (mAb) or bispecific antibody (bsAb) and benzazepine-linker construct, e.g., 10 equivalents, following Scheme A below (Conjugate=antibody construct-benzazepine conjugate). Monomer content and benzazepine-antibody construct ratios (molar ratios) can be determined by methods described herein.

Scheme A:

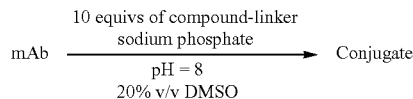

Cysteine-Based Bioconjugation

An antibody construct can be conjugated to a linker via cysteine-based bioconjugation. An antibody construct can be exchanged into an appropriate buffer, for example, phosphate, borate, PBS, Tris-Acetate, Tris-Glycine, HEPES, MOPS, MES, EPS, HEPPS, Histidine, or HEPBS at a concentration of about 2 mg/mL to about 10 mg/mL with an appropriate number of equivalents of a reducing agent, for example, dithiothreitol or tris(2-carboxyethyl)phosphine. The resultant solution can be stirred for an appropriate amount of time and temperature to effect the desired reduction. A compound-linker, e.g., a compound or salt of Formula (IVA), (IVB), or (IVC), described herein can be added as a solution with stirring. Dependent on the physical properties of the benzazepine-linker construct, a co-solvent can be introduced prior to the addition of the benzazepine-linker construct to facilitate solubility. The reaction can be stirred at room temperature for about 1 hour to about 12 hours depending on the observed reactivity. The progression of the reaction can be monitored by liquid chromatography-mass spectrometry (LC-MS). Once the reaction is deemed complete, the remaining free benzazepine-linker construct can be removed by applicable methods and the antibody construct-benzazepine conjugate can be exchanged into the desired formulation buffer. Such cysteine-based conjugates can be synthesized starting with antibody (mAb) and benzazepine-linker construct, e.g., 7 equivalents, using the conditions described in Scheme B below (Conjugate=antibody construct-benzazepine compound conjugate). Monomer content and drug-antibody ratios can be determined by methods described herein.

Scheme B:

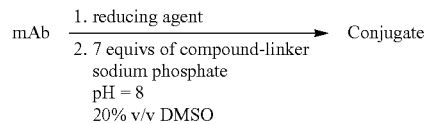

Pharmaceutical Formulations

The compositions, conjugates and methods described herein can be considered useful as pharmaceutical compositions for administration to a subject in need thereof. Pharmaceutical compositions can comprise at least the compounds, salts or conjugates described herein and one or more pharmaceutically acceptable carriers, diluents, excipients, stabilizers, dispersing agents, suspending agents, and/or thickening agents. The composition can comprise the conjugate having an antibody construct and a compound or salt of any one of Formulas (IA), (IB), (IC), (IIA), (IIB), (IIC), (IIIA), (IIIB), (IIIC), (IVA), (IVB), or (IVC) connected via a linker, as described herein. The composition can comprise the conjugate having an antibody construct, a target binding domain, and a compound or salt of any one of Formulas (IA), (IB), (IC), (IIA), (IIB), (IIC), (IIIA), (IIIB), (IIIC), (IVA), (IVB), or (IVC) connected via a linker. The composition can comprise any conjugate described herein. The antibody construct can be an anti-CD40 antibody. A conjugate can comprise an anti-CD40 antibody and a benzazepine. A conjugate can comprise an anti-HER2 antibody and a benzazepine. A conjugate can comprise an anti-TROP2 antibody and a benzazepine. A pharmaceutical composition can comprise at least the compounds, salts or conjugates described herein and one or more of buffers, antibiotics, steroids, carbohydrates, drugs (e.g., chemotherapy drugs), radiation, polypeptides, chelators, adjuvants and/or preservatives.

Pharmaceutical compositions can be formulated using one or more physiologically-acceptable carriers comprising excipients and auxiliaries. Formulation can be modified depending upon the route of administration chosen. Pharmaceutical compositions comprising a compound, salt or conjugate as described herein can be manufactured, for example, by lyophilizing the compound, salt or conjugate, mixing, dissolving, emulsifying, encapsulating or entrapping the conjugate. The pharmaceutical compositions can also include the compounds, salts or conjugates described herein in a free-base form or pharmaceutically-acceptable salt form.

Methods for formulation of the conjugates described herein can include formulating any of the compounds, salts or conjugates described herein with one or more inert, pharmaceutically-acceptable excipients or carriers to form a solid, semi-solid, or liquid composition. Solid compositions can include, for example, powders, tablets, dispersible granules and capsules, and in some aspects, the solid compositions further contain nontoxic, auxiliary substances, for example wetting or emulsifying agents, pH buffering agents, and other pharmaceutically-acceptable additives. Alternatively, the compounds, salts or conjugates described herein can be lyophilized or in powder form for re-constitution with a suitable vehicle, e.g., sterile pyrogen-free water, before use.

Pharmaceutical compositions described herein can comprise at least one active ingredient (e.g., a compound, salt or conjugate). The active ingredients can be entrapped in microcapsules prepared, for example, by coacervation techniques or by interfacial polymerization (e.g., hydroxymethylcellulose or gelatin microcapsules and poly-(methylmethacylate) microcapsules, respectively), in colloidal drug-delivery systems (e.g., liposomes, albumin microspheres, microemulsions, nano-particles and nanocapsules) or in macroemulsions.

Pharmaceutical compositions as described herein often further can comprise more than one active compound (e.g., a compound, salt or conjugate and other agents) as necessary for the particular indication being treated. The active compounds can have complementary activities that do not adversely affect each other. For example, the composition can also comprise a chemotherapeutic agent, cytotoxic agent, cytokine, growth-inhibitory agent, anti-hormonal agent, anti-angiogenic agent, and/or cardioprotectant. Such molecules can be present in combination in amounts that are effective for the purpose intended.

The compositions and formulations can be sterilized. Sterilization can be accomplished by filtration through sterile filtration.

The compositions described herein can be formulated for administration as an injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Injections can be formulated for bolus injection or continuous infusion. Alternatively, the compositions described herein can be lyophilized or in powder form for reconstitution with a suitable vehicle, e.g., sterile pyrogen-free water, before use.

For parenteral administration, the compounds, salts or conjugates can be formulated in a unit dosage injectable form (e.g., use letter solution, suspension, emulsion) in association with a pharmaceutically acceptable parenteral vehicle. Such vehicles can be inherently non-toxic, and non-therapeutic. Vehicles can be water, saline, Ringer's solution, dextrose solution, and 5% human serum albumin. Non-aqueous vehicles such as fixed oils and ethyl oleate can also be used. Liposomes can be used as carriers. The vehicle can contain minor amounts of additives such as substances that enhance isotonicity and chemical stability (e.g., buffers and preservatives).

Sustained-release preparations can also be prepared. Examples of sustained-release preparations can include semipermeable matrices of solid hydrophobic polymers that can contain the compound, salt or conjugate, and these matrices can be in the form of shaped articles (e.g., films or microcapsules). Examples of sustained-release matrices can include polyesters, hydrogels (e.g., poly(2-hydroxyethylmethacrylate), or poly (vinyl alcohol)), polylactides, copolymers of L-glutamic acid and γ ethyl-L-glutamate, non-degradable ethylene-vinyl acetate, degradable lactic acid-glycolic acid copolymers such as the LUPRON DEPO™ (i.e., injectable microspheres composed of lactic acid-glycolic acid copolymer and leuprolide acetate), and poly-D-(−)-3-hydroxybutyric acid.

Pharmaceutical formulations described herein can be prepared for storage by mixing a compound, salt or conjugate with a pharmaceutically acceptable carrier, excipient, and/or a stabilizer. This formulation can be a lyophilized formulation or an aqueous solution. Acceptable carriers, excipients, and/or stabilizers can be nontoxic to recipients at the dosages and concentrations used. Acceptable carriers, excipients, and/or stabilizers can include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

Pharmaceutical formulations of the conjugates described herein may have an average drug-antibody construct ratio ("DAR") selected from about 1 to about 10, wherein the drug is a compound or salt of any one of Formulas (IA), (IB), (IC), (IIA), (IIB), (IIC), (IIIA), (IIIB), (IIIC), (IVA), (IVB), or (IVC). In certain embodiments, the average DAR of the formulation is from about 2 to about 8, such as from about 3 to about 8, such as from about 3 to about 7. In certain embodiments, a pharmaceutical formulation has an average DAR of about 3, about 3.5, about 4, about 4.5, about 5, about 5.5, about 6, or about 6.6.

Therapeutic Applications

The compositions, conjugates and methods of the present disclosure can be useful for a plurality of different subjects including, but are not limited to, a mammal, human, non-human mammal, a domesticated animal (e.g., laboratory animals, household pets, or livestock), non-domesticated animal (e.g., wildlife), dog, cat, rodent, mouse, hamster, cow, bird, chicken, fish, pig, horse, goat, sheep, rabbit, and any combination thereof.

The compositions, conjugates and methods described herein can be useful as a therapeutic, for example, a treatment that can be administered to a subject in need thereof. A therapeutic effect of the present disclosure can be obtained in a subject by reduction, suppression, remission, or eradication of a disease state, including, but not limited to, a symptom thereof. A therapeutic effect in a subject having a disease or condition, or pre-disposed to have or is beginning to have the disease or condition, can be obtained by a reduction, a suppression, a prevention, a remission, or an eradication of the condition or disease, or pre-condition or pre-disease state.

In practicing the methods described herein, therapeutically-effective amounts of the compositions, and conjugates described herein can be administered to a subject in need thereof, often for treating and/or preventing a condition or progression thereof. A pharmaceutical composition can affect the physiology of the subject, such as the immune system, an inflammatory response, or other physiologic affect. A therapeutically-effective amount can vary depending on the severity of the disease, the age and relative health of the subject, the potency of the compounds used, and other factors.

Treat and/or treating can refer to any indicia of success in the treatment or amelioration of the disease or condition. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. Treat can be used herein to refer to a method that results in some level of treatment or amelioration of the disease or condition, and can contemplate a range of results directed to that end, including but not restricted to prevention of the condition entirely.

Prevent, preventing and the like can refer to the prevention of the disease or condition, e.g., tumor formation, in the patient. For example, if an individual at risk of developing a tumor or other form of cancer is treated with the methods of the present disclosure and does not later develop the tumor or other form of cancer, then the disease has been prevented, at least over a period of time, in that individual. Preventing can also refer to preventing re-occurrence of a disease or condition in a patient that has previously been treated for the disease or condition, e.g., by preventing relapse.

A therapeutically effective amount can be the amount of a composition or an active component thereof sufficient to provide a beneficial effect or to otherwise reduce a detrimental non-beneficial event to the individual to whom the composition is administered. A therapeutically effective dose can be a dose that produces one or more desired or desirable (e.g., beneficial) effects for which it is administered, such administration occurring one or more times over a given period of time. An exact dose can depend on the purpose of the treatment, and can be ascertainable by one skilled in the art using known techniques.

The conjugates described herein that can be used in therapy can be formulated and dosages established in a fashion consistent with good medical practice taking into account the disease or condition to be treated, the condition of the individual patient, the site of delivery of the composition, the method of administration and other factors known to practitioners. The compositions described herein can be prepared according to the description of preparation described herein.

Pharmaceutical compositions can be used in the methods described herein and can be administered to a subject in need thereof using a technique known to one of ordinary skill in the art which can be suitable as a therapy for the disease or condition affecting the subject. One of ordinary skill in the art would understand that the amount, duration and frequency of administration of a pharmaceutical composition described herein to a subject in need thereof depends on several factors including, for example but not limited to, the health of the subject, the specific disease or condition of the patient, the grade or level of a specific disease or condition of the patient, the additional therapeutics the subject is being or has been administered, and the like.

The methods and compositions described herein can be for administration to a subject in need thereof. Often, administration of the compositions described herein can include routes of administration, non-limiting examples of administration routes include intravenous, intraarterial, subcutaneous, subdural, intramuscular, intracranial, intrasternal, intratumoral, or intraperitoneally. Additionally, a pharmaceutical composition can be administered to a subject by additional routes of administration, for example, by inhalation, oral, dermal, intranasal, or intrathecal administration.

Compositions and conjugates of the present disclosure can be administered to a subject in need thereof in a first administration, and in one or more additional administrations. The one or more additional administrations can be administered to the subject in need thereof minutes, hours, days, weeks or months following the first administration. Any one of the additional administrations can be administered to the subject in need thereof less than 21 days, or less than 14 days, less than 10 days, less than 7 days, less than 4 days or less than 1 day after the first administration. The one or more administrations can occur more than once per day, more than once per week or more than once per month. The administrations can be weekly, biweekly (every two weeks), every three weeks, monthly or bimonthly.

The compositions, conjugates and methods provided herein can be useful for the treatment of a plurality of diseases, conditions, preventing a disease or a condition in a subject or other therapeutic applications for subjects in need thereof. Often the compositions, conjugates and methods provided herein can be useful for treatment of hyperplastic conditions, including but not limited to, neoplasms, cancers, tumors and the like. The compositions, conjugates and methods provided herein can be useful for specifically targeting TLR8. In one embodiment, the compounds of the present disclosure serve as TLR8 agonists and activate an immune response. In another embodiment, the conjugates of the present disclosure serve as TLR8 agonists and activate an immune response. A condition, such as a cancer, can be associated with expression of a molecule on the cancer cells. Often, the molecule expressed by the cancer cells can comprise an extracellular portion capable of recognition by the antibody construct of the conjugate. A molecule expressed by the cancer cells can be a tumor antigen. An antibody construct portion of the conjugate can recognize a tumor antigen. A tumor antigen can include CD5, CD19, CD20, CD25, CD37, CD30, CD33, CD40, CD45, CAMPATH-1, BCMA, CS-1, PD-L1, B7-H3, B7-DC, HLD-DR, carcinoembryonic antigen (CEA), TAG-72, EpCAM, MUC1, folate-binding protein, A33, G250, prostate-specific membrane antigen (PMSA), ferritin, GD2, GD3, GM2, Le$^y$, CA-125, CA19-9, epidermal growth factor, p185HER2, IL-2 receptor, EGFRvIII (de2-7 EGFR), fibroblast activation protein, tenascin, a metalloproteinase, endosialin, vascular endothelial growth factor, avB3, WT1, LMP2, HPV E6, HPV E7, Her-2/neu, MAGE A3, p53 nonmutant, NY-ESO-1, MelanA/MART1, Ras mutant, gp100, p53 mutant, PR1, bcr-abl, tyronsinase, survivin, PSA, hTERT, a Sarcoma translocation breakpoint protein, EphA2, PAP, ML-IAP, AFP, ERG, NA17, PAX3, ALK, androgen receptor, cyclin B1, polysialic acid, MYCN, RhoC, TRP-2, fucosyl GM1, mesothelin (MSLN), PSCA, MAGE A1, sLe(animal), CYP1B1, PLAV1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, Legumain, Tie 3, VEGFR2, MAD-CT-1, PDGFR-B, MAD-CT-2, ROR2, TRAIL1, MUC16, MAGE A4, MAGE $C_2$, GAGE, EGFR, CMET, HER3, MUC15, CA6, NAPI2B, TROP2, CLDN6, CLDN16, CLDN18.2, CLorf186, RON, LY6E, FRA, DLL3, PTK7, STRA6, TMPRSS3, TMPRSS4, TMEM238, UPK1B, VTCN1, LIV1, ROR1, or Fos-related antigen 1.

As described herein, an antigen binding domain portion of the conjugate may be configured to recognize a molecule expressed by a cancer cell, such as for example, a disease antigen, tumor antigen or a cancer antigen. Often such antigens are known to those of ordinary skill in the art, or newly found to be associated with such a condition, to be commonly associated with, and/or, specific to, such conditions. For example, a disease antigen, tumor antigen or a cancer antigen is, but is not limited to, CD5, CD19, CD20, CD25, CD37, CD30, CD33, CD40, CD45, CAMPATH-1, BCMA, CS-1, PD-L1, B7-H3, B7-DC, HLD-DR, carcinoembryonic antigen (CEA), TAG-72, EpCAM, MUC1, folate-binding protein, A33, G250, prostate-specific membrane antigen (PSMA), ferritin, GD2, GD3, GM2, Le, CA-125, CA19-9, epidermal growth factor, p185HER2, IL-2 receptor, EGFRVIII (de2-7 EGFR), fibroblast activation protein, tenascin, a metalloproteinase, endosialin, vascular endothelial growth factor, avB3, WT1, LMP2, HPV E6, HPV E7, Her-2/neu, MAGE A3, p53 nonmutant, NY-ESO-1, MelanA/MART1, Ras mutant, gp100, p53 mutant, PR1, bcr-abl, tyronsinase, survivin, PSA, hTERT, a Sarcoma translocation breakpoint protein, EphA2, PAP, ML-IAP, AFP, ERG, NA17, PAX3, ALK, androgen receptor, cyclin B1, polysialic acid, MYCN, RhoC, TRP-2, fucosyl GM1, mesothelin (MSLN), PSCA, MAGE A1, sLe(animal), CYP1B1, PLAV1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, Legumain, Tie 3, VEGFR2, MAD-CT-1, PDGFR-B, MAD-CT-2, ROR2, TRAIL1, MUC16, MAGE A4, MAGE $C_2$, GAGE, EGFR, CMET, HER3, MUC15, CA6, NAPI2B, TROP2, CLDN6, CLDN16, CLDN18.2, CLorf186, RON, LY6E, FRA, DLL3, PTK7, STRA6, TMPRSS3, TMPRSS4, TMEM238, UPK1B, VTCN1, LIV1, ROR1, or Fos-related antigen 1. Additionally, such tumor antigens can be derived from the following specific conditions and/or families of conditions, including but not limited to, cancers such as brain cancers, skin cancers, lymphomas, sarcomas, lung cancer, liver cancer, leukemias, uterine cancer, breast cancer, ovarian cancer, cervical cancer, bladder cancer, kidney cancer, hemangiosarcomas, bone cancers, blood cancers, testicular cancer, prostate cancer, stomach cancer, intestinal cancers, pancreatic cancer, and other types of cancers as well as pre-cancerous conditions such as hyperplasia or the like.

Non-limiting examples of cancers can include Acute lymphoblastic leukemia (ALL); Acute myeloid leukemia; Adrenocortical carcinoma; Astrocytoma, childhood cerebellar or cerebral; Basal-cell carcinoma; Bladder cancer; Bone tumor, osteosarcoma/malignant fibrous histiocytoma; Brain cancer; Brain tumors, such as, cerebellar astrocytoma, malignant glioma, ependymoma, medulloblastoma, visual pathway and hypothalamic glioma; Brainstem glioma; Breast cancer; Bronchial adenomas/carcinoids; Burkitt's lymphoma; Cerebellar astrocytoma; Cervical cancer; Cholangiocarcinoma; Chondrosarcoma; Chronic lymphocytic leukemia; Chronic myelogenous leukemia; Chronic myeloproliferative disorders; Colon cancer; Cutaneous T-cell lymphoma; Endometrial cancer; Ependymoma; Esophageal cancer; Eye cancers, such as, intraocular melanoma and retinoblastoma; Gallbladder cancer; Glioma; Hairy cell leukemia; Head and neck cancer; Heart cancer; Hepatocellular (liver) cancer; Hodgkin lymphoma; Hypopharyngeal cancer; Islet cell carcinoma (endocrine pancreas); Kaposi sarcoma; Kidney cancer (renal cell cancer); Laryngeal cancer; Leukemia, such as, acute lymphoblastic, acute myeloid, chronic lymphocytic, chronic myelogenous and, hairy cell; Lip and oral cavity cancer; Liposarcoma; Lung cancer, such as, non-small cell and small cell; Lymphoma, such as, AIDS-related, Burkitt; Lymphoma, cutaneous T-Cell, Hodgkin and Non-Hodgkin, Macroglobulinemia, Malignant fibrous histiocytoma of bone/osteosarcoma; Melanoma; Merkel cell cancer; Mesothelioma; Multiple myeloma/plasma cell neoplasm; Mycosis fungoides; Myelodysplastic syndromes; Myelodysplastic/myeloproliferative diseases; Myeloproliferative disorders, chronic; Nasal cavity and paranasal sinus cancer; Nasopharyngeal carcinoma; Neuroblastoma; Oligodendroglioma; Oropharyngeal cancer; Osteosarcoma/malignant fibrous histiocytoma of bone; Ovarian cancer; Pancreatic cancer; Parathyroid cancer; Pharyngeal cancer; Pheochromocytoma; Pituitary adenoma; Plasma cell neoplasia; Pleuropulmonary blastoma; Prostate cancer; Rectal cancer; Renal cell carcinoma (kidney cancer); Renal pelvis and ureter, transitional cell cancer; Rhabdomyosarcoma; Salivary gland cancer; Sarcoma, Ewing family of tumors; Sarcoma, Kaposi; Sarcoma, soft tissue; Sarcoma, uterine; Sezary syndrome; Skin cancer (non-melanoma); Skin carcinoma; Small intestine cancer; Soft tissue sarcoma; Squamous cell carcinoma; Squamous neck cancer with occult primary, metastatic; Stomach cancer; Testicular cancer; Throat cancer; Thymoma and thymic carcinoma; Thymoma; Thyroid cancer; Thyroid cancer, childhood; Uterine cancer; Vaginal cancer; Waldenstrom macroglobulinemia; Wilms tumor and any combination thereof.

The invention provides any therapeutic compound or conjugate disclosed herein for use in a method of treatment of the human or animal body by therapy. Therapy may be by any mechanism disclosed herein, such as by stimulation of the immune system. The invention provides any therapeutic compound or conjugate disclosed herein for use in stimulation of the immune system, vaccination or immunotherapy, including for example enhancing an immune response. The invention further provides any therapeutic compound or conjugate disclosed herein for prevention or treatment of any condition disclosed herein, for example cancer, autoimmune disease, inflammation, sepsis, allergy, asthma, graft rejection, graft-versus-host disease, immunodeficiency or infectious disease (typically caused by an infectious pathogen).

The invention also provides any therapeutic compound or conjugate disclosed herein for obtaining any clinical outcome disclosed herein for any condition disclosed herein, such as reducing tumour cells in vivo. The invention also provides use of any therapeutic compound or conjugate disclosed herein in the manufacture of a medicament for preventing or treating any condition disclosed herein.

General Synthetic Schemes and Examples

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

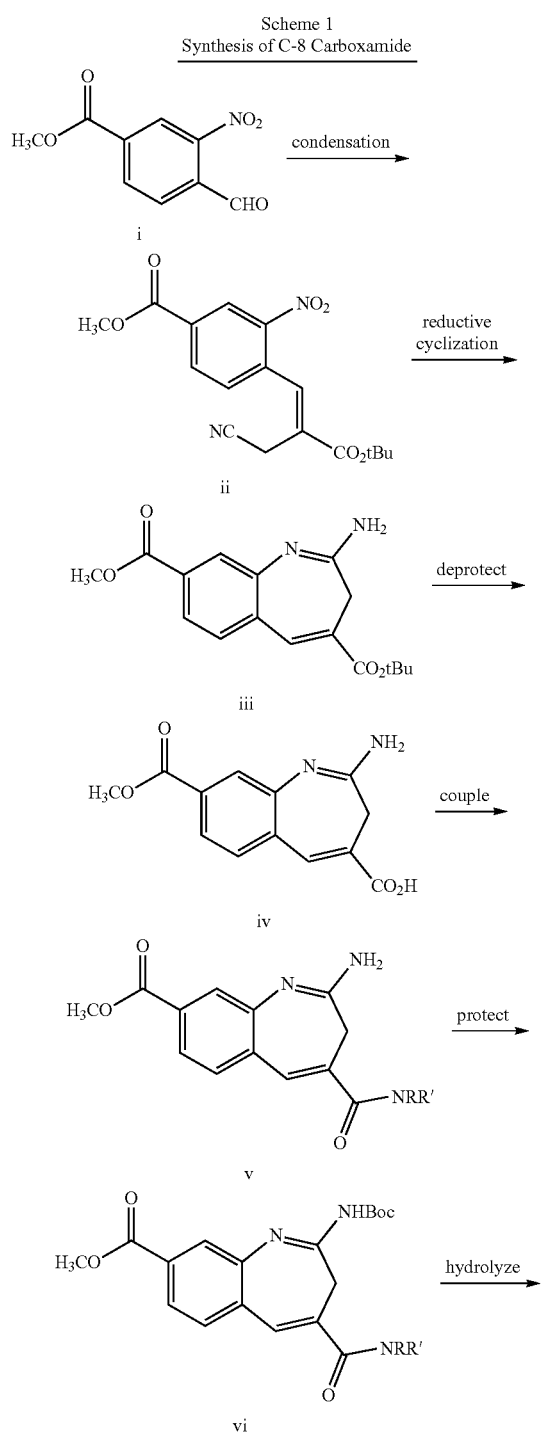

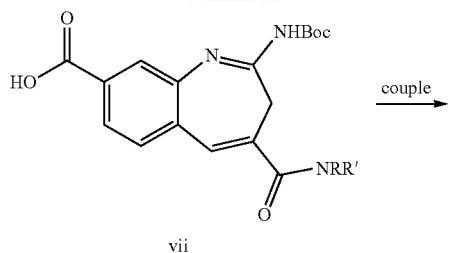

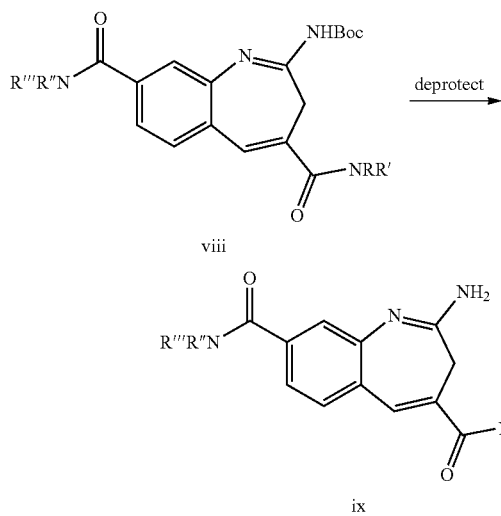

React an aldehyde (i) with an appropriately Wittig reagent, such as tert-butyl 3-cyano-2-(triphenylphosphorylidene)propanoate, at elevated temperatures to afford an olefin (ii), which undergoes reductive cyclization by treating the olefin (ii) with a reducing agent, such as iron powder in hot acetic acid, to afford azepines (iii). Deprotect the C-4 ester group by using a strong acid such as HCl to give compounds (iv), which is in turn coupled with a substituted amine using a coupling agent, such as BOP reagent. Protect the 2-amino substituent of compounds (v) with a tert-butoxycarbonyl group. Hydrolyze the resulting compounds (vi) with reagents such as LiOH in a mixture of THF and methanol to afford compounds (vii). Convert the C-8 carboxylic acid of (vii) to the amide group using known reagents such as HBTU and a tertiary amine base. Acid-mediated deprotection of compounds (viii) using a reagent such as TFA in dichloromethane provides the target compounds (ix).

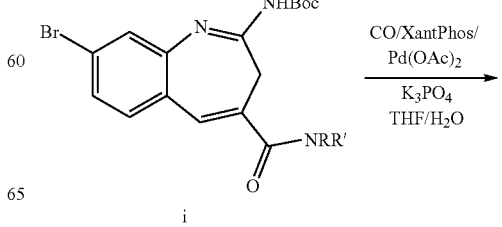

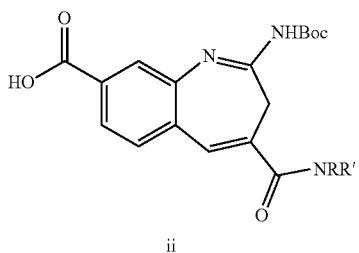

React (i) under standard conditions used for the carbonylation of aryl halides such as carbon monoxide, a palladium catalyst such as Pd(OAc)$_2$ and a ligand such as 4,5-bis(diphenylphosphino)-9,9-dimethylxanthene (XantPhos) and a base such as potassium phosphate in a mixture of THF and water to provide carboxylic acids (ii). Conversion to final products can then be carried out in a manner similar to that described in Scheme 1 (vii→ix).

LiOH to afford the carboxylic acid which is coupled with a substituted amine using a coupling agent, such as BOP reagent to provide compounds (iv). Convert the C-8 carboxylic acid of (v) to the amide group using known reagents such as EDCI/HOBT and a tertiary amine base. Halogen-amine exchange can be effected using standard methodology such as copper-mediated or palladium-catalyzed couplings (benzophenone imine/Pd(II)) to provide C-8 anilines (vi). Functionalization of amines (vi) by acylation or sulfonylation provides anilides (X=C) or sulfonamides (X=SO) compounds (vii). Alternatively, compounds (vii) can be prepared directly through a palladium-mediated coupling of bromide (v) and an appropriately substituted amide or sulfonamide. Acid-mediated deprotection of compounds (vii) using a reagent such as TFA in dichloromethane provides the target compounds (viii).

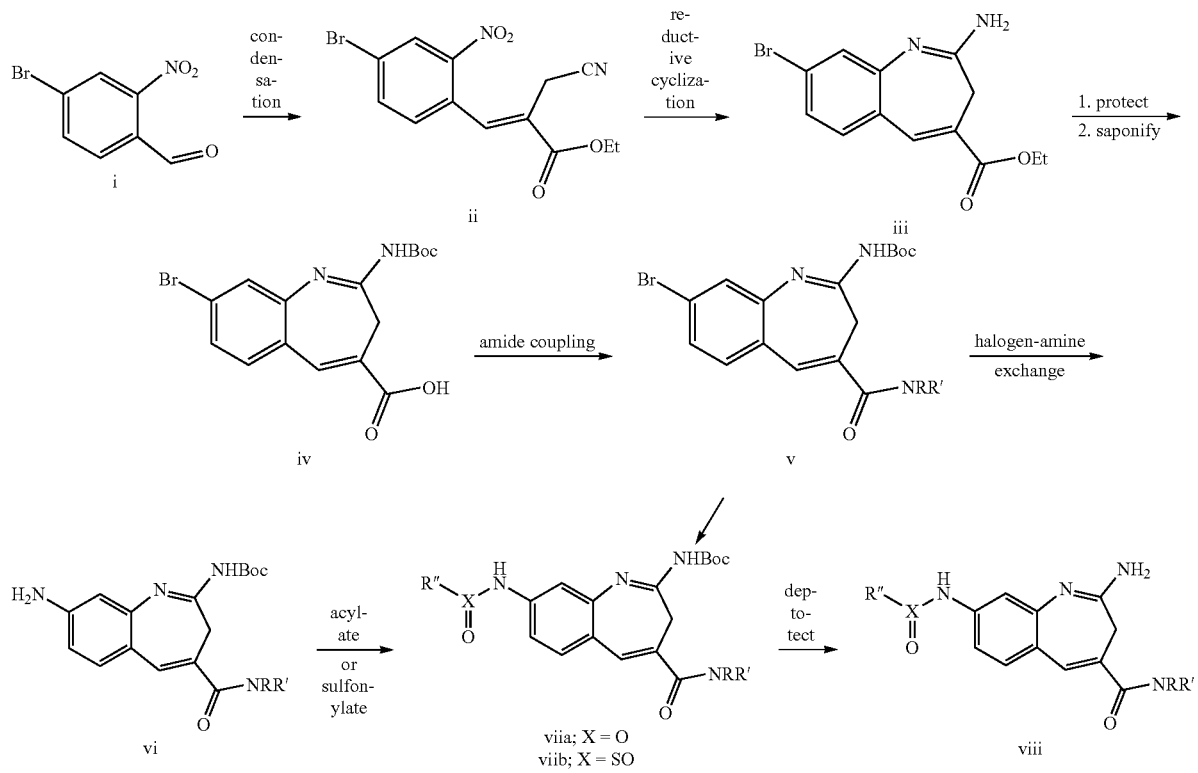

Scheme 3 Synthesis of C-8 Amine Analogs

React an aldehyde (i) with an appropriately Wittig reagent, such as ethyl 3-cyano-2-(triphenylphosphorylidene)propanoate, at ambient temperature to afford an olefin (ii), which undergoes reductive cyclization by treating the olefin (ii) with a reducing agent, such as iron powder in hot acetic acid, to afford azepines (iii). Protect the C-2 amine group by using Boc anhydride to give compounds (iii), which is in turn saponified with an alkaline metal hydroxide such as

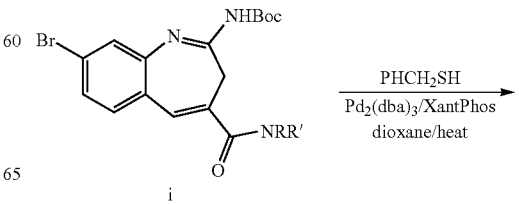

Scheme 4 Synthesis of C-8 Sulfur Analogs

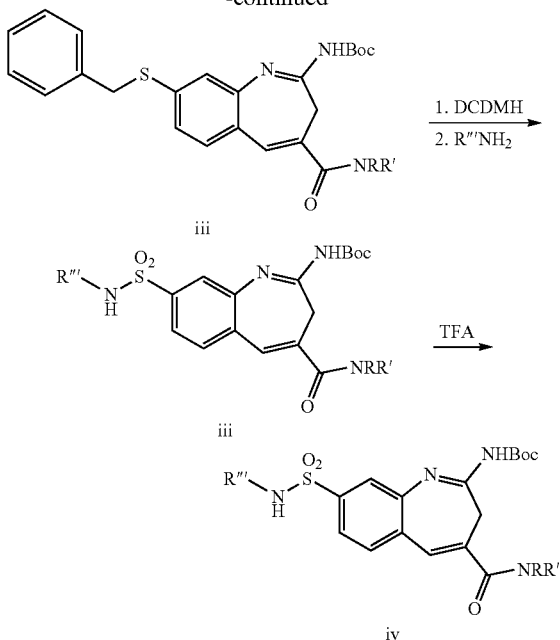

React (i) with benzyl thiol in the presence of a palladium catalyst such as Pd$_2$(dba)$_3$ and a ligand such as XantPhos at elevated temperatures to provide C-8 sulfides (ii). Oxidative chlorination of sulfides (ii) with a reagent such as 1,3-dichloro-5,5-dimethylhydantoin (DCDMH) affords intermediate sulfonyl chlorides which can be reacted with an appropriately substituted amine of structure R'''NH$_2$ to provides sulfonamides (iii). Acid-mediated deprotection of compounds (iii) using a reagent such as TFA in dichloromethane provides the target compounds (iv).

Scheme 5

Synthesis of Linker-Payloads

A linker-payload (LP) can be synthesized by various methods. For example, LP compounds can be synthesized as shown in Scheme 5-1.

Scheme 5-1:

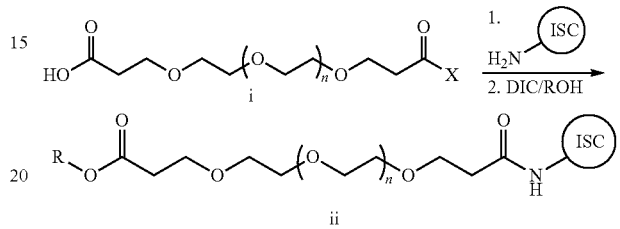

R = NHS, pentafluorophenyl
ISC: immune-stimulatory compound

A PEGylated carboxylic acid (i) that has been activated for amide bond formation can be reacted with an appropriately substituted amine containing immune-stimulatory compound to afford an intermediate amide. Formation of an activated ester (ii) can be achieved by reaction the intermediate amide-containing carboxylic using a reagent such as N-hydroxysuccinimide or pentafluorophenol in the presence of a coupling agent such as diisopropylcarbodiimide (DIC) to provide compounds (ii).

An LP can be synthesized as shown in Scheme 5-2.

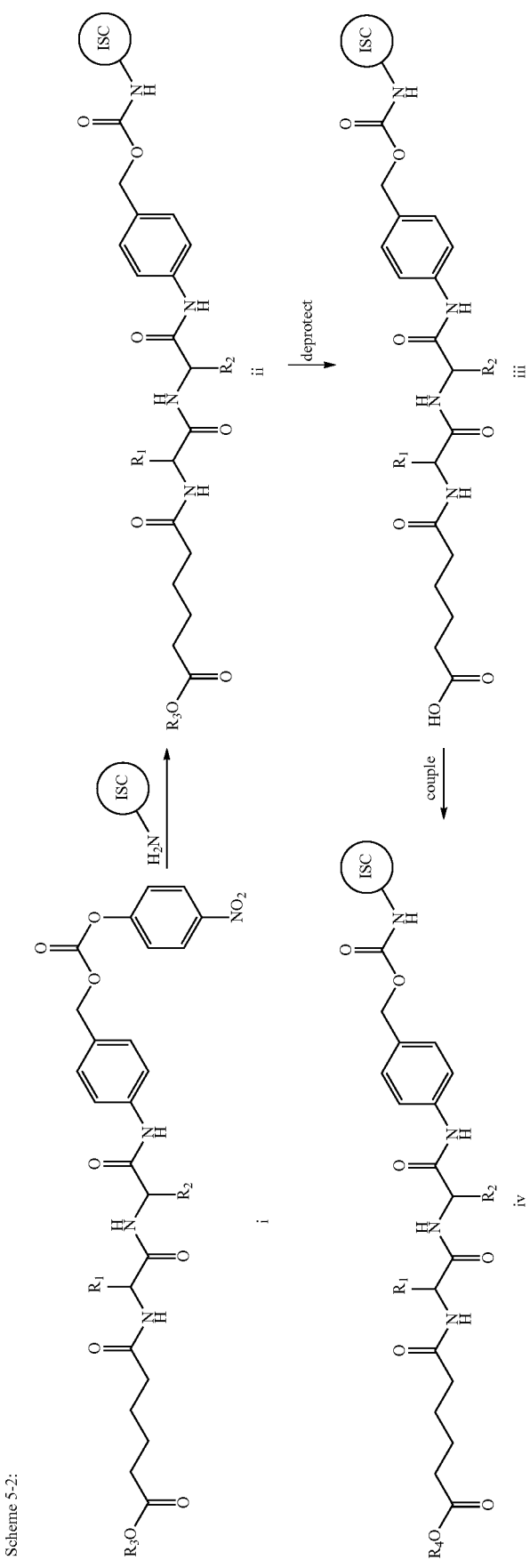
Scheme 5-2:
R4 = NHS, Perfluorofenul
ISC: immune-stimulatory compound An activated carbonate such as (i) can be reacted with an appropriately substituted amine containing immune-stimulatory compound to afford carbamates (ii) which can be deprotected using standard methods based on the nature of the $R_3$ ester group. The resulting carboxylic acid (iii) can then by coupled with an activating agent such as N-hydroxysuccinimide or pentafluorophenol to provide compounds (iv).

An LP compound can be synthesized as shown in Scheme 5-3.

Scheme 5-3:

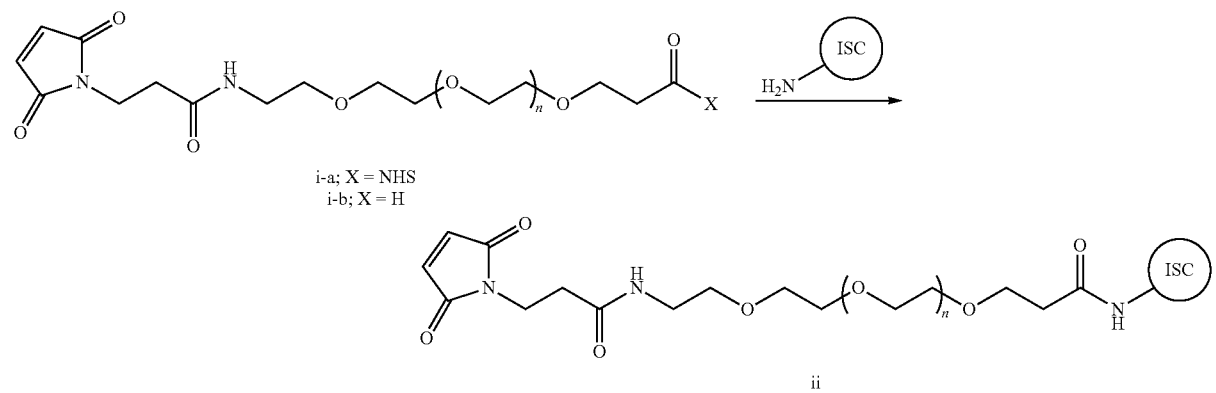

ISC: immune-stimulatory compound

An activated carboxylic ester such as (i-a) can be reacted with an appropriately substituted amine containing immune-modstimulatory compound to afford amides (ii). Alternatively, carboxylic acids of type (i-b) can be coupled to an appropriately substituted amine containing immune-stimulatory compound in the presence of an amide bond forming agent such as dicyclohexycarbodiimde (DCC) to provide the desired LP.

An LP compound can be synthesized by various methods such as that shown in Scheme 5-4.

Scheme 5-4:

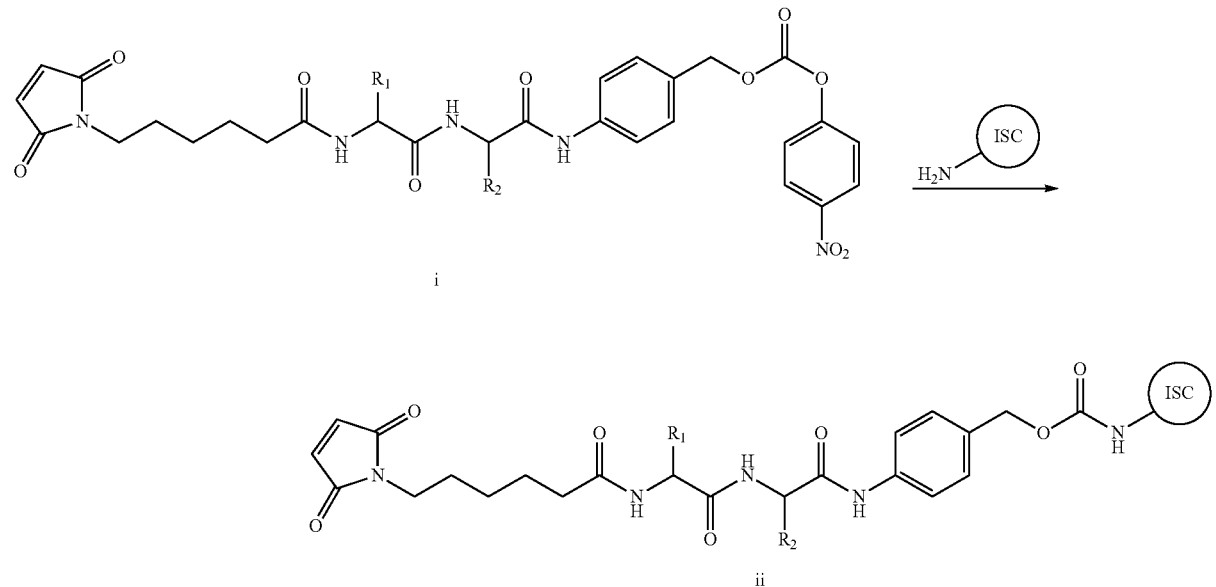

ISC: immune-stimulatory compound

An activated carbonate such as (i) can be reacted with an appropriately substituted amine containing immune-mod-stimulatory compound to afford carbamates (ii) as the target ISC.

An LP compound can also be synthesized as shown in Scheme 5-5.

Scheme 5-5:

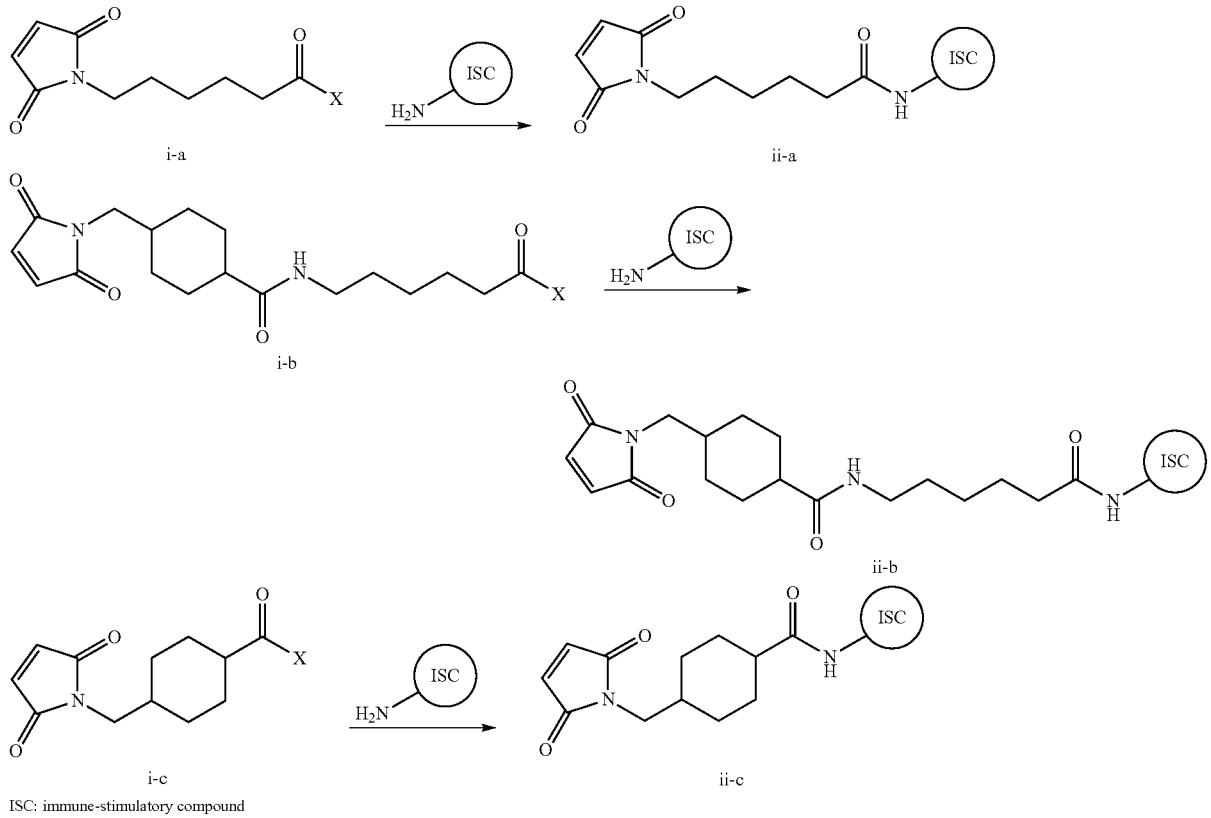

ISC: immune-stimulatory compound

An activated carboxylic acid such as (i-a, i-b, i-c) can be reacted with an appropriately substituted amine containing immune-stimulatory compound to afford amides (ii-a, ii-b, ii-c) as the target linkered payloads (LPs).

Example 1

Synthesis of 2-amino-$N^4$,$N^4$-dipropyl-$N^8$-(1,2,3,4-tetrahydroquinolin-7-yl)-3H-benzo[b]azepine-4,8-dicarboxamide TFA salt (Compound 1.1)

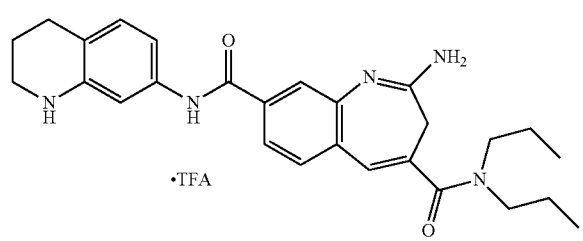 [SMILES: CCCN(CCC)C(=O)C1=Cc2ccc(C(=O)Nc3ccc4c(c3)NCCC4)cc2N=C(N)C1]

Compound 1.1

Step A: Preparation of Int 1.1a

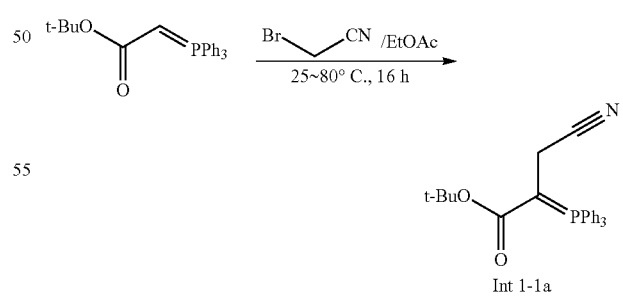

Bromoacetonitrile (8.60 g, 71.7 mmol, 4.78 mL) was added to a solution of tert-butyl (triphenylphosphorylidine) acetate (45.0 g, 119 mmol, 1.00 eq) in EtOAc (260 mL) at 25° C. The reaction was heated at 80° C. for 16 h after which time TLC (DCM:MeOH=10:1; $R_f$=0.4) and LCMS showed the reaction was complete. The mixture was cooled, filtered and washed with EtOAc (200 mL) and concentrated to afford crude Int 1.1a as a red solid which was used directly without purification.

Step B: Preparation of Int 1.1b

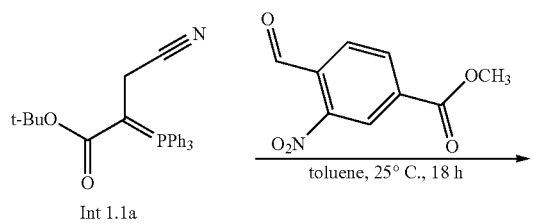

A solution of Int 1.1a (11.4 g, 54.4 mmol, 1.00 eq) and methyl 4-formyl-3-nitrobenzoate (24.8 g, 59.8 mmol, 1.10 eq) in toluene (200 mL) was stirred at 25° C. for 18 h. TLC (petroleum ether:EtOAc=1:2) showed the reaction was completed and the mixture was concentrated to afford crude product which was purified by silica gel chromatography (petroleum ether:EtOAc=10:1 to 8:1 to 4:1) to give Int 1.1b (11.3 g) as yellow solid. $^1$H NMR (CDCl$_3$) δ 8.86 (d, J=1.3 Hz, 1H), 8.40 (dd, J=7.9, 1.3 Hz, 1H), 8.11 (s, 1H), 7.54 (d, J=7.9 Hz, 1H), 3.97-4.05 (m, 3H), 3.27 (s, 2H), 1.60 ppm (s, 9H).

Step C: Preparation of Int 1.1c

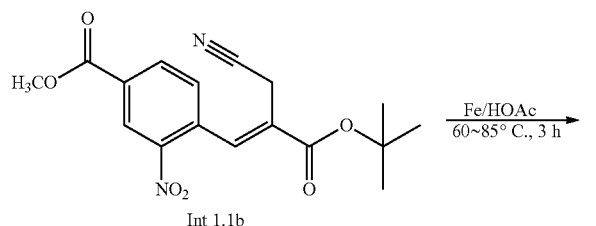

Iron powder (6.79 g, 122 mmol) was added to a solution of Int 1.1b (23.4 g, 20.3 mmol, 1.00 eq) in glacial acetic acid (230 mL) at 60° C. The mixture was stirred at 85° C. for 3 h. TLC (petroleum ether:EtOAc=1:2; R$_f$=0.43) showed the reaction was completed and the mixture was cooled, filtered, washed with acetic acid (100 mL×2) and concentrated. The crude residue was diluted with EtOAc (100 mL) and washed with aq. NaHCO$_3$ (50 mL×3) and dried over Na$_2$SO$_4$, filtered and concentrated. The residue was purified by silica gel chromatography to afford 15.9 g of the Int 1.1c as yellow solid. $^1$H NMR (CDCl$_3$) δ 7.95 (s, 1H), 7.76 (dd, J=8.2, 1.5 Hz, 1H), 7.70 (s, 1H), 7.46 (d, J=8.2 Hz, 1H), 3.93 (s, 3H), 2.99 (s, 2H), 1.56 (s, 9H).

Step D: Preparation of Int 1.1d

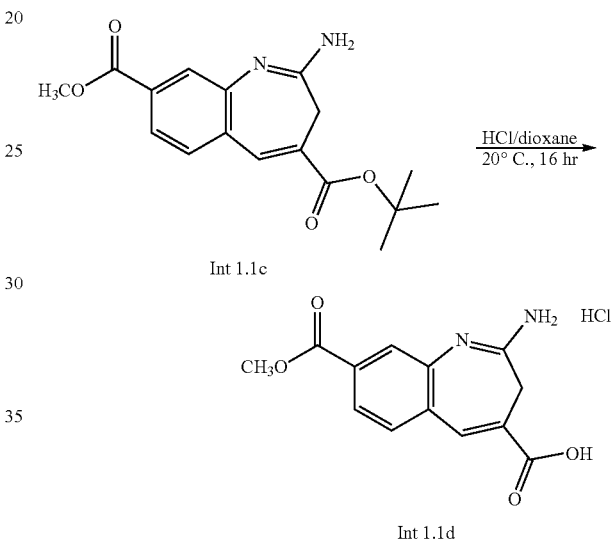

A solution of Int 1.1c (8.00 g, 25.3 mmol) in HCl/dioxane (160 mL) was stirred at 25° C. for 16 h after which time LCMS showed the reaction to be complete. The mixture was concentrated to afford 12.5 g of Int 1.1d as light yellow solid which was used directly without purification. $^1$H NMR (DMSO-d$_6$) δ 13.43 (br s, 1H), 13.00 (br s, 1H), 10.20 (s, 1H), 9.22 (s, 1H), 7.96 (s, 1H), 7.85-7.92 (m, 2H), 7.78-7.83 (m, 1H), 3.90 (s, 3H), 3.52 (s, 2H).

Step E: Preparation of Int 1.1e

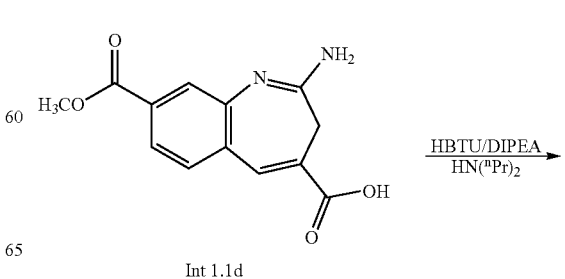

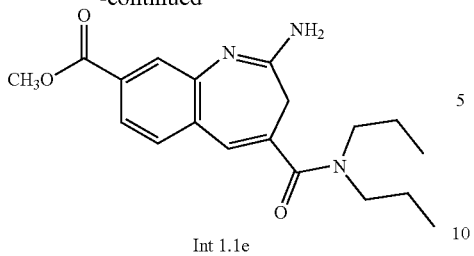

Int 1.1e 5.0 g (13.3 mmol) of HBTU and 7.7 mL (44.4 mmol) of DIPEA were added to a solution containing 3.3 g (11.1 mmol) of Int 1.1d in 60 mL of DMF at 0° C. After 5 minutes, 2.2 g (21.7 mmol) of di-n-propylamine was added and the reaction was stirred to room temperature overnight. The reaction was quenched with 20 mL of saturated NH$_4$Cl and then 20 mL of water. The mixture was extracted with EtOAc (3×30 mL) and the combined organic extracts were washed with brine (2×) then dried over Na$_2$SO$_4$. After removal of the drying agent and concentration of the EtOAc solution, the residue was purified on silica gel (80 g column; 0% to 20% methanol/DCM) to afford 3.0 g of Int 1.1e. $^1$H NMR (CDCl$_3$) δ 7.92 (d, J=1.5 Hz, 1H), 7.86 (dd, J=8.2, 1.5 Hz, 1H), 7.38 (d, J=8.2 Hz, 1H), 6.89 (s, 1H), 3.92 (s, 3H), 3.39 (t, J=7.5 Hz, 4H), 3.22 (s, 2H), 1.68 (m, 4H), 0.91 (bs, 6H). ESI, m/z 343 [M+H].

Step F. Preparation of Int 1.1f

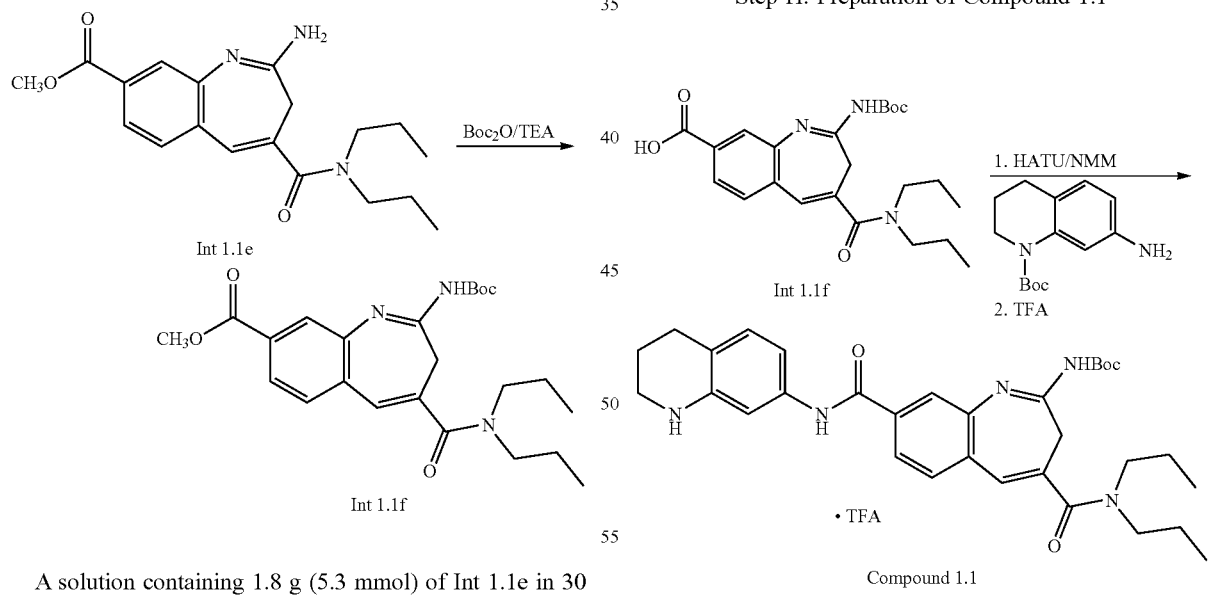

A solution containing 1.8 g (5.3 mmol) of Int 1.1e in 30 mL of dichloromethane was cooled to 0° C. and treated with 2.2 mL (7.9 mmol) of TEA and then 1.7 g (7.9 mmol) of Boc$_2$O. The reaction mixture was stirred to room temperature overnight and then quenched with 10 mL of water. The layers were separated and the aqueous was back extracted with dichloromethane (3×30 mL). The combined organic extracts were washed with brine and dried over Na$_2$SO$_4$. The solvent was removed and the residue was purified by silica gel chromatography (80 g column; 0% to 75% EtOAc/Hexanes) to afford the desired Int 1.1f as a white solid.

Step G: Preparation of Int 1.1g

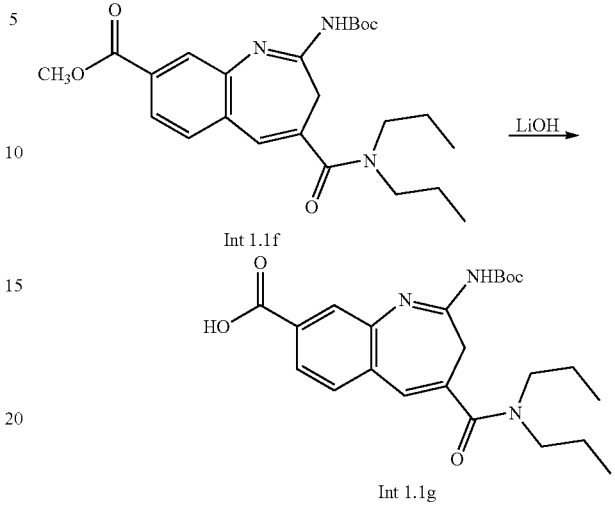

A solution containing 500 mg (1.13 mmol) of Int 1.1f in 10 mL of a 1:1 mixture of THF and water was cooled to 0° C. and treated with 1.7 mL (1.7 mmol) of 1N LiOH. After stirring for 16 h, ice chips were added, followed by enough 5% citric acid solution to effect a precipitate (pH-5.5). The resulting mixture was washed three times with EtOAc and the combined organic extracts were washed with brine and dried over Na$_2$SO$_4$. The solution was evaporated to afford 419 mg of Int 1.1g as a pale yellow solid, which was used without purification.

Step H. Preparation of Compound 1.1

46 mg (0.12 mmol) of HATU was added to a solution containing 43 mg (0.10 mmol) of Int 1.1f in 1.0 mL of DMF. The reaction mixture was stirred for 5 minutes and then treated with 30 mg (0.12 mmol) of 7-N-Boc-amino-1,2,3,4-tetrahydroquinoline and 0.022 mL (0.20 mmol) of NMM. The reaction mixture was stirred for 16 h then treated with 5 mL of saturated NH$_4$Cl solution and 5 mL of water. The resulting mixture was extracted three times with EtOAc and the combined organics were washed with brine then dried over Na₂SO₄. After evaporation of the solvent, the crude oil was dissolved in 3 mL of DCM and then cooled to 0° C. Then, 0.6 mL of TFA was added to the mixture. The mixture was stirred for 4 h, evaporated and the resulting residue was purified by reverse phase chromatography to afford the TFA salt of Compound 1.1 as a white solid. ¹H NMR (CD₃OD) δ 7.96 (s, 1H), 7.95 (s, 1H), 7.85 (d, J=2.4 Hz, 1H), 7.79 (d, J=8.8 Hz, 1H), 7.38 (d, J=7.5 Hz, 1H), 7.25 (d, J=7.5 Hz, 1H), 7.10 (s, 1H), 3.55 (t, J=7.5 Hz, 6H), 3.33 (m, 2H), 2.90 (t, J=6.6 Hz, 2H), 2.10 (m, 1H), 1.69 (m, 4H), 0.77 (bs, 6H). LCMS [M+H]=460.25.

Example 2

Compounds 1.1-1.67

Table 1 shows Compounds 1.1-1.67. Compounds 1.2-1.67 (Table 1) can be prepared in manner similar to that used for the synthesis of Compound 1.1 (Example 1) by using Intermediate 1.1f and an appropriately substituted amine.

TABLE 1

Compounds 1.1-1.67

| Cmpd | Structure and IUPAC | ¹H NMR | M + 1 |
|---|---|---|---|
| 1.1 | 2-amino-N4,N4-dipropyl-N8-(1,2,3,4-tetrahydroquinolin-7-yl)-3H-benzo[b]azepine-4,8-dicarboxamide TFA salt | (CD₃OD) δ 7.96 (s, 1H), 7.95 (s, 1H), 7.85 (d, J = 2.4 Hz, 1H), 7.79 (d, J = 8.8 Hz, 1H), 7.38 (d, J = 7.5 Hz, 1H), 7.25 (d, J = 7.5 Hz, 1H), 7.10 (s, 1H), 3.55 (t, J = 7.5 Hz, 6H), 3.33 (m, 2H), 2.90 (t, J = 6.6 Hz, 2H), 2.10 (1H, 1H), 1.69 (m, 4H), 0.77 (bs, 6H). | 460.3 |
| 1.2 | N⁸-(3-acetylphenyl)-2-amino-N⁴,N⁴-dipropyl-3H-benzo[b]azepine-4,8-dicarboxamide | (CD₃OD) δ 8.35 (s, 1H), 7.97 (dd, J = 1.5, 8.0 Hz, 1H), 7.79 (dd, J = 1.5, 8.8 Hz, 1H), 7.75 (d, J = 1.5 Hz, 1H), 7.63 (dd, J = 1.5, 7.5 Hz, 1H), 7.51 (m, 2H), 6.92 (s, 1H), 3.43 (t, J = 7.5 Hz, 4H), 2.63 (s, 3H), 1.70 (m, 4H), 0.96 (bs, 3H), 0.87 (bs, 3H). | 446.9 |
| 1.3 | 2-amino-N⁴,N⁴-dipropyl-N⁸-(pyridin-3-ylmethyl)-3H-benzo[b]azepine-4,8-dicarboxamide HCl salt | (CD₃OD) δ 8.93 (s, 1H), 8.80 (d, J = 5.5 Hz, 1H), 8.68 (d, J = 8.5 Hz, 1H), 8.11 (m, 1H), 7.97 (d, J = 1.5 Hz, 1H), 7.89 (dd, J = 1.5, 7.5 Hz, 1H), 7.67 (d, J = 7.5 Hz, 1H), 7.08 (s, 1H), 4.84 (s, 2H), 3.44 (bs, 4H), 3.25 (s, 2H), 1.69 (q, J = 7.5 Hz, 4H), 0.92 (bs, 3H), 0.90 (bs, 3H). | 419.9 |
| 1.4 | 2-amino-N⁸-(8-oxo-5,6,7,8-tetrahydronaphthalen-2-yl)-N⁴,N⁴-dipropyl-3H-benzo[b]azepine-4,8-dicarboxamide trifluoroacetate salt | (CD₃OD) δ 8.27 (s, 1H), 7.97 (m, 3H), 7.71 (d, J = 7.5 Hz, 1H), 7.37 (d, J = 7.5 Hz, 1H), 7.11 (s, 1H), 3.55 (m, 4H), 3.28 (s, 2H), 3.00 (t, J = 7.5 Hz, 2H), 2.69 (t, J = 7.5 Hz, 2H), 2.15 (m, 2H), 1.70 (q, J = 7.5 Hz, 4H), 0.98 (bs, 6H). | 473.2 |

TABLE 1-continued

Compounds 1.1-1.67

| Cmpd | Structure and IUPAC | ¹H NMR | M + 1 |
|---|---|---|---|
| 1.5 | 2-amino-N⁸-(5-oxo-5,6,7,8-tetrahydronaphthalen-2-yl)-N⁴,N⁴-dipropyl-3H-benzo[b]azepine-4,8-dicarboxamide trifluoroacetate salt | (CD₃OD) δ 7.99 (m, 3H), 7.85 (s, 1H), 7.71 (m, 2H), 7.15 (s, 1H), 3.50 (m, 4H), 3.30 (s, 2H), 3.03 (t, J = 7.5 Hz, 2H), 2.65 (t, J = 7.5 Hz, 2H), 2.15 (m, 2H), 1.73 (q, J = 7.5 Hz, 4H), 0.97 (bs, 6H). | 473.1 |
| 1.6 | 2-amino-N⁸-(3-(hydrazinecarbonyl)phenyl)-N⁴,N⁴-dipropyl-3H-benzo[b]azepine-4,8-dicarboxamide trifluoroacetate salt | (CD₃OD) δ 8.41 (s, 1H), 7.99 (m, 2H), 7.67 (m, 2H), 7.57 t, J = 8.0 Hz, 1H), 7.12 (s, 1H), 3.65 (m, 5H), 1.66 (m, 4H), 0.96 (bs, 6H). | |
| 1.7 | 2-amino-N⁸-(8-hydroxy-5,6,7,8-tetrahydronaphthalen-2-yl)-N4,N4-dipropyl-3H-benzo[b]azepine-4,8-dicarboxamide trifluoroacetate salt | (DMSO-d₆) δ 10.1 (s, 1H), 7.86 (s, 1H), 7.72 (s, 1H), 7.56 (d, J = 7.7 Hz, 1H), 7.49 (d, J = 7.5 Hz, 1H), 7.58 (d, J = 7.5 Hz, 1H), 7.00 (d, J = 8.1 Hz, 1H), 6.87 (s, 1H), 6.77 (s, 1H), 5.10 (bs, 1H), 4.54 (s, 1H), 3.28 (m, 4H), 3.28 (s, 2H), 2.66 (m, 4H), 1.88 (m, 2H), 1.66-1.32 (m, 6H), 0.87 (bs, 6H). | 475.2 |
| 1.8 | 2-amino-N⁸-(5-hydroxy-5,6,7,8-tetrahydronaphthalen-2-yl)-N⁴,N⁴-dipropyl-3H-benzo[b]azepine-4,8-dicarboxamide trifluoroacetate salt | (CD₃CN) δ 14.0 (bs, 1H), 11.0 (bs, 1H), 8.86 (s, 1H), 7.87 (s, 1H), 7.85 (d, J = 7.7 Hz, 1H), 7.62 (m, 2H), 7.42 (d, J = 7.5 Hz, 1H), 6.98 (s, 1H), 6.77 (s, 1H), 4.68 (s, 1H), 3.28 (m, 4H), 3.15 (m, 4H), 2.76 (m, 2H), 1.88 (m, 3H), 1.61 (m, 4H), 0.92 (bs, 6H). | 475.2 |
| 1.9 | 2-amino-N⁸-(4-(3-hydroxypiperidin-1-yl)phenyl)-N⁴,N⁴-dipropyl-3H-benzo[b]azepine-4,8-dicarboxamide trifluoroacetate salt | (CD₃OD) δ 9.98 (s, 1H), 7.63 (m, 2H), 7.44 (d, J = 8.4 Hz, 1H), 7.39 (d, J = 8.4 Hz, 1H), 6.90 (m, 3H), 6.75 (s, 1H), 4.77 (d, J = 8.4 Hz, 1H), 3.56 (m, 2H), 3.44 (m, 1H), 2.70-2.50 (m, 3H), 1.88 (m, 1H), 1.70 (m, 1H), 1.60 (m, 4H), 1.22 (m, 2H), 0.85 (bs, 6H). | |

TABLE 1-continued

Compounds 1.1-1.67

| Cmpd | Structure and IUPAC | ¹H NMR | M + 1 |
|---|---|---|---|
| 1.10 | 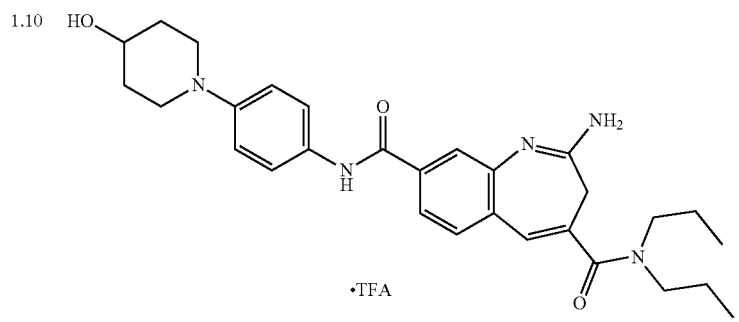<br>2-amino-N⁸-(4-(4-hydroxypiperidin-1-yl)phenyl)-N⁴,N⁴-dipropyl-3H-benzo[b]azepine-4,8-dicarboxamide trifluoroacetate salt | (CD$_3$OD) δ 7.95 (m, 4H), 7.71 (d, J = 8.0 Hz, 1H), 7.55 (d, J = 8.8 Hz, 2H), 7.10 (s, 1H), 4.05 (m, 1H), 3.80 (m, 2H), 3.50 (m, 4H), 3.33 (s, 2H), 2.25 (m, 2H), 1.97 (m, 2H), 1.73 (q, J = 7.5 Hz, 4H), 0.97 (bs, 6H). | |
| 1.11 | 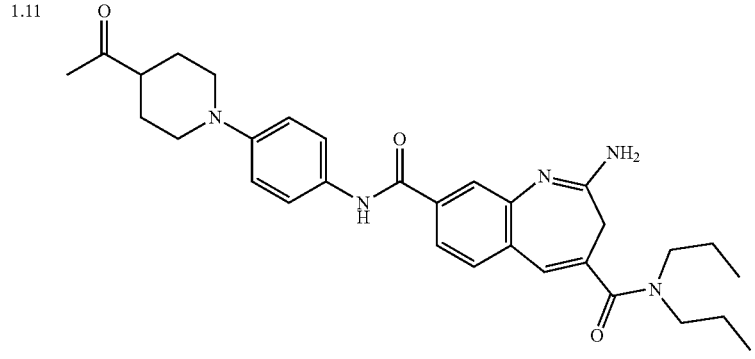<br>N⁸-(4-(4-acetylpiperidin-1-yl)phenyl)-2-amino-N⁴,N⁴-dipropyl-3H-benzo[b]azepine-4,8-dicarboxamide | (CD$_3$OD) δ 7.95 (m, 4H), 7.71 (d, J = 8.0 Hz, 1H), 7.55 (d, J = 8.8 Hz, 2H), 7.10 (s, 1H), 4.05 (m, 1H), 3.80 (m, 2H), 3.50 (m, 4H), 3.33 (s, 2H), 2.25 (m, 2H), 2.15 (s, 3H), 1.97 (m, 2H), 1.73 (q, J = 7.5 Hz, 4H), 0.97 (bs, 6H). | |
| 1.12 | 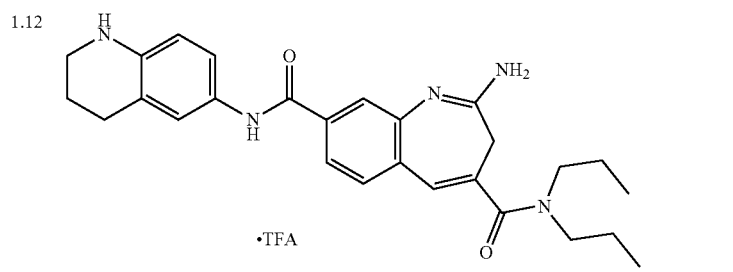<br>2-amino-N⁴,N⁴-dipropyl-N⁸-(1,2,3,4-tetrahydroquinolin-6-yl)-3H-benzo[b]azepine-4,8-dicarboxamide trifluoroacetate salt | (CD$_3$OD) δ 7.95 (m, 2H), 7.71 (m, 3H), 7.18 (m, 1H), 7.11 (s, 1H), 3.43 (m, 4H), 3.50 (m, 2H), 3.28 (s, 2H), 2.96 (t, J = 7.5 Hz, 2H), 2.15 (m, 2H), 1.73 (q, J = 7.5 Hz, 4H), 0.97 (bs, 6H). | 460.2 |
| 1.13 | 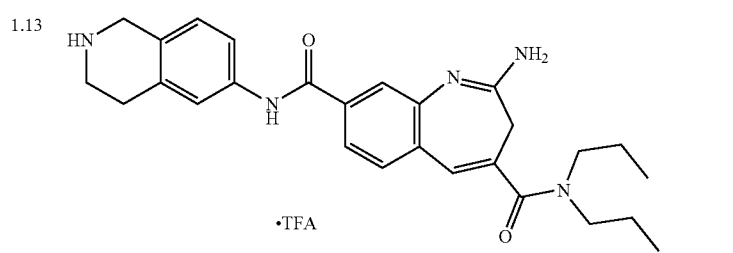<br>2-amino-N⁴,N⁴-dipropyl-N⁸-(1,2,3,4-tetrahydroisoquinolin-6-yl)-3H-benzo[b]azepine-4,8-dicarboxamide trifluoroacetate salt | (CD$_3$OD) δ 7.95 (m, 2H), 7.71-7.61 (m, 3H), 7.27 (d, J = 8.4 Hz, 1H), 7.13 (s, 1H), 4.38 (s, 2H), 3.58-3.45 (m, 6H), 3.40 (s, 2H), 3.15 (t, J = 6.6 Hz, 2H), 1.71 (q, J = 7.5 Hz, 4H), 0.96 (bs, 6H). | 460.2 |

TABLE 1-continued

Compounds 1.1-1.67

| Cmpd | Structure and IUPAC | ¹H NMR | M + 1 |
|---|---|---|---|
| 1.14 | 2-amino-N⁴,N⁴-dipropyl-N⁸-(1,2,3,4-tetrahydro-isoquinolin-7-yl)-3H-benzo[b]azepine-4,8-dicarboxamide trifluoroacetate salt | (CD$_3$OD) δ 7.95 (m, 2H), 7.71-7.61 (m, 3H), 7.27 (d, J = 8.4 Hz, 1H), 7.13 (s, 1H), 4.39 (s, 2H), 3.58-3.45 (m, 6H), 3.40 (s, 2H), 3.14 (t, J = 6.6 Hz, 2H), 1.74 (q, J = 7.5 Hz, 4H), 0.95 (bs, 6H). | 460.2 |
| 1.15 | benzyl (S)-(1-(((5-(2-amino-4-(dipropyl-carbamoyl)-3H-benzo[b]azepine-8-carboxamido)pyridin-3-yl)methyl)amino)-3-methyl-1-oxobutan-2-yl)carbamate | (CD$_3$OD) δ 8.80 (d, J = 2.1 Hz, 1H), 8.29 (s, 1H), 8.21 (s, 1H), 7.72 (s, 1H, 7.58 (dd, J = 1.5, 8.2 Hz, 1H), 7.33-7.23 (m, 5H), 6.90 (s, 1H), 5.11 (d, J = 6.8 Hz, 2H), 4.44 (s, 2H), 3.98 (d, J = 7.0 Hz, 1H), 3.43 (m, 4H), 2.11 (m, 1H), 1.66 (m, 4H), 1.0-0.95 (m, 12H). | 668.3 |
| 1.16 | benzyl (S)-(1-(((5-(2-amino-4-(dipropyl-carbamoyl)-3H-benzo[b]azepine-8-carboxamido)pyridin-3-yl)methyl)amino)-1-oxo-3-phenylpropan-2-yl)carbamate | (CD$_3$OD) δ 8.80 (d, J = 2.1 Hz, 1H), 8.21 (s, 1H), 8.11 (s, 1H), 7.72 (s, 1H), 7.61 (dd, J = 1.5, 8.2 Hz, 1H), 7.45 (d, = 8.2 Hz, 1H), 7.33-7.11 (m, 10H), 6.90 (s, 1H), 5.00 (q, J = 12.6 Hz, 2H), 4.35 (m, 3H), 3.43 (m, 4H), 3.12 (m, 1H), 2.89 (m, 2H), 1.66 (m, 4H), 1.0-0.85 (m, 6H). | 716.3 |
| 1.17 | benzyl (S)-2-(((5-(2-amino-4-(dipropyl-carbamoyl)-3H-benzo[b]azepine-8-carboxamido)pyridin-3-yl)methyl)carbamoyl)pyrrolidine-1-carboxylate | (CD$_3$OD) δ 8.82 (d, J = 2.1 Hz, 1H), 8.69 (s, 1H), 8.33-8.21 (m, 2H), 7.70 (d, J = 17 Hz, 1H), 7.57 (dd, J = 1.5, 8.2 Hz, 1H), 7.45 (d, J = 8.1 Hz, 1H), 7.40-7.21 (m, 5H), 6.90 (s, 1H), 5.00 (q, J = 12.6 Hz, 2H), 4.49 (s, 1H), 4.35 (m, 2H), 3.63-3.53 (m, 2H), 3.45 (m, 4H), 2.85 (m, 1H), 2.31 (m, 1H), 2.10-1.86 (m, 3H), 1.65 (m, 4H), 1.0-0.85 (m, 6H). | 666.5 |

TABLE 1-continued

Compounds 1.1-1.67

| Cmpd | Structure and IUPAC | ¹H NMR | M + 1 |
|---|---|---|---|
| 1.18 | 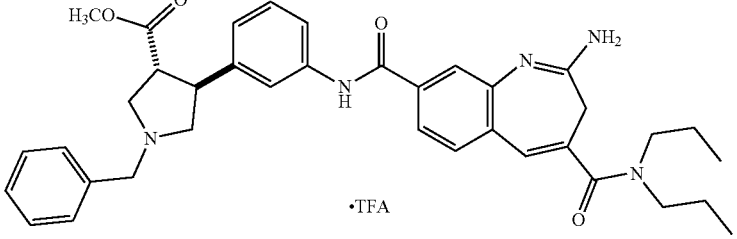<br>methyl (3R,4S)-4-(3-(2-amino-4-(dipropylcarbamoyl)-3H-benzo[b]azepine-8-carboxamido)phenyl)-1-benzylpyrrolidine-3-carboxylate trifluoroacetate salt | (CD₃OD) δ 7.96 (m, 2H), 7.89 (bs, 1H), 7.70 (d, 8.2 Hz, 2H), 7.55 (m, 6H), 7.42 (t, J = 7.5 Hz, 1H), 7.22 (d, J = 7.0 Hz, 1H), 7.11 (s, 1H), 4.53 (s, 2H), 3.90 (m, 3H), 3.70 (s, 3H), 3.51 (m, 4H), 3.37 (s, 2H), 1.70 (q, J = 7.5 Hz, 4H), 1.0-0.85 (m, 6H). | 622.2 |
| 1.19 | 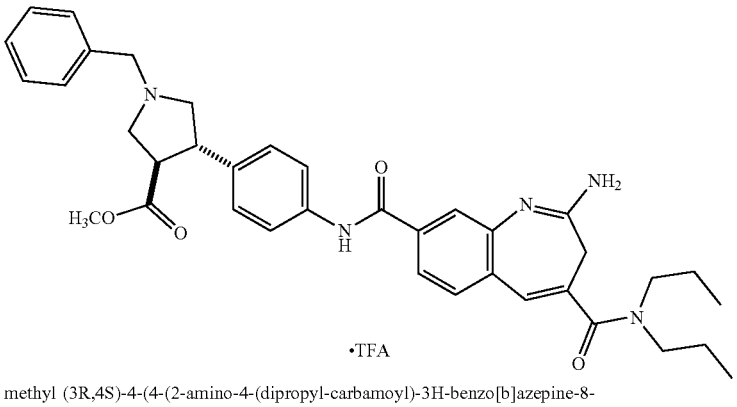<br>methyl (3R,4S)-4-(4-(2-amino-4-(dipropyl-carbamoyl)-3H-benzo[b]azepine-8-carboxamido)phenyl)-1-benzylpyrrolidine-3-carboxylate trifluoroacetate salt | (CD₃OD) δ 7.95 (m, 2H), 7.75 (d, 8.2 Hz, 2H), 7.69 (d, J = 8.5 Hz, 1H), 7.75 (m, 1H), 7.51 (m, 5H), 7.40 (d, J = 7.5 Hz, 1H), 7.10 (s, 1H), 4.51 (s, 2H), 3.90 (m, 3H), 3.68 (s, 3H), 3.51 (m, 4H), 3.37 (s, 2H), 1.70 (q, J = 7.5 Hz, 4H), 0.99-0.92 (m, 6H). | 622.2 |
| 1.20 | 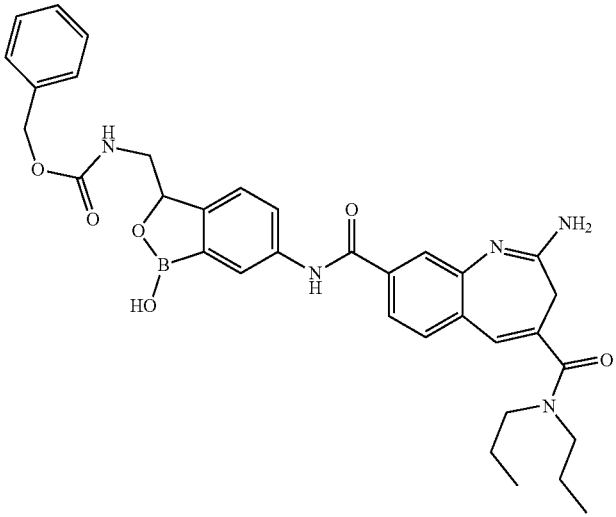 [SMILES: CCCN(CCC)C(=O)C1=Cc2ccc(C(=O)Nc3ccc4c(c3)B(O)OC4CNC(=O)OCc3ccccc3)cc2N=C(N)C1]<br>benzyl ((6-(2-amino-4-(dipropylcarbamoyl)-3H-benzo[b]azepine-8-carboxamido)-1-hydroxy-1,3-dihydrobenzo[c][1,2]oxaborol-3-yl)methyl)carbamate | | 624.3 |
| 1.21 | 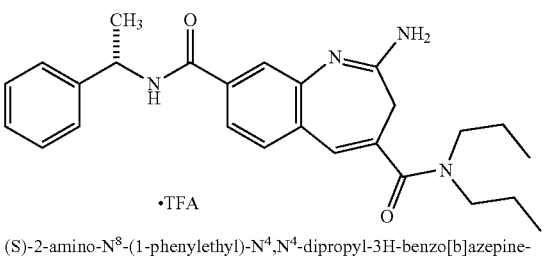<br>(S)-2-amino-N⁸-(1-phenylethyl)-N⁴,N⁴-dipropyl-3H-benzo[b]azepine-4,8-dicarboxamide trifluoroacetate salt | (CD₃OD) δ 7.82 (d, 8.1 Hz, 1H), 7.81 (s, 1H), 7.45 (d, J = 8.1 Hz, 2H), 7.34 (t, J = 7.5 Hz, 2H), 7.27 (d, J = 7.5 Hz, 1H), 7.07 (s, 1H), 5.25 (q, J = 7.0 Hz, 1H), 3.45 (m, 4H), 3.33 (s, 2H), 1.74 (q, J = 7.5 Hz, 4H), 1.52 (d, J = 7.1 Hz, 3H), 0.94 (bs, 3H), 0.91 (bs, 3H). | 433.2 |

TABLE 1-continued

Compounds 1.1-1.67

| Cmpd | Structure and IUPAC | $^1$H NMR | M + 1 |
|---|---|---|---|
| 1.22 | 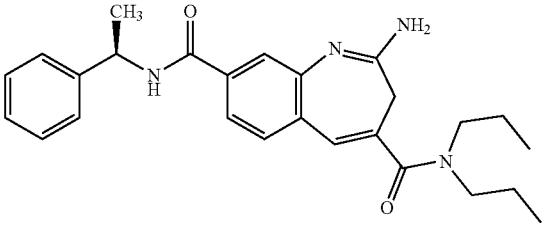 [SMILES: CCCN(CCC)C(=O)C1=Cc2ccc(C(=O)N[C@H](C)c3ccccc3)cc2N=C(N)C1]<br>(R)-2-amino-N$^8$-(1-phenylethyl)-N$^4$,N$^4$-dipropyl-3H-benzo[b]azepine-4,8-dicarboxamide trifluoroacetate salt | (CD$_3$OD) δ 7.82 (d, 8.1 Hz, 1H), 7.81 (s, 1H), 7.45 (d, J = 8.1 Hz, 2H), 7.34 (t, J = 7.5 Hz, 2H), 7.27 (d, J = 7.5 Hz, 1H), 7.07 (s, 1H), 5.25 (q, J = 7.0 Hz, 1H), 3.45 (m, 4H), 3.33 (s, 2H), 1.74 (q, J = 7.5 Hz, 4H), 1.52 (d, J = 7.1 Hz, 3H), 0.94 (bs, 3H), 0.91 (bs, 3H). | 433.2 |
| 1.23 | 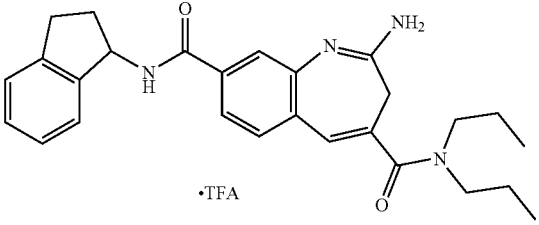 [SMILES: CCCN(CCC)C(=O)C1=Cc2ccc(C(=O)NC3CCc4ccccc43)cc2N=C(N)C1]<br>2-amino-N$^8$-(2,3-dihydro-1H-inden-1-yl)-N$^4$,N$^4$-dipropyl-3H-benzo[b]azepine-4,8-dicarboxamide trifluoroacetate salt | (CD$_3$OD) δ 7.89 (s, 1H), 7.81 (dd, J = 1.8, 8.2 Hz, 1H), 7.61 (d, J = 8.2 Hz, 1H), 7.34 (t, J = 7.5 Hz, 2H), 7.21 (m, 2H), 7.07 (s, 1H), 5.65 (q, J = 7.8 Hz, 1H), 3.48 (m, 4H), 3.28 (s, 2H), 3.01 (m, 1H), 2.95 (m, 1H), 2.62 (m, 1H), 2.02 (m, 1H), 1.68 (q, J = 7.4 Hz, 4H), 0.94 (bs, 3H), 0.91 (bs, 3H). | 445.1 |
| 1.24 | 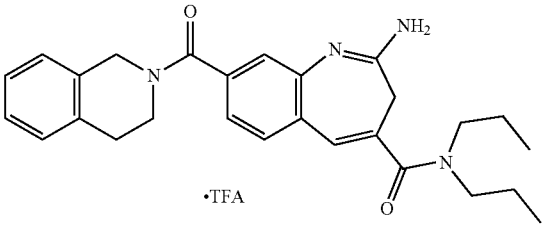 [SMILES: CCCN(CCC)C(=O)C1=Cc2ccc(C(=O)N3CCc4ccccc4C3)cc2N=C(N)C1]<br>2-amino-N,N-dipropyl-8-(1,2,3,4-tetrahydroisoquinoline-2-carbonyl)-3H-benzo[b]azepine-4-carboxamide trifluoroacetate salt | (CD$_3$OD) δ 7.64 (d, J = 8.4 Hz, 1H), 7.44 (m, 2H), 7.23 (m, 4H), 7.06 (s, 1H), 4.64, (m, 1H), 4.00 (m, 1H), 3.71 (m, 1H), 3.48 (m, 4H), 3.28 (s, 2H), 3.01 (m, 1H), 2.95 (m, 1H), 2.62 (m, 1H), 1.98 (s, 1H), 1.71 (q, J = 7.4 Hz, 4H), 1.01 (bs, 3H), 0.95 (bs, 3H). | 445.1 |
| 1.25 | 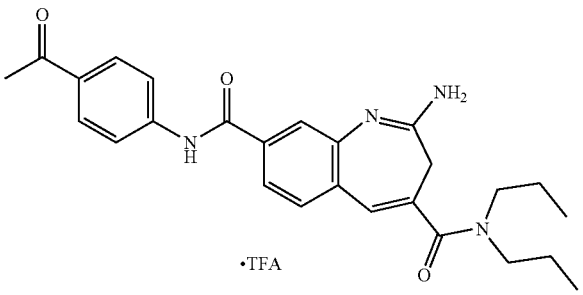 [SMILES: CCCN(CCC)C(=O)C1=Cc2ccc(C(=O)Nc3ccc(C(C)=O)cc3)cc2N=C(N)C1]<br>N$^8$-(4-acetylphenyl)-2-amino-N$^4$,N$^4$-dipropyl-3H-benzo[b]azepine-4,8-dicarboxamide trifluoroacetate salt | (CD$_3$OD) δ 8.04 (d, J = 8.4 Hz, 1H), 7.94 (d, J = 8.0 Hz, 2H), 7.90 (d, J = 8.8 Hz, 2H), 7.69 (d, J = 8.0 Hz, 1H), 7.10 (s, 1H), 3.43 (m, 4H), 3.28 (s, 2H), 2.60 (s, 3H), 1.71 (q, J = 7.5 Hz, 4H), 0.96 (bs, 3H), 0.92 (bs, 3H). | 447.2 |
| 1.26 | 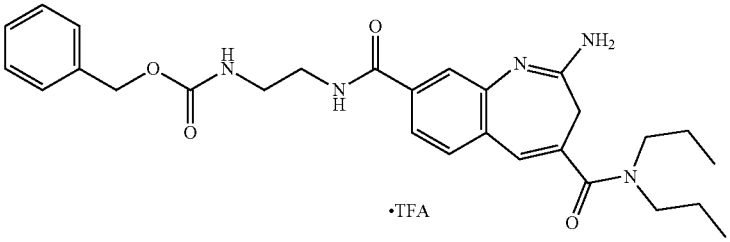 [SMILES: CCCN(CCC)C(=O)C1=Cc2ccc(C(=O)NCCNC(=O)OCc3ccccc3)cc2N=C(N)C1]<br>benzyl (2-(2-amino-4-(dipropylcarbamoyl)-3H-benzo[b]azepine-8-carboxamido)ethyl)carbamate trifluoroacetate salt | (CD$_3$OD) δ 7.80 (d, J = 1.5 Hz, 1H), 7.74 (dd, J = 1.5, 8.0 Hz, 2H), 7.60 (d, J = 8.0 Hz, 1H), 7.31-7.23 (m, 5H), 7.07 (s, 1H), 5.06 (s, 2H), 3.53-3.38 (m, 8H), 3.28 (s, 2H), 1.69 (q, J = 7.5 Hz, 4H), 0.95 (bs, 3H), 0.91 (bs, 3H). | 505.8 |

TABLE 1-continued

Compounds 1.1-1.67

| Cmpd | Structure and IUPAC | ¹H NMR | M + 1 |
|---|---|---|---|
| 1.27 | benzyl (2-(3-(2-amino-4-(dipropylcarbamoyl)-3H-benzo[b]azepine-8-carboxamido)benzamido)ethyl)carbamate | (CD$_3$OD) δ 7.82-7.75 (m, 4H), 7.74 (d, J = 8.0 Hz, 2H), 7.60 (d, J = 8.0 Hz, 1H), 7.45 (m, 1H), 7.31-7.23 (m, 5H), 7.07 (s, 1H), 5.06 (s, 2H), 3.53-3.38 (m, 8H), 3.28 (s, 2H), 1.69 (q, J = 7.5 Hz, 4H), 0.95 (bs, 3H), 0.91 (bs, 3H). | 625.4 |
| 1.28 | 2-amino-N$^8$-((1S,2R)-2-phenylcyclopropyl)-N$^4$,N$^4$-dipropyl-3H-benzo[b]azepine-4,8-dicarboxamide trifluoroacetate salt | (CD$_3$OD) δ 7.83 (s, 1H), 7.79 (d, 8.1 Hz, 1H), 7.61 (d, J = 8.1 Hz, 2H), 7.27 (t, J = 7.5 Hz, 2H), 7.19 (d, J = 7.5 Hz, 1H), 7.06 (s, 1H), 3.45 (m, 4H), 3.28 (s, 2H), 3.00 (m, 1H), 2.21 (m, 1H), 1.68 (q, J = 7.5 Hz, 4H), 1.35 (m, 2H), 0.96 (bs, 3H), 0.91 (bs, 3H). | 444.8 |
| 1.29 | benzyl 6-(2-amino-4-(dipropylcarbamoyl)-3H-benzo[b]azepine-8-carboxamido)-3,4-dihydroisoquinoline-2(1H)-carboxylate | (CD$_3$OD) δ 7.95 (m, 2H), 7.71-7.61 (m, 3H), 7.27 (d, J = 8.4 Hz, 1H), 7.23 (m, 5H), 7.13 (s, 1H), 5.06 (s, 2H), 4.38 (s, 2H), 4.11 (s, 2H), 3.58 (t, J = 7.5 Hz, 2H), 3.28 (s, 2H), 3.15 (t, J = 6.6 Hz, 2H), 1.71 (q, J = 7.5 Hz, 4H), 0.96 (bs, 6H). | 594.4 |
| 1.30 | benzyl 7-(2-amino-4-(dipropylcarbamoyl)-3H-benzo[b]azepine-8-carboxamido)-3,4-dihydroisoquinoline-2(1H)-carboxylate HCl salt | (CD$_3$OD) δ 7.95 (m, 2H), 7.71-7.61 (m, 3H), 7.27 (d, J = 8.4 Hz, 1H), 7.23 (m, 5H), 7.13 (s, 1H), 5.06 (s, 2H), 4.38 (s, 2H), 4.11 (s, 2H), 3.58 (t, J = 7.5 Hz, 2H), 3.28 (s, 2H), 3.15 (t, J = 6.6 Hz, 2H), 1.71 (q, J = 7.5 Hz, 4H), 0.96 (bs, 6H). | 594.4 |

| Cmpd | Structure and IUPAC | ¹H NMR | M + 1 |
|---|---|---|---|
| 1.31 | 2-amino-$N^8$-(3-((3-phenylpropanamido)methyl)phenyl)-$N^4,N^4$-dipropyl-3H-benzo[b]azepine-4,8-dicarboxamide bis TFA salt | (CD$_3$OD) δ 9.15 (s, 1H), 8.63 (bs, 1H), 8.42 (s, 1H), 8.29 (s, 1H), 8.02-7.99 (m, 2H), 7.71 (d, J = 8.5 Hz, 1H), 7.23-7.10 (m, 6H), 4.45 (s, 2H), 3.44 (m, 4H), 3.37 (s, 2H), 2.94 (t, J = 7.5 Hz, 2H), 2.57 (t, J = 7.5 Hz, 2H), 1.61 (q, J = 7.5 Hz, 4H), 0.96 (bs, 3H), 0.91 (bs, 3H). | 566.3 |
| 1.32 | 2-amino-$N^8$-(5-((3-benzylureido)methyl)pyridin-3-yl)-$N^4,N^4$-dipropyl-3H-benzo[b]azepine-4,8-dicarboxamide bis TFA salt | (CD$_3$OD) δ 9.15 (s, 1H), 8.47 (s, 1H), 8.42 (s, 1H), 8.29 (s, 1H), 8.02-7.99 (m, 2H), 7.72 (d, J = 8.0 Hz, 1H), 7.33 (m, 4H), 7.22 (m, 1H), 7.12 (s, 1H), 4.45 (s, 2H), 4.33 (s, 2H), 3.54 (m, 4H), 3.37 (s, 2H), 1.71 (q, J = 7.5 Hz, 4H), 0.97 (bs, 3H), 0.92 (bs, 3H). | 568.3 |
| 1.33 | 2-amino-$N^4,N^4$-dipropyl-$N^8$-(5-((1,2,3,4-tetrahydroquinoline-2-carboxamido)methyl)pyridin-3-yl)-3H-benzo[b]azepine-4,8-dicarboxamide | (CD$_3$OD) δ 8.77 (s, 1H), 8.42 (s, 1H), 8.22 (s, 1H), 8.19 (m, 1H), 7.71 (s, 1H), 7.59 (dd, J = 8.1, 1.8 Hz, 1H), 7.44 (d, J = 8.1 Hz, 1H), 6.99-6.84 (m, 3H), 6.66 (d, J = 8.0 Hz, 1H), 6.55 (t, J = 7.3 Hz, 1H), 4.51 (s, 2H), 4.00 (t, J = 5.2 Hz, 1H), 3.44 (m, 4H), 2.85 (s, 2H), 2.74 (m, 1H), 2.51 (m, 1H), 2.25 (m, 1H), 1.91 (m, 1H), 1.67 (m, 4H), 0.96 (bs, 3H), 0.91 (bs, 3H). | 593.3 |
| 1.34 | 2-amino-$N^4,N^4$-dipropyl-$N^8$-(5-((1,2,3,4-tetrahydroisoquinoline-3-carboxamido)-methyl)pyridin-3-yl)-3H-benzo[b]azepine-4,8-dicarboxamide | (CD$_3$OD) δ 8.80 (d, J = 2.4 Hz, 1H), 8.28 (d, J = 2.1 Hz, 1H), 8.25 (t, J = 2.1 Hz, 1H), 7.72 (d, J = 1.9 Hz, 1H), 7.61 (dd, J = 1.9, 8.1 Hz, 1H), 7.47 (d, J = 8.2 Hz, 1H), 7.13 (m, 3H), 7.05 (m, 1H), 6.90 (s, 1H), 4.50 (s, 2H), 4.05 (q, J = 6.1 Hz, 2H), 3.63 (dd, J = 4.7, 10.5 Hz, 1H), 3.43 (m, 4H), 3.05 (dd, J = 4.7, 16.0 Hz, 1H), 3.02 (m, 1H), 2.83 (d, J = 16.6 Hz, 1H), 1.71 (m, 4H), 1.0-0.85 (m, 6H). | 594.4 |
| 1.35 | (S)-2-amino-$N^8$-(5-((2-amino-3-phenylpropanamido)methyl)pyridin-3-yl)-$N^4,N^4$-dipropyl-3H-benzo[b]azepine-4,8-dicarboxamide | (CD$_3$OD) δ 8.78 (d, J = 2.3 Hz, 1H), 8.15 (s, 1H), 8.11 (s, 1H), 7.72 (s, 1H), 7.61 (dd, J = 1.5, 8.2 Hz, 1H), 7.45 (d, = 8.2 Hz, 1H), 7.23-7.15 (m, 5H), 6.90 (s, 1H), 4.41 (d, J = 15.0 Hz, 1H), 4.34 (d, J = 15.0 Hz, 1H), 3.63 (t, J = 7.5 Hz, 1H), 3.43 (m, 4H), 2.99 (m, 1H), 2.89 (m, 2H), 1.66 (m, 4H), 1.0-0.85 (m, 6H). | 582.2 |

TABLE 1-continued

Compounds 1.1-1.67

| Cmpd | Structure and IUPAC | $^1$H NMR | M + 1 |
|---|---|---|---|
| 1.36 | (R)-2-amino-$N^8$-(5-((2-amino-3-phenyl-propanamido)-methyl)pyridine-3-yl)-$N^4$,$N^4$-dipropyl-3H-benzo[b]azepine-4,8-dicarboxamide | (CD$_3$OD) δ 8.78 (d, J = 2.3 Hz, 1H), 8.15 (s, 1H), 8.11 (s, 1H), 7.72 (s, 1H), 7.61 (dd, J = 1.5, 8.2 Hz, 1H), 7.45 (d, = 8.2 Hz, 1H), 7.23-7.15 (m, 5H), 6.90 (s, 1H), 4.41 (d, J = 15.0 Hz, 1H), 4.34 (d, J = 15.0 Hz, 1H), 3.63 (t, J = 7.5 Hz, 1H), 3.43 (m, 4H), 2.99 (m, 1H), 2.89 (m, 2H), 1.66 (m, 4H), 1.0-0.85 (m, 6H). | 582.2 |
| 1.37 | Phenyl ((5-(2-amino-4-(dipropylcarbamoyl)-3H-benzo[b]azepine-8-carboxamido)pyridin-3-yl)methyl)carbamate | (CD$_3$OD) δ 8.85 (d, J = 2.3 Hz, 1H), 8.35 (s, 1H), 8.31 (s, 1H), 7.72 (s, 1H), 7.95 (m, 2H), 7.72 (d, = 8.5 Hz, 1H), 7.41 (m, 2H), 7.21 (t, J = 7.0 Hz, 1H), 7.15 (d, J = 7.5 Hz, 1H), 7.09 (s, 1H), 4.49 (s, 2H), 3.49 (m, 4H), 1.70 (m, 4H), 1.0-0.85 (m, 6H). | 555.2 |
| 1.38 | 2-amino-$N^8$-(5-((3-amino-3-phenyl-propanamido)methyl)-pyridin-3-yl)-$N^4$,$N^4$-dipropyl-3H-benzo[b]azepine-4,8-dicarboxamide | (CD$_3$OD) δ 8.75 (d, J = 2.1 Hz, 1H), 8.15 (s, 1H), 8.11 (s, 1H), 7.72 (d, J = 2.0 Hz, 1H), 7.61 (dd, J = 1.5, 8.2 Hz, 1H), 7.47 (d, = 8.2 Hz, 1H), 7.33-7.15 (m, 5H), 6.90 (s, 1H), 4.41 (m, 3H), 3.43 (m, 4H), 2.89 (m, 2H), 2.67 (m, 2H), 1.66 (m, 4H), 1.0-0.85 (m, 6H). | 582.2 |
| 1.39 | 2-amino-$N^8$-(5-amino-5,6,7,8-tetrahydro-quinolin-3-yl)-$N^4$,$N^4$-dipropyl-3H-benzo-[b]azepine-4,8-dicarbox-amide | (DMSO) δ 10.3 (s, 1H), 8.68 (s, 1H), 8.26 (s, 1H), 7.68 (s, 1H), 7.50 (d, J = 8.4 Hz, 1H), 7.41 (d, J = 8.4 Hz, 1H), 6.89 (bs, 2H), 6.78 (s, 1H), 3.81 (m, 1H), 3.43 (m, 4H), 2.75 (m, 4H), 1.99 (m, 2H), 1.75 (m, 1H), 1.61 (m, 5H), 0.88 (bs, 6H). | 475.3 |
| 1.40 | Benzyl (3-(2-amino-4-(dipropylcarbamoyl)-3H-benzo[b]azepine-8-carboxamido)-5,6,7,8-tetrahydroquinolin-5-yl)carbamate | (CD$_3$OD) δ 9.25 (d, J = 2.1 Hz, 1H), 8.55 (s, 1H), 8.11 (s, 1H), 8.00 (d, J = 2.0 Hz, 1H), 7.61 (dd, J = 1.5, 8.2 Hz, 1H), 7.33-7.15 (m, 5H), 7.10 (s, 1H), 5.25 (m, 4H), 5.05 (m, 1H), 3.63-3.55 (m, 4H), 3.12 (m, 2H), 2.22 (m, 2H), 1.98 (m, 2H), 1.66 (m, 4H), 1.0-0.85 (m, 6H). | 609.3 |

TABLE 1-continued

Compounds 1.1-1.67

| Cmpd | Structure and IUPAC | ¹H NMR | M + 1 |
|---|---|---|---|
| 1.41 | 2-amino-$N^8$-(5-amino-6,7-dihydro-5H-cyclopenta[b]pyridin-3-yl)-$N^4,N^4$-dipropyl-3H-benzo[b]azepine-4,8-dicarboxamide | (CD$_3$OD) δ 8.75 (d, J = 2.1 Hz, 1H), 8.55 (s, 1H), 7.70 (s, 1H), 7.61 (d, J = 2.0 Hz, 1H), 7.50 (dd, J = 1.5, 8.2 Hz, 1H), 6.90 (s, 1H), 4.70 (m, 1H), 3.63-3.55 (m, 4H), 3.20-2.95 (m, 2H), 2.75 (m, 1H), 2.02 (m, 1H), 1.66 (m, 4H), 1.0-0.85 (m, 6H). | 461.4 |
| 1.42 | Benzyl (3-(2-amino-4-(dipropylcarbamoyl)-3H-benzo[b]azepine-8-carboxamido)-6,7-dihydro-5H-cyclopenta[b]pyridin-5-yl)carbamate | (CD$_3$OD) δ 8.72 (d, J = 2.1 Hz, 1H), 8.11 (s, 1H), 8.05 (s, 1H), 8.00 (d, J = 2.0 Hz, 1H), 7.61 (dd, J = 1.5, 8.2 Hz, 1H), 7.33-7.15 (m, 5H), 7.66 (d, 1H), 7.44-7.20 (m, 5H), 7.10 (s, 1H), 5.25 (m, 1H), 5.15 (s, 1H), 3.63-3.55 (m, 4H), 3.10-2.95 (m, 2H), 2.00 1.66 (m, 4H), 1.0-0.85 (m, 6H). | 595.4 |
| 1.43 | $N^8$-(6-acetylpyridin-3-yl)-2-amino-$N^4,N^4$-dipropyl-3H-benzo[b]azepine-4,8-dicarboxamide | (DMSO) δ 12.3 (s, 1H), 10.9 (s, 1H), 9.89 (s, 1H), 9.17 9s, 1H), 9.06 (s, 1H), 8.45 (d, J = 8.8 Hz, 1H), 8.05-7.95 (m, 3H), 7.77 (d, J = 8.0 Hz, 1H), 7.05 (s, 1H), 3.44 (m, 6H), 2.60 (s, 3H), 1.65 (m, 4H), 0.90 (m, 6H). | 448.2 |
| 1.44 | 2-amino-$N^8$-(3-amino-2,3-dihydro-1H-inden-5-yl)-$N^4,N^4$-dipropyl-3H-benzo[b]azepine-4,8-dicarboxamide | (DMSO) δ 10.1 (s, 1H), 7.90 (s, 1H), 7.75 (s, 1H), 7.50-7.40 (m, 3H), 7.17 (d, J = 8.4 Hz, 1H), 6.90 (bs, 1H), 6.68 (s, 1H), 4.25 (m, 1H), 3.50-3.30 (m, 6H), 2.85-2.65 (m, 4H), 2.40 (m, 1H), 1.65-1.55 (m, 5H), 0.85 (bs, 6H). | 460.3 |
| 1.45 | Benzyl (6-(2-amino-4-(dipropylcarbamoyl)-3H-benzo[b]azepine-8-carboxamido)-2,3-dihydro-1H-inden-1-yl)carbamate | (DMSO) δ 10.1 (s, 1H), 7.72-7.55 (m, 3H), 7.50-7.40 (m, 5H), 7.17 (d, J = 8.4 Hz, 1H), 6.90 (bs, 1H), 6.88 (s, 1H), 5.15 (m, 3H), 3.40 (m, 4H), 2.85-2.65 (m, 4H), 2.40 (m, 1H), 1.80 (m, 1H), 1.65-1.55 (m, 4H), 0.85 (bs, 6H). | 594.3 |

TABLE 1-continued

Compounds 1.1-1.67

| Cmpd | Structure and IUPAC | $^1$H NMR | M + 1 |
|---|---|---|---|
| 1.46 | 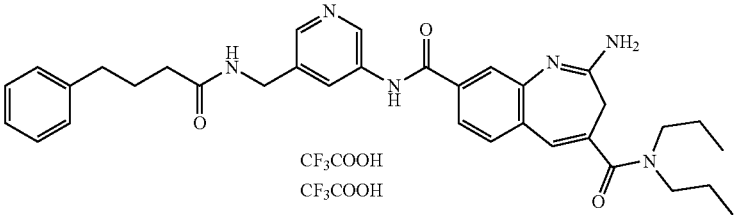 [SMILES: CCCN(CCC)C(=O)C1=Cc2ccc(C(=O)Nc3cncc(CNC(=O)CCCc4ccccc4)c3)cc2N=C(N)C1 ; "CF3COOH" ; "CF3COOH"]<br>2-amino-$N^8$-(5-((4-phenylbutanamido)methyl)pyridin-3-yl)-$N^4,N^4$-dipropyl-3H-benzo[b]azepine-4,8-dicarboxamide bis TFA salt | (CD$_3$OD) δ 9.15 (d, J = 2.1 Hz, 1H), 8.51 (s, 1H), 8.43 (s, 1H), 8.00 (s, 1H), 7.96 (dd, J = 8.4, 2.1 Hz, 1H), 7.71 (d, J = 8.5 Hz, 1H), 7.25-7.11 (m, 6H), 4.50 (s, 2H), 3.46 (m, 4H), 3.37 (s, 2H), 2.64 (t, J = 7.5 Hz, 2H), 2.31 (t, J = 7.5 Hz, 2H), 1.95 (m, 2H), 1.69 (m, 4H), 0.96 (bs, 3H), 0.92 (bs, 3H). | 581.2 |
| 1.47 | 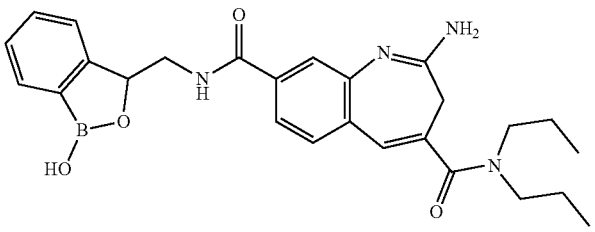 [SMILES: CCCN(CCC)C(=O)C1=Cc2ccc(C(=O)NCC3OB(O)c4ccccc43)cc2N=C(N)C1]<br>2-amino-$N^8$-((1-hydroxy-1,3-dihydro-benzo[c][1,2]oxaborol-3-yl)methyl)-N4,N4-dipropyl-3H-benzo[b]azepine-4,8-dicarboxamide | (CD$_3$OD) δ 7.78 (d, J = 1.5 Hz, 1H), 7.73 (dd, J = 1.5, 8.5 Hz, 1H), 7.66 (d, J = 7.0 Hz, 1H), 7.62 (d, J = 8.5 Hz, 1H), 7.47 (m, 2H), 7.37 (m, 1H), 7.07 (s, 1H), 5.44 (dd, J = 3.5, 8.5 Hz, 1H), 4.00 (dd, J = 3.5, 14.0 Hz, 1H), 3.6-3.4 (m, 7H), 1.69 (m, 4H), 0.95 (bs, 3H), 0.91 (bs, 3H). | 473.2 |
| 1.48 | 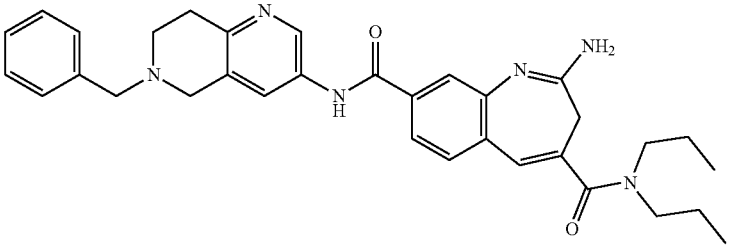 [SMILES: CCCN(CCC)C(=O)C1=Cc2ccc(C(=O)Nc3cnc4c(c3)CN(Cc3ccccc3)CC4)cc2N=C(N)C1]<br>2-amino-$N^8$-(6-benzyl-5,6,7,8-tetrahydro-1,6-naphthyridin-3-yl)-$N^4,N^4$-dipropyl-3H-benzo[b]azepine-4,8-dicarboxamide | (CD$_3$OD) δ 9.33 (s, 1H), 8.89 (s, 1H), 8.09 (s, 1H), 8.05 (d, J = 8.4 Hz, 1H), 7.74 (d, J = 8.4 Hz, 1H), 7.31-7.22 (m, 5H), 7.12 (s, 1H), 4.40 (s, 2H), 4.37 (s, 2H), 3.48 (m, 4H), 3.38-3.28 (m, 8H), 1.71 (q, J = 7.5 Hz, 4H), 0.97-0.92 (bs, 6H). | 551.3 |
| 1.49 | 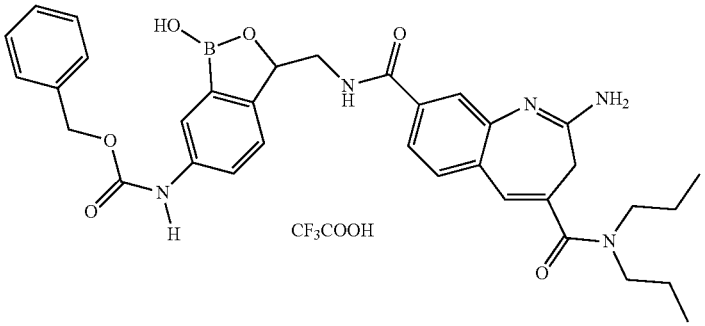 [SMILES: CCCN(CCC)C(=O)C1=Cc2ccc(C(=O)NCC3OB(O)c4cc(NC(=O)OCc5ccccc5)ccc43)cc2N=C(N)C1 ; "CF3COOH"]<br>benzyl (3-((2-amino-4-(dipropylcarbamoyl)-3H-benzo[b]azepine-8-carboxamido)methyl)-1-hydroxy-1,3-dihydrobenzo[c][1.2]oxaborol-6-yl)carbamate TFA salt | (DMSO) δ 12.0 (s, 1H), 9.82 (s, 1H), 9.29 (s, 1H), 8.98 (s, 1H), 8.92 (m, 1H), 7.88-7.83 (m, 3H), 7.65 (d, J = 8.5 Hz, 1H), 7.50 (dd, J = 8.0, .0 Hz, 1H), 7.45-7.33 (m, 6H), 7.01 (s, 1H), 5.30 (m, 1H), 5.15 (s, 2H), 3.70 (m, 1H), 4.40-3.30 (m, 5H), 1.58 (m, 4H), 0.89 (bs, 3H), 0.80 (bs, 3H). | 624 |
| 1.50 | 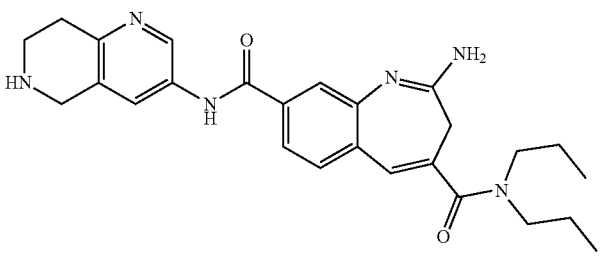 [SMILES: CCCN(CCC)C(=O)C1=Cc2ccc(C(=O)Nc3cnc4c(c3)CNCC4)cc2N=C(N)C1]<br>2-amino-$N^4,N^4$-dipropyl-$N^8$-(5,6,7,8-tetrahydro-1,6-naphthyridin-3-yl)-3H-benzo[b]azepine-4,8-dicarboxamide | (CD$_3$OD) δ 8.68 (s, 1H), 8.00 (s, 1H), 7.70 (s, 1H), 7.58 (dd, J = 8.4, 2.1 Hz, 1H), 7.47 (d, J = 8.4 Hz, 1H), 6.91 (s, 1H), 4.08 (s, 2H), 3.38-3.28 (m, 6H), 2.95 (t, J = 3.0 Hz, 2H), 1.71 (q, J = 7.5 Hz, 4H), 0.97-0.92 (bs, 6H). | 461 |

TABLE 1-continued

Compounds 1.1-1.67

| Cmpd | Structure and IUPAC | ¹H NMR | M + 1 |
|---|---|---|---|
| 1.51 | (S)-2-amino-N[8]-(5-((2-amino-3-methylbutanamido)methyl)pyridin-3-yl)-N[4],N[4]-dipropyl-3H-benzo[b]azepine-4,8-dicarboxamide | (CD$_3$OD) δ 8.78 (d, J = 2.3 Hz, 1H), 8.33 (s, 1H), 8.31 (s, 1H), 7.72 (s, 1H), 7.57 (dd, J = 1.5, 8.2 Hz, 1H), 7.45 (d, = 8.4 Hz, 1H), 6.90 (s, 1H), 4.48 (s, 2H), 3.43 (m, 4H), 2.00 (m, 1H), 1.66 (m, 4H), 1.0-0.85 (m, 12H). | 534 |
| 1.52 | benzyl (3-(2-amino-4-(dipropylcarbamoyl)-3H-benzo[b]azepine-8-carboxamido)-5,6,7,8-tetrahydroquinolin-7-yl)carbamate | (DMSO) δ 10.3 (s, 1H), 8.70 (s, 1H), 7.98 (s, 1H), 7.66 (s, 1H), 7.52-7.35 (m, 6H), 6.90 (bs, 1H), 6.88 (s, 1H), 5.15 (s, 2H), 3.80 (m, 1H), 3.43 (m, 4H), 3.00-2.65 (m, 6H), 2.02 (m, 1H), 1.65-1.55 (m, 4H), 0.85 (bs, 6H). | 609.3 |
| 1.53 | benzyl (3-(2-amino-4-(dipropylcarbamoyl)-3H-benzo[b]azepine-8-carboxamido)-6,7-dihydro-5H-cyclopenta[b]pyridin-6-yl)carbamate | (CD$_3$OD) δ 9.05 (m, 1H), 8.45 (m, 1H), 7.98 (m, 1H), 7.66 (m, 1H), 7.22-7.35 (m, 5H), 7.10 (s, 1H), 5.09 (s, 2H), 4.73 (m, 1H), 3.43 (m, 4H), 3.00-2.65 (m, 2H), 1.72-1.62 (m, 4H), 0.85 (bs, 6H). | 595.3 |
| 1.54 | benzyl 3-(2-amino-4-(dipropylcarbamoyl)-3H-benzo[b]azepine-8-carboxamido)-7,8-dihydro-1,6-naphthyridine-6(5H)-carboxylate | (CD$_3$OD) δ 8.70 (s, 1H), 8.05 (s, 1H), 7.93 (m, 2H), 7.66 (d, J = 7.8 Hz, 1H), 7.42-7.31 (m, 5H), 7.08 (s, 1H), 5.19 (s, 2H), 4.73 (m, 2H), 3.85 (bs, 2H), 3.43 (m, 4H), 3.00-2.95 (m, 2H), 1.72-1.62 (m, 4H), 0.85 (bs, 6H). | 595 |
| 1.55 | benzyl (1-(5-(2-amino-4-(dipropylcarbamoyl)-3H-benzo[b]azepine-8-carboxamido)pyridin-2-yl)piperidin-3-yl)carbamate | (DMSO-d$^6$) δ 12.2 (bs, 1H), 10.2 (s, 1H), 8.50 (s, 1H), 8.00-7.75 (m, 3H), 7.65 (d, J = 7.8 Hz, 1H), 7.43-7.25 (m, 5H), 7.01 (s, 1H), 6.82 (d, J = 8.8 Hz, 1H), 5.04 (s, 2H), 4.21 (d, J = 12 Hz, 1H), 4.04 (d, J = 12 Hz, 1H), 3.55-3.00 (m, 7H), 2.80-2.70 (m, 2H), 2.00-1.40 (m, 8H), 0.85 (bs, 6H). | 638.3 |

TABLE 1-continued

Compounds 1.1-1.67

| Cmpd | Structure and IUPAC | $^1$H NMR | M + 1 |
|---|---|---|---|
| 1.56 | 2-amino-N$^8$-(6-(3-aminopiperidin-1-yl)pyridin-3-yl)-N$^4$,N$^4$-dipropyl-3H-benzo[b]azepine-4,8-dicarboxamide | (DMSO-d$^6$) δ 10.2 (s, 1H), 8.48 (s, 1H), 7.98 (d, J = 7.2 Hz, 1H), 7.65 (s, 1H), 7.45 (m, 2H), 6.82 (d, J = 8.2 Hz, 1H), 4.21 (d, J = 12 Hz, 1H), 3.94 (d, J = 12 Hz, 1H), 2.80-2.70 (m, 4H), 2.00-1.40 (m, 10H), 0.85 (bs, 6H). | 504.2 |
| 1.57 | 2-amino-N$^8$-(6-(4-aminopiperidin-1-yl)pyridin-3-yl)-N$^4$,N$^4$-dipropyl-3H-benzo[b]azepine-4,8-dicarboxamide tris HCl salt | (CD$_3$OD) δ 8.65 (s, 1H), 8.16 (m, 1H), 8.00-7.96 (m, 2H), 7.70 (d, J = 8.0 Hz, 1H), 7.32 (m, 1H), 7.11 (s, 1H), 4.33 (d, J = 13.5 Hz, 2H), 3.47-3.40 (m, 5H), 2.17 (m, 2H), 1.72 (m, 6H), 0.94 (m, 6H). | 504.6 |
| 1.58 | 2-amino-N$^4$,N$^4$-dipropyl-N$^8$-(5-(pyrrolidin-3-yl)pyridin-3-yl)-3H-benzo[b]azepine-4,8-dicarboxamide | (CD$_3$OD) δ 8.84 (J = 1.5 Hz, 1H), 8.42 (d, J = 1.5 Hz, 1H), 8.37 (d, J = 1.5 Hz, 1H), 8.01-7.98 (m, 2H), 7.71 (d, J = 8.0 Hz, 1H), 7.11 (s, 1H), 4.80 (m, 1H), 3.83 (m, 1H), 7.73-3.60 (m, 2H), 3.52-3.44 (m, 2H), 2.57 (m, 1H), 2.18 (m, 1H), 1.71 (q, J = 7.5 Hz, 4H), 0.97 (bs, 3H), 0.92 (bs, 3H). | 475 |
| 1.59 | benzyl (2-(4-((3-(2-amino-4-(dipropylcarbamoyl)-3H-benzo[b]azepine-8-carboxamido)-7,8-dihydro-1,6-naphthyridin-6(5H)-yl)methyl)benzamido)ethyl)carbamate | (CD$_3$OD) δ 8.71 (J = 1.5 Hz, 1H), 8.05 (bs, 1H), 7.95 (m, 2H), 7.87 (m, 2H), 7.70 (d, J = 9.0 Hz, 1H), 7.57 (d, J = 7.5 Hz, 1H), 7.32-7.25 (m, 5H), 7.11 (s, 1H), 5.06 (s, 2H), 3.51-3.46 (m, 6H), 3.37 (m, 4H), 1.69 (q, J = 7.5 Hz, 4H), 0.96 (bs, 3H), 0.92 (bs, 3H). | 771 |

TABLE 1-continued

Compounds 1.1-1.67

| Cmpd | Structure and IUPAC | $^1$H NMR | M + 1 |
|---|---|---|---|
| 1.60 | 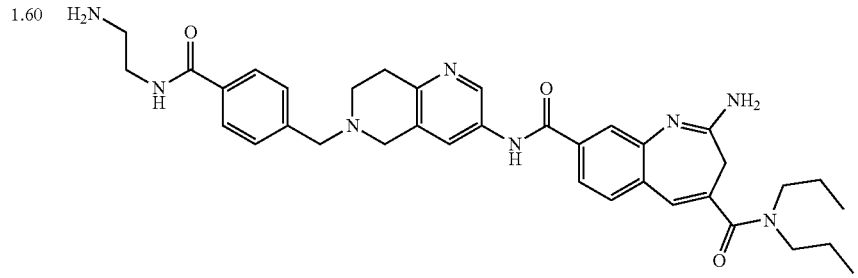<br>2-amino-N$^8$-(6-(4-((2-aminoethyl)carbamoyl)benzyl)-5,6,7,8-tetrahydro-1,6-naphthyridin-3-yl)-N$^4$,N$^4$-dipropyl-3H-benzo[b]azepine-4,8-dicarboxamide | (CD$_3$OD) δ 8.65 (J = 2.5 Hz, 1H), 7.95 (J = 2.5 Hz, 1H), 7.85 (d, J = 8.5 Hz, 2H), 7.68 (d, J = 2.0 Hz, 1H), 7.58-7.53 (m, 3H), 7.44 (d, J = 8.5 Hz, 1H), 6.89 (s, 1H), 3.82 (s, 2H), 3.70 (s, 2H), 3.53 (t, J = 6.0 Hz, 2H), 3.42 (m, 4H), 3.00-2.89 (m, 6H), 1.67 (m, 4H), 0.95-0.87 (m, 6H). | 637.6 |
| 1.61 | 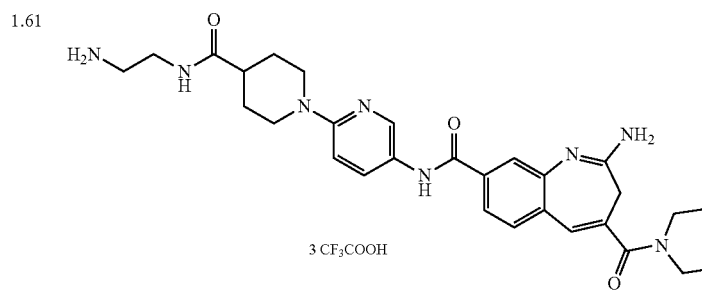<br>3 CF$_3$COOH<br>2-amino-N$^8$-(6-(4-((2-aminoethyl)carbamoyl)piperidin-1-yl)pyridin-3-yl)-N$^4$,N$^4$-dipropyl-3H-benzo[b]azepine-4,8-dicarboxamide tris TFA salt | (CD$_3$OD) δ 8.57 (d, J = 2.5 Hz, 1H), 8.06 (dd, J = 8.0, 2.5 Hz, 1H), 7.96 (s, 1H), 7.94 (d, J = 8.0 Hz, 1H), 7.70 (d, J = 8.0 Hz, 1H), 7.21 (d, J = 8.0 Hz, 1H), 7.11 (s, 1H), 4.25 (d, J = 13.5 Hz, 2H), 3.48-3.44 (m, 6H), 3.17 (m, 2H), 3.06 (t, J = 6.0 Hz, 2H), 2.57 (m, 1H), 1.99-1.95 (m, 2H), 1.82-1.79 (m, 2H), 1.73-1.66 (m, 4H), 0.97 (bs, 3H), 0.91 (bs, 3H). | 575.6 |
| 1.62 | 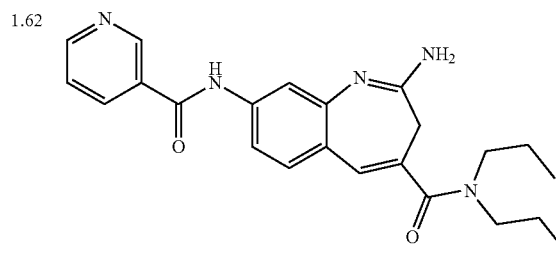<br>2-amino-8-(nicotinamido)-N,N-dipropyl-3H-benzo[b]azepine-4-carboxamide | | |
| 1.63 | 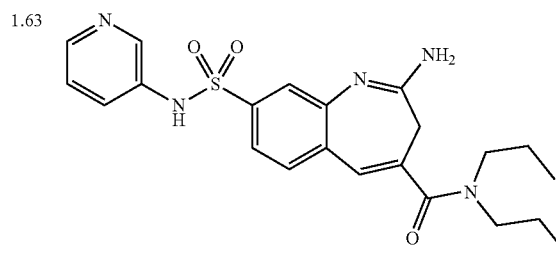<br>2-amino-N,N-dipropyl-8-(N-(pyridin-3-yl)sulfamoyl)-3H-benzo[b]azepine-4-carboxamide | | |
| 1.64 | 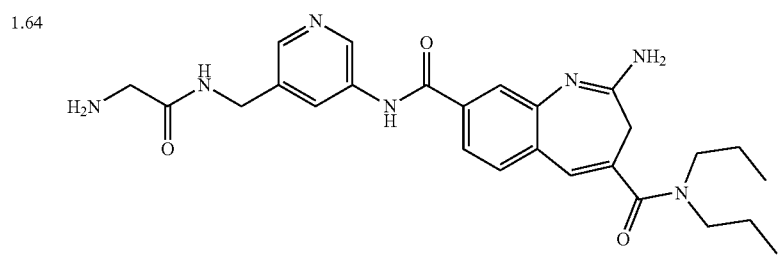<br>2-amino-N8-(5-((2-aminoacetamido)methyl)pyridin-3-yl)-N4,N4-dipropyl-3H-benzo[b]azepine-4,8-dicarboxamide | $^1$H NMR (DMSO-d$^6$) δ 10.4 (s, 1H), 8.85 (d, J = 2.4 Hz, 1H), 8.44 (t, J = 6.0 Hz, 1H), 8.23 (d, 2.0 Hz, 1H), 8.13 (d, t, J = 2.0 Hz, 1H), 7.68 (d, J = 2.0 Hz, 1H), 7.50 (dd, J = 2.0, 8.0 Hz, 1H), 7.41 (d, J = 8.0 Hz, 1H), 6.91 (bs, 2H), 6.79 (s, 1H), 4.33 (d, J = 5.6 Hz, 1H), 3.33 (m, 2H), 3.15 (s, 1H), 2.73 (s, 1H), 1.78 (bs, 1H), 1.56 (m, 4H), 0.84 (bs, 6H). | 492.3 |

TABLE 1-continued

Compounds 1.1-1.67

| Cmpd | Structure and IUPAC | $^1$H NMR | M + 1 |
|---|---|---|---|
| 1.65 | 2-amino-7-methoxy-N4,N4-dipropyl-N8-(5,6,7,8-tetrahydro-1,6-naphthyridin-3-yl)-3H-benzo[b]azepine-4,8-dicarboxamide | | |
| 1.66 | 2-amino-7-fluoro-N4,N4-dipropyl-N8-(5,6,7,8-tetrahydro-1,6-naphthyridin-3-yl)-3H-benzo[b]azepine-4,8-dicarboxamide | | |
| 1.67 | 2-amino-N8-(6-(4-(((3-amino-2,2-difluoropropyl)carbamoyl)benzyl)-5,6,7,8-tetrahydro-1,6-naphthyridin-3-yl)-N4,N4-dipropyl-3H-benzo[b]azepine-4,8-dicarboxamide | | |

Example 3

Synthesis of 8-Substituted Anilides Preparation of 2-amino-8-(nicotinamido)-N,N-dipropyl-3H-benzo[b]azepine-4-carboxamide (Compound 1.62)

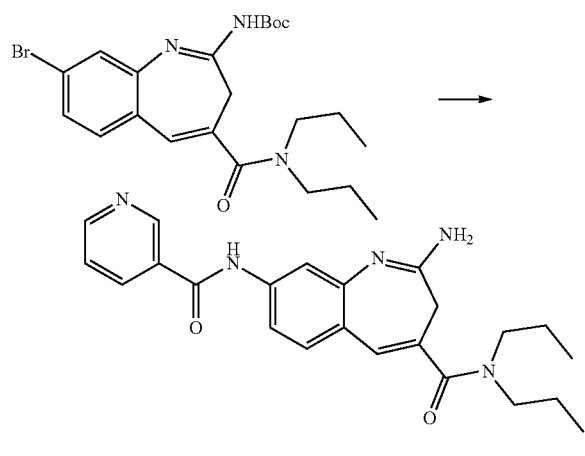

Compound 1.62

Step A: Preparation of Compound 1.62

To a solution containing 46 mg (0.10 mmol) of tert-butyl (8-bromo-4-(dipropylcarbamoyl)-3H-benzo[b]azepin-2-yl)carbamate in 5 mL of DMF was added 65 mg (0.20 mmol) of $Cs_2CO_3$ and 15 mg (0.12 mmol) of nicotinamide. The solution was degassed then treated with 18 mg (0.2 equiv.) of BrettPhos Pd G3 and 11 mg (0.2 equiv.) of BrettPhos and heated at 90° C. for 12 h. The reaction mixture was cooled and chromatographed by preparative HPLC to afford 6 mg of the desired coupled and deprotected compound as an off-white solid. $^1$H NMR (DMSO-d$^6$) δ 10.4 (s, 1H), 9.10 (d, J=1.6 Hz, 1H), 8.76 (d, J=8.0 Hz, 1H), 8.28 (d, J=8.0 Hz, 1H), 7.55 (m, 1H), 7.52 (s, 1H), 7.36 (d, J=8.2 Hz, 1H), 7.27 (d, J=8.0 Hz, 1H), 6.80 (bs, 1H), 6.68 (s, 1H), 3.44 (m, 4H), 2.69 (m, 1H), 1.54 (m, 4H), 0.89 (bs, 6H). LCMS (M+H)=406.2.

Example 4

Synthesis of 8-Substituted Sulfonamides

Preparation of 2-amino-N,N-dipropyl-8-(N-(pyridin-3-yl)sulfamoyl)-3H-benzo[b]azepine-4-carboxamide (Compound 1.63)

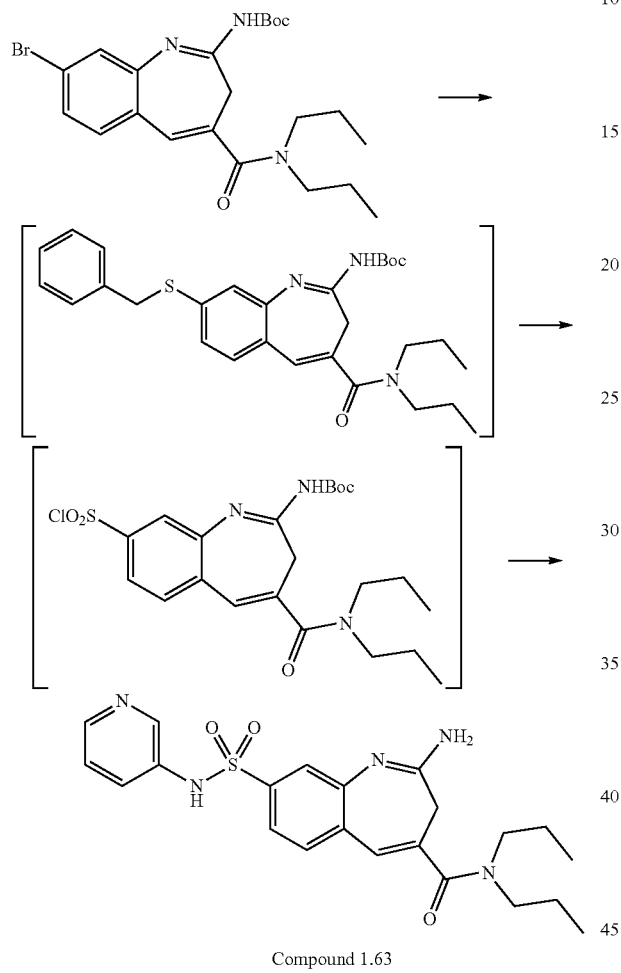

Compound 1.63

Step A: Preparation of Compound 1.63

To a solution containing 460 mg (1.0 mmol) of tert-butyl (8-bromo-4-(dipropylcarbamoyl)-3H-benzo[b]azepin-2-yl)carbamate in 50 mL of dioxane was added 210 mg (2.0 mmol) of N,N-diisopropylethylamine and 140 mg (1.2 mmol) of benzylthiol. The solution was degassed then treated with 180 mg (0.20 mmol) of $Pd_2(dba)_3$ and 116 mg (0.20 mmol) of XantPhos and heated at 90° C. for 6 h. The reaction mixture was cooled and filtered through Celite then chromatographed by reverse phase chromatography to afford 250 mg of the desired thiol ether which was immediately dissolved in DCM (20 ml) and acetic acid (0.5 ml). The resulting solution was cooled in an ice water bath and 1,3-dichloro-5,5-dimethy 2-imidazolidinedione (197 mg, 1.0 mmol) was added. After 2 h the mixture was extracted with DCM and brine and the organics were dried and evaporated. The residue was dissolved in MeCN and treated with 1-methyl-1H-imidazole and 3-aminopyridine at 0° C. and stirred to room temperature over 2 h. The solution was extracted with brine and dried over $Na_2SO_4$. The residue was then dissolved in 4 mL of DCM and treated with 1 mL of TFA and stirred for 2 h. Evaporation of the solvent and purification by reverse phase HPLC afforded 30 mg of the desired compound 1.63. $^1$H NMR (DMSO-d$^6$) δ 10.5 (bs, 1H), 8.32 (s, 1H), 8.25 (d, J=2.0 Hz, 1H), 7.54 (d, 8.0 Hz, 1H), 7.52 (d, J=8.0 Hz, 1H), 7.45 (s, 1H), 7.22 (dd, J=8.0, 2.0 Hz, 1H), 7.07 (m, 2H), 6.73 (s, 1H), 3.30 (m, 4H), 2.95 (s, 2H), 2.11 (s, 1H), 1.54 (m, 4H), 0.85 (bs, 6H). LCMS (M+H)=442.1.

Example 5

Synthesis of Linker-Modified Payloads (LP)

Preparation of 4-((S)-2-((S)-2-(6-(2,5-dioxo-2,5-dihydro-1H-pyrrol-1-yl)hexanamido)-3-methylbutanamido)-5-ureidopentanamido)benzyl ((5-(2-amino-4-(dipropyl-carbamoyl)-3H-benzo[b]azepine-8-carboxamido)pyridin-3-yl)methyl)carbamate (Compound-Linker 2.1)

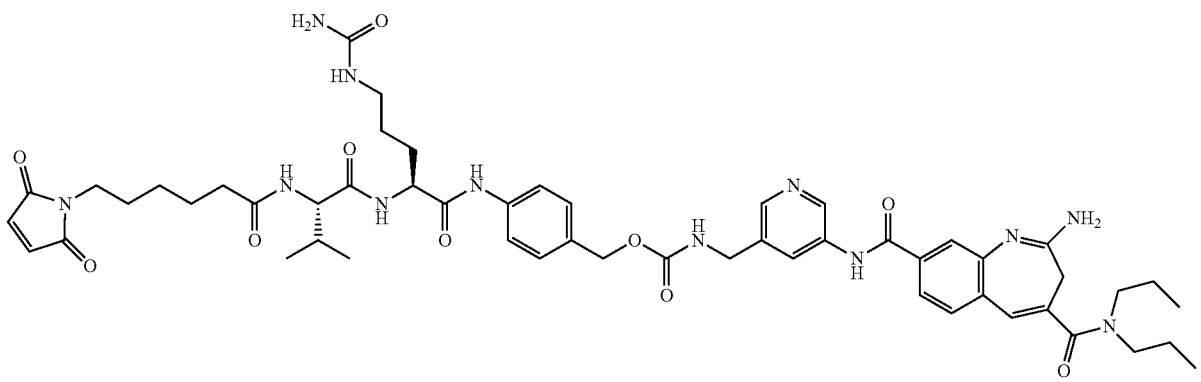

Compound-Linker 2.1

Compound-Linker 2.1

Step A: Preparation of Compound-Linker 2.1

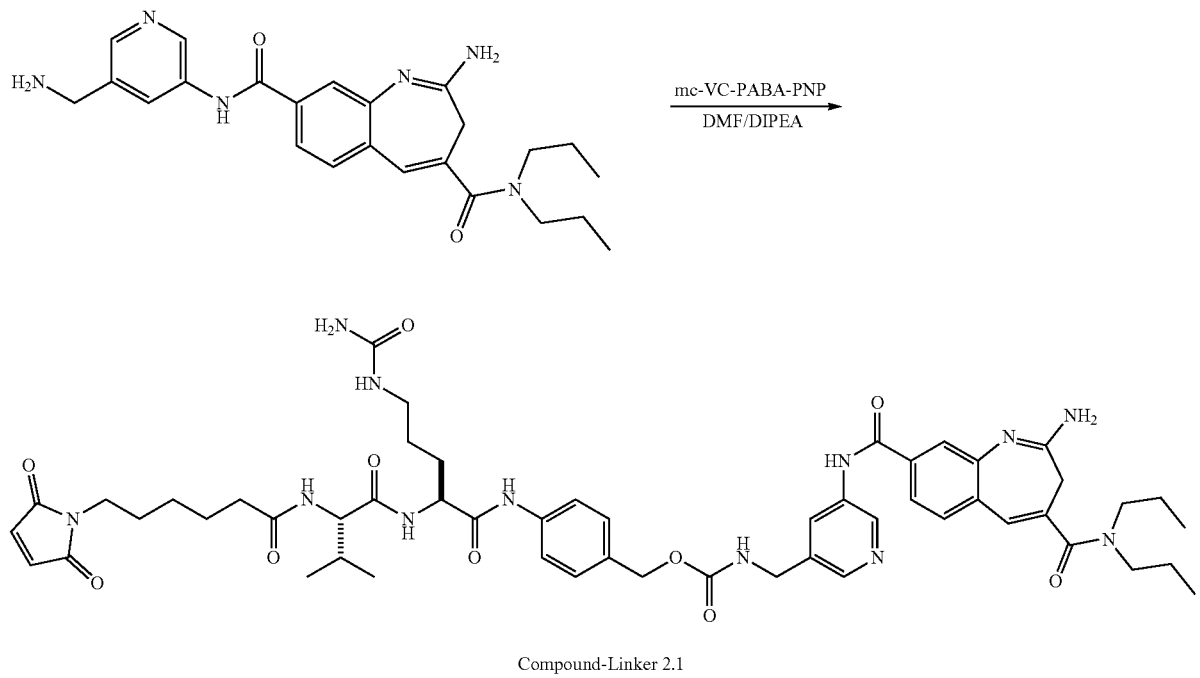 [SMILES: CCCN(CCC)C(=O)C1=Cc2ccc(C(=O)Nc3cncc(CN)c3)cc2N=C(N)C1 ; CCCN(CCC)C(=O)C1=Cc2ccc(C(=O)Nc3cncc(CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1]

Compound-Linker 2.1

54 mg (0.07 mmol) of MC-Val-Cit-PAB-PNP (CAS No. 159857-81-5) was added to a solution containing 40 mg (0.07 mmol) of 2-amino-$N^8$-(5-(aminomethyl)pyridin-3-yl)-$N^4,N^4$-dipropyl-3H-benzo[b]azepine-4,8-dicarboxamide in 1.0 mL of DMF and 32 µL (0.18 mmol) of DIPEA. The reaction mixture was stirred for 16 h then purified directly by reverse phase chromatography (no TFA). The clean fractions were lyophilized to afford 60 mg (71%) of the desired product which was dissolved in 5 mL of DCM and treated with 1 mL of TFA at room temperature. The mixture was stirred for 45 minutes and then evaporated. The resulting residue was purified by reverse phase chromatography (no TFA) to afford 34 mg (62%) of Compound-Linker 2.1 as a white solid. 1H NMR (CD$_3$OD) δ 8.81 (s, 1H), 8.25 (s, 1H), 8.21 (s, 1H), 7.72 (s, 1H), 7.58 (m, 2H), 7.45 (d, J=8.2 Hz, 2H), 7.33 (d, J=8.4 Hz, 2H), 6.91 (s, 1H), 6.75 (s, 2H), 5.08 (s, 2H), 4.49 (m, 1H), 4.39 (m, 2H), 4.14 (d, J=6.5 Hz, 1H), 3.47 (t, J=7.1 Hz, 2H), 3.42 (m, 4H), 3.15 (m, 1H), 3.10 (m, 1H), 2.27 (t, J=7.4 Hz, 2H), 2.05 (m, 1H), 1.88 (m, 1H), 1.75-1.52 (m, 13H), 1.31 (m, 2H), 0.97 (t, J=6.5 Hz, 6H). LCMS [M+H]=1033.

Example 6

Synthesis of Linker-Modified Payloads (LP)

Preparation of 2-amino-$N^8$-(5-((6-(4-((2, 5-dioxo-2, 5-dihydro-1H-pyrrol-1-yl)methyl)cyclohexane-1-carboxamido)hexanamido)methyl)pyridin-3-yl)-$N^4$, $N^4$-dipropyl-3H-benzo[b]azepine-4,8-dicarboxamide (Compound-Linker 2.2)

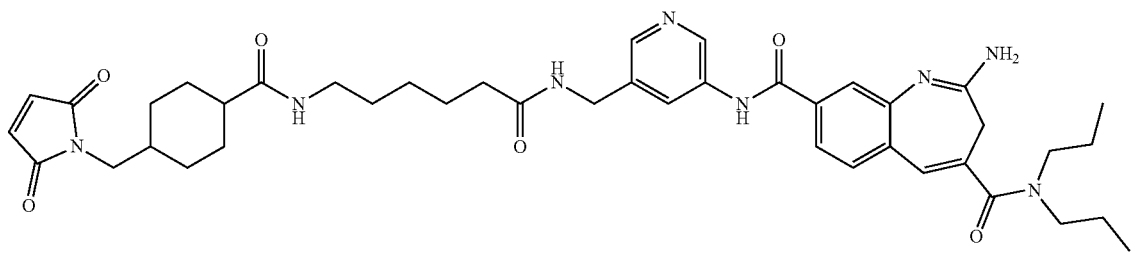 [SMILES: CCCN(CCC)C(=O)C1=Cc2ccc(C(=O)Nc3cncc(CNC(=O)CCCCCNC(=O)C4CCC(CN5C(=O)C=CC5=O)CC4)c3)cc2N=C(N)C1]

Compound-Linker 2.2

Step A: Preparation of Compound-Linker 2.2

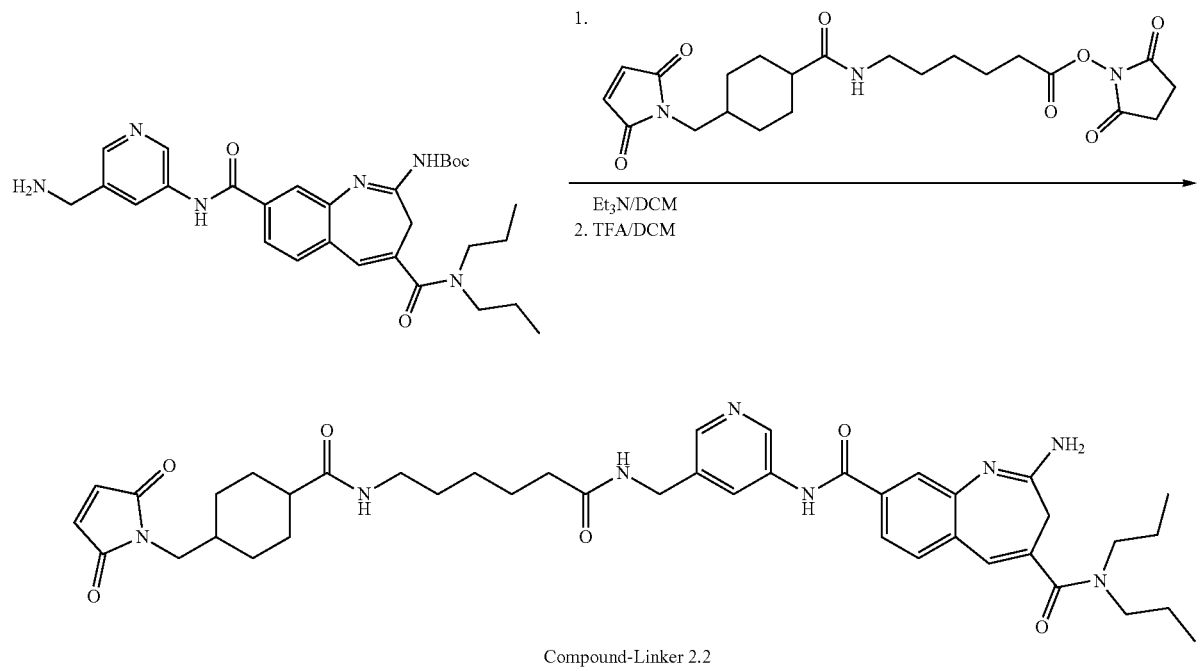

Compound-Linker 2.2

50 mg (0.11 mmol) of N-succinimidyl 6-[[4-(maleimidomethyl)cyclohexyl]carboxamido] caproate (CAS No. 125559-00-4) was added to a solution containing 60 mg (0.11 mmol) of 2-amino-$N^8$-(5-(aminomethyl)pyridin-3-yl)-$N^4,N^4$-dipropyl-3H-benzo[b]azepine-4,8-dicarboxamide in 2.0 mL of DCM and 15 µL (0.11 mmol) of triethylamine. The reaction mixture was stirred for 16 h and then purified directly by reverse phase chromatography (no TFA). The clean fractions were lyophilized to afford the desired product which was dissolved in 5 mL of DCM and treated with 1 mL of TFA at room temperature. The mixture was stirred for 2 h and then evaporated. The resulting residue was purified by reverse phase chromatography (no TFA) to afford 49 mg of Compound-Linker 2.2 as a white solid. $^1$H NMR (CD$_3$OD) δ 8.78 (s, 1H), 8.25 (s, 2H), 7.70 (d, J=1.8 Hz, 1H), 7.58 (dd, J=1.8, 8.1 Hz, 1H), 7.46 (d, J=8.3 Hz, 1H), 6.91 (s, 1H), 6.77 (s, 2H), 4.42 (s, 2H), 3.43 (m, 4H), 3.13 (t, J=6.9 Hz, 2H), 2.85 (d, J=16.6 Hz, 1H), 2.29 (t, J=7.3 Hz, 2H), 2.05 (m, 1H), 1.8-1.6 (m, 12H), 1.51 (m, 1H), 1.37 (m, 4H), 1.11-0.84 (m, 9H). LCMS (M+H)=767.

Example 7

Synthesis of Linker-Modified Payloads (LP)

Example 7A: Preparation of 2-amino-$N^8$-(5-((6-(4-((2,5-dioxo-2,5-dihydro-1H-pyrrol-1-yl)methyl)cyclohexane-1-carboxamido)hexanamido)methyl)pyridin-3-yl)-$N^4,N^4$-dipropyl-3H-benzo[b]azepine-4,8-dicarboxamide (Compound-Linker 2.3)

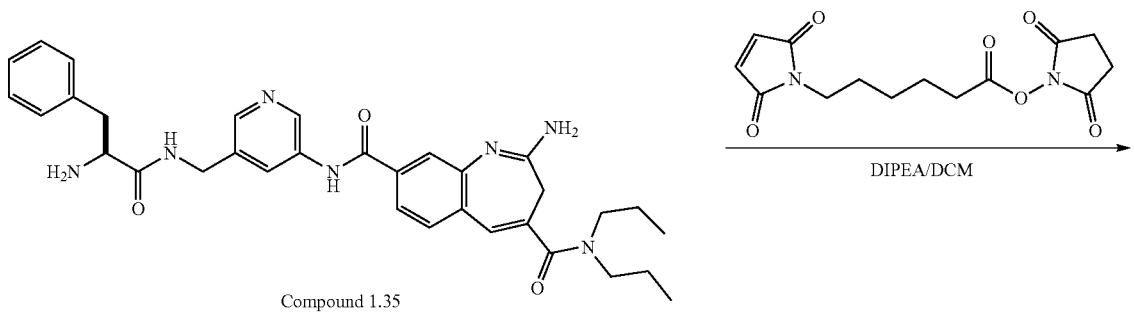

Compound 1.35

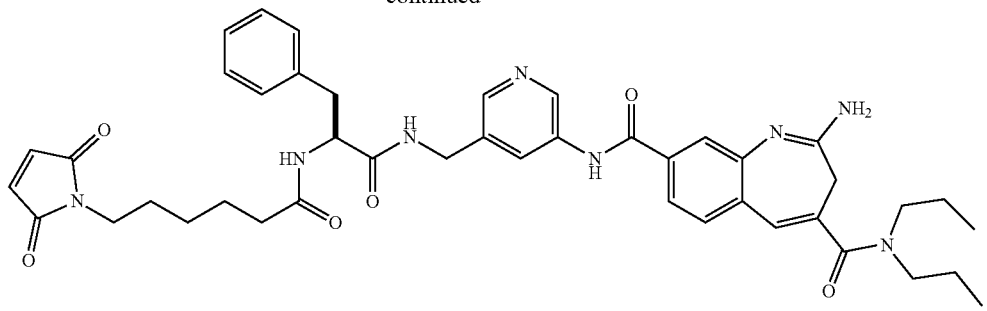

Compound-Linker 2.3

Compound-Linker 2.3

A solution containing 58 mg (0.10 mmol) of Compound 1.35 and 30 mg (0.1 mmol) of 2,5-dioxopyrrolidin-1-yl 6-(2,5-dioxo-2,5-dihydro-1H-pyrrol-1-yl)hexanoate in 2 mL of DCM was treated with 0.07 mL (0.4 mmol) of DIPEA and the reaction was stirred for 4 h at room temperature. The reaction mixture was purified without work-up by reverse phase chromatography to provide 28 mg of Compound-Linker 2.3 as a white solid. $^1$H NMR (CD$_3$OD) δ 8.81 (d, J=2.3 Hz, 1H), 8.19 (d, J=1.9 Hz, 1H), 8.08 (t, J=2.1 Hz, 1H), 7.90 (m, 2H), 7.64 (dd, J=1.9, 8.1 Hz, 1H), 7.25-7.15 (m, 5H), 7.06 (s, 1H), 6.77 (s, 2H), 4.62-4.57 (m, 3H), 4.39 (s, 2H), 3.45-3.40 (m, 4H), 3.39 (t, J=7.5 Hz, 2H), 3.10 (m, 1H), 2.90 (m, 1H), 2.16 (t, J=7.5 Hz, 2H), 1.70 (m, 4H), 1.50 (m, 4H), 1.10 (m, 4H), 0.95 (m, 6H). LCMS (M+H)=775.8.

The following compound-linkers, Compound-Linker 2.4 to 2.7, could be prepared in a manner similar to that described for Compound-Linker 2.3 above by reacting Compound 1.35 with an appropriately substituted linker.

Compound-Linker 2.4

(S)-2-amino-N$^8$-(5-((2-(6-(4-((2,5-dioxo-2,5-dihydro-1H-pyrrol-1-yl)methyl)cyclohexane-1-carboxamido)hexanamido)-3-phenylpropanamido)methyl)pyridin-3-yl)-N$^4$,N$^4$-dipropyl-3H-benzo[b]azepine-4,8-dicarboxamide

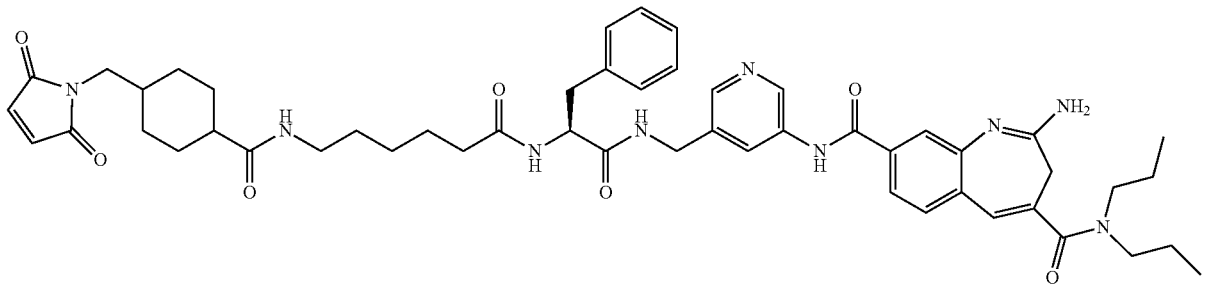 [SMILES: CCCN(CCC)C(=O)C1=Cc2ccc(C(=O)Nc3cncc(CNC(=O)[C@H](Cc4ccccc4)NC(=O)CCCCCNC(=O)C4CCC(CN5C(=O)C=CC5=O)CC4)c3)cc2N=C(N)C1]

From LC-smcc to afford a white solid. $^1$H NMR (CD$_3$OD) δ 8.79 (d, J=2.0 Hz, 1H), 8.17 (d, J=2.0 Hz, 1H), 8.09 (t, J=2.0 Hz, 1H), 7.78 (s, 1H), 7.69 (m, 1H), 7.55 (m, 1H), 7.25-7.15 (m, 5H), 6.96 (s, 1H), 6.79 (s, 2H), 4.62-4.57 (m, 1H), 4.38 (s, 2H), 3.45-3.40 (m, 6H), 3.14 (m, 1H), 3.05 (t, J=7.5 Hz, 2H), 2.90 (m, 1H), 2.18 (t, J=7.5 Hz, 2H), 2.10 (m, 1H), 1.80-1.60 (m, 10H), 1.50-1.30 (m, 6H), 1.20-1.10 (m, 3H), 0.95 (m, 6H). LCMS (M+H)=914.9.

Compound-Linker 2.5

(S)-2-amino-N$^8$-(5-(4-benzyl-24-(2, 5-dioxo-2, 5-dihydro-1H-pyrrol-1-yl)-3,6,22-trioxo-9,12,15,18-tetraoxa-2,5,21-triazatetracosyl)pyridin-3-yl)-N$^4$,N$^4$-dipropyl-3H-benzo[b] azepine-4,8-dicarboxamide

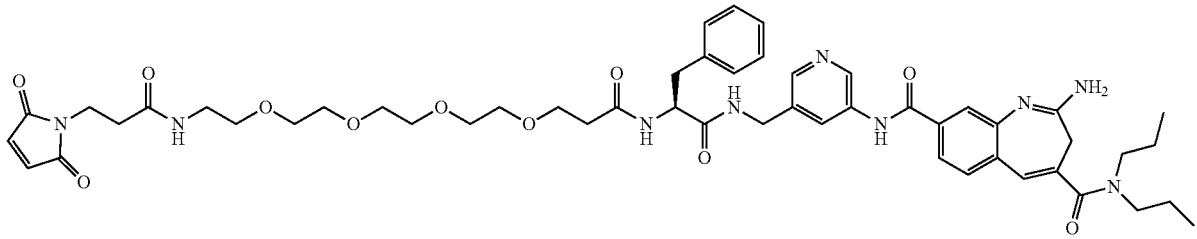 [SMILES: CCCN(CCC)C(=O)C1=Cc2ccc(C(=O)Nc3cncc(CNC(=O)[C@H](Cc4ccccc4)NC(=O)CCOCCOCCOCCOCCNC(=O)CCN4C(=O)C=CC4=O)c3)cc2N=C(N)C1]

From mal-PEG4-NHS to afford a white solid. $^1$H NMR (CD$_3$OD) δ 8.91 (d, J=2.0 Hz, 1H), 8.24 (d, J=2.0 Hz, 1H), 8.15 (t, J=2.0 Hz, 1H), 8.01-7.98 (m, 2H), 7.72 (d, 8.0 Hz, 1H), 7.25-7.15 (m, 5H), 7.12 (s, 1H), 6.78 (s, 2H), 4.60 (m, 1H), 4.43 (s, 2H), 3.73 (t, J=7.5 Hz, 2H), 3.70-3.40 (m, 20H), 3.39 (s, 2H), 3.15 (m, 1H), 2.95 (m, 1H), 2.45 (t, J=7.5 Hz, 2H), 1.70 (q, J=7.5 Hz, 4H), 0.97-0.91 (m, 6H). LCMS (M+H)=980.9.

Compound-Linker 2.6

(S)-2-amino-$N^8$-(5-((2-(4-(4-(2,5-dioxo-2,5-dihydro-1H-pyrrol-1-yl)phenyl)butanamido)-3-phenylpropanamido)methyl)pyridin-3-yl)-$N^4$,$N^4$-dipropyl-3H-benzo[b]azepine-4,8-dicarboxamide, trifluoroacetate salt

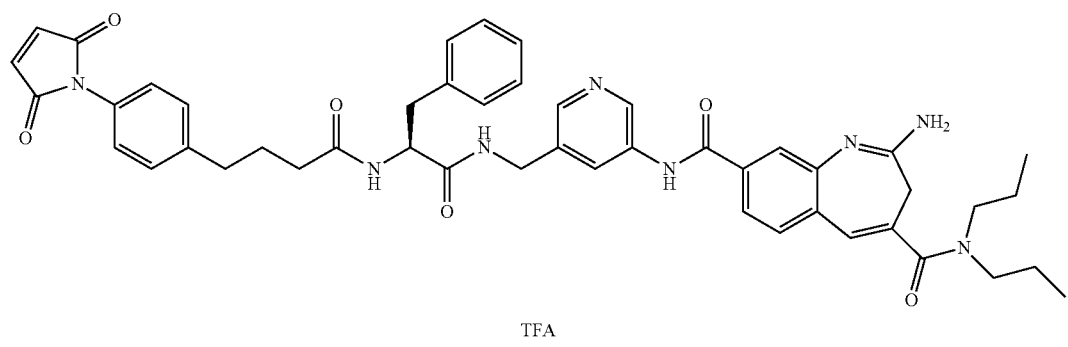 [SMILES: CCCN(CCC)C(=O)C1=Cc2ccc(C(=O)Nc3cncc(CNC(=O)[C@H](Cc4ccccc4)NC(=O)CCCc4ccc(N5C(=O)C=CC5=O)cc4)c3)cc2N=C(N)C1]

From SMPB NHS ester to afford a white solid. $^1$H NMR (CD$_3$OD) δ 8.95 (d, J=2.0 Hz, 1H), 8.63 (d, J=2.0 Hz, 1H), 8.28 (s, 1H), 8.24 (m, 2H), 7.98 (m, 2H), 7.70 (d, J=9.0 Hz, 1H), 7.25-7.15 (m, 9H), 7.16 (s, 1H), 6.94 (s, 2H), 4.60 (m, 1H), 4.51-4.37 (m, 2H), 3.15 (m, 1H), 2.91 (m, 1H), 2.51 (t, J=7.5 Hz, 2H), 2.22 (m, 2H), 1.81 (t, J=7.5 Hz, 2H), 1.70 (q, J=7.5 Hz, 4H), 0.95 (m, 6H). LCMS (M+H)=823.8.

Compound-Linker 2.7

4-((S)-2-((S)-2-(6-(2, 5-dioxo-2, 5-dihydro-1H-pyrrol-1-yl)hexanamido)-3-methylbutanamido)-5-ureidopentanamido)benzyl ((S)-1-(((5-(2-amino-4-(dipropylcarbamoyl)-3H-benzo[b]azepine-8-carboxamido)pyridin-3-yl)methyl)amino)-1-oxo-3-phenylpropan-2-yl)carbamate

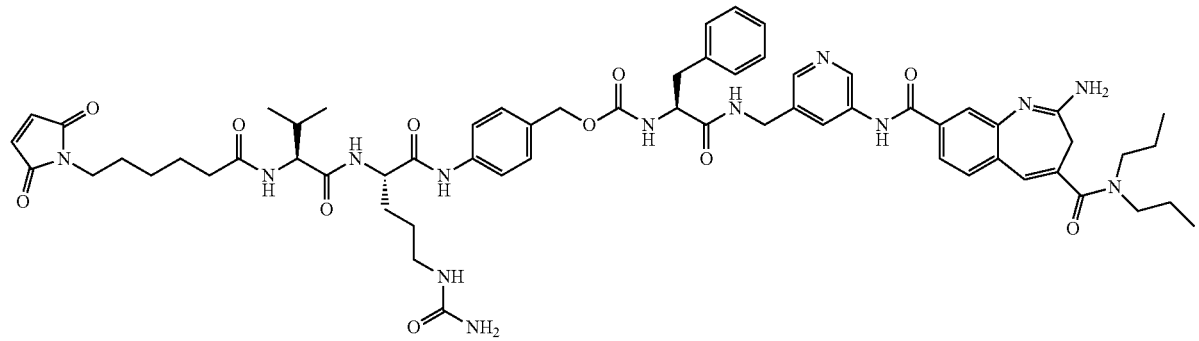 [SMILES: CCCN(CCC)C(=O)C1=Cc2ccc(C(=O)Nc3cncc(CNC(=O)[C@H](Cc4ccccc4)NC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1]

From mc-VC-PABA-PNP to afford a white solid. $^1$H NMR (CD$_3$OD) δ 8.78 (s, 1H), 8.21 (s, 1H), 8.11 (s, 1H), 7.89 (m, 2H), 7.64 (dd, J=1.9, 8.1 Hz, 1H), 7.49 (d, J=8.0 Hz, 2H), 7.25-7.15 (m, 7H), 7.06 (s, 1H), 6.77 (s, 2H), 4.96 (s, 2H), 4.48 (m, 1H), 4.49-4.34 (m, 3H), 4.14 (d, J=7.5 Hz, 1H), 3.46-3.44 (m, 6H), 3.22 (m, 1H), 3.11 (m, 1H), 2.90 (m, 1H), 2.33-2.25 (m, 2H), 2.08 (m, 1H), 1.91 (m, 1H), 1.75-1.50 (m, 13H), 1.30 (m, 2H), 1.00-0.85 (m, 12H). LCMS (M+H)=1181.4.

Compound-Linker 2.8

4-((R)-2-((R)-2-(5-(2, 5-dioxo-2,5-dihydro-1H-pyrrol-1-yl)pentanamido)-3-methylbutanamido)-5-ureidopentanamido)benzyl (2-(1-(5-(2-amino-4-(dipropylcarbamoyl)-3H-benzo[b]azepine-8-carboxamido) pyridin-2-yl)piperidine-4-carboxamido)ethyl) carbamate

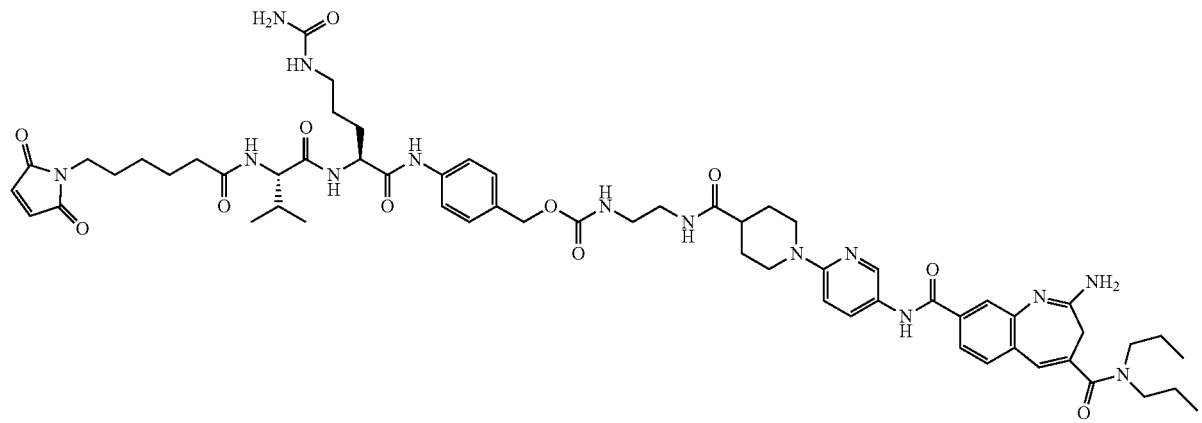 [SMILES: CCCN(CCC)C(=O)C1=Cc2ccc(C(=O)Nc3ccc(N4CCC(C(=O)NCCNC(=O)OCc5ccc(NC(=O)[C@H](CCCNC(N)=O)NC(=O)[C@@H](NC(=O)CCCCCN6C(=O)C=CC6=O)C(C)C)cc5)CC4)nc3)cc2N=C(N)C1]

From Compound 1.61 and mc-VC-PABA-PNP to afford a white solid. $^1$H NMR (CD$_3$OD) δ 10.1 (s, 1H), 9.49 (s, 1H), 9.33 (bs, 2H), 7.88 (d, J=8.0 Hz, 1H), 7.80 (s, 1H), 7.64 (s, 1H), 7.61 (s, 1H), 7.45 (d, J=8.0 Hz, 1H), 7.35 (d, J=8.0 Hz, 1H), 7.02 (s, 1H), 6.85-6.80 (m, 2H), 6.75 (s, 1H), 4.25 m, 2H), 3.54-3.34 (m, 10H), 3.05 (s, 4H), 2.85-2.75 (m, 4H), 2.44 (m, 1H), 1.99 (m, 1H), 1.70-1.60 (m, 12H), 0.95 (bs, 6H).

Compound-Linker 2.9

4-((R)-2-((R)-2-(5-(2, 5-dioxo-2,5-dihydro-1H-pyrrol-1-yl)pentanamido)-3-methylbutanamido)-5-ureidopentanamido)benzyl (1-(5-(2-amino-4-(dipropylcarbamoyl)-3H-benzo[b]azepine-8-carboxamido) pyridin-2-yl)piperidin-4-yl)carbamate

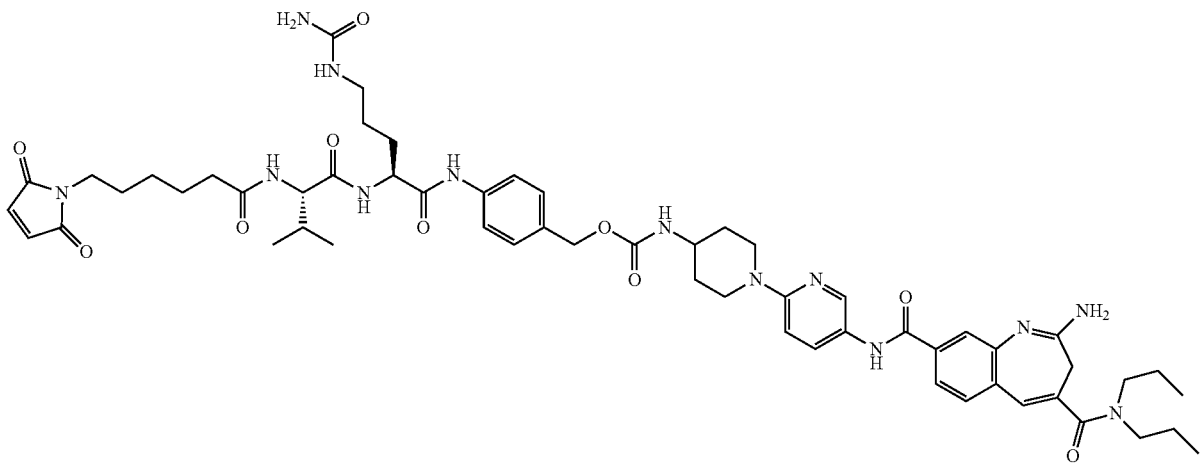 [SMILES: CCCN(CCC)C(=O)C1=Cc2ccc(C(=O)Nc3ccc(N4CCC(NC(=O)OCc5ccc(NC(=O)[C@H](CCCNC(N)=O)NC(=O)[C@@H](NC(=O)CCCCCN6C(=O)C=CC6=O)C(C)C)cc5)CC4)nc3)cc2N=C(N)C1]

From Compound 1.57 and mc-VC-PABA-PNP to afford a white solid. $^1$H NMR (CD$_3$OD) δ 8.37 (d, J=2.5 Hz, 1H), 7.88 (dd, J=8.0, 2.5 Hz, 1H), 7.57-7.54 (m, 3H), 7.43 (d, J=8.0 Hz, 1H), 7.31 (d, J=8.0 Hz, 2H), 6.89 (s, 1H), 6.85-6.80 (m, 1H), 6.78 (s, 2H), 5.03 (s, 2H), 4.45 (m, 2H), 4.12 (m, 3H), 3.65 (m, 1H), 3.54 (t, J=7.5 Hz, 2H), 3.44 (m, 4H), 3.20-2.96 (m, 4H), 2.26 (t, J=7.5 Hz, 2H), 2.05 (m, 1H), 1.99-1.50 (m, 18H), 1.30 (m, 2H), 0.97 (t, J=7.5 Hz, 6H), 0.89 (bs, 6H).

Compound-Linker 2.20

4-((S)-2-((S)-2-(6-(2, 5-dioxo-2, 5-dihydro-1H-pyrrol-1-yl)hexanamido)-3-methylbutanamido)-5-ureidopentanamido)benzyl (2-(((5-(2-amino-4-(dipropylcarbamoyl)-3H-benzo[b]azepine-8-carboxamido)pyridin-3-yl)methyl)amino)-2-oxoethyl)carbamate

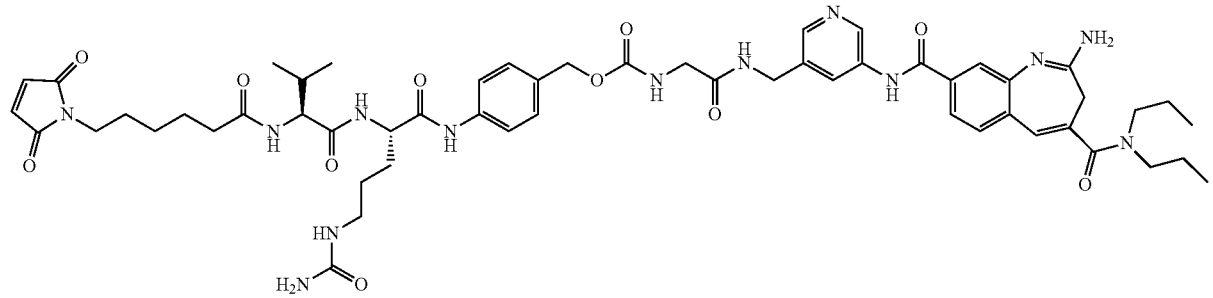 [SMILES: CCCN(CCC)C(=O)C1=Cc2ccc(C(=O)Nc3cncc(CNC(=O)CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1]

From Compound 1.64 and mc-VC-PABA-PNP to afford a white solid. $^1$H NMR (CD$_3$OD) • 8.81 (s, 1H), 8.25 (s, 1H), 8.21 (s, 1H), 7.72 (s, 1H), 7.58 (m, 2H), 7.45 (d, J=8.2 Hz, 2H), 7.33 (d, J=8.4 Hz, 2H), 6.91 (s, 1H), 6.75 (s, 2H), 4.96 (s, 2H), 4.48 (m, 1H), 4.49-4.34 (m, 3H), 4.14 (d, J=7.5 Hz, 1H), 3.46-3.44 (m, 6H), 3.22 (m, 1H), 3.11 (m, 1H), 2.90 (m, 1H), 2.33-2.25 (m, 2H), 2.08 (m, 1H), 1.91 (m, 1H), 1.75-1.50 (m, 13H), 1.30 (m, 2H), 1.00-0.85 (m, 12H). LCMS (M+H)=1090.2.

Compound-Linker 2.21

2-amino-N8-(6-(4-((2-(4-((2, 5-dioxo-2,5-dihydro-1H-pyrrol-1-yl)methyl)cyclohexane-1-carboxamido)ethyl)carbamoyl)piperidin-1-yl)pyridin-3-yl)-N4,N4-dipropyl-3H-benzo[b]azepine-4, 8-dicarboxamide

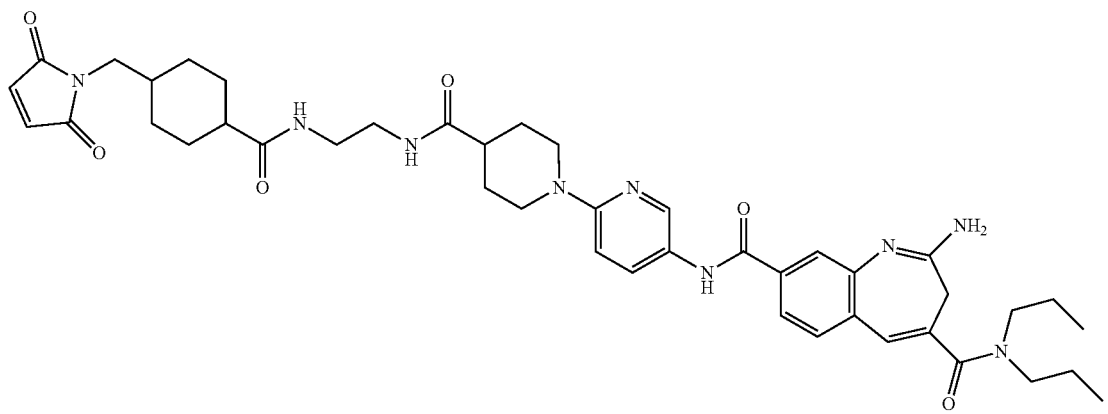 [SMILES: CCCN(CCC)C(=O)C1=Cc2ccc(C(=O)Nc3ccc(N4CCC(C(=O)NCCNC(=O)C5CCC(CN6C(=O)C=CC6=O)CC5)CC4)nc3)cc2N=C(N)C1]

From Compound 1.61 and succinimidyl 4-(N-maleimidomethyl)cyclohexane-1-carboxylate to provide a white solid. ¹H NMR (DMSO-d6) δ 10.1 (s, 1H), 8.46 (s, 1H), 8.61 (bs, 2H), 7.92 (dd, J=8.0, 2.5 Hz, 1H), 7.81 (m, 1H), 7.72 (m, 1H), 7.61 (s, 1H), 7.53 (d, J=8.0 Hz, 1H), 7.41 (d, J=8.0 Hz, 2H), 7.03 (s, 2H), 6.85-6.80 (m, 2H), 6.78 (s, 1H), 4.25 (m, 2H), 3.65 (m, 1H), 3.54 (t, J=7.5 Hz, 2H), 3.44 (m, 4H), 3.20-2.96 (m, 4H), 2.26 (t, J=7.5 Hz, 2H), 2.05 (m, 1H), 1.99-1.50 (m, 18H), 1.30 (m, 2H), 0.97 (t, J=7.5 Hz, 6H), 0.89 (bs, 6H). LCMS (M+H)=794.5.

Example 7B: Synthesis of 4-((S)-2-((S)-2-(6-(2,5-dioxo-2,5-dihydro-1H-pyrrol-1-yl)hexanamido)-3-methylbutanamido)-5-ureidopentanamido)benzyl (2-(4-((3-(2-amino-4-(dipropylcarbamoyl)-3H-benzo[b]azepine-8-carboxamido)-7,8-dihydro-1,6-naphthyridin-6(5H)-yl)methyl)benzamido)ethyl)carbamate (Compound-Linker 2.10)

LC-MS showed mostly desired product with small amount of SM remaining. The reaction mixture was concentrated in vacuo and the residue was diluted with water (45 mL) and saturated NaHCO₃ solution (5 mL) then extracted with EtOAc (3×). The combined extracts were dried (Na₂SO₄), filtered, and concentrated. The residue was absorbed on silica gel and purified by flash column chromatography (ISCO Gold 40 g; dry load, 0-20% CH₂Cl₂/MeOH) to afford 1.32 g of tert-butyl 4-((3-nitro-7,8-dihydro-1,6-naphthyridin-6(5H)-yl)methyl)benzoate as an orange colored syrup. ¹H NMR (DMSO-d⁶) δ 9.15 (d, J=2.5 Hz, 1H), 8.36 (d, J=2.5 Hz, 1H), 7.88 (d, J=8.0 Hz, 2H), 7.49 (d, J=8.0 Hz, 2H), 4.00 (s, 3H), 3.79 (s, 2H), 3.71 (s, 2H), 3.04 (m, 2H), 2.85 (m, 2H), 1.55 (s, 9H).

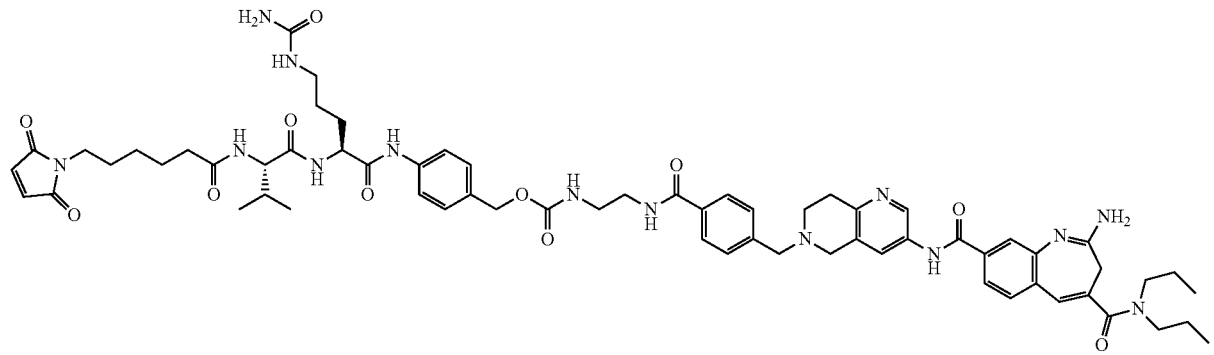 [SMILES: CCCN(CCC)C(=O)C1=Cc2ccc(C(=O)Nc3cnc4c(c3)CN(Cc3ccc(C(=O)NCCNC(=O)OCc5ccc(NC(=O)[C@H](CCCNC(N)=O)NC(=O)[C@@H](NC(=O)CCCCCN6C(=O)C=CC6=O)C(C)C)cc5)cc3)CC4)cc2N=C(N)C1]

Step A: Preparation of Int 7B-1

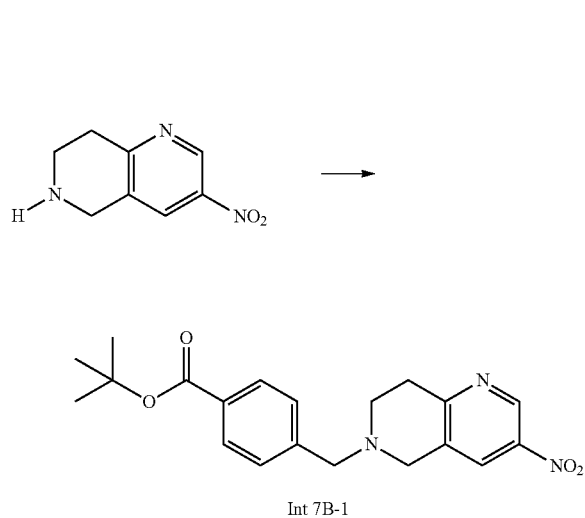

Int 7B-1

To a stirred solution of 3-nitro-5,6,7,8-tetrahydro-1,6-naphthyridine dihydrochloride (1.0 g, 3.97 mmol) and tert-butyl 4-(bromomethyl)benzoate (1.18 g, 4.36 mmol) in DMF (40 mL) cooled in an ice-water bath was added dropwise TEA (2.76 mL, 19.8 mmol). The resulting clear solution was stirred overnight while cooling bath expired.

Step B: Preparation of Int 7B-2

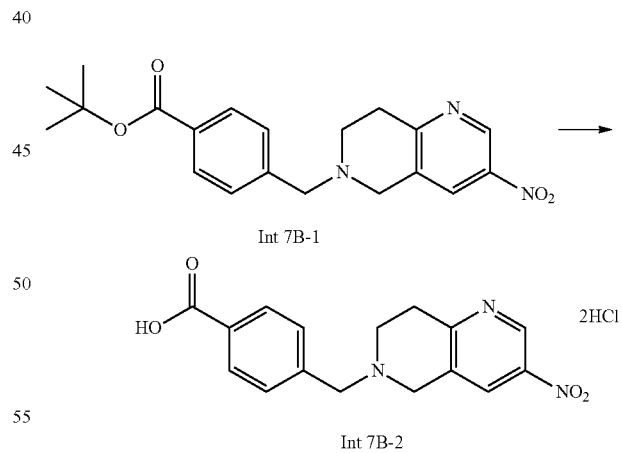

Int 7B-1

Int 7B-2

To a stirred solution of tert-butyl 4-((3-nitro-7,8-dihydro-1,6-naphthyridin-6(5H)-yl)methyl)benzoate (1.32 g, 3.57 mmol) in 27 mL of DCM was added 4M HCl (9 mL, 36.0 mmol) in dioxane at room temperature. The reaction mixture was stirred for 3 h then concentrated under reduced pressure. The residue dried in vacuo to afford a light yellow solid which was used directly without further purification. ¹H NMR (CD₃OD) δ 9.33 (d, J=2.5 Hz, 1H), 8.53 (d, J=2.5 Hz, 1H), 8.19 (d, J=8.0 Hz, 2H), 7.72 (d, J=8.0 Hz, 2H), 4.82 (m, 2H), 4.66 (m, 2H), 4.61 (s, 2H), 3.44 (m, 2H).

Step C: Preparation of Int 7B-3

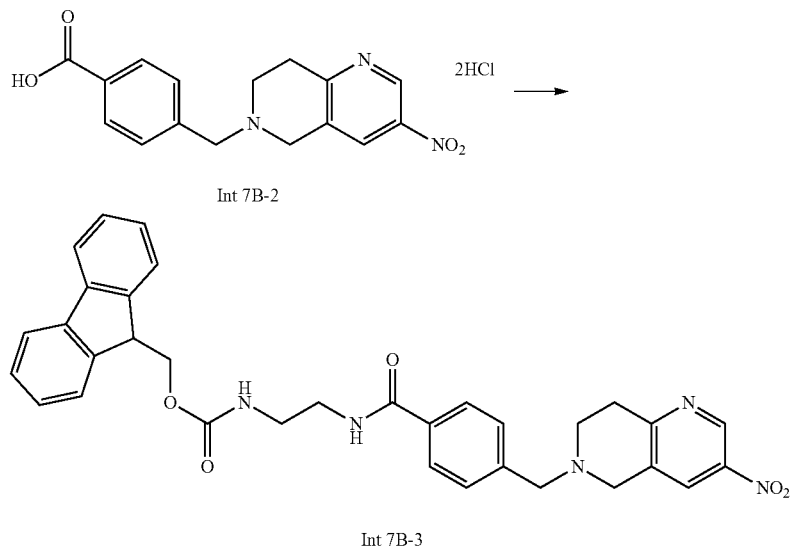 [SMILES: O=C(O)c1ccc(CN2CCc3ncc([N+](=O)[O-])cc3C2)cc1 ; O=C(NCCNC(=O)c1ccc(CN2CCc3ncc([N+](=O)[O-])cc3C2)cc1)OCC1c2ccccc2-c2ccccc21]

To a stirred solution of 4-((3-nitro-7,8-dihydro-1,6-naphthyridin-6(5H)-yl)methyl)benzoic acid dihydrochloride (1.28 g, 3.32 mmol), (9H-fluoren-9-yl)methyl (2-aminoethyl)carbamate hydrochloride (1.060 g, 3.32 mmol), and diisopropylethylamine (4.65 ml, 26.6 mmol) in 30 mL of DCM cooled in an ice-water bath was added dropwise 2,4,6-tripropyl-1,3,5,2,4,6-trioxatriphosphinane 2,4,6-trioxide (T3P®; 3.0 ml, 5.0 mmol). The mixture was stirred overnight while the cooling bath expired. The reaction mixture was partitioned between saturated NaHCO$_3$ and EtOAc. The aqueous layer was extracted with EtOAc (2×) and the combined organic extracts were washed with brine, dried over Na$_2$SO$_4$, filtered and concentrated to give 2.2 g of the desired product as an orange-red solid.

Step D: Preparation of Int 7B-4

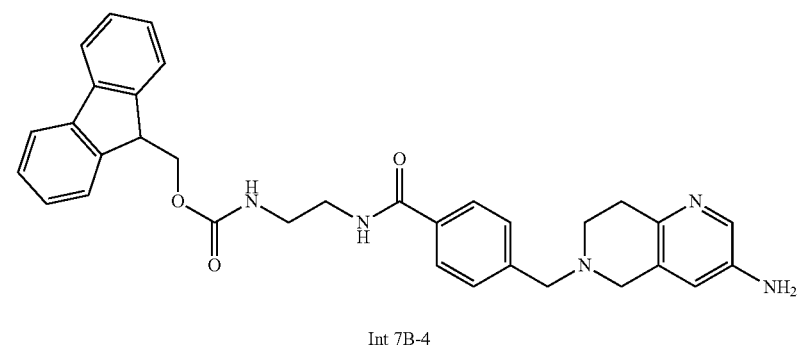

A mixture of (9H-fluoren-9-yl)methyl (2-(4-((3-nitro-7,8-dihydro-1,6-naphthyridin-6(5H)-yl)methyl)benzamido)ethyl)carbamate (2.0 g, 3.5 mmol) and iron (1.930 g, 34.6 mmol) in acetic acid (30 mL)/water (3 mL) was stirred at 50° C. for 45 min. The reaction mixture was cooled to room temperature, filtered and concentrated. The residue was diluted with saturated NaHCO₃ (90 mL) and EtOAc (90 mL). The precipitate was collected, washed with water and EtOAc, and dried in vacuo to afford 1.9 g of a yellow-brown solid which was suspended in 1:1 CH₂Cl₂/MeOH and absorbed on silica gel. Purification by flash column chromatography (ISCO Gold 80 g; dry load, 0-50% B in CH₂Cl₂ gradient, B: 80:18:2 CH₂Cl₂/MeOH/conc. NH₄OH) gave 1.12 g of the desired product as an off-white solid.

Step E: Preparation of Int 7B-5

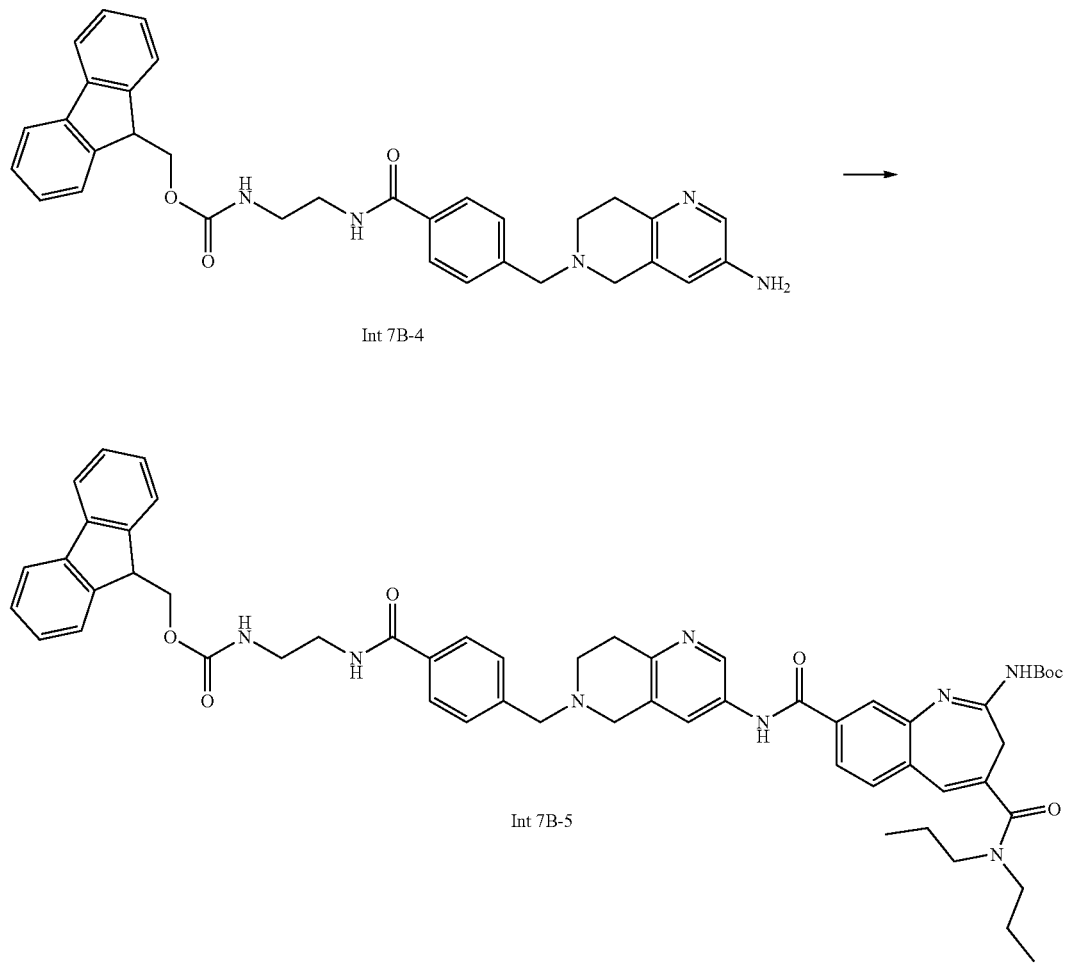

Int 7B-4

Int 7B-5

To a stirred solution of 2-((tert-butoxycarbonyl)amino)-4-(dipropylcarbamoyl)-3H-benzo[b]azepine-8-carboxylic acid (350 mg, 0.815 mmol) in DMF (5 mL) at room temperature was added HATU (341 mg, 0.896 mmol). The reaction was stirred for 15 min before the addition of 669 mg (1.22 mmol) of (9H-fluoren-9-yl)methyl (2-(4-((3-amino-7,8-dihydro-1,6-naphthyridin-6(5H)-yl)methyl)benzamido)ethyl)carbamate in DMF (11 mL) was added. The reaction was stirred for 35 min before the addition of 0.427 mL (2.44 mmol) of Hunig's base. The resulting yellow solution was stirred for 18 h then concentrated in vacuo. The residue was purified by flash column chromatography (ISCO Gold 40 g; dry load, 0-50% B in CH₂Cl₂ gradient, B: 80:18:2 CH₂Cl₂/MeOH/conc. NH₄OH) to afford 435 mg of the desired product as a light yellow solid.

Step F. Preparation of Int 7B-6

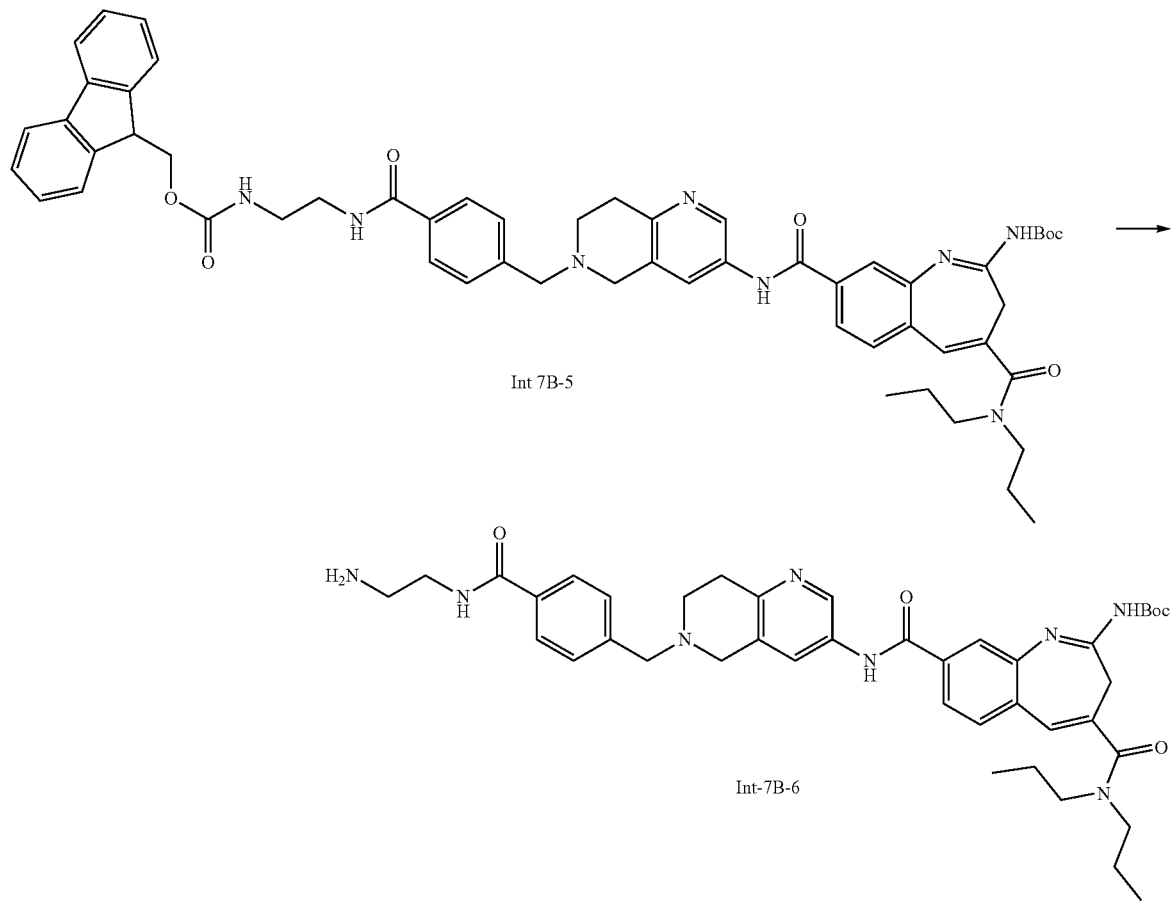

To a stirred solution of tert-butyl (8-((6-(4-((2-((((9H-fluoren-9-yl)methoxy)carbonyl)amino)ethyl)carbamoyl)benzyl)-5,6,7,8-tetrahydro-1,6-naphthyridin-3-yl)carbamoyl)-4-(dipropylcarbamoyl)-3H-benzo[b]azepin-2-yl)carbamate (435 mg, 0.454 mmol) in 3.6 mL of DMF was added 0.90 mL (9.1 mmol) of piperidine at room temperature. The reaction was stirred for 1 h then concentrated. The residue was purified by flash column chromatography (ISCO Gold 24 g, 0-50% B in $CH_2Cl_2$ gradient, B: 80:18:2 $CH_2Cl_2$/MeOH/conc. $NH_4OH$) to afford 241 mg of the desired product as a light yellow solid.

Step G: Preparation of Compound-Linker 2.10

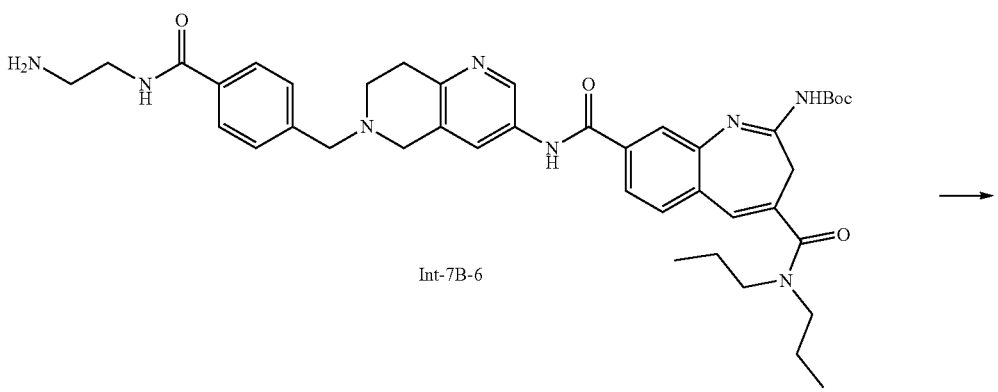

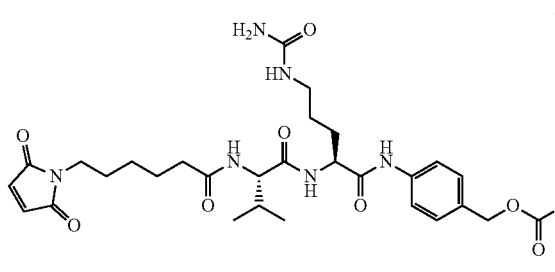

-continued

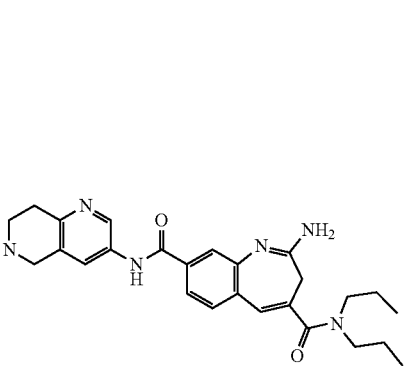

To a stirred solution of tert-butyl (8-((6-(4-((2-aminoethyl)carbamoyl)benzyl)-5,6,7,8-tetrahydro-1,6-naphthyridin-3-yl)carbamoyl)-4-(dipropylcarbamoyl)-3H-benzo[b]azepin-2-yl)carbamate (80 mg, 0.109 mmol) and Hunig's base (0.057 mL, 0.326 mmol) in DMF (3.4 mL) under nitrogen cooled in an ice-water bath was added dropwise a solution of 4-((S)-2-((S)-2-(6-(2,5-dioxo-2, 5-dihydro-1H-pyrrol-1-yl)hexanamido)-3-methylbutanamido)-5-ureidopentanamido)benzyl (4-nitrophenyl) carbonate (80 mg, 0.109 mmol) in DMF (2 mL). The reaction was stirred overnight while cooling bath expired. The reaction mixture was then concentrated and the residue neutralized with saturated NaHCO$_3$ and purified by reverse phase column (Gold C18 30 g; 5-60% CH$_3$CN in water, no TFA). Fractions pooled, concentrated to afford 100 mg of an off-yellow solid which was directly dissolved in 50 mL of DCM and treated with 10 mL of TFA. The resulting solution was stirred for 1 h then concentrated under reduced pressure. The residue was dried in vacuo, neutralized with saturated NaHCO$_3$, and purified by reverse phase column chromatography (ISCO Gold C18 30 g; 5-70% MeCN in water gradient, no TFA). Major fractions were combined and lyophilized to provide 22 mg of an off-white solid. $^1$H NMR (CD$_3$OD) δ 8.67 (d, J=2.5 Hz, 1H), 7.91 (d, J=2.5 Hz, 1H), 7.80 (d, J=8.0 Hz, 1H), 7.69 (d, J=2.5 Hz, 1H), 7.58-7.50 (m, 5H), 7.45 (d, J=8.0 Hz, 1H), 7.26 (d, J=8.5 Hz, 2H), 6.89 (s, 1H), 6.77 (s, 2H), 5.04 (s, 2H), 4.90 (m, 1H), 4.14 (d, J=7.5 Hz, 1H), 3.81 (s, 2H), 3.69 (s, 2H), 3.51-3.40 (m, 8H), 3.34 (m, 2H), 3.22 (m, 1H), 3.11 (m, 2H), 2.97 (m, 2H), 2.90 (m, 3H), 2.25 (t, J=7.5 Hz, 2H), 2.06 (m, 1H), 1.88 (m, 1H), 1.75-1.52 (m, 12H), 1.28 (m, 2H), 0.95 (t, J=7.5 Hz, 6H), 0.89 (bs, 6H). LCMS (M+H)=1235.9.

Example 7C: Synthesis of 4-((S)-2-((S)-2-(6-(2, 5-dioxo-2, 5-dihydro-1H-pyrrol-1-yl)hexanamido)-3-methylbutanamido)-5-ureidopentanamido)benzyl (2-(4-((3-(2-amino-4-(dipropylcarbamoyl)-3H-benzo[b]azepine-8-carboxamido)-7,8-dihydro-1,6-naphthyridin-6(5H)-yl)methyl)benzamido)ethyl)carbamate (Compound-Linker 2.11)

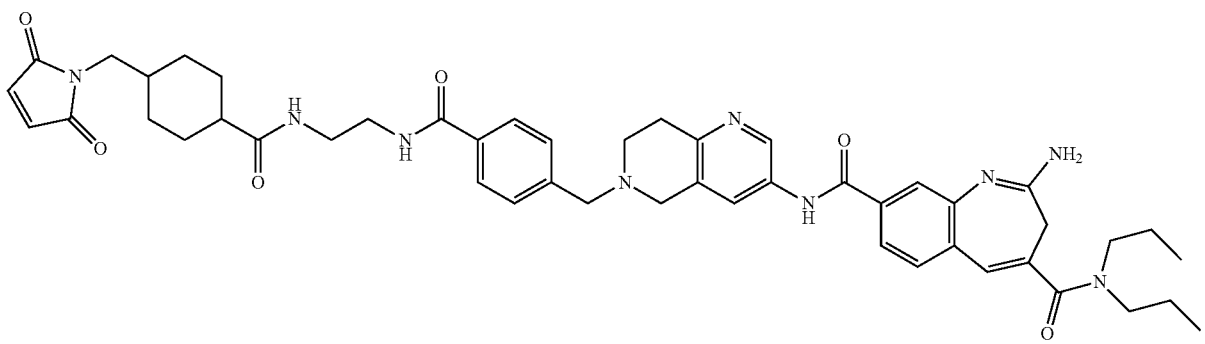 [SMILES: CCCN(CCC)C(=O)C1=Cc2ccc(C(=O)Nc3cnc4c(c3)CN(Cc3ccc(C(=O)NCCNC(=O)C5CCC(CN6C(=O)C=CC6=O)CC5)cc3)CC4)cc2N=C(N)C1]

Step A: Preparation of Compound-Linker 2.11

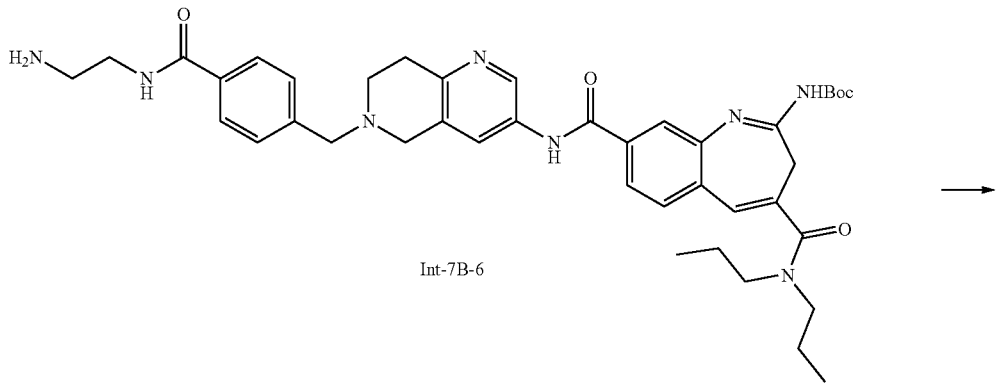

Int-7B-6

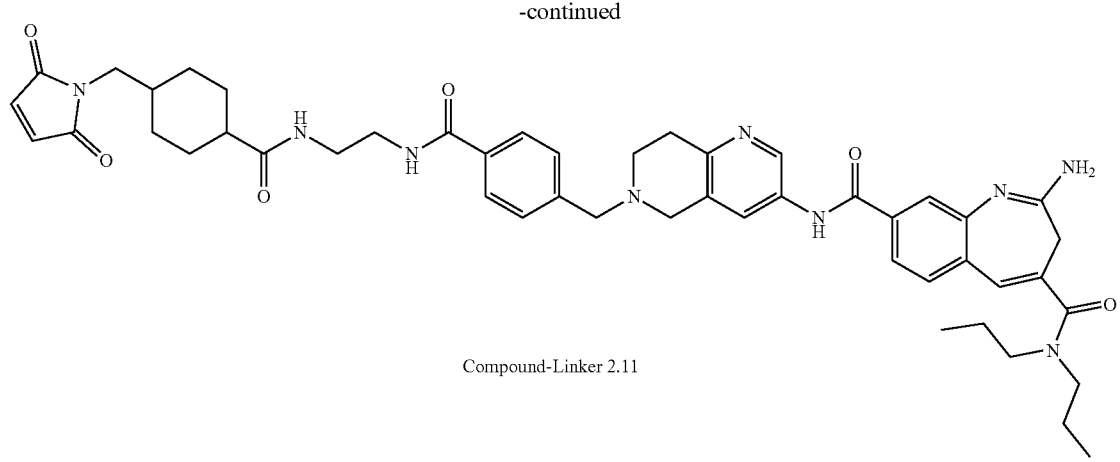

Compound-Linker 2.11

A solution of 84.5 mg (0.115 mmol) of tert-butyl (8-((6-(4-((2-aminoethyl)carbamoyl)benzyl)-5,6,7,8-tetrahydro-1,6-naphthyridin-3-yl)carbamoyl)-4-(dipropylcarbamoyl)-3H-benzo[b]azepin-2-yl)carbamate from step F above, 2,5-dioxopyrrolidin-1-yl 4-((2,5-dioxo-2,5-dihydro-1H-pyrrol-1-yl)methyl)cyclohexane-1-carboxylate (38.3 mg, 0.115 mmol), and Hunig's base (0.040 mL, 0.229 mmol) in DCM (2.5 mL) was stirred at room temperature for 16 h. The reaction mixture was concentrated to dryness and the residue was purified by reverse phase column chromatography (ISCO Gold C18 100 g, 5-70% MeCN in water gradient, no TFA). The desired fractions were pooled and concentrated to provide 79 mg of the desired product as a yellow solid which was subsequently dissolved in 2.5 mL of DCM at room temperature and then treated with TFA (500 µL, 6.49 mmol). After 1 h, the reaction mixture was concentrated, the residue dried in vacuo, neutralized with saturated NaHCO$_3$, and purified by reverse phase column chromatography (ISCO Gold C18 100 g; 5-60% MeCN in water gradient, no TFA).

The main fractions were pooled and concentrated. The residue was lyophilized from MeCN/water to afford 25 mg of the desired product as an off-white solid. $^1$H NMR (CD$_3$OD) δ 8.67 (d, J=2.5 Hz, 1H), 7.91 (d, J=2.5 Hz, 1H), 7.80 (d, J=8.0 Hz, 1H), 7.68 (d, J=2.5 Hz, 1H), 7.55 (dd, J=2.0, 8.0 Hz, 1H), 7.53 (d, J=8.0 Hz, 2H), 7.45 (d, J=8.0 Hz, 1H), 6.89 (s, 1H), 6.77 (s, 2H), 4.57 (s, 1H), 3.81 (s, 2H), 3.49-3.38 (m, 8H), 3.00 (m, 2H), 2.90 (m, 2H), 2.84 (m, 1H), 2.11 (m, 1H), 1.88 (m, 1H), 1.70-1.58 (m, 8H), 1.39 (m, 2H), 1.0-0.89 (m, 10H). LCMS (M+H)=856.8.

Example 7D: Synthesis of Perfluorophenyl 4-((3-((2-(4-((3-(2-amino-4-(dipropylcarbamoyl)-3H-benzo[b]azepine-8-carboxamido)-7,8-dihydro-1,6-naphthyridin-6(5H)-yl)methyl)benzamido)ethyl)thio)-2,5-dioxopyrrolidin-1-yl)methyl)cyclohexane-1-carboxylate tris TFA salt (Compound-Linker 2.12)

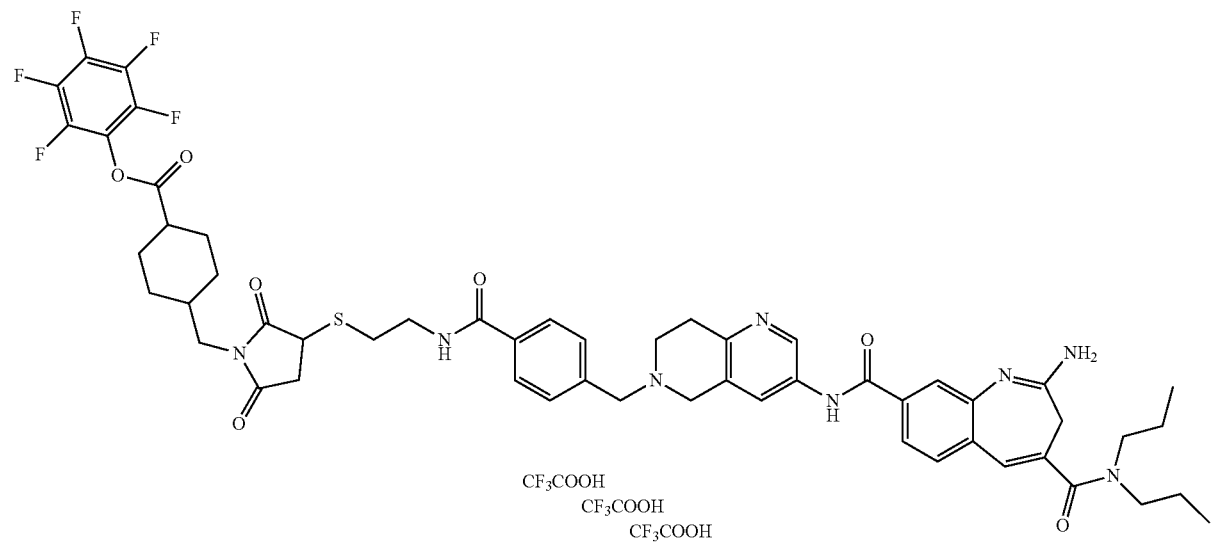 [SMILES: CCCN(CCC)C(=O)C1=Cc2ccc(C(=O)Nc3cnc4c(c3)CN(Cc3ccc(C(=O)NCCSC5CC(=O)N(CC6CCC(C(=O)Oc7c(F)c(F)c(F)c(F)c7F)CC6)C5=O)cc3)CC4)cc2N=C(N)C1 ; "CF3COOH" ; "CF3COOH" ; "CF3COOH"]

CF$_3$COOH
CF$_3$COOH
CF$_3$COOH

Preparation of Compound-Linker 2.12

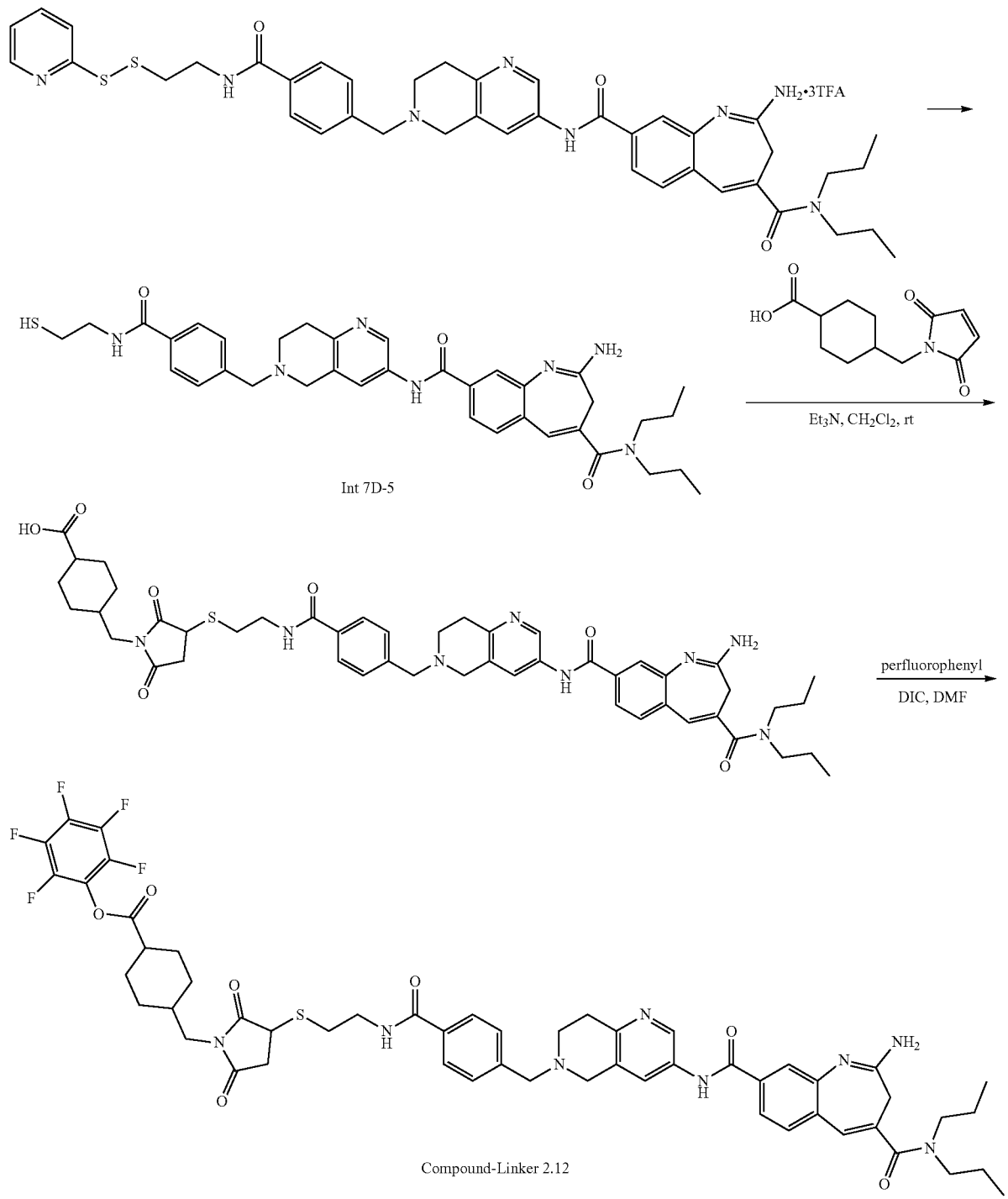

Compound-Linker 2.12

A solution of 2-amino-$N^4$,$N^4$-dipropyl-$N^8$-(6-(4-((2-(pyridin-2-yldisulfanyl)ethyl)carbamoyl)benzyl)-5,6,7,8-tetrahydro-1,6-naphthyridin-3-yl)-3H-benzo[b]azepine-4,8-dicarboxamide (100 mg, 0.090 mmol) (tri-TFA salt) and 3,3',3"-phosphanetriyltripropionic acid hydrochloride (38.9 mg, 0.136 mmol) in 3 mL of 1:1 acetonitrile/water was stirred at room temperature for 0.5 h. The reaction mixture was concentrated in vacuo to dryness to provide Int 7D-1 a yellow foamy solid which was used directly without further any purification. This intermediate was converted to the final compound-linker 2.12 according to the scheme above. $^1$H NMR (CD$_3$OD) δ 8.77 (d, J=2.0 Hz, 1H), 8.22 (d, J=2.5 Hz, 1H), 8.00-7.95 (m, 3H), 7.10 (s, 1H), 4.57 (bs, 2H), 4.47 (bs, 2H), 4.11 (dd, J=9.0, 3.5 Hz, 1H), 3.76-3.62 (m, 3H), 3.45-3.35 (m, 4H), 3.40-3.35 (m, 4H), 3.24-3.18 (m, 4H), 2.98 (m, 1H), 2.71 (m, 1H), 2.54 (d, J=3.5 Hz, 0.5H), 2.50

(d, J=3.5 Hz, 0.5H), 2.15 (m, 2H), 1.83-1.79 (m, 2H), 1.74-1.64 (m, 6H), 1.55-1.45 (m, 2H), 1.17-1.10 (m, 2H), 0.96 (bs, 3H), 0.91 (bs, 3H). LCMS (M+H)=1057.7.

Example 7E: Preparation of 4-((S)-2-((S)-2-(6-(2, 5-dioxo-2,5-dihydro-1H-pyrrol-1-yl)hexanamido)-3-methylbutanamido)-5-ureidopentanamido)benzyl 3-(2-amino-4-(dipropylcarbamoyl)-7-methoxy-3H-benzo[b]azepine-8-carboxamido)-7, 8-dihydro-1,6-naphthyridine-6(5H)-carboxylate TFA salt (Compound-Linker 2.14)

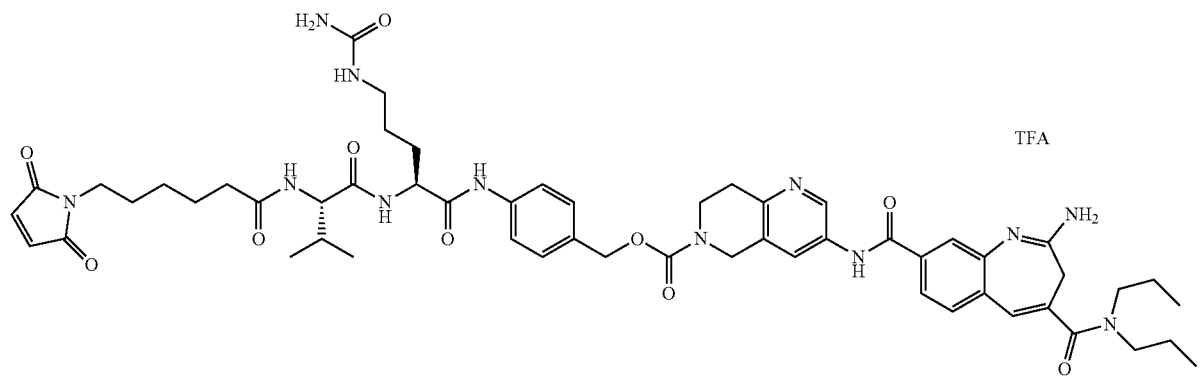 [SMILES: CCCN(CCC)C(=O)C1=Cc2ccc(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1]

Prepared in a manner similar to Compound 1.1 using 2-amino-4-(dipropylcarbamoyl)-3H-benzo[b]azepine-8-carboxylic acid and commercially available tert-Butyl 3-amino-7,8-dihydro-1,6-naphthyridine-6(5H)-carboxylate (CAS No. 355819-02-2).

$^1$H NMR (DMSO-d$^6$) δ 12.1 (s, 1H), 10.4 (s, 1H), 10.0 (s, 1H), 9.14 (s, 1H), 8.73 (d, J=2.4 Hz, 1H), 8.08 (d, J=7.6 Hz, 2H), 7.80 (d, J=8.8 Hz, 1H), 7.70 (s, 1H), 7.60 (d, J=8.4 Hz, 2H), 7.41 (s, 1H), 7.34 (d, J=8.8 Hz, 2H), 7.03 (s, 1H), 7.00 (s, 1H), 5.99 (bs, 1H), 5.07 (s, 2H), 4.65 (m, 4H), 4.40 (m, 2H), 4.21 (m, 2H), 3.97 (s, 3H), 3.74 (bt, 2H), 3.37 (t, J=6.8 Hz, 5H), 3.29 (s, 2H), 3.11-2.95 (m, 4H), 2.22-1.95 (m, 4H), 1.60-1.15 (m, 12H), 0.88 (d, J=7.0 Hz, 6H), 0.82 (d, J=7.0 Hz, 6H). LCMS [M+H]=1090.5. $^{19}$F NMR (DMSO-d$^6$) d -74.5.

Example 7F: Preparation of 4-((S)-2-((S)-2-(6-(2,5-dioxo-2,5-dihydro-1H-pyrrol-1-yl)hexanamido)-3-methylbutanamido)-5-ureidopentanamido)benzyl 3-(2-amino-4-(dipropylcarbamoyl)-7-methoxy-3H-benzo[b] azepine-8-carboxamido)-7, 8-dihydro-1,6-naphthyridine-6(5H)-carboxylate (Compound-Linker 2.15)

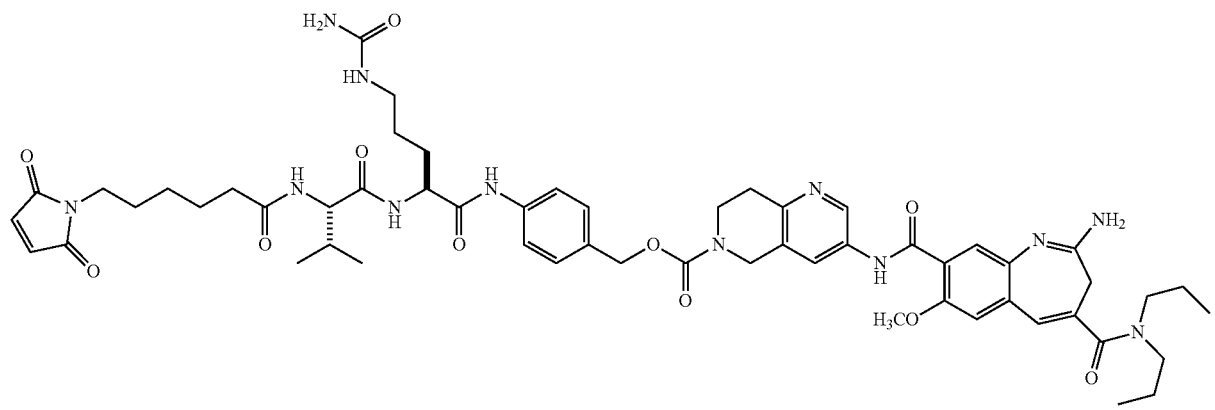 [SMILES: CCCN(CCC)C(=O)C1=Cc2cc(OC)c(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1]

Prepared in a manner similar to Compound 1.1 starting from 2-amino-4-(dipropylcarbamoyl)-7-methoxy-3H-benzo[b]azepine-8-carboxylic acid.

Example 7G: Preparation of 4-((S)-2-((S)-2-(6-(2,5-dioxo-2,5-dihydro-1H-pyrrol-1-yl)hexanamido)-3-methylbutanamido)-5-ureidopentanamido)benzyl 3-(2-amino-4-(dipropylcarbamoyl)-7-fluoro-3H-benzo[b]azepine-8-carboxamido)-7, 8-dihydro-1,6-naphthyridine-6(5H)-carboxylate (Compound-Linker 2.16)

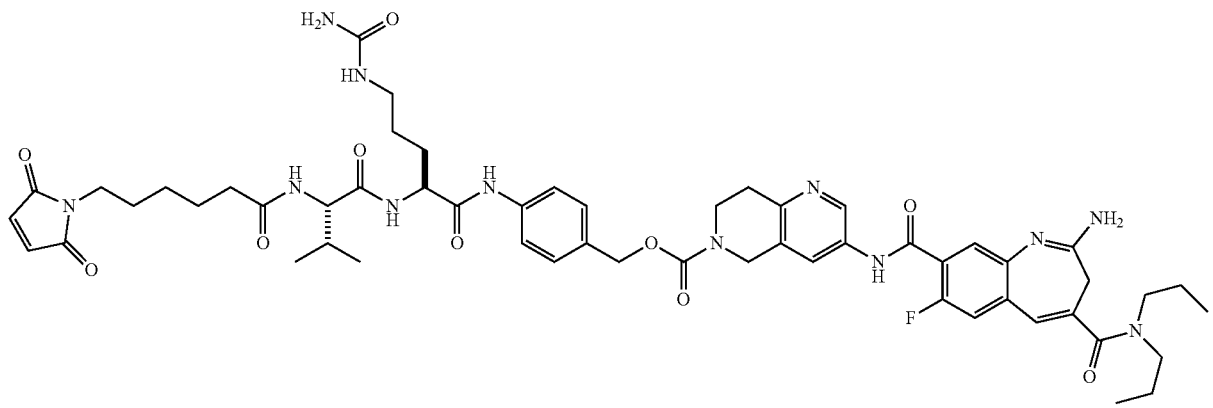 [SMILES: CCCN(CCC)C(=O)C1=Cc2cc(F)c(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1]

Prepared in a manner similar to Compound 1.1 starting from 2-amino-4-(dipropylcarbamoyl)-7-fluoro-3H-benzo[b]azepine-8-carboxylic acid.

$^1$H NMR (DMSO-d$^6$) δ 12.2 (s, 1H), 10.8 (s, 1H), 10.0 (s, 1H), 9.89 (s, 1H), 9.27 (s, 1H), 8.66 (s, 1H), 8.08 (d, J=2.4 Hz, 1H), 8.03 (s, 1H), 7.80 (d, J=8.8 Hz, 2H), 7.70-7.64 (m, 2H), 7.60 (d, J=8.4 Hz, 1H), 7.34 (d, J=8.8 Hz, 2H), 7.02 (s, 1H), 7.00 (s, 2H), 5.99 (bs, 1H), 5.07 (s, 2H), 4.65 (m, 4H), 4.40 (m, 2H), 4.21 (m, 2H), 3.73 (bt, 2H), 3.36 (m, 5H), 3.29 (s, 2H), 3.11-2.95 (m, 4H), 2.22-1.95 (m, 4H), 1.60-1.15 (m, 12H), 0.88 (d, J=7.0 Hz, 6H), 0.82 (d, J=7.0 Hz, 6H). LCMS [M+H]=1079.5.

Example 7F: Preparation of 4-((S)-2-((S)-2-(6-(2,5-dioxo-2,5-dihydro-1H-pyrrol-1-yl)hexanamido)-3-methylbutanamido)-5-ureidopentanamido)benzyl (3-(4-((3-(2-amino-4-(dipropylcarbamoyl)-3H-benzo[b]azepine-8-carboxamido)-7,8-dihydro-1,6-naphthyridin-6(5H)-yl)methyl)benzamido)-2,2-difluoropropyl)carbamate (Compound-Linker 2.17)

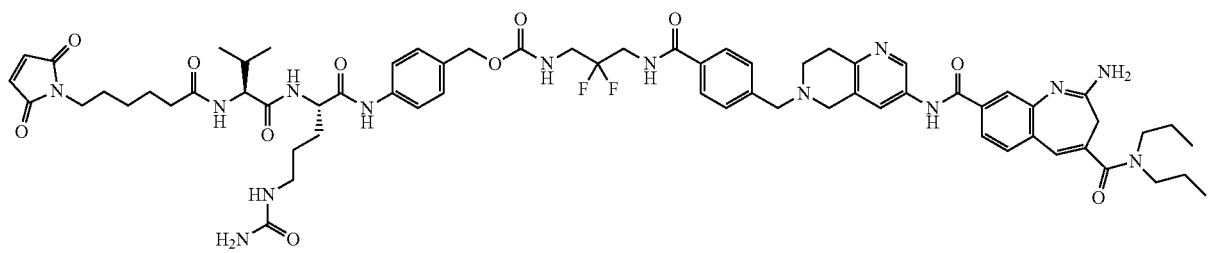 [SMILES: CCCN(CCC)C(=O)C1=Cc2ccc(C(=O)Nc3cnc4c(c3)CN(Cc3ccc(C(=O)NCC(F)(F)CNC(=O)OCc5ccc(NC(=O)[C@H](CCCNC(N)=O)NC(=O)[C@@H](NC(=O)CCCCCN6C(=O)C=CC6=O)C(C)C)cc5)cc3)CC4)cc2N=C(N)C1]

Prepared in a manner similar to Compound 1.1.
Table 2 shows Compound-Linkers 2.1-2.21.

TABLE 2

Compound-Linkers 2.1-2.21

| Compound-Linkers | Structure |
| --- | --- |
| 2.1 | 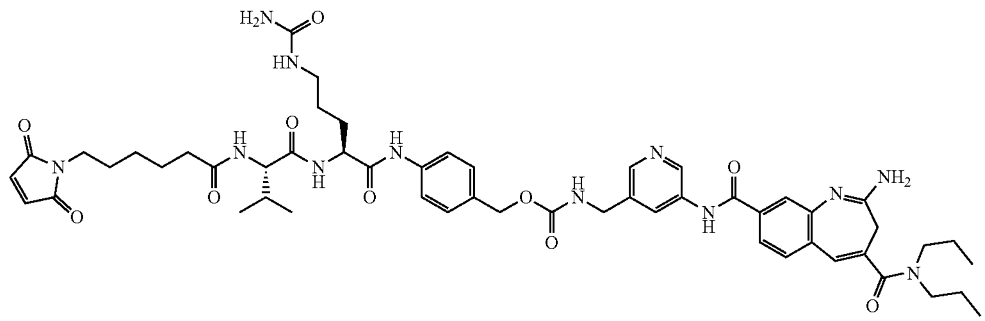 [SMILES: CCCN(CCC)C(=O)C1=Cc2ccc(C(=O)Nc3cncc(CNC(=O)OCc4ccc(NC(=O)[C@H](CCCNC(N)=O)NC(=O)[C@@H](NC(=O)CCCCCN5C(=O)C=CC5=O)C(C)C)cc4)c3)cc2N=C(N)C1] |
| 2.2 | 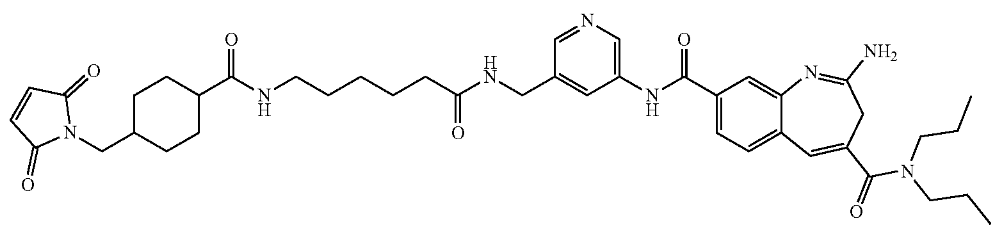 [SMILES: CCCN(CCC)C(=O)C1=Cc2ccc(C(=O)Nc3cncc(CNC(=O)CCCCCNC(=O)C4CCC(CN5C(=O)C=CC5=O)CC4)c3)cc2N=C(N)C1] |
| 2.3 | 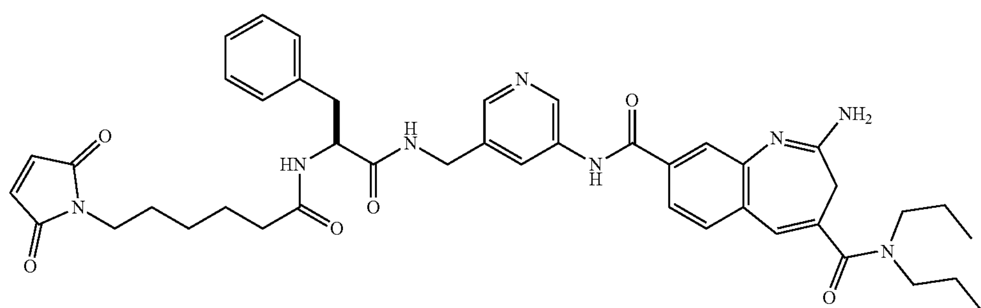 [SMILES: CCCN(CCC)C(=O)C1=Cc2ccc(C(=O)Nc3cncc(CNC(=O)[C@H](Cc4ccccc4)NC(=O)CCCCCN4C(=O)C=CC4=O)c3)cc2N=C(N)C1] |
| 2.4 | 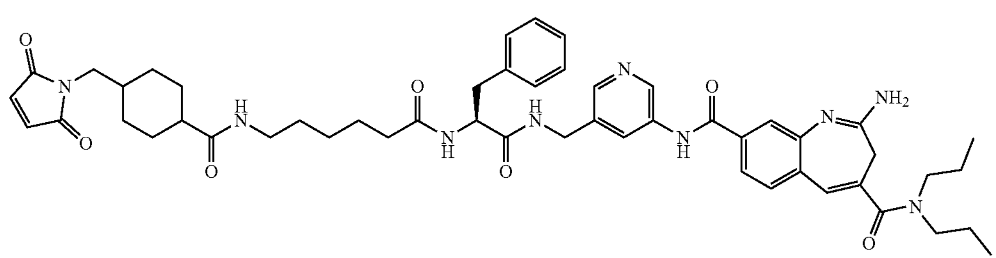 [SMILES: CCCN(CCC)C(=O)C1=Cc2ccc(C(=O)Nc3cncc(CNC(=O)[C@H](Cc4ccccc4)NC(=O)CCCCCNC(=O)C4CCC(CN5C(=O)C=CC5=O)CC4)c3)cc2N=C(N)C1] |
| 2.5 | 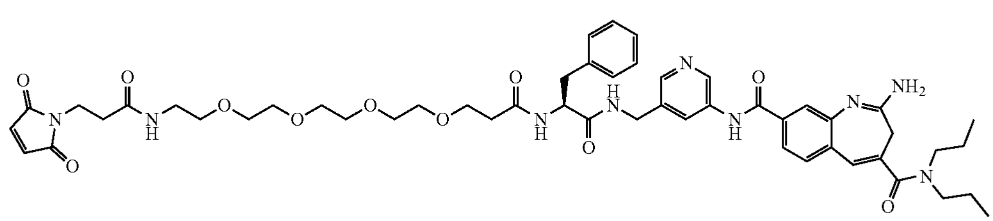 [SMILES: CCCN(CCC)C(=O)C1=Cc2ccc(C(=O)Nc3cncc(CNC(=O)[C@H](Cc4ccccc4)NC(=O)CCOCCOCCOCCOCCNC(=O)CCN4C(=O)C=CC4=O)c3)cc2N=C(N)C1] |

TABLE 2-continued
Compound-Linkers 2.1-2.21
| Compound-Linkers | Structure |
| --- | --- |
| 2.6 | 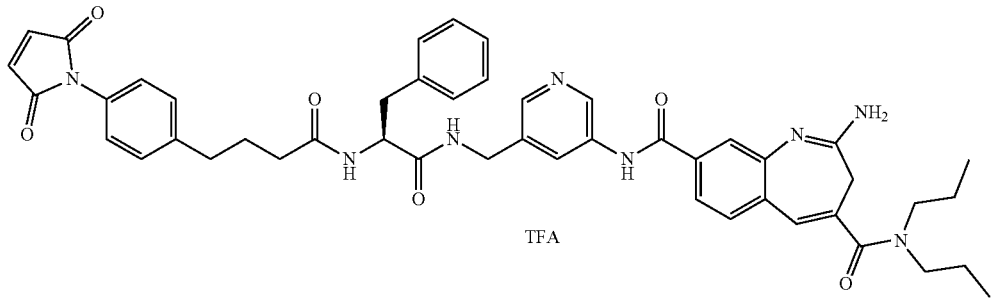 TFA |
| 2.7 | 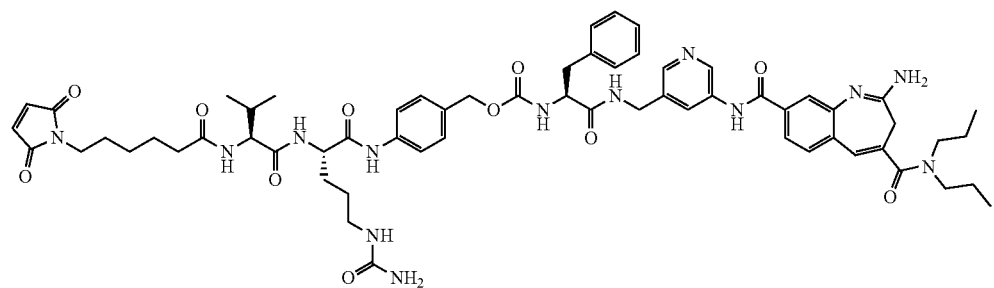 |
| 2.8 | 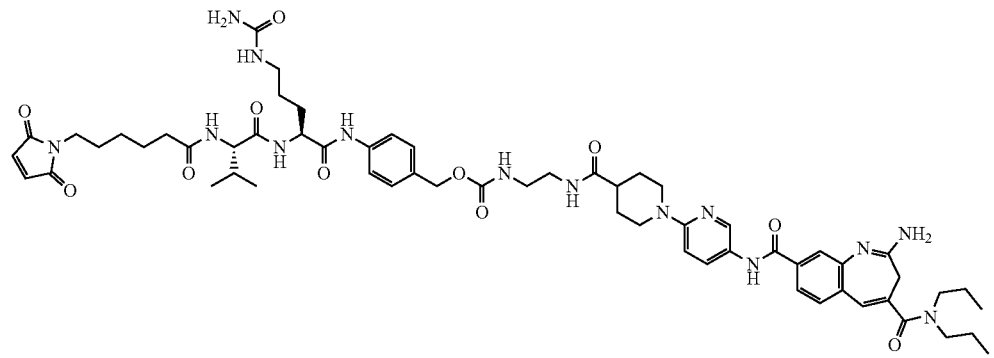 |
| 2.9 | 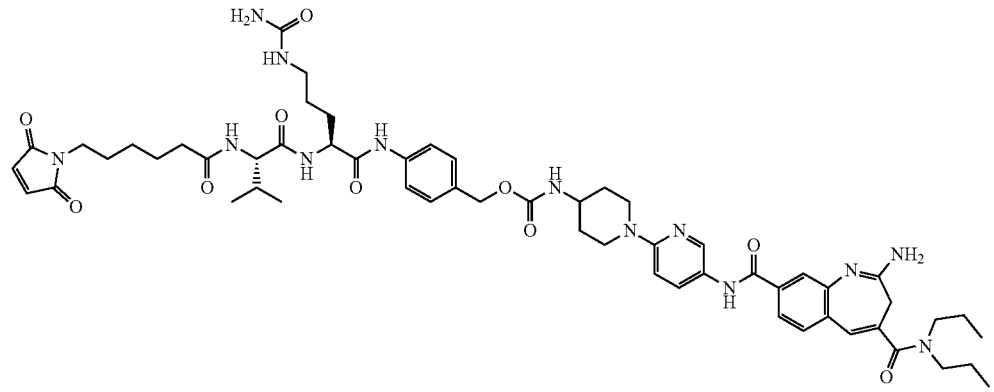 |

TABLE 2-continued

Compound-Linkers 2.1-2.21

| Compound-Linkers | Structure |
| --- | --- |
| 2.10 | 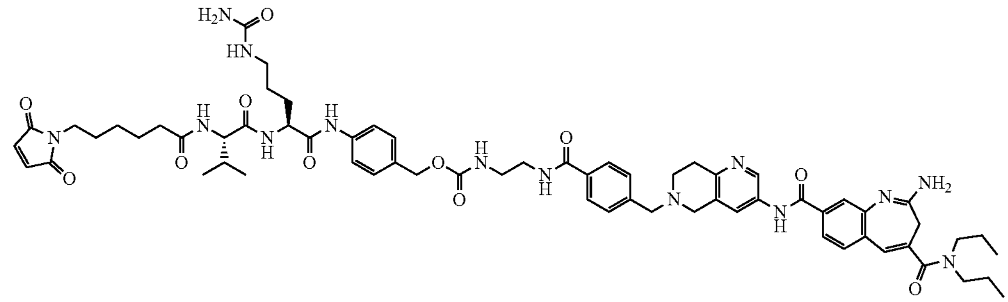 [SMILES: CCCN(CCC)C(=O)C1=Cc2ccc(C(=O)Nc3cnc4c(c3)CN(Cc3ccc(C(=O)NCCNC(=O)OCc5ccc(NC(=O)[C@H](CCCNC(N)=O)NC(=O)[C@@H](NC(=O)CCCCCN6C(=O)C=CC6=O)C(C)C)cc5)cc3)CC4)cc2N=C(N)C1] |
| 2.11 | 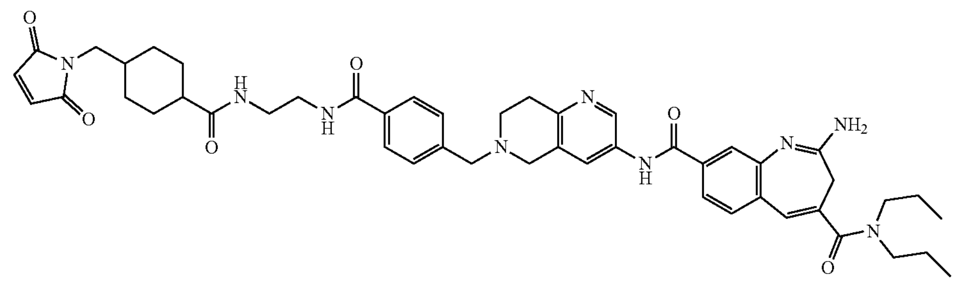 [SMILES: CCCN(CCC)C(=O)C1=Cc2ccc(C(=O)Nc3cnc4c(c3)CN(Cc3ccc(C(=O)NCCNC(=O)C5CCC(CN6C(=O)C=CC6=O)CC5)cc3)CC4)cc2N=C(N)C1] |
| 2.12 | 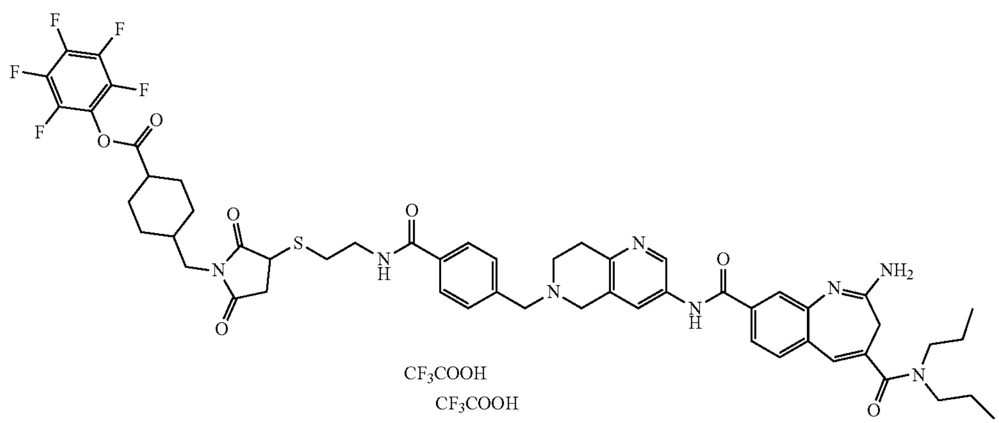 |
| 2.14 | 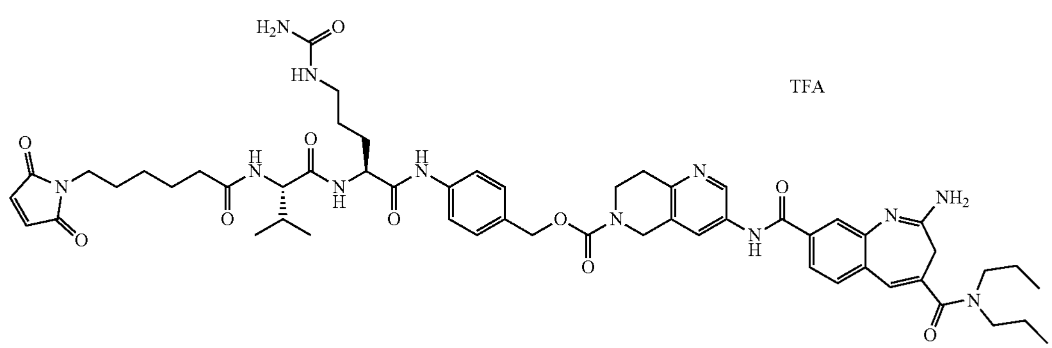 [SMILES: CCCN(CCC)C(=O)C1=Cc2ccc(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1] |

TABLE 2-continued
Compound-Linkers 2.1-2.21
| Compound-Linkers | Structure |
|---|---|
| 2.15 | 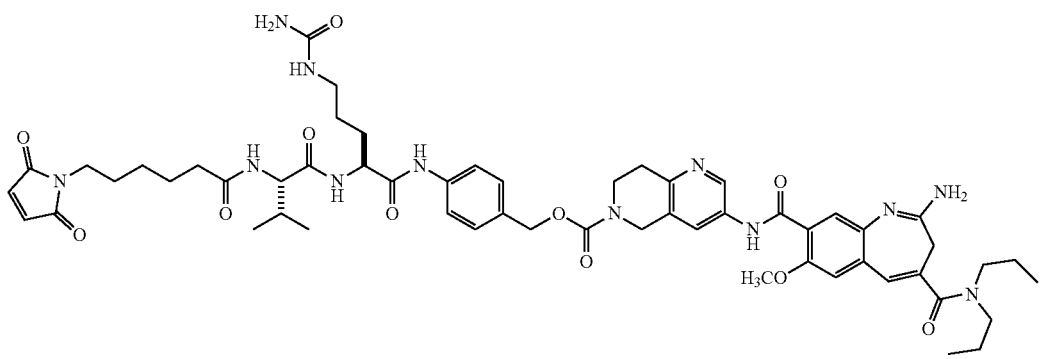 [SMILES: CCCN(CCC)C(=O)C1=Cc2cc(OC)c(C(=O)Nc3cnc4c(c3)CN(C(=O)OCc3ccc(NC(=O)[C@H](CCCNC(N)=O)NC(=O)[C@@H](NC(=O)CCCCCN5C(=O)C=CC5=O)C(C)C)cc3)CC4)cc2N=C(N)C1] |
| 2.16 | 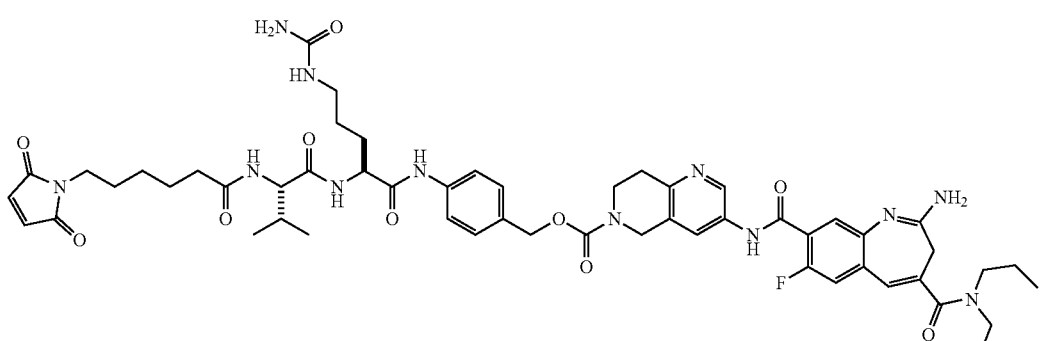 |
| 2.17 | 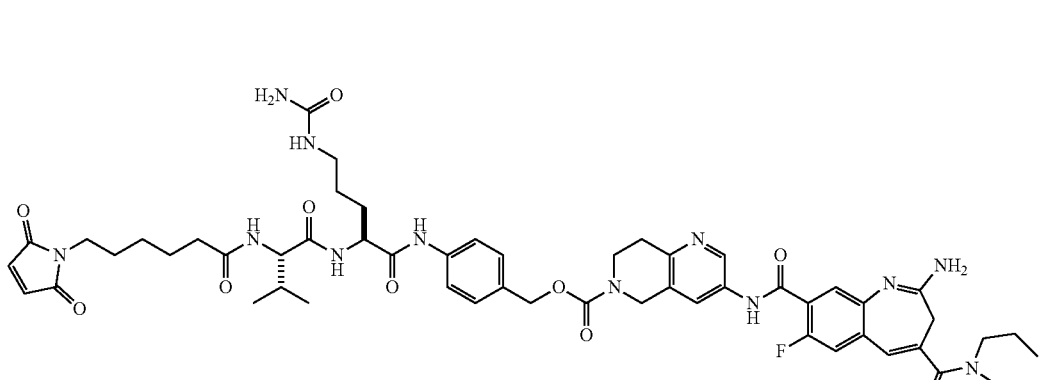 |
| 2.20 | 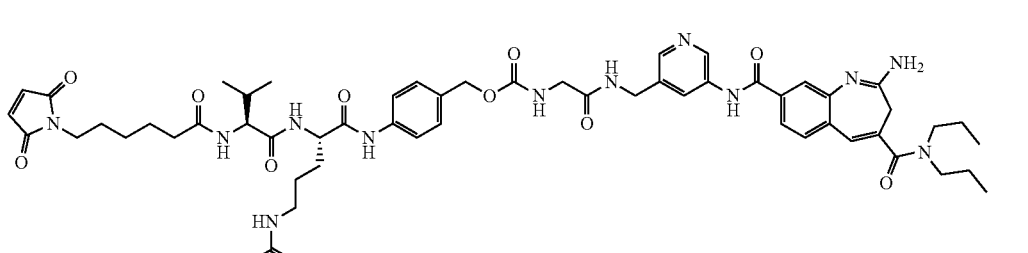 |

TABLE 2-continued

Compound-Linkers 2.1-2.21

| Compound-Linkers | Structure |
|---|---|
| 2.21 | *[chemical structure]* |
| 2.22 | *[chemical structure]* |

Example 8

Synthesis of Antibody Benzazepine Conjugates

Protocol for the Preparation of Antibody Benzazepine Conjugate

The mAb (155 mg, 35.57 mL, 4.38 mg/mL in PBS) was exchanged into HEPES (100 mM, pH 7.0, 1 mM DTPA) via molecular weight cut-off centrifugal filtration (Millipore, 30 kDa). The resultant mAb solution was transferred to a 50 mL conical tube (31.873 mL by weight). The mAb concentration was determined to be 4.39 mg/mL by $A_{280}$ (total mAb content was 140 mg, 3 mg was removed for analytical applications). To the mAb solution was added TCEP (2.0 eq, 1.85 mL, 1 mM stock) at room temperature and the resultant mixture was incubated at 37° C. for 1 hr, with gentle shaking. Upon being cooled to room temperature, a stir bar was added to the reaction tube. With stirring, DMA (10% v/v, 3.0 mL) was added dropwise to the reaction mixture. Compound-Linker 2.1 (7.0 equiv., 647 µL, 10 mM DMA) was added dropwise and the resultant reaction mixture was allowed to stir at ambient temperature for 30 minutes, at which point N-ethyl maleimide (3.0 eq, 100 mM DMA, 28 µL). After an additional 15 minutes of stirring, cysteine (6.0 equiv., 50 mM HEPES, 111 µL) was added. The crude conjugate was then exchanged into PBS and purified by preparative SEC (HiLoad 26/600, Superdex 200pg) using PBS as the mobile phase. The pure fractions were concentrated via molecular weight cut-off centrifugal filtration (Millipore, 30 kDa), sterile filtered and transferred to 15 mL conical tubes. Drug-antibody construct ratios (molar ratios) were determined by methods described in Example 9.

Example 9

General Procedure for the Determination of the Drug-Antibody-Ratios

Hydrophobic Interaction Chromatography

10 µL of a 6 mg/mL solution of the conjugate was injected into an HPLC system set-up with a TOSOH TSKgel Butyl-NPR™ hydrophobic interaction chromatography (HIC) column (2.5 µM particle size, 4.6 mm×35 mm) attached. Then, over the course of 18 minutes, a method was run in which the mobile phase gradient ran from 100% mobile phase A to 100% mobile phase B over the course of 12 minutes, followed by a six-minute re-equilibration at 100% mobile phase A. The flow rate was 0.8 mL/min and the detector was set at 280 nM. Mobile phase A was 1.5 M ammonium sulfate, 25 mM sodium phosphate (pH 7). Mobile phase B was 25% isopropanol in 25 mM sodium phosphate (pH 7). Post-run, the chromatogram was integrated and the molar ratio was determined by summing the weighted peak area.

Mass Spectrometry

One microgram of conjugate was injected into an LC/MS such as an Agilent 6550 iFunnel Q-TOF equipped with an Agilent Dual Jet Stream ESI source coupled with Agilent 1290 Infinity UHPLC system. Raw data is obtained and is deconvoluted with software such as Agilent MassHunter Qualitative Analysis Software with BioConfirm using the Maximum Entropy deconvolution algorithm. The average mass of intact antibody construct immune-stimulatorystimulatorystimulatory compound conjugates was calculated by the software, which used top peak height at 25% for the calculation. This data is then imported into another program to calculate the molar ratio of the conjugate such as Agilent molar ratio calculator.

Example 10

TLR7/TLR8 Reporter Assays

Materials and General Procedures

Reporter cells lines (namely HEK-Blue Null, HEK-Blue hTLR7 and HEK-Blue hTLR8) are obtained from Invivo-Gen. Cells are passed/expanded/stored in liquid nitrogen per supplier's instruction. The cells are typically split twice per week in the growth media of DMEM supplemented with 10% fetal bovine serum, 1× NEAA, 1 mM Pyruvate, 2 mM glutamine, 50 µg/mL penicillin, 50 U/mL streptomycin (each from Gibco) in the presence of the following antibiotics, as shown in Table 3:

TABLE 3

Reporter cell lines treated with antibiotics

| Cell Line | Zeocin | Normocin | Blasticidin |
|---|---|---|---|
| HEK-Blue Null 1 | 100 µg/mL | 100 µg/mL | Not added |
| HEK-Blue hTLR7 | 100 µg/mL | 100 µg/mL | 10 µg/mL |
| HEK-Blue hTLR8 | 100 µg/mL | 100 µg/mL | 30 µg/mL |

General Procedure for In Vitro Small Molecule Screening

Test samples (at desired concentrations diluted in DMEM) are added to the 96-well assay plate, 20 µL per well. Reporter cells are harvested from the tissue culture flasks by incubation in PBS at 37° C. for two minutes after the media in the flask is removed and cells rinsed with PBS. Cells are counted and diluted in the HEK-Blue Detection media at $0.22\times10^6$ cells/mL. Then 180 µL of cells are added to the assay plate containing the 20 µL of test samples, and incubated for 17 hours at 37° C. in a 5% $CO_2$ humidified incubator. Optical density at 640 nm is analyzed using an Envision (Perkin Elmer) plate reader. As described in Table 4, compounds of the disclosure with an $EC_{50}$ value of less than 500 nM have "A" activity, from 500 nM to 1 µM have "B" activity and greater than 1 µM have "C" activity.

TABLE 4

In vitro small molecule screening

| Compound | TLR8 $EC_{50}$ | TLR7 $EC_{50}$ |
|---|---|---|
| 1.15 | A | C |
| 1.16 | B | C |
| 1.17 | A | C |
| 1.18 | C | C |

Example 11

PBMC Screening Assay

Materials and General Procedures

Human peripheral blood mononuclear cells (PBMC) were obtained from BenTek, frozen at $25\times10^6$ cell/mL in 10% DMSO (Sigma) prepared in fetal bovine serum (Gibco) and stored in liquid nitrogen. For culture PBMC were thawed quickly in a 37° C. water bath and diluted into pre-warmed RPMI 1640 (Lonza) supplemented with 10% fetal bovine serum, 2 mM glutamine, 50 µg/mL penicillin, 50 U/mL streptomycin (all from Gibco) and centrifuged for 5 minutes at 500×g. PBMC were suspended into the growth media described above and cultured at a concentration of $1\times10^6$ cells per mL at 37° C. in a 5% $CO_2$ incubator.

General Procedure for In Vitro Small Molecule Screening

PBMC were thawed, suspended at a concentration of $1\times10^6$ cell/mL in growth media and 200 µL was aliquoted into each well of a 96-well plate for a total of $0.2\times10^6$ cells per well. PBMC were incubated for 16-18 hours at 37° C. in a 5% $CO_2$ humidified incubator. The following day PBMC plates were centrifuged at 500×g for 5 minutes and the growth media was removed. 150 µL of twelve concentrations ranging from 1000 to 0.000238 nM of small molecules prepared in growth media were added to PBMC in duplicate and incubated for 24 hours at 37° C. in a 5% $CO_2$ incubator. Prior to supernatant harvest, cells were spun at 500×g for 5 minutes to remove cell debris. TNF-α activity was assessed in the supernatant by ELISA (eBioscience) or HTRF (Cis-Bio) per the manufacturer's instructions. Optical density at 450 nm and 570 nm (ELISA) or luminescence (HTRF) was analyzed using an Envision (Perkin Elmer) plate reader, as shown in Table 5. Compounds of the disclosure with an $EC_{50}$ value of less than 500 nM have "A" activity, from 500 nM to 1 µM have "B" activity and greater than 1 µM to 3 µM have "C" activity.

TABLE 5

In vitro small molecule screening

| Compound | $EC_{50}$ (nM) |
|---|---|
| 1.1 | A |
| 1.2 | A |
| 1.3 | A |
| 1.4 | A |
| 1.5 | A |
| 1.7 | A |
| 1.12 | A |
| 1.13 | A |
| 1.14 | A |
| 1.21 | A |
| 1.22 | A |
| 1.23 | A |
| 1.24 | A |
| 1.25 | A |
| 1.26 | A |
| 1.27 | A |
| 1.28 | A |
| 1.29 | A |
| 1.30 | A |
| 1.31 | A |
| 1.32 | A |
| 1.33 | A |
| 1.34 | A |
| 1.35 | A |
| 1.36 | A |
| 1.37 | A |
| 1.38 | A |
| 1.39 | A |
| 1.47 | B |
| 1.48 | A |
| 1.49 | B |
| 1.50 | A |
| 1.51 | C |
| 1.56 | C |
| 1.57 | A |
| 1.58 | B |
| 1.62 | B |
| 1.63 | B |

Example 12

TNFα Production by PBMCs was Induced by Immune Stimulatory Conjugates

This example shows that immune-stimulatory conjugates can increase production of a pro-inflammatory cytokine, TNFα, by PBMCs in the presence of tumor cells.

PBMCs were isolated from human blood as described above. Briefly, PBMCs were isolated by Ficoll gradient centrifugation, resuspended in RPMI, and plated in 96-well flat bottom microtiter plates (125,000/well). Antigen-expressing tumor cells were then added (25,000/well) along with titrating concentrations of conjugates or unconjugated parental antibodies as controls. After overnight culture, supernatants were harvested, and TNFα levels were determined by AlphaLISA.

Referring to FIG. 1, SKBR3 tumor cells were added to PBMCs, prepared as described above. SKBR3 tumor cells express the tumor antigen HER2. Anti-HER2 TLR8 benzazepine agonist conjugates, either monospecific or bispecific with CD40, and conjugated to various TLR8 benzazepine agonists were added. The conjugates and compound-linkers therein that were used in the study are described in Table 6.

TABLE 6

Exemplary Conjugates and Compound-Linkers Thereof

| Conjugate | Compound-Linker |
| --- | --- |
| Conjugate 1, Conjugate DD, Conjugate FF, Conjugate C | Compound-Linker 2.10 |
| Conjugate 2, Conjugate CC, Conjugate EE, Conjugate B | Compound-Linker 2.8 |
| Conjugate 3, Conjugate F | Compound-Linker 2.7 |
| Conjugate 6, conjugate (Figure 3), conjugate H conjugate I, TLR 8 Agonist (Figures 5 and 6) | Compound-Linker 2.2 |
| Conjugate AA, Conjugate BB, Conjugate A | Compound-Linker 2.1 |
| Conjugate GG, Conjugate BB | Compound-Linker 2.21 |
| Conjugate D | Compound-Linker 2.11 |
| Conjugate E | Compound-Linker 2.9 |
| Conjugate G | Compound-Linker 2.17 |

TNFα production was measured after 24 hours. All of the conjugates were active, stimulating production of TNFα in a dose-dependent manner. In contrast, unconjugated HER2 antibody (HER2 G1WT) and bispecific HER2×CD40 antibody (HER2×CD40) did not stimulate TNFα production.

Figure 2:
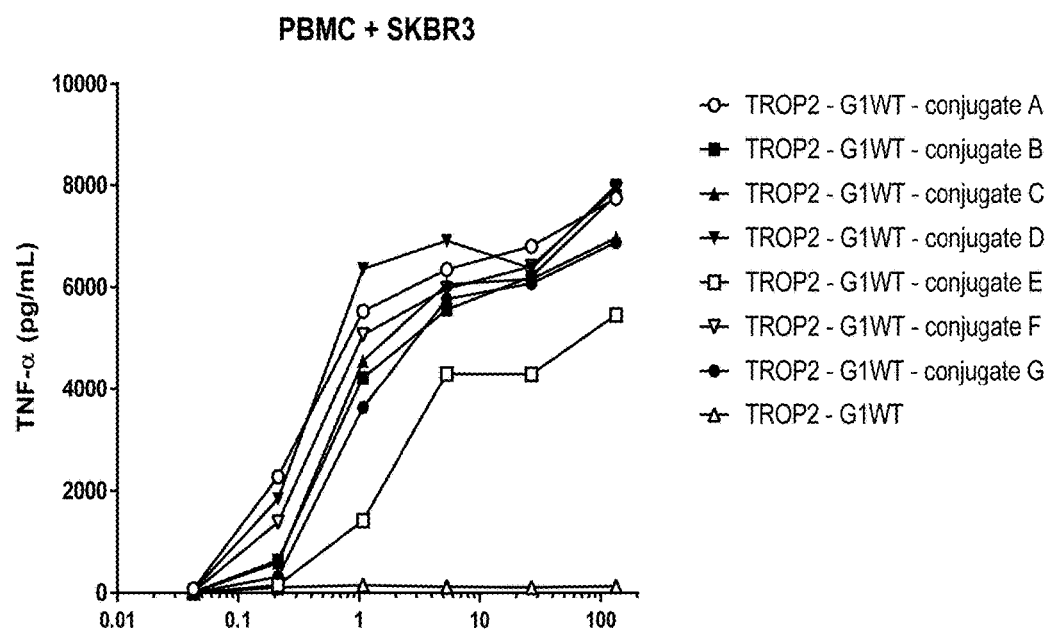
FIG. 2 shows that TROP2-TLR8 agonist conjugates were active in the presence of PBMCs and SKBR3 cells that express HER2, as measured by TNFα production.

Referring to FIG. 2, a similar study was performed using anti-TROP2 conjugates. The conjugate(s) and compound-linkers thereof used in the study are illustrated in Table 6. TROP2 antibodies conjugated to various payloads stimulated the production of TNFα in the presence of PBMCs, while the unconjugated control antibody did not.

Example 13

TNFα Production by Monocytes was Induced by Immune Stimulatory Conjugates

This example shows that immune-stimulatory conjugates can increase the production of a pro-inflammatory cytokine, TNFα, by monocytes in the presence of tumor cells.

Monocytes were prepared as follows: PBMCs were isolated from normal human blood using Ficoll purification, and monocytes were enriched from the PBMCs using Stem Cell Technologies Human Monocyte without CD16 Depletion Negative Selection Kits according to the manufacturer's instructions. Monocytes were then slowly frozen and stored in liquid nitrogen. Prior to assay monocytes were thawed and rested overnight at 37° C. in 5% $CO_2$ in assay media (RPMI 1640 media supplemented with 10% FBS, 50 µg/mL Penicillin, 50 U/mL Streptomycin, 1 mM HEPES, 1× non-essential amino acids, 0.1 mM sodium pyruvate). The following day, monocytes were plated at $4×10^4$ cell/well with or without tumor cells at $4×10^4$ cell/well in 96-well flat bottom plates in assay media described above. After overnight culture, supernatants were harvested, and TNFα levels were determined by AlphaLISA.

Figure 3:
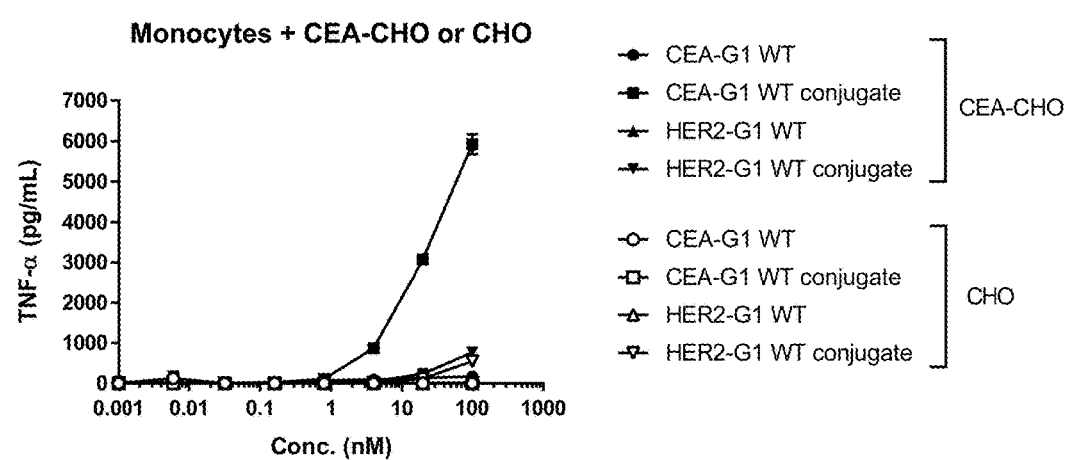
FIG. 3 shows that a CEA-TLR8 agonist conjugate was active in the presence of monocytes and CHO cells engineered to express CEA, while the CEA antibody alone, and the control antibodies and conjugates were not active, as measured by TNFα production.

Referring to FIG. 3, the activity of a CEA TLR8 benzazepine agonist conjugate on CEA-expressing CHO cells, and on control, non-CEA expressing, cells were determined. CEA antibody (CEA-G1 WT), HER2 antibody (HER2-G1 WT antibody) and HER2 conjugate (HER2-G1 WT conjugate) were used as controls. The conjugate and compound-linker therein that was used in the study are described in Table 6. Referring to the figure, only the CEA conjugate exhibited activity, as measured by TNFα production, in the presence of monocytes and tumor cells. The antibodies and conjugates did not stimulate any TNFα production in the presence of CHO cells not expressing detectable HER2 or CEA.

Figure 4:
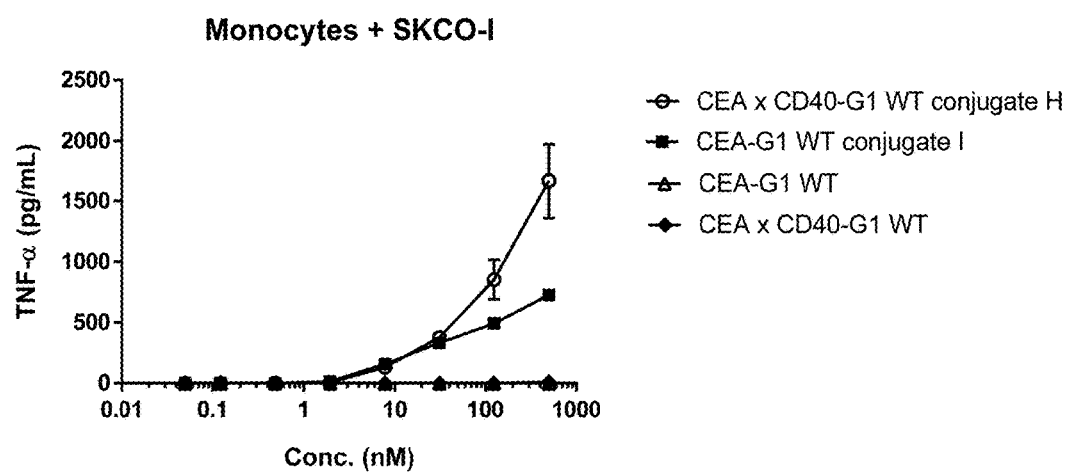
FIG. 4 shows that an anti-CEA-TLR8 agonist conjugate and a CEA×CD40 TLR8 agonist conjugate were active in the presence of monocytes and SKCO-1 cells, as measured by TNFα production.

Referring to FIG. 4, SKCO-1 tumor cells were added to monocytes, prepared as described above. SKCO-1 cells express the tumor antigen CEA. Anti-CEA TLR8 benzazepine agonist conjugates, either monospecific or bispecific with CD40, and conjugated to a TLR8 agonist were added. The conjugates and compound-linkers therein that were used in the study are described in Table 6. TNFα production was measured after 24 hours. Both conjugates were active, stimulating production of TNFα in a dose-dependent manner. Notably the specific CEA×CD40 conjugate was more active. In contrast, unconjugated CEA antibody (CEA-G1 WT) and bispecific CEA×CD40 antibody (CEA×CD40) did not stimulate TNFα production.

Figure 5:
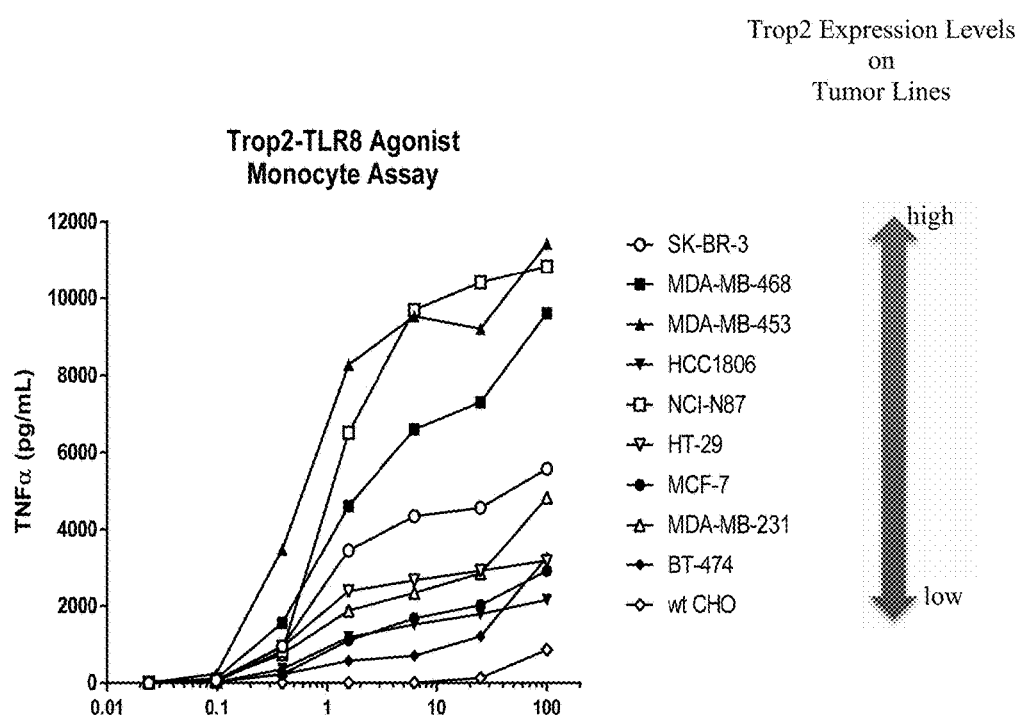
FIG. 5 shows that a TROP TRL8 agonist conjugate was active in a dose-dependent manner on various cell lines expressing TROP2.

Referring to FIG. 5, another study was performed using an anti-TROP2 conjugate and ten different cell lines expressing varying levels of TROP2. The conjugates and compound-linker therein used in the study are described in Table 6. As shown in the figure, the activity of the TROP2-TLR8 benzazepine agonist conjugates, as measured by TNFα production, varied in the dose-dependent manner and generally in accordance with the level of TROP2 expression by the cell line. The control cell line, wt-CHO, does not express detectable levels of TROP2 and little TNFα production was detected when this cell line was used.

Example 14

TNFα Production by Macrophages was Induced by Immune Stimulatory Conjugates

This example shows that immune-stimulatory conjugates can increase the production of a pro-inflammatory cytokine, TNFα, by macrophages in the presence of tumor cells.

Figure 6:
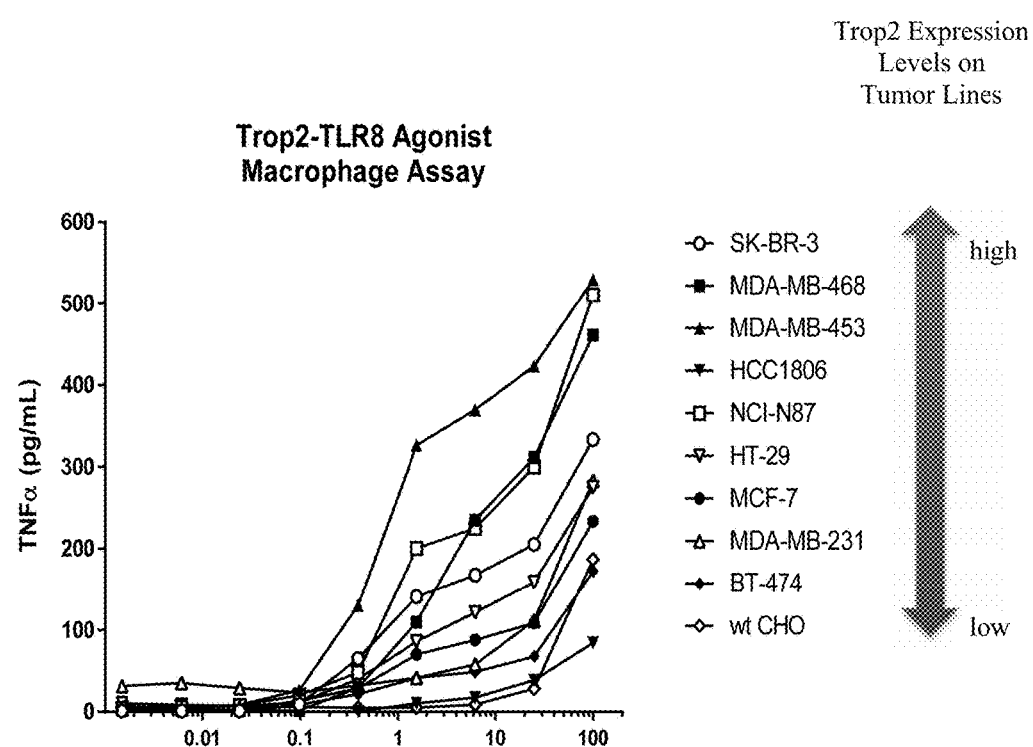
FIG. 6 shows that a TROP2 TLR8 agonist conjugate was active in a dose-dependent manner on various cell lines expressing TROP2.

Macrophages were generated as follows: Monocytes were isolated from human peripheral blood mononuclear cells (PBMCs) using magnetic bead-based negative selection and cultured 7 days in the presence of GM-CSF to generate macrophages. Macrophages were plated in 96-well flat bottom microtiter plates (40,000/well). Antigen-expressing tumor cells were then added (40,000/well) along with titrating concentrations of conjugates or unconjugated parental antibodies as controls. After overnight culture, supernatants were harvested, and TNFα levels were determined by AlphaLISA. Referring to FIG. 6, a study was performed using an anti-TROP2 conjugate and ten different cell lines expressing varying levels of TROP2. The conjugates and compound-linker therein used in the study are illustrated in Table 6. As shown in the figure, the activity of the TROP2-TLR8 benzazepine agonist conjugates, as measured by TNFα production, varied in the dose-dependent manner and generally in accordance with the level of TROP2 expression by the cell line. The control cell line, wt —CHO, does not express detectable levels of TROP2 and little TNFα production was detected when this cell line was used.

Example 15

TNFα Production by PBMCs was Induced by Immune Stimulatory Conjugates

This example shows that immune-stimulatory conjugates can increase production of a pro-inflammatory cytokine, TNFα (TNFα), by PBMCs in the presence of various tumor cell lines.

PBMCs were isolated from human blood as described above. Briefly, PBMCs were isolated by Ficoll gradient centrifugation, resuspended in RPMI, and plated in 96-well flat bottom microtiter plates (125,000/well). Antigen-expressing tumor cells were then added (25,000/well) along with titrating concentrations of conjugates or unconjugated parental antibodies as controls. After overnight culture, supernatants were harvested, and TNFα levels were determined by AlphaLISA.

Anti-TROP2 mAbs (aTROP2) or anti-HER2 mAbs (aHER2) were conjugated to various TLR8 benzazepine agonists attached to linkers. The TLR8 benzazepine agonist-linker compounds are identified by compound number and refer to those in the Examples above.

Figure 7:
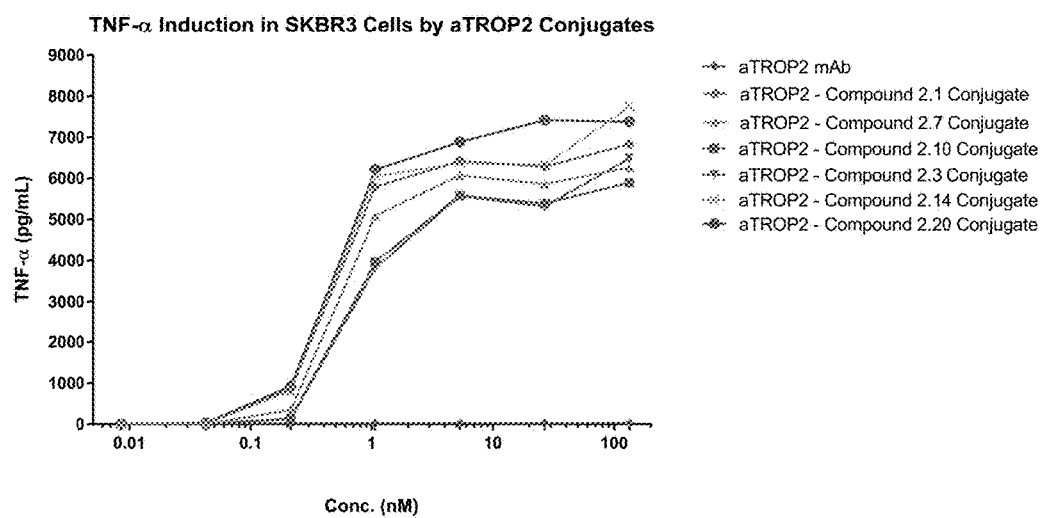
FIG. 7 shows TNF-α induction in SKBR3 cells by aTROP2 conjugates.

Referring to FIG. 7, aTROP2 conjugates and control aTROP2 antibody were added to SKBR3 tumor cells (expressing high levels of TROP2). All of the conjugates were active, stimulating production of TNFα by PBMCs in the presence of antigen positive tumor cells. The control antibody did not stimulate production of TNFα.

Figure 8:
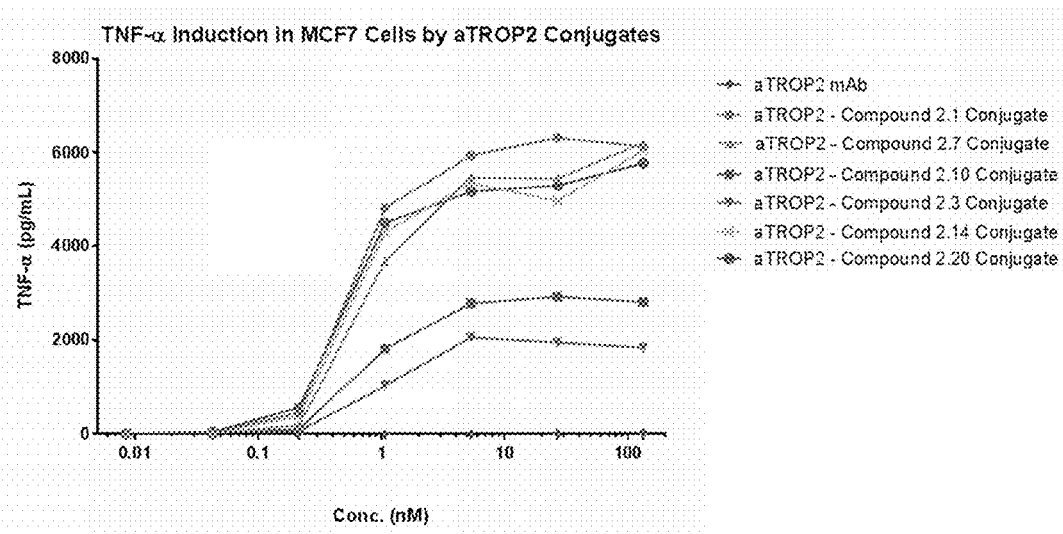
FIG. 8 shows TNF-α induction in MCF7 cells by aTROP2 conjugates.

Referring to FIG. 8, aTROP2 conjugates and control aTROP2 antibody were added to MCF7 tumor cells (expressing moderate levels of TROP2). The conjugates were active, stimulating production of TNFα by PBMCs, although the activity varied depending on the compound attached to the antibody. The control antibody did not stimulate production of TNFα.

Figure 9:
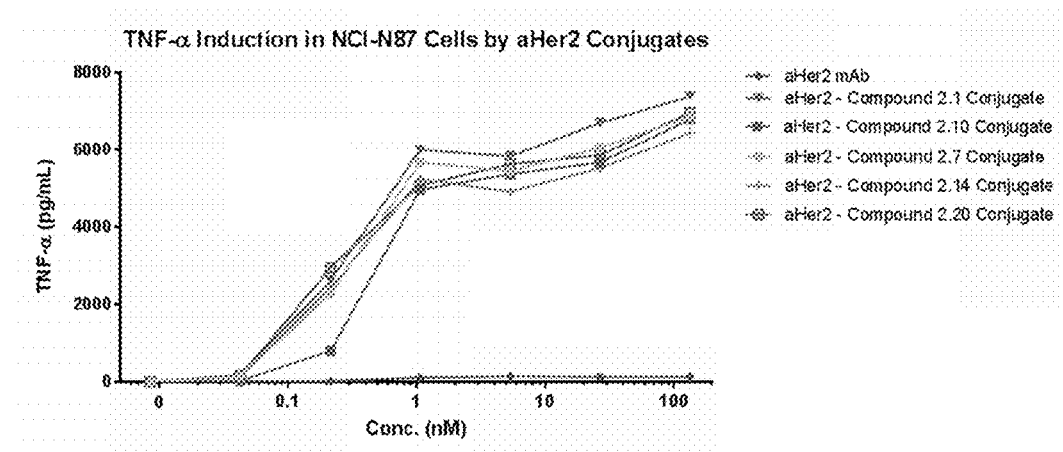
FIG. 9 shows TNF-α induction in NCI-N87 cells by aHER2 conjugates.

Referring to FIG. 9, aHER2 conjugates and control aHER2 antibody were added to NCI-N87 tumor cells (expressing high levels of HER2). All of the conjugates were active, stimulating production of TNFα by PBMCs in the presence of antigen positive tumor cells. The control antibody did not stimulate production of TNFα.

Figure 10:
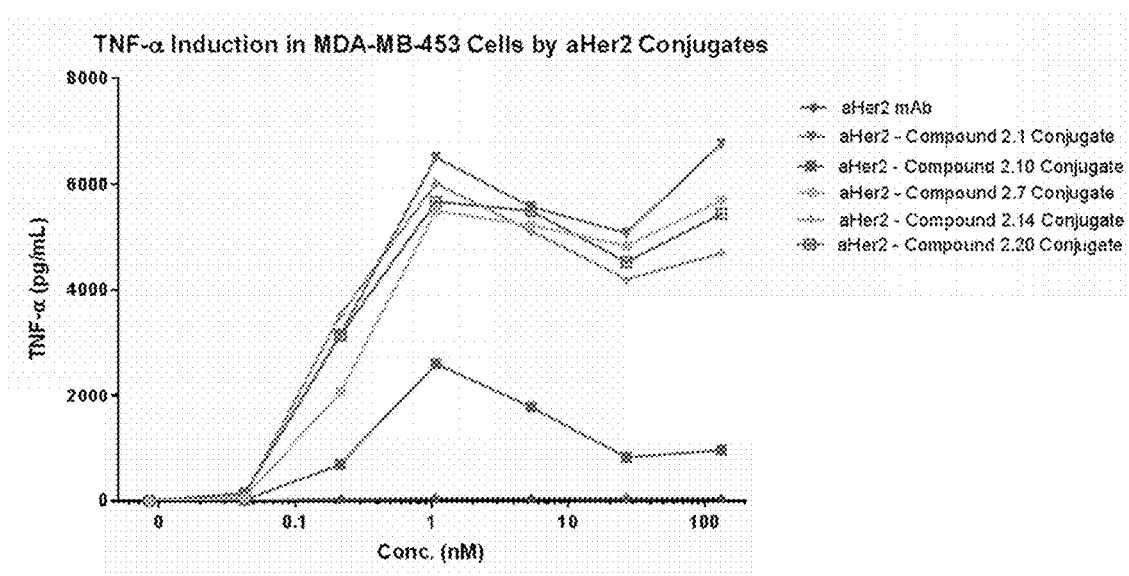
FIG. 10 shows TNF-α induction in MDA-MB-453 cells by aHER2 conjugates.

Referring to FIG. 10, aHER2 conjugates and control aHER2 antibody were added to MDA-MB-453 tumor cells (expressing moderate levels of HER2). All of the conjugates were active, stimulating production of TNFα by PBMCs, although the activity varied depending on the compound attached to the antibody. The control antibody did not stimulate production of TNFα.

Example 16

Antigen Dependent Monocyte Activation by a TROP2-TLR8 Benzazepine Conjugate in a Mouse Model This example shows that a conjugate of a TROP2 antibody attached to a TLR8 benzazepine agonist can activate human monocytes in a mouse model.

Human monocytes were prepared as described above. Trop2$^+$ MDA-MB-453 cells or Trop2$^-$ MiaPaca2 were cultured by standard methods. A TLR8 benzazepine linker payload (LP) was prepared by attaching a MCC (N-maleimidomethyl]cyclohexane-1-carboxylate) linker in place of the mc-vc-PABA linker in Compound-Linker 2.1 to form Compound-Linker 2.22. TROP2-TLR8 benzazepine conjugates were prepared by conjugation of Compound-Linker 2.22 to a TROP2 antibody (sacituzumab) to form a conjugate with an average DAR of about 4.

On Day 1 NOD SCID mice were injected with $5 \times 10^5$ Trop2$^+$ MDA-MB-453 cells or Trop2$^-$ MiaPaca2 cells. Seven to ten days later when the tumor size reached about 300 mm$^3$, the mice were injected intravenously with 5-20 mg/kg of the TROP2-TLR8 benzazepine conjugate or TROP2 antibody alone. Sixteen hours later, $10^6$ human monocytes were injected intratumorally. Four to six hours later, the tumors were harvested and digested. Monocytes were identified by staining for cell surface markers and monocyte activation was determined by intracellular staining for IL-6.

In mice having a TROP2$^+$ tumor and receiving the TROP2-TLR8 benzazepine agonist conjugate, human monocytes were activated. In contrast, in mice having a TROP2-tumor, the TROP2-TLR8 benzazepine agonist conjugate did not cause human monocyte activation. Similarly, the control antibody alone did not cause human monocyte activation in either model.

What is claimed is:

1. A compound represented by the structure of Formula (IIB):

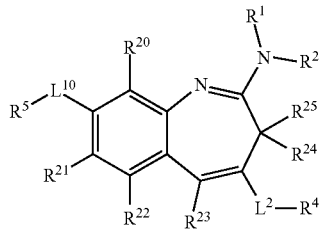

(IIB)

or a pharmaceutically acceptable salt thereof, wherein:

$L^{10}$ is selected from —C(O)—, and —C(O)N($R^{10}$)—*, wherein * represents where $L^{10}$ is bound to $R^5$—;

$L^2$ is selected from —C(O)— and —C(O)N($R^{10}$)—;

$R^1$ and $R^2$ are independently selected from hydrogen; and $C_{1-10}$ alkyl, $C_{2-10}$ alkenyl, and $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)$_2$, —S(O)$R^{10}$, —S(O)$_2R^{10}$, —C(O)$R^{10}$, —C(O)O$R^{10}$, —OC(O)$R^{10}$, —NO$_2$, =O, =S, =N($R^{10}$), and —CN;

$R^4$ is selected from:

—O$R^{10}$, —N($R^{10}$)$_2$, —C(O)N($R^{10}$)$_2$, —C(O)$R^{10}$, —C(O)O$R^{10}$, —S(O)$R^{10}$, and —S(O)$_2R^{10}$; and $C_{1-10}$ alkyl, $C_{2-10}$ alkenyl, $C_{2-10}$ alkynyl, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{3-12}$ carbocycle, and 3- to 12-membered heterocycle; and $C_{3-12}$ carbocycle, and 3- to 12-membered heterocycle, each of which is optionally substituted with one or more substituents independently selected from halogen, —O$R^{10}$, —S$R^{10}$, —C(O)N($R^{10}$)$_2$, —N($R^{10}$)C(O)$R^{10}$, —N($R^{10}$)C(O)N($R^{10}$)$_2$, —N($R^{10}$)$_2$, —C(O)$R^{10}$, —C(O)O$R^{10}$, —OC(O)$R^{10}$, —NO$_2$, =O, =S, =N($R^{10}$), —CN, $C_{1-6}$ alkyl, $C_{2-6}$ alkenyl, and $C_{2-6}$ alkynyl;

$R^5$ is selected from unsaturated $C_{4-8}$ carbocycle; bicyclic carbocycle; and fused 5-5, fused 5-6, and fused 6-6 bicyclic heterocycle, wherein $R^5$ is optionally substituted and wherein substituents are independently selected at each occurrence from:

halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), and —CN; and C$_{1-10}$ alkyl, C$_{2-10}$ alkenyl, C$_{2-10}$ alkynyl, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{3-12}$ carbocycle, and 3- to 12-membered heterocycle; and C$_{3-12}$ carbocycle, and 3- to 12-membered heterocycle, each of which is optionally substituted with one or more substituents independently selected from halogen, —OR$^{10}$, —SR$^{10}$, —C(O)N(R$^{10}$)$_2$, —N(R$^{10}$)C(O)R$^{10}$, —N(R$^{10}$)C(O)N(R$^{10}$)$_2$, —N(R$^{10}$)$_2$, —C(O)R$^{10}$, —C(O)OR$^{10}$, —OC(O)R$^{10}$, —NO$_2$, =O, =S, =N(R$^{10}$), —CN, C$_{1-6}$ alkyl, C$_{2-6}$ alkenyl, and C$_{2-6}$ alkynyl;

R$^{10}$ is independently selected at each occurrence from: hydrogen, —NH$_2$, and —C(O)OCH$_2$C$_6$H$_5$; and C$_{1-10}$ alkyl, C$_{2-10}$ alkenyl, C$_{2-10}$ alkynyl, C$_{3-12}$ carbocycle, and 3- to 12-membered heterocycle, each of which is optionally substituted with one or more substituents independently selected from halogen, —OH, —CN, —NO$_2$, —NH$_2$, =O, =S, —C(O)OCH$_2$C$_6$H$_5$, —NHC(O)OCH$_2$C$_6$H$_5$, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

R$^{20}$, R$^{21}$, R$^{22}$, and R$^{23}$ are independently selected from hydrogen, halogen, OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; and R$^{24}$ and R$^{25}$ are independently selected from hydrogen, halogen, —OR$^{10}$, —SR$^{10}$, —N(R$^{10}$)$_2$, —S(O)R$^{10}$, —S(O)$_2$R$^{10}$, —C(O)R$^{10}$, —C(O)OR$^{10}$, —OC(O)R$^{10}$, —NO$_2$, =O, =S, =N(R$^{10}$), —CN, C$_{1-10}$ alkyl, C$_{2-10}$ alkenyl, and C$_{2-10}$ alkynyl; or R$^{24}$ and R$^{25}$ taken together form an optionally substituted saturated C$_{3-7}$ carbocycle.

2. The compound or salt of claim 1, wherein R$^{20}$, R$^{21}$, R$^{22}$, and R$^{23}$ are independently selected from hydrogen, halogen, —OH, —OR$^{10}$, —NO$_2$, —CN, and C$_{1-10}$ alkyl.

3. The compound or salt of claim 2, wherein R$^{20}$, R$^{21}$, R$^{22}$, and R$^{23}$ are each hydrogen.

4. The compound or salt of claim 1, wherein R$^{24}$ and R$^{25}$ are each hydrogen.

5. The compound or salt of claim 1, wherein R$^1$ and R$^2$ are each hydrogen.

6. The compound or salt of claim 1, wherein L$^{10}$ is selected from —C(O)N(R$^{10}$)—*.

7. The compound or salt of claim 6, wherein R$^{10}$ of —C(O)N(R$^{10}$)—* is selected from hydrogen and C$_{1-6}$ alkyl.

8. The compound or salt of claim 7, wherein L$^{10}$ is —C(O)NH—*.

9. The compound or salt of claim 1, wherein R$^5$ is an optionally substituted 8- to 12-membered bicyclic carbocycle.

10. The compound or salt of claim 1, wherein R$^5$ is an 8- to 12-membered bicyclic carbocycle optionally substituted with one or more substituents independently selected from —OR$^{10}$, —N(R$^{10}$)$_2$, and =O.

11. The compound or salt of claim 10, wherein R$^5$ is an optionally substituted indane, or optionally substituted tetrahydronaphthalene.

12. The compound or salt of claim 1, wherein R$^5$ is selected from an optionally substituted fused 5-5, fused 5-6, and fused 6-6 bicyclic heterocycle.

13. The compound or salt of claim 12, wherein R$^5$ is an optionally substituted fused 5-5, fused 5-6, or fused 6-6 bicyclic heterocycle with one or more substituents independently selected from —C(O)OR$^{10}$, —N(R$^{10}$)$_2$, —OR$^{10}$, and optionally substituted C$_{1-10}$ alkyl.

14. The compound or salt of claim 1, wherein R$^5$ is an optionally substituted fused 6-6 bicyclic heterocycle.

15. The compound or salt of claim 14, wherein the fused 6-6 bicyclic heterocycle is an optionally substituted pyridine-piperidine.

16. The compound or salt of claim 15, wherein L$^{10}$ is bound to a carbon atom of the pyridine of the fused pyridine-piperidine.

17. The compound or salt of claim 1, wherein R$^5$ is selected from tetrahydroquinoline, tetrahydroisoquinoline, tetrahydronaphthyridine, cyclopentapyridine, and dihydrobenzoxaborole, any one of which is optionally substituted.

18. The compound or salt of claim 17, wherein substituents on R$^5$ are independently selected at each occurrence from:

halogen, —OR$^{10}$, —SR$^{10}$, —C(O)N(R$^{10}$)$_2$, —N(R$^{10}$)C(O)R$^{10}$, —N(R$^{10}$)$_2$, —C(O)R$^{10}$, —C(O)OR$^{10}$, —OC(O)R$^{10}$, —NO$_2$, =O, and —CN; and C$_{1-10}$ alkyl optionally substituted with one or more substituents independently selected from halogen, —OR$^{10}$, —SR$^{10}$, —N(R$^{10}$)$_2$, —C(O)R$^{10}$, —C(O)OR$^{10}$, —NO$_2$, =O, and —CN.

19. The compound or salt of claim 1, wherein R$^5$ is not substituted.

20. The compound or salt of claim 1, wherein L$^2$ is —C(O)—.

21. The compound or salt of claim 1, wherein R$^4$ is —N(R$^{10}$)$_2$.

22. The compound or salt of claim 21, wherein R$^{10}$ of —N(R$^{10}$)$_2$ is independently selected at each occurrence from optionally substituted C$_{1-6}$ alkyl.

23. The compound or salt of claim 22, wherein -L$^2$-R$^4$ is

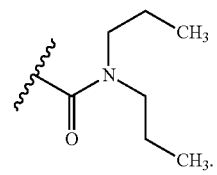

24. The compound or salt of claim 1, wherein the compound is selected from:

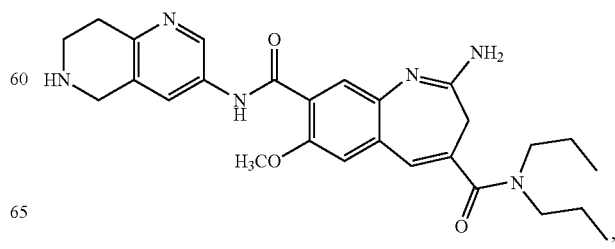

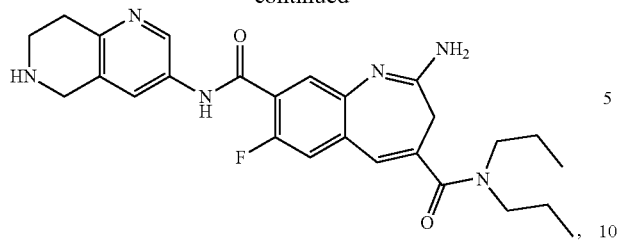

and a salt of any one thereof.

25. The compound or salt of claim 1, wherein
$L^{10}$ is —C(O)N(H)—*,
$L^2$ is —C(O)—,
$R^1$ and $R^2$ are hydrogen;
$R^4$ is —N($R^{10}$)$_2$, wherein $R^{10}$ of —N($R^{10}$)$_2$ is independently selected at each occurrence from optionally substituted $C_{1-6}$ alkyl; and
$R^{20}$, $R^{21}$, $R^{22}$, $R^{23}$, $R^{24}$ and $R^{25}$ are independently selected from hydrogen.

26. The compound or salt of claim 25, wherein $R^5$ is an optionally substituted 8- to 12-membered bicyclic carbocycle.

27. The compound or salt of claim 25, wherein $R^5$ is selected from an optionally substituted fused 5-5, fused 5-6, and fused 6-6 bicyclic heterocycle.

28. The compound or salt of claim 1, wherein the compound is further covalently bound to a linker, $L^3$.

29. The compound or salt of claim 28, wherein $L^3$ is attached, valence permitting, to a substitutable nitrogen atom of the compound represented by the structure of Formula (IIB).

30. The compound or salt of claim 28, wherein $L^3$ is a noncleavable linker.

31. The compound or salt of claim 28, wherein $L^3$ is a cleavable linker.

32. The compound or salt of claim 31, wherein $L^3$ is cleavable by a lysosomal enzyme.

33. The compound or salt of claim 28, wherein $L^3$ is represented by the formula:

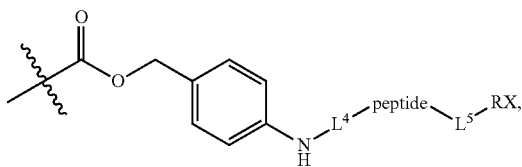

wherein:
$L^4$ represents the C-terminus of the peptide and $L^5$ is selected from a bond, alkylene and heteroalkylene, wherein $L^5$ is optionally substituted with one or more groups independently selected from $R^{32}$, and RX is a reactive moiety; and
$R^{32}$ is independently selected at each occurrence from halogen, —OH, —CN, —O-alkyl, —SH, =O, =S, —NH$_2$, —NO$_2$; and $C_{1-10}$ alkyl, $C_{2-10}$ alkenyl, $C_{2-10}$ alkynyl, each of which is optionally substituted with one or more substituents independently selected from halogen, —OH, —CN, —O— alkyl, —SH, =O, =S, —NH$_2$, and —NO$_2$.

34. The compound or salt of claim 33, wherein RX comprises a maleimide.

35. The compound or salt of claim 33, wherein the peptide of $L^3$ comprises Val-Cit or Val-Ala.

36. The compound or salt of claim 28, wherein $L^3$ is represented by the formula:

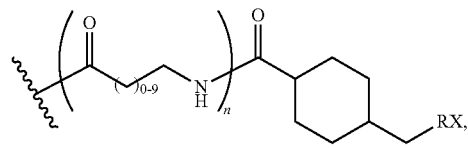

wherein RX comprises a reactive moiety, and n=0-9.

37. The compound or salt of claim 28, wherein $L^3$ is further covalently bound to an antibody construct.

38. The compound or salt of claim 37, wherein $L^3$ is attached to the antibody construct at a lysine or cysteine residue.

39. A pharmaceutical composition comprising the compound or salt of claim 1 and at least one pharmaceutically acceptable excipient.

40. A method of treating cancer, comprising administering to a subject in need thereof an effective amount of the pharmaceutical composition of claim 39.

41. A method of preparing an antibody conjugate of the formula

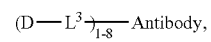

wherein Antibody is an antibody construct and D is a compound or salt of claim 1, wherein $L^3$-D is contacted with an antibody construct.

* * * * *